United States Patent
Liu et al.

(10) Patent No.: US 8,431,607 B2
(45) Date of Patent: Apr. 30, 2013

(54) COMPOUNDS AND COMPOSITIONS AS INHIBITORS OF CANNABINOID RECEPTOR 1 ACTIVITY

(75) Inventors: Hong Liu, San Diego, CA (US); Xiaohui He, San Diego, CA (US); Dean Phillips, San Marcos, CA (US); Xuefeng Zhu, Carlsbad, CA (US); Kunyong Yang, San Diego, CA (US); Thomas Lau, San Diego, CA (US); Baogen Wu, San Diego, CA (US); Yongping Xie, San Diego, CA (US); Truc Ngoc Nguyen, San Diego, CA (US); Xing Wang, San Diego, CA (US)

(73) Assignee: IRM LLC, A Delaware Limited Liability Company, Hamilton (BM)

( * ) Notice: Subject to any disclaimer, the term of this patent is extended or adjusted under 35 U.S.C. 154(b) by 639 days.

(21) Appl. No.: 12/519,147

(22) PCT Filed: Dec. 12, 2007

(86) PCT No.: PCT/US2007/087230
§ 371 (c)(1),
(2), (4) Date: Jan. 27, 2010

(87) PCT Pub. No.: WO2008/076754
PCT Pub. Date: Jun. 26, 2008

(65) Prior Publication Data
US 2010/0234365 A1    Sep. 16, 2010

Related U.S. Application Data

(60) Provisional application No. 60/870,339, filed on Dec. 15, 2006, provisional application No. 60/953,595, filed on Aug. 2, 2007.

(51) Int. Cl.
*A01N 43/50* (2006.01)
*A61K 31/415* (2006.01)
*A61K 31/50* (2006.01)
*A61K 31/501* (2006.01)
*A61K 31/497* (2006.01)
*C07D 401/00* (2006.01)
*C07D 233/00* (2006.01)
*C07D 233/02* (2006.01)
*C07D 241/00* (2006.01)
*C07D 241/02* (2006.01)

(52) U.S. Cl.
USPC ..... 514/391; 514/390; 514/252.1; 546/272.7; 548/300.1; 544/336

(58) Field of Classification Search ............ 514/391, 514/390, 252.1; 546/272.7; 548/300.1; 544/336
See application file for complete search history.

(56) References Cited

U.S. PATENT DOCUMENTS 3,129,228 A    4/1964    Habicht

FOREIGN PATENT DOCUMENTS

| CA | 1053243 | 4/1979 |
|---|---|---|
| EP | 0270093 A2 * | 8/1988 |
| EP | 0270093 | 6/1998 |
| EP | 1165505 | 9/2004 |
| FR | 2097038 | 3/1972 |
| JP | 63264458 | 11/1988 |
| WO | WO 9603386 A1 * | 2/1996 |
| WO | WO2004031160 | 4/2004 |
| WO | WO2004039788 | 5/2004 |
| WO | WO2004058249 | 7/2004 |
| WO | WO2006060461 | 6/2006 |
| WO | WO2006124447 | 11/2006 |
| WO | WO2007020502 | 2/2007 |
| WO | WO2007084319 | 7/2007 |

OTHER PUBLICATIONS

Nadir et al. "Facile Cleavage of N-Arylsulfonyl Bond of N-Arylsulfonyl-imidazolidinone with Magnesium Methanol" J. heterocyclic Chem, 2004, vol. 41, pp. 737-739.*
Machine translation of WO 9603386 claims, pp. 1-9, printed May 17, 2012.*
Database Beilstein; Beilstein Institute for Organic Chemistry, Frankfurt-Main, DE; No. 233033, 1957, Irwin; Wheeler XP002500011.
Database Beilstein; Beilstein Institute for Organic Chemistry, Frankfurt-Main, DE; No. 203272; 1953; Pernot; Willemart; XP002500012.
Database Beilstein; Beilstein Institute for Organic Chemistry, Frankfurt-Main, DE; No. 804179; 1979; Bal'on; Moskaleva; XP002500013.
Database Beilstein; Beilstein Institute for Organic Chemistry, Frankfurt-Main, DE; No. 802066; 1979; Bal'on; Moskaleva; XP002500014.
Database Beilstein; Beilstein Institute for Organic Chemistry, Frankfurt-Main, DE; No. 802065; 1979; Bal'on; Moskaleva; XP002500015.
Database Beilstein; Beilstein Institute for Organic Chemistry, Frankfurt-Main, DE; No. 797466; 1979; Bal'on; Moskaleva; XP002500016.

(Continued)

*Primary Examiner* — Sreeni Padmanabhan
*Assistant Examiner* — Kendra D Carter
(74) *Attorney, Agent, or Firm* — Genomics Institute of the Novartis Research Foundation; Chihang Amy Smith

(57) ABSTRACT

The invention provides compounds, pharmaceutical compositions comprising such compounds and methods of using such compounds to treat or prevent diseases or disorders associated with the activity of Cannabinoid Receptor 1 (CB1).

8 Claims, No Drawings

OTHER PUBLICATIONS

Muccioli, et al., "Synthesis and Activity of 1,3,5-Triphenylimidazolidine-2,4-diones and 1,3,5-Triphenyl-2-thioxoimidazolidin-4-ones: Characterization of New CB1 Cannabinoid Receptor Inverse Agonists/Antagonists", J. Med. Chem., 2006, pp. 872-882, vol. 49, American Chemical Society.

Herweh, et al., "Synthesis and Nuclear Magnetic Resonance Spectra of 2-Oxazolidones", The Journal of Organic Chemistry, Nov. 1968, pp. 4029-4033, vol. 33, No. 11.

Ghosh, et al., "Palladium-Catalyzed Synthesis of N-Aryloxazolidines from Aryl Chlorides", Organic Letters, Jan. 1, 2003, pp. 2207-2210, vol. 5, No. 13, American Chemical Society, Columbus, OH, US.

Baeg, et. Al., "Novel Palladium (II)-Catalyzed Cyclization of Aziridines and Sulfur Diimides", J. Am. Chem. Soc., 1994, pp. 1220-1224, vol. 116, American Chemical Society.

Crowther, et al., "The Formation of Tetrahydro-oxazoles from α-Hydroxy-β-anilino-αβ-diphenylethane and its Homologues", Journal of the Chemical Society, Transactions, 1913, pp. 27-31.

Hayashi, et al., "The stereoselective synthesis of α-substituted b-amino secondary alcohols based on the proline-mediated, asymmetric, three-component Mannich reaction and its application to the formal total synthesis of nikkomycins B and $B_x$", Tetrahedron, 2005, pp. 11393-11404, vol. 61, Elsevier.

Jaunin, et al., "Action des aldéhydes formique at acétique sur les diarylamino-1,2-diphényl-1,2-éthanes", Helvetica Chimica Acta, 1961, pp. 309,-313, vol. 44.

Lee, et al., "DFT Studies on Binding of $Pt(NH_3)_2Cl^+$ to Guanine", Bull. Korean Chem. Soc., 2001, pp. 11-12.

Pernot, et al., "Obtention de pyrrolidines et d'isoindolines d-arylees", Bulletin de la Societe Chimique de France, 1953, pp. 324-326.

Barbon, et al., Zhurnal Organicheskoi Khimii, 1979, pp. 1207-1212, vol. 15.

\* cited by examiner

COMPOUNDS AND COMPOSITIONS AS INHIBITORS OF CANNABINOID RECEPTOR 1 ACTIVITY

CROSS-REFERENCE TO RELATED APPLICATIONS

This application is a 371 U.S. national phase application of international application number PCT/US2007/087230 filed 12 Dec. 2007, which application claims priority to U.S. provisional patent application No. 60/870,339, filed 15 Dec. 2006 and U.S. provisional patent application No. 60/953,595, filed 2 Aug. 2007. The full disclosure of these applications is incorporated herein by reference in its entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of Cannabinoid Receptor 1 (CB1).

2. Background

The cannabinoids are psychoactive ingredients of marijuana, principally delta-9-tetrahydrocannabinol. Two cannabinoid receptors have been cloned, CB1 and CB2. CB1 is predominantly expressed in the central nervous system whereas CB2 is expressed in peripheral tissues, principally in the immune system. Both receptors are members of the G-protein coupled class and their inhibition is linked to adenylate cyclase activity.

The novel compounds of this invention inhibit the activity of CB1 and are, therefore, expected to be useful in the treatment of CB1-associated diseases or disorders such as, but not limited to, psychosis, memory deficit, cognitive disorders, migraine, neuropathy, neuroinflammatory disorders, cerebral vascular accidents, head trauma, anxiety disorders, substance abuse (such as smoking cessation), stress, epilepsy, Parkinson's disease, schizophrenia, osteoporosis, constipation, chronic intestinal pseudo-obstruction, cirrhosis of the liver, asthma, obesity, and other eating disorders associated with excessive food intake.

SUMMARY OF THE INVENTION

In one aspect, the present invention provides a compound of Formula I:

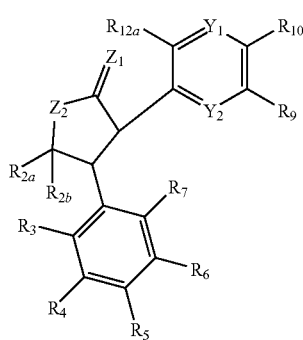

in which:
$Y_1$ is selected from N and $CR_{11}$;
$Y_2$ is selected from N and $CR_8$;
$Z_1$ is selected from S, O, NH, CH—$NO_2$, $NS(O)_2NH_2$, $NC(O)NH_2$, $NS(O)_2CH_3$, N(OH) and N(CN); or C=$Z_1$ of Formula I is replaced with $CH_2$ or $S(O)_2$;
$Z_2$ is selected from O, —$CH_2CHR_{1a}$—, —$OCHR_{1a}$—, —$CR_{1a}R_{1b}$ and —$NR_{1a}$;
$R_{1a}$ is selected from hydrogen, cyano, $C_{1-6}$alkyl, cyano-substituted-$C_{1-6}$alkyl, $C_{2-6}$alkenyl, —$X_1R_{12}$, —$X_1NR_{13}S(O)_2R_{13}$, —$X_1OS(O)_2R_{13}$, —$X_1NR_{13}X_1OR_{13}$, —$X_1OR_{13}$, —$X_1C(O)OR_{13}$, —$X_1S(O)_2R_{12}$, —$X_1S(O)_2NR_{13}C(O)R_{13}$, —$X_1S(O)_2R_{13}$, —$X_1C(O)R_{12}$, —$X_1NR_{13}R_{13}$, —$X_1S(O)_2NR_{13}R_{13}$, —$X_1OC(O)NR_{13}R_{13}$, —$X_1C(O)NR_{12}R_{13}$, —$X_1NR_{13}X_1C(O)NR_{12}$, —$X_1NR_{13}X_1C(O)NR_{13}R_{13}$, —$X_1C(O)NR_{13}X_1C(O)OR_{13}$, —$X_1C(O)NR_{13}X_1NR_{13}R_{13}$, —$X_1C(O)NR_{13}X_1OR_{13}$ and —$X_1C(O)NR_{13}R_{13}$; wherein $R_{12}$ is selected from $C_{6-10}$aryl, $C_{5-10}$heteroaryl, $C_{3-12}$cycloalkyl and $C_{3-10}$heterocycloalkyl; wherein said aryl, heteroaryl, cycloalkyl or heterocycloalkyl of $R_{12}$ is optionally substituted by 1 to 3 radicals independently selected from hydroxy, bis-hydroxy-$C_{1-6}$alkyl-amino, $C_{1-6}$alkyl-amino, $C_{1-6}$alkyl, $C_{1-6}$alkoxy, $C_{1-6}$alkoxy-carbonyl, $C_{1-6}$alkyl-sulphoxy, $C_{1-6}$alkyl-carboxy, $C_{1-6}$alkyl-sulfonyl, halo-substituted-$C_{1-6}$alkyl, halo-substituted-$C_{1-6}$alkoxy, $C_{3-12}$cycloalkyl, $C_{3-10}$heterocycloalkyl, $C_{5-10}$heteroaryl and $C_{6-10}$aryl optionally substituted with 1 to 3 halo radicals; wherein said cycloalkyl, heterocycloalkyl, heteroaryl and aryl substituents of $R_{12}$ can be further optionally substituted with 1 to 3 $C_{1-6}$alkyl radicals; wherein each $R_{13}$ is independently selected from hydrogen, $C_{1-6}$alkyl, hydroxy-$C_{1-6}$alkyl, $C_{6-10}$aryl, $C_{3-10}$heterocycloalkyl; wherein said aryl or heterocycloalkyl of $R_{13}$ is optionally substituted with a group selected from $C_{1-6}$alkyl and $C_{1-6}$alkoxy; wherein each $X_1$ is independently selected from a bond and $C_{1-4}$alkylene; wherein any alkyl of $R_1$ is optionally substituted with cyano;
$R_{1b}$ is selected from hydrogen, $C_{1-6}$alkyl and $C_{2-6}$alkenyl;
$R_{2a}$ is selected from hydrogen, $C_{1-6}$alkyl, halo-substituted-$C_{1-6}$alkyl, $C_{6-10}$aryl, —$X_2NR_{14}X_2NR_{14}R_{14}$, —$X_2NR_{14}C(O)X_2NR_{14}C(O)OR_{14}$, —$X_2NR_{14}X_2R_{15}$, —$X_2OC(O)NR_{14}R_{14}$, —$X_2OC(O)NR_{14}R_{15}$, —$X_2NR_{14}R_{14}$, —$X_2NR_{14}S(O)_2R_{14}$, —$X_2NR_{14}S(O)_2R_{15}$, —$X_2S(O)_{0-2}R_{15}$, —$X_2NR_{14}C(O)R_{14}$, —$X_2NR_{14}C(O)R_{15}$, —$X_2NR_{14}C(O)X_2NR_{14}R_{14}$, —$X_2OSi(R_{14})_3$, —$X_2OC(O)NR_{14}R_{15}$, —$X_2C(O)OR_{14}$, —$X_2OR_{14}$, —$X_2OX_2R_{15}$, —$X_2R_{15}$ and —$X_2C(O)R_{15}$; wherein each $R_{14}$ is independently selected from hydrogen and $C_{1-6}$alkyl; $R_{15}$ is selected from cyano, $C_{6-10}$aryl, $C_{5-10}$heteroaryl, $C_{3-12}$cycloalkyl and $C_{3-10}$heterocycloalkyl; wherein said aryl, heteroaryl, cycloalkyl or heterocycloalkyl of $R_{15}$ is optionally substituted by 1 to 3 radicals independently selected from hydroxy, $C_{1-6}$alkyl, $C_{1-6}$alkoxy, $C_{1-6}$alkyl-sulphoxy, halo-substituted-$C_{1-6}$alkyl, halo-substituted-$C_{1-6}$alkoxy, —$X_3NR_{16}R_{16}$, —$X_3ONR_{16}R_{16}$, —$X_3OR_{16}$, —$X_3S(O)_2R_{16}$, —$X_3NR_{16}C(O)OR_{16}$, —$X_3NR_{16}S(O)_{0-2}R_{16}$, —$X_3R_{16}$, —$X_3C(O)OR_{16}$, —$X_3C(O)NR_{16}R_{16}$, —$X_3OC(O)NR_{16}R_{16}$, —$X_3S(O)_{0-2}NR_{16}R_{16}$, —$X_3C(O)R_{16}$, $C_{6-10}$aryl and $C_{5-10}$heteroaryl; wherein said aryl and heteroaryl substituents of $R_{15}$ are optionally substituted with 1 to 3 halo radicals; each $X_2$ and $X_3$ are independently selected from a bond and $C_{1-4}$alkylene; and each $R_{16}$ is independently selected from hydrogen, $C_{1-6}$alkyl, $C_{6-10}$aryl, $C_{5-10}$heteroaryl, $C_{3-8}$cycloalkyl and $C_{3-12}$heterocycloalkyl; wherein any aryl, heteroaryl, cycloalkyl or heterocycloalkyl of $R_{16}$ is optionally substituted by 1 to 3 radicals independently selected from halo, cyano, $C_{1-6}$alkyl, $C_{1-6}$alkyl-carbonyl-amino and $C_{1-6}$alkoxy;
$R_{2b}$ is selected from hydrogen and $C_{1-6}$alkyl; or $R_{2a}$ and $R_{2b}$ together with the carbon atom to which $R_{2a}$ and $R_{2b}$ are attached form carbonyl;

$R_3$, $R_5$, $R_6$ and $R_7$ are each independently selected from hydrogen, halo and amino;

$R_4$ is selected from hydrogen, halo, hydroxy, $C_{1-6}$alkyl, $C_{1-6}$alkoxy, halo-substituted-$C_{1-6}$alkyl, halo-substituted-$C_{1-6}$alkoxy, hydroxy-substituted-$C_{1-6}$alkyl, hydroxy-substituted-$C_{1-6}$alkoxy, cyano-substituted-$C_{1-6}$alkyl, cyano-substituted-$C_{1-6}$alkoxy, —$OX_5R_{4a}$ and —$OX_5R_{4a}$; wherein $X_5$ is selected from a bond and $C_{1-4}$alkylene; $R_{4a}$ is selected from $C_{1-6}$alkyl, $C_{3-8}$cycloalkyl, $C_{6-10}$aryl and $C_{5-10}$heteroaryl; wherein any cycloalkyl, aryl or heteroaryl of $R_{4a}$ is optionally substituted with 1 to 3 radicals independently selected from halo, cyano, amino, $C_{1-6}$alkyl, $C_{1-6}$alkoxy, halo-substituted-$C_{1-6}$alkyl, halo-substituted-$C_{1-6}$alkoxy, hydroxy-substituted-$C_{1-6}$alkyl, hydroxy-substituted-$C_{1-6}$alkoxy, cyano-substituted-$C_{1-6}$alkyl and cyano-substituted-$C_{1-6}$alkoxy;

$R_8$, $R_9$, $R_{11}$ and $R_{12a}$ are each independently selected from hydrogen, halo, $C_{1-6}$alkyl, $C_{1-6}$alkoxy, halo-substituted-$C_{1-6}$alkyl and halo-substituted-$C_{1-6}$alkoxy;

$R_{10}$ is selected from halo, cyano, $C_{1-6}$alkyl, $C_{1-6}$alkoxy, halo-substituted-$C_{1-6}$alkyl, halo-substituted-$C_{1-6}$alkoxy, —$X_4OR_{17}$, —$X_4S(O)_{0-2}R_{17}$ and —$X_4R_{17}$; wherein $X_4$ is selected from a bond and $C_{1-4}$ alkylene; and $R_{17}$ is selected from $C_{6-10}$aryl and $C_{5-10}$hetyeroaryl; wherein $R_{17}$ is optionally substituted with 1 to 3 halo radicals; and the pharmaceutically acceptable salts, hydrates, solvates and isomers thereof.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of CB1 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which CB1 activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom selected from —O—, —N=,—NR—, —C(O)—, —S—, —S(O)— or —S(O)$_2$—, wherein R is hydrogen, $C_{1-4}$alkyl or a nitrogen protecting group. For example $C_{1-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, 1H-pyridin-2-onyl, 6-oxo-1,6-dihydro-pyridin-3-yl, etc. "$C_{6-10}$aryl$C_{0-4}$alkyl" means an aryl as described above connected via a alkylene grouping. For example, $C_{6-10}$aryl$C_{0-4}$alkyl includes phenethyl, benzyl, etc. Heteroaryl also includes the N-oxide derivatives, for example, pyridine-N-oxide derivatives with the following structure:

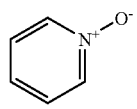

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, 2-oxopyrrolidin-1-yl, 2-oxo-piperidin-1-yl, etc.

"Halogen" (or halo) preferably represents chloro or fluoro, but can also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which inhibition of CB1 activity can prevent, inhibit or ameliorate the pathology and/or symptomology of the diseases, which method comprises administering to the animal a therapeutically effective amount of a compound of Formula I.

In one embodiment, with regard to compounds of Formula I, $R_{1a}$ is selected from cyano, methyl-carbonyl-amino-sulfonyl-ethyl, pyrrolidin-2-onyl-ethyl, imidazolyl-ethyl, oxazolidin-2-only-ethyl, 1-pyrazolyl-ethyl, cyano-methyl, 4'-(4-chlorophenoxy)phenyl, 1,3-dioxanyl-ethyl, allyl, phenyl, pyrazinyl, piperazinyl-sulfonyl-ethyl, azetidinyl-sulfonyl-ethyl, morpholino-sulfonyl-ethyl, pyrrolidinyl-sulfonyl-ethyl, pyrrolidinyl-propyl, pyrrolidinyl-ethyl, piperazinyl-propyl, piperidinyl-sulfonyl-ethyl, pyridazinyl, (5-(4-methoxyphenyl)-1,2,4-oxadiazol-3-yl)methyl, isoxazolyl, piperidinyl-carbonyl-methyl, 3-(N,N-bis(4-methoxyphenyl)sulfamoyl)propyl, methyl-phenyl-sulfonyl, cyanomethyl, 2-oxo-2-(piperidin-1-ylamino)ethyl, propyl-amino-carbonyl-methyl, 2-(carboxymethylamino)-2-oxoethyl), bis-hydroxyethyl-amino-sulfonyl-ethyl, carboxy-methyl-amino-carbonyl-methyl, amino-carbonyl-ethyl, amino-sulfonyl-ethyl, amino-sulfonyl-propyl, methyl-amino-ethyl, piperidinyl-ethyl, piperazinyl-ethyl, methyl-sulfonyl-ethyl, carboxy-methyl, tetrazole-methyl, benzyl, 1,2,4-oxadiazole, 1,2,4-oxadiazole-methyl, 1,2,4-oxadiazole-ethyl, isoxazole-methyl, 2-(2-hydroxyethylamino)-2-oxoethyl, dimethylamino-ethyl-amino-carbonyl-methyl, hydroxyl-ethyl, methoxy-ethyl, hydroxyl-ethyl-amino-ethyl, morpholino-ethyl, methyl-piperazinyl-ethyl, 2-(carbamoyloxy)ethyl, methyl-sulfonyl-oxy-ethyl, morpholino-carbonyl-methyl, methyl-sulfonyl-piperazinyl-ethyl, 2-morpholinoethyl, amino-ethyl, 2-(3,3-dimethylureido)ethyl, morpholino-carbonyl-amino-ethyl, methyl-sulfonyl-amino-ethyl, pyridinyl-methyl, hydroxyl-propyl, 2-(2,6-dimethylmorpholino)ethyl, 2-(2-methylmorpholino)ethyl, methyl-sulfonyl-propyl and morpholino-propyl; wherein said ring systems of $R_{1a}$ are optionally substituted with 1 to 3 radicals independently selected from halo, trifluoromethyl, methyl, bis-hydroxy-ethyl-amino, t-butyl, t-butoxy-carbonyl, hydroxy, methyl-sulfonyl, amino-sulfonyl, diethyl-amino, morpholino, cyclohexyl, pyridinyl, piperidinyl, pyrrolidinyl, piperazinyl optionally substituted with ethyl or methyl-sulfonyl, methoxy-carbonyl and methoxy; and $R_{1b}$ is selected from hydrogen and allyl.

In another embodiment, $R_{2a}$ is selected from (4-(azepan-1-yl-methyl)-1H-1,2,3-triazol-1-yl)methyl, diethyl-amino-pyrrolidinyl-methyl, N,N-methyl-(t-butoxy-carbonyl)-amino-pyrrolidinyl-methyl, (4-(5-cyanopyridin-2-yl)piperazin-1-yl)methyl, 5-cyanopyridinyl-oxy-methyl, (4-(6-methoxypyridin-3-yl)-3-oxopiperazin-1-yl)methyl, (4-(6-methoxypyridin-2-yl)-3-oxopiperazin-1-yl)methyl, (4-(6-methoxypyridin-2-yl)piperazin-1-yl)methyl, 4-t-butoxy-carbonyl-2-oxopiperazin-1-yl)methyl, (4-(4-fluoropyridin-2-yl)piperazin-1-yl)methyl, 5-(1-(tert-butoxycarbonyl)piperidin-4-yl)-2H-tetrazol-2-yl-methyl, 5-(1-(tert-butoxycarbonyl)piperidin-4-yl)-2H-tetrazol-1-yl-methyl, t-butoxy-carbonyl-piperidinyl-methyl, 4-(4-cyanophenyl)-1H-1,2,3-triazol-1-yl, 4-(pyridin-3-yl)-1H-1,2,3-triazol-1-yl, 4-((tetrahydrofuran-3-yloxy)methyl)-1H-1,2,3-triazol-1-yl, 5-phenyl-2H-tetrazol-2-yl, 4-oxadiazolyl-piperidinyl-methyl, 4-(benzyloxycarbonyl)-2-oxopiperazin-1-yl, 4-(1-methyl-1H-imidazol-5-yl)-1H-1,2,3-triazol-1-yl, 4-(3-methyl-1,2,4-oxadiazol-5-yl)-1H-1,2,3-triazol-1-yl, 4-ethoxy-1H-1,2,3-triazol-1-yl, 4-(5-methyl-1,3,4-oxadiazol-2-yl)-1H-1,2,3-triazol-1-yl, 5-(2-ethoxy-2-oxoethyl)-2H-tetrazol-2-yl, 5-(hydroxy-ethyl)-2H-tetrazol-2-yl, (4-(piperidin-1-ylcarbamoyl)-1H-1,2,3-triazol-1-yl)methyl, 1-((tetrahydro-2H-pyran-4-yl)methyl)-1H-1,2,3-triazol-4-yl, 5-(6-methoxy-pyridin-3-yl)-2H-tetrazol-2-yl-methyl, 5-(pyridin-3-yl)-2H-tetrazol-2-yl-methyl, (3-(tetrahydrofuran-3-yl)isoxazol-5-yl)methyl, 5-(morpholino-ethyl)-2H-tetrazol-2-yl, (4-(ethoxy-carbonyl)-1H-1,2,3-triazol-1-yl)methyl, ethyl-sulfonyl-piperazinyl-methyl, (4-(ethyl-sulfonyl-methyl)-1H-1,2,3-triazol-1-yl)methyl, methyl, methyl-piperazinyl-methyl, dimethyl-aminoethyl-amino-methyl, amino-methyl, methyl-sulfonyl-amino-methyl, methoxy-carbonyl, ethoxy-carbonyl, phenyl, hydroxy-methyl, methoxy-methyl, morpholino-methyl, phenyl-sulfonyl-methyl, dimethyl-amino-carbonyl-piperazinyl-methyl, dimethylamino-sulfonyl-piperazinyl-methyl, piperidinyl-methyl, t-butyl-carbamoyl-methyl, t-butoxy-carbonyl-amino-piperidinyl-methyl, phenyl-sulfonyl-amino-methyl, (4-(tetrahydrofuran-2-carbonyl)piperazin-1-yl)methyl, (4-((tetrahydrofuran-2-yl)methyl)piperazin-1-yl)methyl, chloromethyl, morpholino-ethyl-piperazinyl-methyl, t-butoxy-carbonyl-amino-pyrrolidinyl-methyl, thiomorpholinomethyl, amino-pyrrolidinyl-methyl, piperazinyl-methyl, benzyl-amino-methyl, benzyloxy-methyl, 4-fluoro-benzyloxy-methyl, 2,4-difluoro-benzyloxy-methyl, (4-(3,5-difluorophenyl)-1H-1,2,3-triazol-1-yl)methyl, dimethyl-amino-methyl, morpholino-ureido-methyl, (4-methyl-sulfonyl-amino-methyl-1H-1,2,3-triazol-1-yl)methyl, morpholino-carbonyl, propargyl-amino-methyl, phenyl-sulfanyl-methyl, pyridinyl-methyl-amino-methyl, (4-(dimethyl-amino-methyl)-1H-1,2,3-triazol-1-yl)methyl, pyrimidinyl-piperazinyl-methyl, phenyl-pyrazonyl-methyl, (2-(tert-butoxycarbonylamino)-3-methylbutanamido)methyl, (2-amino-3-methylbutanamido)methyl, (4-(3-fluorophenyl)-1H-1,2,3-triazol-1-yl)methyl, (isopropyl-carbamoyloxy)methyl, ((t-butyl)(dimethyl)siloxy)-methyl, imidazoly-propyl-amino-methyl, (3-(2-oxopyrrolidin-1-yl)propylamino)methyl, pyrrolidinyl-ethyl-aminomethyl, pyrrolidinyl-propyl-aminomethyl, (cyclohexyl-carbamoyloxy)methyl, (benzo[d][1,3]dioxol-5-ylcarbamoyloxy)methyl, (1,3-dioxoisoindolin-2-yl)methyl, methyl-carbonyl-amino-methyl, (3-ethylureido)methyl, (tetrahydro-2H-pyran-2-yloxy)methyl, t-butoxy-carbonyl-piperazinyl-methyl, pyridinyl-ethyl-amino-methyl, methyl-carbonyl-piperazinyl-methyl, pyridinyl-piperazinyl-methyl, methoxy-carbonyl-piperazinyl-methyl, ethoxy-carbonyl-piperazinyl-methyl, piperidinyl-methyl-2H-tetrazol-2-yl, 5-chloro-pyridinyl-2-oxy-methyl, 4-phenyl-piperidinyl-methyl, 4-(pyrimidin-2-yl)-piperidinyl-methyl, (5-(pyrazin-2-yl)-2H-tetrazol-2-yl)methyl, (5-(pyridin-2-yl)-2H-tetrazol-2-yl)methyl, (5-(pyridin-2-yl)-1H-tetrazol-1-yl)methyl, 5-(6-methyl-pyridin-3-yl)-1H-tetrazol-1-yl)methyl, (5-(pyrimidin-2-yl)-2H-tetrazol-2-yl)methyl, (4-(pyrazin-2-yl)piperazin-1-yl)methyl, 4-(pyridin-2-yl)-piperidinyl-methyl, 3-t-butoxy-carbonyl-amino-pyrrolidinyl-methyl, (5-(6-chloropyridin-3-yl)-2H-tetrazol-2-yl)methyl, piperidinyl-methyl-1H-1,2,3-triazol-1-yl-methyl, 4-methyl-piperidinyl-methyl-1H-1,2,3-triazol-1-yl-methyl, 4-isopropyl-amino-methyl-1H-1,2,3-triazol-1-yl-methyl, 4-phenyl-1H-imidazol-1-yl, 1H-1,2,3-triazol-1-yl-methyl, 5-(ethoxy-carbonyl)-2H-tetrazol-2-yl, (4-(3,5-dimethylphenyl)-3-oxopiperazin-1-yl)methyl, (5-(imidazo[1,2-a]pyridin-6-yl)-2H-tetrazol-2-yl)methyl, 4-hydroxy-4-phenyl-piperidinyl-methyl, 4-hydroxy-4-(4-chlorophenyl)-piperidinyl-methyl, (5-methyl-2-oxopyridin-1(2H)-yl)methyl, 4-methyl-pyridinyl-2-oxy-methyl, 4-ethoxy-1H-1,2,3-triazol-1-yl-methyl, morpholino-methyl-1H-1,2,3-triazol-1-yl-methyl, diethyl-amino-ethyl-1H-1,2,3-triazol-1-yl-methyl, piperidinyl-ethyl-1H-1,2,3-triazol-1-yl-methyl, piperidinyl-methyl-1H-1,2,3-triazol-1-yl-methyl, diethyl-amino-ethyl-1H-1,2,3-triazol-1-yl-methyl, isopropyl-ethyl-1H-1,2,3-triazol-1-yl-methyl, (4-((3-methyl-1H-pyrazol-1-yl)methyl)-1H-1,2,3-triazol-1-yl)methyl, (4-((4-methyl-1H-pyrazol-1-yl)methyl)-1H-1,2,3-triazol-1-yl)methyl, acetamido-phenyl-1H-1,2,3-triazol-1-yl-methyl, acetyl-1H-1,2,3-triazol-1-yl-methyl, cyclohexyl-methyl-1H-1,2,3-triazol-1-yl-methyl, thienyl-1H-1,2,3-triazol-1-yl-methyl, (2-oxo-4-(pyridin-2-yl)piperazin-1-yl)methyl, (4-(2-methoxyphenyl)-1H-1,2,3-triazol-1-yl)methyl, (4-(3-fluorophenyl)-1H-1,2,3-triazol-1-yl)methyl, (4-(tert-butoxycarbonyl)-1,4-diazepan-1-yl)methyl, ethoxy-carbonyl-piperidinyl-methyl and isobutoxy-carbonyl-piperazinyl-methyl; and $R_{2b}$ is selected from hydrogen and methyl; or $R_{2a}$ and $R_{2b}$ together with the carbon atom to which $R_{2a}$ and $R_{2b}$ are attached form carbonyl.

In another embodiment, $R_3$, $R_5$, $R_6$ and $R_7$ are each independently selected from hydrogen, halo and amino.

In another embodiment, $R_4$ is selected from: hydrogen; trifluoro-methyl; halo; hydroxy; cyano-methoxy; dimethyl-amino-propyl; cyano; cyclopropyl-methoxy; pyrazinyl-oxy optionally substituted with amino; pyridinyl-oxy; pyrimidinyl-oxy; benzoxy; phenoxy optionally substituted with methyl or cyano; ethoxy; tetrazolyl-methoxy optionally substituted with methyl; pyridazinyl-oxy; pyrazinyl-oxy; hydroxy-ethoxy; and methoxy.

In another embodiment, $R_8$, $R_9$, $R_{11}$ and $R_{12a}$ are each independently selected from hydrogen, halo, trifluoromethyl and methyl.

In another embodiment, $R_{10}$ is selected from halo, cyano, methoxy, trifluoromethyl, pyridinyl-oxy, benzoyl, phenoxy, benzyl, pyridazinyl-oxy, phenyl-sulfonyl and pyrimidinyl-oxy; wherein said pyridinyl-oxy, phenyl-sulfonyl, phenoxy, benzoyl, benzyl, pyridazinyl-oxy and pyrimidinyl-oxy can be optionally substituted with 1 to 3 halo radicals.

In another embodiment are compounds selected from: 1-[4-(4-Chloro-phenoxy)-phenyl]-5-phenyl-pyrrolidin-2-one; 5-(4-Amino-3-trifluoromethyl-phenyl)-1-[4-(4-chloro-phenoxy)-phenyl]-pyrrolidin-2-one; 1-[4-(4-Chloro-phenoxy)-phenyl]-5-(3-trifluoromethyl-phenyl)-pyrrolidin-2-one; (S)-3-[4-(4-Chloro-phenoxy)-phenyl]-4-(3-trifluoromethyl-phenyl)-oxazolidin-2-one; 5-(2-Amino-3-trifluoromethyl-phenyl)-1-[4-(4-chloro-phenoxy)-phenyl]-pyrrolidin-2-one; 6-(4-Amino-3-trifluoromethyl-phenyl)-1-[4-(4-chloro-phenoxy)-phenyl]-piperidin-2-one; 3-(4-(4-chlorophenoxy)phenyl)-1-tosyl-4-(3-(trifluoromethyl)phenyl)imidazolidin-2-one; (R)-1-(4-(4-chlorophenoxy)phenyl)-5-phenylimidazolidine-2,4-dione; (S)-1-(4-(4-chlorophenoxy)phenyl)-5-phenylimidazolidine-2,4-dione; 1-[4-(4-Chloro-phenoxy)-phenyl]-5-(3-fluoro-5-trifluoromethyl-phenyl)-pyrrolidin-2-one; (S)-3-[4-(4-Chloro-benzoyl)-phenyl]-4-(3-trifluoromethyl-phenyl)-oxazolidin-2-one; (S)-3-(4-Bromo-phenyl)-4-(3-trifluoromethyl-phenyl)-oxazolidin-2-one; (S)-3-[4-(4-Chloro-phenoxy)-phenyl]-4-(3-fluoro-5-trifluoromethyl-phenyl)-oxazolidin-2-one; (S)-3-(4-Benzyl-phenyl)-4-(3-trifluoromethyl-phenyl)-4-oxazolidin-2-one; 1-[4-(4-Chloro-phenoxy)-phenyl]-3-methyl-5-(S)-phenyl-imidazolidine-2,4-dione; 3-[4-(4-chloro-phenoxy)-phenyl]-1-methyl-4-(3-trifluoromethyl-phenyl)-imidazolidin-2-one; ethyl 2-(3-(4-(4-chlorophenoxy)phenyl)-2-oxo-4-(3-(trifluoromethyl)phenyl)imidazolidin-1-yl)acetate; (S)-ethyl 2-(3-(4-(4-chlorophenoxy)phenyl)-2,5-dioxo-4-phenylimidazolidin-1-yl)acetate; (R)-1-(4-(4-chlorophenoxy)phenyl)-3-methyl-5-phenylimidazolidine-2,4-dione; (4S,5S)-3-(4-(4-chlorophenoxy)phenyl)-5-methyl-4-phenyloxazolidin-2-one; (4S,5S)-3-(4-(4-chlorophenoxy)phenyl)-4,5-diphenyloxazolidin-2-one; (4S,5R)-3-(4-(4-chlorophenoxy)phenyl)-4,5-diphenyloxazolidin-2-one; (4S,5R)-3-(4-(4-chlorophenoxy)phenyl)-5-methyl-4-phenyloxazolidin-2-one; (S)-3-(4-(4-chlorophenoxy)phenyl)-5,5-dimethyl-4-phenyloxazolidin-2-one; (4S,5R)-ethyl 3-(4-(4-chlorophenoxy)phenyl)-2-oxo-4-phenyloxazolidine-5-carboxylate; (4S,5R)-3-(4-(4-chlorophenoxy)phenyl)-4-(3-(trifluoromethyl)phenyl)-5-(hydroxymethyl)oxazolidin-2-one; (4S,5R)-3-(4-(4-chlorophenoxy)phenyl)-5-(hydroxymethyl)-4-phenyloxazolidin-2-one; (4S,5R)-3-(4-(4-chlorophenoxy)phenyl)-5-(methoxymethyl)-4-phenyloxazolidin-2-one; (4S,5R)-3-(4-(4-chlorophenoxy)phenyl)-5-((benzyloxy)methyl)-4-phenyloxazolidin-2-one; ((4S,5R)-3-(4-(4-chlorophenoxy)phenyl)-4-phenyl-2-oxooxazolidin-5-yl)methyl isopropylcarbamate; ((4S,5R)-3-(4-(4-chlorophenoxy)phenyl)-4-phenyl-2-oxooxazolidin-5-yl)methyl cyclohexylmethylcarbamate; ((4S,5R)-3-(4-(4-chlorophenoxy)phenyl)-4-phenyl-2-oxooxazolidin-5-yl) methyl benzo[d][1,3]dioxol-5-ylcarbamate; 2-(((4S,5S)-3-(4-(4-chlorophenoxy)phenyl)-4-phenyl-2-oxooxazolidin-5-yl)methyl)isoindoline-1,3-dione; (4S,5S)-3-(4-(4-chlorophenoxy)phenyl)-5-(aminomethyl)-4-phenyl-oxazolidin-2-one; N-((4S,5S)-3-(4-(4-chloro-phenoxy)-phenyl)-2-oxo-4-phenyl-oxazolidin-5-ylmethyl)-methanesulfonamide; N-(((4S,5S)-3-(4-(4-chlorophenoxy)phenyl)-2-oxo-4-phenyloxazolidin-5-yl)methyl)acetamide; 1-(((4S,5S)-3-(4-(4-chlorophenoxy)phenyl)-2-oxo-4-phenyloxazolidin-5-yl)methyl)-3-ethylurea; (4S,5R)-5-(tert-butyl-dimethyl-silanyloxymethyl)-3-(4-(4-chloro-phenoxy)-phenyl)-4-phenyl-oxazolidin-2-one; (4S,5R)-ethyl 3-(4-(4-chlorophenoxy)phenyl)-4-(3-fluorophenyl)-2-oxooxazolidine-5-carboxylate; (4S,5R)-3-(4-(4-chlorophenoxy)phenyl)-4-(3-fluorophenyl)-5-(hydroxymethyl)oxazolidin-2-one; (S)-4-(4-(4-chlorophenoxy)phenyl)-5-(3-fluorophenyl)morpholin-3-one; (4S,5S)-3-(4-(4-chlorophenoxy)phenyl)-4-(3-fluorophenyl)-5-carboxylate; (4S,5S)-3-(4-(4-chlorophenoxy)phenyl)-4-(3-fluorophenyl)-5-(hydroxymethyl)oxazolidin-2-one; (4S,5S)-3-(4-(4-chlorophenoxy)phenyl)-4-phenyl-5-(hydroxymethyl)oxazolidin-2-one; (2R,3S)-ethyl 4-(4-(4-chlorophenoxy)phenyl)-3-(3-(trifluoromethyl)phenyl)-5-oxomorpholine-2-carboxylate; (2S,3S)-ethyl 4-(4-(4-chlorophenoxy)phenyl)-3-(3-(trifluoromethyl)phenyl)-5-oxomorpholine-2-carboxylate; (4S,5R)-5-((benzyloxy)methyl)-4-(3,5-difluorophenyl)-3-(4-methoxyphenyl)oxazolidin-2-one; (4S,5R)-3-(4-(4-chlorophenoxy)phenyl)-4-(3,5-difluorophenyl)-5-(hydroxymethyl)oxazolidin-2-one; (4S,5R)-3-(4-(4-chlorophenoxy)phenyl)-5-(hydroxymethyl)-4-(3-hydroxyphenyl)oxazolidin-2-one; (5S,6R)-4-(4-(4-chlorophenoxy)phenyl)-6-((benzyloxy)methyl)-5-(3,5-difluorophenyl)morpholin-3-one; (5S,6R)-4-(4-(4-chlorophenoxy)phenyl)-5-(3,5-difluorophenyl)-6-(hydroxymethyl)morpholin-3-one); (4S,5S)-5-((2-(dimethylamino)ethylamino)methyl)-3-(4-(4-chlorophenoxy)phenyl)-4-(3-methoxyphenyl)oxazolidin-2-one; (4S,5S)-5-((2-(pyrrolidin-1-yl)ethylamino)methyl)-3-(4-(4-chlorophenoxy)phenyl)-4-(3-methoxyphenyl)oxazolidin-2-one; (4S,5S)-5-((3-(pyrrolidin-2-one)-1-yl)propylamino)methyl)-3-(4-(4-chlorophenoxy)phenyl)-4-(3,5-difluorophenyl)oxazolidin-2-one; (4S,5S)-5-((3-(1H-imidazol-1-yl)propylamino)methyl)-3-(4-(4-chlorophenoxy)phenyl)-4-(3,5-difluorophenyl)oxazolidin-2-one; (4S,5S)-5-((3-(pyrrolidin-1-yl)propylamino)methyl)-3-(4-(4-chlorophenoxy)phenyl)-4-(3,5-difluorophenyl)oxazolidin-2-one; (4S,5S)-5-((3-(1H-imidazol-1-yl)propylamino)methyl)-3-(4-(4-chlorophenoxy)phenyl)-4-(3-methoxyphenyl)oxazolidin-2-one; (4S,5R)-3-(4-(4-chlorophenoxy)phenyl)-4-(3,5-difluorophenyl)-5-((tetrahydro-2H-pyran-2-yloxy)methyl)oxazolidin-2-one; tert-butyl 4-(((4S,5S)-3-(4-(4-chlorophenoxy)phenyl)-4-(3,5-difluorophenyl)-2-oxooxazolidin-5-yl)methyl)piperazine-1-carboxylate; (4S,5S)-5-((3-(pyridin-3-yl)propylamino)methyl)-3-(4-(4-chlorophenoxy)phenyl)-4-(3,5-difluorophenyl)oxazolidin-2-one; (4S,5R)-3-(4-chlorophenyl)-4-(3-methoxyphenyl)-5-((tetrahydro-2H-pyran-2-yloxy)methyl)oxazolidin-2-one; (4S,5R)-3-(4-(4-chlorophenoxy)phenyl)-4-(3-methoxyphenyl)-5-((tetrahydro-2H-pyran-2-yloxy)methyl)oxazolidin-2-one; (4S,5R)-3-(4-(trifluoromethyl)phenyl)-4-(3,5-difluorophenyl)-5-((tetrahydro-2H-pyran-2-yloxy)methyl)oxazolidin-2-one; (4S,5S)-5-((4-acetylpiperazin-1-yl)methyl)-3-(4-chlorophenyl)-4-(3,5-difluorophenyl)oxazolidin-2-one; (4S,5S)-5-((2-(1H-imidazol-5-yl)ethylamino)methyl)-3-(4-chlorophenyl)-4-(3,5-difluorophenyl)oxazolidin-2-one; (4S,5R)-3-(4-chloro-3-methylphenyl)-4-(3,5-difluorophenyl)-5-((tetrahydro-2H-pyran-2-yloxy)methyl)oxazolidin-2-one; (4S,5R)-3-(4-chloro-3-fluorophenyl)-4-(3,5-difluorophenyl)-5-((tetrahydro-2H-pyran-2-yloxy)methyl)oxazolidin-2-one; tert-butyl 4-(((4S,5S)-3-(4-chlorophenyl)-4-(3-methoxyphenyl)-2-oxooxazolidin-5-yl)methyl)piperazine-1-carboxylate; tert-butyl 4-(((4S,5S)-3-(4-chloro-3-methylphenyl)-4-(3,5-difluorophenyl)-2-oxooxazolidin-5- yl)methyl)piperazine-1-carboxylate; tert-butyl 4-(((4S,5S)-3-(4-chloro-3-(trifluoromethyl)phenyl)-4-(3,5-difluorophenyl)-2-oxooxazolidin-5-yl)methyl)piperazine-1-carboxylate; (4S,5R)-3-(4-chlorophenyl)-4-(3-(trifluoromethyl)phenyl)-5-((tetrahydro-2H-pyran-2-yloxy) methyl)oxazolidin-2-one; (4S,5R)-5-((benzyloxy)methyl)-3-(4-chlorophenyl)-4-(3-(trifluoromethyl)phenyl) oxazolidin-2-one; tert-Butyl 4-(((4S,5S)-3-(4-chlorophenyl)-4-(3-(trifluoromethyl)phenyl)-2-oxooxazolidin-5-yl)methyl)piperazine-1-carboxylate; Methyl 4-(((4S,5S)-3-(4-chlorophenyl)-4-(3-(trifluoromethyl)phenyl)-2-oxooxazolidin-5-yl)methyl)piperazine-1-carboxylate; Ethyl 4-(((4S,5S)-3-(4-chlorophenyl)-4-(3-(trifluoromethyl)phenyl)-2-oxooxazolidin-5-yl)methyl) piperazine-1-carboxylate; isobutyl 4-(((4S,5S)-3-(4-chlorophenyl)-4-(3-(trifluoromethyl)phenyl)-2-oxooxazolidin-5-yl)methyl)piperazine-1-carboxylate; 4-((4S,5R)-4-(3-methoxyphenyl)-2-oxo-5-((tetrahydro-2H-pyran-2-yloxy)methyl)oxazolidin-3-yl)benzonitrile; 4-((4S,5R)-5-((4-fluorobenzyloxy)methyl)-4-(3-(trifluoromethyl)phenyl)-2-oxooxazolidin-3-yl)benzonitrile; (4S,5R)-5-((4-fluorobenzyloxy)methyl)-3-(4-chlorophenyl)-4-(3-fluorophenyl)oxazolidin-2-one; (4S,5R)-5-((4-fluorobenzyloxy)methyl)-3-(4-chlorophenyl)-4-(3-(trifluoromethyl)phenyl)oxazolidin-2-one; (4S,5R)-5-((2,4-difluorobenzyloxy)methyl)-3-(4-chlorophenyl)-4-(3-(trifluoromethyl)phenyl)oxazolidin-2-one; 5-((4S,5R)-5-((4-methoxybenzyloxy)methyl)-4-(3-(trifluoromethyl)phenyl)-2-oxooxazolidin-3-yl)pyridine-2-carbonitrile; (4S,5R)-3-(5-(4-chlorophenoxy)pyrazin-2-yl)-4-(3-(trifluoromethyl)phenyl)-5-(hydroxymethyl)oxazolidin-2-one; (4S,5S)-3-(4-chlorophenyl)-4-(3-(trifluoromethyl)phenyl)-5-((4-(3-fluorophenyl)-1H-1,2,3-triazol-1-yl)methyl)oxazolidin-2-one; (4S,5S)-3-(4-chlorophenyl)-5-((4-((dimethylamino)methyl)-1H-1,2,3-triazol-1-yl)methyl)-4-(3-(trifluoromethyl)phenyl)oxazolidin-2-one; (4S,5S)-3-(4-chlorophenyl)-4-(3-(trifluoromethyl)phenyl)-5-((4-(pyrimidin-2-yl)piperazin-1-yl)methyl)oxazolidin-2-one; (4S,5S)-3-(4-chlorophenyl)-4-(3-(trifluoromethyl)phenyl)-5-((3-phenyl-1H-pyrazol-1-yl)methyl)oxazolidin-2-one; tert-butyl (R)-1-(((4S,5S)-3-(4-(4-chlorophenoxy)phenyl)-2-oxo-4-phenyloxazolidin-5-yl)methylcarbamoyl)-2-methylpropylcarbamate; (2R)—N-(((4S,5S)-3-(4-(4-chlorophenoxy)phenyl)-2-oxo-4-phenyloxazolidin-5-yl)methyl)-2-amino-3-methylbutanamide; (4S,5S)-5-((3-(pyrrolidin-1-yl)propylamino)methyl)-3-(4-(4-chlorophenoxy)phenyl)-4-(3-fluorophenyl)oxazolidin-2-one; (4S,5R)-3-(4-(4-chlorophenoxy)phenyl)-5-(hydroxymethyl)-4-(3-methoxyphenyl)oxazolidin-2-one; (4S,5S)-3-(4-(4-chlorophenoxy)phenyl)-4-(3-fluorophenyl)-5-((4-methylpiperazin-1-yl)methyl)oxazolidin-2-one; (4S,5S)-3-(4-(4-chlorophenoxy)phenyl)-5-(aminomethyl)-4-(3-fluorophenyl)oxazolidin-2-one; ((4S,5R)-3-(4-(4-chlorophenoxy)phenyl)-4-(3-fluorophenyl)-2-oxooxazolidin-5-yl)methyl cyclohexylcarbamate; ((4S,5R)-3-(4-(4-chlorophenoxy)phenyl)-4-(3-fluorophenyl)-2-oxooxazolidin-5-yl)methyl isopropylcarbamate; (4S,5R)-3-(4-(4-chlorophenoxy)phenyl)-5-((benzyloxy)methyl)-4-(3,5-difluorophenyl)oxazolidin-2-one; (4S,5S)-3-(4-(4-chlorophenoxy)phenyl)-5-((dimethylamino)methyl)-4-(3-fluorophenyl)oxazolidin-2-one; N-(((4S,5S)-3-(4-(4-chlorophenoxy)phenyl)-4-(3-fluorophenyl)-2-oxooxazolidin-5-yl)methyl)morpholine-4-carboxamide; (4S,5R)-3-(4-(4-chlorophenoxy)phenyl)-5-(morpholine-4-carbonyl)-4-phenyl-oxazolidin-2-one; (4S,5S)-3-(4-(4-chlorophenoxy)phenyl)-4-(3-fluorophenyl)-5-((prop-2-ynylamino)methyl)oxazolidin-2-one; (4S,5R)-3-(4-(4-chlorophenoxy)phenyl)-4-(3-fluorophenyl)-5-((phenylthio)methyl)oxazolidin-2-one; (4S,5S)-3-[4-(4-Chlorophenoxy)-phenyl]-4-(3-fluoro-phenyl)-5-{[(pyridin-3-ylmethyl)-amino]-methyl}-oxazolidin-2-one; (4S,5S)-3-(4-(4-chlorophenoxy)phenyl)-4-(3-methoxyphenyl)-5-((4-methylpiperazin-1-yl)methyl)oxazolidin-2-one; (4S,5S)-3-[4-(4-Chloro-phenoxy)-phenyl]-4-(3,5-difluoro-phenyl)-5-morpholin-4-ylmethyl-oxazolidin-2-one; (4S,5S)-3-(4-(4-chlorophenoxy)phenyl)-4-(3,5-difluorophenyl)-5-((4-methylpiperazin-1-yl)methyl)oxazolidin-2-one; (4S,5R)-3-(4-(4-chlorophenoxy)phenyl)-4-(3-fluorophenyl)-5-((phenylsulfonyl)methyl)oxazolidin-2-one; (4S,5S)-3-(4-(4-chlorophenoxy)phenyl)-4-(3-fluorophenyl)-5-((4-(tetrahydrofuran-2-carbonyl)piperazin-1-yl)methyl)oxazolidin-2-one; (4S,5S)-3-(4-(4-chlorophenoxy)phenyl)-4-(3-fluorophenyl)-5-((4-((tetrahydrofuran-2-yl)methyl)piperazin-1-yl)methyl)oxazolidin-2-one; (4S,5R)-3-(4-(4-chlorophenoxy)phenyl)-5-(chloromethyl)-4-(3-fluorophenyl)oxazolidin-2-one; (4S,5R)-3-(4-chlorophenyl)-4-(3,5-difluorophenyl)-5-((tetrahydro-2H-pyran-2-yloxy)methyl)oxazolidin-2-one; (4S,5S)-3-(4-(4-chlorophenoxy)phenyl)-4-(3-fluorophenyl)-5-((4-(2-morpholinoethyl)piperazin-1-yl)methyl)oxazolidin-2-one; (4S,5R)-4-(3,5-difluorophenyl)-5-((tetrahydro-2H-pyran-2-yloxy)methyl)-3-p-tolyloxazolidin-2-one; (4S,5R)-3-(4-chlorophenyl)-4-(3,5-difluorophenyl)-5-(hydroxymethyl)oxazolidin-2-one; (4S,5R)-5-((benzyloxy)methyl)-3-(4-chlorophenyl)-4-(3,5-difluorophenyl)oxazolidin-2-one; (4S,5S)-3-(4-chlorophenyl)-4-(3,5-difluorophenyl)-5-(morpholin-4-ylmethyl)oxazolidin-2-one; (4S,5S)-5-((3-(1H-imidazol-1-yl)propylamino)methyl)-3-(4-chlorophenyl)-4-(3,5-difluorophenyl)oxazolidin-2-one; tert-butyl (R)-1-(((4S,5S)-3-(4-(4-chlorophenoxy)phenyl)-4-(3-fluorophenyl)-2-oxooxazolidin-5-yl)methyl)pyrrolidin-3-ylcarbamate; tert-butyl 4-(((4S,5S)-3-(4-(4-chlorophenoxy)phenyl)-4-(3-fluorophenyl)-2-oxooxazolidin-5-yl)methyl)piperazine-1-carboxylate; (4S,5R)-3-(4-(trifluoromethyl)phenyl)-4-(3-fluorophenyl)-5-((tetrahydro-2H-pyran-2-yloxy)methyl)oxazolidin-2-one; (4S,5S)-3-(4-(4-chlorophenoxy)phenyl)-4-(3-fluorophenyl)-5-(thiomorpholinomethyl)oxazolidin-2-one; (4S,5S)-3-(4-(4-chlorophenoxy)phenyl)-5-(((R)-3-aminopyrrolidin-1-yl)methyl)-4-(3-fluorophenyl)oxazolidin-2-one; (4S,5S)-3-(4-(4-chlorophenoxy)phenyl)-4-(3-fluorophenyl)-5-((piperazin-1-yl)methyl)oxazolidin-2-one; (4S,5S)-5-((benzylamino)methyl)-3-(4-(trifluoromethyl)phenyl)-4-(3-fluorophenyl)oxazolidin-2-one; (4S,5R)-3-(4-chlorophenyl)-4-(2,3-difluorophenyl)-5-((tetrahydro-2H-pyran-2-yloxy)methyl)oxazolidin-2-one; (4S,5R)-5-((benzyloxy)methyl)-3-(4-chloro-3-fluorophenyl)-4-(3,5-difluorophenyl)oxazolidin-2-one; 4-(((4S,5S)-3-(3,4-dichlorophenyl)-4-(3-fluorophenyl)-2-oxooxazolidin-5-yl)methyl)-N,N-dimethylpiperazine-1-carboxamide; 4-(((4S,5S)-3-(4-trifluoromethylphenyl)-4-(3-fluorophenyl)-2-oxooxazolidin-5-yl)methyl)-N,N-dimethylpiperazine-1-sulfamide; (4S,5S)-3-(4-(trifluoromethyl)phenyl)-4-(3-fluorophenyl)-5-((piperidin-1-yl)methyl)oxazolidin-2-one; ((4S,5R)-3-(4-chlorophenyl)-4-(3-fluorophenyl)-2-oxooxazolidin-5-yl)methyl tert-butylcarbamate; (4S,5R)-5-((benzyloxy)methyl)-3-(4-(trifluoromethyl)phenyl)-4-(3-fluorophenyl)oxazolidin-2-one; tert-butyl 1-(((4S,5S)-3-(4-chlorophenyl)-4-(3-fluorophenyl)-2-oxooxazolidin-5-yl)methyl)piperidin-4-ylcarbamate; (4S,5S)-3-(4-(4-chlorophenoxy)phenyl)-4-(3-(trifluoromethyl)phenyl)-5-((4-((tetrahydrofuran-2-yl)methyl)piperazin-1-yl)methyl)oxazolidin-2-one; (4S,5R)-3-(4-chlorophenyl)-4-(3-fluoro-5-(trifluoromethyl)phenyl)-5-((tetrahydro-2H-pyran-2- yloxy)methyl)oxazolidin-2-one; ((4S,5R)-3-(4-chlorophenyl)-4-(3-fluorophenyl)-2-oxooxazolidin-5-yl)methyl cyclohexylcarbamate; N-(((4S,5S)-3-(4-chlorophenyl)-4-(3-fluorophenyl)-2-oxooxazolidin-5-yl)methyl)benzenesulfonamide; 4-((4S,5R)-5-((benzyloxy)methyl)-4-(3-fluorophenyl)-2-oxooxazolidin-3-yl)benzonitrile; (4S,5R)-3-(4-(4-chlorophenoxy)phenyl)-4-(3-fluoro-5-(trifluoromethyl) phenyl)-5-(hydroxymethyl)oxazolidin-2-one; (4S,5R)-5-((4-fluorobenzyloxy)methyl)-3-(4-(trifluoromethyl) phenyl)-4-(3-fluorophenyl)oxazolidin-2-one; Ethyl 4-(((4S, 5S)-3-(4-chlorophenyl)-4-(3-fluorophenyl)-2-oxooxazolidin-5-yl)methyl)piperazine-1-carboxylate; (4S, 5R)-5-((4-methylbenzyloxy)methyl)-3-(4-chlorophenyl)-4-(3-(trifluoromethyl)phenyl)oxazolidin-2-one; (4S,5S)-3-(5-(4-chlorophenoxy)pyrazin-2-yl)-4-(3-(trifluoromethyl) phenyl)-5-(morpholinomethyl)oxazolidin-2-one; (4S,5S)-3-(4-chlorophenyl)-4-(3-(trifluoromethyl)phenyl)-5-((4-phenyl-1H-1,2,3-triazol-1-yl)methyl)oxazolidin-2-one; Ethyl 1-(((4S,5S)-3-(4-chlorophenyl)-4-(3-(trifluoromethyl) phenyl)-2-oxooxazolidin-5-yl)methyl)-1H-1,2,3-triazole-4-carboxylate; (4S,5S)-3-(4-chlorophenyl)-4-(3-(trifluoromethyl)phenyl)-5-((4-(3,5-difluorophenyl)-1H-1,2,3-triazol-1-yl)methyl)oxazolidin-2-one; N-((1-(((4S,5S)-3-(4-chlorophenyl)-4-(3-(trifluoromethyl)phenyl)-2-oxooxazolidin-5-yl)methyl)-1H-1,2,3-triazol-4-yl)methyl) methansulfonamide; (S)-2-(3-(4-(4-chlorophenoxy)phenyl)-2-oxo-4-(3-(trifluoromethyl)phenyl)imidazolidin-1-yl) acetonitrile; 3-(4-(4-chlorophenoxy)phenyl)-1-(4-(trifluoromethyl)benzyl)-4-(3-(trifluoromethyl)phenyl) imidazolidin-2-one; 3-[4-(4-Chloro-phenoxy)-phenyl]-1-(3, 5-dimethyl-isoxazol-4-ylmethyl)-4-(3-trifluoromethyl-phenyl)-imidazolidin-2-one; (S)-3-[4-(6-Chloro-pyridazin-3-yloxy)-phenyl]-4-(3-trifluoromethyl-phenyl)-oxazolidin-2-one; (S)-3-(4-(5-chloropyridin-2-yloxy)phenyl)-4-(3-(trifluoromethyl)-phenyl)oxazolidin-2-one; (S)-1-[4-(4-Chloro-phenoxy)-phenyl]-5-(3-trifluoromethyl-phenyl)-imidazolidin-2-one; (R)-1-(4-(4-chlorophenoxy)phenyl)-5-(3-(trifluoromethyl)phenyl)imidazolidin-2-one; (S)-3-[6-(4-Chloro-phenoxy)-pyridin-3-yl]-4-(3-trifluoromethyl-phenyl)-oxazolidin-2-one; (S)-3-(4-(4-chlorophenoxy) phenyl)-1-(4-methoxybenzyl)-4-(3-(trifluoromethyl) phenyl)imidazolidin-2-one; (S)-3-[5-(4-Chloro-phenoxy)-pyrazin-2-yl]-4-(3-trifluoromethyl-phenyl)-oxazolidin-2-one; (S)-1-(6-(4-chlorophenoxy)pyridin-3-yl)-5-(3-(trifluoromethyl)phenyl)imidazolidin-2-one; (S)-1-(5-(4-chlorophenoxy)pyrazin-2-yl)-5-(3-(trifluoromethyl)phenyl) imidazolidin-2-one; (S)-3-[6-(4-Chloro-phenoxy)-pyridin-3-yl]-1-(4-methoxy-benzyl)-4-(3-trifluoromethyl-phenyl)-imidazolidin-2-one; (S)-3-[5-(4-Chloro-phenoxy)-pyrazin-2-yl]-1-(4-methoxy-benzyl)-4-(3-trifluoromethyl-phenyl)-imidazolidin-2-one; (S)-1,3-Bis-[4-(4-chloro-phenoxy)-phenyl]-4-(3-trifluoromethyl-phenyl)-imidazolidin-2-ylidene-cyanamide; (S)-3-[5-(4-Chloro-phenoxy)-pyrazin-2-yl]-1-(4-methoxy-benzyl)-4-(3-trifluoromethyl-phenyl)-imidazolidin-2-ylidene-cyanamide; (S)-2-(3-(5-(4-chlorophenoxy)pyrazin-2-yl)-2-oxo-4-(3-(trifluoromethyl) phenyl)imidazolidin-1-yl)ethanesulfonamide; (S)-3-[4-(4-Chloro-phenoxy)-phenyl]-1-(2-methanesulfonyl-ethyl)-4-(3-trifluoromethyl-phenyl)-imidazolidin-2-one; (S)-2-(3-(4-(4-chlorophenoxy)phenyl)-2-oxo-4-(3-(trifluoromethyl) phenyl)imidazolidin-1-yl)ethanesulfonamide; 2-(3-(4-(4-chlorophenoxy)phenyl)-2-oxo-4-(3-(trifluoromethyl) phenyl)imidazolidin-1-yl)acetic acid; 1-((1H-tetrazol-5-yl)methyl)-3-(4-chlorophenoxy)phenyl)-4-(3-(trifluoromethyl)phenyl)imidazolidin-2-one; 2-(3-(4-(4-chlorophenoxy)phenyl)-2-oxo-4-(3-(trifluoromethyl) phenyl)imidazolidin-1-yl)-N-propylacetamide; 2-(3-(4-(4-chlorophenoxy)phenyl)-2-oxo-4-(3-(trifluoromethyl)phenyl)imidazolidin-1-yl)-N-(piperidin-1-yl)acetamide; 2-(2-(3-(4-(4-chlorophenoxy)phenyl)-2-oxo-4-(3-(trifluoromethyl)phenyl)-imidazolidin-1-yl)acetamido) acetic acid; 2-(3-(4-(4-chlorophenoxy)phenyl)-2-oxo-4-(3-(trifluoromethyl)phenyl)imidazolidin-1-yl)-N-(2-hydroxyethyl)acetamide; 2-(3-(4-(4-chlorophenoxy) phenyl)-2-oxo-4-(3-(trifluoromethyl)phenyl)imidazolidin-1-yl)-N-(2-(dimethylamino)ethyl)acetamide; 3-(4-(4-chlorophenoxy)phenyl)-1-(2-hydroxyethyl)-4-(3-(trifluoromethyl)phenyl)-imidazolidin-2-one; 1-(4-(4-chlorophenoxy)phenyl)-5-(3-(trifluoromethyl)phenyl) imidazolidin-2-imine; 1-(4-(4-chlorophenoxy)phenyl)-5-(3-(trifluoromethyl)phenyl)imidazolidine-2-thione; 2-(3-(4-(4-chlorophenoxy)phenyl)-2-oxo-4-(3-(trifluoromethyl) phenyl)imidazolidin-1-yl)ethyl methanesulfonate; 1-(4-(4-chlorophenoxy)phenyl)-5-(3-(trifluoromethyl)phenyl) imidazolidin-2-one oxime; 3-(4-(4-chlorophenoxy)phenyl)-1-(2-methoxyethyl)-4-(3-(trifluoromethyl)phenyl)-imidazolidin-2-one; 3-(4-(4-chlorophenoxy)phenyl)-1-(2-(2-hydroxyethylamino)ethyl)-4-(3-(trifluoromethyl)phenyl)imidazolidin-2-one; 3-(4-(4-chlorophenoxy)phenyl)-1-(2-morpholinoethyl)-4-(3-(trifluoromethyl)phenyl) imidazolidin-2-one; 3-(4-(4-chlorophenoxy)phenyl)-1-(2-(4-methylpiperazin-1-yl)ethyl)-4-(3-(trifluoromethyl) phenyl)imidazolidin-2-one; 2-(3-(4-(4-chlorophenoxy) phenyl)-2-oxo-4-(3-(trifluoromethyl)phenyl)imidazolidin-1-yl)ethyl carbamate; 3-(4-(4-chlorophenoxy)phenyl)-1-(2-(methylamino)ethyl)-4-(3-(trifluoromethyl)phenyl) imidazolidin-2-one; 3-(4-(4-chlorophenoxy)phenyl)-1-(2-(piperidin-1-yl)ethyl)-4-(3-(trifluoromethyl)phenyl) imidazolidin-2-one; 3-(4-(4-chlorophenoxy)phenyl)-1-(2-(piperazin-1-yl)ethyl)-4-(3-(trifluoromethyl)phenyl)-imidazolidin-2-one; (4R,5S)-methyl 1-(4-(4-chlorophenoxy) phenyl)-2-oxo-5-phenylimidazolidine-4-carboxylate; 1-(4-chlorobenzyl)-3-(4-(4-chlorophenoxy)phenyl)-4-(3-(trifluoromethyl)phenyl)imidazolidin-2-one; 1-benzyl-3-(4-(4-chlorophenoxy)phenyl)-4-(3-(trifluoromethyl)phenyl) imidazolidin-2-one; 3-(4-(4-chlorophenoxy)phenyl)-1-(3-methoxybenzyl)-4-(3-(trifluoromethyl)phenyl) imidazolidin-2-one; 3-(4-(4-chlorophenoxy)phenyl)-1-(2-methoxybenzyl)-4-(3-(trifluoromethyl)phenyl) imidazolidin-2-one; 3-(4-(4-chlorophenoxy)phenyl)-1-(4-methoxyphenyl)-4-(3-(trifluoromethyl)phenyl)-imidazolidin-2-one; 3-(4-(4-chlorophenoxy)phenyl)-1-(2-morpholino-2-oxoethyl)-4-(3-(trifluoromethyl) imidazolidin-2-one; 3-(4-(4-chlorophenoxy)phenyl)-1-(2-(4-(methylsulfonyl)piperazin-1-yl)ethyl)-4-(3-(trifluoromethyl)phenyl)imidazolidin-2-one; 3-(4-(4-chlorophenoxy)phenyl)-1-(2-((2S,6R)-2,6-dimethylmorpholino)ethyl)-4-(3-(trifluoromethyl)phenyl) imidazolidin-2-one; 1-(2-aminoethyl)-3-(4-(4-chlorophenoxy)phenyl)-4-(3-(trifluoromethyl)phenyl) imidazolidin-2-one; 3-(2-(3-(4-(4-chlorophenoxy)phenyl)-2-oxo-4-(3-(trifluoromethyl)phenyl)imidazolidin-1-yl) ethyl)-1,1-dimethylurea; N-(2-(3-(4-(4-chlorophenoxy) phenyl)-2-oxo-4-(3-(trifluoromethyl)phenyl)imidazolidin-1-yl)ethyl)morpholine-4-carboxamide; N-(2-(3-(4-(4-chlorophenoxy)phenyl)-2-oxo-4-(3-(trifluoromethyl) phenyl)imidazolidin-1-yl)ethyl)methanesulfonamide; 3-(4-(4-chlorophenoxy)phenyl)-1-(pyridin-2-ylmethyl)-4-(3-(trifluoromethyl)phenyl)imidazolidin-2-one; 3-(4-(4-chlorophenoxy)phenyl)-1-(pyridin-3-ylmethyl)-4-(3-(trifluoromethyl)phenyl)imidazolidin-2-one; 3-(4-(4-chlorophenoxy)phenyl)-1-(pyridin-4-ylmethyl)-4-(3-(trifluoromethyl)phenyl)imidazolidin-2-one; (S)—N-(3-(4-(4-chlorophenoxy)phenyl)-1-tosyl-4-(3-(trifluoromethyl)

phenyl)imidazolidin-2-ylidene)cyanamide; (S)-3-(4-(4-chlorophenoxy)phenyl)-1-(3-hydroxypropyl)-4-(3-(trifluoromethyl)phenyl)imidazolidin-2-one; (S)—N-(1-(4-(4-chlorophenoxy)phenyl)-5-(3-(trifluoromethyl)phenyl)imidazolidin-2-ylidene)cyanamide; (R)—N-(1-(4-(4-chlorophenoxy)phenyl)-5-(3-(trifluoromethyl)phenyl)imidazolidin-2-ylidene)cyanamide; 3-(4-(4-chlorophenoxy)phenyl)-1-(2-((R)-2-methylmorpholino)ethyl)-4-(3-(trifluoromethyl)phenyl)imidazolidin-2-one; 3-(4-(4-chlorophenoxy)phenyl)-1-(2-((S)-2-methylmorpholino)ethyl)-4-(3-(trifluoromethyl)phenyl)imidazolidin-2-one; (S)—N-(3-(4-(4-chlorophenoxy)phenyl)-1-(2-hydroxyethyl)-4-(3-(trifluoromethyl)phenyl)imidazolidin-2-ylidene)cyanamide; (S)-3-(4-(4-chlorophenoxy)phenyl)-1-(3-(methylsulfonyl)propyl)-4-(3-(trifluoromethyl)phenyl)imidazolidin-2-one; N-(3-(4-(4-chlorophenoxy)phenyl)-1-(2-(methylsulfonyl)ethyl)-4-(3-(trifluoromethyl)phenyl)imidazolidin-2-ylidene)cyanamide; 3-(4-(4-chlorophenoxy)phenyl)-1-(3-morpholinopropyl)-4-(3-(trifluoromethyl)phenyl)imidazolidin-2-one; (S)—N-(3-(4-(4-chlorophenoxy)phenyl)-1-(3-hydroxypropyl)-4-(3-(trifluoromethyl)phenyl)imidazolidin-2-ylidene)cyanamide; N-(3-(4-(4-chlorophenoxy)phenyl)-1-(2-morpholinoethyl)-4-(3-(trifluoromethyl)phenyl)imidazolidin-2-ylidene)cyanamide; N-(3-(4-(4-chlorophenoxy)phenyl)-1-(2-((S)-2-methylmorpholino)ethyl)-4-(3-(trifluoromethyl)phenyl)imidazolidin-2-ylidene)cyanamide; N-(3-(4-(4-chlorophenoxy)phenyl)-1-(3-(methylsulfonyl)propyl)-4-(3-(trifluoromethyl)phenyl)imidazolidin-2-ylidene)cyanamide; (R)-1-(4-(4-chlorophenoxy)phenyl)-5-phenylpyrrolidin-2-one; (R)-1-(5-(4-chlorophenoxy)pyrazin-2-yl)-5-(3-(trifluoromethyl)phenyl)pyrrolidin-2-one; (R)-1-(4-(4-chlorophenoxy)phenyl)-5-(3-methoxyphenyl)pyrrolidin-2-one; (R)-1-(5-(4-chlorophenoxy)pyrazin-2-yl)-5-(3-methoxyphenyl)pyrrolidin-2-one; (R)-1-(4-(4-chlorophenylsulfonyl)phenyl)-5-(3-(trifluoromethyl)phenyl)pyrrolidin-2-one; (R)-1-(4-(4-chlorophenylsulfonyl)phenyl)-5-(3-methoxyphenyl)pyrrolidin-2-one; (R)-1-[4-(4-chlorophenoxy)phenyl]-5-[3-(trifluoromethyl)phenyl]pyrrolidin-2-one; (R)-1-(4-(4-chlorophenoxy)phenyl)-2-(3-(trifluoromethyl)phenyl)pyrrolidine; (R)-1-(4-(4-chlorophenoxy)phenyl)-5-(3-hydroxyphenyl)pyrrolidin-2-one; (R)-5-(3-(2-hydroxyethoxy)phenyl)-1-(4-(4-chlorophenoxy)phenyl)pyrrolidin-2-one; (R)-5-(3-(2-hydroxyethoxy)phenyl)-1-(4-(4-chlorophenylsulfonyl)phenyl)pyrrolidin-2-one; (R)-1-(5-(4-chlorophenoxy)pyrazin-2-yl)-5-(3-hydroxyphenyl)pyrrolidin-2-one; (R)-1-(4-(4-chlorophenoxy)phenyl)-5-(3-cyanomethoxyphenyl)pyrrolidin-2-one; (R)-5-(3-(2-hydroxyethoxy)phenyl)-1-(5-(4-chlorophenoxy)pyrazin-2-yl)pyrrolidin-2-one; (3S,5R)-1-(4-(4-chlorophenoxy)phenyl)-3-allyl-5-(3-(trifluoromethyl)phenyl)pyrrolidin-2-one; (3R,5R)-1-(4-(4-chlorophenoxy)phenyl)-3-allyl-5-(3-(trifluoromethyl)phenyl)pyrrolidin-2-one; (R)-1-(4-(4-chlorophenoxy)phenyl)-3,3-diallyl-5-(3-(trifluoromethyl)phenyl)pyrrolidin-2-one; (R)-5-(3-((1-methyl-1H-tetrazol-5-yl)methoxy)phenyl)-1-(4-(4-chlorophenoxy)phenyl)pyrrolidin-2-one; (R)-5-(3-((2-methyl-2H-tetrazol-5-yl)methoxy)phenyl)-1-(4-(4-chlorophenoxy)phenyl)pyrrolidin-2-one; (3R,5R)-1-(4-(4-chlorophenoxy)phenyl)-5-(3-(trifluoromethyl)phenyl)-3-(2-hydroxyethyl)pyrrolidin-2-one; (3S,5R)-1-(4-(4-chlorophenoxy)phenyl)-5-(3-(trifluoromethyl)phenyl)-3-(2-hydroxyethyl)pyrrolidin-2-one; (R)-2-(3-(1-(4-(4-chlorophenoxy)phenyl)pyrrolidin-2-yl)phenoxy)ethanol; (3S,5R)-1-(4-(4-chlorophenoxy)phenyl)-5-(3-(trifluoromethyl)phenyl)-3-(3-hydroxypropyl)pyrrolidin-2-one; (3R,5R)-1-(4-(4-chlorophenoxy)phenyl)-5-(3-(trifluoromethyl)phenyl)-3-(3-hydroxypropyl)pyrrolidin-2-one; (R)-1-(4-chlorophenyl)-5-(3-methoxyphenyl)pyrrolidin-2-one; (R)-1-(4-chlorophenyl)-5-(3-(pyridazin-3-yloxy)phenyl)pyrrolidin-2-one; (R)-1-(4-chlorophenyl)-5-(3-(pyrazin-2-yloxy)phenyl)pyrrolidin-2-one; (R)-5-(3-(2-hydroxyethoxy)phenyl)-1-(4-chlorophenyl)pyrrolidin-2-one; (3R,5R)-1-(4-(4-chlorophenoxy)phenyl)-5-(3-(trifluoromethyl)phenyl)-3-(2-(methylsulfonyl)ethyl)pyrrolidin-2-one; (3S,5R)-1-(4-(4-chlorophenoxy)phenyl)-5-(3-(trifluoromethyl)phenyl)-3-(2-(methylsulfonyl)ethyl)pyrrolidin-2-one; (S)-methyl 5-(4-chlorophenyl)-4-(3-methoxyphenyl)-1,1-dioxo-1,2,5-thiadiazolidine-2-carboxylate; (S)-2-(4-chlorophenyl)-3-(3-methoxyphenyl)-1,1-dioxo-1,2,5-thiadiazolidine; (R)-5-(3-(cyanomethoxy)phenyl)-1-(4-chlorophenyl)pyrrolidin-2-one; (S)-methyl 5-(4-chlorophenyl)-4-(3-hydroxyphenyl)-1,1-dioxo-1,2,5-thiadiazolidine-2-carboxylate; (S)-3-(2-(4-chlorophenyl)-1,1-dioxo-1,2,5-thiadiazolidin-3-yl)phenol; (S)-2-(4-chlorophenyl)-1,1-dioxo-5-(pyrazin-2-yl)-3-(3-(pyrazin-2-yloxy)phenyl)-1,2,5-thiadiazolidine; (S)-2-(4-chlorophenyl)-1,1-dioxo-3-(3-(pyrazin-2-yloxy)phenyl)-1,2,5-thiadiazolidine; (S)—N,N-bis(4-methoxybenzyl)-3-(5-(4-chlorophenyl)-4-(3-methoxyphenyl)-1,1-dioxo-1,2,5-thiadiazolidin-2-yl)propanesulfamide; (S)-2-(4-chlorophenyl)-1,1-dioxo-5-(3-(methylsulfonyl)propyl)-3-(3-(pyrazin-2-yloxy)phenyl)-1,2,5-thiadiazolidine; (3S,5R)-1-(4-(4-chlorophenoxy)phenyl)-5-(3-(trifluoromethyl)phenyl)-3-(3-(methylsulfonyl)propyl)pyrrolidin-2-one; (S)-2-(5-(4-chlorophenyl)-4-(3-(cyanomethoxy)phenyl)-1,1-dioxo-1,2,5-thiadiazolidin-2-yl)acetonitrile; (S)-2-(4-chlorophenyl)-3-(3-methoxyphenyl)-1,1-dioxo-5-(pyrazin-2-yl)-1,2,5-thiadiazolidine; (S)-2-(4-chlorophenyl)-3-(3-methoxyphenyl)-1,1-dioxo-5-(pyridazin-3-yl)-1,2,5-thiadiazolidine; (S)-2-(4-chlorophenyl)-3-(3-methoxyphenyl)-1,1-dioxo-5-phenyl-1,2,5-thiadiazolidine; (S)-2-(5-(4-chlorophenyl)-4-(3-methoxyphenyl)-1,1-dioxo-1,2,5-thiadiazolidin-2-yl)acetonitrile; (S)-2-(4-chlorophenyl)-3-(3-methoxyphenyl)-1,1-dioxo-5-((3,5-dimethylisoxazol-4-yl)methyl)-1,2,5-thiadiazolidine; (S)-methyl 3-((5-(4-chlorophenyl)-4-(3-methoxyphenyl)-1,1-dioxo-1,2,5-thiadiazolidin-2-yl)methyl)isoxazole-5-carboxylate; (S)-3-((5-(4-chlorophenyl)-4-(3-methoxyphenyl)-1,1-dioxo-1,2,5-thiadiazolidin-2-yl)methyl)-1,2,4-oxadiazole; (S)-3-(2-(4-chlorophenyl)-1,1-dioxo-5-phenyl-1,2,5-thiadiazolidin-3-yl)phenol; (S)-3-(5-(4-chlorophenyl)-1,1-dioxo-4-(3-(pyrazin-2-yloxy)phenyl)-1,2,5-thiadiazolidin-2-yl)propane-1-sulfonamide; (S)-2-(4-chlorophenyl)-1,1-dioxo-5-phenyl-3-(3-(pyrazin-2-yloxy)phenyl)-1,2,5-thiadiazolidine; (S)-4-((5-(4-chlorophenyl)-4-(3-(pyrazin-2-yloxy)phenyl)-1,2,5-thiadiazolidin-2-yl)methyl)-3,5-dimethylisoxazole; (S)-2-(4-chlorophenyl)-5-(4-fluorophenyl)-3-(3-methoxyphenyl)-1,1-dioxo-1,2,5-thiadiazolidine; (R)-1-(5-(4-chlorophenoxy)pyrazin-2-yl)-5-(3-(cyanomethoxy)phenyl)pyrrolidin-2-one; (S)-3-(4-chlorophenyl)-4-(3-(pyrazin-2-yloxy)phenyl)oxazolidin-2-one; (S)-methyl 5-(4-(4-chlorophenoxy)phenyl)-4-(3-methoxyphenyl)-1,2,5-thiadiazolidine-1,1-dioxide-2-carboxylate; (S)-2-(4-chlorophenyl)-3-(3-methoxyphenyl)-1,2,5-thiadiazolidine-1,1-dioxide; (S)-4-(3-(m-tolyloxy)phenyl)-3-(4-chlorophenyl)oxazolidin-2-one; (S)-4-(3-(3-cyanophenoxy)phenyl)-3-(4-chlorophenyl)oxazolidin-2-one; (S)-4-(3-(2-chlorophenoxy)phenyl)-3-(4-chlorophenyl)oxazolidin-2-one; (S)-4-(3-(4-methoxyphenoxy)phenyl)-3-(4-chlorophenyl)oxazolidin-2-one; (S)-4-(3-(2-cyanophenoxy)phenyl)-3-(4-chlorophenyl)oxazolidin-2-one; (S)-4-(3-(4-cyanophenoxy)phenyl)-3-(4-chlorophenyl)oxazolidin-2-one; (S)-3-(4-chlorophenyl)-4-(3-(pyridin-2-yloxy)phenyl)oxazolidin-2-one; (S)-3-(4- chlorophenyl)-4-(3-(pyrimidin-2-yloxy)phenyl)oxazolidin-2-one; (S)-3-(4-chlorophenyl)-4-(3-ethoxyphenyl)oxazolidin-2-one; (S)-3-(4-chlorophenyl)-4-(3-isopropoxyphenyl)oxazolidin-2-one; (S)-3-(4-chlorophenyl)-4-(3-(cyclopropylmethoxy)phenyl)oxazolidin-2-one; (S)-4-(3-(3-(dimethylamino)propoxy)phenyl)-3-(4-chlorophenyl)oxazolidin-2-one; (S)-4-(3-(cyanomethoxy)phenyl)-3-(4-chlorophenyl)oxazolidin-2-one; (S)-4-(3-(2-hydroxyethoxy)phenyl)-3-(4-chlorophenyl)oxazolidin-2-one; (S)-3-(4-chlorophenyl)-4-(3-hydroxyphenyl)oxazolidin-2-one; (S)-3-(4-chlorophenyl)-4-(3-methoxyphenyl)oxazolidin-2-one; 5-(3-(benzyloxy)phenyl)-1-(4-(4-chlorophenoxy)phenyl)imidazolidin-2-one; 3-(4-(4-chlorophenoxy)phenyl)-4-(3-(benzyloxy)phenyl)-1-(2-(methylsulfonyl)ethyl)imidazolidin-2-one; 3-(4-(4-chlorophenoxy)phenyl)-4-(3-hydroxyphenyl)-1-(2-(methylsulfonyl)ethyl)imidazolidin-2-one; 3-(4-(4-chlorophenoxy)phenyl)-1-(2-(methylsulfonyl)ethyl)-4-(3-(pyridin-2-yloxy)phenyl)imidazolidin-2-one; 3-(4-(4-chlorophenoxy)phenyl)-1-(2-(methylsulfonyl)ethyl)-4-(3-(pyrazin-2-yloxy)phenyl)imidazolidin-2-one; 4-(3-(2-cyanophenoxy)phenyl)-3-(4-(4-chlorophenoxy)phenyl)-1-(2-(methylsulfonyl)ethyl)imidazolidin-2-one; 5-(3-(benzyloxy)phenyl)-1-(4-chlorophenyl)imidazolidin-2-one; 4-(3-(benzyloxy)phenyl)-3-(4-chlorophenyl)-1-(2-(methylsulfonyl)ethyl)imidazolidin-2-one; 3-(4-chlorophenyl)-4-(3-hydroxyphenyl)-1-(2-(methylsulfonyl)ethyl)imidazolidin-2-one; 3-(4-chlorophenyl)-1-(2-(methylsulfonyl)ethyl)-4-(3-(pyrazin-2-yloxy)phenyl)imidazolidin-2-one; 4-(3-(2-cyanophenoxy)phenyl)-3-(4-chlorophenyl)-1-(2-(methylsulfonyl)ethyl)imidazolidin-2-one; 3-(4-chlorophenyl)-1-(2-(methylsulfonyl)ethyl)-4-(3-(pyrimidin-2-yloxy)phenyl)imidazolidin-2-one; 3-(4-chlorophenyl)-1-(2-(methylsulfonyl)ethyl)-4-(3-(pyridin-2-yloxy)phenyl)imidazolidin-2-one; 3-(4-chlorophenyl)-1-(2-(methylsulfonyl)ethyl)-4-(3-(pyridin-3-yloxy)phenyl)imidazolidin-2-one; 3-(4-chlorophenyl)-1-(2-(methylsulfonyl)ethyl)-4-(3-(pyridin-4-yloxy)phenyl)imidazolidin-2-one; 3-(4-chlorophenyl)-1-(2-(methylsulfonyl)ethyl)-4-(3-(pyridazin-3-yloxy)phenyl)imidazolidin-2-one; 4-(3-(4-methoxyphenoxy)phenyl)-3-(4-chlorophenyl)-1-(2-(methylsulfonyl)ethyl)imidazolidin-2-one; 4-(3-(5-aminopyrazin-2-yloxy)phenyl)-3-(4-chlorophenyl)-1-(2-(methylsulfonyl)ethyl)imidazolidin-2-one; 3-(4-chlorophenyl)-1-(2-(methylsulfonyl)ethyl)-4-(3-(pyrimidin-5-yloxy)phenyl)imidazolidin-2-one; (4S,5S)-1-((3-(4-chlorophenyl)-4-(3-fluoro-5-(trifluoromethyl)phenyl)-2-oxooxazolidin-5-yl)methyl)-N-(piperidin-1-yl)-1H-1,2,3-triazole-4-carboxamide; (4S,5S)-3-(4-(4-chlorophenoxy)phenyl)-4-(3-fluorophenyl)-5-(morpholinomethyl)oxazolidin-2-one; (4S,5S)-3-(4-(4-chlorophenoxy)phenyl)-5-(morpholinomethyl)-4-(3-(trifluoromethyl)phenyl)oxazolidin-2-one; (4S,5S)-3-(4-(4-chlorophenoxy)phenyl)-4-(3-methoxyphenyl)-5-(morpholinomethyl)oxazolidin-2-one; (4S,5S)-3-(4-chlorophenyl)-5-((4-(ethylsulfonylmethyl)-1H-1,2,3-triazol-1-yl)methyl)-4-(3-fluoro-5-(trifluoromethyl)phenyl)oxazolidin-2-one; ethyl 1-(((4S,5S)-3-(4-chlorophenyl)-4-(3-methoxyphenyl)-2-oxooxazolidin-5-yl)methyl)piperidine-4-carboxylate; tert-butyl 4-(((4S,5S)-3-(4-chlorophenyl)-4-(3-methoxyphenyl)-2-oxooxazolidin-5-yl)methyl)-1,4-diazepane-1-carboxylate; (4S,5S)-3-(4-chlorophenyl)-5-((4-(3-fluorophenyl)-1H-1,2,3-triazol-1-yl)methyl)-4-(3-methoxyphenyl)oxazolidin-2-one; (4S,5S)-3-(4-chlorophenyl)-4-(3-methoxyphenyl)-5-((4-(2-methoxyphenyl)-1H-1,2,3-triazol-1-yl)methyl)oxazolidin-2-one; ethyl 1-(((4S,5S)-3-(4-chlorophenyl)-4-(3-methoxyphenyl)-2-oxooxazolidin-5-yl)methyl)-1H-1,2,3-triazole-4-carboxylate; (4S,5S)-3-(4-chlorophenyl)-5-((4-(ethylsulfonyl)piperazin-1-yl)methyl)-4-(3-methoxyphenyl)oxazolidin-2-one; (4S,5S)-3-(4-chlorophenyl)-5-((4-cyclopentyl-1H-1,2,3-triazol-1-yl)methyl)-4-(3-methoxyphenyl)oxazolidin-2-one; (4S,5S)-3-(4-chlorophenyl)-4-(3-methoxyphenyl)-5-((4-(thiophen-3-yl)-1H-1,2,3-triazol-1-yl)methyl)oxazolidin-2-one; (4S,5S)-3-(4-chlorophenyl)-5-((4-(cyclohexylmethyl)-1H-1,2,3-triazol-1-yl)methyl)-4-(3-methoxyphenyl)oxazolidin-2-one; (4S,5S)-5-((4-acetyl-1H-1,2,3-triazol-1-yl)methyl)-3-(4-chlorophenyl)-4-(3-methoxyphenyl)oxazolidin-2-one; (4S,5S)-3-(4-chlorophenyl)-5-((4-isopentyl-1H-1,2,3-triazol-1-yl)methyl)-4-(3-methoxyphenyl)oxazolidin-2-one; (4S,5S)-3-(4-chlorophenyl)-4-(3-methoxyphenyl)-5-((5-(2-methoxyphenyl)-2H-tetrazol-2-yl)methyl)oxazolidin-2-one; (4S,5S)-3-(4-chlorophenyl)-5-((5-(2-(diethylamino)ethyl)-2H-tetrazol-2-yl)methyl)-4-(3-methoxyphenyl)oxazolidin-2-one; (4S,5S)-3-(4-chlorophenyl)-4-(3-methoxyphenyl)-5-((5-(2-(piperidin-1-yl)ethyl)-2H-tetrazol-2-yl)methyl)oxazolidin-2-one; (4S,5S)-3-(4-chlorophenyl)-5-((4-((diethylamino)methyl)-1H-1,2,3-triazol-1-yl)methyl)-4-(3-methoxyphenyl)oxazolidin-2-one; (4S,5S)-3-(4-chlorophenyl)-4-(3-methoxyphenyl)-5-((4-(piperidin-1-ylmethyl)-1H-1,2,3-triazol-1-yl)methyl)oxazolidin-2-one; (4S,5S)-3-(4-chlorophenyl)-5-(morpholinomethyl)-4-(3-(pyrazin-2-yloxy)phenyl)oxazolidin-2-one; (4S,5S)-3-(4-chlorophenyl)-4-(3-methoxyphenyl)-5-((4-(morpholinomethyl)-1H-1,2,3-triazol-1-yl)methyl)oxazolidin-2-one; (4S,5S)-3-(4-chlorophenyl)-5-((4-((isopropylamino)methyl)-1H-1,2,3-triazol-1-yl)methyl)-4-(3-methoxyphenyl)oxazolidin-2-one; (4S,5S)-3-(4-chlorophenyl)-4-(3,5-difluorophenyl)-5-((4-(ethyl sulfonyl)piperazin-1-yl)methyl)oxazolidin-2-one; ethyl 4-(((4S,5S)-3-(4-chlorophenyl)-4-(3,5-difluorophenyl)-2-oxooxazolidin-5-yl)methyl)piperazine-1-carboxylate; (4S,5S)-3-(4-chlorophenyl)-5-((4-(cyclohexylmethyl)-1H-1,2,3-triazol-1-yl)methyl)-4-(3,5-difluorophenyl)oxazolidin-2-one; (4S,5S)-3-(4-chlorophenyl)-4-(3-methoxyphenyl)-5-((4-(3-methyl-1,2,4-oxadiazol-5-yl)piperidin-1-yl)methyl)oxazolidin-2-one; (4S,5S)-5-((4-acetyl-1H-1,2,3-triazol-1-yl)methyl)-3-(4-chlorophenyl)-4-(3,5-difluorophenyl)oxazolidin-2-one; (4S,5S)-3-(4-chlorophenyl)-4-(3-methoxyphenyl)-5-((4-(5-methyl-1,3,4-oxadiazol-2-yl)piperidin-1-yl)methyl)oxazolidin-2-one; (4S,5S)-5-((4-(azepan-1-ylmethyl)-1H-1,2,3-triazol-1-yl)methyl)-3-(4-chlorophenyl)-4-(3,5-difluorophenyl)oxazolidin-2-one; (4S,5S)-3-(4-chlorophenyl)-4-(3,5-difluorophenyl)-5-((4-((4-methylpiperidin-1-yl)methyl)-1H-1,2,3-triazol-1-yl)methyl)oxazolidin-2-one; (4S,5S)-3-(4-chlorophenyl)-4-(3,5-difluorophenyl)-5-((4-(piperidin-1-ylmethyl)-1H-1,2,3-triazol-1-yl)methyl)oxazolidin-2-one; tert-butyl 1-(((4S,5S)-3-(4-chlorophenyl)-4-(3,5-difluorophenyl)-2-oxooxazolidin-5-yl)methyl)pyrrolidin-3-ylcarbamate; (4S,5S)-3-(4-chlorophenyl)-4-(3,5-difluorophenyl)-5-((4-ethoxy-1H-1,2,3-triazol-1-yl)methyl)oxazolidin-2-one; (4S,5S)-3-(4-chlorophenyl)-5-((5-(6-chloropyridin-3-yl)-2H-tetrazol-2-yl)methyl)-4-(3,5-difluorophenyl)oxazolidin-2-one; (4S,5S)-3-(4-chlorophenyl)-4-(3,5-difluorophenyl)-5-((4-phenylpiperidin-1-yl)methyl)oxazolidin-2-one; (4S,5R)-3-(4-chlorophenyl)-5-((5-chloropyridin-2-yloxy)methyl)-4-(3,5-difluorophenyl)oxazolidin-2-one; (4S,5S)-3-(4-chlorophenyl)-4-(3,5-difluorophenyl)-5-((4-(pyrimidin-2-yl)piperazin-1-yl)methyl)oxazolidin-2-one; (4S,5S)-3-(4-chlorophenyl)-4-(3,5-difluorophenyl)-5-((4-(pyridin-2-yl)piperazin-1-yl)methyl)oxazolidin-2-one; (4S,5S)-3-(4-chlorophenyl)-4-(3,5-difluorophenyl)-5-((4-(3-methyl-1,2,4-oxadiazol-5-yl)piperidin-1-yl)methyl)oxazolidin-2-one;

(4S,5S)-3-(4-chlorophenyl)-4-(3-methoxyphenyl)-5-((4-(pyrazin-2-yl)piperazin-1-yl)methyl)oxazolidin-2-one; ethyl 4-(((4S,5S)-3-(4-chlorophenyl)-4-(3-ethoxyphenyl)-2-oxooxazolidin-5-yl)methyl)piperazine-1-carboxylate; ethyl 4-(((4S,5S)-3-(4-chlorophenyl)-4-(3-isopropoxyphenyl)-2-oxooxazolidin-5-yl)methyl)piperazine-1-carboxylate; (4S,5S)-3-(4-chlorophenyl)-4-(3,5-difluorophenyl)-5-((5-(pyrimidin-2-yl)-2H-tetrazol-2-yl)methyl)oxazolidin-2-one; (4S,5S)-3-(4-chlorophenyl)-4-(3,5-difluorophenyl)-5-((5-(pyrazin-2-yl)-2H-tetrazol-2-yl)methyl)oxazolidin-2-one; (4S,5S)-3-(4-chlorophenyl)-4-(3,5-difluorophenyl)-5-((5-(pyridin-2-yl)-2H-tetrazol-2-yl)methyl)oxazolidin-2-one; (4S,5S)-3-(4-chlorophenyl)-4-(3,5-difluorophenyl)-5-((5-(pyridin-2-yl)-1H-tetrazol-1-yl)methyl)oxazolidin-2-one; (4S,5S)-3-(4-chlorophenyl)-4-(3,5-difluorophenyl)-5-((4-hydroxy-4-phenylpiperidin-1-yl)methyl)oxazolidin-2-one; (4S,5S)-3-(4-chlorophenyl)-5-((4-(4-chlorophenyl)-4-hydroxypiperidin-1-yl)methyl)-4-(3,5-difluorophenyl)oxazolidin-2-one; (4S,5S)-3-(4-chlorophenyl)-4-(3,5-difluorophenyl)-5-((5-methyl-2-oxopyridin-1(2H)-yl)methyl)oxazolidin-2-one; (4S,5R)-3-(4-chlorophenyl)-4-(3,5-difluorophenyl)-5-((4-methylpyridin-2-yloxy)methyl)oxazolidin-2-one; (4S,5S)-3-(4-chlorophenyl)-4-(3,5-difluorophenyl)-5-((5-(imidazo[1,2-a]pyridin-6-yl)-2H-tetrazol-2-yl)methyl)oxazolidin-2-one; (4S,5S)-3-(4-chlorophenyl)-4-(3,5-difluorophenyl)-5-((3-oxo-4-(pyridin-2-yl)piperazin-1-yl)methyl)oxazolidin-2-one; (4S,5S)-3-(4-chlorophenyl)-4-(3,5-difluorophenyl)-5-((4-(pyrazin-2-yl)piperazin-1-yl)methyl)oxazolidin-2-one; (4S,5S)-3-(4-chlorophenyl)-4-(3,5-difluorophenyl)-5-((4-(3,5-dimethylphenyl)-3-oxopiperazin-1-yl)methyl)oxazolidin-2-one; (S)-3-(4-(4-chlorophenoxy)phenyl)-4-(3-(trifluoromethyl)phenyl)-1-(pyrazin-2-yl)imidazolidin-2-one; N-(3-(1-(((4S,5S)-3-(4-chlorophenyl)-4-(3-fluoro-5-(trifluoromethyl)phenyl)-2-oxooxazolidin-5-yl)methyl)-1H-1,2,3-triazol-4-yl)phenyl)acetamide; (4S,5S)-3-(4-chlorophenyl)-4-(3-fluoro-5-(trifluoromethyl)phenyl)-5-((4-((3-methyl-1H-pyrazol-1-yl)methyl)-1H-1,2,3-triazol-1-yl)methyl)oxazolidin-2-one; (4S,5S)-3-(4-chlorophenyl)-4-(3-fluoro-5-(trifluoromethyl)phenyl)-5-((4-((5-methyl-1H-pyrazol-1-yl)methyl)-1H-1,2,3-triazol-1-yl)methyl)oxazolidin-2-one; ethyl 4-(((4S,5S)-3-(4-chlorophenyl)-4-(3-methoxyphenyl)-2-oxooxazolidin-5-yl)methyl)piperazine-1-carboxylate; benzyl 1-(((4S,5S)-3-(4-chlorophenyl)-4-(3-methoxyphenyl)-2-oxooxazolidin-5-yl)methyl)-2-oxopiperidine-4-carboxylate; (4S,5S)-3-(4-chlorophenyl)-4-(3-methoxyphenyl)-5-((4-(pyridin-3-yl)-1H-1,2,3-triazol-1-yl)methyl)oxazolidin-2-one; 4-(1-(((4S,5S)-3-(4-chlorophenyl)-4-(3-methoxyphenyl)-2-oxooxazolidin-5-yl)methyl)-1H-1,2,3-triazol-4-yl)benzonitrile; (4S,5S)-3-(4-chlorophenyl)-4-(3-methoxyphenyl)-5-((4-((tetrahydrofuran-3-yloxy)methyl)-1H-1,2,3-triazol-1-yl)methyl)oxazolidin-2-one; (4S,5S)-3-(4-chlorophenyl)-4-(3-fluorophenyl)-5-((5-phenyl-2H-tetrazol-2-yl)methyl)oxazolidin-2-one; (4S,5S)-3-(4-chlorophenyl)-4-(3-methoxyphenyl)-5-((4-(1-methyl-1H-imidazol-5-yl)-1H-1,2,3-triazol-1-yl)methyl)oxazolidin-2-one; (4S,5S)-3-(4-chlorophenyl)-4-(3-fluoro-5-(trifluoromethyl)phenyl)-5-((4-(3-methyl-1,2,4-oxadiazol-5-yl)-1H-1,2,3-triazol-1-yl)methyl)oxazolidin-2-one; (4S,5S)-3-(4-chlorophenyl)-5-((4-ethoxy-1H-1,2,3-triazol-1-yl)methyl)-4-(3-methoxyphenyl)oxazolidin-2-one; (4S,5S)-3-(4-chlorophenyl)-4-(3-methoxyphenyl)-5-((4-(3-methyl-1,2,4-oxadiazol-5-yl)-1H-1,2,3-triazol-1-yl)methyl)oxazolidin-2-one; (4S,5S)-3-(4-chlorophenyl)-4-(3-methoxyphenyl)-5-((4-(5-methyl-1,3,4-oxadiazol-2-yl)-1H-1,2,3-triazol-1-yl)methyl)oxazolidin-2-one; (4S,5S)-3-(4-chlorophenyl)-4-(3-methoxyphenyl)-5-((5-phenyl-2H-tetrazol-2-yl)methyl)oxazolidin-2-one; ethyl 2-(2-(((4S,5S)-3-(4-chlorophenyl)-4-(3-methoxyphenyl)-2-oxooxazolidin-5-yl)methyl)-2H-tetrazol-5-yl)acetate; (4S,5S)-3-(4-chlorophenyl)-5-((5-(2-hydroxyethyl)-2H-tetrazol-2-yl)methyl)-4-(3-methoxyphenyl)oxazolidin-2-one; (4S,5S)-3-(4-chlorophenyl)-4-(3-methoxyphenyl)-5-((5-(2-morpholinoethyl)-2H-tetrazol-2-yl)methyl)oxazolidin-2-one; (4S,5S)-3-(4-chlorophenyl)-5-((1-(tetrahydro-2H-pyran-4-yl)methyl)-1H-1,2,3-triazol-4-yl)methyl)-4-(3-methoxyphenyl)oxazolidin-2-one; (4S,5S)-3-(4-chlorophenyl)-4-(3-methoxyphenyl)-5-((5-(pyridin-3-yl)-2H-tetrazol-2-yl)methyl)oxazolidin-2-one; (4S,5S)-3-(4-chlorophenyl)-5-((3-(tetrahydrofuran-3-yl)isoxazol-5-yl)methyl)-4-(3-methoxyphenyl)oxazolidin-2-one; tert-butyl 4-((4-(((4S,5S)-3-(4-chlorophenyl)-4-(3-methoxyphenyl)-2-oxooxazolidin-5-yl)methyl)-1H-1,2,3-triazol-1-yl)methyl)piperidine-1-carboxylate; ethyl 2-(((4S,5S)-3-(4-chlorophenyl)-4-(3-methoxyphenyl)-2-oxooxazolidin-5-yl)methyl)-2H-tetrazole-5-carboxylate; (4S,5S)-3-(4-chlorophenyl)-4-(3-methoxyphenyl)-5-((4-phenyl-1H-imidazol-1-yl)methyl)oxazolidin-2-one; (4S,5S)-3-(4-chlorophenyl)-4-(3,5-difluorophenyl)-5-((4-((tetrahydrofuran-3-yloxy)methyl)-1H-1,2,3-triazol-1-yl)methyl)oxazolidin-2-one; (4S,5S)-5-((1H-1,2,3-triazol-1-yl)methyl)-3-(4-chlorophenyl)-4-(3,5-difluorophenyl)oxazolidin-2-one; (4S,5S)-3-(4-chlorophenyl)-4-(3,5-difluorophenyl)-5-((5-(pyridin-3-yl)-2H-tetrazol-2-yl)methyl)oxazolidin-2-one; (4S,5S)-3-(4-chlorophenyl)-4-(3,5-difluorophenyl)-5-((5-((piperidin-1-yl)methyl)-2H-tetrazol-2-yl)methyl)oxazolidin-2-one; (4S,5S)-3-(4-chlorophenyl)-4-(3,5-difluorophenyl)-5-((5-(6-methylpyridin-3-yl)-2H-tetrazol-2-yl)methyl)oxazolidin-2-one; tert-butyl 4-(2-(((4S,5S)-3-(4-chlorophenyl)-4-(3,5-difluorophenyl)-2-oxooxazolidin-5-yl)methyl)-2H-tetrazol-5-yl)piperidine-1-carboxylate; tert-butyl 4-(1-(((4S)-3-(4-chlorophenyl)-4-(3,5-difluorophenyl)-2-oxooxazolidin-5-yl)methyl)-1H-tetrazol-5-yl)piperidine-1-carboxylate; (4S,5S)-3-(4-chlorophenyl)-4-(3,5-difluorophenyl)-5-((4-phenyl-1H-imidazol-1-yl)methyl)oxazolidin-2-one; (4S,5S)-3-(4-chlorophenyl)-4-(3,5-difluorophenyl)-5-((5-(6-methoxypyridin-3-yl)-2H-tetrazol-2-yl)methyl)oxazolidin-2-one; (4S,5S)-3-(4-chlorophenyl)-4-(3-methoxyphenyl)-5-((4-(pyrimidin-2-yl)piperazin-1-yl)methyl)oxazolidin-2-one; (4S,5S)-3-(4-chlorophenyl)-4-(3-methoxyphenyl)-5-((4-(pyridin-2-yl)piperazin-1-yl)methyl)oxazolidin-2-one; (4S,5S)-3-(4-chlorophenyl)-4-(3-isopropoxyphenyl)-5-((5-(pyridin-3-yl)-2H-tetrazol-2-yl)methyl)oxazolidin-2-one; (4S,5S)-3-(4-chlorophenyl)-4-(3-hydroxyphenyl)-5-((5-(pyridin-3-yl)-2H-tetrazol-2-yl)methyl)oxazolidin-2-one; (4S,5S)-3-(4-chlorophenyl)-4-(3-(trifluoromethyl)phenyl)-5-((5-(6-methoxypyridin-3-yl)-2H-tetrazol-2-yl)methyl)oxazolidin-2-one; (4S,5S)-3-(4-chlorophenyl)-4-(3-methoxyphenyl)-5-((5-(6-methylpyridin-3-yl)-2H-tetrazol-2-yl)methyl)oxazolidin-2-one; (4S,5S)-3-(4-chlorophenyl)-5-((5-(6-methoxypyridin-3-yl)-2H-tetrazol-2-yl)methyl)-4-(3-(trifluoromethoxy)phenyl)oxazolidin-2-one; ethyl 4-(((4S,5S)-3-(4-chlorophenyl)-2-oxo-4-(3-(trifluoromethoxy)phenyl)oxazolidin-5-yl)methyl)piperazine-1-carboxylate; (4S,5S)-3-(4-chlorophenyl)-4-(3-hydroxyphenyl)-5-((5-(6-methylpyridin-3-yl)-2H-tetrazol-2-yl)methyl)oxazolidin-2-one; (4S,5S)-3-(4-chlorophenyl)-4-(3-isopropoxyphenyl)-5-((5-(6-methylpyridin-3-yl)-2H-tetrazol-2-yl)methyl)oxazolidin-2-one; (4S,5S)-3-(4-chlorophenyl)-4-(3-methoxyphenyl)-5-((5-(6-methoxypyridin-3-yl)-2H-tetrazol-2-yl)methyl)oxazolidin-2-one; 6-(4-(((4S,5S)-3-(4-chlorophenyl)-4-(3-methoxyphenyl)-2-oxooxazolidin-5-yl)methyl)piperazin-1- yl)pyridine-3-carbonitrile; (4S,5S)-3-(4-chlorophenyl)-4-(3-(2-hydroxyethoxy)phenyl)-5-((5-(6-methoxypyridin-3-yl)-2H-tetrazol-2-yl)methyl)oxazolidin-2-one; (4S,5R)-5-((5-cyanopyridin-2-yloxy)methyl)-3-(4-chlorophenyl)-4-(3-methoxyphenyl)oxazolidin-2-one; 4-(((4S,5S)-3-(4-chlorophenyl)-4-(3-methoxyphenyl)-2-oxooxazolidin-5-yl)methyl)-1-(6-methoxypyridin-3-yl)piperazin-2-one; (4S,5S)-3-(4-chlorophenyl)-4-(3-methoxyphenyl)-5-((4-(6-methoxypyridin-2-yl)piperazin-1-yl)methyl)oxazolidin-2-one; 4-(((4S,5S)-3-(4-chlorophenyl)-4-(3-methoxyphenyl)-2-oxooxazolidin-5-yl)methyl)-1-(6-methoxypyridin-2-yl)piperazin-2-one; tert-butyl 4-(((4S,5S)-3-(4-chlorophenyl)-4-(3-methoxyphenyl)-2-oxooxazolidin-5-yl)methyl)-3-oxopiperazine-1-carboxylate; (4S,5S)-3-(4-chlorophenyl)-5-((4-(4-fluoropyridin-2-yl)piperazin-1-yl)methyl)-4-(3-methoxyphenyl)oxazolidin-2-one; ethyl 3-((4S,5S)-3-(4-chlorophenyl)-4-(3-methoxyphenyl)-2-oxooxazolidin-5-yl)propanoate; (4S,5S)-3-(4-chlorophenyl)-5-((3-(diethylamino)pyrrolidin-1-yl)methyl)-4-(3-fluorophenyl)oxazolidin-2-one; tert-butyl 1-(((4S,5S)-3-(4-chlorophenyl)-4-(3-(trifluoromethyl)phenyl)-2-oxooxazolidin-5-yl)methyl)pyrrolidin-3-ylmethylcarbamate; (S)-3-(4-chlorophenyl)-1-((5-(4-methoxyphenyl)-1,2,4-oxadiazol-3-yl)methyl)-4-(3-(trifluoromethyl)phenyl)imidazolidin-2-one; (S)-3-(4-chlorophenyl)-1-(pyridin-3-ylmethyl)-4-(3-(trifluoromethyl)phenyl)imidazolidin-2-one; (S)-3-(4-chlorophenyl)-1-(4-methoxybenzyl)-4-(3-(trifluoromethyl)phenyl)imidazolidin-2-one; (S)-2-(3-(4-chlorophenyl)-2-oxo-4-(3-(trifluoromethyl)phenyl)imidazolidin-1-yl)ethanesulfonamide; (S)-3-(4-chlorophenyl)-1-(2-hydroxyethyl)-4-(3-(trifluoromethyl)phenyl)imidazolidin-2-one; (S)-3-(4-chlorophenyl)-1-(3-hydroxypropyl)-4-(3-(trifluoromethyl)phenyl)imidazolidin-2-one; (S)-2-(3-(4-chlorophenyl)-2-oxo-4-(3-(trifluoromethyl)phenyl)imidazolidin-1-yl)-N-propylacetamide; (S)-3-(4-chlorophenyl)-1-(2-oxo-2-(piperidin-1-yl)ethyl)-4-(3-(trifluoromethyl)phenyl)imidazolidin-2-one; (S)-2-(3-(4-chlorophenyl)-2-oxo-4-(3-(trifluoromethyl)phenyl)imidazolidin-1-yl)-N-(piperidin-1-yl)acetamide; (S)-tert-butyl 4-(2-(3-(4-chlorophenyl)-2-oxo-4-(3-(trifluoromethyl)phenyl)imidazolidin-1-yl)acetyl)piperazine-1-carboxylate; (S)-3-(4-chlorophenyl)-1-((5-(4-methoxyphenyl)-1,3,4-oxadiazol-2-yl)methyl)-4-(3-(trifluoromethyl)phenyl)imidazolidin-2-one; (S)-3-(4-chlorophenyl)-1-((5-(4-chlorophenyl)oxazol-2-yl)methyl)-4-(3-(trifluoromethyl)phenyl)imidazolidin-2-one; (S)-methyl 3-((3-(4-chlorophenyl)-2-oxo-4-(3-(trifluoromethyl)phenyl)imidazolidin-1-yl)methyl)isoxazole-5-carboxylate; (S)-3-(4-chlorophenyl)-1-(2-morpholinoethyl)-4-(3-(trifluoromethyl)phenyl)imidazolidin-2-one; (S)-3-(4-chlorophenyl)-1-(2-(4-hydroxypiperidin-1-yl)ethyl)-4-(3-(trifluoromethyl)phenyl)imidazolidin-2-one; (S)-3-(4-chlorophenyl)-1-(3-morpholinopropyl)-4-(3-(trifluoromethyl)phenyl)imidazolidin-2-one; (S)-3-(4-chlorophenyl)-1-(2-(4-(methylsulfonyl)piperazin-1-yl)ethyl)-4-(3-(trifluoromethyl)phenyl)imidazolidin-2-one; (S)-1-((5-tert-butyl-1,2,4-oxadiazol-3-yl)methyl)-3-(4-chlorophenyl)-4-(3-(trifluoromethyl)phenyl)imidazolidin-2-one; (S)-3-(4-chlorophenyl)-1-(2-(4-methylpiperazin-1-ylsulfonyl)ethyl)-4-(3-(trifluoromethyl)phenyl)imidazolidin-2-one; (S)-3-(4-chlorophenyl)-1-(2-(piperidin-1-ylsulfonyl)ethyl)-4-(3-(trifluoromethyl)phenyl)imidazolidin-2-one; (S)-3-(4-chlorophenyl)-1-(2-(pyrrolidin-1-ylsulfonyl)ethyl)-4-(3-(trifluoromethyl)phenyl)imidazolidin-2-one; (S)-3-(4-chlorophenyl)-1-(2-(morpholinosulfonyl)ethyl)-4-(3-(trifluoromethyl)phenyl)imidazolidin-2-one; (S)-3-(3-(4-chlorophenyl)-2-oxo-4-(3-(trifluoromethyl)phenyl)imidazolidin-1-yl)propane-1-sulfonamide; (S)-2-(3-(4-chlorophenyl)-2-oxo-4-(3-(trifluoromethyl)phenyl)imidazolidin-1-yl)-N,N-bis(2-hydroxyethyl)ethanesulfonamide; (S)-3-(4-chlorophenyl)-1-((6-morpholinopyridin-3-yl)methyl)-4-(3-(trifluoromethyl)phenyl)imidazolidin-2-one; (S)-3-(4-chlorophenyl)-1-((6-(4-ethylpiperazin-1-yl)pyridin-3-yl)methyl)-4-(3-(trifluoromethyl)phenyl)imidazolidin-2-one; (S)-3-(4-chlorophenyl)-1-((6-(piperidin-1-yl)pyridin-3-yl)methyl)-4-(3-(trifluoromethyl)phenyl)imidazolidin-2-one; (S)-3-(4-chlorophenyl)-1-((6-(pyrrolidin-1-yl)pyridin-3-yl)methyl)-4-(3-(trifluoromethyl)phenyl)imidazolidin-2-one; (S)-1-((6-(bis(2-hydroxyethyl)amino)pyridin-3-yl)methyl)-3-(4-chlorophenyl)-4-(3-(trifluoromethyl)phenyl)imidazolidin-2-one; (S)-3-(4-chlorophenyl)-1-((6-(4-(methylsulfonyl)piperazin-1-yl)pyridin-3-yl)methyl)-4-(3-(trifluoromethyl)phenyl)imidazolidin-2-one; (S)-3-(4-chlorophenyl)-1-(3-(4-(methylsulfonyl)piperazin-1-yl)propyl)-4-(3-(trifluoromethyl)phenyl)imidazolidin-2-one; (4S)-3-(4-chlorophenyl)-1-(3-(3-(diethylamino)pyrrolidin-1-yl)propyl)-4-(3-(trifluoromethyl)phenyl)imidazolidin-2-one; (S)-3-(4-chlorophenyl)-1-(2-(5-cyclohexyl-1,2,4-oxadiazol-3-yl)ethyl)-4-(3-(trifluoromethyl)phenyl)imidazolidin-2-one; (S)-1-(2-(5-tert-butyl-1,2,4-oxadiazol-3-yl)ethyl)-3-(4-chlorophenyl)-4-(3-(trifluoromethyl)phenyl)imidazolidin-2-one; (S)-3-(4-chlorophenyl)-1-(2-(5-(pyridin-3-yl)-1,2,4-oxadiazol-3-yl)ethyl)-4-(3-(trifluoromethyl)phenyl)imidazolidin-2-one; (S)-3-(4-(4-chlorophenoxy)phenyl)-1-(2-(morpholinosulfonyl)ethyl)-4-(3-(trifluoromethyl)phenyl)imidazolidin-2-one; (S)-3-(3-(4-(4-chlorophenoxy)phenyl)-2-oxo-4-(3-(trifluoromethyl)phenyl)imidazolidin-1-yl)propane-1-sulfonamide; (S)-3-(4-(4-chlorophenoxy)phenyl)-1-(2-(4-methylpiperazin-1-ylsulfonyl)ethyl)-4-(3-(trifluoromethyl)phenyl)imidazolidin-2-one; (S)-2-(3-(4-(4-chlorophenoxy)phenyl)-2-oxo-4-(3-(trifluoromethyl)phenyl)imidazolidin-1-yl)-N-(2-hydroxyethyl)ethanesulfonamide; (S)-2-(3-(4-(4-chlorophenoxy)phenyl)-2-oxo-4-(3-(trifluoromethyl)phenyl)imidazolidin-1-yl)-N,N-bis(2-hydroxyethyl)ethanesulfonamide; (S)-1-(4-(4-chlorophenoxy)phenyl)-5-(3-methoxyphenyl)imidazolidin-2-one; (S)-1-(4-(4-chlorophenoxy)phenyl)-5-(3-hydroxyphenyl)imidazolidin-2-one; (S)-2-(3-(4-(4-chlorophenoxy)phenyl)-4-(3-methoxyphenyl)-2-oxoimidazolidin-1-yl)ethanesulfonamide; (S)-1-(4-(4-chlorophenoxy)phenyl)-5-(3-(2-hydroxyethoxy)phenyl)imidazolidin-2-one; (S)-2-(3-(4-(4-chlorophenoxy)phenyl)-4-(3-(2-hydroxyethoxy)phenyl)-2-oxoimidazolidin-1-yl)ethanesulfonamide; (S)—N-(2-(3-(4-(4-chlorophenoxy)phenyl)-2-oxo-4-(3-(trifluoromethyl)phenyl)imidazolidin-1-yl)ethylsulfonyl)acetamide; (S)-3-(4-(4-chlorophenoxy)phenyl)-4-(3-(2-hydroxyethoxy)phenyl)-1-(2-(methylsulfonyl)ethyl)imidazolidin-2-one; tert-butyl 4-((2-((S)-3-(4-(4-chlorophenoxy)phenyl)-4-(3-(trifluoromethyl)phenyl)-2-oxoimidazolidin-1-yl)ethyl)sulfonyl)piperazine-1-carboxylate; (S)-3-(4-(4-chlorophenoxy)phenyl)-4-(3-(trifluoromethyl)phenyl)-1-(2-((piperazin-1-yl)sulfonyl)ethyl)imidazolidin-2-one; (S)-1-(4-chlorophenyl)-5-(3-(pyridazin-3-yloxy)phenyl)imidazolidin-2-one; (S)-3-(4-chlorophenyl)-4-(3-(pyridazin-3-yloxy)phenyl)oxazolidin-2-one; (S)-3-(4-chlorophenyl)-1-(2-(morpholinosulfonyl)ethyl)-4-(3-(pyridazin-3-yloxy)phenyl)imidazolidin-2-one; (S)-3-(4-chlorophenyl)-1-(2-(4-methylpiperazin-1-ylsulfonyl)ethyl)-4-(3-(pyridazin-3-yloxy)phenyl)imidazolidin-2-one; (S)-3-(4-chlorophenyl)-4-(3-(pyridazin-3-yloxy)phenyl)-1-(2-(pyrrolidin-1-ylsulfonyl)ethyl)imidazolidin-2-one; (S)-2-(3-(4-chlorophenyl)-2-oxo-4-(3-(pyridazin-3-yloxy)phenyl)imidazolidin-1-yl)ethanesulfonamide; (S)-3-

(4-chlorophenyl)-4-(3-(2-hydroxyethoxy)phenyl)-1-(2-(methylsulfonyl)ethyl)imidazolidin-2-one; (S)-3-(4-chlorophenyl)-4-(3-(2-hydroxyethoxy)phenyl)-1-(2-(morpholinosulfonyl)ethyl)imidazolidin-2-one; (S)-3-(4-chlorophenyl)-4-(3-(2-hydroxyethoxy)phenyl)-1-(2-(4-methylpiperazin-1-ylsulfonyl)ethyl)imidazolidin-2-one; (S)-3-(4-chlorophenyl)-4-(3-(2-hydroxyethoxy)phenyl)-1-(2-(pyrrolidin-1-ylsulfonyl)ethyl)imidazolidin-2-one; (S)-2-(3-(4-chlorophenyl)-4-(3-(2-hydroxyethoxy)phenyl)-2-oxoimidazolidin-1-yl)ethanesulfonamide; (S)-3-(4-(4-chlorophenoxy)phenyl)-1-(2-(methylsulfonyl)ethyl)-4-(3-(pyrazin-2-yloxy)phenyl)imidazolidin-2-one; (S)-1-(4-(4-chlorophenoxy)phenyl)-5-(3-(pyrazin-2-yloxy)phenyl)imidazolidin-2-one; (S)-2-(3-(4-(4-chlorophenoxy)phenyl)-2-oxo-4-(3-(pyrazin-2-yloxy)phenyl)imidazolidin-1-yl)ethanesulfonamide; (S)-1-(5-(4-chlorophenoxy)pyrazin-2-yl)-5-(3-methoxyphenyl)imidazolidin-2-one; (S)-3-(5-(4-chlorophenoxy)pyrazin-2-yl)-4-(3-methoxyphenyl)-1-(2-(methylsulfonyl)ethyl)imidazolidin-2-one; (S)-1-(2-(azetidin-1-ylsulfonyl)ethyl)-3-(4-(4-chlorophenoxy)phenyl)-4-(3-(trifluoromethyl)phenyl)imidazolidin-2-one; (S)-1-(2-(azetidin-1-ylsulfonyl)ethyl)-3-(4-chlorophenyl)-4-(3-(pyridazin-3-yloxy)phenyl)imidazolidin-2-one; (S)-3-(4-(4-chlorophenoxy)phenyl)-1-(4-(methylsulfonyl)phenyl)-4-(3-(trifluoromethyl)phenyl)imidazolidin-2-one; (S)-3-(4-chlorophenyl)-1-(4-(methylsulfonyl)phenyl)-4-(3-(pyridazin-3-yloxy)phenyl)imidazolidin-2-one; (S)-4-(3-(4-(4-chlorophenoxy)phenyl)-2-oxo-4-(3-(trifluoromethyl)phenyl)imidazolidin-1-yl)benzene sulfonamide; (S)-4-(3-(4-chlorophenyl)-2-oxo-4-(3-(pyridazin-3-yloxy)phenyl)imidazolidin-1-yl)benzenesulfonamide; (S)-methyl 3-(3-(4-(4-chlorophenoxy)phenyl)-2-oxo-4-(3-(trifluoromethyl)phenyl)imidazolidin-1-yl)propanoate; (S)-3-(4-chlorophenyl)-1-(2-(methylsulfonyl)ethyl)-4-(3-(trifluoromethyl)phenyl)imidazolidin-2-one; (S)-3-(3-(4-(4-chlorophenoxy)phenyl)-2-oxo-4-(3-(trifluoromethyl)phenyl)imidazolidin-1-yl)propan amide; (S)—N-(1-(4-(4-chlorophenoxy)phenyl)-5-(3-(trifluoromethyl)phenyl)imidazolidin-2-ylidene)sulfamide; (S)-3-(4-chlorophenyl)-1-(pyrazin-2-yl)-4-(3-(pyrazin-2-yloxy)phenyl)imidazolidin-2-one; (S)—N-(1-(4-(4-chlorophenoxy)phenyl)-5-(3-(trifluoromethyl)phenyl)imidazolidin-2-ylidene)methanesulfonamide; (S)-3-(4-chlorophenyl)-1-(2-(methylsulfonyl)ethyl)-4-(3-(pyridin-2-yloxy)phenyl)imidazolidin-2-one; (4S)-3-(4-(4-chlorophenoxy)phenyl)-1-(2-(1-methylpyrrolidin-2-yl)ethyl)-4-(3-(trifluoromethyl)phenyl)imidazolidin-2-one; (S)-1-(2-(1,3-dioxan-2-yl)ethyl)-3-(4-(4-chlorophenoxy)phenyl)-4-(3-(trifluoromethyl)phenyl)imidazolidin-2-one; 3-(4-(4-chlorophenoxy)phenyl)-1-(2-(2-oxopyrrolidin-1-yl)ethyl)-4-(3-(trifluoromethyl)phenyl)imidazolidin-2-one; 3-(2-(3-(4-(4-chlorophenoxy)phenyl)-2-oxo-4-(3-(trifluoromethyl)phenyl)imidazolidin-1-yl)ethyl)oxazolidin-2-one; 1-(2-(1H-pyrazol-1-yl)ethyl)-3-(4-(4-chlorophenoxy)phenyl)-4-(3-(trifluoromethyl)phenyl)imidazolidin-2-one; 1-(2-(1H-imidazol-1-yl)ethyl)-3-(4-(4-chlorophenoxy)phenyl)-4-(3-(trifluoromethyl)phenyl)imidazolidin-2-one; (S)-1-(4-(4-chlorophenoxy)phenyl)-2-(nitromethylene)-5-(3-(trifluoromethyl)phenyl)imidazolidine; (S)—N-(1-(4-chlorophenyl)-5-(3-(trifluoromethyl)phenyl)imidazolidin-2-ylidene)methanesulfonamide; (S)-3-(4-chlorophenyl)-4-(3-(6-methylpyridin-3-yloxy)phenyl)-1-(2-(methylsulfonyl)ethyl)imidazolidin-2-one; (S)-1-(4-chlorophenyl)-5-(3-(pyrazin-2-yloxy)phenyl)imidazolidin-2-one; (S)-1-(1-(4-(4-chlorophenoxy)phenyl)-5-(3-(trifluoromethyl)phenyl)imidazolidin-2-ylidene)urea; (S)-3-(4-chlorophenyl)-1-(2-(methylsulfonyl)ethyl)-4-(3-(pyrazin-2-yloxy)phenyl)imidazolidin-2-one; (S)-2-(3-(4-chlorophenyl)-2-oxo-4-(3-(pyrazin-2-yloxy)phenyl)imidazolidin-1-yl)ethanesulfonamide; (S)-3-(4-chlorophenyl)-4-(3-(pyrazin-2-yloxy)phenyl)-1-(2-(pyrrolidin-1-ylsulfonyl)ethyl)imidazolidin-2-one; (S)-3-(4-chlorophenyl)-1-(2-(morpholinosulfonyl)ethyl)-4-(3-(pyrazin-2-yloxy)phenyl)imidazolidin-2-one; (S)-3-(4-chlorophenyl)-1-(2-(4-methylpiperazin-1-ylsulfonyl)ethyl)-4-(3-(pyrazin-2-yloxy)phenyl)imidazolidin-2-one; (S)-3-(4-chlorophenyl)-1-(2-(piperazin-1-ylsulfonyl)ethyl)-4-(3-(pyrazin-2-yloxy)phenyl)imidazolidin-2-one; (S)—N-(1-(4-chlorophenyl)-5-(3-(pyrazin-2-yloxy)phenyl)imidazolidin-2-ylidene)methanesulfonamide; (S)—N-(1-(4-chlorophenyl)-5-(3-(2-hydroxyethoxy)phenyl)imidazolidin-2-ylidene)methanesulfonamide; (S)—N-(1-(4-chlorophenyl)-5-(3-(pyrazin-2-yloxy)phenyl)imidazolidin-2-ylidene)sulfamide; (S)—N-(1-(4-chlorophenyl)-5-(3-(pyridazin-3-yloxy)phenyl)imidazolidin-2-ylidene)methanesulfonamide; (S)-1-(2-(1,3-dioxan-2-yl)ethyl)-3-(4-chlorophenyl)-4-(3-(pyrazin-2-yloxy)phenyl)imidazolidin-2-one; (S)-3-(4-(4-chlorophenoxy)phenyl)-4-(3-methoxyphenyl)-1-(2-(methylsulfonyl)ethyl)imidazolidin-2-one; (S)-3-(3-(4-chlorophenyl)-2-oxo-4-(3-(pyrazin-2-yloxy)phenyl)imidazolidin-1-yl)propanamide; (S)—N-3-(4-(4-chlorophenoxy)phenyl)-1-cyano-4-(3-(trifluoromethyl)phenyl)imidazolidin-2-ylidene)cyanamide; (S)-1-(2-(1H-1,2,4-triazol-3-yl)ethyl)-3-(4-chlorophenyl)-4-(3-(pyrazin-2-yloxy)phenyl)imidazolidin-2-one; (S)-3-(3-(4-chlorophenyl)-1-(2-(methylsulfonyl)ethyl)-2-oxoimidazolidin-4-yl)phenoxy)pyrazine-2-carbonitrile; (S)-3-(4-chlorophenyl)-4-(3-(3-ethylpyrazin-2-yloxy)phenyl)-1-(2-(methylsulfonyl)ethyl)imidazolidin-2-one; and (S)-4-(3-(5-aminopyrazin-2-yloxy)phenyl)-3-(4-chlorophenyl)-1-(2-(methylsulfonyl)ethyl)imidazolidin-2-one.

Another embodiment provides for a method of treating a disease mediated by the Cannabinoid-1 receptor (for example, an eating disorder associated with excessive food intake like obesity, bulimia nervosa, and compulsive eating disorders) comprising administration of to a patient in need of such treatment of a therapeutically effective amount of a compound selected from the Summary of the Invention (supra).

Another embodiment provides for a method of preventing obesity in a person at risk for obesity comprising administration to said person of about 0.001 mg to about 100 mg per kg of a compound selected from the Summary of the Invention (supra).

Further compounds of the invention are detailed in the Examples and Table I, infra.

Pharmacology and Utility

Compounds of the invention inhibit the activity of CB1 and, as such, are useful for treating diseases or disorders in which the activity of CB1 contributes to the pathology and/or symptomology of the disease. This invention further provides compounds of this invention for use in the preparation of medicaments for the treatment of diseases or disorders in which CB1 activity contributes to the pathology and/or symptomology of the disease. CB1 mediated diseases or conditions include, but are not limited to, metabolic disorders as well as conditions associated with metabolic disorders including obesity, bulimia nervosa, compulsive eating disorders, diabetes, arteriosclerosis, hypertension, polycystic ovary disease, osteoporosis, cardiovascular disease, osteoarthritis, dermatological disorders, hypertension, insulin resistance, hypercholesterolemia, hypertriglyceridemia, cholelithiasis and sleep disorders, and hyperlipidemic conditions; or psychiatric disorders such as substance abuse, psychosis, depression, anxiety, stress, epilepsy, mania and schizophrenia; or cognitive disorders such as dementia including Alzheimer's disease, memory deficits, short term memory loss and attention deficit disorders; or neurodegenerative disorders such as Parkinson's Disease, cerebral apoplexy and craniocerebral trauma, hypotension, catabolism in connection with pulmonary dysfunction and ventilator dependency; or cardiac dysfunction including valvular disease, myocardial infarction, cardiac hypertrophy and congestive heart failure); or the overall pulmonary dysfunction, transplant rejection, rheumatoid arthritis, migraine, neuropathy, multiple sclerosis, Guillain-Barre syndrome, the inflammatory sequelae of viral encephalitis, cerebral vascular accidents, inflammatory bowel disease, lupus, graft vs. host disease, T-cell mediated hypersensitivity disease, psoriasis, asthma, Hashimoto's thyroiditis, Guillain-Barre syndrome, cancer, contact dermatitis, allergic rhinitis, ischemic or reperfusion injury, head trauma and movement disorders. The compounds are also useful for the treatment of substance abuse disorders, particularly to opiates, alcohol, marijuana, and nicotine including smoking cessation. The compounds are also useful for the treatment of eating disorders by inhibiting excessive food intake and the resulting obesity and complications associated therewith, including left ventricular hypertrophy. The compounds are also useful for the treatment of constipation and chronic intestinal pseudo-obstruction, as well as for the treatment of asthma, osteopororsis, and cirrhosis of the liver.

Marijuana and its derivatives have been used for centuries for medicinal and recreational purposes. A major active ingredient in marijuana and hashish has been determined to be Δ9-Tetrahydrocannabinol (Δ9-THC). The biological action of Δ9-THC and other members of the cannabinoid family occurs through two G-protein coupled receptors termed CB1 and CB2. The CB1 receptor is primarily found in the central and peripheral nervous systems and to a lesser extent in several peripheral organs.

The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to Δ9-THC, including sedation, hypothermia, intestinal immobility, antinociception, analgesia, catalepsy, anti-emesis, and appetite stimulation.

The genes for the respective cannabinoid receptors have each been disrupted in mice. The CB1 receptor knockout mice appeared normal and fertile. They were resistant to the effects of Δ9-THC and demonstrated a strong reduction in the reinforcing properties of morphine and the severity of withdrawal syndrome. They also demonstrated reduced motor activity and hypoalgesia. The CB2 receptor knockout mice were also healthy and fertile. They were not resistant to the central nervous system mediated effects of administered Δ9-THC. There were some effects on immune cell activation, reinforcing the role for the CB2 receptor in immune system functions.

Excessive exposure to Δ9-THC can lead to overeating, psychosis, hypothermia, memory loss, and sedation.

Treatment of asthma with CB1 receptor modulators (such as CB1 inverse agonists) is supported by the finding that presynaptic cannabinoid CB1 receptors mediate the inhibition of noradrenalin release.

Treatment of cirrhosis of the liver with CB1 receptor modulators is supported by the finding that a CB1 receptor modulator will reverse the low blood pressure observed in rats with carbon tetrachloride-induced liver cirrhosis and will lower the elevated mesenteric blood flow and portal vein pressure.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other substances used in the treatment of diseases or disorders, such as, psychosis, memory deficit, cognitive disorders, migraine, neuropathy, neuroinflammatory disorders, cerebral vascular accidents, head trauma, anxiety disorders, stress, epilepsy, Parkinson's disease, schizophrenia, substance abuse disorders such as smoking cessation, osteoporosis, constipation, chronic intestinal pseudo-obstruction, cirrhosis of the liver, asthma, obesity, and other eating disorders associated with excessive food intake, obesity, etc. (see "Pharmacology and Utility", supra). Where the compounds of the invention are administered in conjunction with other therapies, dosages of the co-administered compounds will of course vary depending on the type of co-drug employed, on the specific drug employed, on the condition being treated and so forth.

A combined preparation or pharmaceutical composition can comprise a compound of the invention as defined above or a pharmaceutical acceptable salt thereof and at least one active ingredient selected from:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPAR gamma agonist e.g. GI-262570; Diacylglycerol acetyltransferase (DGAT) inhibitors such as those disclosed in WO 2005044250, WO 2005013907, WO 2004094618 and WO 2004047755;

b) hypolipidemic agents such as 3-hydroxy-3-methyl-glutaryl coenzyme A (HMG-CoA) reductase inhibitors, e.g., lovastatin and related compounds such as those disclosed in U.S. Pat. No. 4,231,938, pitavastatin, simvastatin and related compounds such as those disclosed in U.S. Pat. Nos. 4,448,784 and 4,450,171, pravastatin and related compounds such as those disclosed in U.S. Pat. No. 4,346,227, cerivastatin, mevastatin and related compounds such as those disclosed in U.S. Pat. No. 3,983,140, velostatin, fluvastatin, dalvastatin, atorvastatin, rosuvastatin and related statin compounds disclosed in U.S. Pat. No. 5,753,675, rivastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393,2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5, 491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a SCD-1 inhibitor as disclosed in WO2005011655, a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine;

d) anti-hypertensive agents such as loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; aldosterone synthase inhibitors; and dual ET/AII antagonist such as those disclosed in WO 00/01389.

e) a HDL increasing compound;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and m) an agent interacting with a 5-HT$_3$ receptor and/or an agent interacting with 5-HT$_4$ receptor such as tegaserod described in the U.S. Pat. No. 5,510,353 as example 13, tegaserod hydrogen maleate, cisapride, cilansetron;

n) an agent for treating tobacco abuse, e.g., nicotine receptor partial agonists, bupropion hypochloride (also known under the tradename Zyban®) and nicotine replacement therapies;

o) an agent for treating erectile dysfunction, e.g., dopaminergic agents, such as apomorphine), ADD/ADHD agents (e.g., Ritalin®, Strattera®, Concerta® and Adderall®);

p) an agent for treating alcoholism, such as opioid antagonists (e.g., naltrexone (also known under the tradename ReVia®) and nalmefene), disulfiram (also known under the tradename Antabuse®), and acamprosate (also known under the tradename Campral®)). In addition, agents for reducing alcohol withdrawal symptoms may also be co-administered, such as benzodiazepines, beta-blockers, clonidine, carbamazepine, pregabalin, and gabapentin (Neurontin®);

q) other agents that are useful including anti-inflammatory agents (e.g., COX-2 inhibitors); antidepressants (e.g., fluoxetine hydrochloride (Prozac®)); cognitive improvement agents (e.g., donepezil hydrochloride (Aircept®) and other acetylcholinesterase inhibitors); neuroprotective agents (e.g., memantine); antipsychotic medications (e.g., ziprasidone (Geodon®), risperidone (Risperdal®), and olanzapine (Zyprexa®));

or, in each case a pharmaceutically acceptable salt thereof; and optionally a pharmaceutically acceptable carrier.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

In the following schemes, several methods of preparing the compounds of the present invention are illustrative. One of skill in the art will appreciate that these methods are representative, and in no way inclusive of all methods for preparing the compounds of the present invention. The radicals in the schemes are as described in the Summary of the Invention (supra). In each of the reaction schemes below, R$_1$ is 4-chlorophenyl.

An illustration of the synthesis of the compounds in the present invention of Formula I is given in the following reaction schemes

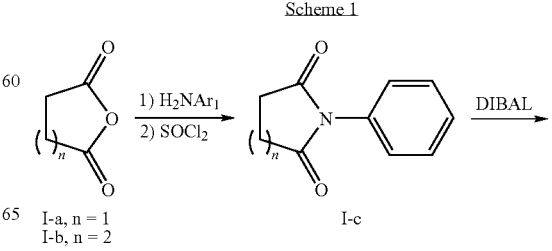

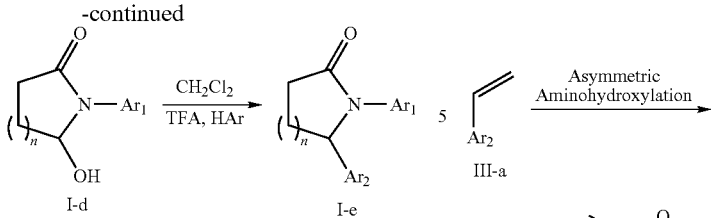

An illustration of the synthesis of the compounds in the present invention of formula I, in which $Z_2$=$CH_2$ and $Z_1$=O, is given in Scheme 1. Succinic anhydride (I-a, n=1) or glutaric anhydride (I-b, n=2) can be converted into I-c by refluxing with the designated aniline in toluene followed by cyclization that is mediated by thionyl chloride. Reduction of I-c with DIBAL in $CH_2Cl_2$ under low temperature (preferably at −78° C.) give I-d, which then undergoes Friedel-Crafts reaction with an appropriate arene under acidic condition to provide I-e.

Scheme 2

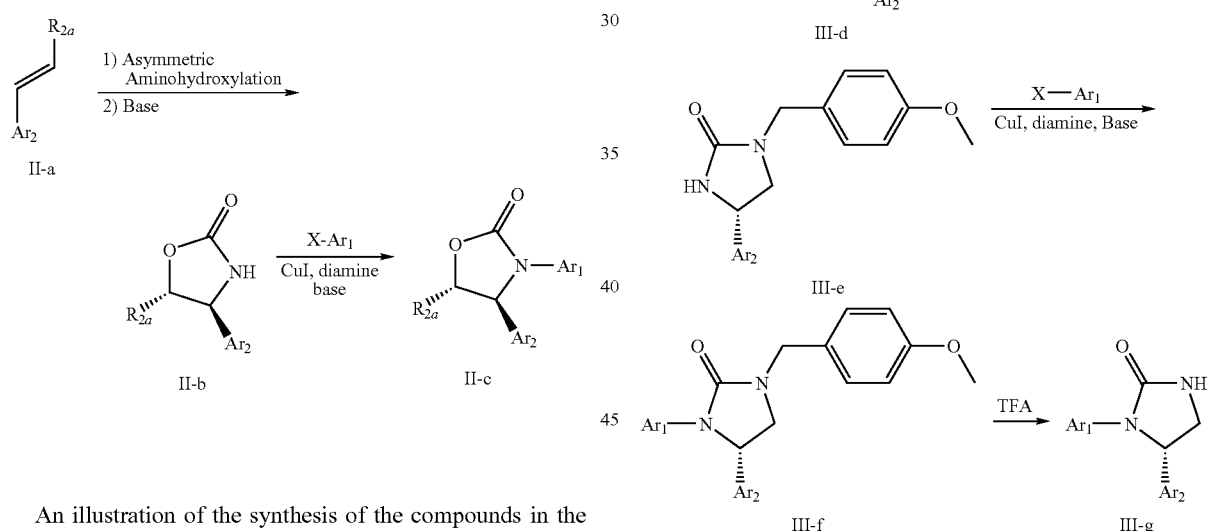

An illustration of the synthesis of the compounds in the present invention of formula I, in which $Z_2$=O and $Z_1$=O, is given in Scheme 2. Oxazolidinone II-b can be synthesized by Sharpless asymmetric aminohydroxylation of alkene II-a followed by cyclization under basic conditions (N. Barta et al. *Org. Lett.* 2000, 2, 2821). 3-aryl oxazolidinones II-c can then be obtained by copper catalyzed N-arylation of II-b. For procedures of Sharpless asymmetric aminohydroxylation, see Sharpless, K. B. et al. (1996). "N-Halocarbamate salts lead to more efficient catalytic asymmetric aminohydroxylation." *Angew. Chem. Int. Ed. Engl.* 35(23/24): 2813-2816; Sharpless, K. B. et al. (1998). "From styrenes to enantiopure α-arylglycines in two steps." *J. Am. Chem. Soc.* 120: 1207-17. For copper mediated N-arylation reactions, see: Buchwald, S. L. et al. (2001). "A general and efficient copper catalyst for the amidation of aryl halides and the N-arylation of nitrogen heterocycles." *J. Am. Chem. Soc.* 123(31): 7727-9.

Scheme 3

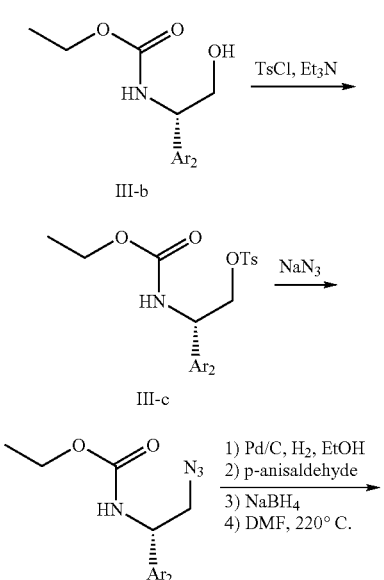

An illustration of the asymmetric synthesis of 1,5-diaryl-imidazolidin-2-one is given in Scheme 3. The hydroxycarbamate III-b can be obtained by a standard Sharpless aminohydroxylation process. Tosylation of the alcohol followed by a nucleophilic substitution with sodium azide provides azide III-d which can then be converted into III-e by a sequence of hydrogenolysis, reductive amination with p-methoxy benzaldehyde followed by in situ cyclization. The resulting imidazolidin-2-one III-e is then subjected to a copper catalyzed N-arylation to provide imidazolidin-2-one III-f, which is then followed by acidic deprotection of the p-methoxybenzyl group to yield III-g.

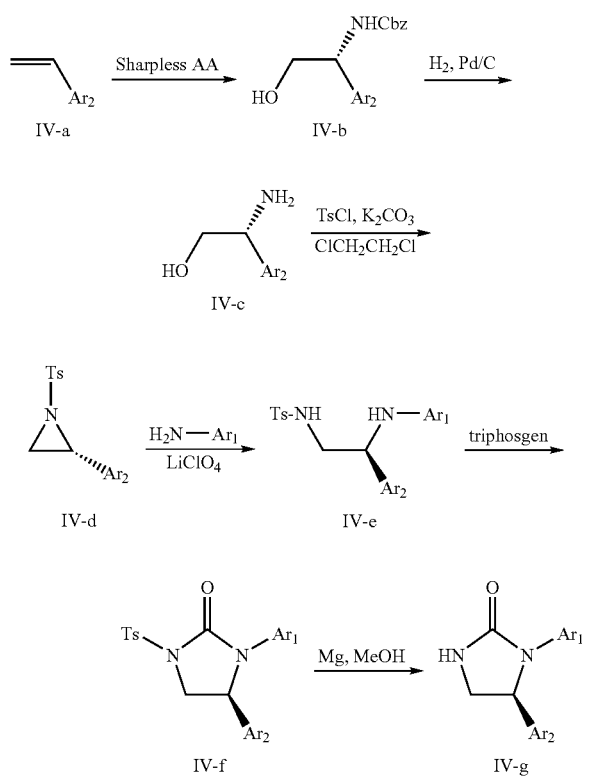

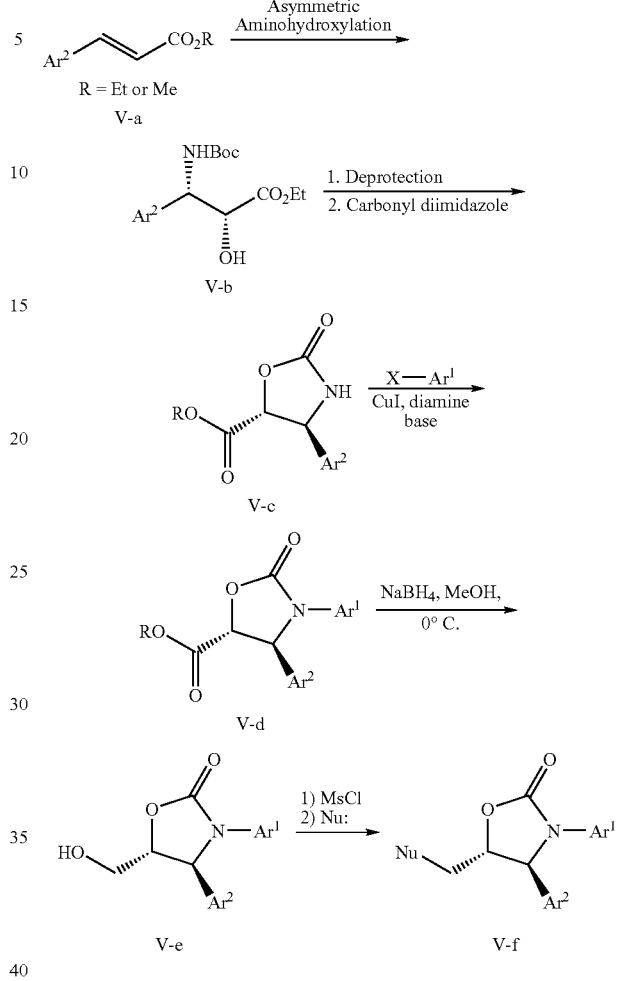

An alternative asymmetric synthesis of 1,5-diaryl-imidazolidin-2-one is given in Scheme 4. Styrene IV-a is converted into aminoalcohol IV-c via a standard Sharpless asymmetric aminohydroxylation (AA) reaction followed by hydrogenolysis to remove the Cbz protection group. Bis-tosylation of IV-c followed by in situ cyclization provides tosyl activated aziridine IV-d, which undergoes a LiClO$_4$-catalyzed configuration-inverted ring opening reaction with aniline Ar$_1$NH$_2$ to provide intermediate IV-e (Yadav, J. S.; Reddy, B. V. S.; Jyothirmai, B.; Murty, M. S. R. *Synlett* 2002, 53). IV-e readily cyclizes with triphosgene to provide compound IV-f. Magnesium reductive cleavage of the N-Ts group in IV-f finishes the desired 1,5-diaryl-imidazolidin-2-one IV-g.

The synthesis of racemic form of IV-g uses the same route with some simplifications, in which the racemic aziridine can be obtained directly from styrene IV-a via an iodine-catalyzed aziridination reaction using Chloramine-T as a nitrogen source (Ando, T.; Kano, D.; Minakata, S.; Ryu, I.; Komatsu, M. *Tedrahedron* 1998, 54, 13485). For other conditions used for aziridination reactions, see J. U. Jeong, B. Tao, I. Sagasser, H. Henniges and K. B. Sharpless, Bromine-Catalyzed Aziridination of Olefins. A Rare Example of Atom-Transfer Redox Catalysis by a Main Group Element, J. Am. Chem. Soc., 120, 6844 (1998); A. V. Gontcharov, H. Liu and K. B. Sharpless, tert-Butylsulfonamide. A New Nitrogen Source for Catalytic Aminohydroxylation and Aziridination of Olefins, *Org. Lett.*, 1, 783 (1999) and references cited therein.

An illustration of the asymmetric synthesis of 5-substituted-4-aryl oxazolidinones is depicted in Scheme 5. Compound V-b is prepared via standard Sharpless aminohydroxylation process (K. L. Reddy and K. B. Sharpless, *J. Am. Chem. Soc.* 1998, 120, 1207). The intermediate carbamate is then deprotected under standard acidic conditions, which is then followed by conversion into oxazolidinone V-c with carbonyl diimidazole, or a suitable equivalent. Copper-catalyzed N-arylation yields V-d. The carboxylate ester is then reduced with sodium borohyride to give alcohol V-e, which can then be converted in to V-f via nucleophilic replacement of a corresponding mesylate with a suitable nucleophile (e.g. amines, thiol and etc.).

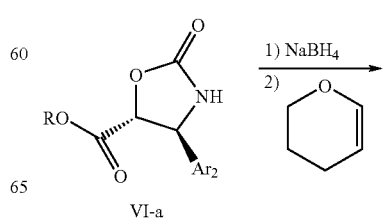

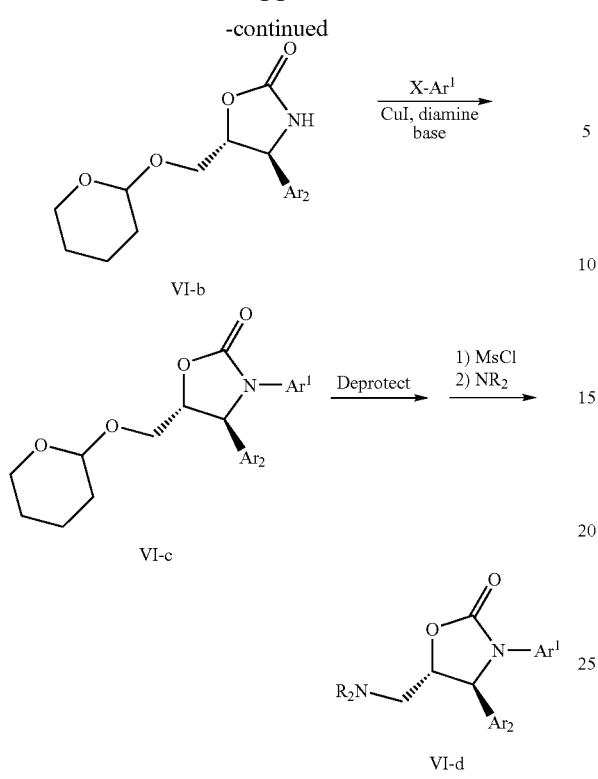

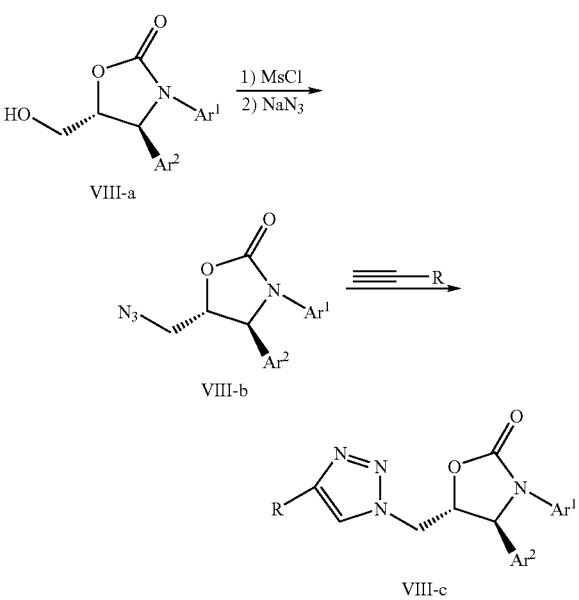

An alternative synthesis of 5-substituted-4-aryl oxazolidinones is shown in Scheme 6. Oxazolidinone-5-carboxylic ester VI-a is treated with sodium borohydride to give the intermediate alcohol which is then converted into tetrahydropyranyl (THP) ether VI-b. Copper catalyzed N-arylation gives VI-c, which is then subjected to acidic deprotection of the THP group, followed mesylation and nucleophilic displacement (for example, with a amine $R_2NH$) to give the 5-substituted analogues VI-d.

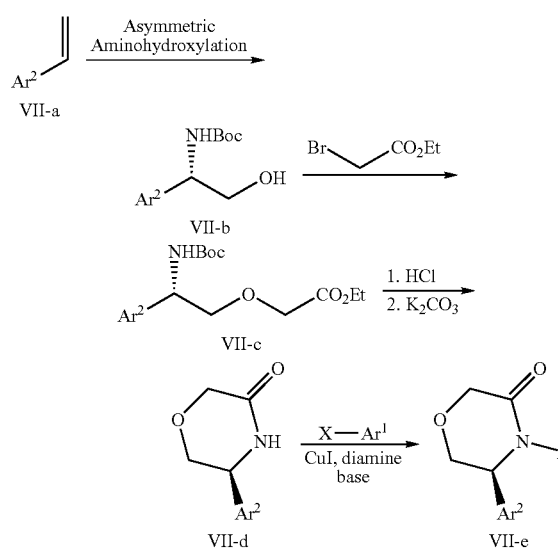

An illustration of the asymmetric synthesis of morpholinones is depicted in Scheme 7. Asymmetric aminohydroxlation of styrene VII-a is followed by conversion into ether VII-c. Deprotection of the t-butoxycarbamate group is followed by base-mediated cyclization to give morpholinone VII-d. Copper mediated N-arylation gives the morpholinone VII-e.

An illustration of the conversion of oxazolidinone VIII-a into the corresponding 1,2,3-triazole derivatives VIII-c is depicted in Scheme 8. The alcohol VIII-a is first converted into the requisite mesylate, which is then treated with sodium azide to give azide VIII-b. The azide is then subjected to copper mediated cycloaddition with an alkyne RCCH to give triazole VIII-c. For an efficient synthesis of 1,2,3-triazoles from azide and alkyne, see: P. Wu, A. K. Feldman, A. K. Nugent, C. J. Hawker, A. Scheel, B. Voit, J. Pyun, J. M. J. Fréchet, K. B. Sharpless and V. V. Fokin, Efficiency and Fidelity in a Click Chemistry Route to Triazole Dendrimers via the Cu(I)-Catalyzed Ligation of Azides and Alkynes, *Angew. Chem. Int. Ed.,* 43, 3928 (2004). For an efficient synthesis of tetrazoles from azide and nitrile, see: Z. P. Demko and K. B. Sharpless, An Intramolecular [2+3] Cycloaddition Route to Fused 5-Heterosubstituted Tetrazoles, *Org. Lett.,* 3, 4091 (2001); Z. P. Demko and K. B. Sharpless, Preparation of 5-Substituted-1H-Tetrazoles from Nitriles in Water, *J. Org. Chem.,* 66, 7945 (2001). For reviews on click chemistry in drug discovery, see: H. C. Kolb and K. B. Sharpless, The Growing Impact of Click Chemistry on Drug Discovery, *Drug Discovery Today,* 8, 1128 (2003); H. C. Kolb, M. G. Finn and K. B. Sharpless, Click Chemistry: Diverse Chemical Function From a Few Good Reactions, *Angew. Chem.,* 40, 2004 (2001).

Scheme 9

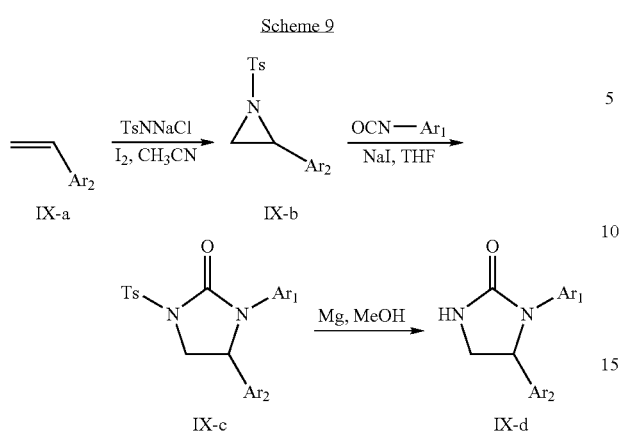

An alternative racemic synthesis of 1,5-diaryl-imidazolidin-2-one is described in Scheme 9. Styrene IX-a is converted into aziridine IX-b via an iodine-catalyzed aziridination reaction using Chloramine-T as a nitrogen source (Ando, T.; Kano, D.; Minakata, S.; Ryu, I.; Komatsu, M. *Tedrahedron* 1998, 54, 13485). Aziridine IX-b undergoes a regioselective cycloaddition reaction with aryl isocyanate OCN—Ar$_2$ to form compound IX-c (Nadir, U. K.; Basu, N. *Tedrahedron Lett.* 1992, 33, 7949). Magnesium reductive cleavage of the Ts group furnishes the desired 1,5-diaryl-imidazolidin-2-one IX-d.

Scheme 10

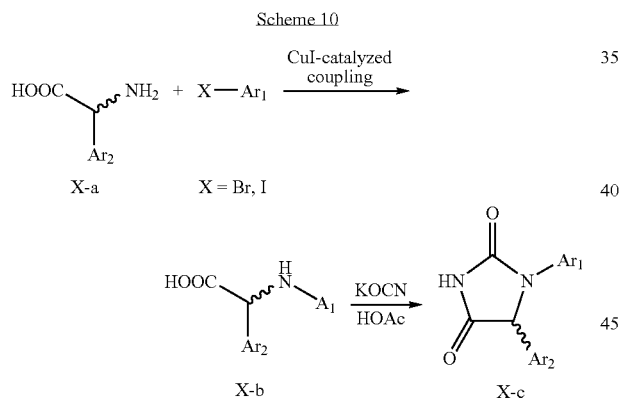

An illustration of the synthesis of 1,5-diaryl-imidazolidine-2,4-dione is given in Scheme 10. N-Aryl amino acid X-b is synthesized from α-amino acid X-a and aryl halide under the CuI-catalyzed coupling reaction condition described in Ma, D.; Zhang, Y.; Yao, J.; Wu, S.; Tao, F. *J. Am. Chem. Soc.* 1998, 120, 12459. Compound X-b is cyclized with potassium cyanate in acidic media to finish 1,5-diaryl-imidazolidine-2,4-dione X-c.

Scheme 11

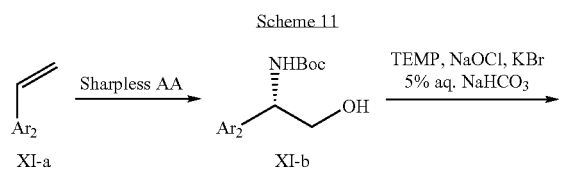

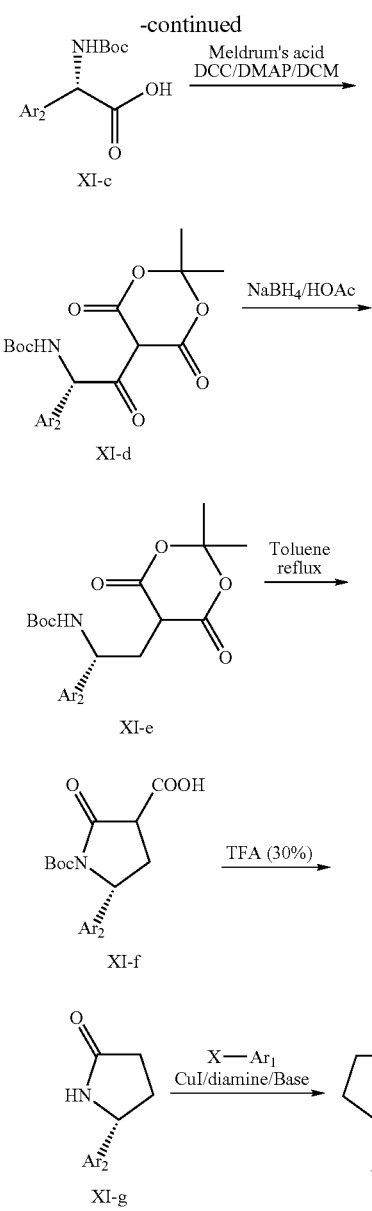

An illustration of the asymmetric synthesis of 5-aryl substituted pyrrolidin-2-one exemplified by structure XI-h is depicted in Scheme 11. N-Boc-protected α-arylglycines XI-c is be easily prepared via the standard Sharpless two-step process from styrenes XI-a (K. L. Reddy and K. B. Sharpless, *J. Am. Chem. Soc.* 1998, 120, 1207). The monoalkylated Meldrum's acid XI-e is obtained from XI-c by condensed with Meldrum's acid, followed by complete reduction of its keto functionality (M. Smrcina, P. Majer, E. Majerova, T. A. Guerassina and M. A. Eissenstat, *Tetrahedron Lett.* 1997, 53, 12867; B. Hin, P. Majer and T. Tsukamoto, *J. Org. Chem.* 2002, 67, 7365). XI-e undergoes thermal ring closure to a N-Boc-protected 3-carboxy pyrrolidin-2-one XI-f, which can be further transformed into 5-aryl substituted pyrrolidin-2-one XI-g upon treatment with TFA. Buchwald copper-catalyzed N-arylation yields XI-h in good yields.

Scheme 12

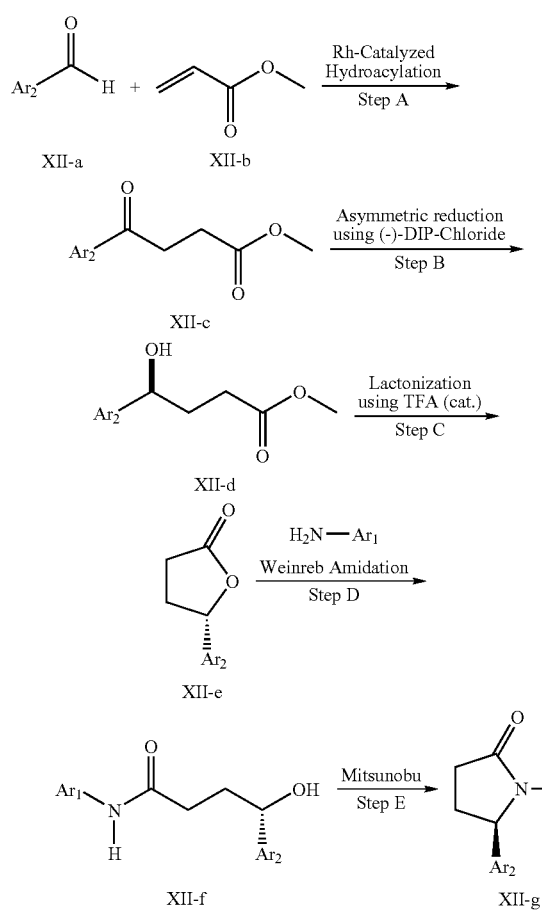

An alternative asymmetric synthesis of 5-aryl substituted pyrrolidin-2-one exemplified by structure XII-g is depicted in scheme 12. γ-Ketoester XII-c can be prepared using a Rh-catalyzed chelation assisted hydroacylation of aromatic aldehyde XII-a with methyl acrylate XII-b (Eun-Ae Jo and Chul-Ho Jun, *Eur. J. Org. Chem.* 2006, 2504-2507). Asymmetric reduction of XII-c using (−)-B-chlorodiisopinocamphenylborane ((−)-DIP-Chloride) affords hydroxyl ester XII-d, which is then converted into the corresponding lactone XII-e (P. V. Ramachandran, S. Pitre, and H. C. Brown, *J. Org. Chem.* 2002, 67, 5315-5319.). A Weinreb amidation and Mitsunobu cyclodehydration yields the 5-aryl substituted pyrrolidin-2-one in good yield and enantiomeric purity (I. M. Bell, D. C. Beshore, S, N. Gallicchio, and T. M. Williams, *Tetrahedron Lett.* 2000, 41, 1141-1145).

Several new synthetic methods have recently been introduced that have made the copper catalyzed cross-coupling of most nitrogen containing functional groups to sp²-halides more accessible. (Ley et al. *Angew. Chem. Int. Ed.* 2003, 42, 5400). The majority of these new methods employ a variety of multidentate copper chelators that make the construction of sp²-carbon-heteroatom bonds more facile. (Buchwald et al. *J. Org. Chem.* 2004, 59, 5578 and references cited therein). Despite these advances, relatively high heat (≧100° C.) and long reaction times (≧24 h) are still mandatory to obtain good results. Therefore, methods with improved reactivity, broader reaction scope, and substrate tolerance are still in demand. Since many groups have exploited the donor ligand effects to improve the cross-coupling, attention has shifted away from the other vital components in the reaction. A non-obvious replacement of the conventional bases ($K_2CO_3$, $K_3PO_4$, $Cs_2CO_3$) with the milder cesium fluoride catalyzes the coupling of a number of amides, carbamates, and nitrogen heterocycles to aryl iodides, in many cases at room temperature. Furthermore, substrates that were incompatible with the copper catalyzed reaction employing the stronger bases may be compatible with CsF.

Optimized conditions for substrates that were incompatible with the conventional conditions (CuI, diamine, $K_3PO_4$ or $K_2CO_3$, 100-110° C.) were determined with simpler substrates. Weaker bases, such as $KHCO_3$, KOAc, or CsF, would avoid unwanted side reactions. Screening of these bases revealed efficient coupling of oxazolidinone 1 with aryl iodide 2 to give the product 3 in good yield at 100° C. (Scheme 1). Cesium fluoride required only 2 h, whereas $KHCO_3$ and KOAc required 18 h. When the same reactants were treated with CsF at 25° C. for 18 h, a nearly quantitative yield of 3 was obtained. Further experiments revealed that THF, ACN, or EtOAc (Table 2) were optimal solvents for this reaction and that a minimum of 2-2.5 equivalents of CsF were required. Since CsF showed an improved ability to promote the CuI-catalyzed reaction in this model system, its ability to promote the coupling of other substrates was investigated.

Scheme 13. Modified Buchwald Couplings with Weak Bases

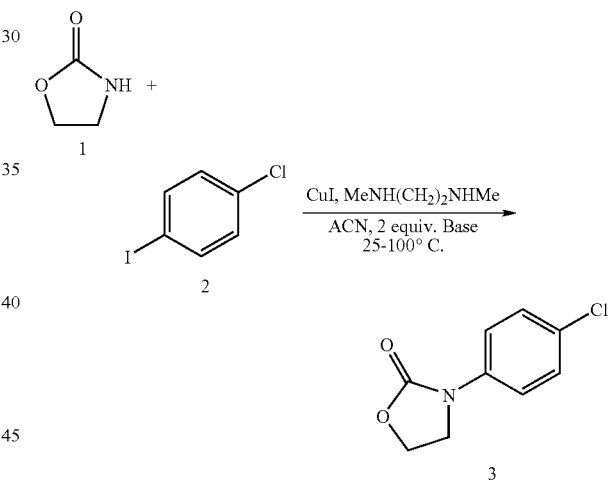

| Base | % Yield |
|------|---------|
| $KHCO_3$ | 89 (18 h) |
| KOAc | 80 (18 h) |
| CsF | 81 (2 h) |
| CsF | 99 (18 h, RT) |

A number of control reactions were performed to show that the effect cannot simply be attributed to the presence of cesium or to fluoride, but to a synergy between CsF and CuI. When CsF is replaced by KF, $K_2CO_3$, or $Cs_2CO_3$ the yield was significantly lower at 25° C. (Table 3, Entries 5-7) and at 100° C. (Table 3, Entry 5). These reduced yields could be attributed to the reduced solubility of these salts at room temperature in ethyl acetate compared to the solubility of CsF. However, when KF and $K_2CO_3$ are combined with a substoichiometric quantity of CsF, a 3.5 to 10-fold increase in yield was observed (Table 3, Entries 8, 9). These results suggest that some synergic effect exist between CsF and CuI to account for the dramatic increase in yield.

TABLE 2

Solvent Screen for N-Arylation Reaction using CsF as Base[a]

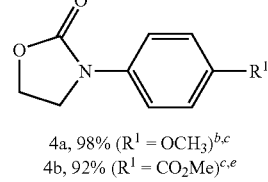

| Entry | Solvent | 100° C.[b] | 60° C.[b] | 25° C.[b] |
|---|---|---|---|---|
| 1 | EtOAc | 99 | 99 | 99 |
| 2 | THF | 98 | 99 | 92 |
| 3 | ACN | 99 | 94 | 90 |
| 4 | DMSO | 94 | — | — |
| 5 | DME | 84 | — | — |
| 6 | DMF | 81 | — | 55 |
| 7 | Dioxane | 73 | — | — |
| 8 | Toluene | 59 | — | — |

TABLE 3

CsF Condition Screening for the N-Arylation Reaction[a]

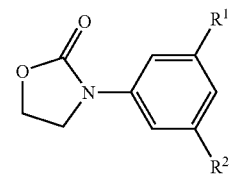

| Entry | Conditions | Yield | Entry | Conditions | Yield |
|---|---|---|---|---|---|
| 1 | 2 eq. CsF | 99 | 6 | 2 eq. K$_2$CO$_3$ | 12 |
| 2 | 1.5 eq. CsF | 55 | 7 | 2 eq. Cs$_2$CO$_3$ | trace[d] |
| 3 | 1.2 eq. CsF | 43 | 8 | 2 eq. K$_2$CO$_3$ + 0.2 eq. CsF | 43 |
| 4 | 1.0 eq. CsF | 23 | 9 | 2 eq. KF + 0.2 eq. CsF | 40 |
| 5 | 2 eq. KF | 4; 21[c] | 10 | 2 eq. CsBr | 9 |

[a]Conditions: 1.1 equivalents 1, 1.0 equivalents 2, 2 mL EtOAc;
[b]% isolated yield;
[c]100° C., 16 h;
[d]as detected by LC-MS.

The reactions of several amides relevant to the claimed compounds with various aryl iodides is detailed in Table 4. These reactions were performed at 1 mmol scale with 2.5 equivalents of CsF, 5 mol % CuI, and 10 mmol % N,N'-dimethylethylenediamine in either THF or EtOAc typically for 18-24 h. We found that most amides and carbamates coupled very efficiently to aryl iodides with p- or m-substituents at 25° C., with only 4u requiring heating to 60° C. (Table 4). The efficiency of these conditions on 10 mmol scale was demonstrated at 60° C. with example 4b, proving that these conditions may be scalable. Electron-poor and electron-rich aryl halides coupled with near equal efficiency under these conditions. Overall, excellent substrate tolerance and selectivity were observed. Example 4i is noteworthy as no halide exchange was observed with these conditions. The slightly reduced yield for 4n could be explained by the steric hindrance imposed by the methyl group, or to perhaps the slightly higher expected pKa for the starting amide compared to its des-methyl congener. The proximal ester group in example 4o probably aided the formation of the Cu-coordinated intermediate, leading to a nearly quantitative yield. Furthermore, no racemization or hydrolysis was observed with these conditions, but was a problem with the conventional bases. Aryl halides with o-substituents are known to suppress the N-arylation of most substrates; this limitation was overcome by coupling those substrates at 85-100° C. (Table 4, 4f-g).

TABLE 4

Substrate Scope with Iodides

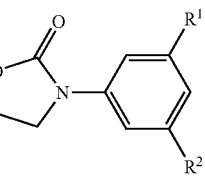

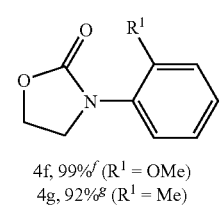

4a, 98% (R$^1$ = OCH$_3$)[b,c]
4b, 92% (R$^1$ = CO$_2$Me)[c,e]

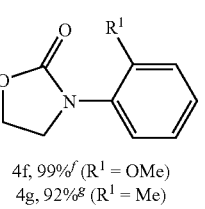

4c, 94% (R$^1$, R$^2$ = Me)
4d, 93% (R$^1$ = Ac)
4e, 99% (R$^1$ = F)

4f, 99%[f] (R$^1$ = OMe)
4g, 92%[g] (R$^1$ = Me)

TABLE 4-continued
Substrate Scope with Iodides

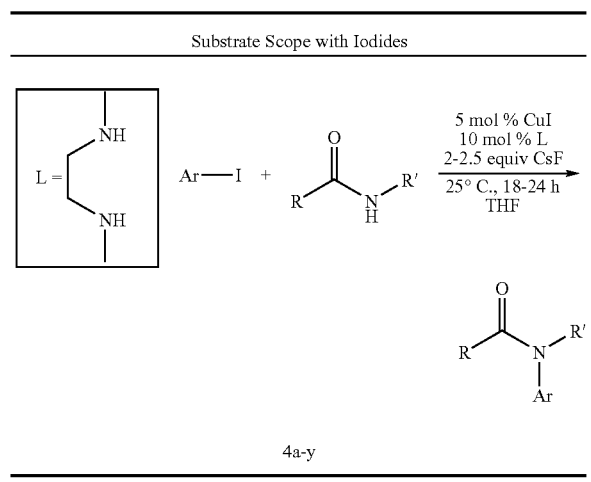

4a-y

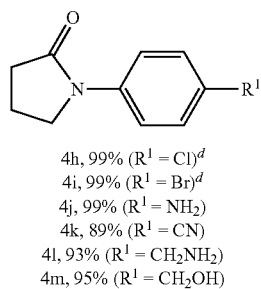

4h, 99% ($R^1$ = Cl)[d]
4i, 99% ($R^1$ = Br)[d]
4j, 99% ($R^1$ = $NH_2$)
4k, 89% ($R^1$ = CN)
4l, 93% ($R^1$ = $CH_2NH_2$)
4m, 95% ($R^1$ = $CH_2OH$)

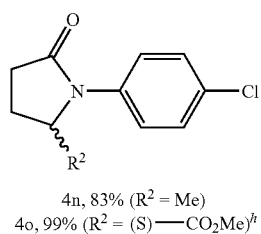

4n, 83% ($R^2$ = Me)
4o, 99% ($R^2$ = (S)—$CO_2Me$)[h]

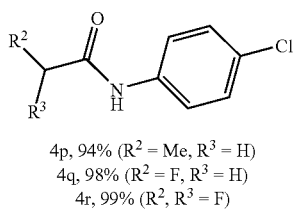

4p, 94% ($R^2$ = Me, $R^3$ = H)
4q, 98% ($R^2$ = F, $R^3$ = H)
4r, 99% ($R^2$, $R^3$ = F)

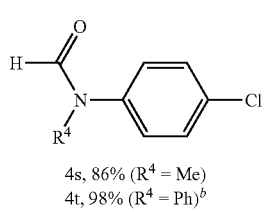

4s, 86% ($R^4$ = Me)
4t, 98% ($R^4$ = Ph)[b]

TABLE 4-continued
Substrate Scope with Iodides

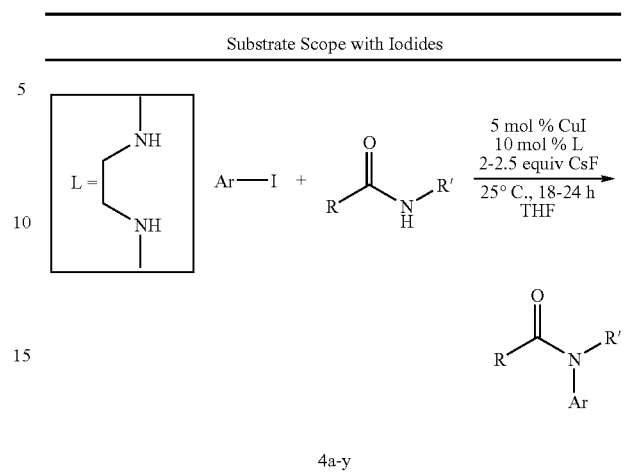

4a-y

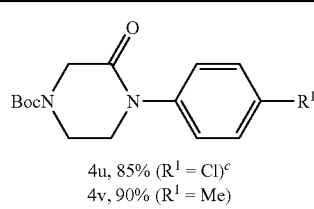

4u, 85% ($R^1$ = Cl)[c]
4v, 90% ($R^1$ = Me)

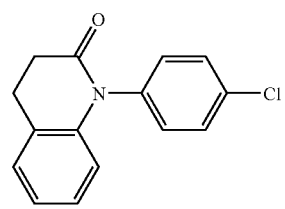

4w, 91%[d]

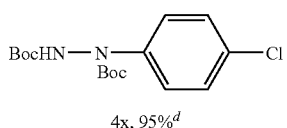

4x, 95%[d]

[a] Yields refer to isolated yields.
[b] 83% at 25° C.
[c] 60° C.
[d] in EtOAc.
[e] 10 mmol scale.
[f] in ACN at 85° C.
[g] in ACN at 100° C.
[h] 86% ee The amidation of aryl bromides is summarized in Table 5. Aryl and heteroaryl bromides usually require higher reaction temperatures and/or longer reaction times than the corresponding aryl iodides. Even though a number of new ligands have been introduced by several groups to reduce these barriers, none have so far completely succeeded. When aryl bromides were subjected to our CsF promoted conditions, we obtained good to excellent results in most cases when the substrates were treated 100° C. (Table 5).

TABLE 5

Substrate Scope with Aryl Bromides

Ar—Br + R-C(O)-N(H)-R' → (5 mol % CuI, 10 mol % L, 2-2.5 equiv CsF, 100° C., 18-24 h, ACN) → R-C(O)-N(Ar)-R'

5a-5f 5a, 91%

5b, 77%

5c, 97%

5d, 83%

5e, 68%

5f, 78%[b]

[a] Yields refer to isolated yields.
[b] DMA 110° C.

In summary, the advantages of CsF mediated coupling are as follows:

a. Cesium fluoride (CsF) promoted N-arylation reactions proceed well at room temperature with a variety of substrates whereas, for other bases, elevated temperatures are required.

b. CsF is compatible with most N-arylation reaction conditions in the art, yet CsF promotes the coupling at lower temperatures and shorter reaction times than the reported conditions.

c. The weaker basicity of CsF offers greater versatility in promoting the C—N coupling reaction of base sensitive substrates; and d. The convenience of the milder reaction conditions proves to be more useful in combinatorial or parallel reaction formats and in large scale syntheses.

Consequently, an embodiment of the present invention provides for a process of preparing a compound of the Summary of the Invention with a greater than 80% yield. Said compound contains an aryl bonded directly to a group selected from an amide, a carbamate and a nitrogen containing heterocycle forming a compound of Formula I. The process comprises: reacting an aryl-halide with an amide, a carbamate or a nitrogen containing heterocycle in the presence of a copper catalyst; cesium fluoride; and a solvent. The reaction is carried out at a temperature of less than or equal to 100° C. and requires less than or equal to 24 hours for completion.

In a further embodiment, the copper catalyst is copper iodide.

In a further embodiment, the solvent is selected from THF, CAN, DMSO, DME, DMF, Dioxane, toluene and EtOAc.

In a further embodiment, the reaction is carried out at a temperature of less than or equal to 75° C.

In a further embodiment, the reaction is carried out at a temperature of less than or equal to 50° C.

In a further embodiment, the reaction is carried out at a temperature of less than or equal to 25° C.

In a further embodiment, the reaction takes between 18 and 24 hours for completion.

Detailed descriptions of the synthesis of compounds of the Invention are given in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme 1-12; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following Examples that illustrate the preparation of compounds of the invention.

Example 2 and Example 5

5-(4-Amino-3-trifluoromethyl-phenyl)-1-[4-(4-chloro-phenoxy)-phenyl]-pyrrolidin-2-one and 5-(2-Amino-3-trifluoromethyl-phenyl)-1-[4-(4-chloro-phenoxy)-phenyl]-pyrrolidin-2-one

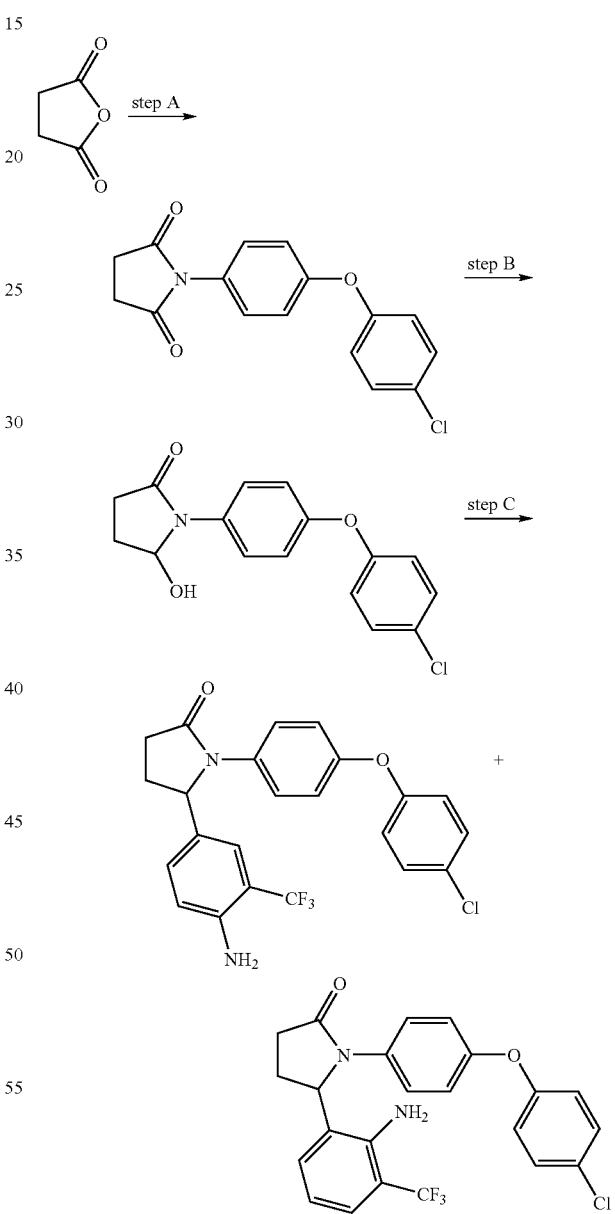

Step A: A mixture of succinic anhydride (250 mg, 2.50 mmol) and 4-amino-4'-chloro diphenylether (500 mg, 2.27 mml) in toluene is heated to 110° C. for 14 h. and cooled down to room temperature. SOCl$_2$ (1.5 mL) is added into the mixture and stirred at room temperature for 8 h. After the solvent is removed under vacuum, the residue is treated with saturated NaHCO₃ aqueous solution (20 mL) and extracted with CHCl₃ (3×50 mL). The combined organic layer is washed with brine and dried (MgSO₄). After filtering the drying agent, the filtrate is concentrated and purified by flash column chromatography (silica gel, EtOAc/hexane 30%~80%) to provide 1-[4-(4-chloro-phenoxy)-phenyl]-pyrrolidine-2,5-dione as white solid (570 mg, 83%).

Step B: A solution of 1-[4-(4-chloro-phenoxy)-phenyl]-pyrrolidine-2,5-dione (100 mg, 0.33 mmol) in anhydrous CH₂Cl₂ (1.5 mL) is cooled down to −78° C. in a dry ice bath. DIBAL-H (0.6 mL, 1 M solution in hexane, 0.66 mmol) is added into the solution dropwise under N₂. After the addition, the mixture is stirred at the same temperature for 10 min and quenched by H₂O (10 mL). The mixture is warmed up to room temperature and extracted with CH₂Cl₂ (3×10 mL). The combined organic layer is washed with brine and dried (MgSO₄). After filtering the drying agent, the filtrate is concentrated and purified by flash column chromatography (silica gel, EtOAc) to provide the (±)-1-[4-(4-chloro-phenoxy)-phenyl]-5-hydroxy-pyrrolidin-2-one as off white solid (72 mg, 72%).

Step C: To a mixture of 1-[4-(4-chloro-phenoxy)-phenyl]-5-hydroxy-pyrrolidin-2-one (10 mg, 0.033 mmol) and TFA (0.2 mL) in CH₂Cl₂ (0.8 mL) is added 3-trifluoroaniline (50 mL). After stirring at 40° C. for 14 h, the mixture is cooled and concentrated. The resulted residue is treated with saturated NaHCO₃ aqueous solution (1 mL) and extracted with EtOAc (3×3 mL). The combined organic layers is concentrated and purified by preparative LC/MS to provide the title compound 5-(4-amino-3-trifluoromethyl-phenyl)-1-[4-(4-chloro-phenoxy)-phenyl]-pyrrolidin-2-one as major product (11 mg, 75%, example 2) and 5-(2-amino-3-trifluoromethyl-phenyl)-1-[4-(4-chloro-phenoxy)-phenyl]-pyrrolidin-2-one as minor product (2.52 mg, 17%, example 5). Example 2: ¹H NMR (CDCl₃, 400 MHz) δ 7.27 (d, 2H), 7.23 (d, 1H), 7.17 (d, 2H), 7.14 (dd, 1H), 6.89 (d, 2H), 6.88 (d, 2H), 6.71 (d, 1H), 6.02 (br, 2H), 5.14 (dd, 1H), 2.64-3.0 (m, 3H), 2.05-2.13 (m, 1H); HPLC-MS calculated for $C_{23}H_{18}ClF_3N_2O_2$ (M+H⁺) 447.1, found 447.1. Example 5: ¹H NMR (CDCl₃, 400 MHz) δ 7.40 (d, 3H), 7.25 (d, 2H), 7.15 (d, 2H), 7.14 (dd, 1H), 6.90 (d, 2H), 6.88 (d, 2H), 6.76 (t, 1H), 5.25 (dd, 1H), 4.24 (br, 2H), 2.56-2.80 (m, 3H), 2.05-2.18 (m, 1H); HPLC-MS calculated for $C_{23}H_{18}ClF_3N_2O_2$ (M+H⁺) 447.1, found 447.1.

Example 3

1-[4-(4-Chloro-phenoxy)-phenyl]-5-(3-trifluoromethyl-phenyl)-pyrrolidin-2-one

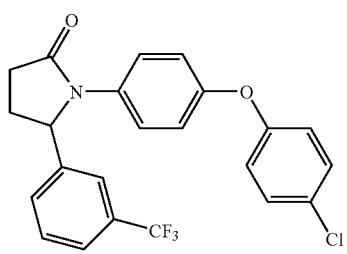 [SMILES: O=C1CCC(c2cccc(C(F)(F)F)c2)N1c1ccc(Oc2ccc(Cl)cc2)cc1]

A solution of t-butyl nitrite (4.62 mg, 0.045 mmol) in DMF (0.2 mL) is heated to 65° C. while 5-(4-amino-3-trifluoromethyl-phenyl)-1-[4-(4-chloro-phenoxy)-phenyl]-pyrrolidin-2-one (10 mg, 0.022 mmol) in DMF (0.2 mL) is added in dropwise. The resulted mixture is stirred at 65° C. for an extra 5 min and then cooled down to room temperature. The reaction mixture is treated with 2 N HCl (5 mL) and extracted with EtOAc (3×3 mL). The combined organic layers is concentrated and purified by flash column chromatography (silica gel, EtOAc/hexane 0~50%) to provide the title compound 1-[4-(4-chloro-phenoxy)-phenyl]-5-(3-trifluoromethyl-phenyl)-pyrrolidin-2-one as colorless oil (~7 mg, 72%). ¹H NMR (CDCl₃, 400 MHz) δ 7.53 (d, 1H), 7.47 (s, 1H), 7.46 (d, 1H), 7.41 (t, 1H), 7.31 (d, 2H), 7.25 (d, 2H), 6.88 (d, 2H), 6.86 (d, 2H), 5.28 (t, 1H), 2.60-2.80 (m, 3H), 1.99-2.02 (m, 1H); HPLC-MS calculated for $C_{23}H_{17}ClF_3NO_2$ (M+H⁺) 432.1, found 432.1.

Example 4

(S)-3-[4-(4-Chloro-phenoxy)-phenyl]-4-(3-trifluoromethyl-phenyl)-oxazolidin-2-one

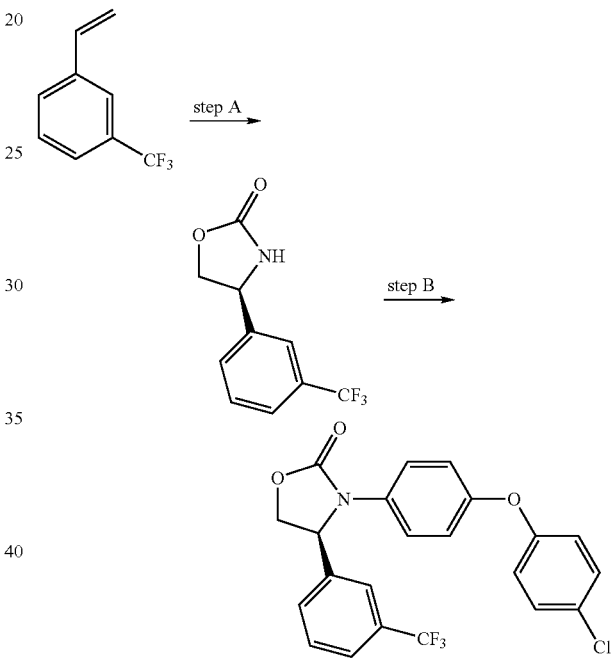

Step A: (S)-(3-Trifluoromethyl-phenyl)-oxazolidin-2-one can be synthesized from 3-trifluoromethylstyrene by using the method reported by N. Barta et al. (*Org. Lett.* 2000, 2, 2821). HPLC-MS calculated for $C_{10}H_8F_3NO_2$ (M+H⁺) 232.1, found 232.1.

Step B: A mixture of 4(S)-(3-trifluoromethyl-phenyl)-oxazolidin-2-one (10 mg, 0.043 mmol), 4-chloro-4'-iodo-diphenyl ether (17.1 mg, 0.052 mmol), K₃PO₄ (18 mg, 0.086 mmol), catalytic amount of CuI and trans-1,2-cyclohexyldiamine in dioxane (0.5 mL) is degassed and heated to 100° C. under N₂ for 2 h. After cooling down to room temperature, the mixture is treated with saturated aqueous NH₄Cl solution (3 mL) and extracted with EtOAc (3×3 mL). The combined organic layers is concentrated and purified by flash column chromatography (silica gel, EtOAc/hexane 0~50%) to provide the titled compound (S)-3-[4-(4-chloro-phenoxy)-phenyl]-4-(3-trifluoromethyl-phenyl)-oxazolidin-2-one as colorless oil (9 mg, 48%). ¹H NMR (CDCl₃, 400 MHz) δ 7.61 (t, 1H), 7.55 (s, 1H), 7.52 (d, 2H), 7.30 (d, 2H), 7.25 (d, 2H), 6.90 (d, 2H), 6.87 (d, 2H), 5.42 (dd, 1H), 4.83 (t, 1H), 4.21 (dd, 1H); HPLC-MS calculated for $C_{22}H_{15}ClF_3NO_3$ (M+H⁺) 434.1, found 434.1.

Example 7

3-(4-(4-chlorophenoxy)phenyl)-1-tosyl-4-(3-(trifluoromethyl)phenyl)imidazolidin-2-one

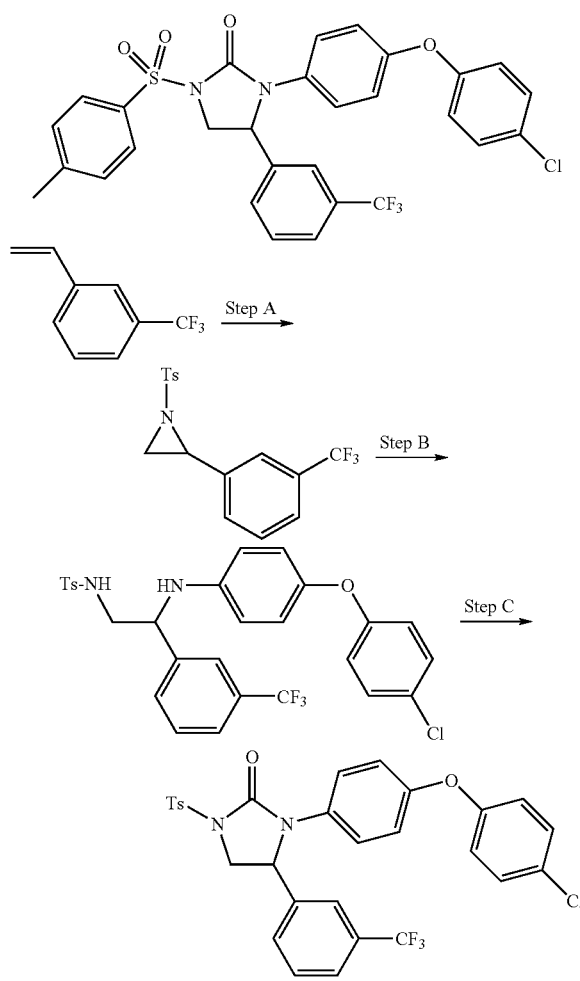

Step A: 3-(Trifluoromethyl)styrene (1.70 mL, 11.5 mmol) is added to a mixture of iodine (0.29 g, 1.15 mmol) and Chloramine-T (3.12 g, 11.5 mmol) in acetonitrile (35 mL). The reaction mixture is stirred at room temperature under a nitrogen atmosphere overnight, then taken in $H_2O$ (200 mL) and extracted with $CH_2Cl_2$ (3×100 mL). The combined organic layer is washed with brine, dried over $MgSO_4$, concentrated and purified by silica gel chromatography (0~20% EtOAc/Hexanes) to provide 1-tosyl-2-(3-(trifluoromethyl) phenyl)aziridine (3.44 g, 88% yield) as a colorless oil product.

Step B: To a solution of 1-tosyl-2-(3-(trifluoromethyl)phenyl)aziridine (2.29 g, 6.71 mmol) in $Et_2O$ (13.5 mL) are added 4-(4-chlorophenoxy)aniline (1.47 g, 6.71 mmol) and $LiClO_4$ (0.36 g, 3.36 mmol). The reaction mixture is stirred at room temperature overnight. After removal of the solvent, the crude N-(2-(4-(4-chlorophenoxy)phenylamino)-2-(3-(trifluoromethyl)phenyl)ethyl)-4-methylbenzenesulfonamide is used in next step without further purification.

Step C: To a solution of the crude product from Step B in acetonitrile (13.5 mL) at 0° C. are added triphosgen (1.33 g, 4.47 mmol) and TEA (1.87 mL, 13.4 mmol). The reaction mixture is heated at 80° C. for 1.5 h. After cooling down to room temperature, the reaction mixture is taken in $H_2O$ (100 mL) and extracted with EtOAc (3×50 mL). The combined organic layer is washed with brine, dried over $MgSO_4$, concentrated and purified by silica gel chromatography (0~50% EtOAc/Hexanes) to provide the title compound (2.64 g, 67% yield for two steps) as a white solid product; $^1H$ NMR ($CDCl_3$, 400 MHz) δ 7.96 (d, 2H), 7.58 (d, 1H), 7.47 (t, 1H), 7.41 (m, 2H), 7.36 (d, 2H), 7.23 (d, 2H), 7.19 (d, 2H), 6.83 (m, 4H), 5.22 (dd, 1H), 4.37 (dd, 1H), 3.81 (dd, 1H), 2.46 (s, 3H); HPLC-MS calculated for $C_{29}H_{22}ClF_3N_2O_4S$ ($M+H^+$) 587.1, found 587.1.

Example 9

(S)-1-[4-(4-chloro-phenoxy)-phenyl]-5-(S)-phenyl-imidazolidine-2,4-dione

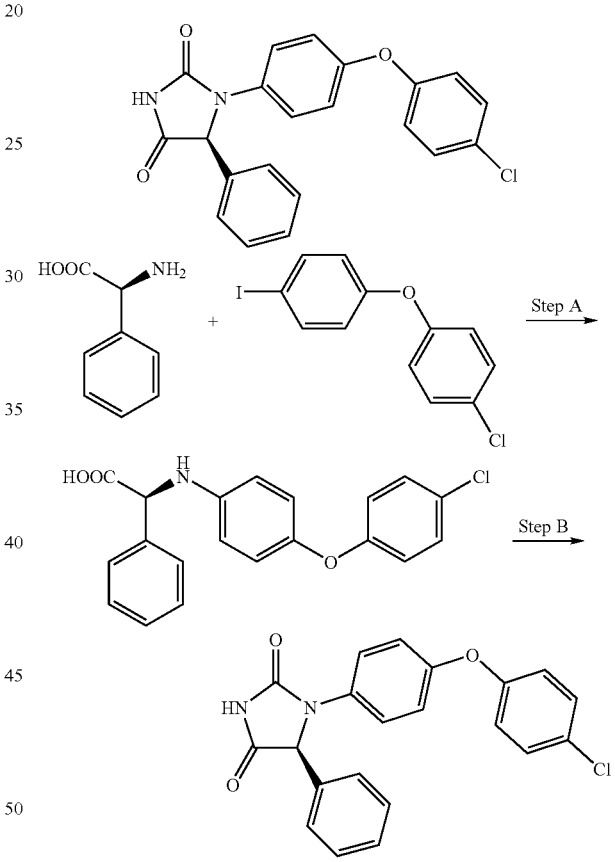

Step A: A reaction tube charged with L-phenylglycine (151.2 mg, 1.00 mmol), 4-(4-chloro-phenoxy)-iodobenzene (165.3 mg, 0.50 mmol), $K_2CO_3$ (103.7 mg, 0.75 mmol), and CuI (9.5 mg, 0.05 mmol) is purged with nitrogen. Anhydrous dimethylacetamide (0.6 mL) is added via syringe. The reaction mixture is heated at 90° C. overnight before removal of the solvent in vacuo. The residue is used directly in next step without further purification.

Step B: The reaction residue from step A is taken in acetic acid (5.0 mL) and potassium cyanate (324.5 mg, 4.00 mmol) is added. The reaction mixture is heated at 80° C. for 1 h before removal of the solvent. The residue is basified with saturated $NaHCO_3$ aqueous solution at 0° C. and extracted with ethyl acetate. The combined ethyl acetate layer is dried over MgSO₄, concentrated, and purified by silica gel chromatography to provide (S)-1-[4-(4-chloro-phenoxy)-phenyl]-5-phenyl-imidazolidine-2,4-dione (49.1 mg, 26% yield for two steps) as a yellow solid product; ¹H NMR (CDCl₃, 400 MHz) δ 7.78 (br, 1H), 7.39-7.33 (m, 7H), 7.26 (d, 2H), 6.91 (d, 2H), 6.89 (d, 2H), 5.48 (s, 1H); HPLC-MS calculated for $C_{21}H_{15}ClN_2O_3$ (M+H⁺) 379.1, found 379.1.

Example 13

(S)-3-[4-(4-Chloro-phenoxy)-phenyl]-4-(3-fluoro-5-trifluoromethyl-phenyl)-oxazolidin-2-one

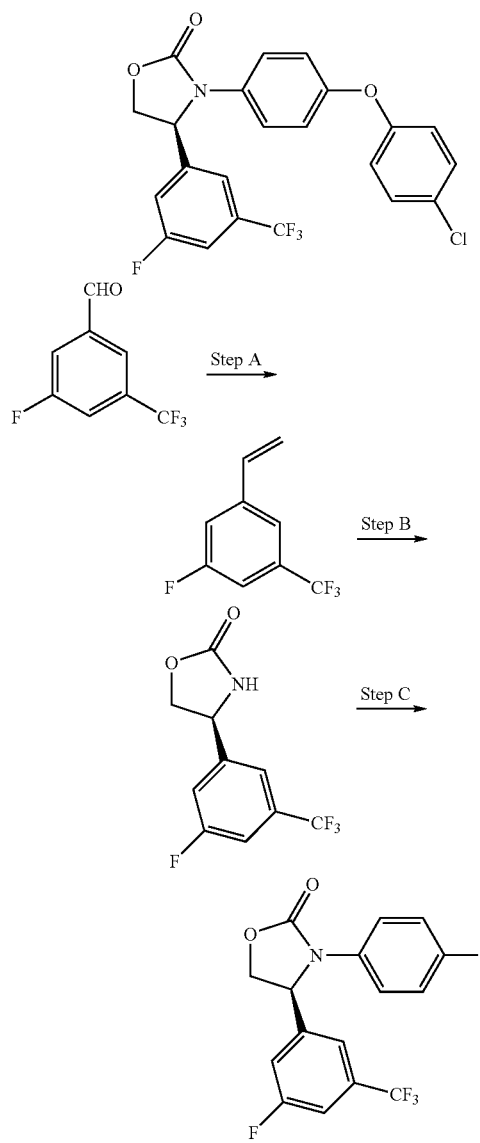

Step A: In a 100 mL round bottom flask is added methyltriphenylphosphonium bromide (2.79 g, 7.8 mmol) and anhydrous ethyl ether (40 mL). The suspension is then cooled down to −78° C. and BuLi (6.77 mmol, 4.23 mL 1.6 M solution in hexane) is added dropwise. After the addition, the bright yellow mixture is warmed up to 0° C. and stirred for 30 min and cooled down to −78° C. again. To this mixture, a solution of 3-fluoro-5-trifluoromethyl-benzaldehyde (1 g, 5.2 mmol) in anhydrous ethyl ether (6 mL) is added drop by drop. After the addition, the mixture is slowly warmed up to room temperature and stirred for 14 hr. The precipitate is removed by filtration and washed with ethyl ether (2×5 mL). The filtrate is concentrated by distilling off ethyl ether at ~60° C. bath temperature. The resulted higher boiling point liquid is purified by pass through a short column (silica gel) with hexane. After removing the hexane under vacuum (~150 mmHg), the resulted crude 1-fluoro-3-trifluoromethyl-5-vinyl-benzene is used directly for next step.

Step B: (S)-(3-fluoro-5-trifluoromethyl-phenyl)-oxazolidin-2-one can be prepared from 1-fluoro-3-trifluoromethyl-5-vinyl-benzene by following the methods described in example 4, step A.

Step C: (S)-3-[4-(4-Chloro-phenoxy)-phenyl]-4-(3-fluoro-5-trifluoromethyl-phenyl)-oxazolidin-2-one can be prepared by following methods described in example 4, step B. ¹H NMR (CDCl₃, 400 MHz) δ 7.20-7.37 (m, 7H), 6.92 (d, 2H), 6.89 (d, 2H), 5.42 (q, 1H), 4.84 (t, 1H), 4.20 (q, 1H); HPLC-MS calculated for $C_{22}H_{14}ClF_4NO_3$ (M+H⁺) 452.1, found 452.1.

Example 14

(S)-3-(4-Benzyl-phenyl)-4-(3-trifluoromethyl-phenyl)-4-oxazolidin-2-one

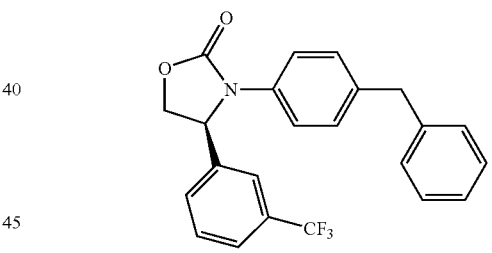

A mixture of (S)-3-(4-bromo-phenyl)-4-(3-trifluoromethyl-phenyl)-oxazolidin-2-one (20 mg, 0.052 mmol), 2-benzyl-4,4,5,5-tetramethyl-[1,3,2]dioxaborolane (17 mg, 0.078 mmol), Pd(dppf)₂Cl₂ (4 mg, 0.005 mmol) and Cs₂CO₃ (34 mg, 0.104 mmol) in anhydrous DMF (0.5 mL) is degassed and heated to 100° C. for 24 h. After cooling down to room temperature, the mixture is treated with saturated aqueous NH₄Cl solution (3 mL) and extracted with EtOAc (3×3 mL). The combined organic layers is concentrated and purified by preparative LC/MS and preparative thin layer chromatography sequentially to provide the title compound. ¹H NMR (CDCl₃, 400 MHz) δ 7.59 (t, 1H), 7.54 (s, 1H), 7.49 (d, 2H), 7.27 (d, 2H), 7.24 (d, 2H), 7.18 (t, 1H), 7.11 (d, 2H), 7.09 (d, 2H), 5.42 (q, 1H), 4.81 (t, 1H), 4.18 (q, 1H); HPLC-MS calculated for $C_{23}H_{18}F_3NO_2$ (M+H⁺) 398.1, found 398.1.

Example 15

1-[4-(4-Chloro-phenoxy)-phenyl]-3-methyl-5-(S)-phenyl-imidazolidine-2,4-dione

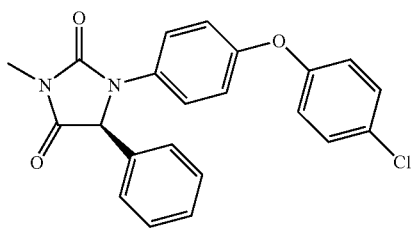 [SMILES: CN1C(=O)[C@H](c2ccccc2)N(c2ccc(Oc3ccc(Cl)cc3)cc2)C1=O]

To a solution of 1-[4-(4-chloro-phenoxy)-phenyl]-5-(S)-phenyl-imidazolidine-2,4-dione (10.0 mg, 0.026 mmol) in anhydrous DMF (0.5 mL) are added $K_2CO_3$ (7.3 mg, 0.052 mmol) and MeI (4.93 µL, 0.078 mmol). The reaction mixture is stirred at room temperature overnight before removal of the solvent. The residue is purified by preparative LC/MC to provide the title compound; $^1$H NMR (CDCl$_3$, 400 MHz) δ 7.42-7.31 (m, 7H), 7.26 (d, 2H), 6.90 (m, 4H), 5.42 (s, 1H), 3.16 (s, 3H); HPLC-MS calculated for $C_{22}H_{17}ClN_2O_3$ (M+H$^+$) 393.1, found 393.1.

Example 16

3-[4-(4-chloro-phenoxy)-phenyl]-1-methyl-4-(3-trifluoromethyl-phenyl)-imidazolidin-2-one

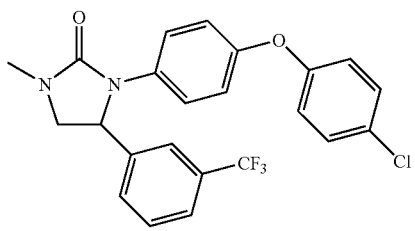 [SMILES: CN1CC(c2cccc(C(F)(F)F)c2)N(c2ccc(Oc3ccc(Cl)cc3)cc2)C1=O]

To a solution of 1-[4-(4-chloro-phenoxy)-phenyl]-5-(3-trifluoromethyl-phenyl)-imidazolidin-2-one (20.0 mg, 0.046 mmol) in anhydrous DMF (0.5 mL) is added NaH (2.2 mg, 60% dispersion in mineral oil, 0.055 mmol) at 0° C. The reaction mixture is stirred at room temperature for 30 minutes before MeI (8.63 µL, 0.138 mmol) is added. The mixture is stirred at room temperature for 2 hours and then partitioned between water and ethyl acetate. The organic layer is concentrated and purified by preparative LC/MC to provide the title compound; HPLC-MS calculated for $C_{23}H_{18}ClF_3N_2O_2$ (M+H$^+$) 447.1, found 447.1.

Example 20

(4S,5S)-3-(4-(4-chlorophenoxy)phenyl)-5-methyl-4-phenyloxazolidin-2-one

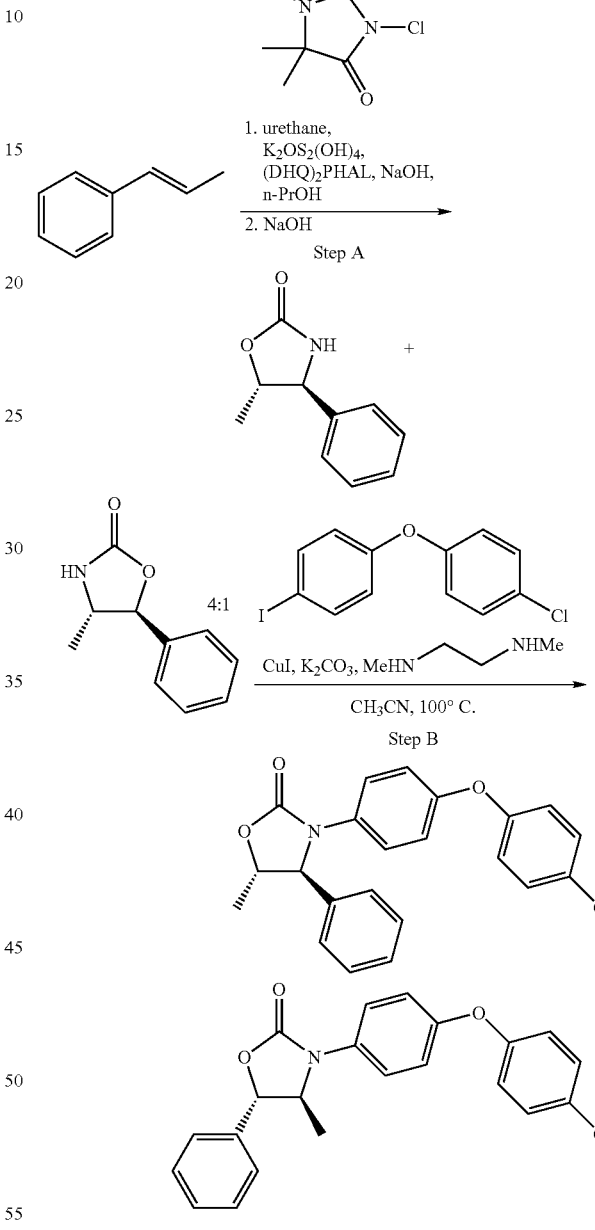

Step A: To a 100 mL flask was added 7 mL of a 0.556M NaOH solution (3.9 mmol), 3.5 mL n-propanol, 1,3-dichloro-5,5-dimethylhydantoin (394 mg, 2.0 mmol), and ethyl carbamate (356 mg, 4.0 mmol). In a separate flask, potassium osmate (11 mg, 0.03 mmol) was dissolved in 0.2 mL of the NaOH solution (0.1 mmol). To a third flask was added trans-β-methylstyrene (0.168 mL, 1.3 mmol), 1 mL n-propanol, and (DHQ)$_2$PHAL (23 mg, 0.03 mmol). This solution was added to the first flask, followed by the osmate solution. The reaction was stirred at ambient temperature for 3 h, at which point NaOH (160 mg, 4 mmol) was added and the reaction was stirred for an additional h. The reaction was quenched with a slight excess of sodium sulfite, and diluted with water and ethyl acetate. The aqueous phase was extracted once with ethyl acetate and the organic phases combined, washed with brine, dried (MgSO$_4$), and concentrated. Flash chromatography (0-30% ethyl acetate/hexanes) afforded 195 mg (84%) of the product as a 3.4:1 mixture of regioisomers of the oxazolidinones.

Step B: The oxazolidinone from Step A was placed into a 20 mL reaction vessel and subsequently treated with 1-(4-iodophenoxy)-4-chlorobenzene (1.1 eq), copper iodide (0.1 eq), N,N'-dimethylethylenediamine (0.2 eq), and potassium carbonate (2 eq). The reaction vessel was capped, evacuated and back-filled with nitrogen twice, and heated to 100° C. overnight. The reaction was subsequently cooled to room temperature, quenched with excess 1 M HCl, extracted with ethyl acetate, washed with brine, then dried over MgSO$_4$, and concentrated. Flash chromatography (0-30% ethyl acetate/hexanes) gave the title compounds. 58 mg isolated (61% overall yield) as a white solid. Example 20: $^1$H NMR (acetone-d6) δ (ppm) 7.46-7.49 (m, 4H), 7.32-7.42 (m, 5H), 6.93-6.98 (m, 4H), 5.24 (d, 1H, J=6.6 Hz), 4.46 (p, 1H, J=6.3 Hz), 1.58 (d, 3H, J=6.2 Hz). HPLC-MS calculated C22H18ClNO3 (M+H$^+$): 380.8, found: 380.8. Regioisomer: $^1$H NMR (acetone-d6) δ (ppm) 7.52-7.58 (m, 4H), 7.39-7.50 (m, 7H), 7.02-7.11 (m, 4H), 5.27 (d, 1H, J=6.8 Hz), 4.48 (p, 1H, J=6.3 Hz), 1.44 (d, 3H, J=6.1 Hz). HPLC-MS calculated C$_{22}$H$_{18}$ClNO$_3$ (M+H$^+$): 380.8, found: 380.8.

Example 26

(4S,5R)-3-(4-(4-chlorophenoxy)phenyl)-4-(3-(trifluoromethyl)phenyl)-5-(hydroxymethyl)-oxazolidin-2-one

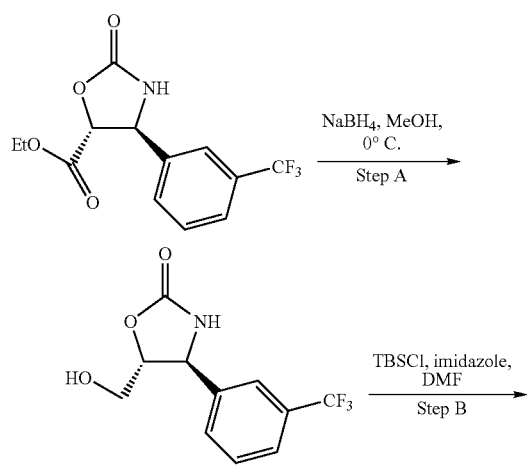

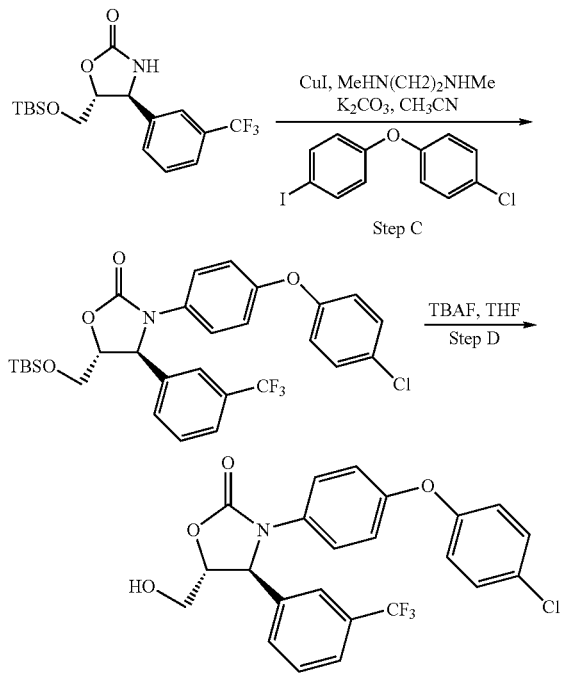

Step A: (4S,5R)-ethyl 4-(3-(trifluoromethyl)phenyl)-2-oxooxazolidine-5-carboxylate (650 mg, 2.1 mmol), was dissolved in 8 mL dry MeOH under nitrogen and cooled to 0° C. NaBH$_4$ (162 mg, 4.3 mmol) was added and the reaction was stirred 1 h, as judged complete by TLC. Saturated ammonium chloride was added carefully to quench, and the suspension was diluted with water and ethyl acetate. The organic phase was washed with brine, dried (MgSO$_4$), and concentrated to give 380 mg of a colorless oil that was used without purification.

Step B: To the alcohol from Step A in 3 mL DMF was added imidazole (130 mg, 1.91 mmol) and TBSCl (160 mg, 1.05 mmol). The reaction was stirred at ambient temperature overnight, at which point saturated NaHCO$_3$ was added to quench. Aqueous extracted once with ethyl acetate and the organic was dried (MgSO$_4$), and concentrated. Flash chromatography (0-30% ethyl acetate/hexanes) provided 241 mg (67%) of a white solid.

Step C: Reaction performed as described in Example 20.

Step D: To the TBS ether (13 mg, 0.02 mmol) in THF at 0° C. was added TBAF (0.034 mL, 0.03 mmol). The reaction was stirred for 30 min at this temperature as judged complete by TLC. Saturated ammonium chloride was added to quench, followed by dilution with water and ethyl acetate. The organic phase was washed with brine, dried (MgSO$_4$), and concentrated. Flash chromatography (0-40% ethyl acetate/hexanes) gave 8 mg (80%) of the title compound as a colorless oil. $^1$H NMR (CDCl$_3$) δ (ppm) 7.51-7.61 (m, 4H), 7.30 (d, 2H, J=9.0 Hz). 7.25 (d, 2H, J=8.9 Hz), 6.88 (t, 4H, J=9.1 Hz), 5.43 (d, 1H, J=6.3 Hz), 4.39-4.42 (m, 1H), 4.08 (dd, 1H, J=12.8, 3.2 Hz), 3.84 (dd, 1H, J=12.8, 3.0 Hz). HPLC-MS calculated C$_{23}$H$_{17}$ClF$_3$NO$_4$ (M+H$^+$): 464.1, found: 464.1.

Example 28

(4S,5R)-3-(4-(4-chlorophenoxy)phenyl)-5-(methoxymethyl)-4-phenyloxazolidin-2-one

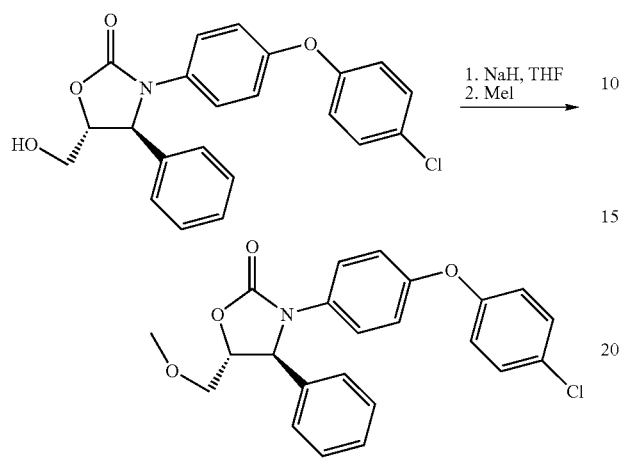

To (4S,5R)-3-(4-(4-chlorophenoxy)phenyl)-5-(hydroxymethyl)-4-phenyloxazolidin-2-one (14 mg, 0.035 mmol) in THF (1 mL) was added NaH (~5 mg) and the reaction was stirred for 10 min. at room temperature. Iodomethane (~0.01 mL) was added and the reaction was stirred for an additional 2 h. NaHCO$_3$ aqueous solution was added to quench, followed by dilution with water and ethyl acetate. The organic phase was washed with brine, dried (MgSO$_4$), and concentrated. Flash chromatography (0-30% ethyl acetate/hexanes) yielded 8 mg (57%) of the title compound as a colorless oil. $^1$H NMR (CDCl$_3$) δ (ppm) 7.23-7.32 (m, 7H), 7.16-7.19 (m, 2H), 6.78-6.82 (m, 4H), 5.16 (d, 1H, J=5.7 Hz), 4.36 (dd, 1H, J=9.3, 3.9 Hz), 3.63 (ddd, 2H, J=18.4, 11.0, 4.1), 3.41 (s, 3H). HPLC-MS calculated C$_{23}$H$_{20}$ClNO$_4$ (M+H$^+$): 410.1, found: 410.1.

Example 30

((4S,5R)-3-(4-(4-chlorophenoxy)phenyl)-4-phenyl-2-oxooxazolidin-5-yl)methyl isopropylcarbamate

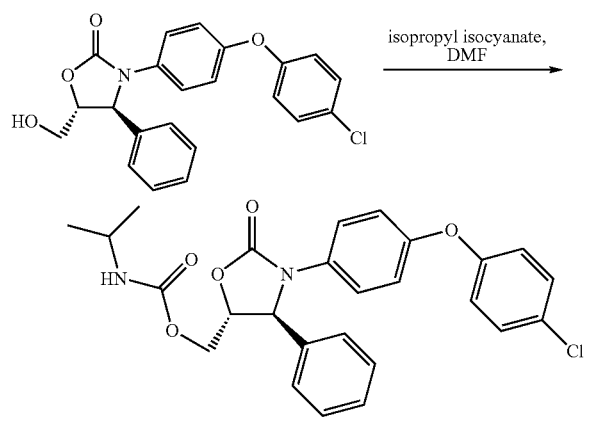

To (4S,5R)-3-(4-(4-chlorophenoxy)phenyl)-5-(hydroxymethyl)-4-phenyloxazolidin-2-one (33 mg, 0.08 mmol) in 0.3 mL DMF was added isopropyl isocyanate (0.015 mL, 0.16 mmol). The reaction was stirred for 3 h at room temperature until reaction completed as judged by TLC. Water and ethyl acetate were added and the phases separated. The organic phase was washed with brine, dried (MgSO$_4$), and concentrated. 13 mg (33%) of the title compound was obtained as a white solid after Prep-LC purification (10-90 Acetonitrile/water (0.05% ammonium acetate). $^1$H NMR (CDCl$_3$) δ (ppm) 7.30-7.39 (m, 7H), 7.23-7.26 (m, 2H), 6.84-6.90 (m, 4H), 5.14 (d, 1H, J=5.6 Hz), 4.67 (d, 1H, J=7.2 Hz), 4.34-4.53 (m, 3H), 3.77-3.85 (m, 1H), 1.17 (d, 3H, J=6.5 Hz), 1.13 (d, 3H, J=6.5 Hz). HPLC-MS calculated C$_{26}$H$_{25}$ClN$_2$O$_5$ (M+H$^+$): 481.2, found: 481.1.

Example 33

2-(((4S,5S)-3-(4-(4-chlorophenoxy)phenyl)-4-phenyl-2-oxooxazolidin-5-yl)methyl)isoindoline-1,3-dione

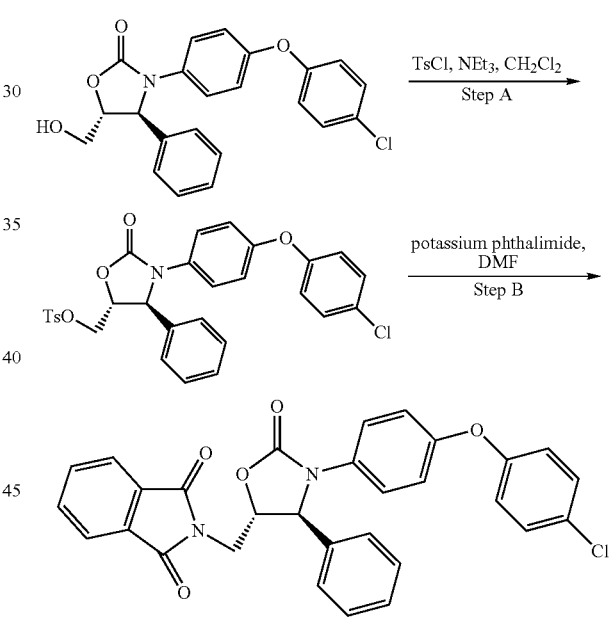

To (4S,5R)-3-(4-(4-chlorophenoxy)phenyl)-5-(hydroxymethyl)-4-phenyloxazolidin-2-one (161 mg, 0.4 mmol) and triethylamine (0.17 mL, 1.2 mmol) in dichloromethane (3 mL) was added tosyl chloride (93 mg, 0.48 mmol). The reaction mixture was stirred for 17 h at ambient temperature and quenched with NaHCO$_3$ aqueous solution. Water and dichloromethane were added. The organic phase was separated, dried (MgSO$_4$), and concentrated. Flash chromatography (0-30% ethyl acetate/hexanes) yielded 196 mg (89%) of the title compound as a colorless oil that crystallized on standing. $^1$H NMR (CDCl$_3$) δ (ppm) 7.85-7.88 (m, 2H), 7.75-7.78 (m, 2H), 7.22-7.31 (m, 9H), 6.83-6.88 (m, 4H), 5.21 (d, 1H, J=5.4 Hz), 4.72 (dd, 1H, J=11.5, 5.9 Hz), 4.16 (d, 2H, J=6.0 Hz). HPLC-MS calculated C$_{30}$H$_{21}$ClN$_2$O$_5$ (M+H$^+$): 525.1, found: 525.1.

Example 34

(4S,5S)-3-(4-(4-chlorophenoxy)phenyl)-5-(aminomethyl)-4-phenyl-oxazolidin-2-one

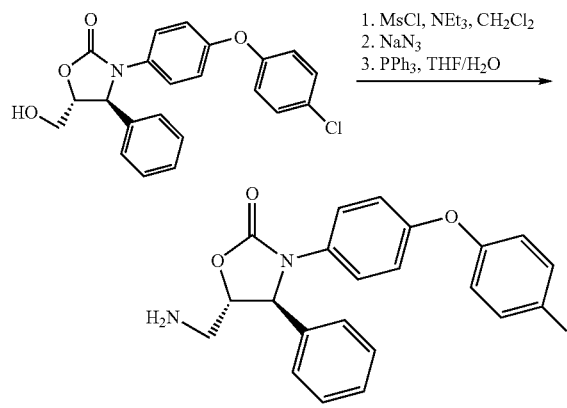

1. MsCl, NEt₃, CH₂Cl₂
2. NaN₃
3. PPh₃, THF/H₂O

To (4S,5R)-3-(4-(4-chlorophenoxy)phenyl)-5-(hydroxymethyl)-4-phenyloxazolidin-2-one (44 mg, 0.11 mmol) and triethylamine (0.046 mL, 0.33 mmol) in dichloromethane (1.5 mL) at 0° C. was added mesyl chloride (0.012 mL, 0.15 mmol). The reaction mixture was stirred at this temperature for 20 min until reaction complete as judged by TLC, and then was quenched with NaHCO₃ aqueous solution. The aqueous layer was extracted (2× dichloromethane) and the organics combined, dried (MgSO₄), and concentrated. The oil was taken up in 2 mL DMF and treated with NaN₃ (14 mg, 0.2 mmol) at 70° C. for 5 h (monitored by analytical LC/MS). The reaction was cooled to room temperature, and then quenched with water. Ethyl acetate was added and the organic was washed with brine, dried (MgSO₄), and concentrated. The oil was re-dissolved in THF/water (10:1, 1 mL) and treated with triphenylphosphine (34 mg, 0.12 mmol). The reaction was stirred at room temperature overnight and then concentrated. Flash chromatography (0-5% MeOH/dichloromethane) gave 35 mg (80%, 3 steps) of a the title compound as colorless oil that crystallized on standing. ¹H NMR (acetone-d₆) δ (ppm) 7.49-7.53 (m, 2H), 7.30-7.46 (m, 7H), 6.92-6.97 (m, 4H), 5.48 (d, 1H, J=4.8 Hz), 4.55 (dd, 1H, J=9.5, 4.7 Hz), 3.64 (dd, 2H, J=4.9, 1.6 Hz). HPLC-MS calculated $C_{22}H_{19}ClN_2O_3$ (M+H⁺): 395.1, found: 395.1.

Example 35

N-((4S,5S)-3-(4-(4-chloro-phenoxy)-phenyl)-2-oxo-4-phenyl-oxazolidin-5-ylmethyl)-methanesulfonamide

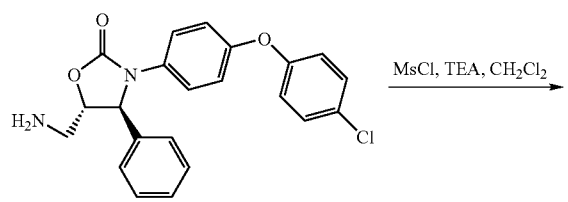

MsCl, TEA, CH₂Cl₂

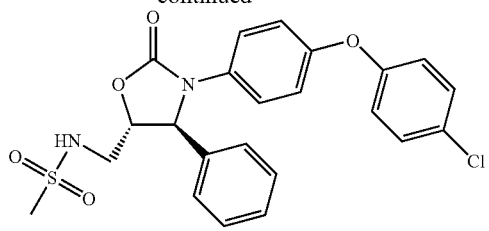

To a solution of (4S,5S)-3-(4-(4-chlorophenoxy)phenyl)-5-(aminomethyl)-4-phenyl-oxazolidin-2-one (14 mg, 0.035 mmol) and triethylamine (0.01 mL, 0.07 mmol) in dichloromethane (0.4 mL) at 0° C. was added mesyl chloride (0.005 mL, 0.05 mmol). The reaction mixture was stirred for 10 min and was then quenched with saturated NaHCO₃ aqueous solution. Water and dichloromethane was added and the organic was washed with brine, dried (MgSO₄), and concentrated. Purification by prep-LC (10-90% Acetonitrile/water (0.05% ammonium acetate) gave 5 mg (31%). ¹H NMR (acetone-d₆) δ (ppm) 7.45-7.51 (m, 4H), 7.32-7.42 (m, 5H), 6.94-6.97 (m, 4H), 6.66 (t, 1H, J=6.6 Hz), 5.56 (d, 1H, J=5.6 Hz), 4.51, (dd, 1H, J=10.1, 4.7 Hz), 3.59-3.72 (m, 2H), 3.04 (s, 3H). HPLC-MS calculated $C_{23}H_{21}ClN_2O_5S$ (M+H⁺): 473.1, found: 473.1.

Example 38

(4S,5R)-5-(tert-butyl-dimethyl-silanyloxymethyl)-3-(4-(4-chloro-phenoxy)-phenyl)-4-phenyl-oxazolidin-2-one

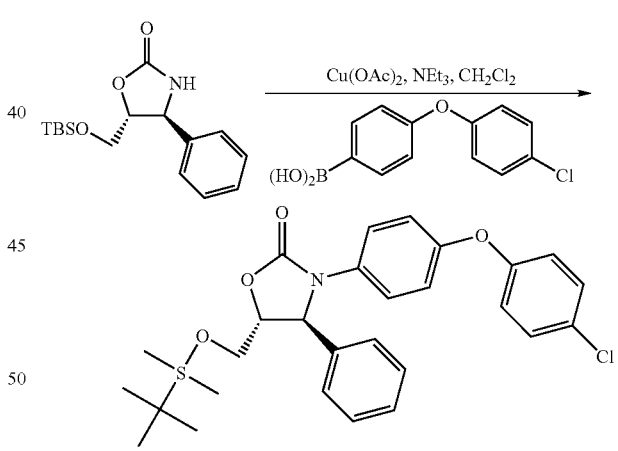

Cu(OAc)₂, NEt₃, CH₂Cl₂

A stirring solution of the oxazolidinone (31 mg, 0.1 mmol) in dichloromethane was treated with the boronic acid (50 mg, 0.2 mmol), triethylamine (40 μL, 0.3 mmol), and copper II acetate (36 mg, 0.2 mmol). Stirred at room temperature until complete, then filtered through celite, diluted with ethyl acetate, washed with 1 M HCl, then dried over magnesium sulfate, filtered and concentrated. Purified on silica gel (10-30% ethyl aceate/hexanes) to give the title compound (5 mg, 10%) as a colorless oil. ¹H NMR (CDCl₃) δ (ppm) 7.24-7.37 (m, 9H), 6.86-6.89 (m, 4H), 5.26 (d, 1H, J=4.7 Hz), 4.35 (d, 1H, J=3.5 Hz), 3.95 (dd, 1H, J=11.6, 3.9 Hz), 3.86 (d, 1H, J=11.5 Hz), 0.89 (s, 9H,), 0.12 (s, 6H). HPLC-MS calculated $C_{28}H_{32}ClNO_4Si$ (M+H⁺): 510.2, found: 510.2.

Example 39 and Example 42

(4S,5R)-ethyl 3-(4-(4-chlorophenoxy)phenyl)-4-(3-fluorophenyl)-2-oxooxazolidine-5-carboxylate; (4S,5S)-ethyl 3-(4-(4-chlorophenoxy)phenyl)-4-(3-fluorophenyl)-2-oxooxazolidine-5-carboxylate

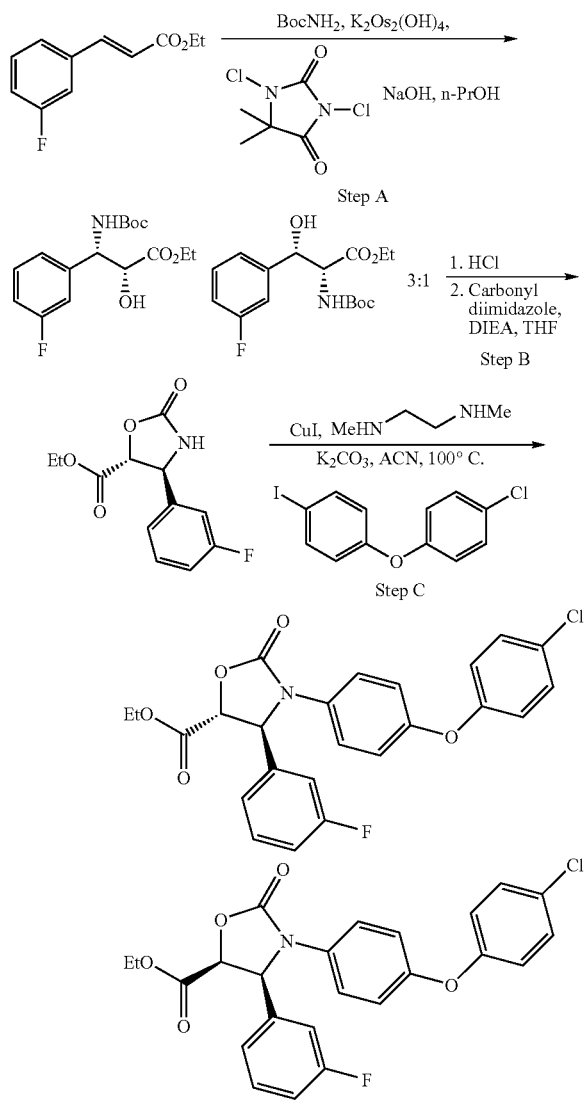

Step A: In a 500 mL round bottom flask was placed sodium hydroxide (1.19 g, 29.8 mmol) and water (70 mL). Once the sodium hydroxide had dissolved, a 2.0 mL aliquot was removed and was used to dissolve potassium osmate (213 mg, 0.58 mmol, 6 mol %) in a 4 dram vial containing a stir bar. Then, n-propanol (50 mL) was added to the hydroxide solution, followed by addition of t-butyl carbamate (3.48 g, 29.8 mmol), and 1,3-dichloro-5,5-dimethylimidazolidine-2,4-dione (2.93 g, 14.9 mmol). The mixture was stirred vigorously at 0° C. To a separate flask was dissolved (E)-ethyl 3-(3-fluorophenyl)acrylate (1.87 g, 9.6 mmol), (DHQ)$_2$PHAL (450 mg, 0.58 mmol, 6 mol %) in n-propanol (25 mL). This solution was then added to the previously prepared solution, which was subsequently followed by addition of the osmate solution. After 2 h, the reaction was quenched with sodium sulfite (slight excess), and water (50 mL). The contents were then partitioned with ethyl acetate and the aqueous layer was removed and extracted with ethyl acetate (2×100 mL). The combined organics were then washed with brine (50 mL), dried over magnesium sulfate, filtered, concentrated in vacuo, and then purified on silica gel with 30% ethyl acetate/70% hexanes to give the product (2.68 g, 85%) as a white solid as a 3:1 mixture of regioisomers. HPLC-MS calculated for $C_{16}H_{22}FNO_5$ (M+Na$^+$) 350.2, found 350.1, $C_{11}H_{14}FNO_3$ (M-Boc+H$^+$) 227.1, found 227.1.

Step B: The product from step A was dissolved in dichloromethane (24 mL) and treated with a 4.0M solution of HCl in dioxane (12 mL) and stirred overnight. The solvents were evaporated in vacuo, and the residue was then suspended in tetrahydrofuran (40 mL) and treated with diisopropylethylamine (DIEA) (4.23 mL, 24 mmol) followed by carbonyldiimidazole (1.64 g, 10.1 mmol). The mixture was heated to reflux for 3 h, and was then cooled to room temperature, diluted with ethyl acetate (30 mL) and water (30 mL) and then acidified with 0.5 M HCl (15 mL). The layers were separated, and the aqueous layer was extracted with ethyl acetate (2×50 mL). The combined organics were dried over magnesium sulfate, filtered and concentrated. The crude mixture was purified on silica gel with methanol/dichloromethane (3-7% methanol gradient) to give 1.2 g (88%) of product as a mixture of regioisomers. HPLC-MS calculated for $C_{12}H_{12}FNO_4$ (M+H$^+$) 254.1, found 254.0.

Step C: To a 20 mL reaction tube fitted with a screw cap was added (4S,5R)-ethyl 4-(3-fluorophenyl)-2-oxazolidinone-5-carboxylate (120 mg, 0.47 mmol) and acetonitrile (2.5 mL). 1-chloro-4-(4-iodophenoxy)-benzene (196 mg, 0.60 mmol) was then added, followed by copper iodide (25 mg, 0.13 mmol), N,N'-dimethylethylenediamine (0.03 mL, 0.28 mmol), and potassium carbonate (162 mg, 1.18 mmol). The system was sealed and evacuated and back-filled with nitrogen three times, then heated to 100° C. for 4 h. The reaction was cooled to room temperature, quenched with 1M HCl (3 mL) and extracted with ethyl acetate. The combined organics were washed once with brine, dried over magnesium sulfate, filtered and concentrated in vacuo. Purification on silica gel (20% ethyl acetate/80% hexanes) gave 76.1 mg of (4S,5R)-ethyl 3-(4-(4-chlorophenoxy)phenyl)-4-(3-fluorophenyl)-2-oxooxazolidine-5-carboxylate (Example 39) and 27.5 mg of (4S,5S)-ethyl 3-(4-(4-chlorophenoxy)phenyl)-4-(3-fluorophenyl)-2-oxooxazolidine-5-carboxylate (Example 42) (48% overall yield). Trans-isomer: $^1$H NMR (d$_6$ acetone) δ (ppm) 7.54 (d, J=9.1 Hz, 2H), 7.53-7.47 (m, 1H), 7.38 (d, J=8.9 Hz, 2H), 7.37-7.31 (m, 2H), 7.19-7.14 (m, 1H), 7.00-6.97 (m, 4H), 5.83 (d, J=5.1 Hz, 1H), 5.00 (d, J=5.1 Hz, 1H), 4.37-4.30 (m, 2H), 1.34 (t, J=7.1 Hz, 3H); HPLC-MS calculated $C_{24}H_{19}ClFNO_5$ (M+H$^+$): 456.1, found: 456.0. Cis-isomer: $^1$H NMR (d$_6$ acetone) δ (ppm) 7.55 (d, J=9.1 Hz, 2H), 7.46-7.41 (m, 1H), 7.38 (d, J=8.9 Hz, 2H), 7.21 (d, J=7.8 Hz, 1H), 7.17-7.01 (m, 2H), 7.00-6.97 (m, 4H), 6.13 (d, J=9.4 Hz, 1H), 5.61 (d, J=9.4 Hz, 1H), 3.88-3.82 (m, 1H), 3.75-3.68 (m, 1H), 0.92 (t, J=7.1 Hz, 3H); HPLC-MS calculated $C_{24}H_{19}ClFNO_5$ (M+H$^+$): 456.1, found: 456.0.

Example 41

(S)-4-(4-(4-chlorophenoxy)phenyl)-5-(3-fluorophenyl)morpholin-3-one

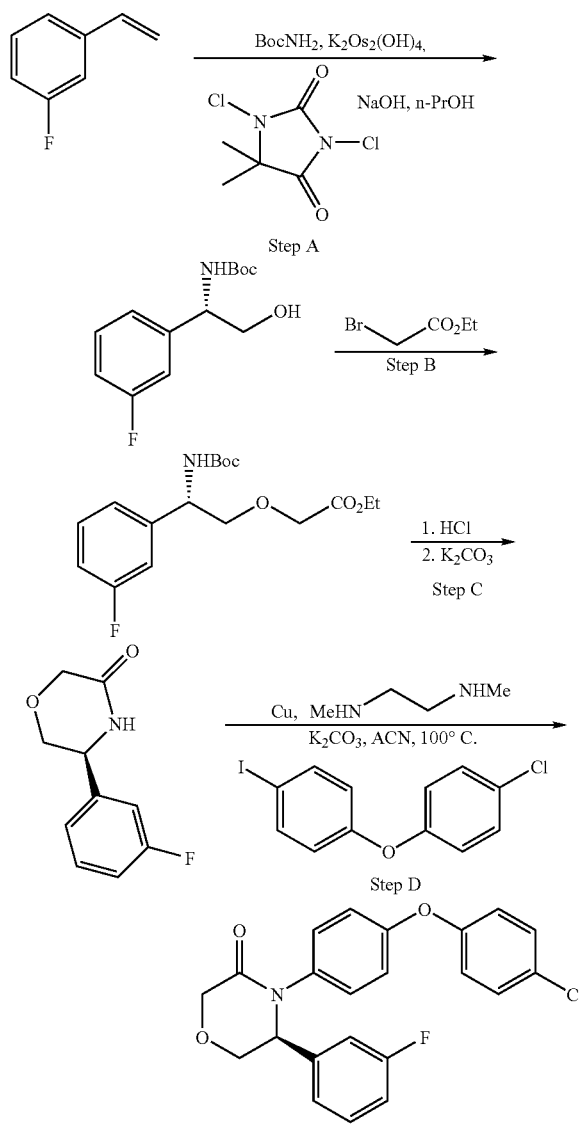

Step A: was performed as described in Example 20 to give tert-butyl (S)-1-(3-fluorophenyl)-2-hydroxyethylcarbamate (27% yield). HPLC-MS calculated for $C_{13}H_{18}FNO_3$ (M+Na$^+$) 278.2, found 278.1, $C_8H_{10}FNO$ (M-Boc+H$^+$) 155.1, found 155.1.

Step B: Tert-butyl (S)-1-(3-fluorophenyl)-2-hydroxyethylcarbamate (256 mg, 1.0 mmol) was dissolved in acetonitrile (10 mL) and treated with cesium carbonate (391 mg, 1.2 mmol) and ethyl bromoacetate (0.14 mL, 1.25 mmol). The mixture was heated to 100° C. for 30 min, then cooled to room temperature, acidified, and extracted with ethyl acetate. Purification on silica gel (15%-40% ethyl acetate/hexanes) gave 69 mg of tert-butyl (S)-2-((ethoxycarbonyl)methoxy)-1-(3-fluorophenyl)ethylcarbamate as a colorless glass. HPLC-MS calculated for $C_{17}H_{24}FNO_5$ (M+H$^+$) 342.2, found 342.1.

Step C: In a 10 mL round bottom flask was added tert-butyl (S)-2-((ethoxycarbonyl)methoxy)-1-(3-fluorophenyl)ethylcarbamate (69 mg, 0.2 mmol), dichloromethane (1.5 mL), and trifluoroacetic acid (0.5 mL). The solution was stirred at room temperature overnight then concentrated to dryness. The residue was then dissolved in tetrahydrofuran (2 mL) and subsequently treated with DIEA (0.5 mL) and potassium carbonate (excess) and heated 50° C. for 1 h. Upon cooling to room temperature, the reaction solution was diluted with water (3 mL) and extracted with ethyl acetate. The combined organics were dried over magnesium sulfate, filtered and concentrated. Purification on silica gel (40% ethyl acetate/hexanes) gave (S)-5-(3-fluorophenyl)morpholin-3-one (37 mg, 95%) as a colorless oil. HPLC-MS calculated for $C_{10}H_{10}FNO_2$ (M+H$^+$) 196.2, found 196.1.

Step D: was performed according to the method (Step C) described in Example 39/42 to give the title compound (53%) as a colorless oil. $^1$H NMR (d$_6$ acetone) δ (ppm) 7.39-7.29 (m, 5H), 7.26-7.21 (m, 2H), 7.06-7.01 (m, 1H), 6.99-6.96 (m, 2H), 6.94-6.90 (m, 2H), 5.26 (app t, J=3.8 Hz, 1H), 4.47 (d, J=16.6 Hz, 1H), 4.35 (dd, J=12.0, 3.8 Hz, 1H), 4.16 (d, J=16.5 Hz, 1H), 4.02 (dd, J=11.9, 3.9 Hz, 1H); HPLC-MS calculated $C_{22}H_{22}ClFNO_3$ (M+H$^+$): 398.1, found: 398.0.

Example 48

(4S,5R)-3-(4-(4-chlorophenoxy)phenyl)-4-(3,5-difluorophenyl)-5-(hydroxymethyl)oxazolidin-2-one

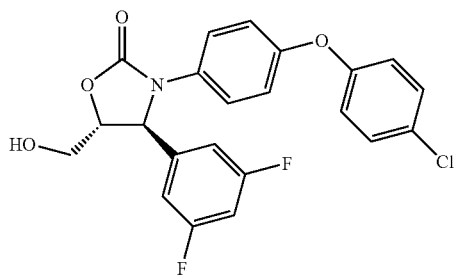 [SMILES: O=C1O[C@@H](CO)[C@H](c2cc(F)cc(F)c2)N1c1ccc(Oc2ccc(Cl)cc2)cc1]

The title compound was obtained as a colorless oil from 1-((E)-3-(benzyloxy)prop-1-enyl)-3,5-difluorobenzene by the same method that is described for Example 39. (4S,5R)-3-(4-(4-chlorophenoxy)phenyl)-5-((benzyloxy)methyl)-4-(3,5-difluorophenyl)oxazolidin-2-one (Example 96) was placed into a 25 mL round bottom flask and dissolved in 7 mL ethanol:ethyl acetate (1:1) and treated with palladium on carbon (10% by weight, 73 mg). The vessel was sealed with a rubber septum and charged with hydrogen. The reaction was stirred for 2 h, then filtered on celite, evaporated to dryness and purified on silica gel (20-30% ethyl acetate/hexanes) to give the title compound as a colorless oil that solidified on standing. $^1$H NMR (acetone-d$_6$) δ (ppm) 7.53 (d, J=9.1 Hz, 2H), 7.37 (d, J=9.0 Hz, 2H), 7.21-7.16 (m, 2H), d, J=6.15 Hz, 2H), 7.02-6.93 (m, 5H), 5.58 (d, J=5.4 Hz, 1H), 4.55 (t, J=5.8 Hz, 1H), 4.45 (ddd, J=5.6, 3.7, 3.6), 3.97 (ddd, J=12.3, 5.6, 3.8 Hz, 1H), 3.90 (ddd, J=12.3, 5.6, 3.8 Hz, 1H); HPLC-MS calculated $C_{22}H_{16}ClF_2NO_4$ (M+H$^+$): 432.1, found: 432.0.

Example 49

(4S,5R)-3-(4-(4-chlorophenoxy)phenyl)-5-(hydroxymethyl)-4-(3-hydroxyphenyl)oxazolidin-2-one

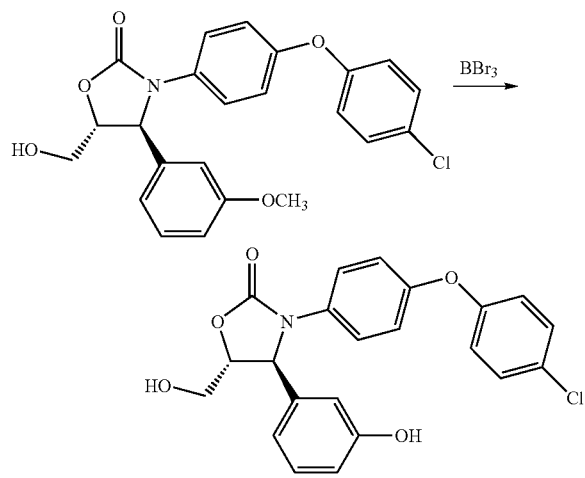

(4S,5R)-3-(4-(4-chlorophenoxy)phenyl)-5-(hydroxymethyl)-4-(3-methoxyphenyl)oxazolidin-2-one (Example 91) was dissolved in dichlormethane, cooled to −78° C., and treated with boron tribromide (1M solution, 2.1 eq). After 10 min, the cooling bath was removed, and the reaction mixture is stirred for 1 h. The reaction was then quenched with water, extracted with ethyl acetate, dried over magnesium sulfate, filtered, concentrated, and purified on silica gel (2-5% methanol/dichlormethane) to give the title compound. $^1$H NMR (acetone-d$_6$) δ (ppm) 8.36 (s, 1H), 7.42 (d, J=9.1 Hz, 2H), 7.23 (d, J=9.0 Hz, 2H), 7.09 (t, J=7.9 Hz, 1H), 6.85-6.81 (m, 4H), 6.77 (d, J=7.6 Hz, 1H), 6.74 (m, 1H), 6.67 (dd, J=8.1, 2.4 Hz, 1H), 5.39 (d, J=5.2 Hz, 1H), 4.49 (t, J=5.9 Hz, 1H), 4.36 (ddd, J=5.6, 3.7, 3.4), 3.96 (ddd, J=12.4, 5.7, 3.6 Hz, 1H), 3.85 (ddd, J=12.3, 5.6, 3.8 Hz, 1H); HPLC-MS calculated C$_{22}$H$_{18}$ClNO$_5$ (M+H$^+$): 411.1, found: 410.0.

Example 52

(4S,5S)-5-((2-(dimethylamino)ethylamino)methyl)-3-(4-(4-chlorophenoxy)phenyl)-4-(3-methoxyphenyl)oxazolidin-2-one

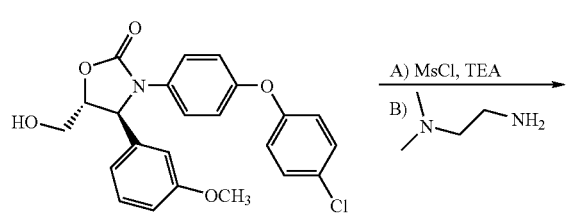

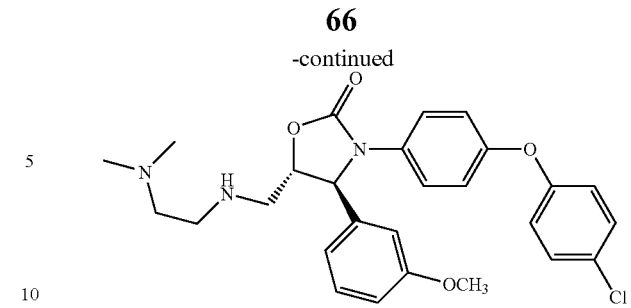

Step A: (4S,5R)-3-(4-(4-chlorophenoxy)phenyl)-5-(hydroxymethyl)-4-(3-methoxyphenyl)oxazolidin-2-one (Example 91) (130 mg, 0.31 mmol) was dissolved in dichloromethane and treated with triethylamine (TEA, 0.1 mL, 0.62 mmol) and was then cooled to 0° C. Methanesulfonyl chloride (0.025 mL, 0.32 mmol) was then added and after 30 min, the reaction was quenched with 3 mL 1M HCl and diluted with dichloromethane. After extraction with dichloromethane, the organics were combined, dried over magnesium sulfate, filtered and concentrated. The product was carried forward without purification.

Step B: The product from Step A (0.04 mmol) was dissolved in DMF (0.5 mL) and treated with N,N-dimethylethylene diamine (0.4 mmol) at 100° C. overnight. The cooled solution was subsequently purified by preparatory LC-MS (C-18, 10-90% ACN/water (0.05% TFA) to give the title compound as a colorless oil. $^1$H NMR (acetone-d$_6$) δ (ppm) 7.53-7.49 (m, 2H), 7.38-7.36 (m, 2H), 7.30 (t, J=7.9 Hz, 1H), 7.06 (t, J=2.0 Hz, 1H), 7.01 (d, J=7.7 Hz, 1H), 6.98-6.94 (m, 4H), 6.90-6.88 (m, 1H), 5.61 (d, J=5.6 Hz, 1H), 4.89 (ddd, J=6.5, 5.6, 5.6 Hz, 1H) 3.93-3.83 (m, 2H), 3.89-3.74 (m, 9H), 3.10 (br s, 6H), 2.10-2.05 (obscured by solvent); HPLC-MS calculated C$_{27}$H$_{30}$ClN$_3$O$_4$ (M+H$^+$): 496.2, found: 496.2.

Example 64

(4S,5S)-5-((4-acetylpiperazin-1-yl)methyl)-3-(4-chlorophenyl)-4-(3,5-difluorophenyl)oxazolidin-2-one

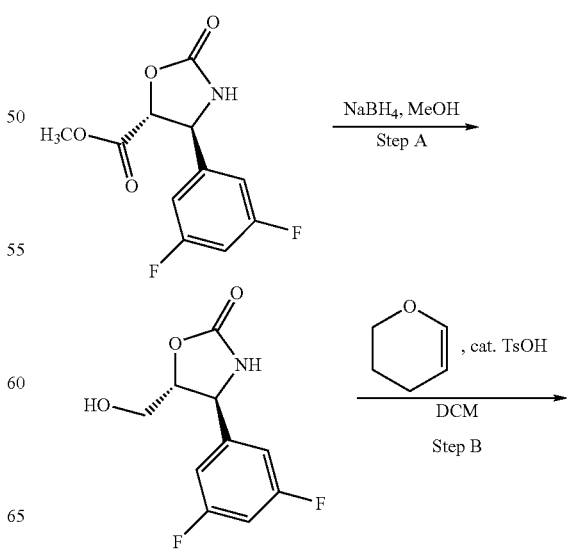

-continued

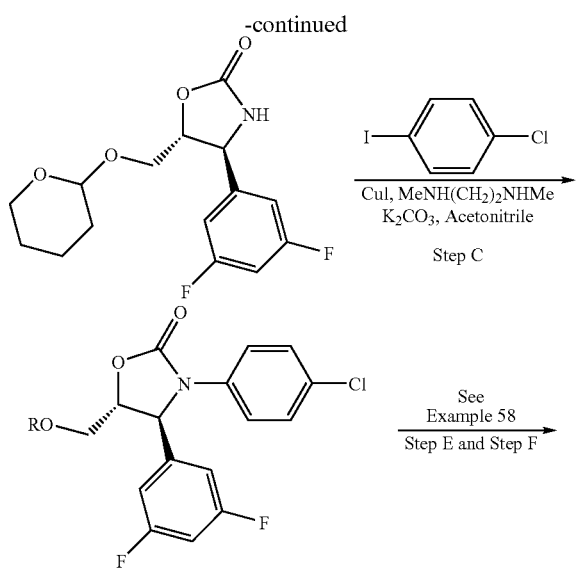

Step A: (4S,5R)-methyl 4-(3,5-difluorophenyl)-2-oxooxazolidine-5-carboxylate (prepared according to Example 39 from (E)-methyl 3-(3,5-difluorophenyl)acrylate) (11 mmol) was dissolved in methanol (70 mL) and cooled to 0° C. NaBH$_4$ (407 mg, 11 mmol) was then added and the reaction mixture was stirred for 30 min. and then was quenched with 0.1 M HCl (20 mL) and concentrated by 80-90% on rotary evaporator. The contents were then extracted with ethyl acetate. The combined organics were washed with brine, then dried over magnesium sulfate, filtered and concentrated. Carried forward without purification.

Step B: The product from Step A was dissolved in dichloromethane (to a concentration of 0.2 M) and treated with 3,4-dihydro-2H-pyran (1.2 eq) and catalytic p-toluenesulfonic acid (0.1 eq). After 2 h the reaction was quenched with aq. sodium bicarbonate and diluted with dichloromethane and transferred to an extraction funnel. The organic layer was removed, the aqueous layer was extracted once with dichloromethane, and the combined organics were dried, filtered, concentrated and purified on silica gel with 40% ethyl acetate/hexanes→50% ethyl acetate/hexanes to give the pure product.

Step C: The reaction was performed as described for Example 39 (Step C) using 4-chloro-1-iodobenzene instead of 1-(4-iodophenoxy)-4-chlorobenzene. The crude product was purified on silica gel (30% ethyl acetate/hexanes) to give the desired product.

Step D: The THP group was removed under standard conditions (T. W. Greene and P. G. M. Wuts, Protective groups in Organic Synthesis, 1999.).

Steps E and F: The title compound was prepared by mesylation followed by nucleophilic replacement with 1-acetylpiperizine using the methods described for Example 52 to give the product as a colorless oil. $^1$H NMR (acetone-d6) δ (ppm) 7.51-7.49 (m, 2H), 7.35-7.32 (m, 2H), 7.24-7.22 (m, 2H), 7.00 (tt, J=9.1, 2.3 Hz, 1H), 5.63 (d, J=6.5 Hz, 1H), 4.65 (ddd, J=ddd, J=6.5, 5.4, 3.2 Hz, 1H), 3.81-3.58 (m, 5H), 3.28-3.16 (m, 4H), 2.07 (part. obs. s, 3H); HPLC-MS calculated C$_{22}$H$_{22}$ClF$_2$N$_3$O$_3$ (M+H$^+$): 450.1, found: 450.1.

Example 72

(4S,5R)-5-((benzyloxy)methyl)-3-(4-chlorophenyl)-4-(3-(trifluoromethyl)phenyl)oxazolidin-2-one

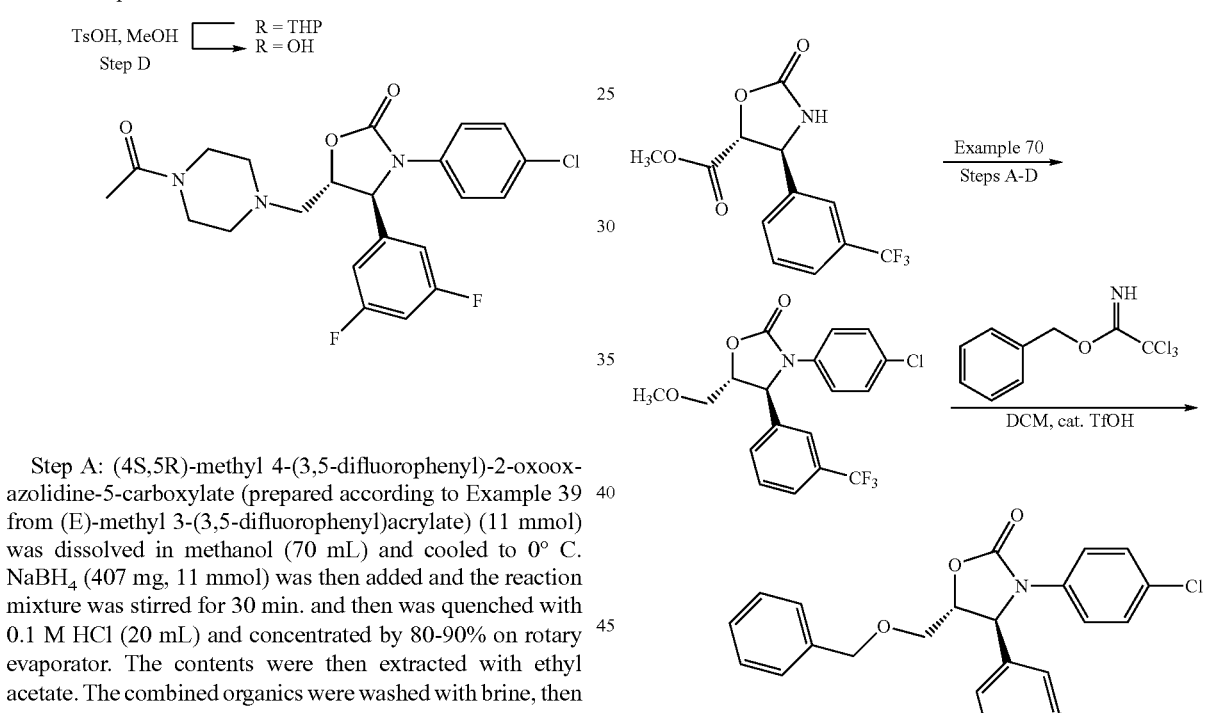

(4S,5R)-3-(4-chlorophenyl)-4-(3-(trifluoromethyl)phenyl)-5-(hydroxymethyl)-oxazolidin-2-one (0.08 mmol), prepared according to the method described for Example 64, in dichloromethane (1 mL) was treated with benzyltrichloroacetimidate (0.09 mmol) and catalytic trifluoromethane sulfonic acid. The reaction was stirred overnight, and was then purified on silica gel (10-30% ethyl acetate/hexanes) to give the title compound. $^1$H NMR (acetone-d6) δ (ppm) 7.82 (s, 1H), 7.74 (d, J=7.6 Hz, 1H) 7.68 (d, J=7.7 Hz, 1H), 7.65-7.61 (m, 1H), 7.54-7.52 (m, 2H), 7.37-7.28 (m, 6H), 5.72 (d, J=5.3 Hz, 1H), 4.71-4.62 (m, 3H), 3.95 (d, J=3.8 Hz, 2H); HPLC-MS calculated C$_{24}$H$_{19}$ClF$_3$NO$_3$ (M+H$^+$): 462.1, found: 461.9.

Example 83

(4S,5R)-3-(5-(4-chlorophenoxy)pyrazin-2-yl)-4-(3-(trifluoromethyl)phenyl)-5-(hydroxymethyl)oxazolidin-2-one

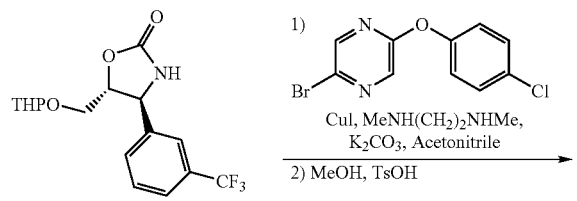

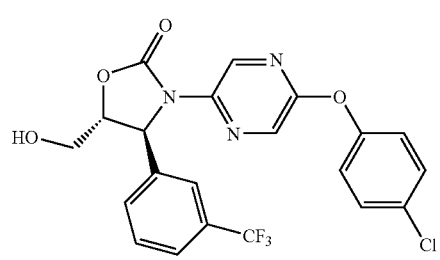

(4S,5R)-4-(3-(trifluoromethyl)phenyl)-5-((tetrahydro-2H-pyran-2-yloxy)methyl)-oxazolidin-2-one (prepared as in Example 64, Steps A and B) (54 mg, 0.16 mmol) was added to a 10 mL reaction vessel with a screw cap and charged with acetonitrile (0.5 mL), 2-(4-chlorophenoxy)-5-bromopyrazine (47 mg, 0.16 mmol), copper (I) iodide (14 mg, 0.074 mmol), N,N'-dimethylethylenediamine (0.014 mL, 0.15 mmol), and potassium carbonate (44 mg, 0.32 mmol). The vessel was sealed, evacuated and back-filled with nitrogen twice, and then heated to 110° C. in a microwave for 30 min. The reaction mixture was cooled to room temperature, quenched with 1 M HCl, and extracted with ethyl acetate. The organic layer was dried, filtered and concentrated to give the crude intermediate which was immediately dissolved in methanol (5 mL) and treated with excess toluenesulfonic acid for 1 h. The reaction was quenched with 1 mL triethylamine, then concentrated to dryness and purified on silica gel (30% ethyl acetate/hexanes) to give the title compound as a white solid. $^1$H NMR (acetone-$d_6$) 600 MHz δ (ppm) 8.91 (d, J=1.3 Hz, 1H), 8.05 (d, 1.3 Hz, 1H), 7.83 (s, 1H), 7.76 (d, J=7.6 Hz, 1H), 7.67 (d, J=7.8 Hz, 1H), 7.63 (t, J=7.7 Hz, 1H), 7.43 (d, J=8.8 Hz, 2H), 7.18 (d, J=8.8 Hz, 2H), 5.86 (d, J=5.0 Hz, 1H), 4.61 (ddd, J=5.4, 3.5, 3.0, 1H), 4.58 (t, J=5.7 Hz, 1H), 4.02 (ddd, J=12.4, 5.5, 3.5 z, 1H), 3.94 (ddd, J=12.3, 5.9, 3.5 Hz, 1H); HPLC-MS calculated $C_{21}H_{15}ClF_3N_3O_4S$ (M+H$^+$): 466.1, found 466.1.

Example 84

(4S,5S)-3-(4-chlorophenyl)-4-(3-(trifluoromethyl)phenyl)-5-((4-(3-fluorophenyl)-1H-1,2,3-triazol-1-yl)methyl)oxazolidin-2-one

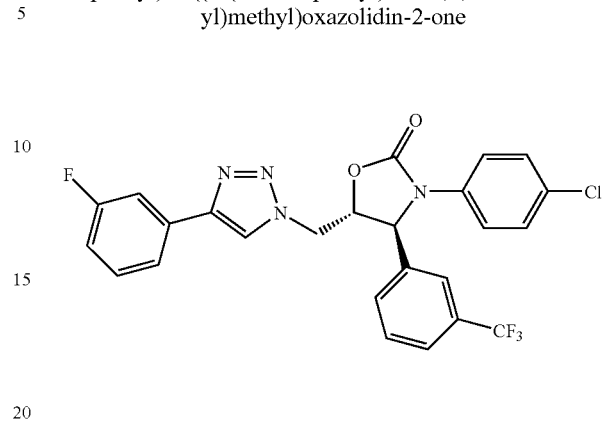

(4S,5R)-3-(4-chlorophenyl)-4-(3-(trifluoromethyl)phenyl)-5-(hydroxymethyl)oxazolidin-2-one (from Example 72) was converted into (4S,5S)-5-(azidomethyl)-3-(4-chlorophenyl)-4-(3-(trifluoromethyl)phenyl)oxazolidin-2-one as described in Example 34. The azide (0.076 mmol) was then dissolved in t-butanol:water (2:1, 0.5 mL) and treated with 3-fluorophenylacetylene (0.076 mmol), followed by copper (II) sulfate pentahydrate (0.4 mg) and sodium ascorbate (0.75 mg). After stirring for 2 h, the reaction mixture was quenched with water and extracted with ethyl acetate, dried over magnesium sulfate, filtered and concentrated. Purification on silica gel (30% ethyl acetate/hexanes) gave the title compound as a colorless oil. $^1$H NMR (acetone-d6) δ (ppm) 8.57 (s, 1H), 7.88 (s, 1H), 7.79 (d, J=7.7 Hz, 1H), 7.72-7.70 (m, 2H), 7.67-7.63 (m, 2H), 7.50-7.44 (m, 3H), 7.30-7.28 (m, 2H), 7.11 (td, J=8.5, 2.3 Hz, 1H), 5.81 (d, J=5.2 Hz, 1H), 5.22-5.16 (m, 2H), 5.07 (ddd, J=5.5, 5.5, 4.4 Hz, 1H), 4.73-4.64 (m, 3H), 4.01 (d, J=3.6 Hz, 2H); HPLC-MS calculated $C_{25}H_{17}ClF_4N_4O_2$ (M+H$^+$): 517.1, found: 517.1.

Example 87

(4S,5S)-3-(4-chlorophenyl)-4-(3-(trifluoromethyl)phenyl)-5-((3-phenyl-1H-pyrazol-1-yl)methyl)oxazolidin-2-one

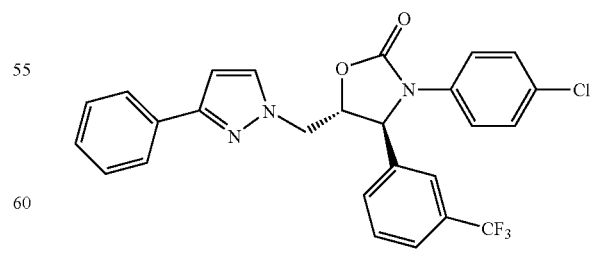

Same as Example 73 by treating 3-phenyl-1H-pyrazole with 1 eq. of sodium hydride in dimethylformamide followed by addition of the corresponding mesylate, prepared using the methods described in Example 52, to give the title compound as a colorless oil. $^1$H NMR (acetone-d6) δ (ppm) 7.82 (d, J=2.3 Hz, 1H), 7.79 (d, J=7.7 Hz, 1H), 7.76-7.74 (m, 2H), 7.71 (d, J=7.6 Hz, 1H), 7.67 (d, J=7.6 Hz, 1H), 7.62 (t, J=7.6 Hz, 1H), 7.42-7.40 (m, 2H), 7.36-7.33 (m, 2H), 7.28-7.26 (m, 2H), 7.19-7.18 (m, 2H), 5.90 (d, J=4.7 Hz, 1H), 4.95 (q, J=4.6 Hz, 1H), 4.85 (dd, J=14.6, 4.6 Hz, 1H), 4.79 (dd, J=14.6, 4.7 Hz, 1H); HPLC-MS calculated $C_{26}H_{19}ClF_3N_3O_2$ (M+H$^+$): 498.1, found: 498.1.

Example 88 tert-butyl (R)-1-(((4S,5S)-3-(4-(4-chlorophenoxy)phenyl)-2-oxo-4-phenyloxazolidin-5-yl)methylcarbamoyl)-2-methylpropylcarbamate

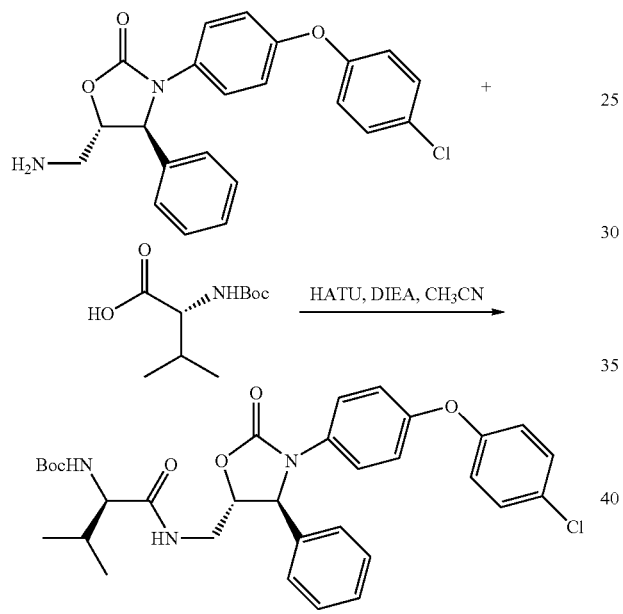

To a stirred solution of Boc-D-valine (12 mg, 0.06 mmol), HATU (22 mg, 0.06 mmol), and DIEA (29 µL, 0.16 mmol) in acetonitrile (0.2 mL) was added the amine (20 mg, 0.05 mmol) in 0.1 mL acetonitrile. The reaction mixture was stirred 3 h as judged complete by TLC, and was then diluted with saturated aq. NH$_4$Cl and ethyl acetate. The organic was washed with brine, dried over magnesium sulfate, filtered and concentrated. Purified on silica gel (0-5% methanol/dichloromethane) to give the title compound (30 mg, 100%) as a colorless oil. $^1$H NMR (CDCl$_3$) δ (ppm) 7.34-7.37 (m, 4H), 7.28-7.33 (m, 3H), 7.22-7.25 (m, 2H), 6.83-6.88 (m, 4H), 6.58 (t, 1H, J=6.1 Hz), 5.12 (d, 1H, J=7.2 Hz), 4.89 (d, 1H, J=6.8 Hz), 4.42 (ddd, 1H, J=7.3, 3.8, 3.8 Hz), 3.93-4.00 (m, 2H), 3.59 (d, 1H, J=14.1 Hz), 2.19 (sextet, 1H, J=6.8 Hz), 1.38 (s, 9H), 0.97 (d, 3H, J=6.8 Hz), 0.90 (d, 3H, J=6.8 Hz). HPLC-MS calculated $C_{32}H_{36}ClN_3O_6$ (M+H$^+$): 594.2, found: 594.2.v

Example 89

(2R)—N-(((4S,5S)-3-(4-(4-chlorophenoxy)phenyl)-2-oxo-4-phenyloxazolidin-5-yl)methyl)-2-amino-3-methylbutanamide

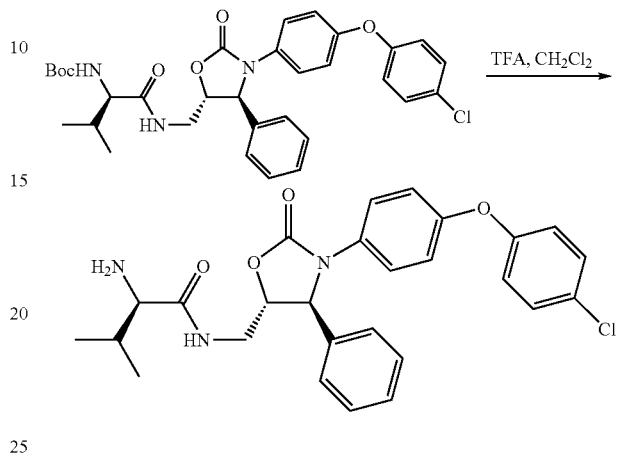

TFA (20 µL) was added to a cooled (0° C.) solution of the Boc-amine (25 mg, 0.04 mmol) in dichloromethane (1 mL). The reaction was stirred 30 min as judged complete by TLC, and quenched with saturated NaHCO$_3$. The solution was diluted with ethyl acetate, washed with brine, dried over magnesium sulfate, filtered and concentrated. HPLC purification (0-90% acetonitrile/water) gave the title compound (11 mg, 53%) as a white film. $^1$H NMR (CDCl$_3$) δ (ppm) 8.18 (br s, 1H), 7.21-7.37 (m, 9H), 6.83-6.86 (m, 4H), 5.13 (d, 1H, J=6.3 Hz), 4.46-4.50 (m, 1H), 3.82-3.89 (m, 1H), 3.62-3.68 (m, 1H), 3.48 (br s, 1H), 2.31-2.39 (m, 1H), 1.0 (d, 3H, J=7.0 Hz), 0.86 (d, 3H, J=6.9 Hz). HPLC-MS calculated $C_{27}H_{28}ClN_3O_4$ (M+H$^+$): 494.2, found: 494.2.

Example 99

(4S,5R)-3-(4-(4-chlorophenoxy)phenyl)-5-(morpholine-4-carbonyl)-4-phenyl-oxazolidin-2-one

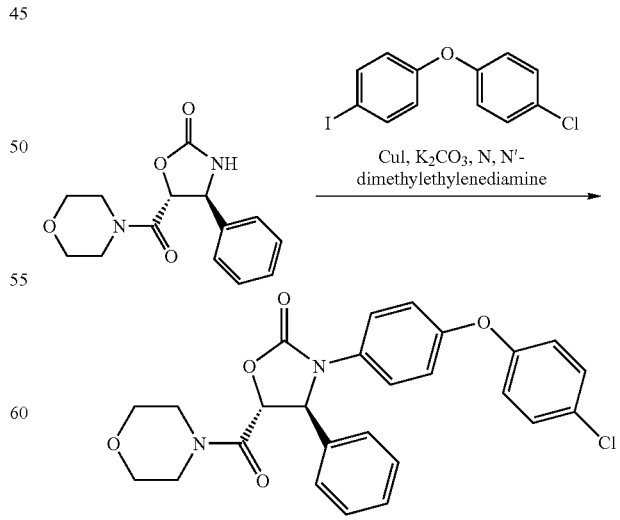

A solution of (4S,5R)-morpholin-2-oxo-4-phenyloxazolidine-5-carboxamide (obtained by the method described in Example 39 from (E)-1-morpholino-3-phenylprop-2-en-1-one) (131 mg, 0.47 mmol), aryl iodide (155 mg, 0.47 mmol), CuI (14 mg. 0.07 mmol), and potassium carbonate (118 mg, 0.85 mmol) in dry acetonitrile (0.6 mL) was purged with nitrogen in a tube fitted with a screw-cap. The diamine (15 µL, 0.14 mmol) was added and the reaction was heated to 100° C. with stirring overnight. The reaction mixture was cooled, diluted with ethyl acetate, filtered through a short plug of silica and concentrated. Purified on silica gel (0-40% ethyl aceate/hexanes) to give the title compound as a white solid. $^1$H NMR (CDCl$_3$) δ (ppm) 7.33-7.37 (m, 7H), 7.23-7.27 (m, 2H), 6.85-6.91 (m, 4H), 6.09 (d, 1H, J=5.8 Hz), 4.87 (d, 1H, J=5.8 Hz), 3.81-3.86 (m, 1H), 3.67-3.78 (m, 5H), 3.51-3.57 (m, 1H), 3.42-3.49 (m, 1H). HPLC-MS calculated $C_{26}H_{23}ClN_2O_5$ (M+H$^+$): 479.1, found: 479.1.

Example 101

(4S,5R)-3-(4-(4-chlorophenoxy)phenyl)-4-(3-fluorophenyl)-5-((phenylthio)methyl)oxazolidin-2-one

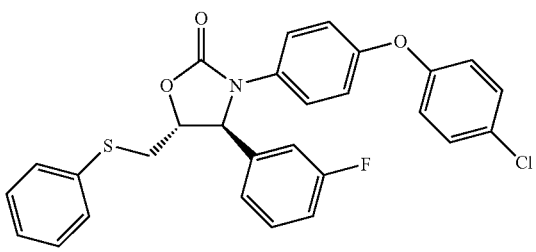 [SMILES: O=C1O[C@@H](CSc2ccccc2)[C@H](c2cccc(F)c2)N1c1ccc(Oc2ccc(Cl)cc2)cc1]

((4S,5R)-3-(4-(4-chlorophenoxy)phenyl)-4-(3-fluorophenyl)-2-oxooxazolidin-5-yl)methyl methanesulfonate (0.3 mmol, prepared by the methods described in example 34) was dissolved in ethanol (1.5 mL) and treated with benzenethiol (0.6 mmol) and triethylamine (0.6 mmol). The reaction mixture was heated to 75° C. for 8 h, then was cooled to room temperature, diluted with ethyl acetate, washed with 1M HCl and then purified on silica gel (10-30% ethyl acetate/hexanes) to give the title compound as a colorless oil. $^1$H NMR (CDCl$_3$) δ (ppm) 7.31-7.37 (m, 5H), 7.24-7.29 (m, 5H), 7.08 (d, 1H, J=7.7 Hz), 6.97-7.04 (m, 2H), 6.86-6.91 (m, 4H), 5.21 (d, 1H, J=4.0 Hz), (ddd, 1H, J=8.4, 4.0, 4.0 Hz), 3.46 (dd, 1H, J=14.2, 3.9 Hz), 3.22 (dd, 1H, J=14.2, 8.7 Hz). HPLC-MS calculated $C_{28}H_{21}ClFNO_3S$ (M+H$^+$): 506.1, found 506.1.

Example 106

(4S,5R)-3-(4-(4-chlorophenoxy)phenyl)-4-(3-fluorophenyl)-5-((phenylsulfonyl)methyl)oxazolidin-2-one

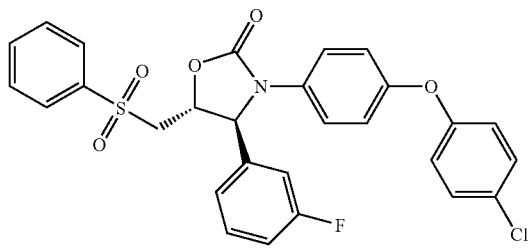 [SMILES: O=C1O[C@@H](CS(=O)(=O)c2ccccc2)[C@H](c2cccc(F)c2)N1c1ccc(Oc2ccc(Cl)cc2)cc1]

(4S,5R)-3-(4-(4-chlorophenoxy)phenyl)-4-(3-fluorophenyl)-5-((phenylthio)methyl)oxazolidin-2-one (Example 101, 0.3 mmol) was dissolved in dichloromethane (12 mL) and treated with m-chloroperbenzoic acid (77%, 1.2 mmol, 4 eq) at room temperature for 1 h. The reaction was diluted with dichloromethane and washed with aq. Sodium bicarbonate solution and then a solution of sodium metabisulfite (2×). The organic layer was dried over magnesium sulfate, filtered and concentrated to dryness. The product was purified on silica gel (30% ethyl acetate/hexanes) to give the title compound as a white solid. $^1$H NMR (acetone-d$_6$) δ (ppm) 7.95 (d, J=7.5 Hz, 2H), 7.79-7.75 (m, 1H), 7.68-7.64 (m, 2H), 7.49-7.44 (m, 3H), 7.38-7.31 (m, 4H), 7.16-7.11 (dt, J=8.5, 2.6 Hz, 1H), 6.97-6.93 (m, 4H), 5.61 (d, J=5.6 Hz, 1H), 4.81 (dd, J=11.9, 5.3 Hz, 1H), 4.14-4.02 (m, 2H); HPLC-MS calculated $C_{28}H_{21}ClFNO_5S$ (M+H$^+$) 538.1, found 538.1.

Example 109

(4S,5R)-3-(4-(4-chlorophenoxy)phenyl)-5-(chloromethyl)-4-(3-fluorophenyl)oxazolidin-2one

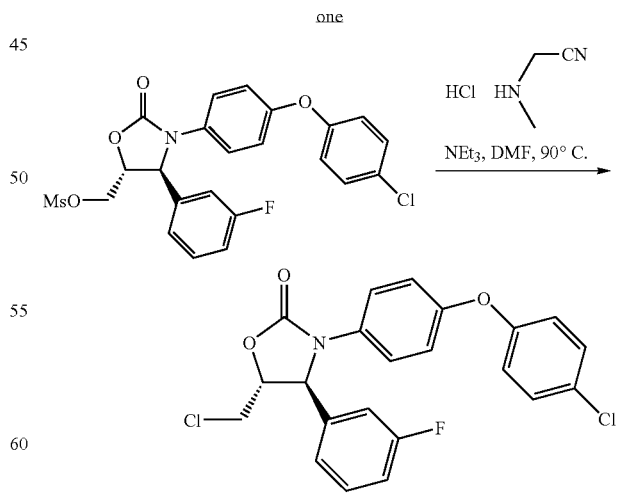

To a solution of the mesylate, prepared using the methods described in example 34 (35 mg, 0.07 mmol) and triethylamine (0.125 mL, 0.9 mmol) in DMF (0.3 mL) was added methylaminoacetonitrile hydrochloride (76 mg, 0.7 mmol).

The reaction was heated to 90° C. and stirred for 3 h. After cooling, and dilution with water and ethyl acetate, the organic was washed successively with 1 M HCl, brine, dried over magnesium sulfate, filtered and concentrated. HPLC purification (0-90% acetonitrile/water) gave 16 mg (53%) of the title compound as a colorless oil. $^1$H NMR (acetone-$d_6$) δ (ppm) 7.52-7.56 (m, 2H), 7.47 (ddd, 1H, J=8.1, 8.1, 6.0 Hz), 7.31-7.42 (m, 4H), 7.10-7.15 (m, 1H), 6.95-6.99 (m, 4H), 5.55 (d, 1H, J=4.8 Hz), 4.75 (q, 1H, J=4.4 Hz), 4.10-4.17 (m, 2H). HPLC-MS calculated $C_{22}H_{16}Cl_2FNO_3$ (M+H$^+$): 432.1, found: 432.1.

Example 135

N-(((4S,5S)-3-(4-chlorophenyl)-4-(3-fluorophenyl)-2-oxooxazolidin-5-yl)methyl)benzenesulfonamide

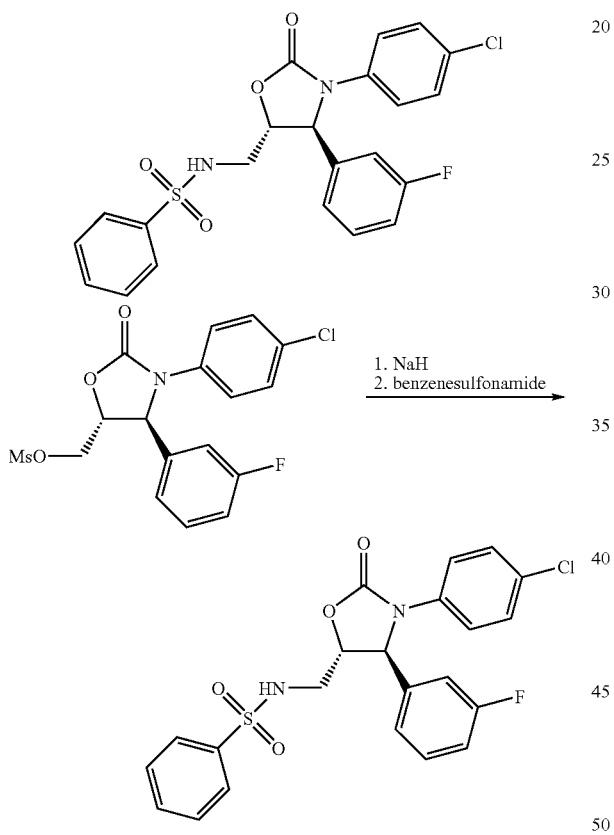

Sodium hydride (9 mg, 0.21 mmol) was added to a cooled (0° C.) solution of benzenesulfonamide (34 mg, 0.21 mmol) in DMF (1 mL) under nitrogen. The reaction mixture was stirred for 5 min, at which point the mesylate (from (4S,5R)-3-(4-chlorophenyl)-4-(3-fluorophenyl)-5-(hydroxymethyl)oxazolidin-2-one) (72 mg 0.18 mmol) was added and the cooling bath removed, and the reaction was heated to 80° C. with stirring for 4 h. The reaction mixture was cooled and quenched with saturated aqueous solution of NH$_4$Cl. Ethyl acetate was added and the organic phase was washed with brine, dried over magnesium sulfate, filtered and concentrated. HPLC purification (0-90% acetonitrile/water) gave the title compound (10 mg, 12%) as a colorless oil. $^1$H NMR (acetone-$d_6$) δ (ppm) 7.91-7.94 (m, 2H), 7.66-7.70 (m, 1H), 7.59-7.63 (m, 2H), 7.47-7.50 (m, 2H), 7.42-7.46 (m, 1H), 7.30-7.34 (m, 2H), 7.28 (d, 1H, J=7.8 Hz), 7.24 (ddd, 1H, J=9.7, 2.5, 2.5 Hz), 7.19 (t, 1H, J=6.5 Hz), 7.08-7.13 (m, 1H), 5.60 (d, 1H, J=5.8 Hz), 4.49 (ddd, 1H, J=5.7, 4.6, 4.6), 3.46-3.50 (m, 2H). HPLC-MS calculated $C_{22}H_{18}ClFN_2O_4S$ (M+H$^+$): 461.1, found: 461.1.

Example 149

(S)-3-[4-(6-Chloro-pyridazin-3-yloxy)-phenyl]-4-(3-trifluoromethyl-phenyl)-oxazolidin-2-one

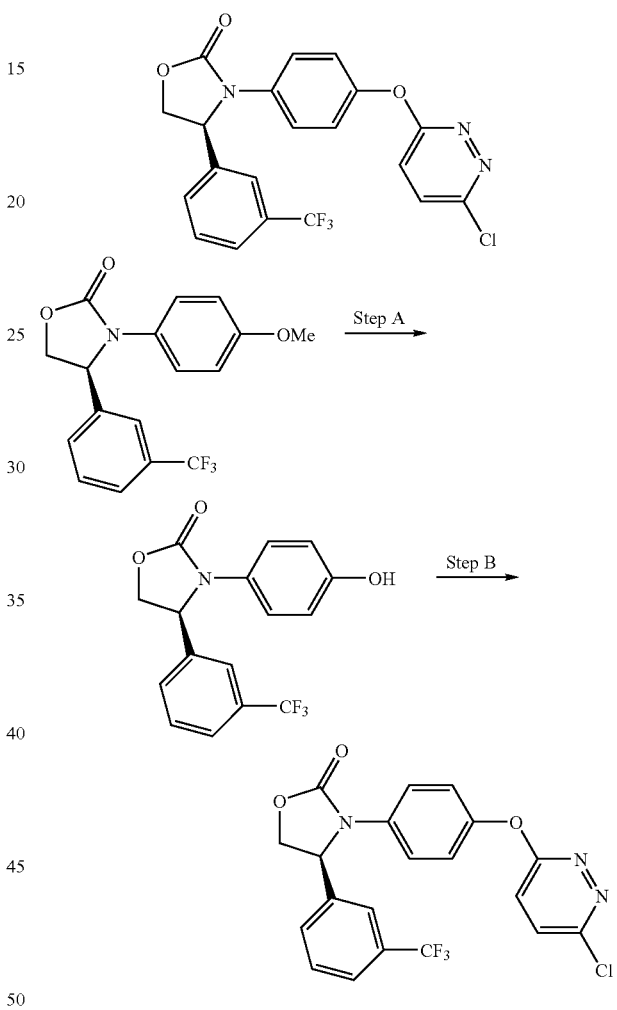

Step A: A solution of (S)-3-(4-methoxy-phenyl)-4-(3-trifluoromethyl-phenyl)-oxazolidin-2-one (57 mg, 0.169 mmol, prepared from (S)-4-(3-trifluoromethyl-phenyl)-oxazolidin-2-one and 1-iodo-4-methoxy-benzene using the same condition as example 4) in CH$_2$Cl$_2$ (1 mL) is cooled down to −78° C. in a dry ice bath when BBr$_3$ (0.371 mmol, 1M in CH$_2$Cl$_2$) is added into the mixture dropwise. After the addition, the mixture is allowed to warm up to 0° C. and stirred for 1 h. The reaction is then quenched at 0° C. by adding MeOH (0.5 mL) and diluted with water (2 mL). After extraction with CH$_2$Cl$_2$ (3×2 mL), the combined organic layers were concentrated and purified by a flash column chromatography (silica gel, EtOAc/hexane 0~50%) to provide the desired (S)-3-(4-hydroxy-phenyl)-4-(3-trifluoromethyl-phenyl)-oxazolidin-2-one (47 mg, 86%). HPLC-MS calculated for $C_{16}H_{12}F_3NO_3$ (M+H$^+$) 324.1, found 324.1.

Step B: A mixture of (S)-3-(4-hydroxy-phenyl)-4-(3-trifluoromethyl-phenyl)-oxazolidin-2-one (20 mg, 0.062 mmol), 3,6-dichloropyradazine (18.5 mg, 0.124 mmol) and K$_2$CO$_3$ (17 mg, 0.124 mmol) in DMF (0.5 mL) is heated to 80° C. for 2 h and then cooled down to room temperature. The mixture is then treated with saturated NH$_4$Cl aqueous solution (4 mL) and extracted with EtOAc (3×2 mL). The combined organic layers were then concentrated and purified by preparative LC/MS to provide the desired product (S)-3-[4-(6-Chloro-pyridazin-3-yloxy)-phenyl]-4-(3-trifluoromethyl-phenyl)-oxazolidin-2-one. $^1$H NMR (CDCl$_3$, 400 MHz) δ 7.50~7.63 (m, 4H), 7.47 (d, 1H), 7.42 (d, 2H), 7.09~7.15 (m, 3H), 5.46 (dd, 1H), 4.82 (t, 1H), 4.19 (dd, 1H); HPLC-MS calculated for C$_{20}$H$_{13}$ClF$_3$N$_3$O$_3$ (M+H$^+$) 436.1, found 436.1.

Example 151

(S)-1-[4-(4-Chloro-phenoxy)-phenyl]-5-(3-trifluoromethyl-phenyl)-imidazolidin-2-one

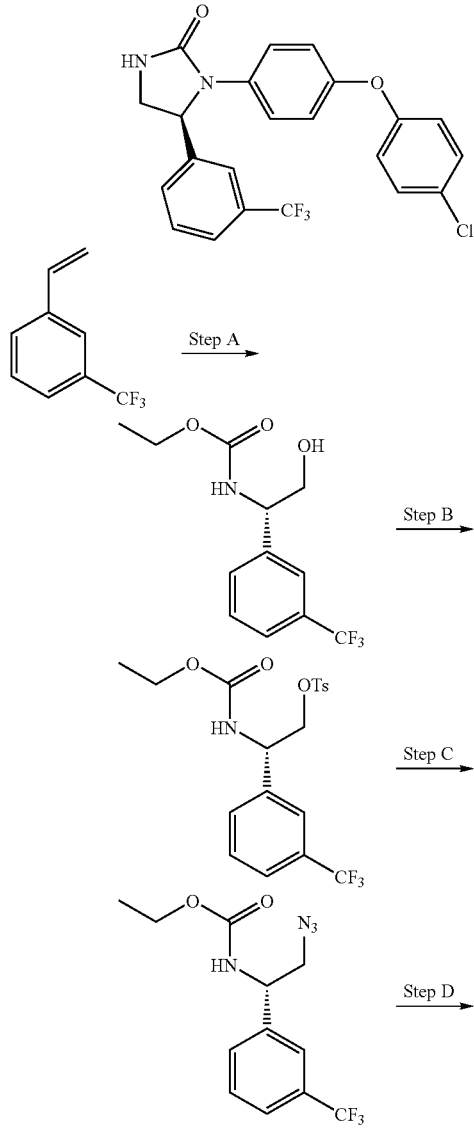

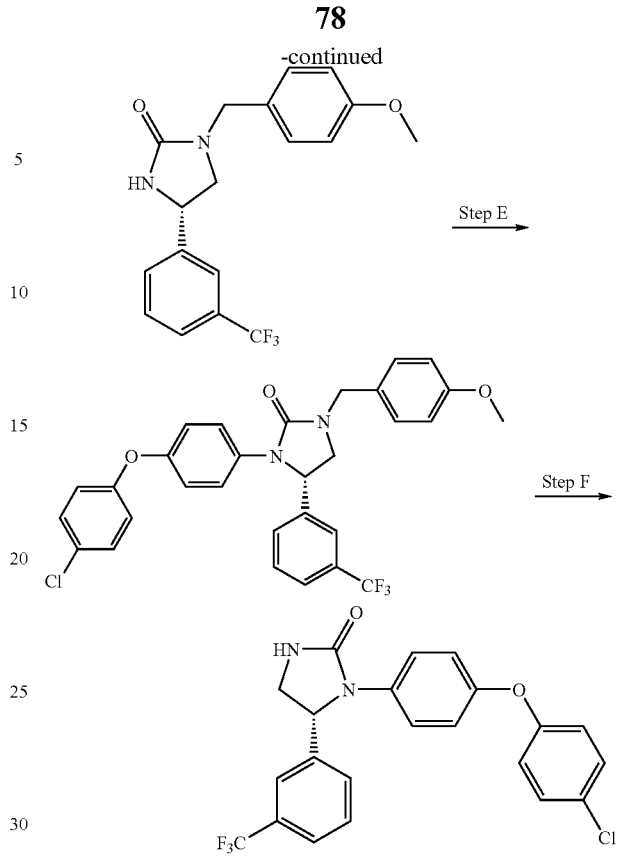

Step A: To a solution of urethane (7.76 g, 87.1 mmol) in n-propanol (~100 mL) is added freshly prepared NaOH (0.5 M, 174.2 mL, 87.1 mmol). The mixture is stirred at room temperature for 5 min before the addition of 1,3-dichloro-5,5-dimethyl-imidazolidine-2,4-dione (8.57 g, 43.5 mmol). After the resulted mixture is stirred at room temperature for 10 min, a solution of 3-trifluorostyrene (5.00 g, 29.0 mmol) and (DHQ)$_2$PHAL (564 mg, 0.72 mmol) in n-propanol (70 mL) is added into the solution. Right after the addition, K$_2$OsO$_4$.2H$_2$O (241 mg, 0.72 mmol) in 0.5 M NaOH (2 ml) is added into the mixture and the resulted brownish solution is stirred at room temperature for 14 h. The yellowish reaction mixture is then diluted with water (200 ml) and poured into a separatory funnel. After extraction with EtOAc (3×200 ml), the combined organic layer is washed with brine and dried (MgSO$_4$). After removing the drying agent, the solution is concentrated and purified by flash column chromatography (silica gel, EtOAc/hexane 0%~65%) to provide the desired (S)-[2-hydroxy-1-(3-trifluoromethyl-phenyl)-ethyl]-carbamic acid ethyl ester as colorless oil (6.1 g, 75%). $^1$H NMR (CDCl$_3$, 400 MHz) δ 7.58 (s, 1H), 7.56 (d, 1H), 7.52 (d, 1), 7.50 (t, 1H), 5.49 (d, 1H), 4.89 (br, 1H), 4.12 (m, 2H), 3.94 (br, 1H), 3.86 (br, 1H), 1.98 (br, 1H), 1.25 (t, 3H); HPLC-MS calculated for C$_{12}$H$_{14}$F$_3$NO$_3$ (M+H$^+$) 228.1, found 228.1.

Step B: To an ice cooled solution of [2-hydroxy-1-(3-trifluoromethyl-phenyl)-ethyl]-carbamic acid ethyl ester (6.1 g, 22.0 mmol) in CH$_2$Cl$_2$ (50 mL) is added p-toluenesulfonyl chloride (4.40 g, 23.1 mmol) and Et$_3$N (3.11 g, 30.8 mmol) slowly. After the addition, the mixture is allowed to warm up to room temperature and stirred for 14 h. The mixture is then poured into water (200 ml) and extracted with CH$_2$Cl$_2$ (3×100 ml). The combined organic layer is washed with brine and dried (MgSO$_4$). After removing the drying agent, the solution is concentrated and purified by a wash column (silica gel, 0~45% EtOAc/hexane) to provide the desired product (S)-toluene-4-sulfonic acid 2-ethoxycarbonylamino-2-(3-trifluoromethyl-phenyl)-ethyl ester as a colorless oil (7.5 g, 79%). $^1$H NMR (CDCl$_3$, 400 MHz) δ 7.64 (d, 2H), 7.53 (m, 1H), 7.43 (m, 3H), 7.27 (d, 2H), 5.40 (br, 1H), 5.03 (m, 1H), 4.31 (dd, 1H), 4.21 (dd, 1H), 4.14 (q, 2H), 2.43 (s, 3H), 1.26 (t, 3H); HPLC-MS calculated for C$_{19}$H$_{20}$F$_3$NO$_5$S (M+H$^+$) 432.1, found 432.1.

Step C: To a solution of (S)-toluene-4-sulfonic acid 2-ethoxycarbonylamino-2-(3-trifluoromethyl-phenyl)-ethyl ester (7.50 g, 17.4 mmol) in DMF (70 mL) is added NaN$_3$ (1.70 g, 26.1 mmol). The suspension is then heated to 70° C. for 2 h. and then cooled down to room temperature. The majority of the DMF is removed under vacuum and the resulted residue is treated with water (200 mL) and extracted with EtOAc (3×150 mL). The combined organic layer is washed with brine and dried (MgSO$_4$). After removing the drying agent, the solution is concentrated and purified by a wash column (silica gel, EtOAc/hexane 0%~45%) to provide the desired product (S)-[2-Azido-1-(3-trifluoromethyl-phenyl)-ethyl]-carbamic acid ethyl ester as colorless oil (4.6 g, 88%). $^1$H NMR (CDCl$_3$, 400 MHz) δ 7.56 (m, 2H), 7.52 (m, 2H), 5.29 (br, 1H), 4.98 (m, 1H), 4.13 (m, 2H), 3.73 (q, 1H), 3.67 (q, 2H), 1.25 (t, 3H); HPLC-MS calculated for C$_{12}$H$_{13}$F$_3$N$_4$O$_2$ (M+H$^+$) 303.1, found 303.1.

Step D: To a solution of (S)-[2-azido-1-(3-trifluoromethyl-phenyl)-ethyl]-carbamic acid ethyl ester (4.60 g, 15.2 mmol) in EtOH (200 mL) is added 10% Pd/C (~200 mg). The resulted mixture is then degassed and filled with H$_2$ and stirred at room temperature under H$_2$ for 14 h. The mixture is then filtered through a pat of Celite to remove the Pd/C and washed with EtOH (3×10 mL). The filtrate is concentrate to provide the crude (S)-[2-amino-1-(3-trifluoromethyl-phenyl)-ethyl]-carbamic acid ethyl ester (~4.0 g, 95%), which is used for next step without further purification.

Crude (S)-[2-amino-1-(3-trifluoromethyl-phenyl)-ethyl]-carbamic acid ethyl ester from above is dissolved in anhydrous EtOH (100 mL). p-Anisaldehyde (2.07 g, 15.2 mmol) is added into the solution and stirred at room temperature for 5 h before the addition of NaBH$_4$ (0.82 g, 21.8 mmol) at 0° C. The mixture is then warmed up to room temperature and stirred for 14 hr. After the solvent is removed under vacuum, the residue is treated with saturated NH$_4$Cl aqueous solution (50 mL) and extracted with EtOAc (3×150 mL). The combined organic layer is washed with brine and dried (MgSO$_4$). After removing the drying agent, the solution is concentrated to provide the crude (S)-[2-(4-methoxy-benzylamino)-1-(3-trifluoromethyl-phenyl)-ethyl]-carbamic acid ethyl ester as colorless oil (~6.0 g) which is used directly for next step.

The crude material obtained from above (6.0 g) is dissolved in DMF (75 mL) and transferred into a microwave reaction vessel and heated to 220° C. for 15 min in a microwave reactor. The solvent DMF is removed under vacuum and the residue is treated with water (200 mL) and extracted with EtOAc (3×150 mL). The combined organic layer is washed with brine and dried (MgSO$_4$). After removing the drying agent, the solution is concentrated and purified by a wash column (silica gel, EtOAc/hexane 0%~85%) to provide the desired product (S)-1-(4-methoxy-benzyl)-4-(3-trifluoromethyl-phenyl)-imidazolidin-2-one as colorless oil (4.7 g, 92%). $^1$H NMR (CDCl$_3$, 400 MHz) δ 7.51 (m, 4H), 7.18 (d, 2H), 6.85 (d, 2H), 5.22 (br, 1H), 4.79 (t, 1H), 4.40 (d, 1H), 4.27 (d, 1H), 3.79 (s, 3H), 3.68 (t, 1H), 3.05 (dd, 1H); HPLC-MS calculated for C$_{18}$H$_{17}$F$_3$N$_2$O$_2$ (M+H$^+$) 351.1, found 351.1.

Step E: A mixture of (S)-1-(4-methoxy-benzyl)-4-(3-trifluoromethyl-phenyl)-imidazolidin-2-one (1.7 g, 4.86 mmol), 4-(4-clorophenoxy)-iodobenzene, (1.77 g, 5.35 mmol), CuI (93 mg, 0.49 mmol), trans-N,N'-dimethyl-cyclohexane-1,2-diamine (119 mg, 0.97 mmol) and K$_3$PO$_4$ (2.06 g, 9.72 mmol) in DMF (17 mL) is degassed and heated to 110° C. under N$_2$ for 16 h. After cooling down to room temperature, the mixture was poured into water (200 mL) and extracted with EtOAc (3×50 mL). The combined organic layer is washed with brine and dried (MgSO$_4$). After removing the drying agent, the solution is concentrated and purified by flash column chromatography (silica gel, EtOAc/hexane 0%~80%) to provide the desired product (S)-3-[4-(4-chloro-phenoxy)-phenyl]-1-(4-methoxy-benzyl)-4-(3-trifluoromethyl-phenyl)-imidazolidin-2-one (example 154) as a white solid (2.1 g, 78%). $^1$H NMR (CDCl$_3$, 400 MHz) δ 7.51 (m, 2H), 7.44 (m, 2H), 7.34 (d, 2H), 7.23 (m, 4H), 6.87 (m, 6H), 5.17 (dd, 1H), 4.53 (d, 1H), 4.37 (d, 1H), 3.79 (s, 3H), 3.76 (t, 1H), 3.07 (dd, 1H); HPLC-MS calculated for C$_{30}$H$_{24}$ClF$_3$N$_2$O$_3$ (M+H$^+$) 553.1, found 553.1.

Step F: (S)-3-[4-(4-chloro-phenoxy)-phenyl]-1-(4-methoxy-benzyl)-4-(3-trifluoromethyl-phenyl)-imidazolidin-2-one (2.1 g, 3.8 mmol) is treated with TFA (15 mL) at room temperature for 14 h. The excess of TFA is removed under vacuum and the residue is treated with saturated NaHCO$_3$ aqueous solution (50 mL) and extracted with EtOAc (3×100 mL). The combined organic layer is washed with brine and dried (MgSO$_4$). After removing the drying agent, the solution is concentrated and purified by flash column chromatography (silica gel, EtOAc/hexane 0%~70%) to provide the desired product (S)-1-[4-(4-chloro-phenoxy)-phenyl]-5-(3-trifluoromethyl-phenyl)-imidazolidin-2-one as white crystals (1.5 g, 91%). $^1$H NMR (CDCl$_3$, 400 MHz) δ 7.45~7.58 (m, 4H), 7.29 (d, 2H), 7.23 (d, 2H), 6.87 (m, 4H), 5.34 (dd, 1H), 4.82 (br, 1H), 4.01 (t, 1H), 3.35 (dd, 1H); HPLC-MS calculated for C$_{22}$H$_{16}$ClF$_3$N$_2$O$_2$ (M+H$^+$) 433.1, found 433.1.

Example 153

(S)-3-[6-(4-Chloro-phenoxy)-pyridin-3-yl]-4-(3-trifluoromethyl-phenyl)-oxazolidin-2-one

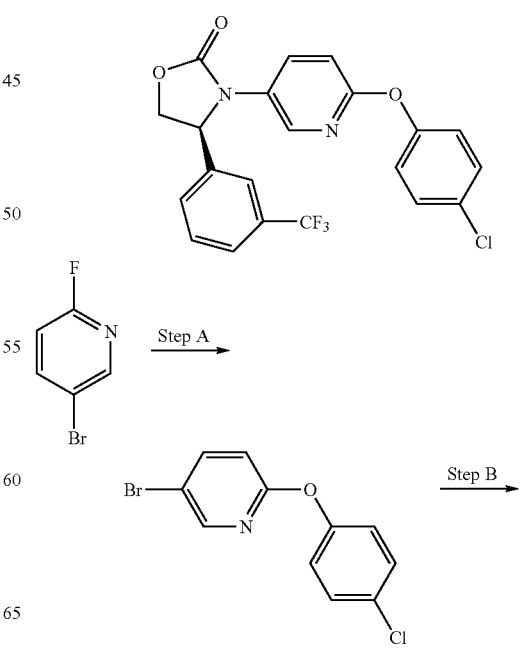

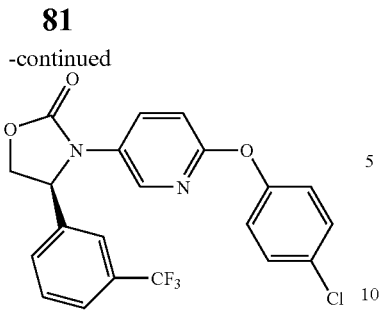

Step A: To a solution of 5-bromo-2-fluoro-pyridine (176 mg, 1.00 mmol) in DMF (2 mL) is added 4-chlorophenol (141 mg, 1.1 mmol) and $K_2CO_3$ (209 mg, 1.5 mmol). The resulted mixture is then heated to 85° C. and stirred for 14 h. the mixture is cooled down to room temperature and treated with saturated $NH_4Cl$ aqueous solution (15 mL) and extracted with EtOAc (3×20 mL). The combined organic layer is washed with brine and dried ($MgSO_4$). After removing the drying agent, the solution is concentrated and purified by flash column chromatography (silica gel, EtOAc/hexane 0%~30%) to provide the desired product 5-bromo-2-(4-chloro-phenoxy)-pyridine (220 mg, 78%). HPLC-MS calculated for $C_{11}H_7BrClNO$ (M+H$^+$) 283.9, found 283.9.

Step B: (S)-3-[6-(4-Chloro-phenoxy)-pyridin-3-yl]-4-(3-trifluoromethyl-phenyl)-oxazolidin-2-one is prepared from (S)-4-(3-trifluoromethyl-phenyl)-oxazolidin-2-one and 5-bromo-2-(4-chloro-phenoxy)-pyridine using the same conditions as example 4. $^1$H NMR (CDCl$_3$, 400 MHz) δ 8.03 (dd, 1H), 7.88 (d, 1H), 7.62 (d, 1H), 7.45~7.55 (m, 3H), 7.3 (d, 2H), 7.01 (d, 2H), 5.40 (dd, 1H), 4.85 (t, 1H), 4.24 (dd, 1H); HPLC-MS calculated for $C_{21}H_{15}ClF_3N_3O_2$ (M+H$^+$) 435.1, found 435.1.

Example 155

(S)-3-[5-(4-Chloro-phenoxy)-pyrazin-2-yl]-4-(3-trifluoromethyl-phenyl)-oxazolidin-2-one

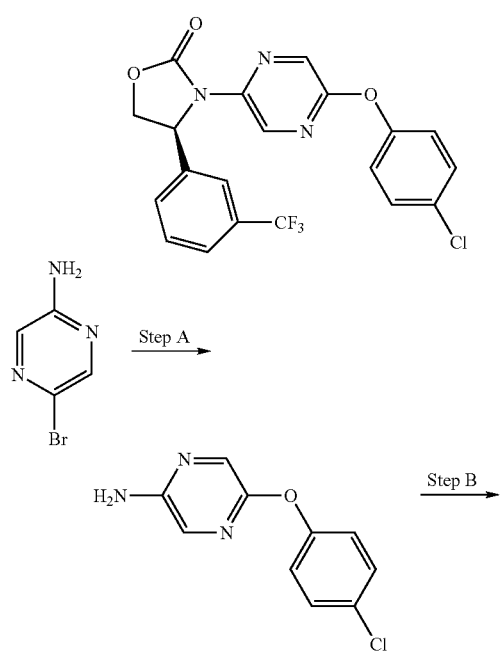

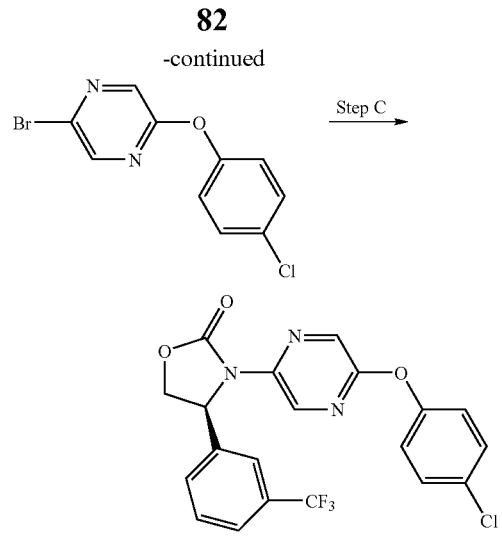

Step A: A mixture of 5-amino-2-bromopyrazine (2.0 g, 11.5 mmol), 4-chlorophenol (1.61 g, 12.5 mmol), $Cs_2CO_3$ (5.0 g, 15.4 mmol), CuI (0.21 g, 1.1 mmol), N,N-dimethylglycin (0.11 g, 1.1 mmol) in dioxane (22 mL) is degassed and heated to 115° C. under $N_2$ for 2 h. After cooling down to room temperature, the mixture is diluted with EtOAc (200 mL) and water (200 mL). The solid is removed by filtration and washed with EtOAc (2×10 mL). The filtrate is put into a separatory funnel for extraction (EtOAc, 3×100 mL). The combined organic layer is washed with brine and dried ($MgSO_4$). After removing the drying agent, the solution is concentrated and purified by flash column chromatography (silica gel, EtOAc/hexane 0%~45%) to provide the desired product 5-(4-chloro-phenoxy)-pyrazin-2-ylamine (1.8 g, 74%). HPLC-MS calculated for $C_{10}H_8ClN_3O$ (M+H$^+$) 222.0, found 222.0.

Step B: To a mixture of 5-(4-chloro-phenoxy)-pyrazin-2-ylamine (1.0 g, 4.52 mmol), CuBr (0.65 g, 4.52 mmol) and CuBr$_2$ (3.03 g, 13.6 mmol) in DMF (20 mL) at 0° C. is added tert-butyl nitrite (1.4 g, 13.6 mmol) dropwise. After the resulted mixture is stirred at room temperature for 14 h, it is poured into a 0.05 N HCl aqueous solution (200 mL) and extracted with EtOAc (3×100 mL). The combined organic layer is washed with brine and dried ($MgSO_4$). After removing the drying agent, the solution is concentrated and purified by flash column chromatography (silica gel, EtOAc/hexane 0%~30%) to provide the desired product 2-bromo-5-(4-chloro-phenoxy)-pyrazine as yellowish crystal (1.2 g, 93%). HPLC-MS calculated for $C_{10}H_6BrClN_2O$ (M+H$^+$) 284.9, found 284.9.

Step C: (S)-3-[5-(4-Chloro-phenoxy)-pyrazin-2-yl]-4-(3-trifluoromethyl-phenyl)-oxazolidin-2-one is prepared from 4-(3-trifluoromethyl-phenyl)-oxazolidin-2-one and 2-bromo-5-(4-chloro-phenoxy)-pyrazine using the same conditions as example 4. $^1$H NMR (CDCl$_3$, 400 MHz) δ 8.98 (d, 1H), 7.95 (d, 1H), 7.47~7.62 (m, 4H), 7.34 (d, 2H), 7.04 (d, 2H), 5.82 (dd, 1H), 4.88 (t, 1H), 4.35 (dd, 1H); HPLC-MS calculated for $C_{20}H_{13}ClF_3N_3O_3$ (M+H$^+$) 436.1, found 436.1.

Example 163

(S)-3-[4-(4-Chloro-phenoxy)-phenyl]-1-(2-methane-sulfonyl-ethyl)-4-(3-trifluoromethyl-phenyl)-imidazolidin-2-one

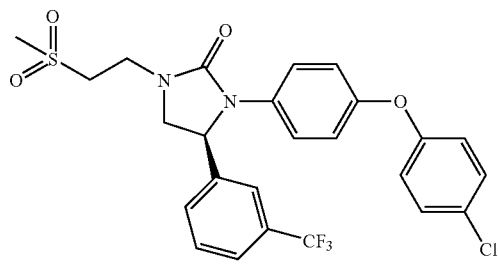 [SMILES: CS(=O)(=O)CCN1C[C@H](c2cccc(C(F)(F)F)c2)N(c2ccc(Oc3ccc(Cl)cc3)cc2)C1=O]

A solution of (S)-1-[4-(4-chloro-phenoxy)-phenyl]-5-(3-trifluoromethyl-phenyl)-imidazolidin-2-one (1.5 g, 3.47 mmol) in anhydrous DMF (20 mL) is cooled down to 0° C. in an ice bath when NaH (194 mg, 60% in mineral oil, 4.86 mmol) is added into the solution portion wise. After the addition, the mixture is stirred at 0° C. for 10 min when a solution of vinyl methylsulfone (736 mg, 6.94 mmol) in DMF (5 mL) is added into the mixture. The resulted mixture is allowed to warm up to room temperature and stir for 1 h. The mixture is then poured into 10% $NH_4Cl$ aqueous solution (~300 mL) and extracted with EtOAc (3×100). The combined organic layer is washed with brine and dried ($MgSO_4$). After removing the drying agent, the solution is concentrated and purified by flash column chromatography (silica gel, EtOAc/hexane 0%~100%) to provide the desired product (S)-3-[4-(4-chloro-phenoxy)-phenyl]-1-(2-methanesulfonyl-ethyl)-4-(3-trifluoromethyl-phenyl)-imidazolidin-2-one as white solid (1.18 g, 63%) with the recovery of the starting material (S)-1-[4-(4-chloro-phenoxy)-phenyl]-5-(3-trifluoromethyl-phenyl)-imidazolidin-2-one (~300 mg). $^1$H NMR ($CDCl_3$, 400 MHz) δ 7.45~7.58 (m, 4H), 7.29 (d, 2H), 7.23 (d, 2H), 6.87 (m, 4H), 5.27 (dd, 1H), 4.07 (t, 1H), 3.80~4.10 (m, 2H), 3.28~3.40 (m, 3H), 3.01 (s, 3H); HPLC-MS calculated for $C_{25}H_{22}ClF_3N_2O_4S$ (M+H$^+$) 539.1, found 539.1.

Example 164

(S)-2-(3-(4-(4-chlorophenoxy)phenyl)-2-oxo-4-(3-(trifluoromethyl)phenyl)imidazolidin-1-yl)ethanesulfonamide

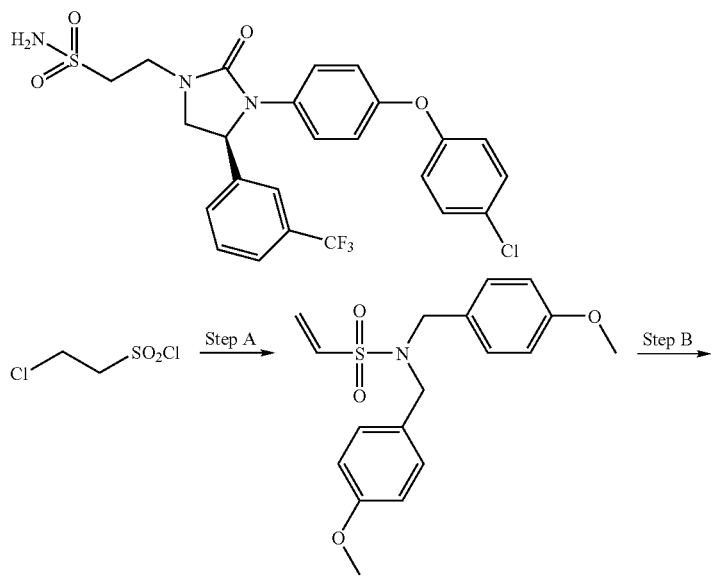

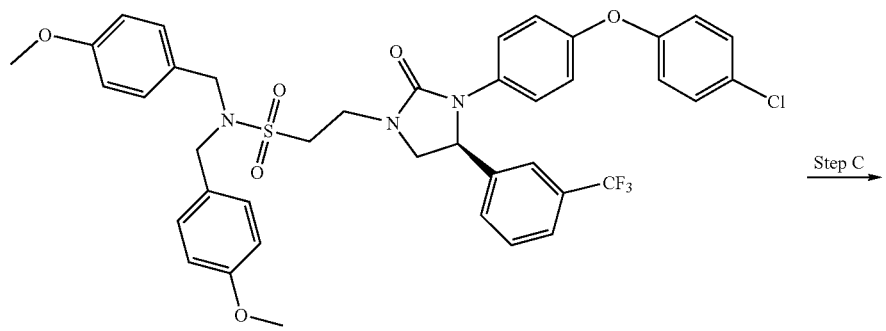

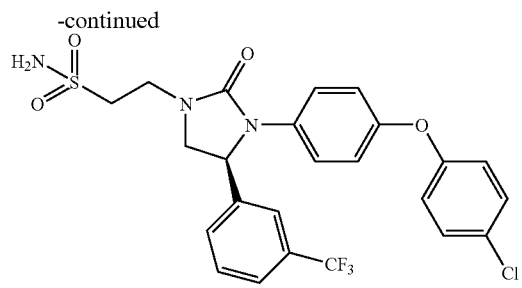

Step A: To a solution of 2-chloro-ethanesulfonyl chloride (223 mg, 1.37 mmol) in anhydrous $CH_2Cl_2$ (3 mL) at 0° C. is added bis-(4-methoxy-benzyl)-amine (370 mg, 1.44 mmol) followed by $Et_3N$ (304 mg, 3.01 mmol). After the addition, the mixture is allowed to warm up to room temperature and stirred for 5 h. The mixture is then poured into water (5 mL) and extracted with $CH_2Cl_2$ (3×5 mL). The combined organic layer is concentrated and purified by flash column chromatography (silica gel, EtOAc/hexane 0%~30%) to provide the desired product N,N-bis(4-methoxybenzyl)ethenesulfonamide as colorless oil. (300 mg, 63%).

Step B: (S)-2-(3-(4-(4-chlorophenoxy)phenyl)-2-oxo-4-(3-(trifluoromethyl)phenyl)-imidazolidin-1-yl)-N,N-bis(4-methoxybenzyl)ethanesulfonamide is prepared using the methods described in example 163. HPLC-MS calculated for $C_{40}H_{37}ClF_3N_3O_6S$ (M+H$^+$) 780.2, found 780.2.

Step C: A solution of (S)-2-(3-(4-(4-chlorophenoxy)phenyl)-2-oxo-4-(3-(trifluoromethyl)-phenyl)imidazolidin-1-yl)-N,N-bis(4-methoxybenzyl)ethanesulfonamide (2.2 g, 2.82 mmol) in TFA (30 mL) is stirred at room temperature for 14 h. Excess of TFA is removed under vacuum. The residue is treated with saturated $NaHCO_3$ aqueous solution (30 mL) and extracted with EtOAc (3×50 mL). The combined organic layer is washed with brine and dried ($MgSO_4$). After removing the drying agent, the solution is concentrated and purified by flash column chromatography (silica gel, EtOAc/hexane 0%~90%) to provide the desired product (S)-2-(3-(4-(4-chlorophenoxy)phenyl)-2-oxo-4-(3-(trifluoromethyl)phenyl)-imidazolidin-1-yl)ethanesulfonamide as white solid (1.2 g, 83%). $^1$H NMR (CDCl$_3$, 400 MHz) δ 7.55~7.62 (m, 3H), 7.48 (t, 1H), 7.24 (d, 2H), 7.22 (d, 2H), 6.85 (m, 4H), 5.47 (s, 2H), 5.28 (dd, 1H), 3.90~4.03 (m, 3H), 3.40 (dd, 1H), 3.28~3.35 (m, 2H); HPLC-MS calculated for $C_{24}H_{21}ClF_3N_3O_4S$ (M+H$^+$) 540.1, found 540.1.

Example 165

2-(3-(4-(4-chlorophenoxy)phenyl)-2-oxo-4-(3-(trifluoromethyl)phenyl)imidazolidin-1-yl)acetic acid

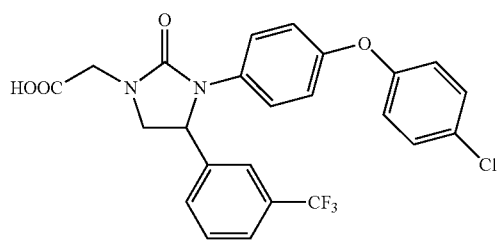 [SMILES: O=C(O)CN1CC(c2cccc(C(F)(F)F)c2)N(c2ccc(Oc3ccc(Cl)cc3)cc2)C1=O]

To a solution of ethyl 2-(3-(4-(4-chlorophenoxy)phenyl)-2-oxo-4-(3-(trifluoromethyl)phenyl)imidazolidin-1-yl)acetate (12.0 mg, 0.023 mmol) in EtOH (0.5 mL) is added 1N NaOH aqueous solution (115 μL, 0.12 mmol). The mixture is stirred at room temperature overnight before removal of the solvent. The residue is purified by preparatory LC/MS to provide the title compound; HPLC-MS calculated for $C_{26}H_{22}ClF_3N_2O_4$ (M+H$^+$) 491.1, found 491.1.

Example 166

1-((1H-tetrazol-5-yl)methyl)-3-(4-(4-chlorophenoxy)phenyl)-4-(3-(trifluoromethyl)phenyl)imidazolidin-2-one

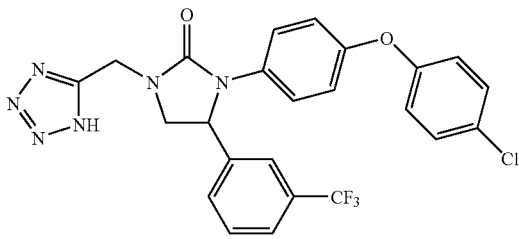 [SMILES: O=C1N(Cc2nnn[nH]2)CC(c2cccc(C(F)(F)F)c2)N1c1ccc(Oc2ccc(Cl)cc2)cc1]

To a solution of 2-(3-(4-(4-chlorophenoxy)phenyl)-2-oxo-4-(3-(trifluoromethyl)phenyl)-imidazolidin-1-yl)acetonitrile (21.8 mg, 0.046 mmol) in DMF (1.0 mL) are added NaN$_3$ (60 mg, 0.92 mmol) and NH$_4$Cl (49 mg, 0.92 mmol). The reaction mixture is heated at 220° C. for 15 min in a microwave reactor. After cooling down to room temperature and removal of the solvent, the residue is purified by preparatory LC/MS to provide the title compound; $^1$H NMR (CDCl$_3$, 400 MHz) δ 7.58-7.45 (m, 4H), 7.26 (d, 2H), 7.19 (d, 2H), 6.87 (m, 4H), 5.24 (dd, 1H), 4.95 (d, 1H), 4.69 (d, 1H), 4.10 (t, 1H), 3.48 (dd, 1H); HPLC-MS calculated for $C_{24}H_{18}ClF_3N_6O_2$ (M+H$^+$) 515.1, found 515.1.

Example 167

2-(3-(4-(4-chlorophenoxy)phenyl)-2-oxo-4-(3-(trifluoromethyl)phenyl)imidazolidin-1-yl)-N-propylacetamide

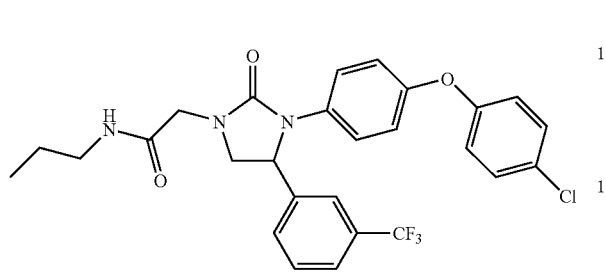

To a solution of 2-(3-(4-(4-chlorophenoxy)phenyl)-2-oxo-4-(3-(trifluoromethyl)phenyl)-imidazolidin-1-yl)acetic acid (16.0 mg, 0.0326 mmol), HATU (18.6 mg, 0.0489 mmol) and $^i$Pr$_2$NEt (17.0 µL, 0.0978 mmol) in DMF (0.5 mL) is added propylamine (5.36 µL, 0.0652 mmol). The reaction mixture is stirred at room temperature overnight before removal of the solvent. The residue is purified by preparative LC/MS to provide the title compound; HPLC-MS calculated for $C_{27}H_{25}ClF_3N_3O_3$ (M+H$^+$) 532.2, found 532.2.

Example 169

2-(2-(3-(4-(4-chlorophenoxy)phenyl)-2-oxo-4-(3-(trifluoromethyl)phenyl)-imidazolidin-1-yl)acetamido)acetic acid

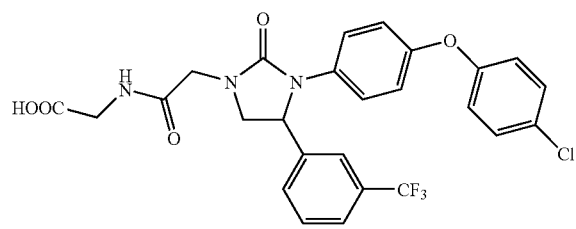 [SMILES: O=C(O)CNC(=O)CN1CC(c2cccc(C(F)(F)F)c2)N(c2ccc(Oc3ccc(Cl)cc3)cc2)C1=O]

tert-Butyl 2-(2-(3-(4-(4-chlorophenoxy)phenyl)-2-oxo-4-(3-(trifluoromethyl)phenyl)-imidazolidin-1-yl)acetamido)acetate (20.0 mg, 0.0332 mmol) is dissolved in a mixture solvent of DCM (0.4 mL) and TFA (0.4 mL). The reaction mixture is stirred at room temperature for 3 h before removal of the solvent. The residue is purified by reparative LC/MS to provide the title compound; HPLC-MS calculated for $C_{26}H_{21}ClF_3N_3O_5$ (M+H$^+$) 548.1, found 548.1.

Example 172

3-(4-(4-chlorophenoxy)phenyl)-1-(2-hydroxyethyl)-4-(3-(trifluoromethyl)phenyl)-imidazolidin-2-one

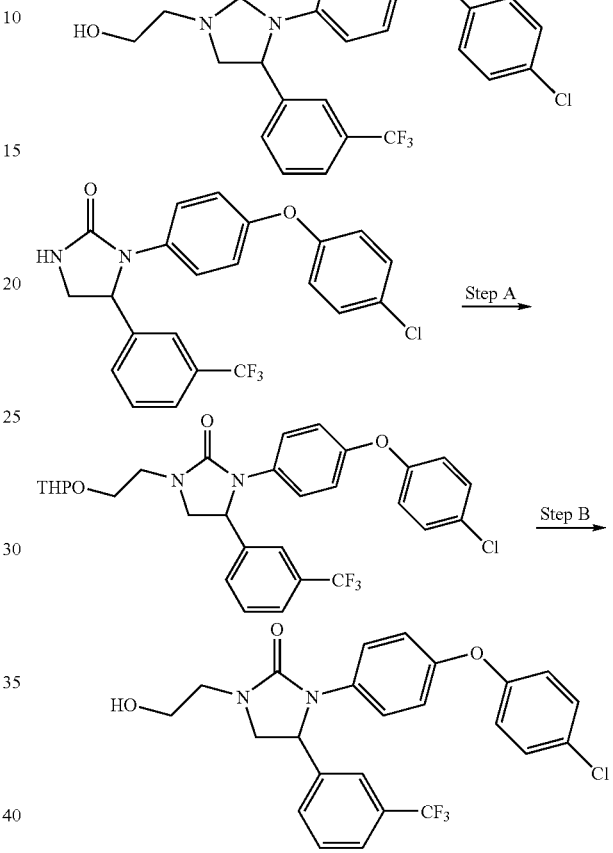

Step A: To a solution of 1-(4-(4-chlorophenoxy)phenyl)-5-(3-(trifluoromethyl)phenyl)imidazolidin-2-one (300 mg, 0.69 mmol) in DMF (3.5 mL) at 0° C. is slowly added NaH (60% dispersion in mineral oil, 33.3 mg, 0.83 mmol). The reaction mixture is stirred at 0° C. for 30 min before 2-(2-bromoethoxy)tetrahydro-2H-pyran (208 µL, 1.38 mmol) is added. The mixture is then stirred at room temperature for 2 h before quenched with H$_2$O (40 mL) and extracted with EtOAc (3×20 mL). The combined organic layer is washed with brine and dried over MgSO$_4$. After removal of the drying agent and solvent, the crude 3-(4-(4-chlorophenoxy)phenyl)-1-(2-(tetrahydro-2H-pyran-2-yloxy)ethyl)-4-(3-(trifluoromethyl)phenyl)imidazolidin-2-one is used in next step without further purification.

Step B: The crude product from Step A is dissolved in MeOH (3.5 mL) and p-TSA (6.6 mg, 0.035 mmol) is added. The reaction mixture is stirred at room temperature for 2 h before removal of the solvent. The residue is purified by silica gel chromatography (40~90% EtOAc/Hexanes) to provide the title compound (271 mg, 82% in two steps) as a colorless oil-like product; $^1$H NMR (CDCl$_3$, 400 MHz) δ 7.57-7.44 (m, 4H), 7.29 (d, 2H), 7.23 (d, 2H), 6.86 (m, 4H), 5.27 (dd, 1H), 4.06 (t, 1H), 3.85 (t, 2H), 3.55 (m, 1H), 3.43 (m, 1H), 3.36 (dd, 1H); HPLC-MS calculated for $C_{24}H_{20}ClF_3N_2O_3$ (M+H$^+$) 477.1, found 477.1.

Example 173

1-(4-(4-chlorophenoxy)phenyl)-5-(3-(trifluoromethyl)phenyl)imidazolidin-2-imine

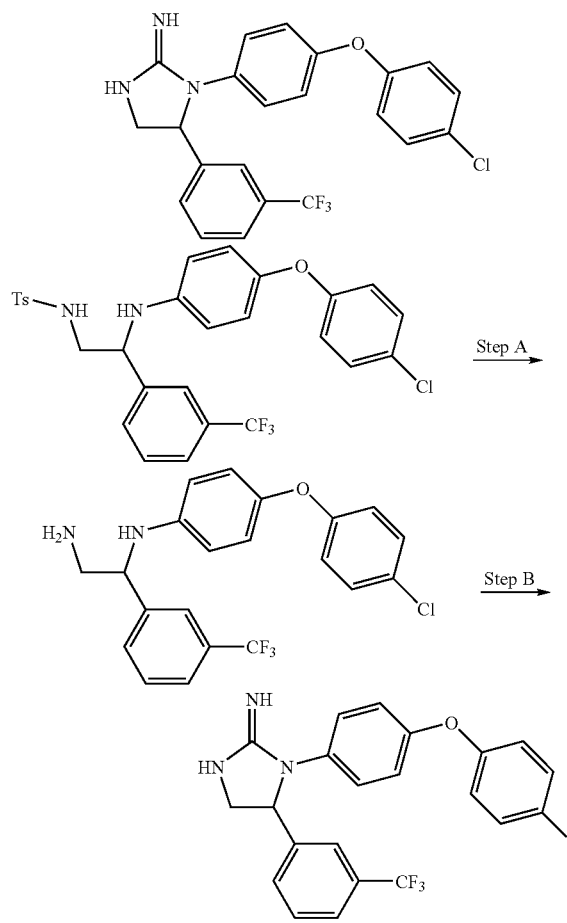

Step A: A solution of N-(2-(4-(4-chlorophenoxy)phenylamino)-2-(3-(trifluoromethyl)phenyl)ethyl)-4-methylbenzenesulfonamide (358 mg, 0.638 mmol) and phenol (180 mg, 1.92 mmol) in 30 wt % HBr in acetic acid (3.5 mL) is heated at 80° C. for 2 h. After cooling down to room temperature, most of the solvent is removed under vacuo. The residue is then quenched with cold saturated NaHCO$_3$ aqueous solution (40 mL) and extracted with EtOAc (3×20 mL). The combined organic layer is concentrated and purified by reverse phase HPLC to provide N$^1$-(4-(4-chlorophenoxy)phenyl)-1-(3-(trifluoromethyl)phenyl)ethane-1,2-diamine (128 mg, 49% yield) as a light yellow oil-like product.

Step B: To a solution of N$^1$-(4-(4-chlorophenoxy)phenyl)-1-(3-(trifluoromethyl)phenyl)ethane-1,2-diamine (20.0 mg, 0.0492 mmol) in EtOH (0.5 mL) are added cyanogen bromide (6.2 mg, 0.0590 mmol) and TEA (8.22 µL, 0.0590 mmol). The reaction mixture is heated at 80° C. for 2 h before removal of the solvent. The residue is purified by preparatory LC/MS to provide the title compound; $^1$H NMR (CDCl$_3$, 400 MHz) δ 7.65-7.50 (m, 4H), 7.33 (d, 2H), 7.01 (d, 2H), 6.94 (m, 4H), 5.24 (dd, 1H), 4.30 (t, 1H), 3.79 (dd, 1H); HPLC-MS calculated for C$_{22}$H$_{17}$ClF$_3$N$_3$O (M+H$^+$) 432.1, found 432.1.

Example 174

1-(4-(4-chlorophenoxy)phenyl)-5-(3-(trifluoromethyl)phenyl)imidazolidine-2-thione

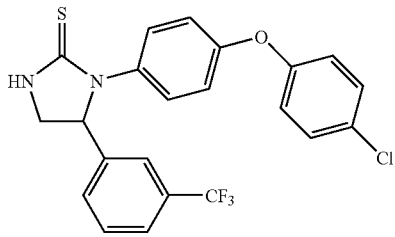 [SMILES: FC(F)(F)c1cccc(C2CNC(=S)N2c2ccc(Oc3ccc(Cl)cc3)cc2)c1]

To a solution of N$^1$-(4-(4-chlorophenoxy)phenyl)-1-(3-(trifluoromethyl)phenyl)ethane-1,2-diamine (127 mg, 0.312 mmol) in EtOH (2.0 mL) are added CS$_2$ (188 µL, 3.12 mmol) and $^i$Pr$_2$NEt (272 µL, 1.56 mmol). The reaction mixture is heated at 80° C. overnight before removal of the solvent. The residue is purified by silica gel chromatography (0~40% EtOAc/Hexanes) to provide the title compound (95.9 mg, 69% yield) as a white solid product; HPLC-MS calculated for C$_{22}$H$_{16}$ClF$_3$N$_2$OS (M+H$^+$) 449.1, found 449.1.

Example 175

2-(3-(4-(4-chlorophenoxy)phenyl)-2-oxo-4-(3-(trifluoromethyl)phenyl)imidazolidin-1-yl)ethyl methanesulfonate

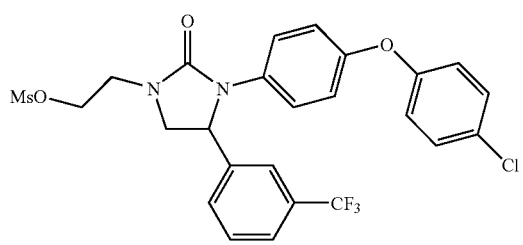 [SMILES: CS(=O)(=O)OCCN1CC(c2cccc(C(F)(F)F)c2)N(c2ccc(Oc3ccc(Cl)cc3)cc2)C1=O]

To a solution of 3-(4-(4-chlorophenoxy)phenyl)-1-(2-hydroxyethyl)-4-(3-(trifluoromethyl)phenyl)imidazolidin-2-one (340 mg, 0.713 mmol) in DCM (3.5 mL) at 0° C. are added MsCl (111 µL, 1.43 mmol) and TEA (199 µL, 1.43 mmol). The reaction mixture is stirred at room temperature overnight before removal of the solvent. The residue is taken in H$_2$O (40 mL) and extracted with EtOAc (3×20 mL). The combined organic layer is washed with brine, dried over MgSO$_4$, concentrated, and purified by silica gel chromatography (20~70% EtOAc/hexanes) to provide the title compound (337 mg, 85% yield) as a colorless oil-like product; HPLC-MS calculated for C$_{25}$H$_{22}$ClF$_3$N$_2$O$_5$S (M+H$^+$) 555.1, found 555.1.

Example 176

1-(4-(4-chlorophenoxy)phenyl)-5-(3-(trifluoromethyl)phenyl)imidazolidin-2-one oxime

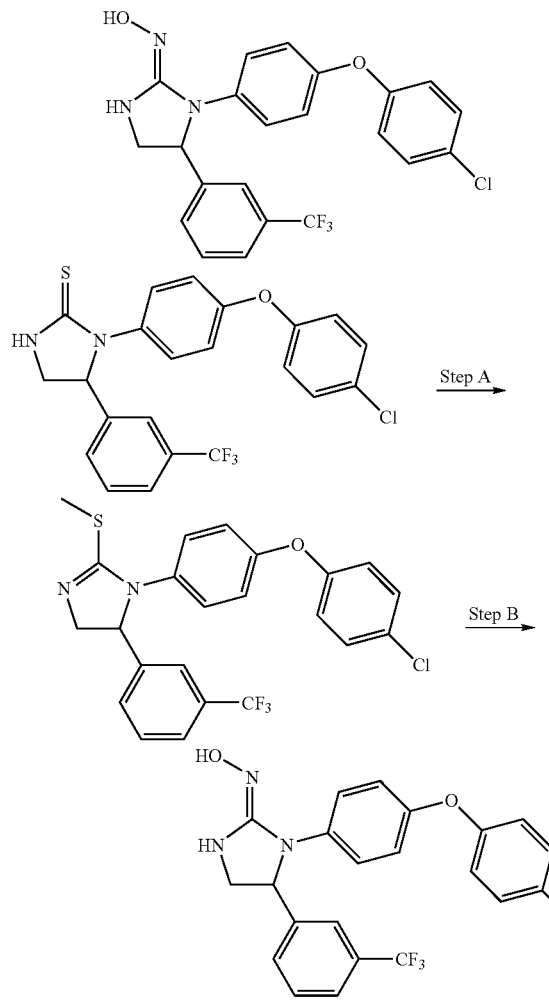

Step A: To a solution of 1-(4-(4-chlorophenoxy)phenyl)-5-(3-(trifluoromethyl)phenyl)imidazolidine-2-thione (10.0 mg, 0.0223 mmol) in MeOH (0.5 mL) is added MeI (6.94 µL, 0.111 mmol). The reaction mixture is heated at 80° C. for 1 h before removal of the solvent. The crude 1-(4-(4-chlorophenoxy)phenyl)-2-(methylthio)-5-(3-(trifluoromethyl)phenyl)-4,5-dihydro-1H-imidazole is used in next step without further purification; HPLC-MS calculated for $C_{23}H_{18}ClF_3N_2OS$ (M+H$^+$) 463.1, found 463.1.

Step B: To a solution of the crude product from previous step in MeOH (0.5 mL) are added NH$_2$OH.HCl (7.7 mg, 0.111 mmol) and K$_2$CO$_3$ (15.4 mg, 0.111 mmol). The reaction mixture is heated at 80° C. for 1 h before removal of the solvent. The residue is purified by preparatory TLC to provide the title compound; HPLC-MS calculated for $C_{22}H_{17}ClF_3N_3O_2$ (M+H$^+$) 448.1, found 448.1.

Example 177

3-(4-(4-chlorophenoxy)phenyl)-1-(2-methoxyethyl)-4-(3-(trifluoromethyl)phenyl)-imidazolidin-2-one A solution of 2-(3-(4-(4-chlorophenoxy)phenyl)-2-oxo-4-(3-(trifluoromethyl)phenyl)-imidazolidin-1-yl)ethyl methanesulfonate (10.0 mg, 0.0180 mmol) in MeOH (0.3 mL) is heated at 60° C. overnight. After removal of the solvent the residue is purified by preparatory LC/MS to provide the title compound; $^1$H NMR (CDCl$_3$, 400 MHz) δ 7.56-7.44 (m, 4H), 7.30 (d, 2H), 7.23 (d, 2H), 6.86 (m, 4H), 5.22 (dd, 1H), 4.07 (t, 1H), 3.57 (m, 3H), 3.49 (m, 1H), 3.36 (dd, 1H), 3.34 (s, 3H); HPLC-MS calculated for $C_{25}H_{22}ClF_3N_2O_3$ (M+H$^+$) 491.1, found 491.1.

Example 178

3-(4-(4-chlorophenoxy)phenyl)-1-(2-(2-hydroxyethylamino)ethyl)-4-(3-(trifluoromethyl)-phenyl)imidazolidin-2-one

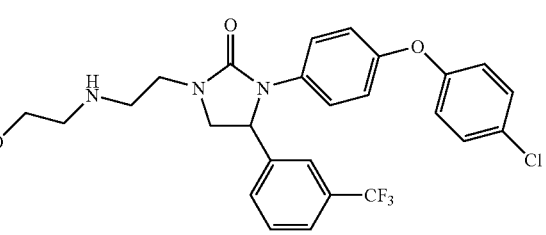

To a solution of 2-(3-(4-(4-chlorophenoxy)phenyl)-2-oxo-4-(3-(trifluoromethyl)phenyl)imidazolidin-1-yl)ethyl methanesulfonate (12.0 mg, 0.0216 mmol) in THF (0.3 mL) is added 2-aminoethanol (6.53 µL, 0.108 mmol). The reaction mixture is heated at 80° C. for 2 h before removal of the solvent. The residue is purified by preparatory LC/MS to provide the title compound; HPLC-MS calculated for $C_{26}H_{25}ClF_3N_3O_3$ (M+H$^+$) 520.2, found 520.2.

Example 181

2-(3-(4-(4-chlorophenoxy)phenyl)-2-oxo-4-(3-(trifluoromethyl)phenyl)imidazolidin-1-yl)ethyl carbamate

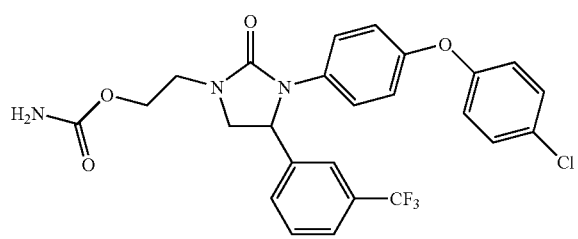 [SMILES: NC(=O)OCCN1CC(c2cccc(C(F)(F)F)c2)N(c2ccc(Oc3ccc(Cl)cc3)cc2)C1=O]

To a solution of 3-(4-(4-chlorophenoxy)phenyl)-1-(2-hydroxyethyl)-4-(3-(trifluoromethyl)phenyl)imidazolidin-2-one (10.0 mg, 0.021 mmol) in DCM (0.3 mL) are added sodium cyanate (5.5 mg, 0.084 mmol) and TFA (6.46 µL, 0.084 mmol). The mixture is stirred at room temperature overnight before removal of the solvent. The residue is purified by preparatory TLC to provide the title compound; HPLC-MS calculated for $C_{25}H_{21}ClF_3N_3O_4$ (M+H$^+$) 520.1, found 520.1.

Example 184

3-(4-(4-chlorophenoxy)phenyl)-1-(2-(piperazin-1-yl)ethyl)-4-(3-(trifluoromethyl)phenyl)-imidazolidin-2-one

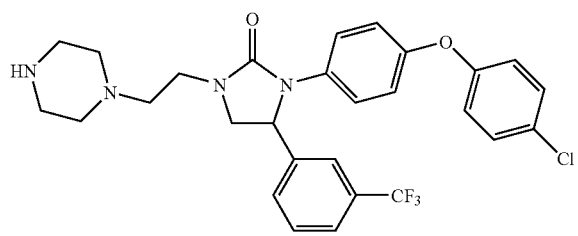 [SMILES: O=C1N(CCN2CCNCC2)CC(c2cccc(C(F)(F)F)c2)N1c1ccc(Oc2ccc(Cl)cc2)cc1]

tert-butyl 4-(2-(3-(4-(4-chlorophenoxy)phenyl)-2-oxo-4-(3-(trifluoromethyl)phenyl)imidazo-lidin-1-yl)ethyl)piperazine-1-carboxylate (15 mg, 0.023 mmol) is dissolved in a mixture solvent of DCM (0.2 mL) and TFA (0.2 mL). The reaction mixture is stirred at room temperature for 15 min before removal of the solvent. The residue is purified by reparative LC/MS to provide the title compound; HPLC-MS calculated for $C_{28}H_{28}ClF_3N_4O_2$ (M+H$^+$) 545.2, found 545.2.

Example 185

(4R,5S)-methyl 1-(4-(4-chlorophenoxy)phenyl)-2-oxo-5-phenylimidazolidine-4-carboxylate

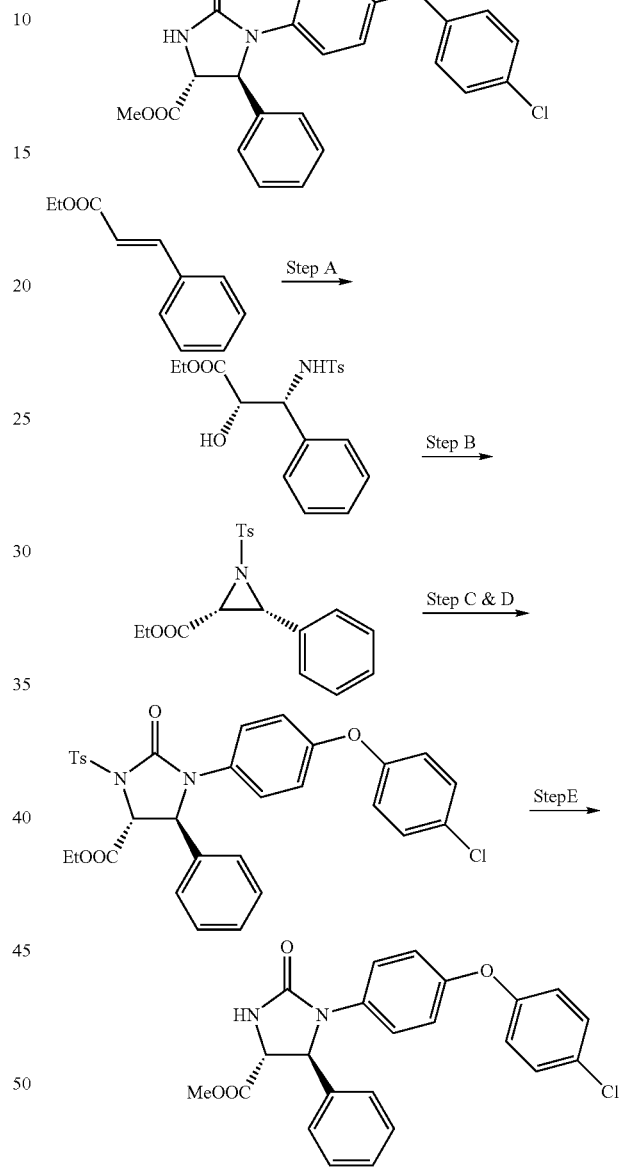

Step A: (2S,3R)-ethyl 2-hydroxy-3-(4-methylphenylsulfonamido)-3-phenylpropanoate is synthesized from ethyl cinnamate, using the Sharpless Asymmetric Aminohydroxylation (AA) conditions described in Li, G.; Chang, H.-T.; Sharpless, K. B. *Angew. Chem. Int. Ed. Engl.* 1996, 35, 451.

Step B: (2R,3R)-ethyl 3-phenyl-1-tosylaziridine-2-carboxylate is synthesized from (2S,3R)-ethyl 2-hydroxy-3-(4-methylphenylsulfonamido)-3-phenylpropanoate, using the cyclodehydration conditions described in Rubin, A. E.; Sharpless, K. B. *Angew. Chem. Int. Ed. Engl.* 1997, 36, 2637.

Step C and D: (4R,5S)-ethyl 1-(4-(4-chlorophenoxy)phenyl)-2-oxo-5-phenyl-3-tosylimidazolidine-4-carboxylate is synthesized from (2R,3R)-ethyl 3-phenyl-1-tosylaziridine-2-carboxylate, using the conditions described in Example 7, Step B and C.

Step E: To a solution of (4R,5S)-ethyl 1-(4-(4-chlorophenoxy)phenyl)-2-oxo-5-phenyl-3-tosylimidazolidine-4-carboxylate (15.0 mg, 0.025 mmol) in MeOH (0.5 mL) is added magnesium powder (6.2 mg, 0.25 mmol). The reaction mixture is heated in a sealed tube at 80° C. for 1 h. After cooling down to room temperature, the mixture is quenched with saturated NH$_4$Cl aqueous solution (5 mL) and extracted with EtOAc (3×3 mL). The combined organic layer is concentrated and purified by preparatory TLC to provide the title compound; $^1$H NMR (CDCl$_3$, 400 MHz) δ 7.39-7.32 (m, 7H), 7.23 (d, 2H), 6.86 (m, 4H), 5.43 (d, 1H), 5.26 (br, 1H), 4.08 (d, 1H), 3.87 (s, 3H); HPLC-MS calculated for C$_{23}$H$_{19}$ClN$_2$O$_4$ (M+H$^+$) 423.1, found 423.1.

Example 190

3-(4-(4-chlorophenoxy)phenyl)-1-(4-methoxyphenyl)-4-(3-(trifluoromethyl)phenyl)-imidazolidin-2-one

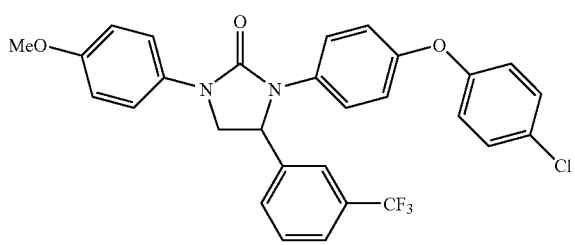 [SMILES: COc1ccc(N2CC(c3cccc(C(F)(F)F)c3)N(c3ccc(Oc4ccc(Cl)cc4)cc3)C2=O)cc1]

A reaction tube charged with 1-(4-(4-chlorophenoxy)phenyl)-5-(3-(trifluoromethyl)phenyl)imidazolidin-2-one (20.0 mg, 0.0462 mmol), 4-iodoanisole (13.0 mg, 0.0554 mmol), K$_3$PO$_4$ (19.6 mg, 0.0924 mmol), and catalytic amount of CuI is purged with nitrogen. 1,4-Dioxane (0.5 mL) and catalytic amount of trans-1,2-diaminocyclohexane are added via syringe. The reaction mixture is heated at 100° C. overnight, cooled down to room temperature, quenched with saturated NH$_4$Cl aqueous solution (5 mL), and extracted with EtOAc (3×3 mL). The combined organic layer is concentrated and purified by preparatory LC/MS to provide the title compound; HPLC-MS calculated for C$_{29}$H$_{22}$ClF$_3$N$_2$O$_3$ (M+H$^+$) 539.1, found 539.1.

Example 194

1-(2-aminoethyl)-3-(4-(4-chlorophenoxy)phenyl)-4-(3-(trifluoromethyl)phenyl)imidazolidin-2-one

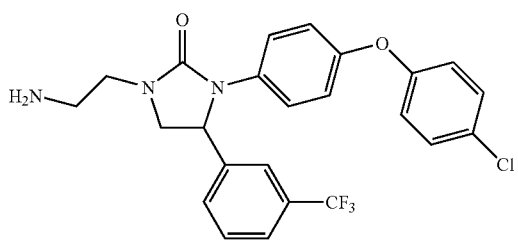 [SMILES: NCCN1CC(c2cccc(C(F)(F)F)c2)N(c2ccc(Oc3ccc(Cl)cc3)cc2)C1=O]

2-(3-(4-(4-Chlorophenoxy)phenyl)-2-oxo-4-(3-(trifluoromethyl)phenyl)-imidazolidin-1-yl)ethyl methanesulfonate (85.0 mg, 0.153 mmol) is dissolved in a mixture solvent of $^i$PrOH (0.5 mL) and concentrated ammonia aqueous solution (0.5 mL). The reaction mixture is heated at 80° C. for 2 h, cooled down to room temperature, taken in H$_2$O (10 mL), and extracted with EtOAc (3×5 mL). The combined organic layer is dried over MgSO$_4$ and evaporated in vacuo to provide the crude title compound (69.7 mg, 96% yield) as a colorless oil-like product; HPLC-MS calculated for C$_{24}$H$_{21}$ClF$_3$N$_3$O$_2$ (M+H$^+$) 476.1, found 476.1.

Example 201

(S)—N-(3-(4-(4-chlorophenoxy)phenyl)-1-tosyl-4-(3-(trifluoromethyl)phenyl)imidazolidin-2-ylidene)cyanamide

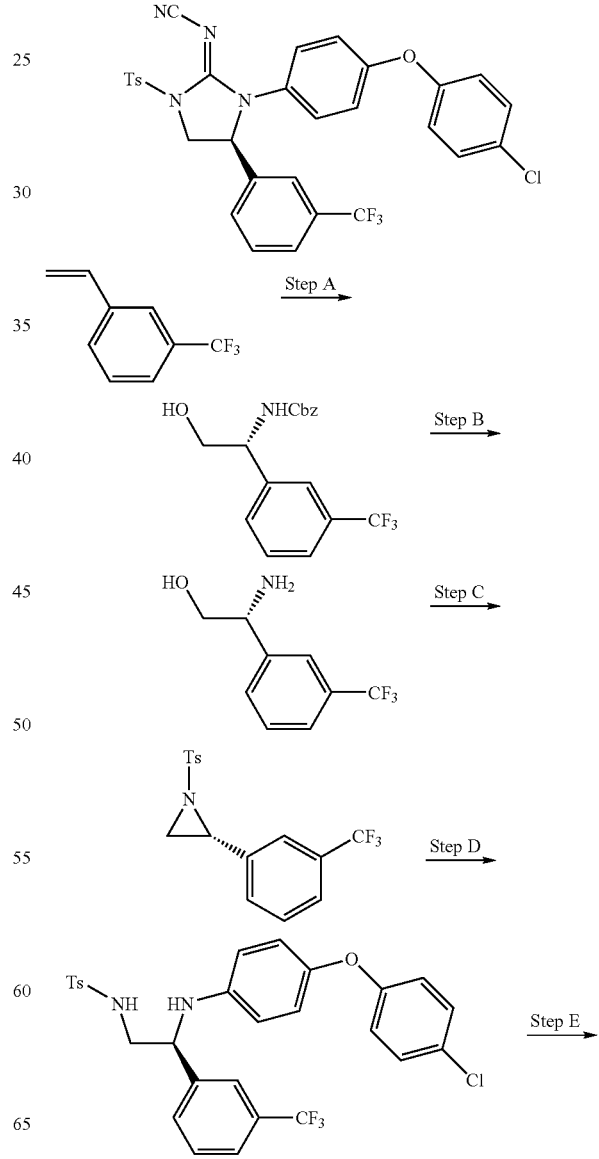

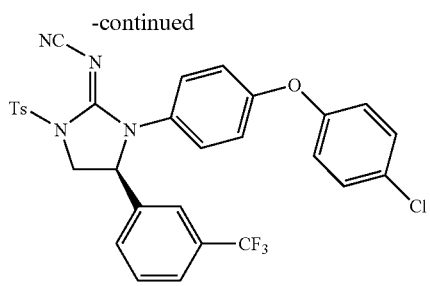

Step A: (R)-Benzyl 2-hydroxy-1-(3-(trifluoromethyl)phenyl)ethylcarbamate is synthesized from 3-(trifluoromethyl)styrene, using the Sharpless Asymmetric Aminohydroxylation (AA) conditions described in Li, G.; Angert, H. H.; Sharpless, K. B. *Angew. Chem. Int. Ed. Engl.* 1996, 35, 2813, as a white solid product (35% yield); $^1$H NMR (CDCl$_3$, 400 MHz) δ 7.57-7.46 (m, 4H), 7.36 (m, 5H), 5.61 (d, 1H), 5.11 (m, 2H), 4.91 (br, 1H), 3.94 (dd, 1H), 3.86 (dd, 1H); HPLC-MS calculated for C$_{17}$H$_{16}$F$_3$NO$_3$ (M+H$^+$) 340.1, found 340.1.

Step B: To a solution of (R)-Benzyl 2-hydroxy-1-(3-(trifluoromethyl)phenyl)ethylcarbamate (4.54 g, 13.4 mmol) in MeOH (100 mL) is slowly added 10 wt % Pd/C (454 mg). The reaction mixture is stirred at room temperature under hydrogen (balloon) for 1.5 h, filtered through celite, and evaporated in vacuo to provide crude (R)-2-amino-2-(3-(trifluoromethyl)phenyl)ethanol (2.70 g, 98% yield) as a white solid product; $^1$H NMR (CDCl$_3$, 400 MHz) δ 7.62 (s, 1H), 7.55 (m, 2H), 7.47 (t, 1H), 4.15 (dd, 1H), 3.77 (dd, 1H), 3.57 (dd, 1H); HPLC-MS calculated for C$_9$H$_{10}$F$_3$NO (M+H$^+$) 206.1, found 206.1.

Step C: To a solution of the crude product from Step B (1.11 g, 5.45 mmol) in 1,2-dichloroethane (25 mL) at 0° C. are added K$_2$CO$_3$ (2.26 g, 16.4 mmol) and TsCl (2.60 g, 13.6 mmol). The reaction mixture is stirred at room temperature overnight. If reaction is not done at this point, additional K$_2$CO$_3$ (0.75 g, 5.45 mmol) and TsCl (1.04 g, 5.45 mmol) are added and the reaction mixture is stirred for another 24 h. After removal of the solvent, the residue is taken in cold saturated NaHCO$_3$ aqueous solution (100 mL) and extracted with EtOAc (3×50 mL). The combined organic layer is washed with brine, dried over MgSO$_4$, concentrated, and purified by silica gel chromatography (0~35% EtOAc/Hexanes) to provide (R)-1-tosyl-2-(3-(trifluoromethyl)phenyl)aziridine (1.74 g, 94% yield); $^1$H NMR (CDCl$_3$, 400 MHz) δ 7.88 (d, 2H), 7.54 (m, 1H), 7.43 (m, 3H), 7.36 (d, 2H), 3.81 (dd, 1H), 3.01 (d, 1H), 2.45 (s, 3H), 2.39 (d, 1H); HPLC-MS calculated for C$_{16}$H$_{14}$F$_3$NO$_2$S (M+H$^+$) 342.1, found 342.1.

Step D: To a solution of the aziridine product from Step C (1.13 g, 3.31 mmol) in Et$_2$O (6.6 mL) are added 4-(4-chlorophenoxy)aniline (0.73 g, 3.31 mmol) and LiClO$_4$ (176 mg, 1.66 mmol). The reaction mixture is stirred at room temperature overnight. After removal of the solvent, the crude (S)—N-(2-(4-(4-chlorophenoxy)phenylamino)-2-(3-(trifluoromethyl)-phenyl)ethyl)-4-methylbenzenesulfonamide is used in next step without further purification.

Step E: The crude product from Step D is dissolved in DMF (16.5 mL). Cyanogen bromide (1.75 g, 16.6 mmol) and K$_2$CO$_3$ (2.29 g, 16.6 mmol) are added. The reaction mixture is heated at 100° C. for 2 h, cooled down to room temperature, taken in H$_2$O (160 mL), and extracted with EtOAc (3×80 mL). The combined organic layer is washed with brine, dried over MgSO$_4$, and evaporated in vacuo.

The residue is then dissolved in 1,4-dioxane (16.5 mL). Cyanogen bromide (1.75 g, 16.6 mmol) and K$_2$CO$_3$ (2.29 g, 16.6 mmol) are added. The reaction mixture is heated at 100° C. for 2 h, cooled down to room temperature, taken in H$_2$O (160 mL), and extracted with EtOAc (3×80 mL). The combined organic layer is washed with brine, dried over MgSO$_4$, concentrated, and purified by silica gel chromatography (10~40% EtOAc/Hexanes) to provide the title compound (1.06 g, 52% yield for two steps) as a light yellow solid product; $^1$H NMR (CDCl$_3$, 400 MHz) δ 7.98 (d, 2H), 7.66 (d, 1H), 7.53 (t, 1H), 7.43 (m, 3H), 7.36 (s, 1H), 7.26 (d, 2H), 6.91 (m, 4H), 6.85 (d, 2H), 5.00 (dd, 1H), 4.59 (dd, 1H), 4.09 (dd, 1H), 2.51 (s, 3H); HPLC-MS calculated for C$_{30}$H$_{22}$ClF$_3$N$_4$O$_3$S (M+H$^+$) 611.1, found 611.1.

Example 203

(S)—N-(1-(4-(4-chlorophenoxy)phenyl)-5-(3-(trifluoromethyl)phenyl)imidazolidin-2-ylidene)cyanamide

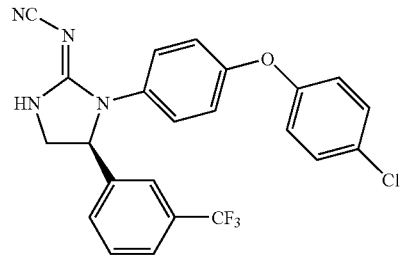

To a solution of (S)—N-(3-(4-(4-chlorophenoxy)phenyl)-1-tosyl-4-(3-(trifluoromethyl)-phenyl)imidazolidin-2-ylidene)cyanamide (1.06 g, 1.73 mmol) in MeOH (17 mL) is added magnesium powder (0.42 g, 17.3 mmol). The reaction mixture is heated to reflux for 45 min. After cooling down to room temperature, the mixture is quenched with saturated NH$_4$Cl aqueous solution (150 mL) and extracted with EtOAc (3×75 mL). The combined organic layer is washed with brine, dried over MgSO$_4$, concentrated, and purified by silica gel chromatography (20~70% EtOAc/Hexanes) to provide the title compound (0.62 g, 78% yield) as a white solid product; $^1$H NMR (CDCl$_3$, 400 MHz) δ 7.60 (m, 1H), 7.51 (m, 3H), 7.27 (d, 2H), 7.15 (d, 2H), 6.88 (m, 4H), 6.65 (br, 1H), 5.40 (dd, 1H), 4.21 (t, 1H), 3.63 (dd, 1H); HPLC-MS calculated for C$_{23}$H$_{16}$ClF$_3$N$_4$O (M+H$^+$) 457.1, found 457.1.

Example 208

(S)-3-(4-(4-chlorophenoxy)phenyl)-1-(3-(methylsulfonyl)propyl)-4-(3-(trifluoromethyl)phenyl)imidazolidin-2-one

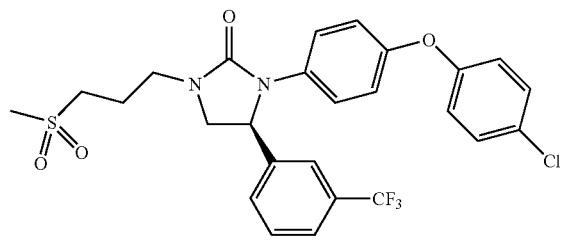

-continued

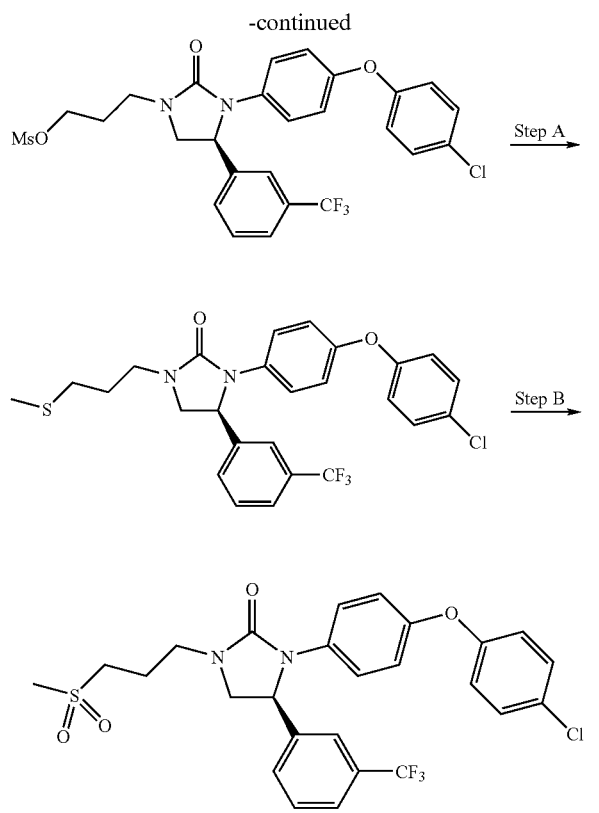

Step A

Step B

Example 215

(R)-1-[4-(4-chlorophenoxy)phenyl]-5-phenylpyrroli-din-2-one

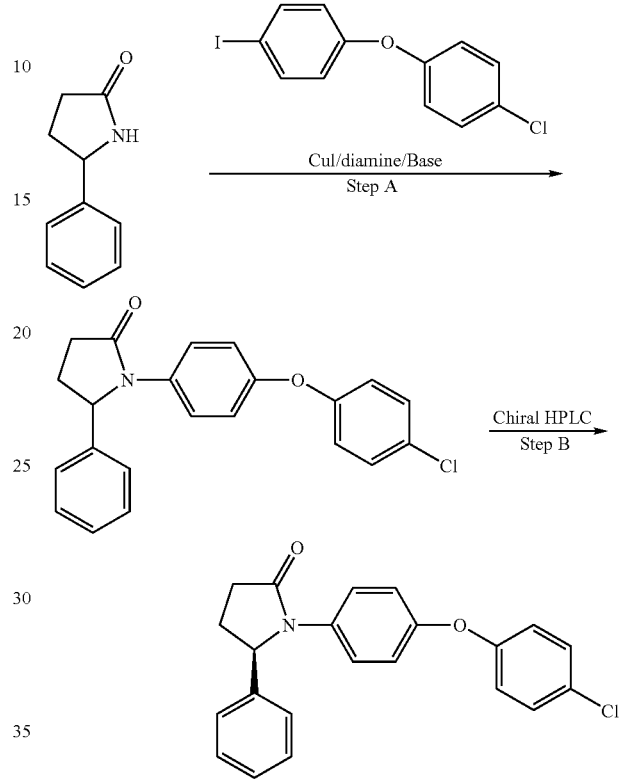

Step A: To a solution of (S)-3-(3-(4-(4-chlorophenoxy)phenyl)-2-oxo-4-(3-(trifluoromethyl)phenyl)imidazolidin-1-yl)propyl methanesulfonate (2.22 g, 3.90 mmol) in THF (20 mL) is added NaSCH$_3$ (0.55 g, 7.80 mmol). The reaction mixture is heated to reflux for 2 h, cooled down to room temperature, taken in H$_2$O (100 mL), and extracted with EtOAc (3×50 mL). The combined organic layer is washed with brine and dried over MgSO$_4$. After removal of the drying agent and solvent, the crude (S)-3-(4-(4-chlorophenoxy)phenyl)-1-(3-(methylthio)propyl)-4-(3-(trifluoromethyl)phenyl)imidazolidin-2-one is used in next step without further purification.

Step B: The crude product from Step A is dissolved in DCM (40 mL) and m-CPBA (77%, 2.62 g, 11.7 mmol) is added. The reaction mixture is stirred at room temperature overnight before removal of the solvent. The residue is taken in saturated NaHCO$_3$ aqueous solution (100 mL) and extracted with EtOAc (3×50 mL). The combined organic layer is washed with brine, dried over MgSO$_4$, concentrated, and purified by silica gel chromatography (40-90% EtOAc/hexanes) to provide the title compound (1.47 g, 68% yield for two steps) as a colorless oil-like product; $^1$H NMR (CDCl$_3$, 400 MHz) δ 7.56 (m, 2H), 7.49 (m, 2H), 7.25 (m, 4H), 6.87 (m, 4H), 5.27 (dd, 1H), 4.00 (t, 1H), 3.59 (m, 1H), 3.43 (m, 1H), 3.28 (dd, 1H), 3.11 (m, 2H), 2.94 (s, 3H), 2.15 (m, 2H); HPLC-MS calculated for C$_{26}$H$_{24}$ClF$_3$N$_2$O$_4$S (M+H$^+$) 553.1, found 553.1.

Step A (Method 1, Using Standard Buchwald Coupling Conditions): To a 10 mL reaction tube fitted with a screw cap is charged with 5-phenylpyrrolidin-2-one (26.8 mg, 0.166 mmol), 1-(4-iodophenoxy)-4-chlorobenzene (66 mg, 0.199 mmol, 1.2 eq), copper iodide (6.3 mg, 0.033 mmol, 0.2 eq), K$_3$PO$_4$ (70.6 mg, 0.333 mmol, 2.0 eq), trans-cyclohexane-1,2-diamine (3.8 mg, 0.033 mmol, 0.2 eq) and 1,4-dioxane (2 mL). The system is degassed with argon then sealed and heated to 110° C. for 20 h. The reaction is cooled to room temperature, dissolved in ethyl acetate and washed with water and brine. The organic phase is dried over Na$_2$SO$_4$, filtered and concentrated in vacuo. Purification on silica gel (0-33% ethyl acetate in hexane) gives 1-[4-(4-chlorophenoxy)phenyl]-5-phenylpyrrolidin-2-one as a slightly brown oil (30.0 mg, 50%).

Step A (Method 2, Using CsF as Base): To a 10 mL reaction tube fitted with a screw cap is charged with 5-phenylpyrrolidin-2-one (80.5 mg, 0.5 mmol), 1-(4-iodophenoxy)-4-chlorobenzene (248 mg, 0.75 mmol, 1.5 eq), copper iodide (5.0 mg, 0.025 mmol, 0.05 eq), CsF (189 mg, 1.25 mmol, 2.5 eq), N1,N2-dimethylethane-1,2-diamine (5.5 µL, 0.05 mmol, 0.1 eq) and ethyl acetate (1 mL). The system is degassed with argon then sealed and heated to 85° C. for 20 h. The reaction is cooled to room temperature, filtered and concentrated in vacuo. Purification on silica gel (0-33% ethyl acetate in hexane) gives 1-[4-(4-chlorophenoxy)phenyl]-5-phenylpyrrolidin-2-one as a colorless oil (182 mg, 100%).

Step B: The product obtained in step A is then subjected to chiral HPLC, giving (R)-1-[4-(4-chlorophenoxy)phenyl]-5- phenylpyrrolidin-2-one as a colorless oil, along with its (S)-enantiomer. $^1$H NMR (CDCl$_3$) δ (ppm) 7.41-7.32 (m, 4H), 7.31-7.23 (m, 5H), 6.92-6.87 (m, 4H), 5.24 (dd, J=7.4, 4.6 Hz, 1H), 2.82-2.78 (m, 1H), 2.71-2.58 (m, 2H), 2.10-2.01 (m, 1H). HPLC-MS calculated C$_{22}$H$_{18}$ClNO$_2$ (M+H$^+$): 364.11, found: 364.10.

Example 221

(R)-1-[4-(4-chlorophenoxy)phenyl]-5-[3-(trifluoromethyl)phenyl]pyrrolidin-2-one

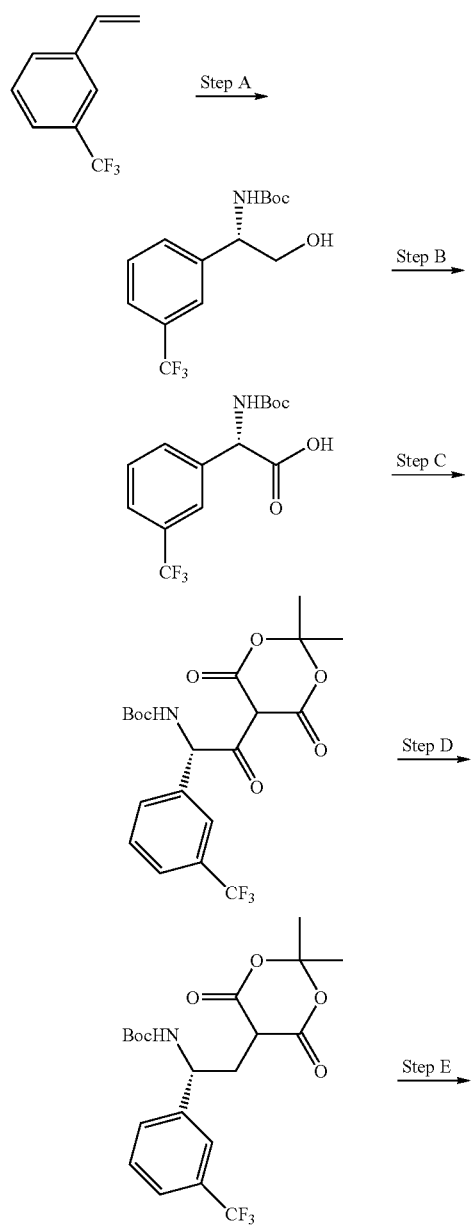

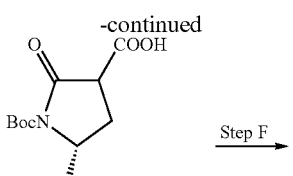

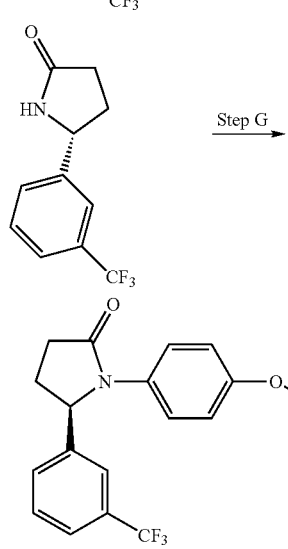

Step A: A 500 mL round-bottomed flask is charged with tert-butyl carbamate (5.42 g, 46.0 mmol) and n-PrOH (48 mL). To this stirred solution is added freshly prepared aqueous solution of NaOH (1.84 g, 46.0 mmol in 75 mL of H$_2$O), followed by 1,3-dichloro-5,5-dimethylhydantoin (4.54 g, 23.0 mmol). After 5 min a solution of (DHQ)$_2$PHAL (584 mg, 0.75 mmol, 5 mol %) in n-PrOH (42 mL) is added. 3-Trifluoromethylstyrene (2.58 g, 15.0 mmol, dissolved in 60 mL of n-PrOH) is then added, followed by K$_2$OsO$_2$(OH)$_4$ (221 mg, 0.6 mmol, 4 mol %). The resulting solution is stirred at rt for 2 h. The reaction mixture is then cooled in an ice-bath, and the reaction is quenched by the addition of sodium sulfite (4.41 g, 35.0 mmol) and stirred for 1 h. Evaporation to remove most of n-PrOH, the aqueous solution is extracted with ethyl acetate (4×100 mL). The combined organic phases were washed with water (50 mL), brine (50 mL), dried over anhydrous Na$_2$SO$_4$, and concentrated and then purified on silica gel (eluent: 0-33% ethyl acetate in hexane) to give tert-butyl (S)-1-[3-(trifluoromethyl)phenyl]-2-hydroxyethylcarbamate (2.42 g, 53%) as a colorless oil. HPLC-MS calculated for C$_9$H$_{11}$F$_3$NO (M-Boc+H$^+$) 206.07, found 206.10.

Step B: The tert-butyl (S)-1-[3-(trifluoromethyl)phenyl]-2-hydroxyethylcarbamate (4.83 g, 15.8 mmol) is dissolved in acetone (120 mL) and added to an aqueous 5% NaHCO$_3$ solution (42 mL). This magnetically stirred heterogeneous mixture is cooled to 0° C. and treated sequentially with KBr (0.192 g, 1.62 mmol) and TEMPO (2.61 g, 16.8 mmol). Sodium hypochloride (4-6%, 39 mL, ca. 20 mmol) is then added dropwise over a period of 15 min, while the mixture is vigorously stirred and maintained at 0° C. After 1 h, additional sodium hypochloride (7.8 mL, ca. 4 mmol) is added, and stiffing is continued at 0° C. for another hour followed by addition of 5% NaHCO$_3$ solution (60 mL). When the acetone is removed on a rotary evaporator, the resulting aqueous layer is washed twice with ether to remove TEMPO impurities, acidified to pH 6 with 10% citric acid, and extracted with ethyl acetate (4×100 mL). The combined organic phases were washed with water (50 mL), brine (50 mL), dried over anhydrous $Na_2SO_4$, and concentrated to give pure acid (4.62 g, 91%) as a colorless oil.

Step C: The N-Boc-protected amino acid obtained in Step B (2.0 g, 6.26 mmol) is dissolved with Meldrum's acid (0.97 g, 6.89 mmol) and DMAP (1.23 g, 10.01 mmol) in DCM (30 mL). The reaction mixture is cooled to below 0° C. and a solution of DCC (1.56 g, 7.51 mmol) in DCM (15 mL) is added dropwise over 30 min. The mixture is stirred at 0° C. for 6 h, then it is left at <0° C. overnight. After filtration to remove dicyclohexylurea the reaction mixture is washed with 5% $KHSO_4$ (4×50 mL) and brine (50 mL) and dried in the refrigerator with $Na_2SO_4$. Filtered, the resulting solution is used for the next step without characterization or further purification.

Step D: The solution obtained from Step C is cooled to below 0° C. and AcOH (4.13 g, 68.3 mmol) is added. Then $NaBH_4$ is added in small potions while stirring over 30 min. The mixture is stirred at 0° C. for 6 h, then it is left at <0° C. overnight. The reaction mixture is then washed with brine (3×20 mL) and water (2×20 mL). The organic phase is dried over anhydrous $Na_2SO_4$, and concentrated to dryness and then purified on silica gel (0-40% ethyl acetate in hexane) to give tert-butyl (R)-1-[3-(trifluoromethyl)phenyl]-2-(2,2-dimethyl-4,6-dioxo-1,3-dioxan-5-yl)ethylcarbamate (1.76 g, 65% overall yield for two steps) as a white solid. HPLC-MS calculated for $C_{20}H_{24}F_3NO_6$ (M+Na$^+$) 454.16, found 453.80.

Step E: The mixture of tert-butyl (R)-1-[3-(trifluoromethyl)phenyl]-2-(2,2-dimethyl-4,6-dioxo-1,3-dioxan-5-yl)ethylcarbamate (520 mg, 1.21 mmol) and toluene (15 mL) is stirred at 110° C. for 3 h. Concentration to give (5R)-1-(tert-butoxycarbonyl)-5-[3-(trifluoromethyl)phenyl]-2-oxopyrrolidine-3-carboxylic acid as a colorless oil. This product is used for the next step without further purification. HPLC-MS calculated for $C_{12}H_{10}F_3NO_3$ (M-Boc+H$^+$) 274.06, found 274.10.

Step F: The mixture of (5R)-1-(tert-butoxycarbonyl)-5-[3-(trifluoromethyl)phenyl]-2-oxopyrrolidine-3-carboxylic acid obtained in Step E (ca. 1.21 mmol) and 30% TFA in DCM (6 mL) is stirred at rt for 30 min. The reaction mixture is then dissolved in DCM (120 mL), washed with saturated aq. $NaHCO_3$ (40 mL) and brine (40 mL) and dried over $Na_2SO_4$. Concentration to give (R)-5-[3-(trifluoromethyl)phenyl]pyrrolidin-2-one as a slight brown solid (278 mg, 100% overall yield for two steps). This product is used for the next step without further purification. HPLC-MS calculated for $C_{11}H_{10}F_3NO$ (M+H$^+$) 230.07, found 230.00.

Step G: To a 10 mL reaction tube fitted with a screw cap is charged with (R)-5-[3-(trifluoromethyl)phenyl]pyrrolidin-2-one (90 mg, 0.39 mmol) and 1,4-dioxane (3 mL). 1-(4-iodophenoxy)-4-chlorobenzene (157 mg, 0.47 mmol) is then added, followed by copper iodide (15 mg, 0.078 mmol), N,N'-1,2-trans-dimethylcyclohexane-1,2-diamine (11.2 mg, 0.078 mmol), and $K_3PO_4$ (167 mg, 0.78 mmol). The system is degassed with argon then sealed and heated to 110° C. for 28 h. The reaction is cooled to room temperature, dissolved in ethyl acetate and washed with water and brine. The organic phase is dried over $Na_2SO_4$, filtered and concentrated in vacuo. Purification on silica gel (0-30% ethyl acetate in hexane) gave (R)-1-[4-(4-chlorophenoxy)phenyl]-5-[3-(trifluoromethyl)phenyl]pyrrolidin-2-one as a slightly yellow oil (102 mg, 60%). $^1$H NMR (CDCl$_3$) δ (ppm) 7.60-7.50 (m, 1H), 7.49-7.37 (m, 3H), 7.34-7.28 (m, 2H), 7.27-7.21 (m, 2H), 6.91-6.67 (m, 4H), 5.28 (dd, J=6.8, 5.6 Hz, 1H), 2.84-2.59 (m, 3H), 2.07-1.94 (m, 1H). HPLC-MS calculated for $C_{23}H_{17}ClF_3NO_2$ (M+H$^+$) 432.09, found 432.10.

Example 222

(R)-1-[4-(4-chlorophenoxy)phenyl]-2-[3-(trifluoromethyl)phenyl]pyrrolidine

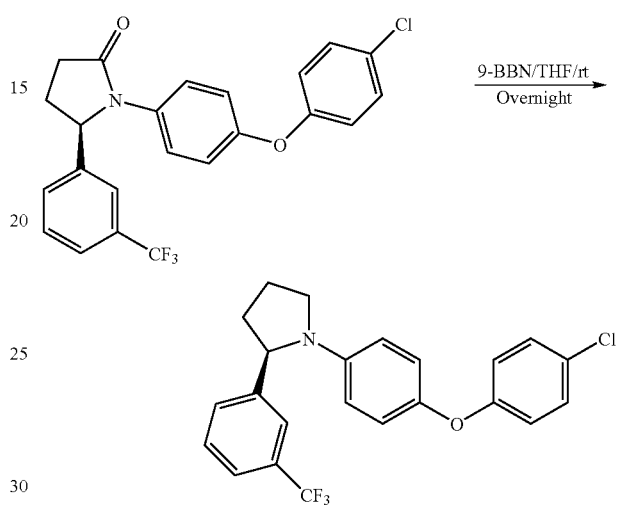

A mixture of (R)-1-[4-(4-chlorophenoxy)phenyl]-5-[3-(trifluoromethyl)phenyl]pyrrolidin-2-one (6.4 mg, 0.015 mmol), THF (0.5 mL) and 9-BBN (0.5 M in hexane, 0.5 mL) is stirred at room temperature overnight. After concentration, the residue is purified on silica gel (0-30% ethyl acetate in hexane) to give the title compound (5.1 mg, 82%) as a colorless oil. HPLC-MS calculated for $C_{23}H_{19}ClF_3NO$ (M+H$^+$) 418.11, found 418.10.

Example 228

(R)-5-[3-(2-hydroxyethoxy)phenyl]-1-[5-(4-chlorophenoxy)pyrazin-2-yl]pyrrolidin-2-one

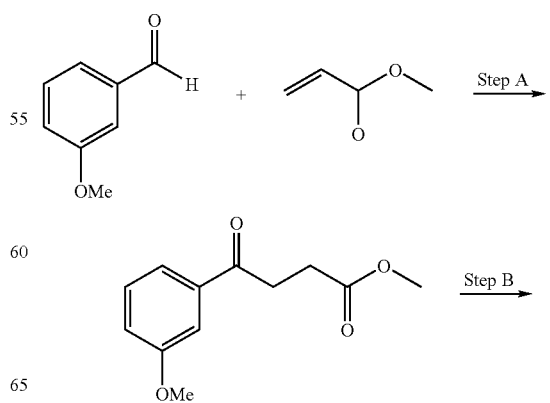

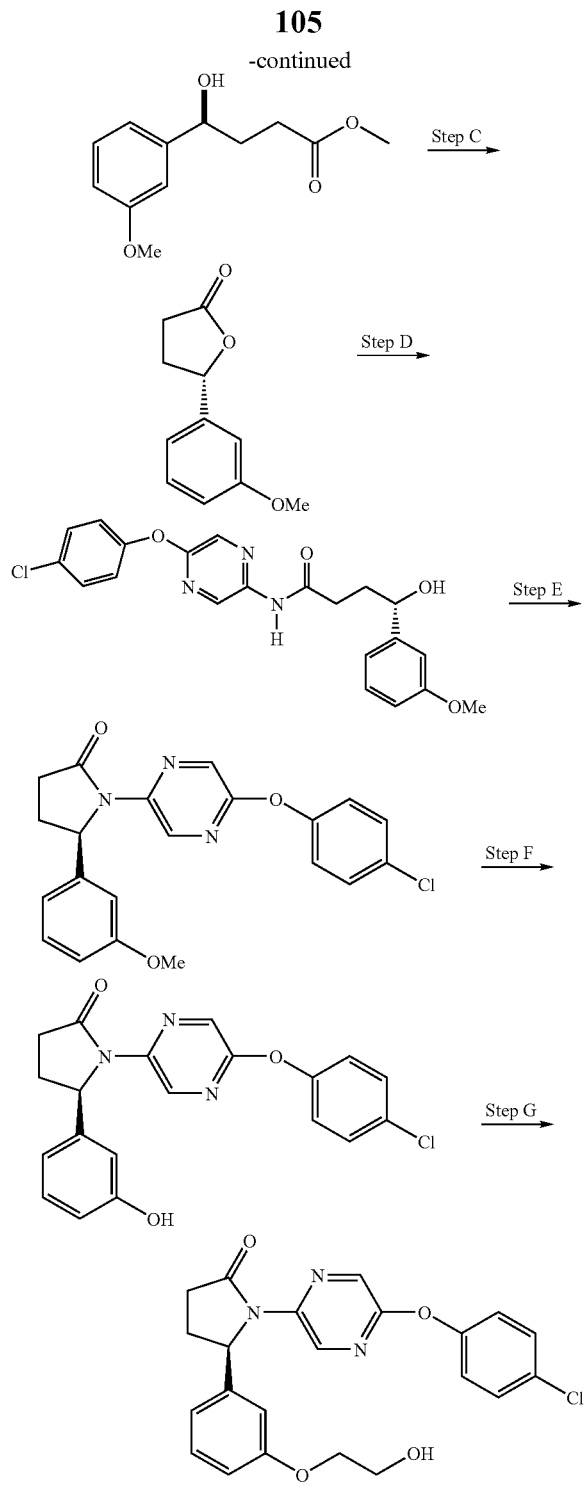

clear reddish brown oil. $^1$H NMR (CDCl$_3$, 400 MHz) δ 7.57 (d, J=9.5 Hz, 1H), 7.51 (dd, J=3.0, 2.0 Hz, 1H), 7.38 (t, J=10.0 Hz, 1H), 7.12 (ddd, J=10.5, 3.5, 1.0 Hz, 1H), 3.85 (s, 3H), 3.71 (s, 3H), 3.32 (t, J=8.5 Hz, 2H), 2.77 (t, J=8.5 Hz, 2H).

Step B: A dried, 25 mL round-bottom flask equipped magnetic stirring bar is cooled to room temperature under a stream of nitrogen. To this is added (−)-DIP-Chloride (6.76 mmol, 2.17 g, 1.2 eq) and THF (10 mL), and the mixture is cooled to −25° C., followed by the addition of methyl 4-(3-methoxyphenyl)-4-oxobutanoate (5.63 mmol). The resulting mixture is then stirred at −20° C. to −30° C. for 10 h. Then, diethanolamine (12.39 mmol, 2.2 eq) is added at −20° C., and the mixture is warmed to room temperature and stirred overnight. This mixture is then filtered, evaporated, and the residue is purified on silica gel (0-33% ethyl acetate in hexane) to give (S)-methyl 4-hydroxy-4-(3-methoxyphenyl)butanoate (985 mg, 79%; >95% based on recovered starting material) as a clear colorless oil. $^1$H NMR (CDCl$_3$) δ 7.33-7.27 (m, 1H), 6.92-6.84 (m, 3H), 5.52-5.46 (m, 1H), 3.82 (s, 1H), 3.48 (s, 1H), 2.71-2.61 (m, 3H), 2.26-2.12 (m, 1H).

Step C: The (S)-methyl 4-hydroxy-4-(3-methoxyphenyl)butanoate (985 mg) is dissolved in CH$_2$Cl$_2$ (10 mL), and the solution is cooled to 0° C. Trifluoroacetic acid (~4 drops) is added and the mixture is stirred for 8 h at room temperature to complete the lactonization. The reaction is quenched with aqueous sodium bicarbonate, and the organic layer is washed with water, dried (Na$_2$SO$_4$), and concentrated to yield 827 mg (100%) of (S)-dihydro-5-(3-methoxyphenyl)furan-2(3H)-one as a colorless oil.

Step D: To a stirred solution of 5-(4-chlorophenoxy)pyrazin-2-amine (149 mg, 0.67 mmol) in dry CH$_2$Cl$_2$ (1.5 mL) at room temperature, under argon, is added trimethylaluminum (0.335 mL of a 2.0 N solution in toluene, 0.67 mmol) dropwise. The resulting mixture is stirred for 15 min, then (S)-dihydro-5-(3-methoxyphenyl)furan-2(3H)-one (107 mg, 0.555 mmol) in CH$_2$Cl$_2$ (1.5 mL) is added slowly and stirring is continued at ambient temperature for 3 days. The reaction is quenched carefully with 10% aqueous citric acid (0.5 mL) at 0° C. The mixture is then partitioned between saturated aqueous NaHCO$_3$ (10 mL) and CH$_2$Cl$_2$ (10 mL). The aqueous layer is extracted further with CH$_2$Cl$_2$ (3×10 mL). The combined organic extracts are dried over Na$_2$SO$_4$, filtered, and concentrated in vacuo. The residue is then purified on silica gel (0-75% ethyl acetate in hexane) to give (S)—N-[5-(4-chlorophenoxy)pyrazin-2-yl]-4-hydroxy-4-(3-methoxyphenyl)butanamide (230 mg, 100%) as a white solid.

Step E: Tri-n-butylphosphine (0.178 mL, 0.72 mmol) is added to a solution of di-tert-butyl azodicarboxylate (167 mg, 0.72 mmol) in dry THF (1.5 mL) at room temperature. The resulting mixture is stirred for 5 min at room temperature, then added dropwise to a solution of (S)—N-[5-(4-chlorophenoxy)pyrazin-2-yl]-4-hydroxy-4-(3-methoxyphenyl)butanamide (194 mg, 0.47 mmol) in THF (1.5 mL) at 0° C. and under argon. The reaction mixture is allowed to warm slowly to ambient temperature and stirred for 1.5 h, then partitioned between saturated aqueous NaHCO$_3$ (5 mL) and CH$_2$Cl$_2$ (10 mL). The aqueous layer is extracted with CH$_2$Cl$_2$ (3×10 mL). The combined organic extracts are dried over Na$_2$SO$_4$, filtered, and concentrated in vacuo. The residue is then purified on silica gel (0-33% ethyl acetate in hexane) to give (R)-1-[5-(4-chlorophenoxy)pyrazin-2-yl]-5-(3-methoxyphenyl)pyrrolidin-2-one (130 mg, 70%) as a colorless oil. $^1$H NMR (CDCl$_3$, 400 MHz) δ 9.11 (d, J=1.2 Hz), 7.99 (d, Step A: A screw-capped tube equipped with a magnetic stir bar is charged with m-anisaldehyde (3.04 mL, 25 mmol), methyl acrylate (4.50 mL, 50 mmol), (PPh$_3$)$_3$RhCl (1.16 g, 1.25 mmol), 2-amino-3-picoline (1.06 mL, 10 mmol), and benzoic acid (702 mg, 5 mmol). The reaction mixture is stirred at 130° C. for 3 days. After cooling to room temperature, the resulting mixture is dissolved in diethyl ether and ished with water and brine. The organic phase is then dried over Na$_2$SO$_4$ and concentrated. The residue is then purified on silica gel (10-30% ethyl acetate in hexane) to give methyl 4-(3-methoxyphenyl)-4-oxobutanoate (5.02 g, 90%) as a J=1.6 Hz, 1H), 7.37-7.31 (m, 1H), 7.22 (t, J=8.0 Hz, 1H), 7.07-7.02 (m, 2H), 6.81-6.72 (m, 3H), 5.68 (dd, J=8.2, 3.8 Hz, 1H), 3.77 (s, 3H), 2.89-2.74 (m, 1H), 2.72-2.57 (m, 2H), 2.10-1.99 (m, 1H). HPLC-MS calculated $C_{21}H_{18}ClN_3O_3$ (M+H$^+$): 396.11, found: 396.10.

Step F: A mixture of (R)-1-[5-(4-chlorophenoxy)pyrazin-2-yl]-5-(3-methoxyphenyl)pyrrolidin-2-one (286 mg, 0.72 mmol), DCM (10 mL) and BBr$_3$ (1M in DCM, 4 mL) is stirred at room temperature for 1 h. The reaction mixture is then diluted with DCM (120 mL), washed with saturated NaHCO$_3$ (20 mL) and brine (20 mL) and dried over Na$_2$SO$_4$. After concentrating, the residue is purified on silica gel (0-33% ethyl acetate in hexane) to give (R)-1-[5-(4-chlorophenoxy)pyrazin-2-yl]-5-(3-hydroxyphenyl)pyrrolidin-2-one (276 mg, 100%) as a white solid. HPLC-MS calculated for $C_{20}H_{16}ClN_3O_3$ (M+H$^+$) 382.09, found 382.10.

Step G: A mixture of (R)-1-[5-(4-chlorophenoxy)pyrazin-2-yl]-5-(3-hydroxyphenyl)pyrrolidin-2-one (276 mg, 0.72 mmol), acetone (9 mL), K$_2$CO$_3$ (996 mg, 7.2 mmol) and 2-iodoethanol (1.86 g, 10.8 mmol) is stirred at 70° C. for 65 h. Then, acetone is removed by evaporation and the residue is dissolved in ethyl acetate (120 mL), washed with brine (20 mL) and dried over Na$_2$SO$_4$. After concentration, the residue is purified on silica gel (0-50% ethyl acetate in hexane) to give the title compound (215 mg, 70%) as a colorless oil. $^1$H NMR (CDCl$_3$, 400 MHz) δ 9.12 (s, 1H), 7.99 (s, 1H), 7.37-7.32 (m, 2H), 7.22 (t, J=7.6 Hz, 1H), 7.08-7.03 (m, 2H), 6.84-6.74 (m, 3H), 5.68 (dd, J=8.0, 3.2 Hz, 1H), 4.09-3.99 (m, 2H), 3.98-3.92 (m, 2H), 2.89-2.75 (m, 1H), 2.72-2.58 (m, 2H), 2.09-1.98 (m, 1H). HPLC-MS calculated for $C_{22}H_{20}ClN_3O_4$ (M+H$^+$) 426.12, found 426.10.

Example 243 and Example 244

(3R,5R)-1-[4-(4-chlorophenoxy)phenyl]-5-[3-(trifluoromethyl)phenyl]-3-[2-(methylsulfonyl)ethyl]pyrrolidin-2-one & (3S,5R)-1-[4-(4-chlorophenoxy)phenyl]-5-[3-(trifluoromethyl)phenyl]-3-[2-(methylsulfonyl)ethyl]pyrrolidin-2-one

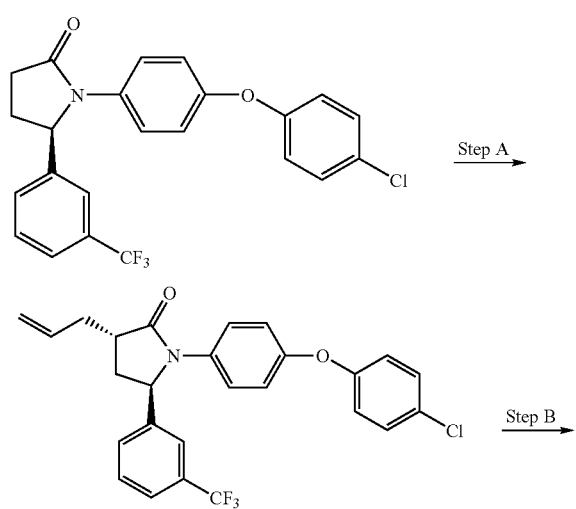

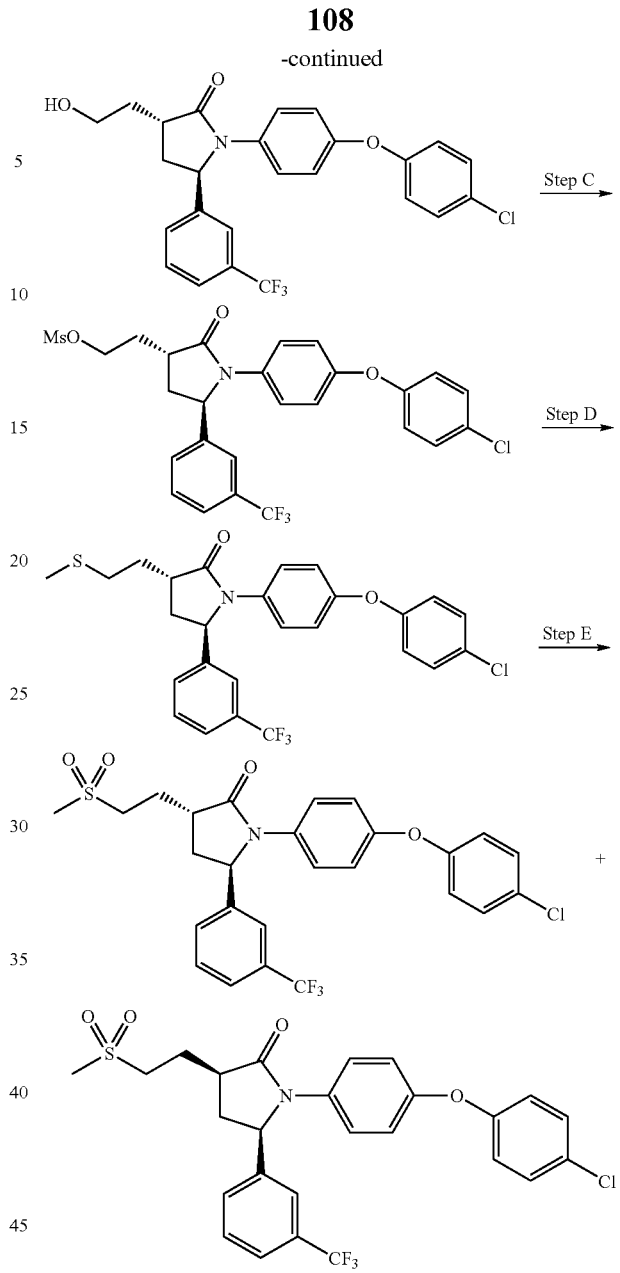

Step A: A solution of (R)-1-[4-(4-chlorophenoxy)phenyl]-5-[3-(trifluoromethyl)phenyl]pyrrolidin-2-one (67 mg, 0.155 mmol) in THF (1 mL) is cooled to 0° C., then LiHMDS (0.31 mL, 1.0 M in THF, 0.31 mmol) is added. After addition, the resulting solution is further stirred at 0° C. for 45 min. Then allyl iodide (52 mg, 0.31 mmol) is added at 0° C. The resulting mixture is stirred at 0° C. for 1 h and 45 min, then the reaction is quenched with saturated NH$_4$Cl solution (0.2 mL). THF is removed by evaporation and then the residue is dissolved in CH$_2$Cl$_2$ (40 mL), washed with brine (10 mL) and dried over Na$_2$SO$_4$. After concentration, the residue is purified on silica gel (0-50% ethyl acetate in hexane) to give (3S,5R)-1-[4-(4-chlorophenoxy)phenyl]-3-allyl-5-[3-(trifluoromethyl)phenyl]pyrrolidin-2-one (58.5 mg, 80%) and its (3R)-diastereomer (6.5 mg, 9%) as a colorless oil. HPLC-MS calculated for $C_{26}H_{21}ClF_3NO_2$ (M+H$^+$) 472.12, found 472.10.

Step B: (3S,5R)-1-[4-(4-chlorophenoxy)phenyl]-3-allyl-5-[3-(trifluoromethyl)phenyl]pyrrolidin-2-one (56 mg, 0.119 mmol) is dissolved in 3 mL of a 2:1 mixture of CH$_2$Cl$_2$-

MeOH and is cooled to −78° C. Ozone is bubbled through the solution until a blue color persisted and then nitrogen is bubbled through until it is clear. NaBH$_4$ (2.5 eq) is added and the reaction mixture is allowed to warm to room temperature. The mixture is stirred for 2 h, and then most of the solvent is removed by evaporation in vacuo. Water is added (10 mL) and the aqueous layer is extracted with ethyl acetate (5×10 mL). The combined extracts are washed with brine (10 mL), dried over Na$_2$SO$_4$, filtered and evaporated. The residue is purified on silica gel (0-55% ethyl acetate in hexane) to give (3R,5R)-1-[4-(4-chlorophenoxy)phenyl]-5-[3-(trifluoromethyl)phenyl]-3-(2-hydroxyethyl)pyrrolidin-2-one (51 mg, 89%) as a colorless oil. $^1$H NMR (CDCl$_3$, 400 MHz) δ 7.51-7.46 (m, 1H), 7.44-7.37 (m, 2H), 7.36-7.30 (m, 3H), 7.21-7.16 (m, 2H), 6.87-6.78 (m, 4H), 5.21 (dd, J=10.5, 2.0 Hz, 1H), 3.85-3.68 (m, 2H), 2.97-2.85 (m, 1H), 2.45-2.32 (m, 1H), 2.26-2.15 (m, 2H), 2.10-1.98 (m, 1H), 1.80-1.69 (m, 1H). HPLC-MS calculated for C$_{25}$H$_{21}$ClF$_3$NO$_3$ (M+H$^+$) 476.12, found 476.10.

Step C: To a solution of (3R,5R)-1-[4-(4-chlorophenoxy)phenyl]-5-[3-(trifluoromethyl)phenyl]-3-(2-hydroxyethyl)pyrrolidin-2-one (50 mg, 0.105 mmol) in DCM (2 mL) at 0° C. is added MsCl (26 µL) and TEA (50 µL). The reaction mixture is stirred at room temperature for 45 min before removal of the solvent. The residue is purified on silica gel (0-50% ethyl acetate in hexane) to give 2-{(3R,5R)-1-[4-(4-chlorophenoxy)phenyl]-5-[3-(trifluoromethyl)phenyl]-2-oxopyrrolidin-3-yl}ethyl methanesulfonate (54.3 mg, 93%) as a colorless oil.

Step D: To a solution of 2-{(3R,5R)-1-[4-(4-chlorophenoxy)phenyl]-5-[3-(trifluoromethyl)phenyl]-2-oxopyrrolidin-3-yl}ethyl methanesulfonate (54.3 mg, 0.098 mmol) in THF (2 mL) is added NaSMe (excess). The reaction mixture is stirred at room temperature for 64 h before removal of the solvent. The crude (3R,5R)-1-[4-(4-chlorophenoxy)phenyl]-5-[3-(trifluoromethyl)phenyl]-3-[2-(methylthio)ethyl]pyrrolidin-2-one is used in next step without further purification.

Step E: The crude product from Step D is dissolved in CH$_2$Cl$_2$ (3 mL) and m-CPBA (77%, excess) is added at 0° C. The reaction mixture is stirred at room temperature overnight before removal of the solvent. The residue is dissolved in CH$_2$Cl$_2$ (60 mL) and washed with saturated NaHCO$_3$ aqueous solution (10 mL) and brine (10 mL). The organic layer is dried over Na$_2$SO$_4$, concentrated, and purified on silica gel (0-75% ethyl acetate in hexane) to give as (3R,5R)-1-[4-(4-chlorophenoxy)phenyl]-5-[3-(trifluoromethyl)phenyl]-3-[2-(methylsulfonyl)ethyl]pyrrolidin-2-one as a colorless oil (33 mg, 63% for two steps) $^1$H NMR (CDCl$_3$, 400 MHz) δ 7.58-7.53 (m, 1H), 7.51-7.44 (m, 2H), 7.41-7.36 (m, 3H), 7.28-7.23 (m, 2H), 6.93-6.85 (m, 4H), 5.27 (dd, J=10.5, 2.5 Hz, 1H), 3.48 (ddd, J=17.5, 13.5, 7.0 Hz, 1H), 3.21 (ddd, J=17.5, 13.0, 6.5 Hz, 1H), 3.00-2.88 (m, 1H), 2.95 (s, 3H), 2.53-2.37 (m, 1H), 2.37-2.24 (m, 2H), 2.23-2.12 (m, 1H). HPLC-MS calculated for C$_{26}$H$_{23}$ClF$_3$NO$_4$S (M+H$^+$) 538.10, found 538.10; and (3S,5R)-1-[4-(4-chlorophenoxy)phenyl]-5-[3-(trifluoromethyl)phenyl]-3-[2-(methyl-sulfonyl)ethyl]pyrrolidin-2-one as a colorless oil (15 mg, 28% for two steps) $^1$H NMR (CDCl$_3$, 400 MHz) δ 7.52-7.47 (m, 1H), 7.45-7.34 (m, 3H), 7.27-7.21 (m, 2H), 7.21-7.16 (m, 2H), 6.89-6.81 (m, 4H), 5.21 (dd, J=11.5, 8.0 Hz, 1H), 3.52 (ddd, J=17.5, 12.5, 7.0 Hz, 1H), 3.29 (ddd, J=17.5, 12.0, 7.0 Hz, 1H), 2.97 (s, 3H), 2.96-2.84 (m, 2H), 2.46-2.34 (m, 1H), 2.26-2.12 (m, 1H), 1.76-1.65 (m, 1H). HPLC-MS calculated for C$_{26}$H$_{23}$ClF$_3$NO$_4$S (M+H$^+$) 538.10, found 538.10.

Example 254

(3S,5R)-1-[4-(4-chlorophenoxy)phenyl]-5-[3-(trifluoromethyl)phenyl]-3-[3-(methylsulfonyl)propyl]pyrrolidin-2-one

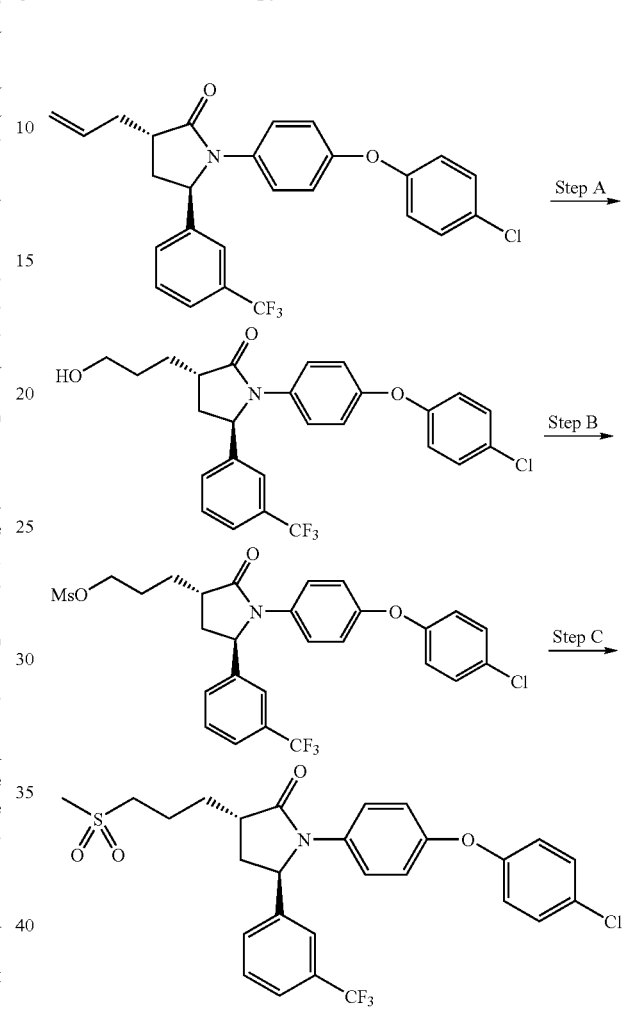

Step A: To a solution of (3S,5R)-1-[4-(4-chlorophenoxy)phenyl]-3-allyl-5-[3-(trifluoromethyl)phenyl]pyrrolidin-2-one (61.5 mg, 0.13 mmol) in dry THF (1 mL) at 0° C. and argon is added dropwise a 9-BBN solution (0.57 mL, 0.5 M in hexane). After the addition is complete, the reaction mixture is stirred at 0° C. for 2 h and at room temperature for 3 h. The mixture is then cooled to 0° C. and treated with a 3M NaOH (0.3 mL). The oxidation is carried out by slow addition of 35% H$_2$O$_2$ (0.3 mL) at 0° C. The reaction mixture is stirred at 0° C. for 1 h and then at room temperature overnight. The resulting solution is poured into ethyl acetate (50 mL), washed with brine (10 mL), dried over Na$_2$SO$_4$, filtered and evaporated. The residue is purified on silica gel (0-50% ethyl acetate in hexane) to give (3S,5R)-1-[4-(4-chlorophenoxy)phenyl]-5-[3-(trifluoromethyl)phenyl]-3-(3-hydroxypropyl)pyrrolidin-2-one (64 mg, 100%) as a colorless oil. $^1$H NMR (CDCl$_3$, 400 MHz) δ 7.60-7.51 (m, 1H), 7.50-7.43 (m, 2H), 7.43-7.35 (m, 3H), 7.28-7.22 (m, 2H), 6.93-6.83 (m, 4H), 5.24 (dd, J=10.5, 3.0 Hz, 1H), 3.70 (t, J=7.2 Hz, 2H), 2.87-2.75 (m, 1H), 2.45-2.33 (m, 1H), 2.26-2.16 (m, 1H), 2.11-1.98 (m, 1H), 1.87 (s, br, 1H), 1.75-1.58 (m, 3H). HPLC-MS calculated for C$_{26}$H$_{23}$ClF$_3$NO$_3$ (M+H$^+$) 490.13, found 490.10.

Step B: To a solution of (3S,5R)-1-[4-(4-chlorophenoxy)phenyl]-5-[3-(trifluoromethyl)phenyl]-3-(3-hydroxypropyl)pyrrolidin-2-one (34 mg, 0.070 mmol) in DCM (3 mL) at 0° C. is added MsCl (50 µL) and TEA (100 µL). The reaction mixture is stirred at room temperature overnight before removal of the solvent. The residue is purified on silica gel (0-50% ethyl acetate in hexane) to give 3-{(3S,5R)-1-[4-(4-chlorophenoxy)phenyl]-5-[3-(trifluoromethyl)phenyl]-2-oxopyrrolidin-3-yl}propyl methanesulfonate (39.1 mg, 99%) as a colorless oil.

Step C: To a solution of 3-{(3S,5R)-1-[4-(4-chlorophenoxy)phenyl]-5-[3-(trifluoromethyl)phenyl]-2-oxopyrrolidin-3-yl}propyl methanesulfonate (39.1 mg, 0.069 mmol) in THF (1 mL) is added NaSMe (excess). The reaction mixture is stirred at room temperature for 16 h before removal of the solvent. The crude product is then dissolved in $CH_2Cl_2$ (1 mL) and m-CPBA (77%, excess) is added at 0° C. The reaction mixture is stirred at room temperature for 1 h before removal of the solvent. The residue is dissolved in $CH_2Cl_2$ (60 mL) and washed with saturated $NaHCO_3$ aqueous solution (10 mL) and brine (10 mL). The organic layer is dried over $Na_2SO_4$, concentrated, and purified on a silica gel (0-75% ethyl acetate in hexane) to give the title compound as a colorless oil (33.1 mg, 87%). $^1$H NMR (CDCl$_3$, 400 MHz) δ 7.57-7.53 (m, 1H), 7.51-7.44 (m, 2H), 7.43-7.36 (m, 3H), 7.28-7.22 (m, 2H), 6.93-6.85 (m, 4H), 5.25 (dd, J=10.5, 2.5 Hz, 1H), 3.12-3.03 (m, 2H), 2.92 (s, 3H), 2.85-2.74 (m, 1H), 2.46-2.34 (m, 1H), 2.24 (ddd, J=16.0, 10.0, 3.0 Hz, 1H), 2.16-1.94 (m, 3H), 1.79-1.67 (m, 1H). HPLC-MS calculated for $C_{27}H_{25}ClF_3NO_4S$ (M+H$^+$) 552.11, found 552.10.

Example 269

(S)-3-(4-chlorophenyl)-4-(3-(pyrazin-2-yloxy)phenyl)oxazolidin-2-one

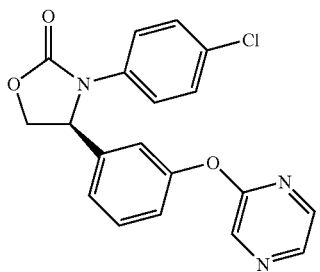 [SMILES: O=C1OC[C@H](c2cccc(Oc3cnccn3)c2)N1c1ccc(Cl)cc1]

Reference: Org Lett 2003, 5(21), 3799. A small reaction tube fitted with a screw cap containing a septum is charged with (S)-3-(4-chlorophenyl)-4-(3-hydroxyphenyl)-oxazolidin-2-one (0.06 mmol), 2-bromopyrazine (0.076 mmol), CuI (0.04 mmol), N,N-dimethylglycine (0.04 mmol), $Cs_2CO_3$ (0.13 mmol) and 1,4-dioxane (1 mL) is stirred at 120° C. for 18 h. The reaction mixture is then cooled to room temperature and filtered through a Whatman 0.42 µM filter and purified by preparative HPLC (C-18, 10-90% ACN/water (0.05% TFA)). $^1$H NMR (CDCl$_3$, 400 MHz) δ 8.41 (d, J=1.2 Hz, 1H), 8.29 (d, J=2.8 Hz, 1H), 8.04 (dd, J=2.8, 1.2 Hz, 1H), 7.43 (t, J=8.0 Hz, 1H), 7.34 (d, J=8.8 Hz, 2H), 7.24 (d, J=8.2 Hz, 2H), 7.12-7.19 (m, 2H), 7.10 (s, 1H), 5.37 (dd, J=8.8, 6.0 Hz, 1H), 4.80 (t, J=8.8 Hz, 1H), 4.26 (dd, J=8.8, 6.0 Hz, 1H); HPLC-MS calculated for $C_{19}H_{14}ClN_3O_3$ (M+H$^+$) 368.1, found 368.1.

The above procedure is also applied towards the preparation of Example 278, Example 292, Example 297, Examples 300-303, and Examples 305-306. See Table for spectral data.

Example 270

(S)-methyl 5-(4-(4-chlorophenoxy)phenyl)-4-(3-methoxyphenyl)-1,2,5-thiadiazolidine-1,1-dioxide-2-carboxylate

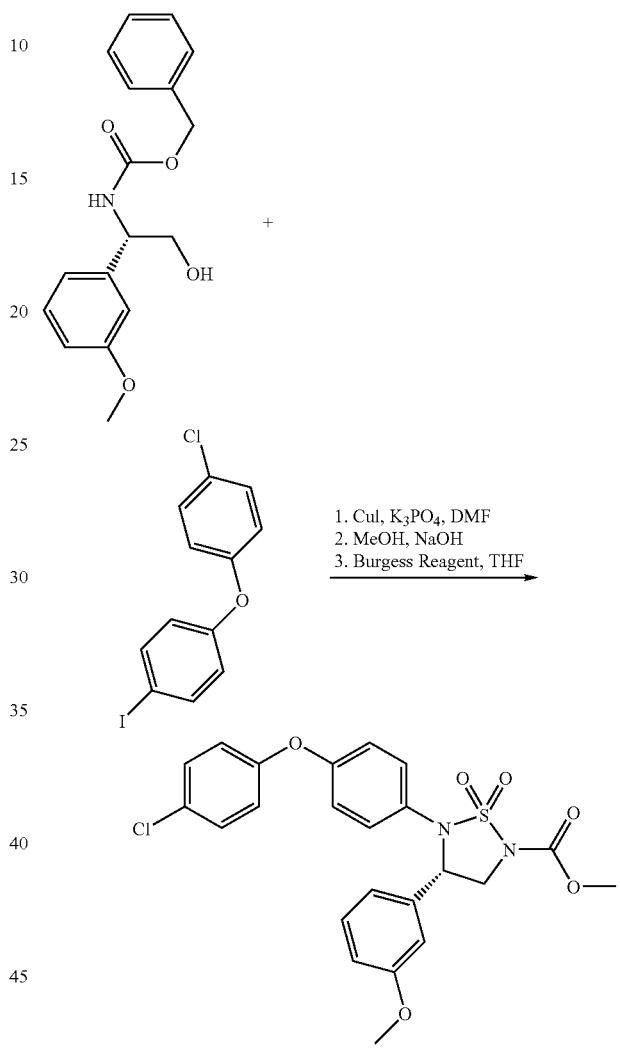

Step 1: To a dry round bottom flask is added [2-hydroxy-1-(3-methoxy-phenyl)ethyl]-carbamic acid benzyl ester (300 mg, 1 mmol), 1-(4-chlorophenoxy)-4-iodobenzene (330 mg, 1 mmol), $K_3PO_4$ (210 mg), 1,2-cyclohexanediamine (15 µL) and CuI (20 mg), and DMF (5 mL). The mixture is evacuated and back-filled with nitrogen three times. The reaction mixture is heated to 110° C. for 7 h. The reaction is then cooled to room temperature, diluted with EtOAc (50 mL), washed with 1N HCl, and brine, subsequently dried over MgSO$_4$, filtered, and concentrated to give the crude product, which is purified by flash chromatography on silica gel (EtOAc/Hex: 1/2) to provide 3-[4-(4-chlorophenoxy)phenyl]-4-(3-methoxyphenyl)-oxazolidin-2-one (304 mg).

Step 2: A solution of the product from step 1 (293 mg) in 3 mL of NaOH/MeOH (10%, w/w) is heated to 60° C. for 6 h, then subsequently cooled to room temperature and concentrated. The residue is dissolved in EtOAc (30 ml) and is washed with brine, and dried over MgSO$_4$, filtered, and concentrated to give the crude product, which is by purified flash chromatography on silica gel (EtOAc/Hex: 1/1) to provide 2-[4-(4-chloro-phenoxy)-phenylamino]-2-(3-methoxy-phenyl)-ethanol (202 mg).

Step 3: A solution of the Step 2 product (185 mg) in 10 ml THF is treated with Burgess' reagent (310 mg, 2.5 eq) in 3 mL THF. The reaction mixture is heated to reflux for 8 h, then cooled to room temperature. DCM (30 mL) is added to the mixture which is then washed with 1N HCl, brine, then dried over MgSO$_4$, filtered, concentrated, and purified by flash chromatography on silica gel (EtOAc/Hex: 1/1) to afford 208 mg of the title compound. $^1$H NMR (CDCl$_3$, 400 MHz) δ 7.27-7.31 (4H, m), 7.22 (1H, t, J=8.0 Hz), 6.87-6.93 (6H, m), 6.81 (1H, dd, J=2.8, 0.8 Hz), 5.05 (1H, dd, J=9.6, 6.4 Hz), 4.25 (1H, dd, J=6.0, 1.6 Hz), 3.95 (3H, s), 3.81 (1H, t, J=6.0 Hz), 3.72 (3H, s); HPLC-MS calculated for C$_{23}$H$_{21}$ClN$_2$O$_6$S (M+H$^+$): 489.1, found 489.1.

See reference: K. C. Nicolaou et al *Angew. Chem. Int. Ed.* 2002, 41, 3806.

Example 271

(S)-2-(4-(4-chlorophenoxy)phenyl)-3-(3-methoxyphenyl)-1,2,5-thiadiazolidine-1,1-dioxide

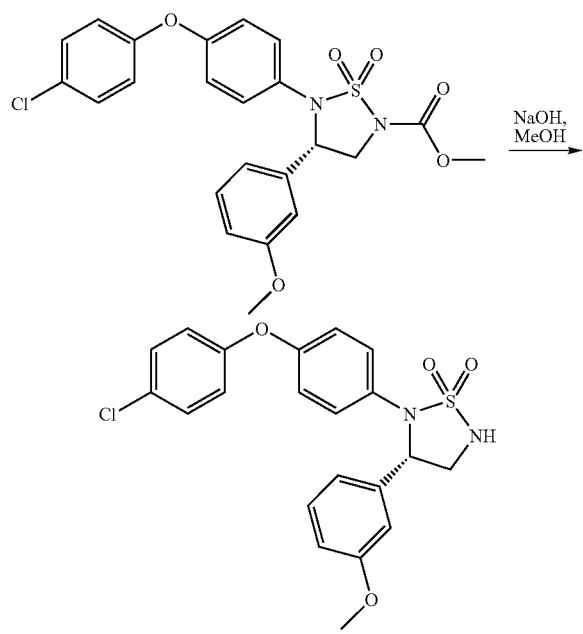

A solution of (S)-methyl 5-(4-(4-chlorophenoxy)phenyl)-4-(3-methoxyphenyl)-1,2,5-thiadiazolidine-1,1-dioxide-2-carboxylate (24 mg) in MeOH/20% NaOH—H$_2$O/THF (2/1/1) is stirred at room temperature for 1 h. The reaction mixture is neutralized with 1N HCl and extracted with EtOAc (3×10 mL). The combined extracts are washed with brine and dried. Concentration and purification of the residue by flash chromatography (EtOAc/Hex: 1:1) afford 17 mg of the title compound. $^1$H NMR (CDCl$_3$) δ 7.23-7.30 (3H, m), 7.18-7.21 (2H, d, J=6.8 Hz), 6.97 (1H, br s), 6.85-6.92 (5H, m), 6.83 (1H, dd, J=2.4, 0.8 Hz), 5.13 (1H, t, J=6.4 Hz), 4.69 (1H, J=8.0 Hz), 3.98 (1H, m), 3.78 (3H, s), 3.45 (1H, m); HPLC-MS calculated for C$_{21}$H$_{19}$ClN$_2$O$_4$S (M+H$^+$): 431.1, found 431.1

General Procedure I

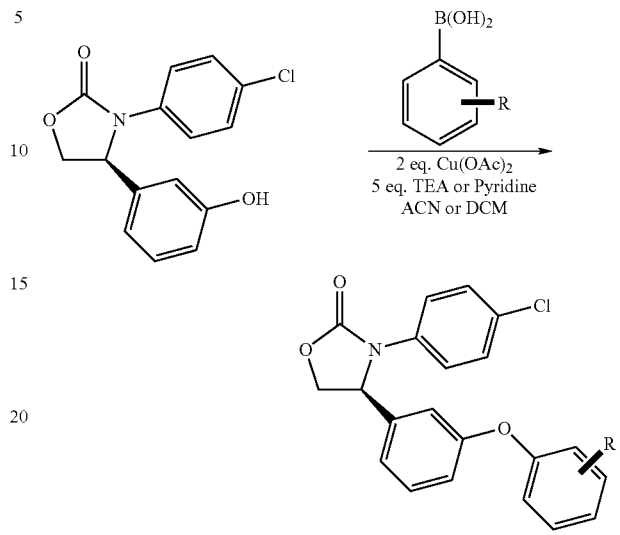

General Method for O-Arylation of (S)-3-(4-chlorophenyl)-4-(3-hydroxyphenyl)oxazolidin-2-one with Boronic Acids. Reference to O-Arylation with Boronic Acids: *Tetrahedron Lett.* 1998, 39, 2933-2936. To a septum cap tube is combined 4 Å powder molecular sieves, phenol (0.10 mmol, 1 equiv.), phenyl boronic acid (2 equiv.), Cu(OAc)$_2$ (2 equiv.), triethylamine or pyridine (5 equiv.) in anhydrous acetonitrile or dichloromethane (1 mL). The mixture is stirred at room temperature for 18-42 h. The mixture is then filtered through a Whatman 0.42 μM filter and purified by preparatory LC-MS purification (C-18, 10-90% ACN/water (0.05 TFA)) to give the title compound.

Example 272

(S)-4-(3-(m-tolyloxy)phenyl)-3-(4-chlorophenyl)oxazolidin-2-one

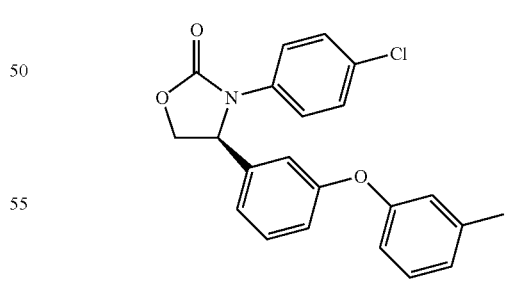

The title compound is prepared by the general O-arylation procedure with 3-methylphenylboronic acid to give the title compound. HPLC-MS calculated for C$_{22}$H$_{18}$ClNO$_3$ (M+H$^+$): 380.1, found 380.1.

The above O-arylation procedure is applied towards the preparation of Example 273, Example 274, Example 275, and Example 304. See Table for spectral data.

Example 276

(S)-4-(3-(2-cyanophenoxy)phenyl)-3-(4-chlorophenyl)oxazolidin-2-one

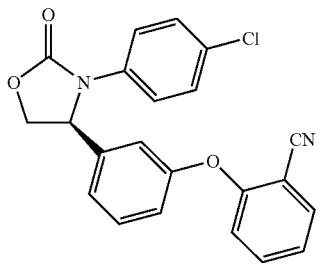 [SMILES: N#Cc1ccccc1Oc1cccc([C@H]2COC(=O)N2c2ccc(Cl)cc2)c1]

To (S)-3-(4-chlorophenyl)-4-(3-hydroxyphenyl)oxazolidin-2-one (0.07 mmol) is added $K_2CO_3$ (0.14 mmol) and 2-fluorobenzonitrile (0.08 mmol) in DMSO (1 mL). The mixture is degassed with $N_2$ (2×) and stirred at 80° C. for 2-3 hours. The mixture is filtered through a Whatman 0.42 μM filter and purified by preparatory LC-MS (C-18, 10-90% ACN/water (0.05% TFA)). HPLC-MS calculated for $C_{22}H_{15}ClN_2O_3$ (M+H$^+$): 391.1, found 391.0.

Example 279

(S)-3-(4-chlorophenyl)-4-(3-(pyrimidin-2-yloxy)phenyl)oxazolidin-2-one

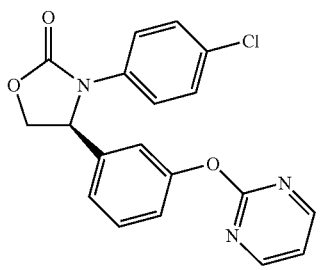 [SMILES: O=C1OC[C@H](c2cccc(Oc3ncccn3)c2)N1c1ccc(Cl)cc1]

To (S)-3-(4-chlorophenyl)-4-(3-hydroxyphenyl)oxazolidin-2-one (0.05 mmol) is added $Cs_2CO_3$ (0.1 mmol) and 2-chloropyrimidine (0.06 mmol) in DMF (1 mL). The mixture is stirred at 80° C. for 3 h then cooled to room temperature and filtered through Whatman 0.42 μM filter and purified by preparative HPLC (C-18, 10-90% ACN/water (0.05% TFA)). HPLC-MS calculated for $C_{19}H_{14}ClN_3O_3$ (M+H$^+$): 368.0, found 368.0.

The same procedure is applied towards the preparation of Example 299. See Table for spectral data.

Example 280

(S)-3-(4-chlorophenyl)-4-(3-ethoxyphenyl)oxazolidin-2-one

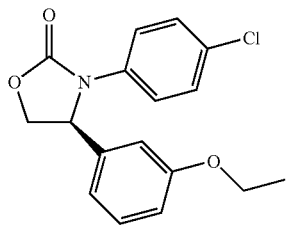 [SMILES: CCOc1cccc([C@H]2COC(=O)N2c2ccc(Cl)cc2)c1]

To (S)-3-(4-chlorophenyl)-4-(3-hydroxyphenyl)oxazolidin-2-one (0.07 mmol), $K_2CO_3$ (0.37 mmol) in DMF (0.5 mL) is added iodoethane (0.14 mmol) and the reaction stirred at 60° C. overnight, then cooled to room temperature, filtered through a Whatman 0.42 μM filter and purified by preparative HPLC (C-18, 10-90% ACN/water (0.05% TFA)). HPLC-MS calculated for $C_{17}H_{16}ClNO_3$ (M+H$^+$): 318.1, found 318.0.

This procedure is applied towards the preparation of Example 281 (LDN547), Example 282 (LDN548), Example 283, Example 284, and Example 285. See Table for structures and spectral data.

Example 288

1-(4-(4-chlorophenoxy)phenyl)-5-(3-(benzyloxy)phenyl)imidazolidin-2-one

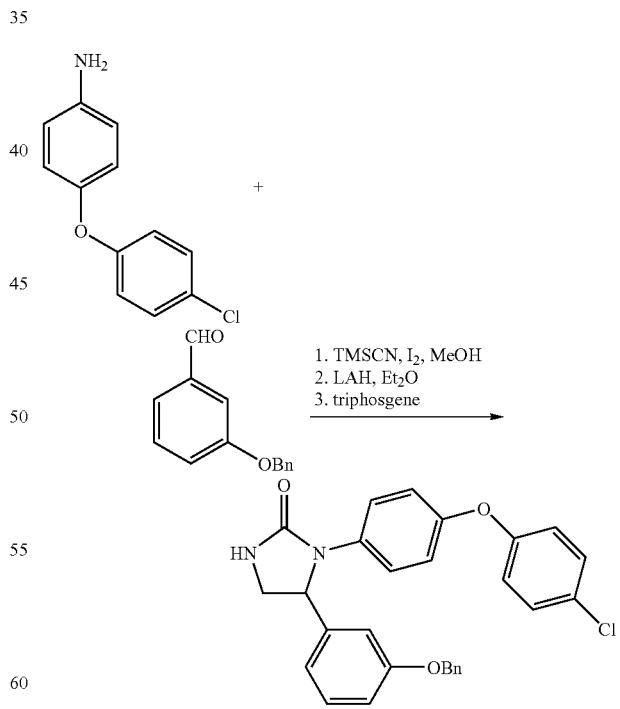

Step 1: Reference to α-amino nitrile synthesis: *Synlett*, 2005, 8, 1325. A methanol solution (50 mL) of 3-benzyloxybenzaldehyde (5 g, 23.6 mmol), 4-amino-4-chlorodiphenyl ether (5.7 g, 25.9 mmol), iodine (120 mg, 0.47 mmol) and trimethylsilylcyanide (3.8 mL, 28.3 mmol) is stirred at room temperature for 18 h. The precipitate that formed is collected and rinsed with ethyl acetate/hexane (1:4) to obtain ~7 g (67%) of 2-(4-(4-chlorophenoxy)phenylamino)-2-(3-(benzyloxy)phenyl)acetonitrile as a light brown solid.

Step 2: A suspension of the α-amino nitrile (3 g, 6.8 mmol) from Step 1 in ether is cooled to −78° C. and is treated with lithium aluminum hydride (1.0 M solution in ether, 27.2 mmol) via slow addition. The cooling bath is removed and the reaction is allowed to warm to room temperature. Upon completion, 500 μL of water is added at 0° C. and the mixture stirred for 15 min. The mixture is filtered through a bed of Celite and the filtrate concentrated and purified by silica gel chromatography (eluting with 7N NH$_3$ in IPA/methanol/dichloromethane 0.1:1:9) to give 1.5 g of 4-(4-chlorophenoxy)-N-(2-amino-1-(3-(benzyloxy)phenyl)ethyl)benzenamine as an oily brownish foam (50%).

Step 3: To the diamine (440 mg, 0.98 mmol) from Step 2, and triethylamine (330 μL, 2.4 mmol) in THF (20 mL) is added triphosgene (180 mg, 0.6 mmol) in THF at 0° C. After complete addition, the mixture is quenched with water and THF is removed by evaporation. The residue is extracted with ethyl acetate and washed with water. Evaporation of the organics gives a solid which is triturated with ethyl acetate, filtered, and washed with 40% ethyl acetate/hexane to give 279 mg of the title compound. Purification of the filtrate gives an additional 127 mg of product (combined yield, 88%). HPLC-MS calculated for $C_{28}H_{23}ClN_2O_3$ (M+H$^+$): 471.1, found 471.1.

Example 289

3-(4-(4-chlorophenoxy)phenyl)-4-(3-(benzyloxy)phenyl)-1-(2-(methylsulfonyl)ethyl)imidazolidin-2-one

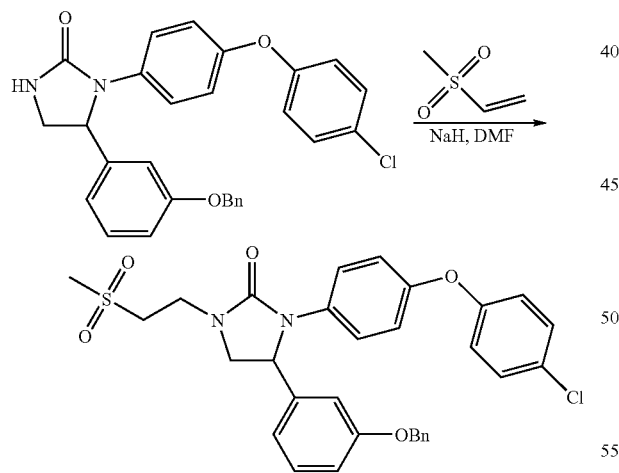

To 1-(4-(4-chlorophenoxy)phenyl)-5-(3-(benzyloxy)phenyl)imidazolidin-2-one (Example 288) (200 mg, 0.42 mmol) in 5 mL DMF is added sodium hydride (19 mg, 0.47 mmol) followed by methyl vinyl sulfone (41 μL, 0.47 mmol). After 30 minute, the reaction is cooled to 0° C. and sat. ammonium chloride is added slowly to the reaction mixture. The reaction mixture is extracted with ethyl acetate (2×) and purified by flash chromatography gives 171 mg (71%) of the title compound. HPLC-MS calculated for $C_{31}H_{29}ClN_2O_5S$ (M+H$^+$): 577.2, found 577.2.

Example 290

3-(4-(4-chlorophenoxy)phenyl)-4-(3-hydroxyphenyl)-1-(2-(methylsulfonyl)ethyl)imidazolidin-2-one

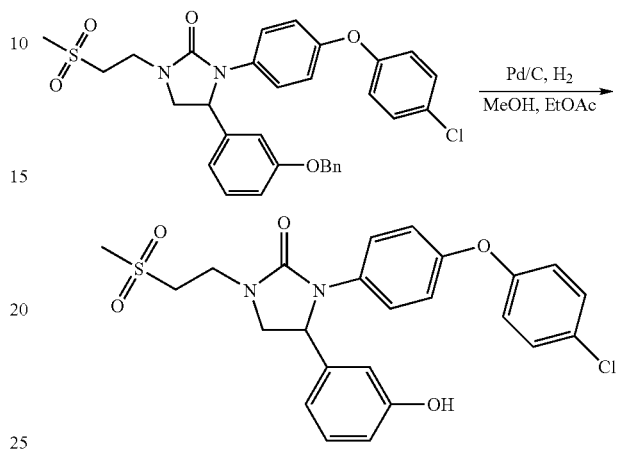

To 3-(4-(4-chlorophenoxy)phenyl)-4-(3-(benzyloxy)phenyl)-1-(2-(methylsulfonyl)ethyl)imidazolidin-2-one (Example 289) (200 mg, 0.35 mmol) in methanol/ethyl acetate (1:3) is added 20 mg Pd/C. The mixture is stirred under H$_2$ atmosphere for 30 minutes. Filtration through a bed of celite and evaporation yields 178 mg of the title compound as a white solid. $^1$H NMR (CDCl$_3$) δ 7.32-7.29 (m, 2H), 7.25-7.19 (m, 2H), 7.19-7.15 (m, 1H), 6.88-6.83 (m, 4H), 6.79-6.73 (m, 3H), 5.10 (dd, J=9.2, 5.6 Hz, 1H), 3.97-3.88 (m, 2H), 3.75-3.68 (m, 1H), 3.38 (dd, J=8.8, 6.0 Hz, 1H), 3.36 (t, J=6.4 Hz, 2H), 3.01 (s, 3H); HPLC-MS calculated for $C_{24}H_{23}ClN_2O_5S$ (M+H$^+$): 487.1, found 487.1.

Example 291

3-(4-(4-chlorophenoxy)phenyl)-1-(2-(methylsulfonyl)ethyl)-4-(3-(pyridin-2-yloxy)phenyl)imidazolidin-2-one

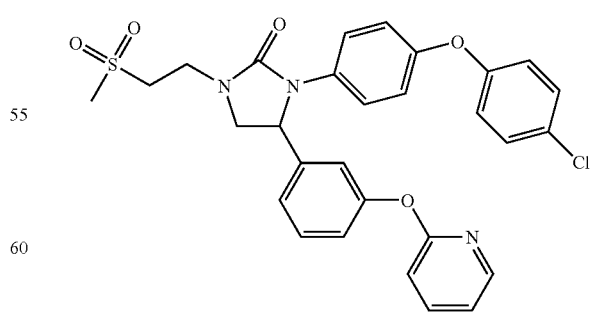

The title compound is prepared as described in Example 269 from Example 290 and 2-bromopyridine. HPLC-MS calculated for $C_{29}H_{26}ClN_3O_5S$ (M+H$^+$): 564.0, found 564.0.

Example 293

4-(3-(2-cyanophenoxy)phenyl)-3-(4-(4-chlorophenoxy)phenyl)-1-(2-(methylsulfonyl)ethyl)imidazolidin-2-one

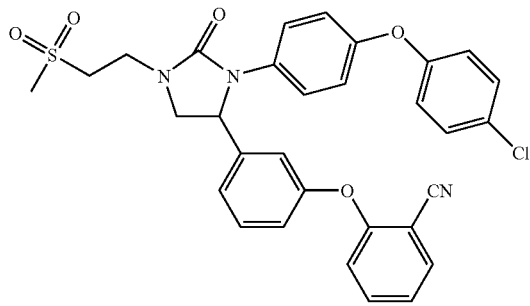 [SMILES: CS(=O)(=O)CCN1CC(c2cccc(Oc3ccccc3C#N)c2)N(c2ccc(Oc3ccc(Cl)cc3)cc2)C1=O]

The title compound is prepared as described in Example 276 from Example 290 and 2-fluorobenzonitrile. $^1$H NMR (CDCl$_3$) δ 7.66 (dd, J=7.6, 1.6 Hz, 1H), 7.45-7.40 (m, 1H), 7.40-7.36 (m, 2H), 7.27-7.23 (m, 3H), 7.18-7.13 (m, 2H), 7.01-6.98 (m, 2H), 6.90-6.86 (m, 4H), 6.68 (dd, J=8.8, 0.8 Hz, 1H), 5.22 (dd, J=9.2, 6.8 Hz, 1H), 4.06 (t, J=9.2 Hz, 1H), 3.90-3.76 (m, 2H), 3.44-3.29 (m, 3H), 3.00 (s, 3H); HPLC-MS calculated for C$_{31}$H$_{26}$ClN$_3$O$_5$S (M+H$^+$): 588.1, found 588.1.

The same procedure is applied towards the preparation of Example 298. See Table for spectral data.

Example 294

5-(3-(benzyloxy)phenyl)-1-(4-chlorophenyl)imidazolidin-2-one

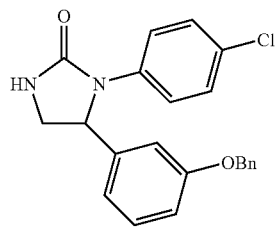 [SMILES: O=C1NCC(c2cccc(OCc3ccccc3)c2)N1c1ccc(Cl)cc1]

The title compound is prepared as described for Example 288, replacing 4-amino-4-chlorodiphenyl ether with 4-chloroaniline. HPLC-MS calculated for C$_{22}$H$_{19}$ClN$_2$O$_2$ (M+H$^+$): 379.1, found 379.1.

Example 295

4-(3-(benzyloxy)phenyl)-3-(4-chlorophenyl)-1-(2-(methylsulfonyl)ethyl)-imidazolidin-2-one

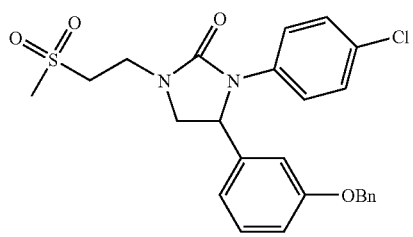 [SMILES: CS(=O)(=O)CCN1CC(c2cccc(OCc3ccccc3)c2)N(c2ccc(Cl)cc2)C1=O]

The title compound is prepared as described for Example 289 from Example 294. HPLC-MS calculated for C$_{25}$H$_{25}$ClN$_2$O$_4$S (M+H$^+$): 485.1, found 485.1.

Example 296

3-(4-chlorophenyl)-4-(3-hydroxyphenyl)-1-(2-(methyl sulfonyl)ethyl)imidazolidin-2-one

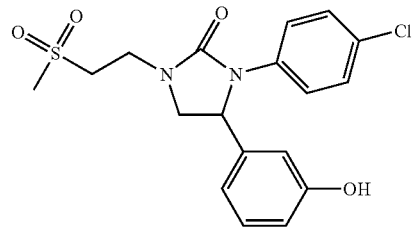 [SMILES: CS(=O)(=O)CCN1CC(c2cccc(O)c2)N(c2ccc(Cl)cc2)C1=O]

The title compound is prepared as described for Example 290 from Example 295. HPLC-MS calculated for C$_{18}$H$_{19}$ClN$_2$O$_4$S (M+H$^+$): 395.1, found 395.1.

Example 307

(4S,5S)-1-((3-(4-chlorophenyl)-4-(3-fluoro-5-(trifluoromethyl)phenyl)-2-oxooxazolidin-5-yl)methyl)-N-(piperidin-1-yl)-1H-1,2,3-triazole-4-carboxamide

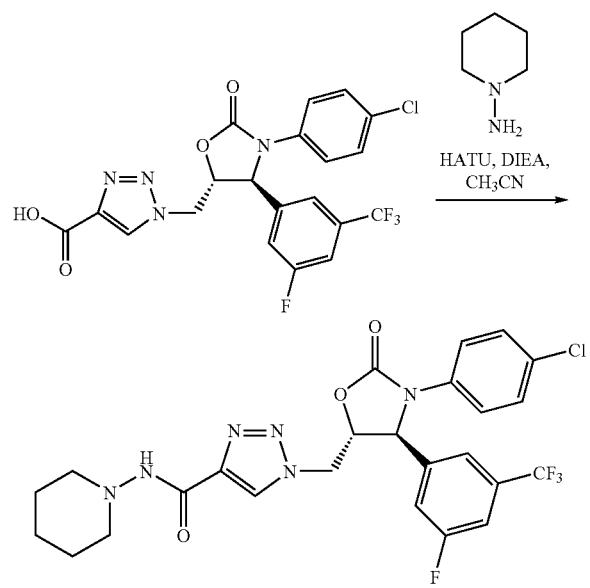

(4S,5S)-1-((3-(4-Chlorophenyl)-4-(3-fluoro-5-(trifluoromethyl)phenyl)-2-oxooxazolidin-5-yl)methyl)-1H-1,2,3- triazole-4-carboxylic acid (40 mg, 0.082 mmol) is dissolved in CH$_3$CN (2 mL) and is successively treated with DIEA (14 µL, 0.082 mmol) and HATU (31 mg, 0.082 mmol) at ambient temperature. After 5 minutes, 1-aminopiperidine (10 µL, 0.097 mmol) is added and the reaction stirred for 2 h as judged complete by LC-MS. The reaction is quenched with 1 mL 1M HCl and diluted with water and ethyl acetate. The organic layer is washed successively with NaHCO$_3$, brine, dried over MgSO$_4$, filtered and concentrated. Purification by flash chromatography on silica gel (0-5% methanol/dichloromethane) gives the title compound (17 mg, 37%) as a white film. $^1$H NMR (acetone-d$_6$, 400 MHz) δ 8.49 (s, 1H), 8.39 (s, 1H), 7.72 (s, 1H), 7.66 (d, 1H, J=9.2 Hz), 7.52 (d, 1H, J=8.5 Hz), 7.45-7.49 (m, 2H), 7.30-7.33 (m, 2H), 5.85 (d, 1H, J=5.5 Hz), 5.21 (d, 2H, J=5.6 Hz), 5.11 (q, 1H, J=5.6 Hz), 2.89 (t, 4H, J=5.3 Hz), 1.65 (pentet, 4H, J=6.0 Hz), 1.48-1.51 (m, 1H), 1.39-1.45 (m, 1H). HPLC-MS calculated C$_{25}$H$_{23}$ClF$_4$N$_6$O$_3$ (M+H$^+$): 567.2, found: 567.2.

Example 311

(4S,5S)-3-(4-chlorophenyl)-5-((4-(ethylsulfonylmethyl)-1H-1,2,3-triazol-1-yl)methyl)-4-(3-fluoro-5-(trifluoromethyl)phenyl)oxazolidin-2-one

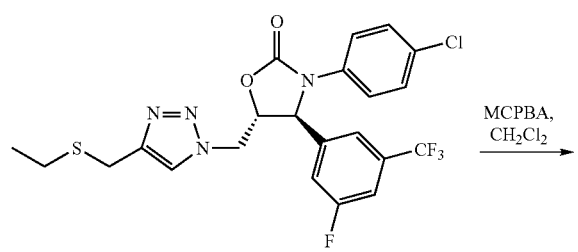

Meta-chloroperbenzoic acid (MCPBA) (60 mg, 0.27 mmol) is added to a solution of the sulfide (35 mg, 0.068 mmol) in CH$_2$Cl$_2$ (3 mL) at room temperature and stirred for 2 h. The reaction is quenched with Na$_2$S$_2$O$_3$ and diluted with water. The organic layer is then washed with NaHCO$_3$, dried over MgSO$_4$, filtered and concentrated. Preparative HPLC purification (C-18, 10-80% ACN/water (0.05 TFA)) gives the title compound (33 mg, 89%) as a colorless oil. $^1$H NMR (acetone-d$_6$, 400 MHz) δ 8.20 (s, 1H), 7.76 (s, 1H), 7.67 (d, 1H, J=9.2 Hz), 7.53 (d, 1H, J=8.5 Hz), 7.43-7.49 (m, 2H), 7.29-7.35 (m, 2H), 5.83 (d, 1H, J=5.4 Hz), 5.14-5.23 (m, 2H), 5.08 (ddd, 1H, J=5.8, 5.8, 4.3 Hz), 4.47 (s, 2H), 2.98 (q, 2H, J=7.5 Hz), 1.28 (t, 3H, J=7.5 Hz). HPLC-MS calculated C$_{22}$H$_{19}$ClF$_4$N$_4$O$_4$S (M+H$^+$): 547.1, found: 547.1.

Example 324

(4S,5S)-3-(4-chlorophenyl)-5-((5-(2-(diethylamino)ethyl)-2H-tetrazol-2-yl)methyl)-4-(3-methoxyphenyl)oxazolidin-2-one

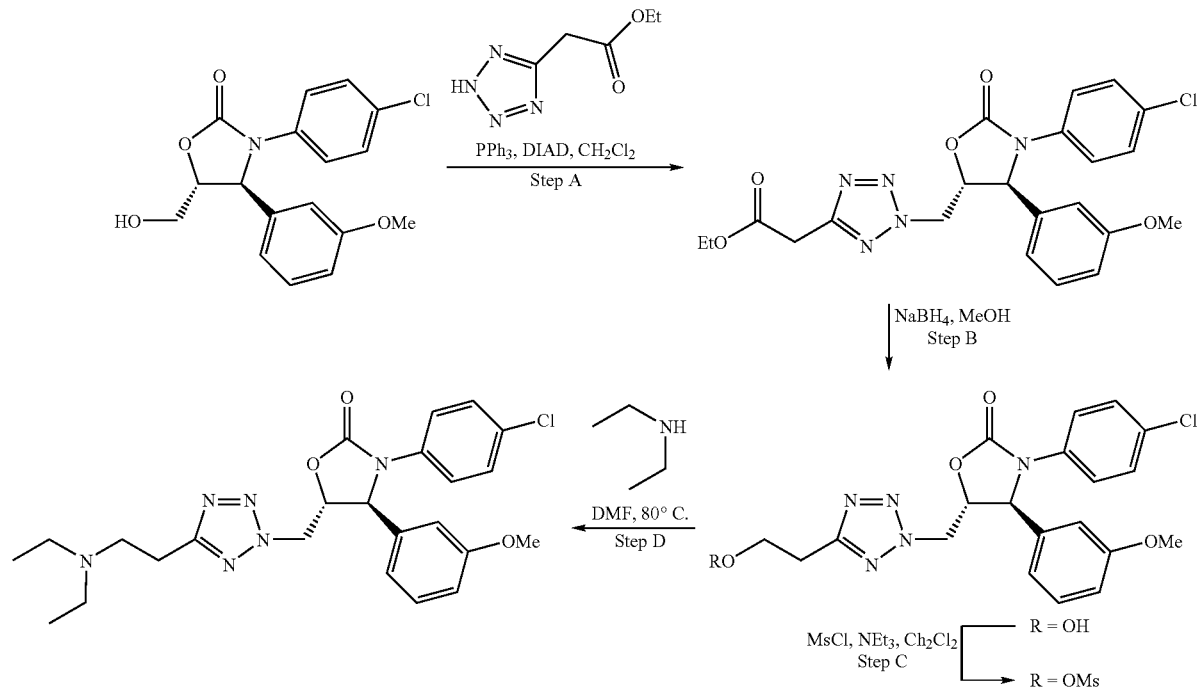

Step A: To a stirred solution of (4S,5R)-3-(4-chlorophenyl)-5-(hydroxymethyl)-4-(3-methoxyphenyl)oxazolidin-2-one (prepared according to Step D of Example 64) (325 mg, 0.97 mmol) and ethyl 2-(2H-tetrazol-5-yl)acetate (303 mg, 1.94 mmol) in $CH_2Cl_2$ at 0° C. is added triphenylphosphine (509 mg, 1.94 mmol) under an atmosphere of nitrogen. DIAD (380 µL, 1.94 mmol) is added dropwise and the cooling bath is removed, which allowed the reaction to warm to ambient temperature while stirring overnight. The reaction is concentrated and the residue purified by flash chromatography on silica gel (0-40% ethyl acetate/hexanes) to give 431 mg of the product as a colorless oil.

Step B: $NaBH_4$ (137 mg, 3.64 mmol) is added to a methanol (4 mL) solution of the ester from Step A at 0° C. under a nitrogen atmosphere. The cooling bath is removed and the reaction is stirred at ambient temperature for 3 h. The reaction is quenched with a saturated solution of $NH_4Cl$ and diluted with water and ethyl acetate. The organic is washed with brine, dried over $MgSO_4$, filtered and concentrated. Purification on silica gel (0-5% methanol/dichloromethane) gives 369 mg of the product as a colorless oil.

Step C: Methanesulfonyl chloride (73 µL, 0.94 mmol) is added to a $CH_2Cl_2$ (4 mL) solution of the alcohol from Step B and $NEt_3$ (236 µL, 1.7 mmol) at ambient temperature. After 30 minutes, the reaction is quenched with a saturated solution of $NH_4Cl$. The aqueous phase is extracted once with $CH_2Cl_2$ and the combined organics are dried over $MgSO_4$, filtered and concentrated to give 440 mg of the mesylate as a colorless oil.

Step D: Performed as in Step B of Example 52 and purified by preparative HPLC (C-18, 10-80% ACN/water (0.05% TFA)) to give 14 mg of the title compound as a colorless oil. $^1$H NMR (acetone-$d_6$, 400 MHz) δ 7.43-7.47 (m, 2H), 7.28-7.33 (m, 3H), 7.04 (t, 1H, J=2.2 Hz), 6.98-6.99 (m, 1H), 6.91 (ddd, 1H, J=8.3, 2.6, 0.8 Hz), 5.61 (d, 1H, J=5.0 Hz), 5.32 (dd, 1H, J=14.6, 5.7 Hz), 5.25 (dd, 1H, J=14.6, 5.7 Hz), 4.99 (ddd, 1H, J=5.6, 5.6, 4.2 Hz), 3.78 (s, 3H), 2.88-2.91 (m, 2H), 2.70-2.74 (m, 2H), 2.51 (q, 4H, J=7.1 Hz), 0.95 (t, 6H, J=7.1 Hz). HPLC-MS calculated $C_{24}H_{29}ClN_6O_3$ (M+H$^+$): 485.2, found: 485.2.

Example 326

(4S,5S)-3-(4-chlorophenyl)-5-((4-((diethylamino)methyl)-1H-1,2,3-triazol-1-yl)methyl)-4-(3-methoxyphenyl)oxazolidin-2-one

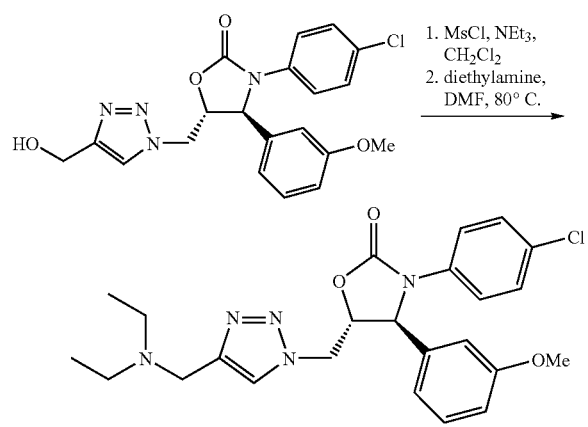

The alcohol is prepared as described in Example 84 using propargyl alcohol. The title compound is prepared as described in Steps C and D in Example 324 with purification by flash chromatography on silica gel (0-5% methanol/dichloromethane), yielding 15 mg. $^1$H NMR (acetone-$d_6$, 400 MHz) δ 8.39 (br s, 1H), 7.47-7.50 (m, 2H), 7.26-7.31 (m, 3H), 7.03 (t, 1H, J=2.0 Hz), 6.97 (d, 1H, J=7.8 Hz), 6.88 (ddd, 1H, J=8.3, 2.6, 0.8 Hz), 5.57 (d, 1H, J=4.8 Hz), 5.06-5.16 (m, 2H), 4.92 (q, 1H, J=4.8 Hz), 4.12 (br s, 2H), 3.77 (s, 3H), 2.75 (br s, 4H), 1.23 (t, 6H, J=6.7 Hz). HPLC-MS calculated $C_{24}H_{28}ClN_5O_3$ (M+H$^+$): 470.2, found: 470.2.

Example 334

(4S,5S)-3-(4-chlorophenyl)-4-(3-methoxyphenyl)-5-((4-(3-methyl-1,2,4-oxadiazol-5-yl)piperidin-1-yl)methyl)oxazolidin-2-one

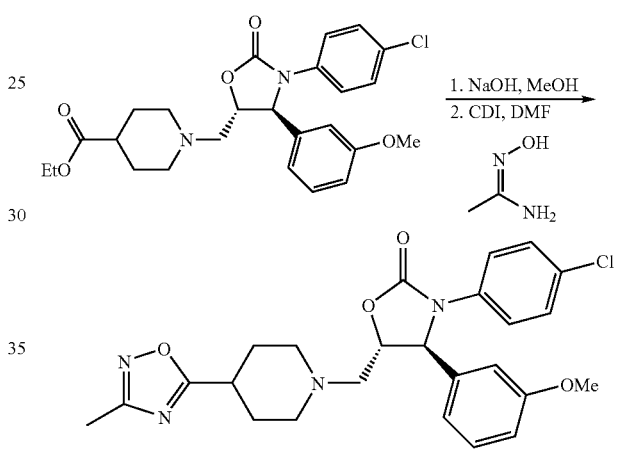

Step 1: The ester (196 mg, 0.41 mmol, prepared using the methods described for Example 64) is dissolved in MeOH/water (3 mL, 3:1) and NaOH added (40 mg, 1 mmol). The reaction is stirred at 50° C. for 1 hour, as judged complete by LC-MS, and cooled to room temperature. The reaction is brought to pH 2 using 1M HCl, extracted 3×$CH_2Cl_2$, dried over $MgSO_4$, filtered and concentrated to give 120 mg of a white solid that is used without purification.

Step 2: The acid from Step 1 is dissolved in DMF (1 mL) under $N_2$. N,N'-carbonyldiimidazole (CDI, 45 mg, 0.28 mmol) is added and the reaction is stirred 30 minutes at ambient temperature, at which point acetamidoxime (20 mg, 0.28 mmol) is added and stirred for 4 h. An additional 45 mg of CDI is added and the reaction is stirred at 100° C. overnight. The reaction is cooled and diluted with water and dichloromethane. The organic phase is washed successively with 1M HCl, $NaHCO_3$, brine, dried over $MgSO_4$, filtered and concentrated. Purification by preparative HPLC (C-18, 10-70% ACN/water (0.05% TFA)) gives 15 mg of the title compound as a colorless oil. $^1$H NMR (acetone-$d_6$, 400 MHz) δ 7.52-7.56 (m, 2H), 7.27-7.31 (m, 3H), 7.01-7.04 (m, 2H), 6.87 (ddd, 1H, J=8.3, 2.5, 0.9 Hz), 5.45 (d, 1H, J=5.6 Hz), 4.52 (q, 1H, J=5.7 Hz), 3.77 (s, 3H), 2.83-3.05 (m, 7H), 2.41 (dt, 1H, J=11.1, 2.1 Hz), 2.33 (dt, 1H, J=11.1, 2.1 Hz), 2.30 (s, 3H), 1.75-1.94 (m, 2H). HPLC-MS calculated $C_{25}H_{27}ClN_4O_4$ (M+H$^+$): 483.2, found: 483.2.

Example 336

(4S,5S)-3-(4-chlorophenyl)-4-(3-methoxyphenyl)-5-((4-(5-methyl-1,3,4-oxadiazol-2-yl)piperidin-1-yl)methyl)oxazolidin-2-one

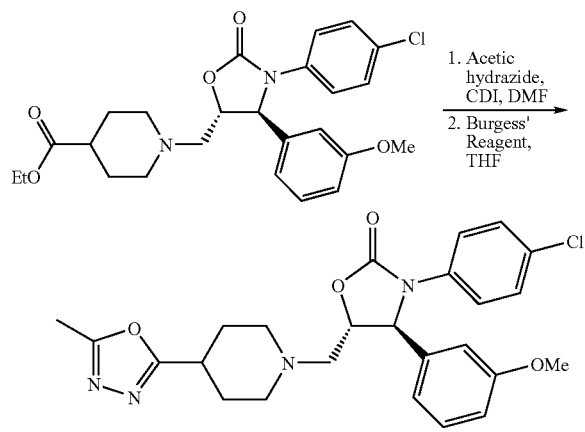

Step 1: CDI (30 mg, 0.18 mmol) is added to a solution of the acid (prepared in Example 334, 75 mg, 0.168 mmol) and stirred 30 minutes at ambient temperature. Acetic hydrazide (14 mg, 0.18 mmol) is added and the reaction is heated to 90° C. with stirring for 16 h. The reaction is cooled and diluted with water and ethyl acetate. The organic is washed with brine, dried over MgSO$_4$, filtered and concentrated to give 28 mg of a white film that is used without purification.

Step 2: Burgess' reagent (53 mg, 0.22 mmol) is added to a solution of the diacylhydrazine from Step 1 in THF under N$_2$. The reaction is stirred at reflux for 3 h, cooled, and concentrated. Purification of the residue by preparatory LC-MS (C-18, 10-80% ACN/water (0.05% TFA)) gives 5 mg of the product as a white solid. $^1$H NMR (acetone-d$_6$, 400 MHz) δ 7.52-7.55 (m, 2H), 7.27-7.29 (m, 2H), 7.00-7.02 (m, 2H), 6.86-6.88 (m, 1H), 5.44 (dd, 1H, J=5.3, 2.4 Hz), 4.50-4.54 (m, 1H), 3.77 (s, 3H), 2.85-3.05 (m, 6H), 2.45 (s, 3H), 2.30-2.40 (m, 2H), 1.96-2.00 (m, 1H), 1.74-1.91 (m, 2H). HPLC-MS calculated C$_{25}$H$_{27}$ClN$_4$O$_4$ (M+H$^+$): 483.2, found: 483.2.

Example 344

(4S,5R)-3-(4-chlorophenyl)-5-((5-chloropyridin-2-yloxy)methyl)-4-(3,5-difluorophenyl)oxazolidin-2-one

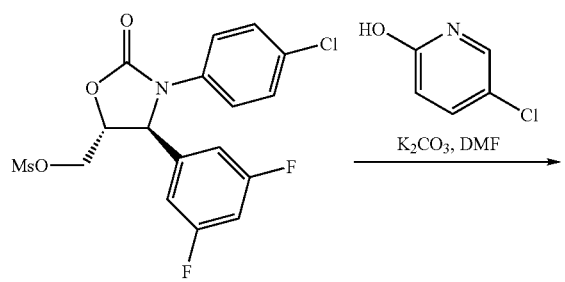

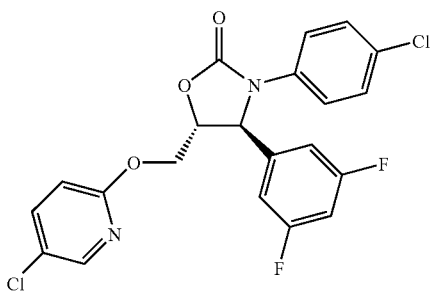

The ((4S,5R)-3-(4-chlorophenyl)-4-(3,5-difluorophenyl)-2-oxooxazolidin-5-yl)methyl methanesulfonate (49 mg, 0.117 mmol), 5-chloropyridin-2-ol (45 mg, 0.35 mmol), and K$_2$CO$_3$ (48 mg, 0.35 mmol) are dissolved in DMF (1.0 mL) and stirred at 35° C. for 2 h, as judged complete by LC-MS. The reaction is diluted with water and ethyl acetate. The organic is washed with brine, dried over MgSO$_4$, filtered and concentrated. Separation of the N- and O-alkylated products by preparative HPLC (C-18, 10-80% ACN/water (0.05% TFA)) gave 2.5 mg of the desired product. $^1$H NMR (acetone-d$_6$, 400 MHz) δ 8.15 (d, 1H, J=2.7 Hz), 7.76 (dd, 1H, J=8.8, 2.7 Hz), 7.54-7.57 (m 2H), 7.32-7.36 (m, 2H), 7.22-7.28 (m, 2H), 7.02 (tt, 1H, J=9.1, 2.3 Hz), 6.86 (d, 1H, J=8.8 Hz), 5.77 (d, 1H, J=5.6 Hz), 4.85 (ddd, 1H, J=5.2, 4.0, 4.0 Hz), 4.72-4.79 (m, 2H). HPLC-MS calculated C$_{21}$H$_{14}$Cl$_2$F$_2$N$_2$O$_3$ (M+H$^+$): 451.0, found: 451.0.

This procedure is applied towards the preparation of Example 410.

Example 363

(S)-3-(4-(4-chlorophenoxy)phenyl)-1-(pyrazin-2-yl)-4-(3-(trifluoromethyl)phenyl)-imidazolidin-2-one

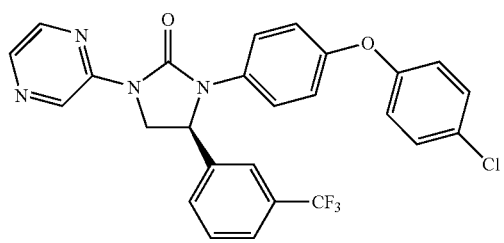 [SMILES: O=C1N(c2cnccn2)C[C@H](c2cccc(C(F)(F)F)c2)N1c1ccc(Oc2ccc(Cl)cc2)cc1]

To a solution of (S)-1-(4-(4-chlorophenoxy)phenyl)-5-(3-(trifluoromethyl)phenyl)imidazolidin-2-one (20.0 mg, 0.046 mmol) in DMF (0.5 mL) are added Cs$_2$CO$_3$ (30.1 mg, 0.092 mmol) and chloropyrazine (8.25 µL, 0.092 mmol). The reaction mixture is heated at 100° C. overnight, and additional Cs$_2$CO$_3$ (30.1 mg, 0.092 mmol) and chloropyrazine (8.25 µL, 0.092 mmol) are added. After heating at 100° C. for another 8 h, the reaction mixture is quenched with H$_2$O (5 mL) and extracted with EtOAc (3×3 mL). The combined organic layer is evaporated under vacuo and purified by preparatory LC/MS to provide the title compound; HPLC-MS calculated for C$_{26}$H$_{18}$ClF$_3$N$_4$O$_2$ (M+H$^+$) 511.1, found 511.1.

Example 368 benzyl 1-(((4S,5S)-3-(4-chlorophenyl)-4-(3-methoxyphenyl)-2-oxoöxazolidin-5-yl)methyl)-2-oxopiperidine-4-carboxylate

Example 376

(4S,5S)-3-(4-chlorophenyl)-4-(3-methoxyphenyl)-5-((4-(3-methyl-1,2,4-oxadiazol-5-yl)-1H-1,2,3-triazol-1-yl)methyl)oxazolidin-2-one

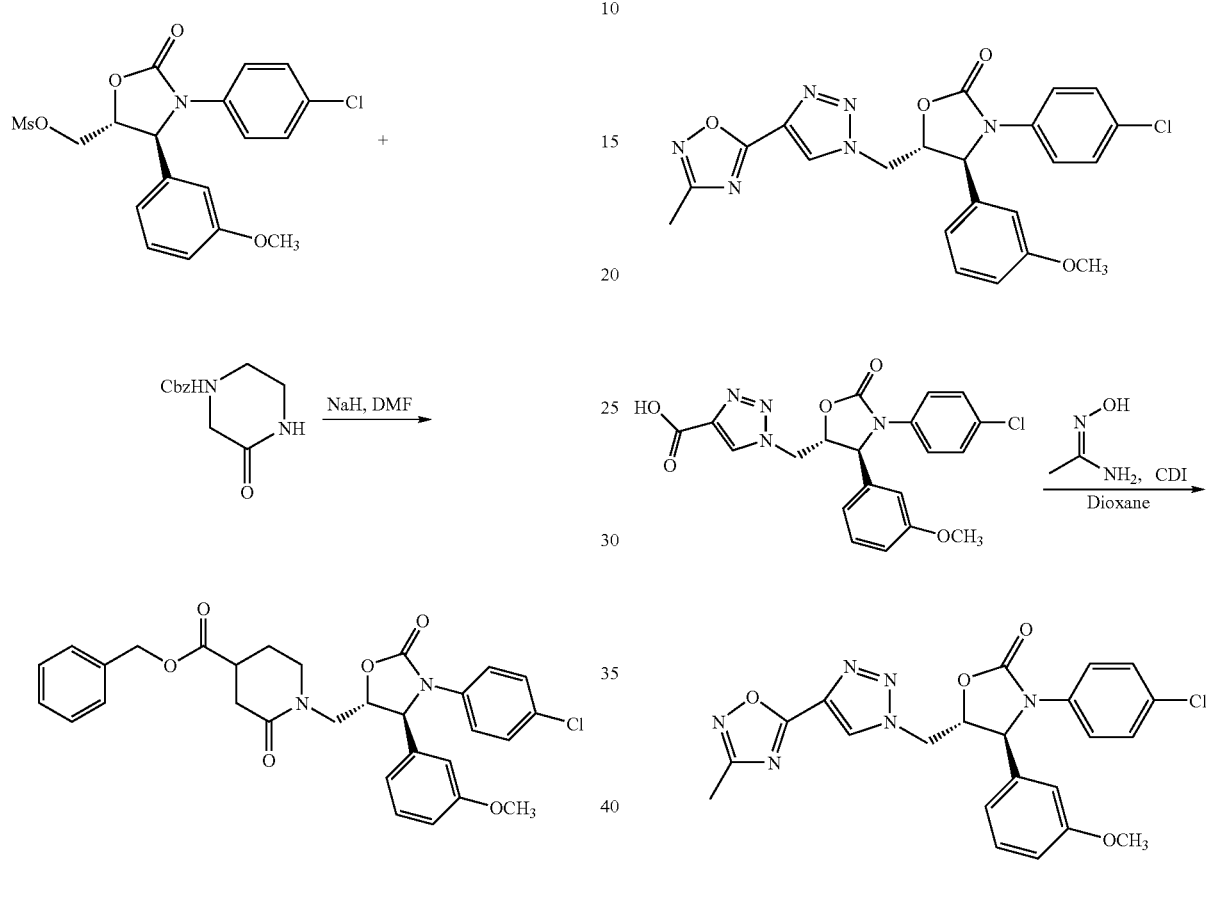

A suspension of sodium hydride (7 mg, 0.18 mmol) in DMF (0.5 mL) is cooled to 0° C. Benzyl 3-oxopiperazine-1-carboxylate (40 mg, 0.1 mmol) is added slowly to the suspension, which is then stirred for 10 min. ((4S,5R)-3-(4-Chlorophenyl)-4-(3-methoxyphenyl)-2-oxoöxazolidin-5-yl) methyl methanesulfonate in DMF (0.5 mL) is then added dropwise to the suspension of the amidate and is subsequently allowed to warm to room temperature overnight and is then quenched with 0.1 M HCl and extracted with ethyl acetate. The combined organics are dried over MgSO₄, filtered, and concentrated. The crude product is purified by preparative HPLC (C-18, 10-90% ACN/water (0.05% TFA)) to give the title compound as an oil. $^1$H NMR (acetone-$d_6$, 400 MHz) δ 7.47-7.25 (m, 9H), 7.05 (t, J=2.0 Hz, 1H), 7.01 (d, J=7.7 Hz, 1H), 6.85 (ddd, J=8.3, 2.6, 0.9 Hz, 1H), 5.44 (d, J=6.2 Hz, 1H), 5.13 (s, 2H), 4.64 (ddd, J=6.2, 5.2, 4.8 Hz, 1H), 4.09-4.07 (m, 2H) 3.97-3.95 (m, 2H), 3.78-3.57 (m, 7H); HPLC-MS calculated $C_{29}H_{28}ClN_3O_6$ (M+H⁺) 550.2, found 550.2.

The procedure is applied towards the preparation of Example 414.

Reference for 1,2,4-oxadiazole formation: *Bioorg. Med. Chem. Lett.* 1999, 9, 209. A solution of 1-(((4S,5S)-3-(4-chlorophenyl)-4-(3-methoxyphenyl)-2-oxoöxazolidin-5-yl) methyl)-1H-1,2,3-triazole-4-carboxylic acid (32 mg, 0.07 mmol) in dioxane (0.5 mL) is treated with N,N'-carbonyldiimidazole and stirred at room temperature for 30 min. Acetamide oxime (10 mg, 0.13 mmol) is then added and the mixture stirred for 2 h at room temperature then at 100° C. for 18 h. The reaction solution is then diluted with acetonitrile and filtered through a Whatman 0.42 µM and purified by preparative HPLC (C-18, 10-90% ACN/water (0.05% TFA)) HPLC to give the title compound. $^1$H NMR (acetone-$d_6$, 400 MHz) δ 8.93 (s, 1H), 7.47-7.44 (m, 2H), 7.33-7.28 (m, 3H), 7.05-7.00 (m, 2H), 6.88 (ddd, J=7.9, 2.5, 0.8 Hz, 1H), 5.62 (d, J=5.0 Hz, 1H), 5.25-5.24 (m, 2H), 5.03 (ddd, J=5.7, 5.5, 4.9 Hz, 1H) 3.76 (s, 3H), 2.40 (s, 3H); HPLC-MS calculated $C_{22}H_{19}ClN_6O_4$ (M+H⁺) 467.1, found 467.1.1.

Example 377

(4S,5S)-3-(4-chlorophenyl)-4-(3-methoxyphenyl)-5-((4-(5-methyl-1,3,4-oxadiazol-2-yl)-1H-1,2,3-triazol-1-yl)methyl)oxazolidin-2-one

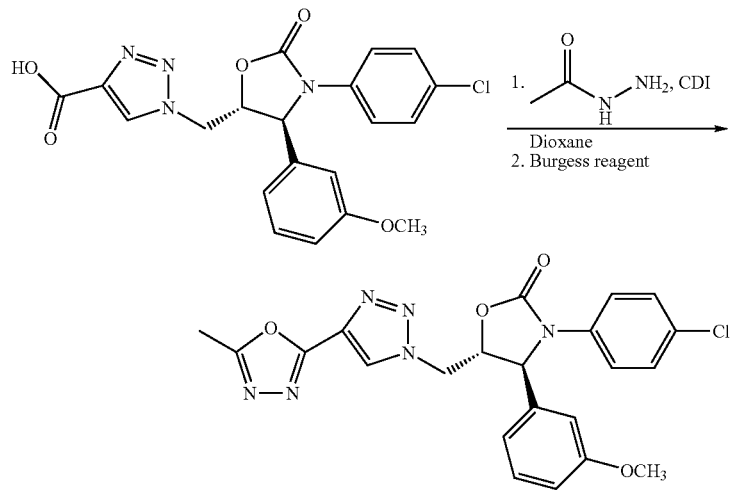

A solution of 1-(((4S,5S)-3-(4-chlorophenyl)-4-(3-methoxyphenyl)-2-oxooxazolidin-5-yl)methyl)-1H-1,2,3-triazole-4-carboxylic acid (32 mg, 0.07 mmol) in dioxane (0.5 mL) is treated with N,N'-carbonyldiimidazole and stirred at room temperature for 30 min. Acetylhydrazide (10 mg, 0.13 mmol) is then added and the mixture stirred for 2 h at room temperature. Burgess' reagent (67 mg, 0.28 mmol) is then added followed by THF (0.5 mL) and the mixture heated to 65° C. overnight. The cooled reaction is then evaporated to dryness and purified by flash chromatography (4 g RediSep flash cartridge, 0-1.5% methanol/DCM) to give the title compound as a white solid. $^1$H NMR (acetone-$d_6$, 400 MHz) δ 8.81 (s, 1H), 7.47-7.44 (m, 2H), 7.33-7.28 (m, 3H), 7.04-7.00 (m, 2H), 6.88 (ddd, J=8.3, 2.5, 0.8 Hz, 1H), 5.62 (d, J=5.9 Hz, 1H), 5.23-5.21 (m, 2H), 5.03 (ddd, J=5.7, 5.4, 4.8 Hz, 1H) 3.77 (s, 3H), 2.59 (s, 3H); HPLC-MS calculated $C_{22}H_{19}ClN_6O_4$ (M+H$^+$) 467.1, found 467.1.1.

Example 378

(4S,5S)-3-(4-chlorophenyl)-4-(3-methoxyphenyl)-5-((5-phenyl-2H-tetrazol-2-yl)methyl)oxazolidin-2-one

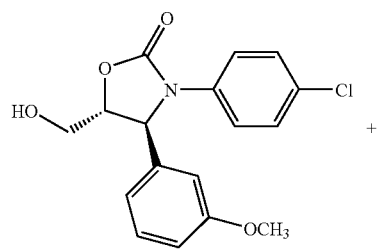

(4S,5R)-3-(4-Chlorophenyl)-5-(hydroxymethyl)-4-(3-methoxyphenyl)oxazolidin-2-one (40 mg, 0.12 mmol) and phenyltetrazole (17 mg, 0.12 mmol) are dissolved in DCM (1 mL), cooled to 0° C. and are then subsequently treated with triphenylphosphine (29 mg, 0.11 mmol) and diisopropylazodicarboxylate (0.024 mL, 0.12 mmol). The mixture is allowed to stir to room temperature overnight and is then purified by flash chromatography (4 g Redisep cartridge, 10-30% Ethyl acetate-hexanes) to give the title compound. $^1$H NMR (acetone-$d_6$, 400 MHz) δ 8.05-8.03 (m, 2H), 7.54-7.50 (m, 3H), 7.47-7.43 (m, 2H), 7.32 (t, J=7.9 Hz, 1H), 7.30-7.24 (m, 2H), 7.09 (t, J=2.08 Hz, 1H), 7.05-7.03 (app d, J=7.8 Hz, 1H), 6.90 (ddd, J=8.3, 2.6, 0.9 Hz, 1H), 5.72 (d, J=5.1 Hz, 1H), 5.50 (dd, J=14.7, 8.7 Hz, 1H), 5.43 (dd, J=14.7, 10.6 Hz, 1H), 5.12-5.08 (m, 1H), 3.76 (s, 3H); HPLC-MS calculated $C_{24}H_{20}ClN_5O_3$ (M+H$^+$) 462.1, found 462.1.

Example 380

(4S,5S)-3-(4-chlorophenyl)-5-((5-(2-hydroxyethyl)-2H-tetrazol-2-yl)methyl)-4-(3-methoxyphenyl)oxazolidin-2-one

Example 381

(4S,5S)-3-(4-chlorophenyl)-4-(3-methoxyphenyl)-5-((5-(2-morpholinoethyl)-2H-tetrazol-2-yl)methyl)oxazolidin-2-one

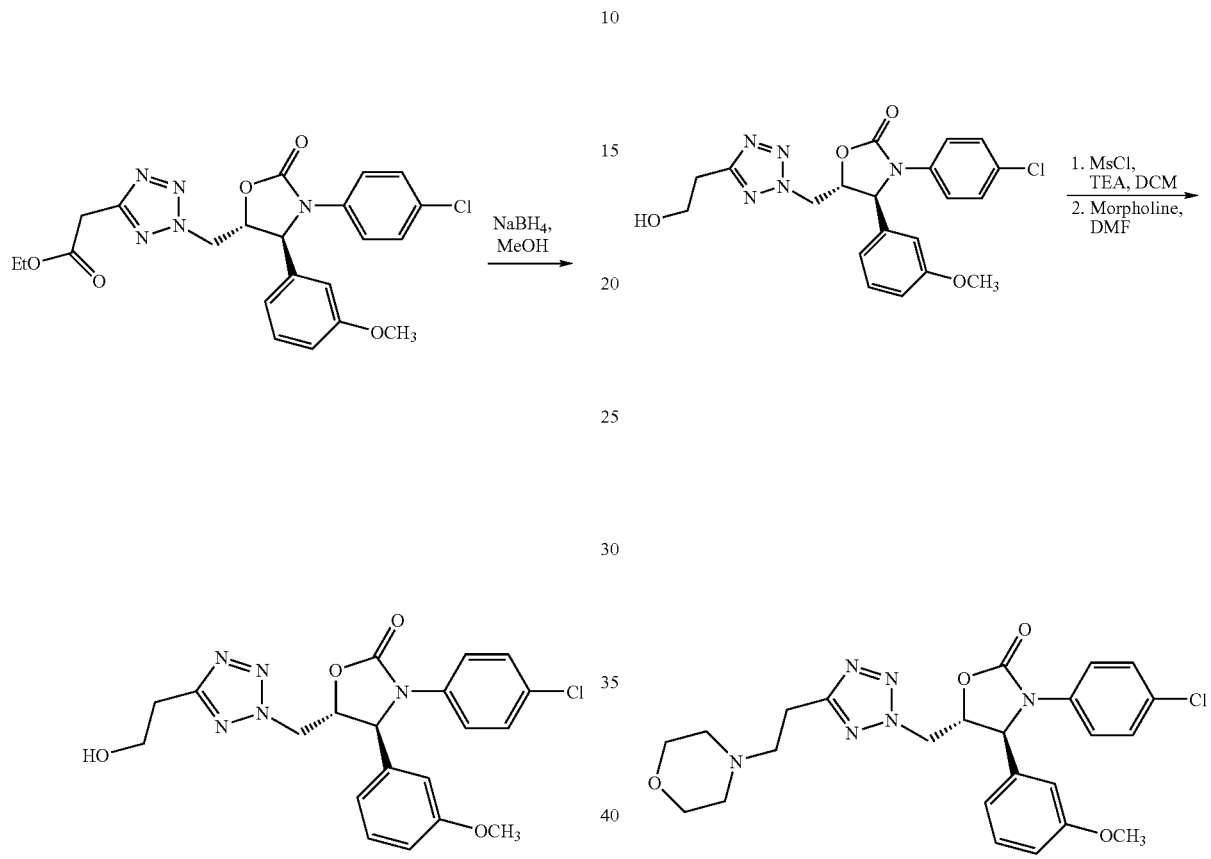

A solution of ethyl 2-(2-(((4S,5S)-3-(4-chlorophenyl)-4-(3-methoxyphenyl)-2-oxooxazolidin-5-yl)methyl)-2H-tetrazol-5-yl)acetate (50 mg, 0.11 mmol) [Example 379] in MeOH (1 mL) is treated with excess sodium borohydride at room temperature for 30 min. The reaction is quenched with 1 mL 0.1 M HCl and extracted with EtOAc (3×5 mL). The combined organics are dried over MgSO$_4$, filtered and concentrated to give the title compound. $^1$H NMR (acetone-d$_6$, 400 MHz) δ 7.47-7.43 (m, 2H), 7.33-7.29 (m, 3H), 7.04 (app t, J=2.0 Hz, 1H), 7.00-6.98 (app d, J=7.7 Hz, 1H), 6.90 (ddd, J=8.3, 2.6, 0.9 Hz, 1H), 5.60 (d, J=5.2 Hz, 1H), 5.33 (dd, J=14.6, 6.2 Hz, 1H), 5.25 (dd, J=14.6, 4.1 Hz, 1H), 4.99 (ddd, J=6.2, 5.2, 4.1 Hz, 1H), 3.89-3.76 (m, 6H), 2.99 (t, J=6.3 Hz, 2H), HPLC-MS calculated C$_{20}$H$_{20}$ClN$_5$O$_4$ (M+H$^+$) 430.1, found 430.1.

A solution of (4S,5S)-3-(4-chlorophenyl)-5-((5-(2-hydroxyethyl)-2H-tetrazol-2-yl)methyl)-4-(3-methoxyphenyl)oxazolidin-2-one (47 mg, 0.11 mmol) in DCM is cooled to 0° C. and treated with methanesulfonyl chloride (10 µL, 0.13 mmol) followed by triethylamine (36 µL, 0.26 mmol). After 30 min., the reaction is quenched with water and extracted with DCM, then dried over Na$_2$SO$_4$, filtered, and concentrated to give the crude product. The crude product is then dissolved in DMF (1 mL) and treated with excess morpholine (48 µL, 0.55 mmol) and heated to 100° C. overnight. The cooled reaction is then quenched with water, basified to pH 10 and extracted with EtOAc. The crude product is purified by preparative HPLC (C-18, 10-90% ACN/water (0.05% TFA)) to give the title compound. $^1$H NMR (acetone-d$_6$, 400 MHz) δ 7.47-7.43 (m, 2H), 7.34-7.29 (m, 3H), 7.04 (app t, J=2.0 Hz, 1H), 7.00-6.98 (app d, J=7.7 Hz, 1H), 6.90 (ddd, J=8.3, 2.6, 0.9 Hz, 1H), 5.61 (d, J=5.0 Hz, 1H), 5.33 (dd, J=14.6, 5.6 Hz, 1H), 5.25 (dd, J=14.6, 4.1 Hz, 1H), 4.99 (ddd, J=5.6, 5.1, 4.2 Hz, 1H), 3.78 (s, 3H), 3.55 (t, J=4.6 Hz, 4H), 2.99-2.93 (m, 2H), 2.59-2.55 (m, 2H), 2.40-2.37 (m, 4H); HPLC-MS calculated C$_{24}$H$_{27}$ClN$_6$O$_4$ (M+H$^+$) 499.2, found 499.2.

Example 382

(4S,5S)-3-(4-chlorophenyl)-5-((1-((tetrahydro-2H-pyran-4-yl)methyl)-1H-1,2,3-triazol-4-yl)methyl)-4-(3-methoxyphenyl)oxazolidin-2-one

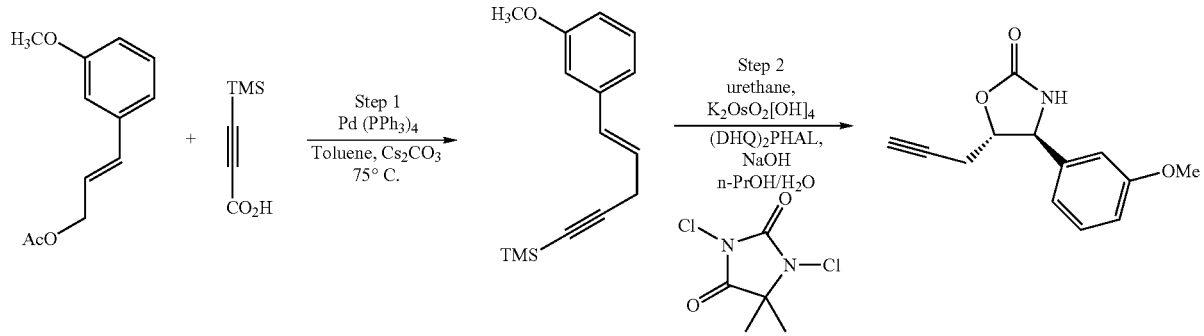

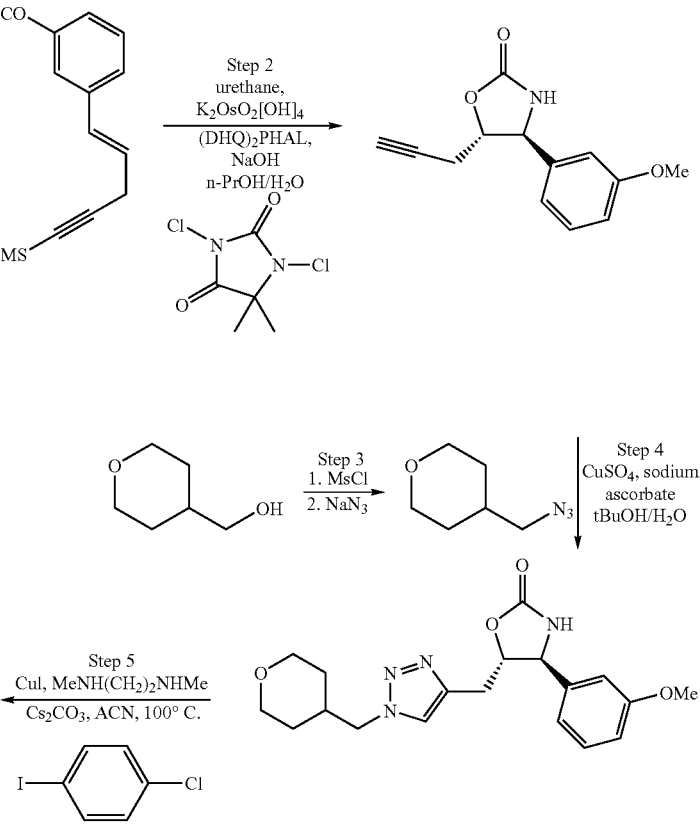

Step 1: To a dried 40 mL scintillation vial fitted with a Teflon coated cap is added 3-methoxycinnamyl acetate (619 mg, 3.0 mmol), toluene (20 mL), 3-(trimethylsilyl)propiolic acid (512 mg, 3.6 mmol), cesium carbonate (1.17 g, 3.6 mmol), and tetrakis(triphenylphosphine)palladium (0) (346 mg, 0.3 mmol, 10 mol %). The vessel is evacuated and back-filled with Argon and then heated to 75° C. for 18 h. Upon cooling to room temperature, the reaction mixture is quenched with $H_2O$ (5 mL) and extracted with diethyl ether (2×10 mL). The combined organics are washed with brine, dried over $MgSO_4$, filtered, and concentrated. The crude oil is purified by flash chromatography (12 g RediSep flash cartridge, hexanes to 1.5% ethyl acetate/hexanes) to give 307 mg (42%) of ((E)-5-(3-methoxyphenyl)pent-4-en-1-ynyl)trimethylsilane as an oil. $^1$H NMR (acetone-$d_6$, 400 MHz) δ 7.23 (d, J=8.1 Hz, 1H), 6.99-6.97 (m, 2H), 6.80 (m, 1H), 6.65 (dt, J=15.7, 1.7 Hz, 1H), 6.26 (dt, J=15.7, 5.7 Hz, 1H), 3.8 (s, 3H), 3.19 (dd, J=5.7, 1.8 Hz, 2H), 0.16 (s, 9H). Reference: Tunge, J. A.; rayabarapu, D. K. *J. Am. Chem. Soc.* 2005, 127, 13510-13511.

Step 2: Performed according to Example 20, Step A to give (4S,5S)-4-(3-methoxyphenyl)-5-(prop-2-ynyl)oxazolidin-2-one. HPLC-MS calculated $C_{13}H_{13}NO_3$ 232.1, found 232.1.

Step 3: To a 25 mL round bottom flask is placed (tetrahydro-2H-pyran-4-yl)methanol (350 mg, 3 mmol), followed by dichloromethane (DCM, 15 mL). The solution is cooled to 0° C. and is then treated with methanesulfonyl chloride (0.24 mL, 3.15 mmol) and triethylamine (0.88 mL, 6.3 mmol). The reaction is complete after 30 min. and is then quenched with water and diluted with DCM (10 mL). The layers are then partitioned, and the aqueous layer is extracted with DCM (3×10 mL). The combined organics are dried over $Na_2SO_4$, filtered and concentrated. The crude mesylate is then dissolved in DMF (10 mL), to which sodium azide (410 mg, 6.3 mmol) is added and then heated to 75° C. for 4 h. The reaction is then cooled to room temperature, quenched with water (10 mL) and extracted with diethyl ether (3×20 mL). The combined organics are then washed with water (3×10 mL), dried over $MgSO_4$, filtered, and concentrated to give 4-(azidomethyl)-tetrahydro-2H-pyran as a colorless liquid. $^1$H NMR ($CDCl_3$, 400 MHz) δ 4.01-3.97 (m, 2H), 3.39 (td, J=11.9, 2.1 Hz, 2H), 3.18 (d, J=6.8 Hz, 2H), 1.86-1.75 (m, 1H), 1.67-1.64 (m, 2H), 1.40-1.29 (m, 2H).

Step 4: To an 8 mL reaction tube is placed (4S,5S)-4-(3-methoxyphenyl)-5-(prop-2-ynyl)oxazolidin-2-one (25 mg, 0.11 mmol), 1:1 tBuOH:$H_2O$ (0.5 mL), 4-(azidomethyl)-tetrahydro-2H-pyran (21 mg, 0.15 mmol), $CuSO_4$ $5H_2O$ (catalytic), and sodium ascorbate (catalytic). The mixture is heated to 40° C. for 18 h, then quenched with water (2 mL) and extracted with EtOAc (3×5 mL). The combined organics are washed with 1M HCl (2 mL), then brine (3 mL), and are then dried over $MgSO_4$, filtered, and concentrated to give the crude product as an oil, which is carried forward without further purification. HPLC-MS calculated $C_{19}H_{24}N_4O_4$ (M+H$^+$): 373.2, found: 373.2.

Step 5: Performed according to Example 39, Step C to give the title compound. $^1$H NMR (acetone-$d_6$, 400 MHz) δ 7.87 (s, 1H), 7.46-7.42 (m, 2H), 7.29-7.25 (m, 3H), 6.92-6.88 (m, 2H), 6.85 (ddd, J=8.2, 2.5, 0.9 Hz, 1H), 5.45 (d, J=4.9 Hz, 1H), 4.67 (ddd, J=5.4, 5.4, 5.0 Hz, 1H), 4.27 (d, J=7.2 Hz, 2H), 3.83-3.74 (m, 5H), 3.32 (d, J=5.4 Hz, 2H), 3.21 (dddd, J=11.7, 11.7, 2.2, 2.2 Hz, 2H), 1.40-1.18 (m, 5H); HPLC-MS calculated $C_{25}H_{27}ClN_4O_4$ (M+H$^+$) 483.2, found 483.2.

Example 385 is prepared in the same manner as Step 5 above from tert-butyl 4-(azidomethyl)piperidine-1-carboxylate.

Example 384

(4S,5S)-3-(4-chlorophenyl)-5-((3-(tetrahydrofuran-3-yl)isoxazol-5-yl)methyl)-4-(3-methoxyphenyl)oxazolidin-2-one

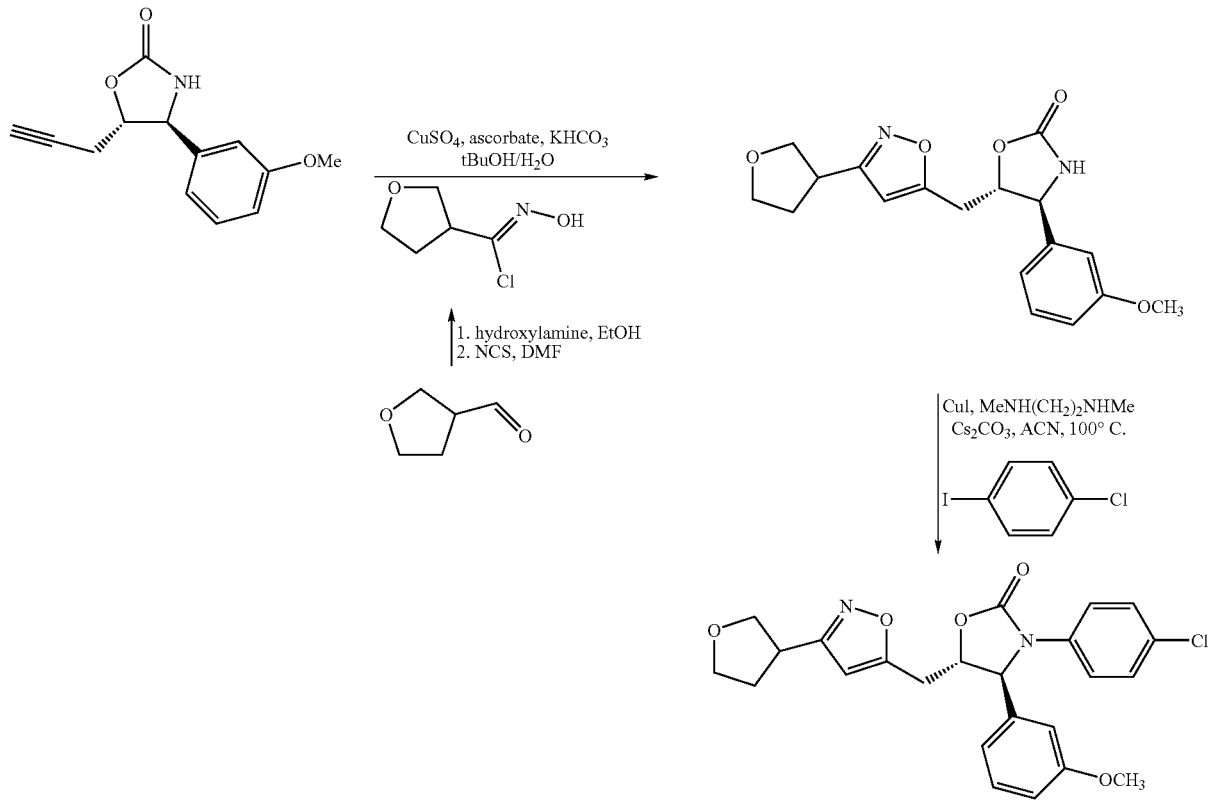

To a small reaction tube fitted with a screw cap is placed (4S,5S)-4-(3-methoxyphenyl)-5-(prop-2-ynyl)oxazolidin-2-one (50 mg, 0.22 mmol) in tBuOH/water (1:1, 1.5 mL). Successively, copper(II) sulfate pentahydrate (2 mg, 0.012 mmol), sodium ascorbate (12 mg, 0.06 mmol), potassium bicarbonate (92 mg, 0.92 mmol), and the freshly prepared product described above are then added. After stirring at room temperature for 2 h, the reaction is then quenched with sat. ammonium chloride, and extracted with EtOAc. The combined organics are washed with brine, dried over MgSO$_4$, filtered, and concentrated to give the crude product, which is carried forward without purification. Next, in a small reaction tube fitted with a screw cap is placed the crude intermediate, acetonitrile (1 mL), 4-chloro-1-iodobenzene (62 mg, 0.26 mmol), copper iodide (3 mg, 0.04 mmol), N,N'-dimethylethylenediamine (9.3 μL, 0.08 mmol), and cesium carbonate (143 mg, 0.44 mmol). The vessel is evacuated and back-filled with nitrogen, then heated to 85° C. for 4 h. The reaction is N-hydroxytetrahydrofuran-3-carbimidoyl chloride: Tetrahydrofuran-3-carboxaldehyde (50% solution in water, 2.5 mL, 12.5 mmol) in ethanol (5.0 mL) is stirred with hydroxylamine-hydrochloride (1.3 g, 18.7 mmol) for 3 h. The reaction is quenched with 0.1 M HCl and extracted with EtOAc, dried over MgSO$_4$, filtered, and concentrated to give the oxime as a colorless oil. A solution of the oxime (115 mg, 1.0 mmol) in DMF (1 mL) is then treated with N-chlorosuccinimide (147 mg, 1.1 mmol) at 40° C. for 2 h. The reaction is then cooled to room temperature, poured on to ice water and extracted with diethyl ether (3×10 mL). The combined organics are dried over MgSO$_4$, filtered, and concentrated to give tetrahydrofuran-3-carbonyl chloride oxime, which is used without further purification.

then cooled to room temperature and quenched with sat. ammonium chloride, extracted with EtOAc, dried over MgSO$_4$, filtered, and concentrated. The title compound is obtained after purification by preparative HPLC (C-18, 10-90% ACN/water (0.05% TFA)). $^1$H NMR (acetone-$d_6$, 400 MHz) δ (mixture of diastereomers) 8.67 (overlp s, 1H), 7.50-7.43 (m, 2H), 7.30-7.27 (m, 2H), 6.97-6.96 (m, 2H), 6.90-6.87 (m, 1H), 5.45 (d, J=4.8 Hz, 0.2H), 5.40 (d, J=5.8 Hz, 0.8H), 4.92-4.89 (m, 0.2H), 4.68-4.63 (m, 0.8H), 4.05 (m, 1H), 3.97-3.68 (m, 7H), 2.34-2.01 (m, 2H); HPLC-MS calculated $C_{23}H_{23}ClN_2O_5$ (M+H$^+$) 455.1, found 455.1. For references to Copper catalyzed synthesis of 3,5-disubstituted isoxazoles, see Hansen, T. V.; Wu, P.; Fokin, V. V. *J. Org. Chem.* 2005, 70, 7791-7764; Himo, F.; Lovell, T.; Hilgraf, R.;

Rostovtsev, V. V.; Noodleman, L.; Sharpless, K. B.; Fokin, V. V. *J. Am. Chem. Soc.* 2005, 127, 210-216.

Example 386 ethyl 2-(((4S,5S)-3-(4-chlorophenyl)-4-(3-methoxyphenyl)-2-oxooxazolidin-5-yl)methyl)-2H-tetrazole-5-carboxylate

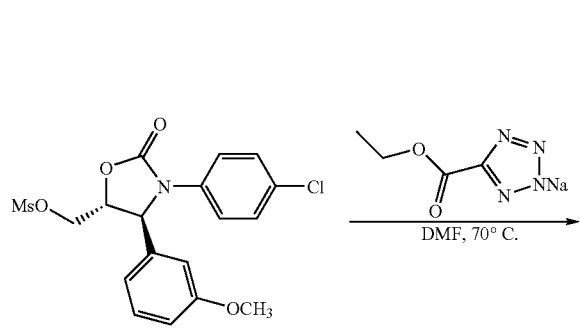

A small reaction tube fitted with a screw cap is charged with ((4S,5R)-3-(4-chlorophenyl)-4-(3-methoxyphenyl)-2-oxooxazolidin-5-yl)methyl methanesulfonate (50 mg, 0.12 mmol) and DMF (1 mL). Ethyl 1H-tetrazole-5-carboxylate, sodium salt (39 mg, 0.24 mmol) is added and the mixture is heated to 70° C. overnight. The cooled reaction is quenched with water, extracted with EtOAc, combined organics are washed with brine, dried over MgSO$_4$, filtered, concentrated, and purified by flash chromatography (12 g Redisep cartridge, 30-50% EtOAc/hexanes) to give the title compound. $^1$H NMR (acetone-d$_6$, 400 MHz) δ 7.53-7.43 (m, 2H), 7.34-7.28 (m, 3H), 7.10-7.08 (m, 1H), 7.06-7.00 (m, 2H), 6.92-6.90 (m, 1H), 5.67 (d, J=5.3 Hz, 1H), 5.52 (dd, J=(ddd, J=14.6, 6.5 Hz, 1H), 5.47-5.41 (m, 1H), 5.11-4.99 (m, 1H), 4.46-4.41 (m, 2H), 3.76 (s, 3H), 1.39-1.35 (m, 3H); HPLC-MS calculated C$_{21}$H$_{20}$ClN$_5$O$_5$ (M+H$^+$) 458.1, found 458.1.

Example 387

(4S,5S)-3-(4-chlorophenyl)-4-(3-methoxyphenyl)-5-((4-phenyl-1H-imidazol-1-yl)methyl)oxazolidin-2-one

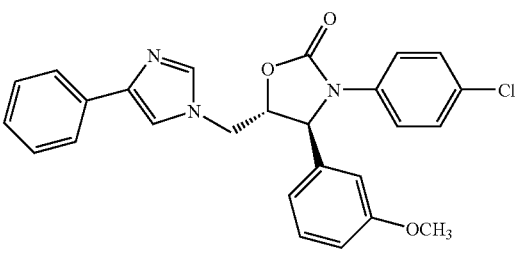 [SMILES: COc1cccc([C@H]2[C@H](Cn3cnc(-c4ccccc4)c3)OC(=O)N2c2ccc(Cl)cc2)c1]

A small reaction tube fitted with a screw cap is charged with ((4S,5R)-3-(4-chlorophenyl)-4-(3-methoxyphenyl)-2-oxooxazolidin-5-yl)methyl methanesulfonate (50 mg, 0.12 mmol) and DMF (1 mL). Phenylimidazole (35 mg, 0.24 mmol) is added followed by cesium carbonate (39 mg, 0.12 mmol) and the mixture is heated to 70° C. overnight. The reaction is then cooled to room temperature, quenched with water and extracted with EtOAc. The combined organics are washed with water, dried over MgSO$_4$, filtered, concentrated, and purified by preparative HPLC (C-18, 10-90% ACN/water (0.05% TFA)) to give the title compound. $^1$H NMR (acetone-d$_6$, 400 MHz) δ 7.80-7.78 (m, 3H), 7.68 (d, J=1.2 Hz, 1H), 7.46-7.42 (m, 2H), 7.34-7.17 (m, 6H), 6.96-6.93 (m, 2H), 6.89 (ddd, J=8.2, 2.5, 0.8 Hz, 1H), 5.46 (d, J=5.2 Hz, 1H), 4.83 (ddd, J=6.0, 5.0, 5.0 Hz, 1H), 4.70-4.69 (m, 2H), 3.72 (s, 3H); HPLC-MS calculated C$_{26}$H$_{22}$ClN$_3$O$_3$ (M+H$^+$) 460.1, found 460.1.

Example 389

(4S,5S)-5-((1H-1,2,3-triazol-1-yl)methyl)-3-(4-chlorophenyl)-4-(3,5-difluorophenyl)oxazolidin-2-one

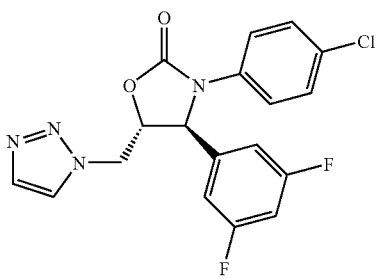 [SMILES: O=C1O[C@@H](Cn2ccnn2)[C@H](c2cc(F)cc(F)c2)N1c1ccc(Cl)cc1]

The title compound is obtained as a side-product applying the procedure described for Example 84 with propiolic acid used in place of 3-fluorophenylacetylene. $^1$H NMR (acetone-d$_6$, 400 MHz) δ 8.11 (br s, 1H), 7.72 (br s, 1H), 7.49-7.42 (m, 2H), 7.33-7.30 (m, 2H), 7.22-7.15 (m, 2H), 7.04-6.99 (m, 1H), 5.65 (d, J=5.3 Hz, 1H), 5.13-5.11 (m, 2H), 4.99-4.97 (m, 1H); HPLC-MS calculated C$_{18}$H$_{13}$ClF$_2$N$_4$O$_2$ (M+H$^+$): 391.1, found: 391.1.

Example 391

(4S,5S)-3-(4-chlorophenyl)-4-(3,5-difluorophenyl)-5-((5-((piperidin-1-yl)methyl)-2H-tetrazol-2-yl)methyl)oxazolidin-2-one

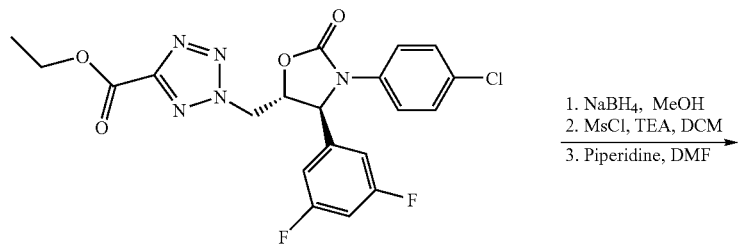

1. NaBH$_4$, MeOH
2. MsCl, TEA, DCM
3. Piperidine, DMF

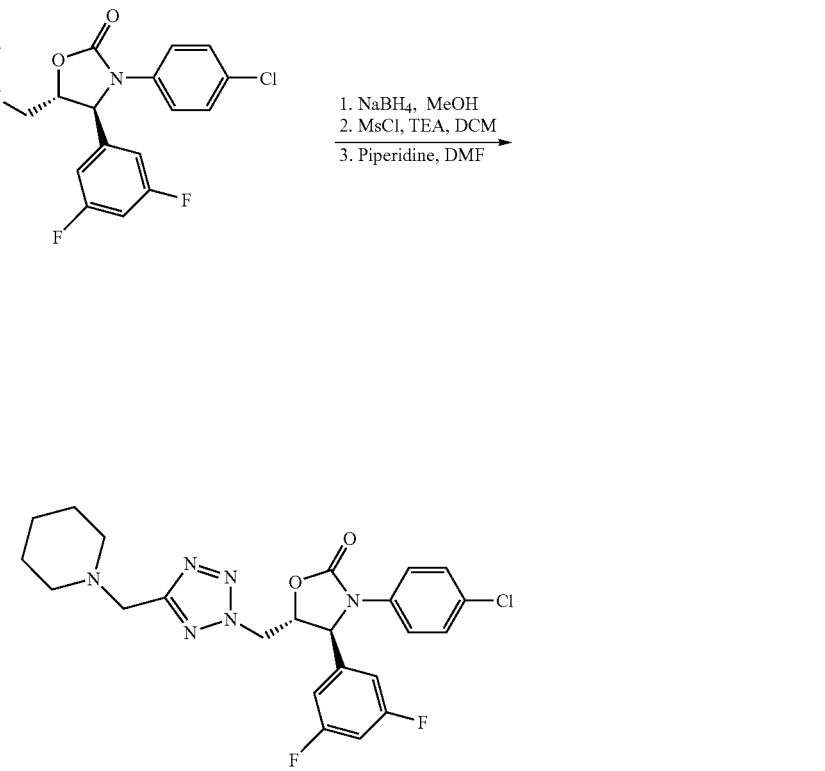

To a 10 mL round bottom flask is placed ethyl 2-(((4S,5S)-3-(4-chlorophenyl)-4-(3,5-difluorophenyl)-2-oxooxazolidin-5-yl)methyl)-2H-tetrazole-5-carboxylate (37 mg, 0.08 mmol; prepared as described in Example 386) and MeOH (0.5 mL). Sodium borohydride (5 mg, 0.135 mmol) is added and the mixture is stirred for 10 min., then quenched with water and extracted with EtOAc, dried over MgSO$_4$, filtered, and concentrated. The crude product is then dissolved in DCM (0.5 mL), cooled to 0° C., and treated with methanesulfonyl chloride (7 µL, 0.08 mmol) and triethylamine (22 µL, 0.16 mmol). After 30 min the reaction is quenched with 0.1 M HCl, extracted with EtOAc, dried over MgSO$_4$, filtered, and concentrated. The crude mesylate is then dissolved in DMF (0.5 mL) and is treated with piperidine (79 µL, 0.8 mmol) at 90° C. overnight; the reaction is then cooled to room temperature and purified by preparative HPLC (C-18, 10-90% ACN/water (0.05% TFA)). $^1$H NMR (acetone-d$_6$, 400 MHz) (mixture of tetrazole regioisomers) δ 7.52 (dd, J=14.5, 9.0, Hz, 2H), 7.35-7.31 (m, 2H), 7.23-7.21 (m, 2H), 7.05-6.99 (m, 1H), 5.78 (d, J=5.2 Hz, 1H), 5.39 (dd, J=14.7, 5.6 Hz, 1H), 5.33 (dd, J=14.7, 4.2 Hz, 1H), 5.14-5.08 (m, 1H), 3.70 (d (gem), J=14.0 Hz, 2H), 2.37-2.35 (m, 4H), 1.49-1.29 (m, 6H); HPLC-MS calculated C$_{23}$H$_{23}$ClF$_2$N$_6$O$_2$ (M+H$^+$) 489.2, found 489.2.

Example 392

(4S,5S)-3-(4-chlorophenyl)-4-(3,5-difluorophenyl)-5-((5-(6-methylpyridin-3-yl)-2H-tetrazol-2-yl)methyl)oxazolidin-2-one

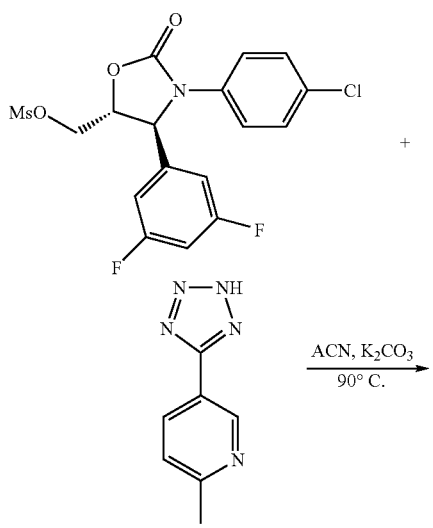

ACN, K$_2$CO$_3$
90° C.

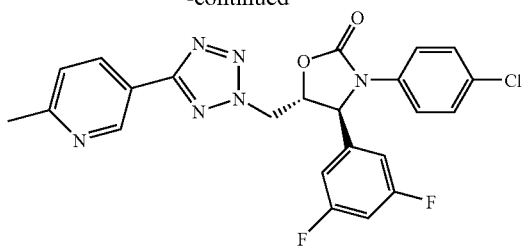

To a small reaction tube is placed ((4S,5R)-3-(4-chlorophenyl)-4-(3,5-difluorophenyl)-2-oxooxazolidin-5-yl)methyl methanesulfonate (50 mg, 0.12 mmol), ACN (1 mL), 2-methyl-5-(2H-tetrazol-5-yl)pyridine (39 mg, 0.24 mmol), and potassium carbonate (33 mg, 0.24 mmol). The tube is capped and the reaction is heated to 90° C. for 4 h. The reaction is then quenched with water (2 mL), and extracted with EtOAc, dried over MgSO$_4$, filtered, and concentrated. The product is purified by flash chromatography (12 g Redisep, 0-10% MeOH/DCM) to give the title compound. $^1$H NMR (acetone-d$_6$, 400 MHz) δ 9.18 (br s, 1H), 8.39 (d, J=8.1 Hz, 1H), 7.58 (br s, 1H), 7.47-7.44 (m, 2H), 7.29-7.23 (m, 2H), 7.02 (dddd, J=9.1, 9.1, 2.3, 2.3 Hz, 1H), 5.87 (d, J=5.0 Hz, 1H), 5.54 (dd, J=14.7, 5.8 Hz, 1H), 5.46 (dd, J=14.7, 4.0 Hz, 1H), 5.12 (ddd, J=5.7, 5.1, 4.0 Hz, 1H), 2.65 (s, 3H); HPLC-MS calculated C$_{23}$H$_{17}$ClF$_2$N$_6$O$_2$ (M+H$^+$) 483.1, found 483.0.

This procedure is applied toward the preparation of Example 393, Example 394, Example 396, Example 401, Example 402, Example 403, and Example 407 from the requisite tetrazoles and mesylates.

Example 399

(4S,5S)-3-(4-chlorophenyl)-4-(3-isopropoxyphenyl)-5-((5-(6-methylpyridin-3-yl)-2H-tetrazol-2-yl)methyl)oxazolidin-2-one

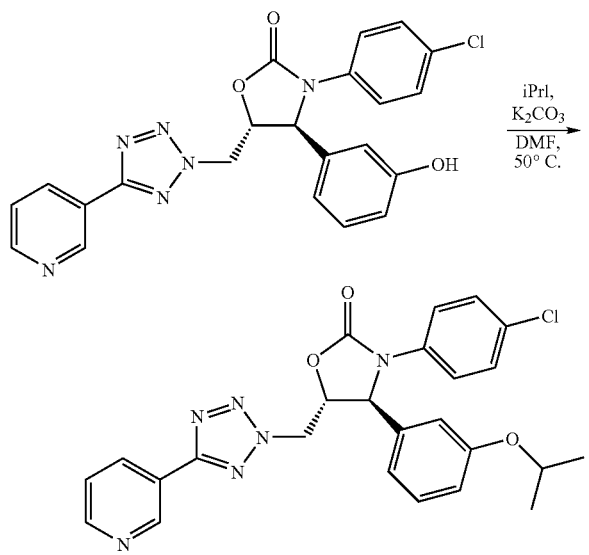

A small reaction tube fitted with screw cap containing a septa is charged with (4S,5S)-3-(4-chlorophenyl)-4-(3-hydroxyphenyl)-5-((5-(pyridin-3-yl)-2H-tetrazol-2-yl)-methyl)oxazolidin-2-one (25 mg, 0.055 mmol) and DMF (0.5 mL). Potassium carbonate (25 mg, 0.18 mmol) and 2-iodopropane (18 μL, 0.18 mmol) are then added and the vessel is heated to 50° C. for 4 h, then cooled to room temperature. The reaction is quenched with water, and extracted with EtOAc, dried over MgSO$_4$, filtered and concentrated. The title compound is then obtained after flash chromatography (12 g Redisep, 30-50% EtOAc/hexanes). $^1$H NMR (acetone-d$_6$, 400 MHz) δ 9.22 (br, s 1H), 8.72 (br, s, 1H), 8.33 (ddd, J=8.0, 1.8, 1.8 Hz, 1H), 7.52 (dd, J=7.9, 4.8 Hz, 1H), 7.46-7.42 (m, 2H), 7.32 (t, J=7.6 Hz, 1H), 7.27-7.24 (m, 2H), 7.09 (app t, J=1.9 Hz, 1H), 7.04 (d, J=7.7 Hz, 1H), 6.86 (ddd, J=8.3, 2.5, 0.8 Hz, 1H), 5.72 (d, J=5.0 Hz, 1H), 5.51 (dd, J=14.7, 5.9 Hz, 1H), 5.44 (dd, J=14.7, 4.1 Hz, 1H), 5.12 (ddd, J=5.8, 5.0, 4.2 Hz, 1H), 4.60 (septet, J=6.0 Hz, 1H), 1.24 (d, J=6.0 Hz, 3H, 1.21 (d, J=6.0 Hz, 3H); HPLC-MS calculated C$_{25}$H$_{23}$ClN$_6$O$_3$ (M+H$^+$) 491.2, found 491.2.

This procedure is applied towards the syntheses of Example 406 and Example 409.

Example 400

(4S,5S)-3-(4-chlorophenyl)-4-(3-hydroxyphenyl)-5-((5-(pyridin-3-yl)-2H-tetrazol-2-yl)methyl)oxazolidin-2-one

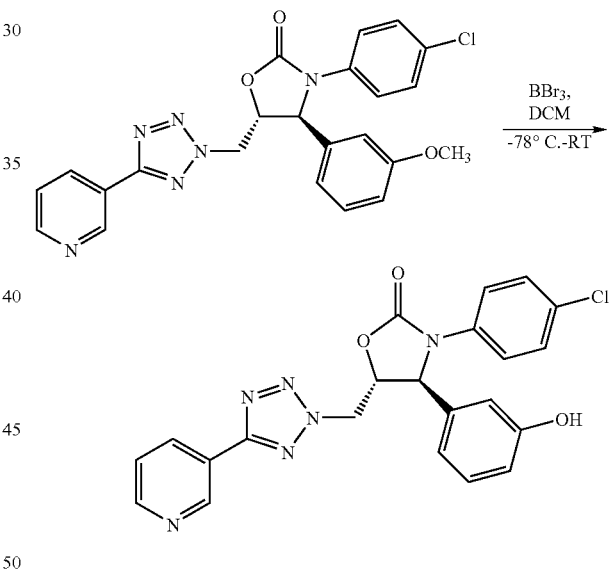

To a 10 mL round bottom flask is charged with (4S,5S)-3-(4-chlorophenyl)-4-(3-methoxyphenyl)-5-((5-(pyridin-3-yl)-2H-tetrazol-2-yl)methyl)oxazolidin-2-one (264 mg, 0.57 mmol) and DCM (6 mL) and is cooled to −78° C. Boron tribromide (1M, 2.3 mL, 2.3 mmol) is then added dropwise, and after 30 min. the cooling bath is removed and the reaction is allowed to warm to room temperature. The reaction is quenched with water (5 mL), basified to pH 10 with 1N NaOH, and extracted with DCM. The combined organics are dried over Na$_2$SO$_4$, filtered, and concentrated. Purified on 40 g Redisep silica gel cartridge with 5% MeOH/DCM to give the title compound. $^1$H NMR (acetone-d$_6$) δ 9.21 (s, 1H), 8.72 (dd, J=4.8, 1.7 Hz, 1H), 8.60 (br s, 1H), 8.36 (ddd, J=6.1, 1.9, 1.9 Hz, 1H), 7.58 (dd, J=8.0, 5.0, 0.8 Hz, 1H), 7.46-7.42 (m, 2H), 7.27-7.22 (m, 3H), 6.95 (d, J=7.6 Hz, 1H), 6.92 (t, J=2.2 Hz, 1H), 6.82 (ddd, J=8.1, 2.4, 0.9 Hz, 1H), 5.67 (d, J=4.7 Hz, 1H), 5.50 (dd, J=14.7, 5.8 Hz, 1H), 5.42 (dd, J=14.7, 3.9 Hz, 1H), 5.12 (ddd, J=5.8, 4.6, 4.0 Hz, 1H), HPLC-MS calculated C$_{22}$H$_{17}$ClN$_6$O$_3$ (M+H$^+$) 449.1, found 449.0.

This procedure is applied towards the preparation of Example 405.

Example 411

4-(((4S,5S)-3-(4-chlorophenyl)-4-(3-methoxyphenyl)-2-oxooxazolidin-5-yl)methyl)-1-(6-methoxypyridin-3-yl)piperazin-2-one

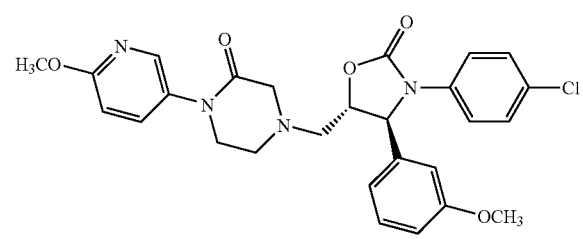 [SMILES: COc1cccc([C@H]2[C@H](CN3CCN(c4ccc(OC)nc4)C(=O)C3)OC(=O)N2c2ccc(Cl)cc2)c1]

The title compound is prepared according to Example 52, Step B with 1-(6-methoxypyridin-3-yl)piperazin-2-one (prepared via copper-mediated cross-coupling, for a review see *Angew. Chem. Int. Ed.* 2003, 42, 5400). $^1$H NMR (acetone-d$_6$, 400 MHz) δ 8.10 (d, J=2.6 Hz, 1H), 7.64 (dd, J=8.8, 2.7 Hz, 1H), 7.55-7.53 (m, 2H), 7.33-7.29 (m, 3H), 7.08 (dd, J=2.2, 1.8 Hz, 1H), 7.04 (d, J=7.7 Hz, 1H), 6.87 (dd, J=8.3, 1.8 Hz, 1H), 5.52 (d, J=5.9 Hz, 1H), 4.62 (q, J=5.8 Hz, 1H), 3.88 (s, 3H), 3.77 (s, 3H), 3.70 (dddd, J=18.6, 12.8, 6.3, 4.9 Hz, 2H), 3.43 (d, J=16.3 Hz, 1H), 3.36 (d, J=16.3 Hz, 1H), 3.10 (dd, J=13.5, 5.5 Hz, 1H), 3.06-2.98 (m, 3H); HPLC-MS calculated C$_{27}$H$_{27}$ClN$_4$O$_5$ (M+H$^+$) 523.2, found 523.0.

Example 412

(4S,5S)-3-(4-chlorophenyl)-4-(3-methoxyphenyl)-5-((4-(6-methoxypyridin-2-yl)piperazin-1-yl)methyl)oxazolidin-2-one

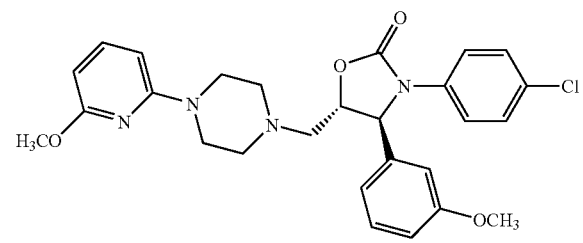 [SMILES: COc1cccc([C@H]2[C@H](CN3CCN(c4cccc(OC)n4)CC3)OC(=O)N2c2ccc(Cl)cc2)c1]

The title compound is prepared according to Example 52, Step B with 1-(6-methoxypyridin-2-yl)piperazine (prepared via palladium-catalyzed cross-coupling, see *Tetrahedron Lett.* 2004, 45, 2057). $^1$H NMR (acetone-d$_6$, 400 MHz) δ 7.55-7.52 (m, 2H), 7.42 (t, J=8.0 Hz, 1H) 7.33-7.28 (m, 3H), 7.05-7.03 (m, 2H), 6.89-6.86 (m, 1H), 6.27 (d, J=8.1 Hz, 1H), 6.01 (d, J=7.8 Hz, 1H), 5.49 (d, J=5.7 Hz, 1H), 4.57 (q, J=5.7 Hz, 1H), 3.80 (s, 3H), 3.77 (s, 3H), 3.72 (ddd, J=5.0, 4.5, 4.5 Hz, 4H), 2.98 (dd, J=13.4, 5.9 Hz, 1H), 2.88 (dd, J=13.4, 5.7 Hz, 1H), 2.69 (t, J=5.0 Hz, 4H); HPLC-MS calculated C$_{27}$H$_{29}$ClN$_4$O$_4$ (M+H$^+$) 509.2, found 509.0.

Example 416 ethyl 3-((4S,5S)-3-(4-chlorophenyl)-4-(3-methoxyphenyl)-2-oxooxazolidin-5-yl)propanoate

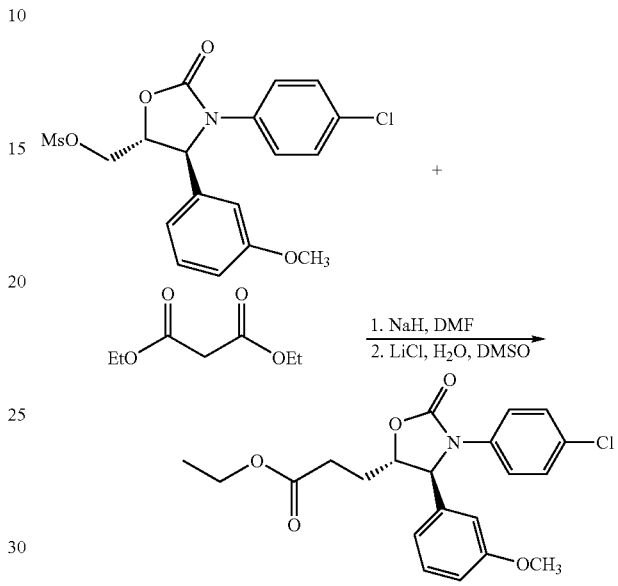

A dried 25 mL round bottom flask is charged with diethyl malonate (0.11 mL, 0.75 mmol) and DMF (5 mL) and is cooled to 0° C. Sodium hydride (33 mg, 0.83 mmol) is then added portion-wise and after 5 min ((4S,5R)-3-(4-chlorophenyl)-4-(3-methoxyphenyl)-2-oxooxazolidin-5-yl)methyl methanesulfonate (205 mg, 0.5 mmol) in DMF (2 mL) is then slowly added to the solution of the malonate anion. The reaction is then heated to 100° C., and after 2.5 h the reaction is subsequently cooled to room temperature, quenched with 0.1 M HCl, extracted with diethyl ether, dried over MgSO$_4$, filtered, and concentrated. The crude product is purified by flash chromatography (12 g Redisep cartridge, 5-100% EtOAc/hexanes) to give 86 mg of the malonate adduct. The intermediate is then transferred to a small reaction tube, dissolved in DMSO (1 mL), and charged with lithium chloride (12 mg, 0.28 mmol) and water (3 μL, 0.14 mmol). The tube is capped and heated to 160° C. overnight. The reaction is then cooled to room temperature, diluted with water, extracted with EtOAc, dried over MgSO$_4$, filtered, and concentrated. The crude is purified by flash chromatography (4 g Redisep cartridge, 5-100% EtOAc/hexanes) to give the title compound. $^1$H NMR (acetone-d$_6$, 400 MHz) δ 7.52-7.48 (m, 2H), 7.32-7.27 (m, 3H), 7.05-7.03 (dd, J=2.2, 1.9 Hz, 1H), 7.01 (d, J=7.7 Hz, 1H), 6.88 (ddd, J=8.2, 2.5, 0.7 Hz, 1H), 5.35 (d, J=6.1 Hz, 1H), 4.57 (ddd, J=6.9, 6.0, 6.0 Hz, 1H), 4.06 (q, J=7.1 Hz, 2H), 3.77 (s, 3H), 2.63-2.50 (m, 2H), 2.29-2.15 (m, 2H), 1.18 (t, J=7.1 Hz, 3H); HPLC-MS calculated C$_{21}$H$_{22}$ClNO$_5$ (M+H$^+$) 404.1, found 404.1.

Example 419

(S)-3-(4-chlorophenyl)-1-((5-(4-methoxyphenyl)-1,2,4-oxadiazol-3-yl)methyl)-4-(3-(trifluoromethyl)phenyl)imidazolidin-2-one

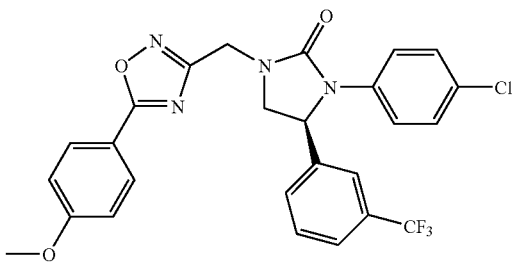 [SMILES: COc1ccc(-c2nc(CN3C[C@H](c4cccc(C(F)(F)F)c4)N(c4ccc(Cl)cc4)C3=O)no2)cc1]

A solution of (S)-1-(4-chlorophenyl)-5-(3-(trifluoromethyl)phenyl)imidazolidin-2-one (40 mg, 0.117 mmol, prepared by following the same procedure as described in example 151 using 1-(trifluoromethyl)-3-vinylbenzene as the starting material.) in anhydrous DMF (2 mL) is cooled down to 0° C. in an ice bath when NaH (17 mg, 60% in mineral oil, 0.423 mmol) is added into the solution portion wise. After the addition, the mixture is stirred at 0° C. for 10 min when a solution of 3-(chloromethyl)-5-(4-methoxyphenyl)-1,2,4-oxadiazole (31.6 mg, 0.141 mmol) in DMF (1 mL) is added into the mixture. The resulted mixture is allowed to warm up to room temperature and stir for 1 h. The residue is purified by preparatory LC/MS to provide the title compound; $^1$H NMR (CD$_3$OD, 400 MHz) δ 7.95 (d, J=9.2 Hz, 2H), 7.62 (s, 1H), 7.57 (d, J=7.6 Hz, 1H), 7.48-7.39 (m, 2H), 7.31 (d, J=9.2 Hz, 2H), 7.13 (d, J=8.8 Hz, 2H), 7.00 (d, J=8.8 Hz, 1H), 5.50 (dd, J=9.2, 6.0 Hz, 1H), 4.68 (m, 2H), 4.07 (t, J=9.2 Hz, 1H), 3.78 (s, 3H), 3.41 (dd, J=9.0, 6.0 Hz, 1H); HPLC-MS calculated for C$_{26}$H$_{21}$ClF$_3$N$_4$O$_3$ (M+H$^+$) 529.1, found 529.0.

Example 432

(S)-3-(4-chlorophenyl)-1-(2-morpholinoethyl)-4-(3-(trifluoromethyl)phenyl)imidazolidin-2-one

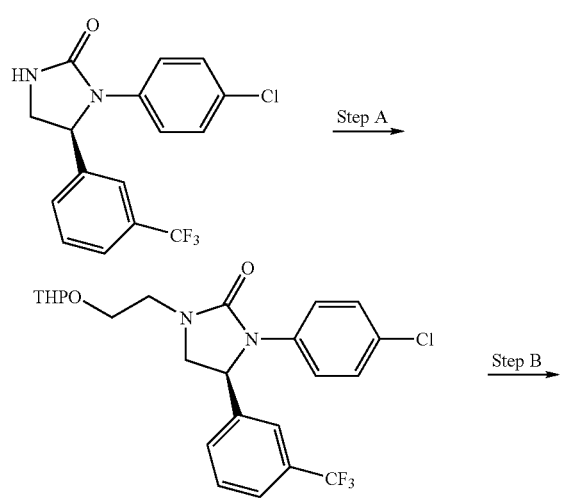

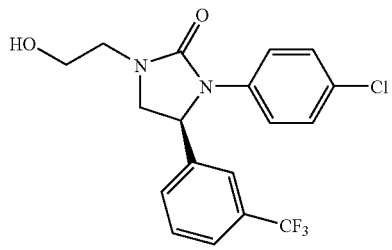

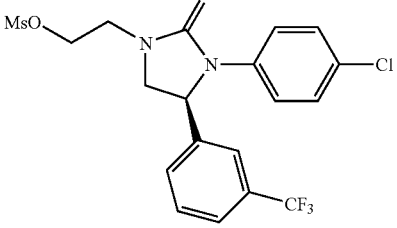

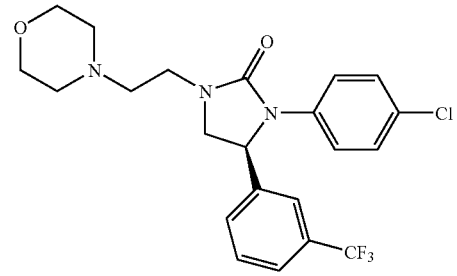

Step A and B: Follow the procedure as described in example 172 using (S)-1-(4-chlorophenyl)-5-(3-(trifluoromethyl)phenyl)imidazolidin-2-one as the starting material to give (S)-3-(4-chlorophenyl)-1-(3-hydroxypropyl)-4-(3-(trifluoromethyl)phenyl)imidazo-lidin-2-one. $^1$H NMR (CDCl$_3$, 400 MHz) δ 7.50-7.39 (m, 4H), 7.23 (d, J=8.8 Hz, 2H), 7.13 (d, J=9.2 Hz, 2H), 5.22 (dd, J=9.2, 6.4 Hz, 1H), 3.99 (t, J=9.2 Hz, 1H), 3.78 (t, J=5.0 Hz, 2H), 3.51-3.32 (m, 2H), 3.30 (dd, J=9.0, 6.2 Hz, 1H); HPLC-MS calculated for C$_{18}$H$_{17}$ClF$_3$N$_2$O$_2$ (M+H$^+$) 385.0, found 385.0.

Step C: Follow the procedure as described in example 175 using (S)-3-(4-chlorophenyl)-1-(3-hydroxypropyl)-4-(3-(trifluoromethyl)phenyl)imidazolidin-2-one as the starting material to give (S)-2-(3-(4-chlorophenyl)-2-oxo-4-(3-(trifluoromethyl)phenyl)imidazolidin-1-yl)ethyl methanesulfonate: HPLC-MS calculated for C$_{19}$H$_{19}$ClF$_3$N$_2$O$_4$ (M+H$^+$) 463.0, found 463.0.

Step D: To a solution of (S)-2-(3-(4-chlorophenyl)-2-oxo-4-(3-(trifluoromethyl)phenyl)imidazolidin-1-yl)ethyl methanesulfonate (30 mg, 0.065 mmol) in anhydrous dichloromethane (3 mL) is added morpholine (16.9 mg, 0.194 mmol). After 3 h at room temperature, the residue is purified by preparatory LC/MS to provide the title compound; $^1$H NMR (CD$_3$OD, 400 MHz) δ 7.71 (s, 1H), 7.62-7.53 (m, 3H), 7.43 (d, J=9.2 Hz, 2H), 7.25 (d, J=9.2 Hz, 2H), 5.58 (dd, J=9.2, 6.2 Hz, 1H), 4.04 (t, J=9.2 Hz, 1H), 3.95-4.59 (m, 6H), 3.49-3.26 (m, 4H), 3.24 (dd, J=9.0, 6.2 Hz, 1H), 3.19-3.01 (m, 2H); HPLC-MS calculated for C$_{22}$H$_{24}$ClF$_3$N$_3$O$_2$ (M+H$^+$) 454.1, found 454.0.

Example 438

(S)-3-(4-chlorophenyl)-1-(2-(piperidin-1-ylsulfonyl)ethyl)-4-(3-(trifluoromethyl)phenyl)imidazolidin-2-one

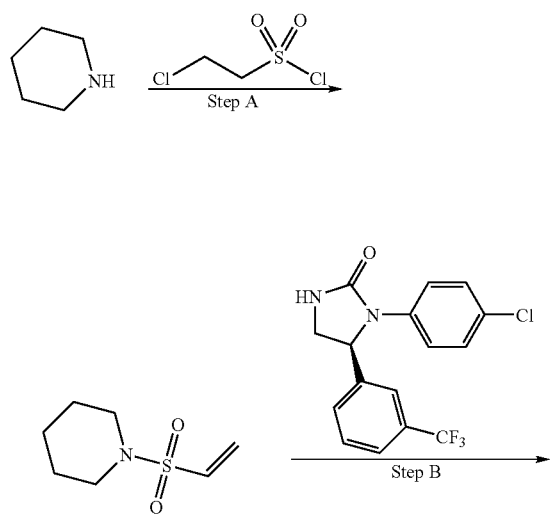

Step A: Triethylamine (683 mg, 6.75 mmol) is added to a solution of piperidine (274 mg, 3.22 mmol) and 2-chloroethanesulfonyl chloride (500 mg, 3.07 mmol) in dichloromethane (8 mL). The reaction is stirred for 2 h at room temperature. The reaction is diluted with ethyl acetate, sat. sodium bicarbonate solution is added. The organic layer is washed with brine and dried with MgSO$_4$. The solvents is removed under vacuum to afford crude 1-(vinylsulfonyl)piperidine which is used directly in the next step without further purification. HPLC-MS calculated for $C_7H_{14}NO_2S$ (M+H$^+$) 176.0, found 176.0.

Step B: Follow the same procedure as described in example 419 using 1-(vinylsulfonyl)piperidine as the starting material. $^1$H NMR (CD$_3$OD, 400 MHz) δ 7.59 (s, 1H), 7.54-7.40 (m, 3H), 7.27 (d, J=9.2 Hz, 2H), 7.12 (d, J=9.2 Hz, 2H), 5.43 (dd, J=9.4, 6.2 Hz, 1H), 3.97 (t, J=9.2 Hz, 1H), 3.73-3.60 (m, 2H), 3.35 (dd, J=8.8, 6.4 Hz, 1H), 3.20-3.13 (m, 6H), 1.56-1.52 (m, 6H); HPLC-MS calculated for $C_{23}H_{26}ClF_3N_3O_3S$ (M+H$^+$) 516.1, found 516.1.

Example 445

(S)-3-(4-chlorophenyl)-1-((6-(piperidin-1-yl)pyridin-3-yl)methyl)-4-(3-(trifluoromethyl)phenyl)imidazolidin-2-one

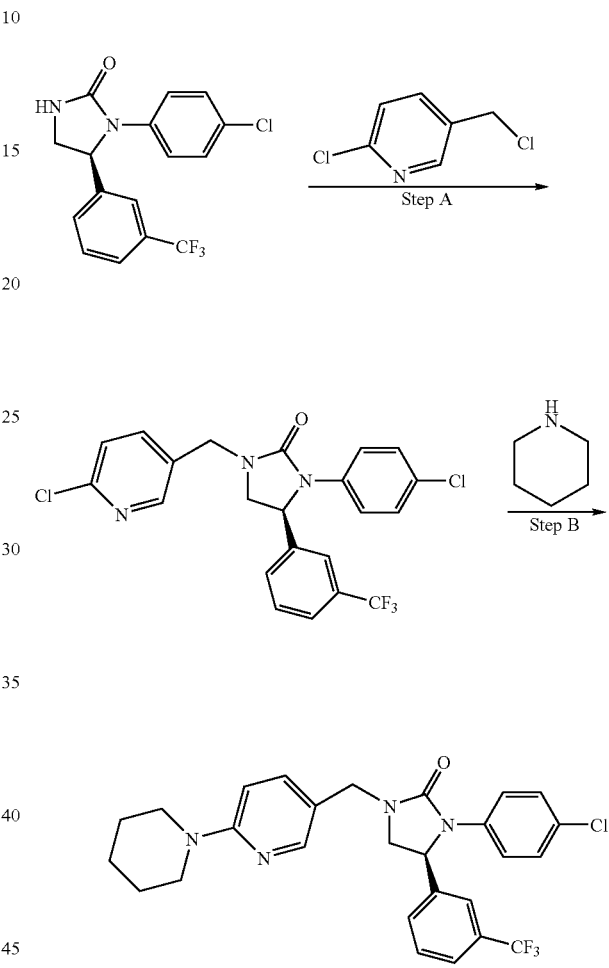

Step A: Follow the same procedure as described in example 419 using 2-chloro-5-(chloromethyl)pyridine as the starting material. HPLC-MS calculated for $C_{22}H_{17}Cl_2F_3N_3O$ (M+H$^+$) 466.0, found 466.0.

Step B: A mixture of (S)-3-(4-chlorophenyl)-1-((6-chloropyridin-3-yl)methyl)-4-(3-(trifluoromethyl)phenyl)imidazolidin-2-one (34 mg, 0.073 mmol), piperidine (0.5 mL) and pyridine (2 mL) are heated for 2 days at 130° C. The residue is purified by preparatory LC/MS to provide the title compound; $^1$H NMR (CD$_3$OD, 400 MHz) δ 7.89 (dd, J=9.6, 6.4 Hz, 1H), 7.75 (d, J=1.6 Hz, 1H), 7.50-7.41 (m, 4H), 7.32-7.27 (m, 3H), 7.15 (d, J=9.2 Hz, 2H), 5.45 (dd, J=9.2, 6.4 Hz, 1H), 4.34 (s, 2H), 3.88 (t, J=9.2 Hz, 1H), 3.60-3.58 (m, 4H), 3.16 (dd, J=9.0, 6.2 Hz, 1H), 1.72-1.61 (m, 6H); HPLC-MS calculated for $C_{27}H_{26}ClF_3N_4O$ (M+H$^+$) 515.1, found 515.1.

Example 451

(S)-3-(4-chlorophenyl)-1-(2-(5-cyclohexyl-1,2,4-oxadiazol-3-yl)ethyl)-4-(3-(trifluoromethyl)phenyl)imidazolidin-2-one

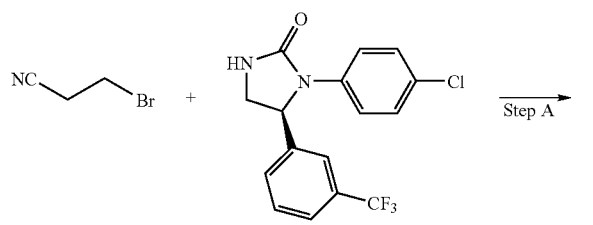

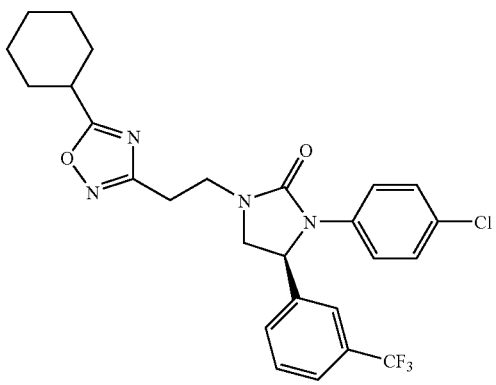

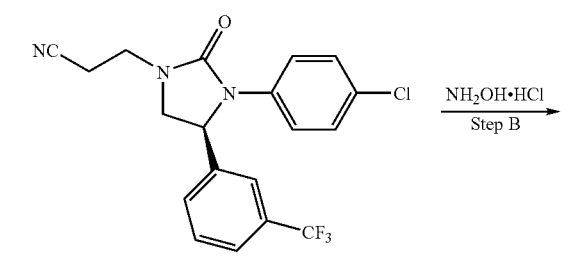

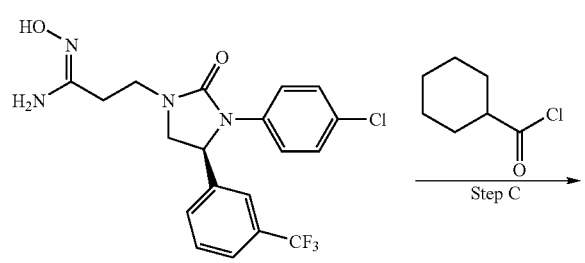

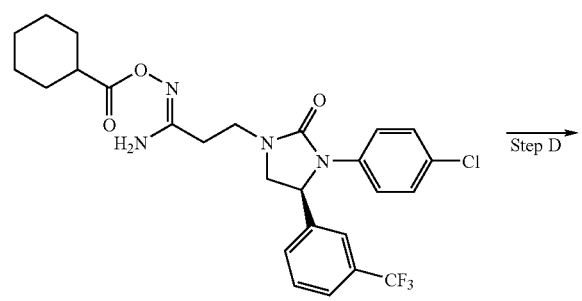

Step A: Follow the same procedure as described in example 419 using 3-bromopropanenitrile as the starting material. HPLC-MS calculated for $C_{16}H_{13}ClF_3N_2O$ (M+H$^+$) 394.0, found 394.0.

Step B: A mixture of (S)-3-(3-(4-chlorophenyl)-2-oxo-4-(3-(trifluoromethyl)-phenyl)imidazolidin-1-yl)propanenitrile (97 mg, 0.25 mmol), hydroxylamine hydrogen chloride (85.5 mg, 1.23 mmol), K$_2$CO$_3$ (187 mg, 1.35 mmol) and anhydrous ethanol (4 mL) are refluxed for 2 days. The solvent is removed under vacuum. The residue is taken into ethyl acetate, washed with sat. NaHCO$_3$ and brine. The organic phase is dried by Mg$_2$SO$_4$. The solvent is removed under vacuum to afford crude (S)-3-(3-(4-chlorophenyl)-2-oxo-4-(3-(trifluoromethyl)phenyl)imidazolidin-1-yl)-N'-hydroxypropanimidamide which is used directly in the next step without further purification. HPLC-MS calculated for $C_{19}H_{19}ClF_3N_4O_2$ (M+H$^+$) 427.1, found 427.1.

Step C: (S)-3-(3-(4-chlorophenyl)-2-oxo-4-(3-(trifluoromethyl)phenyl)-imidazolidin-1-yl)-N'-hydroxypropanimidamide (28.7 mg, 0.067 mmol) is dissolved in dichloromethane (2 mL). Cyclohexanecarbonyl chloride (14.8 mg, 0.10 mmol) and diisopropyl ethylamine (26.3 mg, 0.20 mmol) are then added. The reaction is stirred for 3 h at room temperature. The reaction is diluted with ethyl acetate followed by quenching with sat. sodium bicarbonate solution. The organic layer is washed with brine and dried with MgSO$_4$. The solvents is removed under vacuum to afford crude (S)-3-(3-(4-chlorophenyl)-2-oxo-4-(3-(trifluoromethyl)phenyl)imidazolidin-1-yl)-N'-(cyclohexanecarbonyloxy)propanimidamide which is used directly in the next step without further purification. HPLC-MS calculated for $C_{26}H_{29}ClF_3N_4O_3$ (M+H$^+$) 537.1, found 537.1.

Step D: The crude product from step C is dissolved in anhydrous THF and tetrabutylammonium fluoride (67 uL) is added. The mixture is flushed with N$_2$ and sealed in a microwave tube. The tube is put into a microwave reactor and heated to 100° C. for 5 min. The residue is purified by preparatory LC/MS to provide the title compound; HPLC-MS calculated for $C_{26}H_{27}ClF_3N_4O_2$ (M+H$^+$) 519.1, found 519.1.

Example 455

(S)-3-(3-(4-(4-chlorophenoxy)phenyl)-2-oxo-4-(3-(trifluoromethyl)phenyl)imidazolidin-1-yl)propane-1-sulfonamide

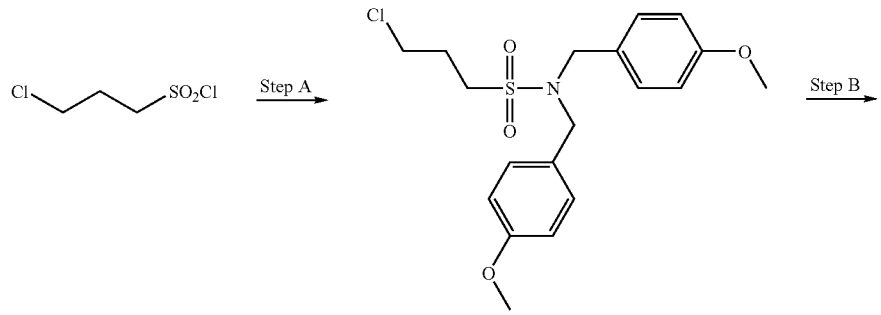

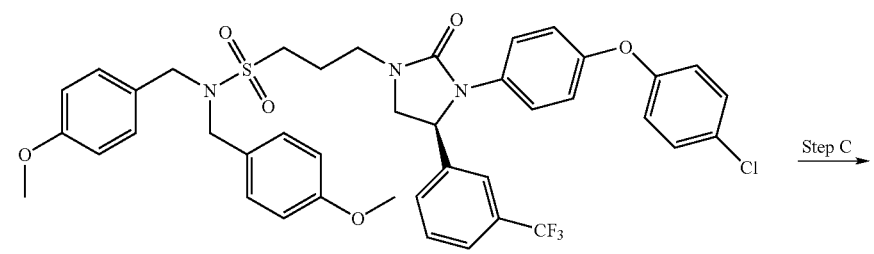

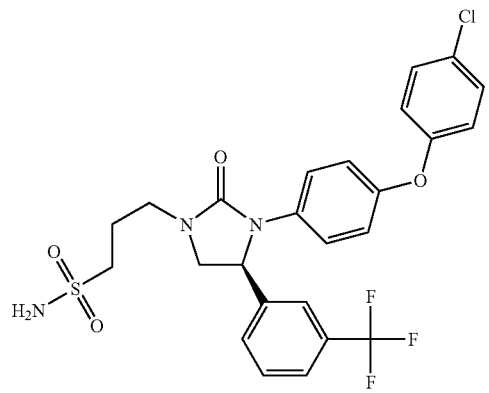

Step A: To a solution of 3-chloropropane-1-sulfonyl chloride (1.46 g, 8.22 mmol) in anhydrous $CH_2Cl_2$ (20 mL) at 0° C. is added bis-(4-methoxy-benzyl)-amine (2.22 g, 8.63 mmol) followed by $Et_3N$ (1.68 g, 10.69 mmol). After the addition, the mixture is allowed to warm to room temperature and is stirred for 2 h. The mixture is then poured into water (50 mL) and is extracted with $CH_2Cl_2$ (3×50 mL). The combined organic layers are concentrated and purified by flash column chromatography (silica gel, EtOAc/hexane 0%~50%) to provide 3-chloro-N,N-bis(4-methoxybenzyl)propane-1-sulfonamide as colorless oil. (2.7 g, 84%).

Step B: To a solution of 3-chloro-N,N-bis(4-methoxybenzyl)propane-1-sulfonamide (30.0 mg, 0.075 mmol) and (S)-1-(4-(4-chloro-phenoxy)-phenyl)-5-(3-(trifluoromethyl)-phenyl)-imidazolidin-2-one (20.0 mg, 0.046 mmol) in DMF (0.8 mL) is added $Cs_2CO_3$ (22 mg, 0.069 mmol) and KI (1 mg). The resulted mixture is stirred at 80° C. for 14 h and is cooled down to room temperature. The mixture is poured into water (5 mL) and extracted with EtOAc (3×3 mL). The combined organic layers are concentrated and purified by flash column chromatography to provide (S)-3-(3-(4-(4-chlorophenoxy)phenyl)-2-oxo-4-(3-(trifluoromethyl)phenyl)imidazolidin-1-yl)-N,N-bis(4-methoxybenzyl)propane-1-sulfonamide (30 mg, 82%). HPLC-MS calculated for $C_{41}H_{39}ClF_3N_3O_6S$ (M+H$^+$) 794.2, found 794.2.

Step C: The title compound is prepared by the same method as described in example 164 Step C. HPLC-MS calculated for $C_{25}H_{23}ClF_3N_3O_4S$ (M+H$^+$) 554.1, found 554.1.

Example 457 and Example 458

(S)-2-(3-(4-(4-chlorophenoxy)phenyl)-2-oxo-4-(3-(trifluoromethyl)phenyl)imidazolidin-1-yl)-N-(2-hydroxyethyl)ethanesulfonamide and (S)-2-(3-(4-(4-chlorophenoxy)phenyl)-2-oxo-4-(3-(trifluoromethyl)phenyl)imidazolidin-1-yl)-N,N-bis(2-hydroxyethyl)ethanesulfonamide

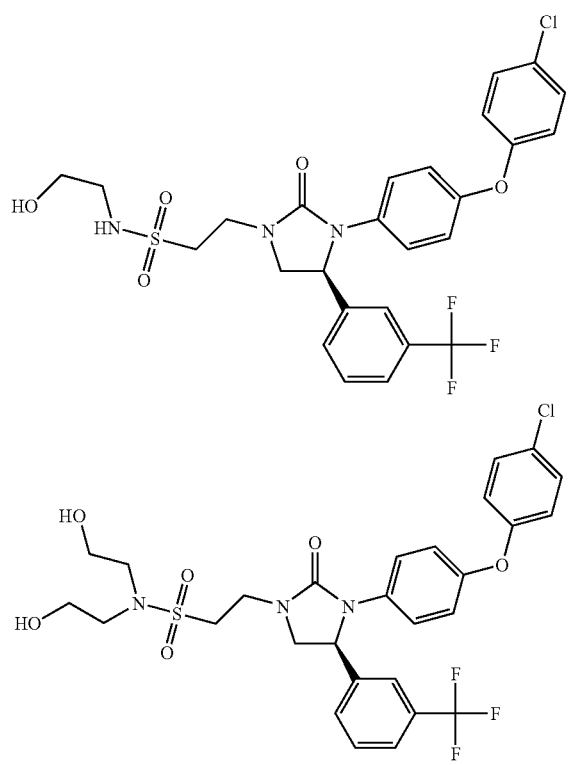

To a solution of (S)-2-[3-[4-(4-chloro-phenoxy)-phenyl]-2-oxo-4-(3-trifluoromethyl-phenyl)-imidazolidin-1-yl]-ethanesulfonic acid amide (20 mg, 0.037 mmol) in acetonitrile (0.5 mL) is added Cs$_2$CO$_3$ (18 mg, 0.056 mmol) followed by 2-(2-bromoethoxy)tetrahydro-2H-pyran (12 mg, 0.056 mmol) and KI (1 mg). The resulting mixture is stirred at 60° C. for 14 h and is then cooled to room temperature. The mixture is then treated with water (5 mL) and extracted with EtOAc (3×3 mL). The combined organic layers are concentrated and the residue is dissolved in MeOH (1 mL). To the MeOH solution is added catalytic pTSA (~1 mg). The resulting mixture is then stirred at room temperature for 1 h and treated with sat. NaHCO$_3$ solution (3 mL). After extracting with EtOAc (3×3 mL), the combined organic layers are concentrated and purified by thin layer chromatography (silica gel, 85% EtOAc/hexane) to provide Example 457: HPLC-MS calculated for C$_{26}$H$_{25}$ClF$_3$N$_3$O$_5$S (M+H$^+$) 584.1, found 584.1; and Example 458: $^1$H NMR (CDCl$_3$, 400 MHz) δ 7.45-7.60 (m, 4H), 7.24 (d, J=8.8 Hz, 4H), 6.86 (d, J=8.8 Hz, 2H), 6.85 (d, J=8.8 Hz, 2H), 5.26 (dd, J=9.2, 6.4 Hz, 1H), 4.05 (t, J=9.2 Hz, 1H), 3.72-3.90 (m, 6H), 3.55 (br s, 2H), 3.48 (t, J=5.2 Hz, 4H), 3.43 (t, J=6.8 Hz, 2H), 3.36 (dd, J=8.8, 6.4 Hz, 1H); HPLC-MS calculated for C$_{28}$H$_{29}$ClF$_3$N$_3$O$_6$S (M+H$^+$) 628.1, found 628.1.

Example 459

(S)-1-(4-(4-chlorophenoxy)phenyl)-5-(3-methoxyphenyl)imidazolidin-2-one

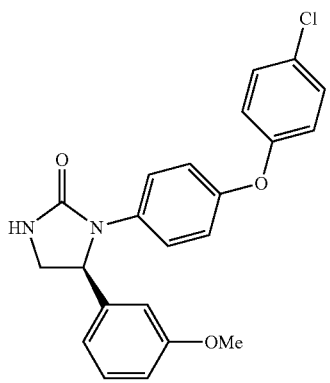 [SMILES: COc1cccc([C@H]2CNC(=O)N2c2ccc(Oc3ccc(Cl)cc3)cc2)c1]

The title compound is prepared by following the same procedure as described in example 151 using 1-methoxy-3-vinylbenzene as the starting material. $^1$H NMR (CDCl$_3$, 400 MHz) δ 7.33 (d, J=9.2 Hz, 2H), 7.25 (t, J=7.6 Hz, 1H), 7.23 (d, J=8.8 Hz, 2H), 6.91 (d, J=7.6 Hz, 1H), 6.84-6.89 (m, 5H), 6.82 (d, J=8.8 Hz, 1H), 5.24 (dd, J=9.2, 6.4 Hz, 1H), 4.83 (br s, 1H), 3.95 (t, J=8.8 Hz, 1H), 3.77 (s, 3H), 3.35 (dd, J=8.4, 6.8 Hz, 1H); HPLC-MS calculated for C$_{22}$H$_{19}$ClN$_2$O$_3$ (M+H$^+$) 395.1, found 395.1.

Example 460

(S)-1-(4-(4-chlorophenoxy)phenyl)-5-(3-hydroxyphenyl)imidazolidin-2-one

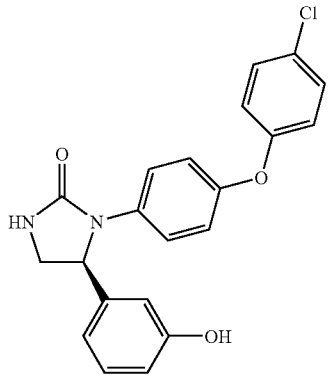 [SMILES: O=C1NC[C@H](c2cccc(O)c2)N1c1ccc(Oc2ccc(Cl)cc2)cc1]

A solution of (S)-1-(4-(4-chlorophenoxy)phenyl)-5-(3-methoxyphenyl)-imidazolidin-2-one (99 mg, 0.25 mmol) in CH$_2$Cl$_2$ (2 mL) is cooled to −78° C. when BBr$_3$ (1 mmol, 1 mL of 1M solution in CH$_2$Cl$_2$) is added drop wise. After the addition, the mixture is warmed to 0° C. and stirred for 1 h when MeOH (0.5 mL) is added into the mixture to quench the reaction. The reaction mixture is then treated with water (3 mL) and extracted with EtOAc (3×5 mL). The combined organic layers are concentrated and purified by flash column chromatography (silica gel, 0-100% EtOAc/hexane) to provide the titled compound as a white solid (84 mg, 88%). HPLC-MS calculated for C$_{21}$H$_{17}$ClN$_2$O$_3$ (M+H$^+$) 381.1, found 381.1.

Example 462

(S)-1-(4-(4-chlorophenoxy)phenyl)-5-(3-(2-hydroxy-ethoxy)phenyl)imidazolidin-2-one

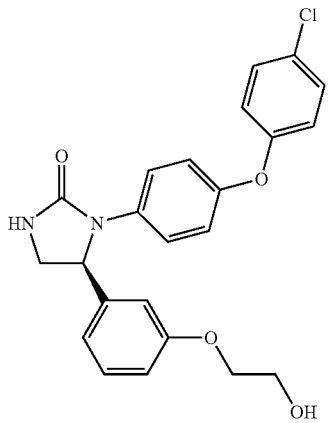 [SMILES: O=C1NC[C@H](c2cccc(OCCO)c2)N1c1ccc(Oc2ccc(Cl)cc2)cc1]

To a solution of (S)-1-(4-(4-chlorophenoxy)phenyl)-5-(3-hydroxyphenyl)-imidazolidin-2-one (26 mg, 0.068 mmol) in acetonitrile (2 mL) is added $Cs_2CO_3$ (50 mg, 0.15 mmol) followed by 2-(2-bromoethoxy)tetrahydro-2H-pyran (30 mg, 0.14 mmol). The resulting mixture is stirred at room temperature for 24 h and is then treated with water (5 mL) and extracted with EtOAc (3×3 mL). The combined organic layers are concentrated and the residue is dissolved in MeOH (1 mL). To the MeOH solution is added catalytic amount of pTSA (~1 mg). The resulting mixture is stirred at room temperature for 1 h and is then treated with sat. $NaHCO_3$ solution (3 mL). After extracting with EtOAc (3×3 mL), the combined organic layers are concentrated and purified by preparative thin layer chromatography (silica gel, 85% EtOAc/hexane) to provide the title compound as a white solid. $^1$H NMR ($CDCl_3$, 400 MHz) δ 7.33 (d, J=9.2 Hz, 2H), 7.22-7.27 (m, 3H), 6.89 (d, J=7.6 Hz, 1H), 6.81-6.88 (m, 6H), 5.23 (dd, J=8.8, 6.0 Hz, 1H), 4.90 (br s, 1H), 3.92-4.08 (m, 5H), 2.34 (dd, J=8.8, 6.4 Hz, 1H), 2.03 (t, J=5.6 Hz, 1H); HPLC-MS calculated for $C_{23}H_{21}ClN_2O_4$ (M+H$^+$) 425.1, found 425.1.

Example 463

(S)-2-(3-(4-(4-chlorophenoxy)phenyl)-4-(3-(2-hydroxyethoxy)phenyl)-2-oxoimidazolidin-1-yl)ethanesulfonamide

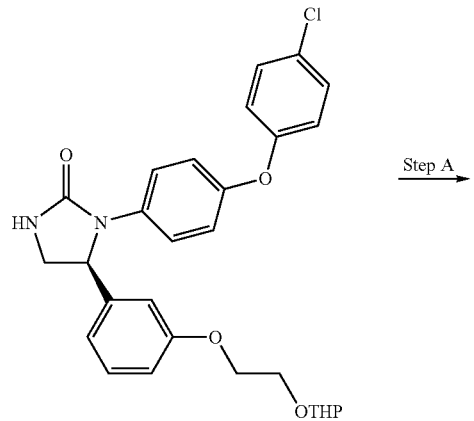

Step A

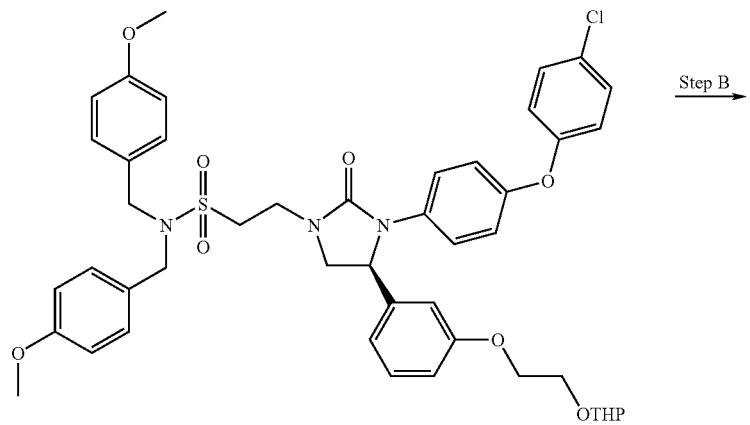

Step B

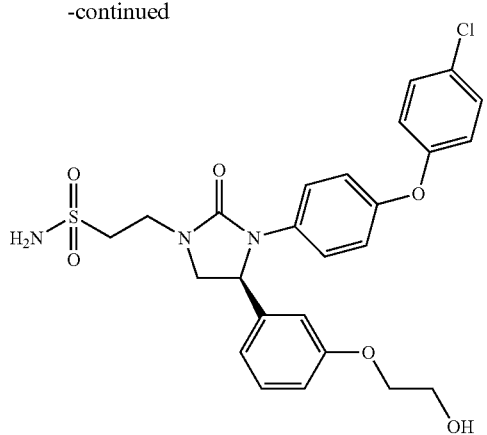

Step A: 2-((4S)-3-(4-(4-chlorophenoxy)phenyl)-2-oxo-4-(3-(2-(tetrahydro-2H-pyran-2-yloxy)ethoxy)phenyl)imidazolidin-1-yl)-N,N-bis(4-methoxybenzyl)ethane-sulfonamide is prepared from (Example 462) and ethenesulfonic acid bis-(4-methoxy-benzyl)-amide (example 164) by using the same procedure described in Example 164 step B.

Step B: A solution of 2-((4S)-3-(4-(4-chlorophenoxy)phenyl)-2-oxo-4-(3-(2-(tetrahydro-2H-pyran-2-yloxy)ethoxy)phenyl)imidazolidin-1-yl)-N,N-bis(4-methoxybenzyl)-ethane-sulfonamide (40 mg, 0.046 mmol) in TFA (1 mL) is stirred at room temperature for 2 h and is then concentrated. The residue is dissolved in MeOH (1 mL) and NaOH (0.09 mmol, 1M aqueous solution) is added. The mixture is stirred at room temperature for 14 h and is treated with water (3 mL) and extracted with EtOAc (3×3 ml). The combined organic layers are concentrated and purified by flash column chromatography (silica gel, 0-100% EtOAc/hexane) to provide the title compound as a white solid (20 mg, 81%). $^1$H NMR (CDCl$_3$, 400 MHz) δ 7.21-7.28 (m, 5H), 6.81-6.97 (m, 7H), 5.67 (s, 2H), 5.16 (dd, J=9.2, 6.8 Hz, 1H), 3.98-4.08 (m, 2H), 3.92 (m, 3H), 3.75-3.80 (m, 2H), 3.26-3.41 (m, 3H), 2.37 (br s, 1H); HPLC-MS calculated for C$_{25}$H$_{26}$ClN$_3$O$_6$S (M+H$^+$) 532.1, found 532.1.

Example 464

(S)—N-(2-(3-(4-(4-chlorophenoxy)phenyl)-2-oxo-4-(3-(trifluoromethyl)phenyl)imidazolidin-1-yl)ethyl-sulfonyl)acetamide

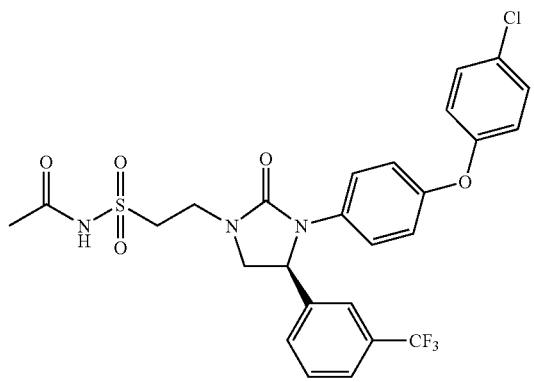 [SMILES: CC(=O)NS(=O)(=O)CCN1C[C@H](c2cccc(C(F)(F)F)c2)N(c2ccc(Oc3ccc(Cl)cc3)cc2)C1=O]

To a solution of (S)-2-[3-[4-(4-chloro-phenoxy)-phenyl]-2-oxo-4-(3-trifluoromethyl-phenyl)-imidazolidin-1-yl] ethanesulfonic acid amide (20 mg, 0.037 mmol) and acetyl chloride (6 mg, 0.076 mmol) in anhydrous CH$_2$Cl$_2$ (1 mL) is added triethylamine (7.7 mg, 0.076 mmol). The mixture is stirred at room temperature for 14 h and is then concentrated to dryness. The residue is dissolved in EtOH and treated with NaOH (0.074 mmol, 1 M aqueous solution) for 1 h. The mixture is then treated with water (3 mL) and extracted with EtOAc (3×3 mL). The combined organic layers are concentrated and purified by flash column chromatography to provide the title compound as a white solid. $^1$H NMR (CDCl$_3$, 400 MHz) δ 7.56 (m, 3H), 7.48 (m, 1H), 7.24 (d, J=8.8 Hz, 2H), 7.20 (d, J=8.8 Hz, 2H), 6.86 (d, J=9.2 Hz, 2H), 6.85 (d, J=8.8 Hz, 2H), 5.26 (dd, J=9.2, 6.8 Hz, 1H), 4.00 (t, J=9.2 Hz, 1H), 3.75-3.90 (m, 2H), 3.55-3.65 (m, 2H), 3.36 (dd, J=8.8, 6.8 Hz, 1H), 2.17 (s, 3H); HPLC-MS calculated for C$_{26}$H$_{23}$ClF$_3$N$_3$O$_5$S (M+H$^+$) 582.1, found 582.1.

Example 468

(S)-1-(4-chlorophenyl)-5-(3-(pyridazin-3-yloxy)phenyl)imidazolidin-2-one

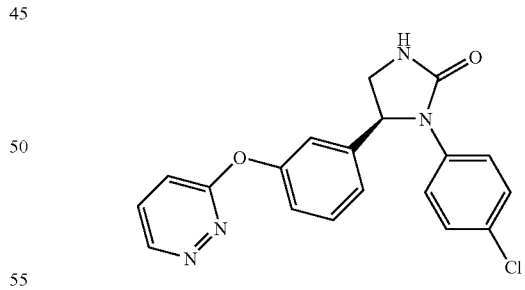

To a solution of (S)-1-(4-chlorophenyl)-5-(3-hydroxyphenyl)imidazolidin-2-one (210 mg, 0.73 mmol, prepared by using a similar procedure as described in Example 460) and 3-chloropyradazine (167 mg, 1.46 mmol) in DMF (2 mL) is added Cs$_2$CO$_3$ (354 mg, 1.09 mmol). The mixture is stirred at 80° C. for 14 h and is then cooled to room temperature. The reaction mixture is then treated with water (20 mL) and extracted with EtOAc (3×15 ml). The combined organic layers are washed with brine and dried (MgSO$_4$). After removing the drying agent, the solution is concentrated and purified by flash column chromatography (silica gel, 0%~10% MeOH/

CH$_2$Cl$_2$) to provide the title compound. $^1$H NMR (CDCl$_3$, 400 MHz) δ 8.95 (dd, J=4.4, 1.2 Hz, 1H), 7.49 (dd, J=8.8, 4.4 Hz, 1H), 7.32-7.40 (m, 3H), 7.10-7.20 (m, 6H), 5.28 (dd, J=8.0, 4.8 Hz, 1H), 4.70 (br s, 1H), 3.97 (t, J=8.8 Hz, 1H), 3.41 (dd, J=8.8, 6.0 Hz, 1H); HPLC-MS calculated for C$_{19}$H$_{15}$ClN$_4$O$_2$ (M+H$^+$) 367.1, found 367.1.

Example 490

(S)-methyl 3-(3-(4-(4-chlorophenoxy)phenyl)-2-oxo-4-(3-(trifluoromethyl)phenyl)imidazolidin-1-yl)propanoate

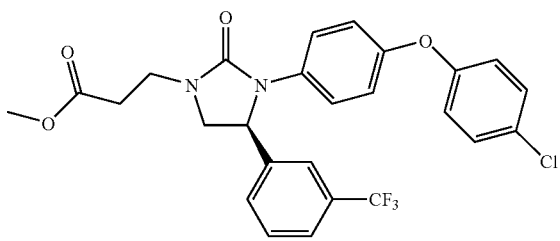 [SMILES: COC(=O)CCN1C[C@H](c2cccc(C(F)(F)F)c2)N(c2ccc(Oc3ccc(Cl)cc3)cc2)C1=O]

The title compound is prepared by the method described in Example 163, using methyl acrylate instead of vinyl methylsulfone; HPLC-MS calculated for C$_{26}$H$_{22}$ClF$_3$N$_2$O$_4$ (M+H$^+$) 519.1, found 519.1.

Example 493

(S)—N-(1-(4-(4-chlorophenoxy)phenyl)-5-(3-(trifluoromethyl)phenyl)imidazolidin-2-ylidene)sulfamide

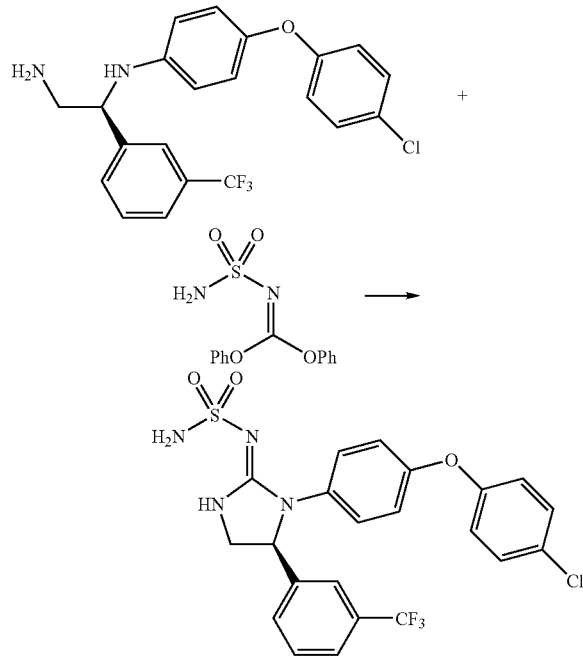

Diphenyl sulfamoylcarbonimidate: To a solution of sulfamide (100.9 mg, 1.05 mmol) in anhydrous acetonitrile (3.3 mL) is slowly added dichlorodiphenoxymethane (269.1 mg, 1.00 mmol) at 0° C. The reaction mixture is stirred at room temperature overnight before removal of the solvent. The residue is purified by chromatography to provide diphenyl sulfamoylcarbonimidate (280.2 mg, 96% yield) as a white solid product; HPLC-MS calculated for C$_{13}$H$_{12}$N$_2$O$_4$S (M+H$^+$) 293.1, found 293.1.

The title compound is prepared by condensing diphenyl sulfamoylcarbonimidate (27.0 mg, 0.091 mmol) with (S)—N$^1$-(4-(4-chlorophenoxy)-phenyl)-1-(3-(trifluoromethyl)phenyl)ethane-1,2-diamine (37.0 mg, 0.091 mmol) [prepared from Example 173 Step A] $^i$PrOH (1.0 mL) at 80° C. for 2 h; then K$_2$CO$_3$ (25.1 mg, 0.182 mmol) is added and the reaction mixture is heated at 80° C. for another 2 h, then cooled, quenched with H$_2$O (5 mL), and extracted with EtOAc (3×3 mL). The combined organic layer is concentrated and purified by preparatory TLC to provide the title compound as a white solid; $^1$H NMR (CDCl$_3$, 400 MHz) δ 7.59-7.47 (m, 4H), 7.26 (d, J=9.2 Hz, 2H), 7.15 (m, 3H), 6.86 (m, 4H), 5.31 (dd, J=9.6, 7.6 Hz, 1H), 4.65 (br, 2H), 4.18 (t, J=9.6 Hz, 1H), 3.59 (dd, J=9.6, 7.6 Hz, 1H); HPLC-MS calculated for C$_{22}$H$_{18}$ClF$_3$N$_4$O$_3$S (M+H$^+$) 511.1, found 511.1.

Example 495

(S)—N-(1-(4-(4-chlorophenoxy)phenyl)-5-(3-(trifluoromethyl)phenyl)imidazolidin-2-ylidene)methanesulfonamide

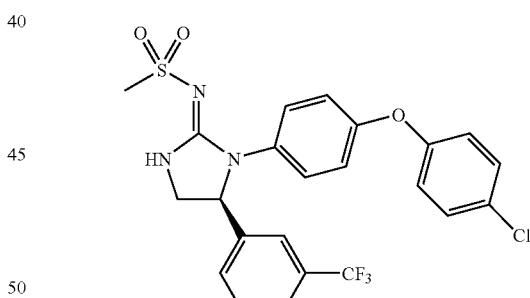

The title compound is prepared by the method described in Example 493, using methanesulfonamide instead of sulfamide and changing the reaction condition from room temperature overnight to heating at 100° C. overnight in Step A; $^1$H NMR (CDCl$_3$, 400 MHz) δ 7.59-7.47 (m, 4H), 7.27 (d, J=9.2 Hz, 2H), 7.16 (d, J=9.2 Hz, 2H), 6.89 (d, J=9.2 Hz, 2H), 6.85 (d, J=9.2 Hz, 2H), 5.31 (dd, J=9.6, 7.6 Hz, 1H), 4.17 (t, J=9.6 Hz, 1H), 3.58 (dd, J=9.6, 7.6 Hz, 1H), 3.02 (s, 3H); HPLC-MS calculated for C$_{23}$H$_{19}$ClF$_3$N$_3$O$_3$S (M+H$^+$) 510.1, found 510.1.

Example 503

(S)-1-(4-(4-chlorophenoxy)phenyl)-2-(nitromethyl-ene)-5-(3-(trifluoromethyl)phenyl)imidazolidine

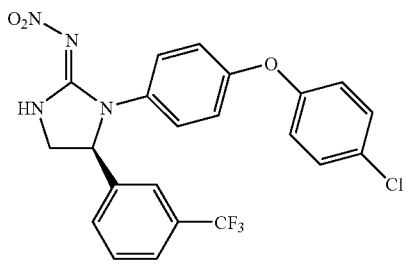 [SMILES: O=[N+]([O-])/N=C1\NC[C@H](c2cccc(C(F)(F)F)c2)N1c1ccc(Oc2ccc(Cl)cc2)cc1]

1,1-Bis(methylthio)-2-nitroethylene (13.1 mg, 0.079 mmol) and (S)—N$^1$-(4-(4-chlorophenoxy)phenyl)-1-(3-(trifluoromethyl)phenyl)ethane-1,2-diamine prepared from Example 173 Step A (16.1 mg, 0.040 mmol) are dissolved in $^i$PrOH (0.4 mL) and heated at 80° C. for 2 h. The solvent is removed and the residue is purified by preparatory LC/MS to provide the title compound; HPLC-MS calculated for $C_{23}H_{17}ClF_3N_3O_3$ (M+H$^+$) 476.1, found 476.1.

Example 507

(S)-1-(1-(4-(4-chlorophenoxy)phenyl)-5-(3-(trifluoromethyl)phenyl)imidazolidin-2-ylidene)urea

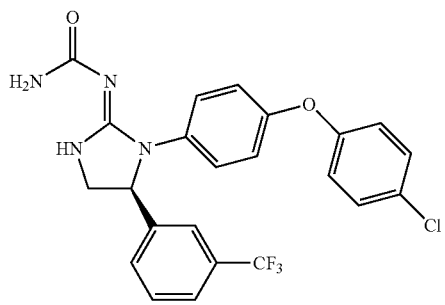 [SMILES: NC(=O)/N=C1\NC[C@H](c2cccc(C(F)(F)F)c2)N1c1ccc(Oc2ccc(Cl)cc2)cc1]

(S)—N-(1-(4-(4-Chlorophenoxy)phenyl)-5-(3-(trifluoromethyl)phenyl)-imidazo-lidin-2-ylidene)cyanamide prepared from Example 203 (12.0 mg, 0.026 mmol) is dissolved in a mixed solvent of 4N HCl solution (0.5 mL) and acetonitrile (0.5 mL). The reaction mixture is heated at 80° C. for 30 minutes. The solvent is removed en vacuo and the residue is purified by preparatory LC/MS to provide the title compound; $^1$H NMR (CDCl$_3$, 400 MHz) δ 9.35 (br, 1H), 7.71 (br, 1H), 7.67-7.51 (m, 4H), 7.30 (d, J=8.8 Hz, 2H), 6.95 (m, 4H), 6.84 (d, J=8.8 Hz, 2H), 5.67 (br, 1H), 5.25 (t, J=9.2 Hz, 1H), 4.46 (t, J=10.4 Hz, 1H), 3.97 (t, J=9.2 Hz, 1H); HPLC-MS calculated for $C_{23}H_{18}ClF_3N_4O_2$ (M+H$^+$) 475.1, found 475.1.

Example 521

(S)—N-(3-(4-(4-chlorophenoxy)phenyl)-1-cyano-4-(3-(trifluoromethyl)phenyl)imidazo-lidin-2-ylidene)cyanamide

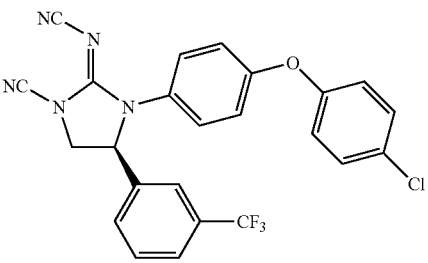

To a solution of (S)—N-(1-(4-(4-chlorophenoxy)phenyl)-5-(3-(trifluoromethyl)-phenyl)imidazolidin-2-ylidene)cyanamide [prepared from Example 203] (15.0 mg, 0.033 mmol) in 1,4-dioxane (0.5 mL) is treated with excess BrCN and K$_2$CO$_3$. The reaction mixture is heated at 100° C. for 2 h, cooled, then quenched with H$_2$O (5 mL) and extracted with EtOAc (3×3 mL). The combined organics are evaporated en vacuo and purified by preparatory LC/MS followed by preparatory TLC to provide the title compound; HPLC-MS calculated for $C_{24}H_{15}ClF_3N_5O$ (M+H$^+$) 482.1, found 482.1.

Example 522

(S)-1-(2-(1H-1,2,4-triazol-3-yl)ethyl)-3-(4-chlorophenyl)-4-(3-(pyrazin-2-yloxy)phenyl)imidazolidin-2-one

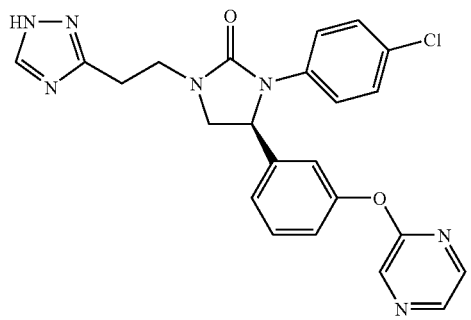 [SMILES: O=C1N(CCc2nc[nH]n2)C[C@H](c2cccc(Oc3cnccn3)c2)N1c1ccc(Cl)cc1]

(S)-3-(3-(4-Chlorophenyl)-2-oxo-4-(3-(pyrazin-2-yloxy)phenyl)imidazolidin-1-yl)propanamide (30.0 mg, 0.069 mmol) is dissolved in DMF-DMA (0.5 mL) and heated at 100° C. for 1.5 h. The solvent is removed en vacuo and the residue is then dissolved in acetic acid (0.5 mL) and treated with excess hydrazine monohydrate. The reaction mixture is heated at 100° C. for 1 h, and then the solvent is removed under vacuum and the residue is purified by preparatory LC/MS to provide the title compound; HPLC-MS calculated for $C_{23}H_{20}ClN_7O_2$ (M+H$^+$) 462.1, found 462.1.

By repeating the procedures described in the above examples, using appropriate starting materials, the following compounds of Formula I, as identified in Table 1, are obtained.

TABLE 1

| Compound Number | Structure | Physical Data $^1$H NMR 400 MHz (CDCl$_3$) and/or MS (m/z) |
|---|---|---|
| 1 | 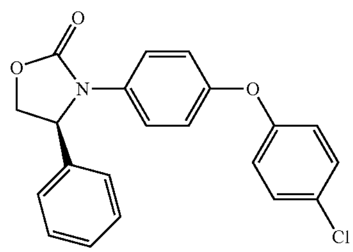 [SMILES: O=C1OC[C@H](c2ccccc2)N1c1ccc(Oc2ccc(Cl)cc2)cc1] | $^1$H NMR (CDCl$_3$, 400 MHz) δ 7.28-7.37 (m, 7H), 7.25 (d, 2H), 7.46 (d, 1H), 7.41 (t, 1H), 7.31 (d, 2H), 7.25 (d, 2H), 6.88 (d, 2H), 6.87 (d, 2H), 5.34 (dd, 1H), 4.79 (t, 1H), 4.22 (dd, 1H); HPLC-MS calculated for C$_{21}$H$_{16}$ClNO$_3$ (M + H$^+$) 366.1, found 366.1. |
| 5 | 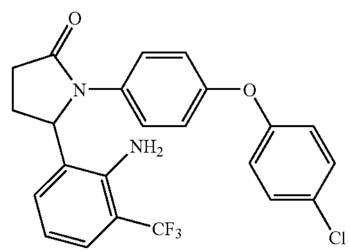 [SMILES: Nc1c(C2CCC(=O)N2c2ccc(Oc3ccc(Cl)cc3)cc2)cccc1C(F)(F)F] | $^1$H NMR (CDCl$_3$, 400 MHz) δ 7.40 (d, 3H), 7.25 (d, 2H), 7.15 (d, 2H), 7.14 (dd, 1H), 6.90 (d, 2H), 6.88 (d, 2H), 6.76 (t, 1H), 5.25 (dd, 1H), 4.24 (br, 2H), 2.56-2.80 (m, 3H), 2.05-2.18 (m, 1H); HPLC-MS calculated for C$_{23}$H$_{18}$ClF$_3$N$_2$O$_2$ (M + H$^+$) 447.1, found 447.1. |
| 6 | 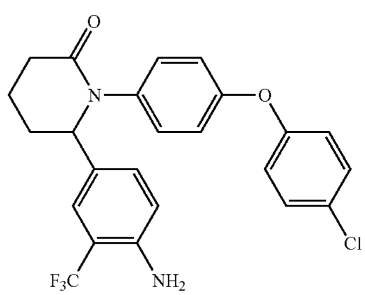 [SMILES: Nc1ccc(C2CCCC(=O)N2c2ccc(Oc3ccc(Cl)cc3)cc2)cc1C(F)(F)F] | $^1$H NMR (CDCl$_3$, 400 MHz) δ 7.25 (d, 2H), 7.17 (s, 1H), 7.16 (d, 1H), 7.02 (d, 2H), 6.88 (d, 2H), 6.84 (d, 2H), 6.67 (d, 1H), 4.87 (t, 1H), 2.65-2.70 (m, 2H), 2.26-2.31 (m, 1H), 1.80-1.96 (m, 3H); HPLC-MS calculated for C$_{24}$H$_{20}$ClF$_3$N$_2$O$_2$ (M + H$^+$) 461.1, found 461.1 |
| 8 | 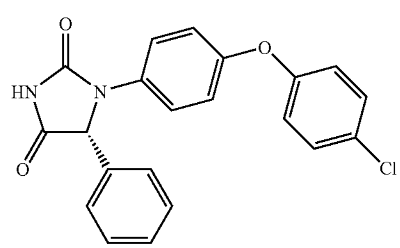 [SMILES: O=C1NC(=O)N(c2ccc(Oc3ccc(Cl)cc3)cc2)[C@@H]1c1ccccc1] | $^1$H NMR (CDCl$_3$, 400 MHz) δ 7.78 (br, 1H), 7.39-7.33 (m, 7H), 7.26 (d, 2H), 6.91 (d, 2H), 6.89 (d, 2H), 5.48 (s, 1H); HPLC-MS calculated for C$_{21}$H$_{15}$ClN$_2$O$_3$ (M + H$^+$) 379.1, found 379.1. |
| 10 | 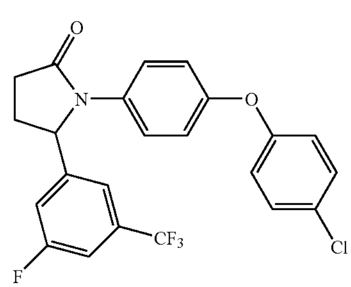 [SMILES: O=C1CCC(c2cc(F)cc(C(F)(F)F)c2)N1c1ccc(Oc2ccc(Cl)cc2)cc1] | $^1$H NMR (CDCl$_3$, 400 MHz) δ 7.20-7.33 (m, 7H), 7.11 (d, 1H), 6.90 (d, 2H), 6.88 (d, 2H), 5.27 (q, 1H), 2.6-2.8 (m, 3H), 1.98-2.03 (m, 1H); HPLC-MS calculated for C$_{23}$H$_{16}$ClF$_4$NO$_2$ (M + H$^+$) 450.1, found 450.1. |

TABLE 1-continued

| Compound Number | Structure | Physical Data $^1$H NMR 400 MHz (CDCl$_3$) and/or MS (m/z) |
|---|---|---|
| 11 | 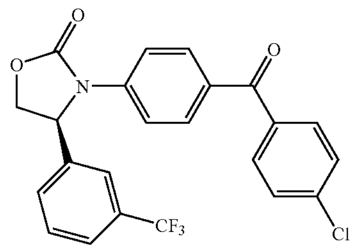 [SMILES: O=C(c1ccc(Cl)cc1)c1ccc(N2C(=O)OC[C@@H]2c2cccc(C(F)(F)F)c2)cc1] | $^1$H NMR (CDCl$_3$, 400 MHz) δ 7.73 (d, 2H), 7.69 (d, 2H), 7.63 (d, 1H), 7.48-7.58 (m, 5H), 7.44 (d, 2H), 5.54 (q, 1H), 4.88 (t, 1H), 4.25 (q, 1H); HPLC-MS calculated for C$_{23}$H$_{15}$ClF$_3$NO$_3$ (M + H$^+$) 446.1, found 446.1. |
| 12 | 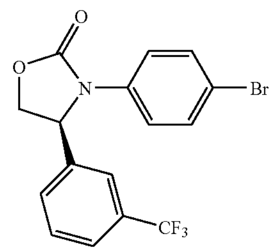 [SMILES: O=C1OC[C@H](c2cccc(C(F)(F)F)c2)N1c1ccc(Br)cc1] | HPLC-MS calculated for C$_{16}$H$_{11}$BrF$_3$NO$_2$ (M + H$^+$) 386.0, found 386.0. |
| 17 | 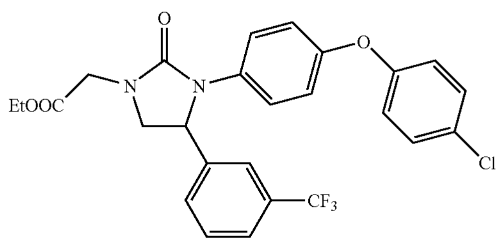 [SMILES: CCOC(=O)CN1CC(c2cccc(C(F)(F)F)c2)N(c2ccc(Oc3ccc(Cl)cc3)cc2)C1=O] | HPLC-MS calculated for C$_{26}$H$_{22}$ClF$_3$N$_2$O$_4$ (M + H$^+$) 519.1, found 519.1. |
| 18 | 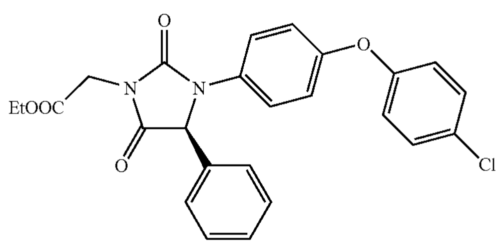 [SMILES: CCOC(=O)CN1C(=O)[C@H](c2ccccc2)N(c2ccc(Oc3ccc(Cl)cc3)cc2)C1=O] | HPLC-MS calculated for C$_{25}$H$_{21}$ClN$_2$O$_5$ (M + H$^+$) 465.1, found 465.1. |
| 19 | 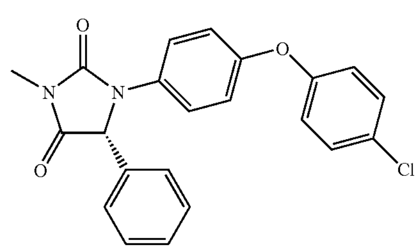 [SMILES: CN1C(=O)[C@@H](c2ccccc2)N(c2ccc(Oc3ccc(Cl)cc3)cc2)C1=O] | HPLC-MS calculated for C$_{22}$H$_{17}$ClN$_2$O$_3$ (M + H$^+$) 393.1, found 393.1. |
| 21 | 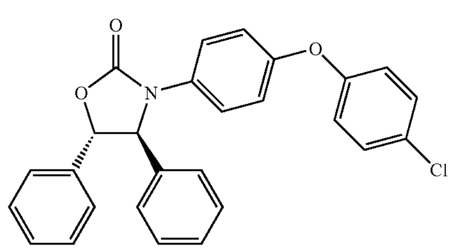 [SMILES: O=C1O[C@@H](c2ccccc2)[C@H](c2ccccc2)N1c1ccc(Oc2ccc(Cl)cc2)cc1] | $^1$H NMR (CDCl$_3$) δ (ppm) 7.41-7.44 (m, 4H), 7.23-7.39 (m, 10H), 6.85-6.88 (m, 4H), 5.33 (d, 1H, J = 6.6 Hz), 5.13 (d, 1H, J = 6.6 Hz). HPLC-MS calculated C$_{27}$H$_{20}$ClNO$_3$ (M + H$^+$): 442.9, found: 442.9. |

TABLE 1-continued

| Compound Number | Structure | Physical Data $^1$H NMR 400 MHz (CDCl$_3$) and/or MS (m/z) |
|---|---|---|
| 22 | 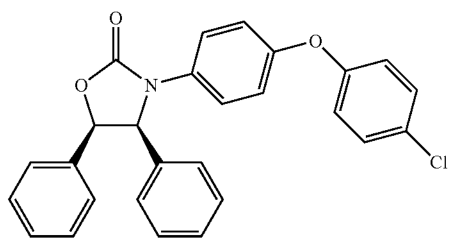 [SMILES: O=C1O[C@H](c2ccccc2)[C@H](c2ccccc2)N1c1ccc(Oc2ccc(Cl)cc2)cc1] | $^1$H NMR (CDCl$_3$) δ (ppm) 7.44 (d, 2H, J = 8.3 Hz), 7.24-7.29 (m, 2H), 7.10 (d, 6H, J = 12.3 Hz), 7.01 (s, 2H), 6.86-6.90 (m, 6H), 6.00 (d, 1H, =7.4 Hz), 5.51 (d, 1H, J = 7.8 Hz). HPLC-MS calculated C$_{27}$H$_{20}$ClNO$_3$ (M + H$^+$): 442.9, found: 442.9. $^1$H NMR (CDCl$_3$) δ (ppm) 7.41-7.44 (m, 4H), 7.23-7.39 (m, 10H), 6.85-6.88 (m, 4H), 5.33 (d, 1H, J = 6.6 Hz), 5.13 (d, 1H, J = 6.6 Hz). |
| 23 | 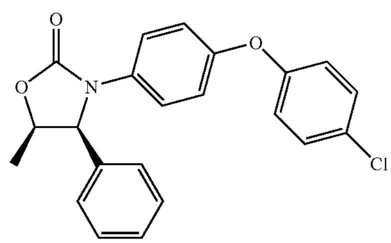 [SMILES: C[C@H]1OC(=O)N(c2ccc(Oc3ccc(Cl)cc3)cc2)[C@H]1c1ccccc1] | $^1$H NMR (acetone-d$_6$) δ (ppm) 7.58 (d, 2H, J = 9.1 Hz), 7.40-7.44 9m, 3H), 7.31-7.38 (m, 4H), 6.95 (dd, 4H, J = 9.1, 1.4 Hz), 5.65 (d, 1H, J = 7.8 Hz), 5.14 (dq, 1H, J = 6.5, 1.3 Hz), 0.96 (d, 3H, J = 6.5 Hz). HPLC-MS calculated C$_{22}$H$_{18}$ClNO$_3$ (M + H$^+$): 380.8, found: 380.8. |
| 24 | 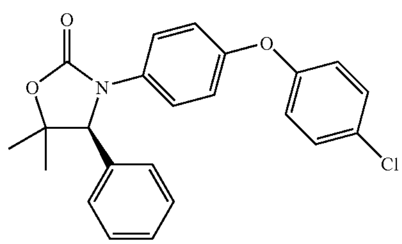 [SMILES: CC1(C)OC(=O)N(c2ccc(Oc3ccc(Cl)cc3)cc2)[C@H]1c1ccccc1] | $^1$H NMR (acetone-d$_6$) δ (ppm) 7.55 (d, 2H, J = 9.1 Hz), 7.33-7.42 (m, 7H), 6.94 (d, 4H, J = 8.9 Hz), 5.38 (s, 1H), 1.69 (s, 3H), 0.97 (s, 3H). HPLC-MS calculated C$_{23}$H$_{20}$ClNO$_3$ (M + H$^+$): 394.1, found: 394.1. $^1$H NMR (acetone-d$_6$) δ (ppm) 7.58 (d, 2H, J = 9.1 Hz), 7.40-7.44 9m, 3H), 7.31-7.38 (m, 4H), 6.95 (dd, 4H, J = 9.1, 1.4 Hz), 5.65 (d, 1H, J = 7.8 Hz), 5.14 (dq, 1H, J = 6.5, 1.3 Hz), 0.96 (d, 3H, J = 6.5 Hz). HPLC-MS calculated C$_{22}$H$_{18}$ClNO$_3$ (M + H$^+$): 380.8, found: 380.8. |
| 25 | 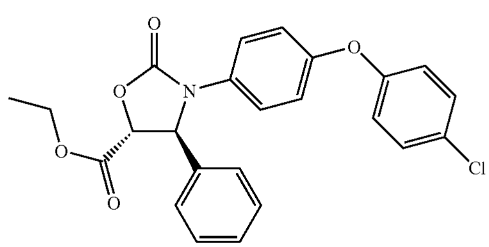 [SMILES: CCOC(=O)[C@@H]1OC(=O)N(c2ccc(Oc3ccc(Cl)cc3)cc2)[C@H]1c1ccccc1] | $^1$H NMR (acetone-d$_6$) δ (ppm) 7.48-7.54 (m, 4H), 7.43 (t, 2H, J = 7.0 Hz), 7.35-7.39 (m, 3H), 6.96 (dd, 4H, J = 8.8, 1.5 Hz), 5.75 (d, 1H, 4.7 Hz), 4.93 (d, 1H, J = 4.7 Hz), 4.28-4.36 (m, 2H), 1.32 (t, 3H, J = 7.1 Hz). HPLC-MS calculated C$_{24}$H$_{20}$ClNO$_5$ (M + H$^+$): 438.1, found: 438.1. |
| 27 | 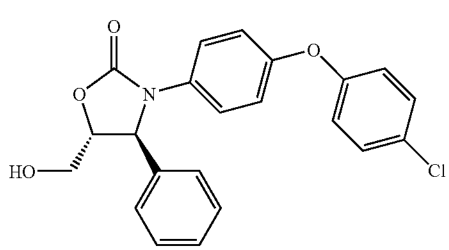 [SMILES: O=C1O[C@@H](CO)[C@H](c2ccccc2)N1c1ccc(Oc2ccc(Cl)cc2)cc1] | $^1$H NMR (CDCl$_3$) δ (ppm) 7.24-7.32 (m, 7H), 7.16-7.20 (m, 2H), 6.78-6.81 (m, 4H), 5.25 (dd, 1H, J = 6.4, 1.1 Hz), 4.34-4.37 (m, 1H), 3.99 (ddd, 1H, J = 12.8, 2.5, 2.3 Hz), 3.74 (ddd, 1H, J = 12.8, 2.7, 2.3 Hz). HPLC-MS calculated C$_{22}$H$_{18}$ClNO$_4$ (M + H$^+$): 396.1, found: 396.1. |

TABLE 1-continued

| Compound Number | Structure | Physical Data $^1$H NMR 400 MHz (CDCl$_3$) and/or MS (m/z) |
|---|---|---|
| 29 | 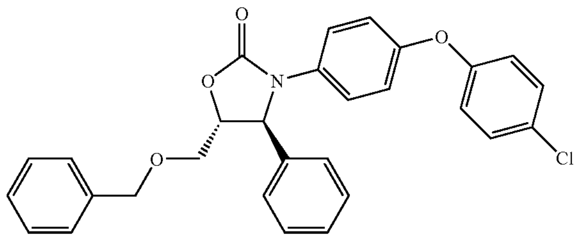 [SMILES: O=C1O[C@@H](COCc2ccccc2)[C@H](c2ccccc2)N1c1ccc(Oc2ccc(Cl)cc2)cc1] | $^1$H NMR (CDCl$_3$) δ (ppm) 7.20-7.29 (m, 9H), 7.13-7.18 (m, 5H), 6.75-6.79 (m, 4H), 5.13 (d, 1H, J = 5.6 Hz), 4.61 (d, 1H, J = 12.0 Hz), 4.53 (d, 1H, J = 12.0 Hz), 4.35-4.38 (m, 1H), 3.73 (dd, 1H, J = 11.0 4.1 Hz), 3.65 (dd, 1H, J = 11.0, 3.6 Hz). HPLC-MS calculated C$_{29}$H$_{24}$ClNO$_4$ (M + H$^+$): 486.1, found: 486.1. |
| 31 | 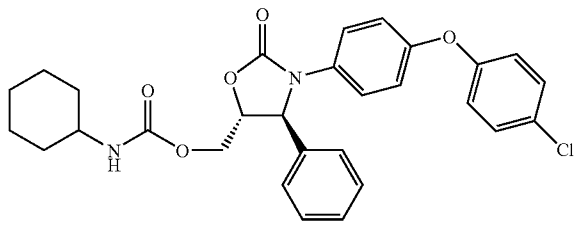 [SMILES: O=C(NC1CCCCC1)OC[C@@H]1OC(=O)N(c2ccc(Oc3ccc(Cl)cc3)cc2)[C@H]1c1ccccc1] | $^1$H NMR (acetone-d$_6$) δ (ppm) 7.45-7.48 (m, 4H), 7.32-7.42 (m, 5H), 6.97 (d, 4H, J = 8.7 Hz), 6.42 (d, 1H, J = 7.8 Hz), 5.42 (d, 1H, J = 5.6 Hz), 4.55 (dd, 1H, J = 8.5, 4.7 Hz), 4.46 (dd, 1H, J = 12.5, 4.6 Hz), 4.37 (dd, 1H, J = 12.4, 3.3 Hz), 3.34-3.43 (m, 1H), 1.81-1.89 (m, 2H), 1.69-1.73 (m, 2H), 1.56-1.60 (m, 2H), 1.08-1.36 (m, 4H). HPLC-MS calculated C$_{29}$H$_{29}$ClN$_2$O$_5$ (M + H$^+$): 521.2, found: 521.2. |
| 32 | 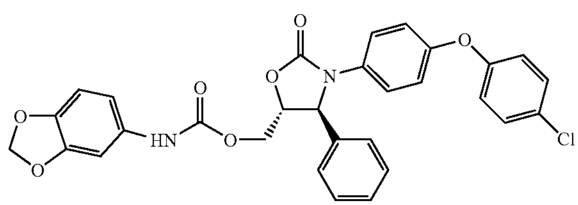 [SMILES: O=C(Nc1ccc2c(c1)OCO2)OC[C@@H]1OC(=O)N(c2ccc(Oc3ccc(Cl)cc3)cc2)[C@H]1c1ccccc1] | $^1$H NMR (acetone-d$_6$) δ (ppm) 8.90 (s, 1H), 7.48-7.51 (m, 4H), 7.32-7.42 (m, 5H), 7.21 (s, 1H), 6.90-6.96 (m, 5H), 6.76 (d, 1H, J = 8.2 Hz), 5.96 (s, 2H), 5.52 (d, 1H, J = 5.8 Hz), 4.63-4.67 (m, 1H), 4.57 (dd, 1H, J = 12.4, 4.6 Hz), 4.51 (dd, 1H, J = 12.4, 3.3 Hz). HPLC-MS calculated C$_{30}$H$_{23}$ClN$_2$O$_7$ (M + H$^+$): 559.1, found: 559.1. |
| 36 | 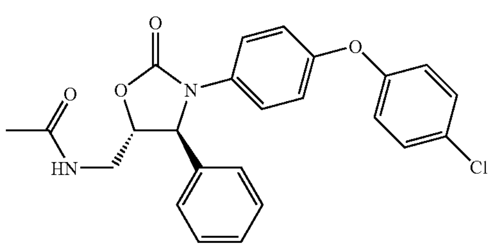 [SMILES: CC(=O)NC[C@@H]1OC(=O)N(c2ccc(Oc3ccc(Cl)cc3)cc2)[C@H]1c1ccccc1] | $^1$H NMR (acetone-d$_6$) δ (ppm) 7.59 (s, 1H), 7.42-7.46 (m, 4H), 7.30-7.41 (m, 5H), 6.92-6.97 (m, 4H), 5.38 (d, 1H, J = 6.0 Hz), 4.44 (dd, 1H, J = 10.6, 4.7 Hz), 3.78 (ddd, 1H, J = 14.5, 6.6, 5.0), 3.62 (ddd, 1H, J = 14.5, 5.6, 4.6 Hz), 1.95 (s, 3H). HPLC-MS calculated C$_{24}$H$_{21}$ClN$_2$O$_4$ (M + H$^+$): 437.1, found: 437.1. $^1$H NMR (acetone-d$_6$) δ (ppm) 7.49-7.53 (m, 2H), 7.30-7.46 (m, 7H), 6.92-6.97 (m, 4H), 5.48 (d, 1H, J = 4.8 Hz), 4.55 (dd, 1H, J = 9.5, 4.7 Hz), 3.64 (dd, 2H, J = 4.9, 1.6 Hz). HPLC-MS calculated C$_{22}$H$_{19}$ClN$_2$O$_3$ (M + H$^+$): 395.1, found: 395.1. |
| 37 | 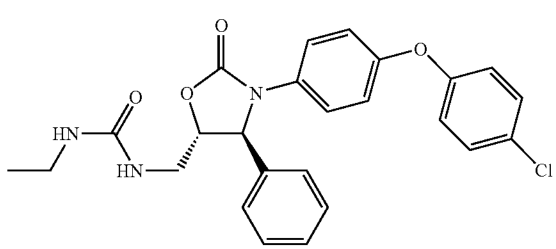 [SMILES: CCNC(=O)NC[C@@H]1OC(=O)N(c2ccc(Oc3ccc(Cl)cc3)cc2)[C@H]1c1ccccc1] | $^1$H NMR (acetone-d$_6$) δ (ppm) 7.44-7.47 (m, 4H), 7.32-7.41 (m, 5H), 6.93-6.97 (m, 4H), 5.91 (t, 1H, J = 6.5 Hz), 5.66 (t, 1H, J = 5.1 Hz), 5.49 (d, 1H, J = 5.5 Hz), 4.39 (dd, 1H, J = 9.8, 4.4 Hz), 3.75 (ddd, 1H, J = 14.7, 6.7, 4.2 Hz), 3.54 (ddd, 1H, J = 14.7, 5.7, 4.6 Hz), 3.17 (m, 2H), 1.04 (t, 3H, J = 7.2 Hz). HPLC-MS calculated C$_{25}$H$_{24}$ClN$_3$O$_4$ (M + H$^+$): 466.2, found: 466.1. |

| Compound Number | Structure | Physical Data $^1$H NMR 400 MHz (CDCl$_3$) and/or MS (m/z) |
|---|---|---|
| 40 | 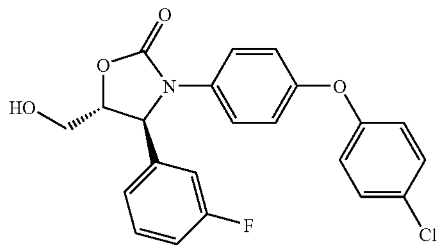 [SMILES: O=C1O[C@@H](CO)[C@H](c2cccc(F)c2)N1c1ccc(Oc2ccc(Cl)cc2)cc1] | $^1$H NMR (d$_6$ acetone) δ (ppm) 7.54 (d, J = 9.1 Hz, 2H), 7.48-7.43 (m, 1H), 7.37 (d, J = 8.9 Hz, 2H), 7.31 (d, J = 7.7 Hz, 1H), 7.29-7.25 (m, 1H), 7.13-7.08 (m, 1H), 6.98-6.95 (m, 4H), 5.55 (d, J = 5.6 Hz, 1H), 4.53 (t, J = 5.9 Hz, 1H), 4.43-4.40 (m, 1H), 4.00-3.94 (m, 1H), 3.91-3.85 (m, 1H); HPLC-MS calculated C$_{22}$H$_{17}$ClFNO$_4$ (M + H$^+$): 414.1, found: 414.0. |
| 43 | 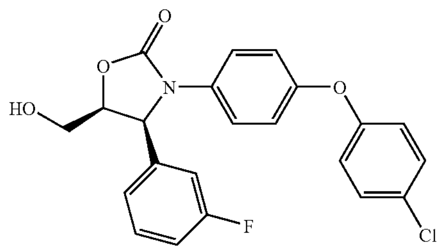 [SMILES: O=C1O[C@H](CO)[C@H](c2cccc(F)c2)N1c1ccc(Oc2ccc(Cl)cc2)cc1] | $^1$H NMR (d$_6$ acetone) δ (ppm) 7.58 (d, J = 9.1 Hz, 2H), 7.46-7.42 (m, 1H), 7.37 (d, J = 8.9 Hz, 2H), 7.21-7.10 (m, 2H), 6.98-6.95 (m, 4H), 5.82 (d, J = 8.3 Hz, 1H), 5.08-5.02 (m, 1H), 4.11 (t, J = 5.3 Hz, 1H), 3.36-3.30 (m, 2H); HPLC-MS calculated C$_{22}$H$_{17}$ClFNO$_4$ (M + H$^+$): 414.1, found: 414.0. |
| 44 | 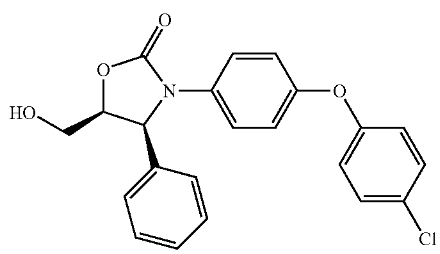 [SMILES: O=C1O[C@H](CO)[C@H](c2ccccc2)N1c1ccc(Oc2ccc(Cl)cc2)cc1] | $^1$H NMR (d$_6$ acetone) δ (ppm) 7.57 (d, J = 9.2 Hz, 1H), 7.52 (d, J = 9.2 Hz, 1H), 7.47-7.33 (m, 7H), 6.96-6.93 (m, 4H), 5.76 (d, J = 8.0 Hz, 1H), 5.04-4.99 (m, 1H), 4.40-4.37 (m, 1H), 3.94 (dd, J = 12.4, 3.6 Hz, 1H), 3.87 (dd, J = 12.4, 3.6 Hz, 1H); HPLC-MS calculated C$_{22}$H$_{18}$ClNO$_4$ (M + H$^+$): 396.1, found: 396.0. |
| 45 | 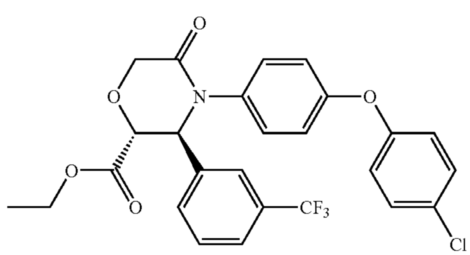 [SMILES: CCOC(=O)[C@@H]1OCC(=O)N(c2ccc(Oc3ccc(Cl)cc3)cc2)[C@H]1c1cccc(C(F)(F)F)c1] | $^1$H NMR (acetone-d6) δ (ppm) 7.84 (d, J = 7.2 Hz, 1H), 7.81 (s, 1H), 7.70-7.66 (m, 2H), 7.41-7.38 (m, 2H), 7.28-7.25 (m, 2H), 7.00-6.95 (m, 4H), 5.64 (d, J = 3.1 Hz, 1H), 4.86 (d, J = 3.1 Hz, 1H), 4.58 (s, 2H), 4.32 (q, J = 7.1 Hz, 2H), 1.29 (t, J = 7.1 Hz, 3H); HPLC-MS calculated C$_{26}$H$_{21}$ClF$_3$NO$_5$ (M + H$^+$: 520.1, found: 520.0. |
| 46 | 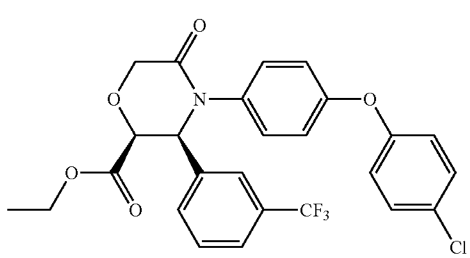 [SMILES: CCOC(=O)[C@H]1OCC(=O)N(c2ccc(Oc3ccc(Cl)cc3)cc2)[C@H]1c1cccc(C(F)(F)F)c1] | $^1$H NMR (acetone-d6) δ (ppm) 7.77 (d, J = 7.6 Hz, 1H), 7.68-7.57 (m, 3H), 7.41-7.38 (m, 2H), 7.28-7.25 (m, 2H), 7.01-6.98 (m, 2H), 6.94-6.90 (m, 2H), 5.41 (d, J = 3.6 Hz, 1H), 5.27 (d, J = 3.6 Hz, 1H), 4.66 (d, J = 16.8 Hz, 1H), 4.47 (d, J = 16.8 Hz, 1H), 4.03-3.92 (m, 2H), 1.06 (t, J = 7.2 Hz, 3H); HPLC-MS calculated C$_{26}$H$_{21}$ClF$_3$NO$_5$ (M + H$^+$: 520.1, found: 520.0. |

TABLE 1-continued

| Compound Number | Structure | Physical Data<br>$^1$H NMR 400 MHz (CDCl$_3$) and/or MS (m/z) |
|---|---|---|
| 47 | 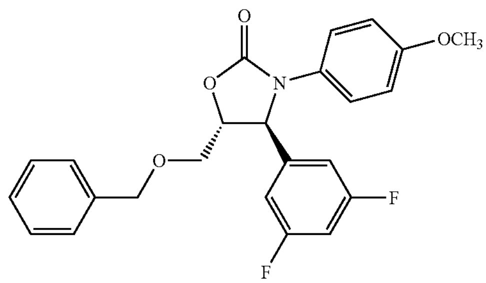 [SMILES: COc1ccc(N2C(=O)O[C@@H](COCc3ccccc3)[C@@H]2c2cc(F)cc(F)c2)cc1] | $^1$H NMR (CDCl$_3$) δ (ppm) 7.44-7.29 (m, 7H), 7.18-7.13 (m, 2H), 7.01-6.95 (m, 1H), 6.87-6.85 (m, 2H), 5.54 (d, 1H, J = 5.7 Hz), 4.69 (d, 1H, J = 12.0 Hz), 4.66 (d, 1H, J = 12.0 Hz), 4.38 (m, 1H), 3.94 (m, 2H), 3.75 (s, 3H). HPLC-MS calculated C$_{24}$H$_{21}$F$_2$NO$_4$ (M + H$^+$): 426.1, found: 426.1 |
| 50 | 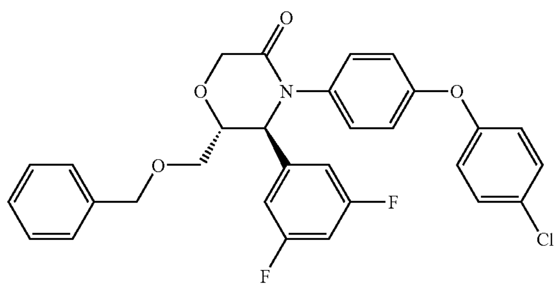 [SMILES: O=C1CO[C@@H](COCc2ccccc2)[C@H](c2cc(F)cc(F)c2)N1c1ccc(Oc2ccc(Cl)cc2)cc1] | $^1$H NMR (CDCl$_3$) δ (ppm) 7.38-7.36 (m, 2H), 7.34-7.23 (m, 7H), 7.12-7.09 (m, 2H), 6.94-6.88 (m, 5H), 5.32 (d, J = 8.1 Hz, 1H), 4.59-4.50 (m, 3H), 4.36 (d, J = 16.4 Hz, 1H), 4.26-4.22 (m, 1H), 3.70 (dd, J = 11.1, 3.0 Hz, 1H), 3.58 (dd, J = 11.1 5.0 Hz, 1H); HPLC-MS calculated C$_{30}$H$_{24}$ClF$_2$NO$_4$ (M + H$^+$): 536.1, found: 536.1. |
| 51 | 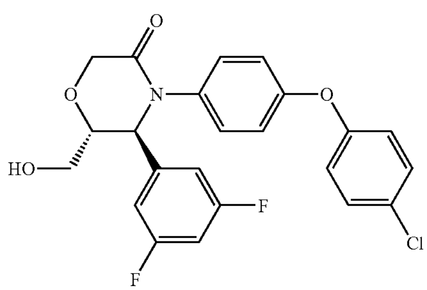 [SMILES: O=C1CO[C@@H](CO)[C@H](c2cc(F)cc(F)c2)N1c1ccc(Oc2ccc(Cl)cc2)cc1] | $^1$H NMR (CDCl$_3$) δ (ppm) 7.38-7.36 (m, 2H), 7.29-7.25 (m, 2H), 7.15-7.10 (m, 2H), 6.94-6.87 (m, 5H), 5.31 (d, J = 8.1 Hz, 1H), 4.55 (d, J = 16.4 Hz, 1H), 4.35 (d, J = 16.4 Hz, 1H), 4.06 (ddd, J = 8.2, 5.1, 3.1 Hz, 1H), 3.70 (dd, J = 12.2, 3.1, 1H), 3.58 (dd, J = 12.2, 5.2 Hz, 1H); HPLC-MS calculated C$_{23}$H$_{18}$ClF$_2$NO$_4$ (M + H$^+$): 446.1, found: 446.0.. |
| 53 | 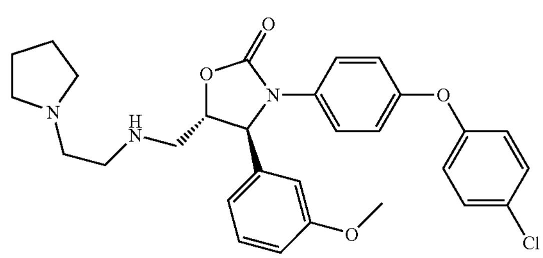 [SMILES: COc1cccc([C@H]2[C@H](CNCCN3CCCC3)OC(=O)N2c2ccc(Oc3ccc(Cl)cc3)cc2)c1] | $^1$H NMR (acetone-d$_6$) δ (ppm) 7.55-7.51 (m, 2H), 7.39-7.37 (m, 2H), 7.31 (t, J = 7.9 Hz, 1H), 7.08 (t, J = 2.0 Hz, 1H), 7.03 (d, J = 7.7 Hz, 1H), 7.00-6.95 (m, 4H), 6.92-6.89 (m, 1H), 5.64 (d, J = 5.4 Hz, 1H), 4.92 (ddd, J = 6.6, 5.2, 5.2 Hz, 1H) 3.93-3.83 (m, 2H), 3.81-3.70 (m, 7H), 3.60 (br s, 4H), 2.15 (m, 4H); HPLC-MS calculated C$_{29}$H$_{32}$ClN$_3$O$_4$ (M + H$^+$): 522.2, found: 522.2. |
| 54 | 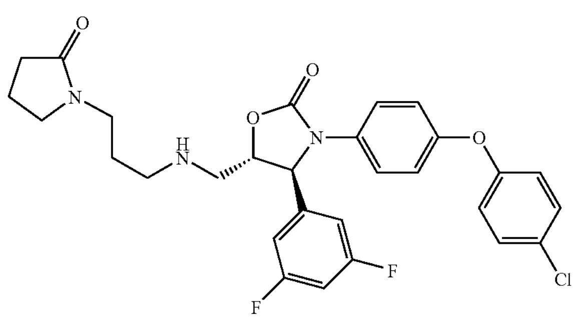 [SMILES: O=C1CCCN1CCCNC[C@@H]1OC(=O)N(c2ccc(Oc3ccc(Cl)cc3)cc2)[C@H]1c1cc(F)cc(F)c1] | $^1$H NMR (acetone-d$_6$) δ (ppm) 7.55-7.49 (m, 2H), 7.39-7.35 (m, 2H), 7.31-7.27 (m, 2H), 7.03-6.94 (m, 5H), 5.81 (d, J = 6.5 Hz, 1H), 4.99 (ddd, J = 6.6, 6.3. 4.1 Hz, 1H), 3.78 (dd, J = 13.7 4.0 Hz, 1H), 3.73 (dd, J = 13.7, 6.7 Hz, 1H), 3.54-3.42 (m, 4H), 3.26 (td, J = 6.8, 2.5 Hz, 2H), 2.35 (t, J = 8.2 Hz, 2H), 2.15-2.07 (part. Obs. By solvent, 4H); HPLC-MS calculated C$_{29}$H$_{28}$ClF$_2$N$_3$O$_4$ (M + H$^+$): 557.1, found: 557.1. |

TABLE 1-continued

| Compound Number | Structure | Physical Data $^1$H NMR 400 MHz (CDCl$_3$) and/or MS (m/z) |
|---|---|---|
| 55 | 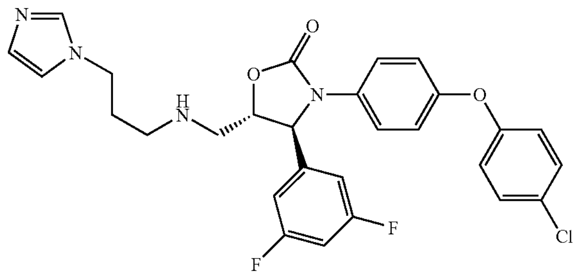 [SMILES: O=C1O[C@@H](CNCCCn2ccnc2)[C@H](c2cc(F)cc(F)c2)N1c1ccc(Oc2ccc(Cl)cc2)cc1] | $^1$H NMR (acetone-d$_6$) δ (ppm) 9.00 (br s, 1H), 7.80 (br s, 1H), 7.66 (br s, 1H), 7.52-7.48 (m, 2H), 7.38-7.35 (m, 2H), 7.25-7.21 (m, 2H), 7.03-6.94 (m, 5H), 5.77 (d, J = 6.0 Hz, 1H), 4.99 (ddd, J = 6.8, 6.0. 4.1 Hz, 1H), 4.66 (t, J = 6.8 Hz, 1H), 3.87-3.77 (m, 2H), 3.49-3.41 (m, 2H), 2.68-2.60 (m, 2H); HPLC-MS calculated C$_{28}$H$_{25}$ClF$_2$N$_4$O$_3$ (M + H$^+$): 539.2, found: 539.2. |
| 56 | 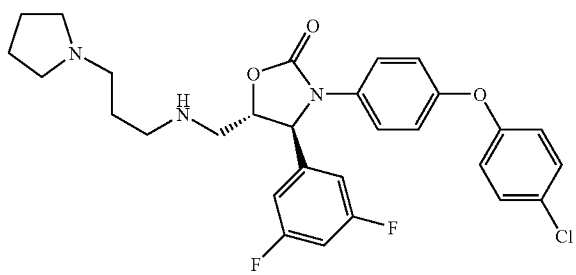 [SMILES: O=C1O[C@@H](CNCCCN2CCCC2)[C@H](c2cc(F)cc(F)c2)N1c1ccc(Oc2ccc(Cl)cc2)cc1] | $^1$H NMR (acetone-d$_6$) δ (ppm) 7.54-7.50 (m, 2H), 7.41-7.37 (m, 2H), 7.28-7.25 (m, 2H), 7.05-6.96 (m, 5H), 5.77 (d, J = 6.0 Hz, 1H), 4.99 (ddd, J = 6.0, 5.5. 5.5 Hz, 1H), 3.88-3.17 (m, 10H), 2.46 (quintet, J = 7.2 Hz, 2H), 2.10-2.07 (m, 4H); HPLC-MS calculated C$_{29}$H$_{30}$ClF$_2$N$_3$O$_3$ (M + H$^+$): 542.2, found: 542.2 |
| 57 | 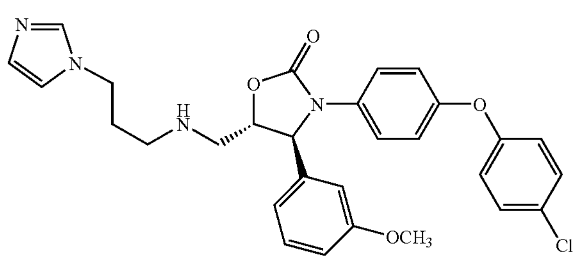 [SMILES: COc1cccc([C@H]2[C@H](CNCCCn3ccnc3)OC(=O)N2c2ccc(Oc3ccc(Cl)cc3)cc2)c1] | $^1$H NMR (acetone-d$_6$) δ (ppm) 9.06 (br s, 1H), 7.80 (br s, 1H), 7.66 (br s, 1H),) 7.50-7.47 (m, 2H), 7.38-7.36 (m, 2H), 7.28 (t, J = 8.0 Hz, 1H), 7.06-7.05 (m, 1H), 7.01 (d, J = 7.6 Hz, 1H), 6.98-6.94 (m, 4H), 6.90-6.88 (m, 1H), 5.60 (d, J = 5.7 Hz, 1H), 4.89 (app q, J = 6.2, 1H), 4.66 (t, J = 6.9 Hz, 2H), 3.82-3.78 (m, 2H), 3.76 (s, 3H), 3.48 (app quintet, J = 6.8 Hz, 2H), 2.65 (t, J = 7.0 Hz, 2H); HPLC-MS calculated C$_{29}$H$_{29}$ClN$_4$O$_4$ (M + H$^+$): 533.2, found: 433.2. |
| 58 | 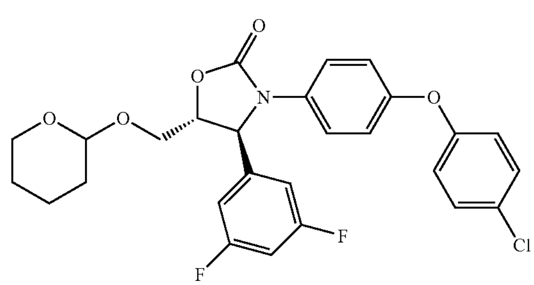 [SMILES: O=C1O[C@@H](COC2CCCCO2)[C@H](c2cc(F)cc(F)c2)N1c1ccc(Oc2ccc(Cl)cc2)cc1] | $^1$H NMR (acetone-d$_6$) δ (ppm) 7.57-7.54 (m, 2H), 7.40-7.38 (m, 2H), 7.23-7.21 (m, 2H), 7.06-6.90 (m, 5H), 5.63-5.60 (ovlp d, 1H), 4.79-4.74 (ovlp dd, 1H), 4.63-4.61 (ovlp ddd, 1H), 4.14-4.10 (ovlp dd, 1H), 3.91-3.84 (m, 2H), 3.55-3.48 (m, 1H), 1.78-1.47 (m, 7H); HPLC-MS calculated C$_{27}$H$_{24}$ClF$_2$NO$_5$ (M + H$^+$-THP): 431.1, found: 431.1. |
| 59 | 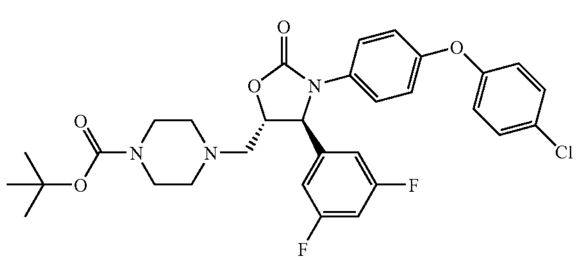 [SMILES: CC(C)(C)OC(=O)N1CCN(C[C@@H]2OC(=O)N(c3ccc(Oc4ccc(Cl)cc4)cc3)[C@H]2c2cc(F)cc(F)c2)CC1] | $^1$H NMR (acetone-d$_6$) δ (ppm) 7.52 (d, J = 9.0 Hz, 2H), 7.37 (d, J = 8.9 Hz, 2H), 7.24-7.19 (m, 2H), 7.07-6.95 (m, 5H), 5.55 (d, J = 5.9 Hz, 1H), 4.56 (dd, J = 9.9, 4.9 Hz, 1H), 3.39-3.35 (m, 5H), 2.96 (dd, J = 13.5, 6.2 Hz, 1H), 2.88 (partially obs. By HOD, dd, J = 13.5, 5.4 Hz, 1H), 2.53 (app t, J = 5.0 Hz, 4H), 1.41 (s, 9H); HPLC-MS calculated C$_{31}$H$_{32}$ClF$_2$N$_3$O$_5$ (M + H$^+$): 600.2, found: 544.1 (M-tBu + H). |

TABLE 1-continued

| Compound Number | Structure | Physical Data<br>¹H NMR 400 MHz (CDCl₃) and/or MS (m/z) |
|---|---|---|
| 60 | 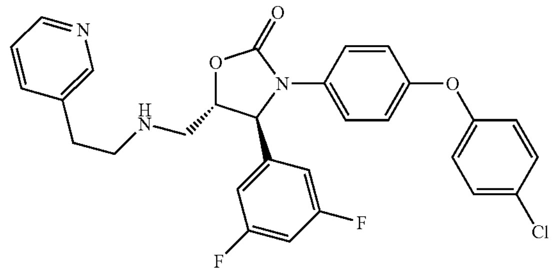 [SMILES: O=C1O[C@@H](CNCCc2cccnc2)[C@H](c2cc(F)cc(F)c2)N1c1ccc(Oc2ccc(Cl)cc2)cc1] | ¹H NMR (acetone-d₆) δ (ppm) 8.48 (br s, 1H), 8.40 (m, 1H), 7.67-7.64 (m, 1H), 7.49-7.47 (m, 2H), 7.39-7.36 (m, 2H), 7.24 (dd, J = 7.7, 4.7 Hz, 1H), 7.12-7.09 (m, 2H), 7.00-6.97 (m, 5H), 5.52 (d, J = 5.6 Hz, 1H), 4.45 (ddd, J = 5.4, 5.0, 5.0 Hz, 1H), 4.21 (dd, J = 5.4, 4.6 Hz, 1H), 3.15 (dd, J = 13.2, 4.9 Hz, 1H), 3.10 (dd, J = 13.2, 4.8 Hz, 1H), 3.04-2.97 (m, 2H); HPLC-MS calculated $C_{29}H_{24}ClF_2N_3O_3$ (M + H⁺): 536.2, found: 536.2. |
| 61 | 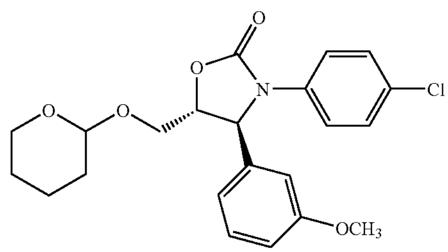 [SMILES: COc1cccc([C@H]2[C@H](COC3CCCCO3)OC(=O)N2c2ccc(Cl)cc2)c1] | ¹H NMR (acetone-d₆) δ (ppm) 7.54 (d, J = 8.4 Hz, 2H), 7.33-7.29 (m, 3H), 7.02-6.99 (m, 2H), 6.88 (d, J = 8.0 Hz 1H), 5.49-5.46 (ovlp, d, J = 5.0 Hz, 1H), 4.75-4.71 (m, 1H), 4.54-4.53 (m, 1H), 4.08-4.03 (m, 1H), 3.89-3.77 (m, 2H), 3.77 (s, 3H), 3.53-3.47 (m, 1H), 1.78-1.47 (m, 7H); HPLC-MS calculated $C_{22}H_{24}ClNO_5$ (M + H⁺(-THP)): 334.1, found: 334.1. |
| 62 | 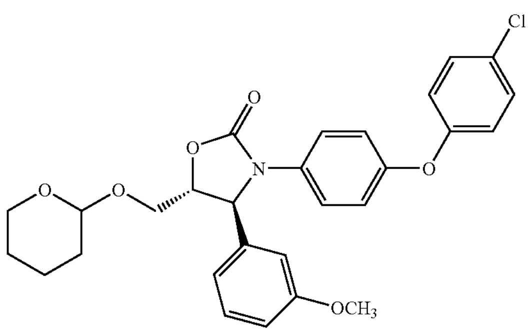 [SMILES: COc1cccc([C@H]2[C@H](COC3CCCCO3)OC(=O)N2c2ccc(Oc3ccc(Cl)cc3)cc2)c1] | ¹H NMR (acetone-d₆) δ (ppm) 7.53 (d, J = 9.2 Hz, 2H), 7.36 (d, J = 8.8 Hz, 2H), 7.32 (t, J = 7.9 Hz, 1H), 7.04-6.88 (m, 7H) 5.48-5.43 (diasteromers, d, J = 5.3 Hz, 1H), 4.75-4.71 (m, 1H), 4.54-4.53 (m, 1H), 4.08-4.03 (m, 1H), 3.89-3.77 (m, 2H), 3.77 (s, 3H), 3.53-3.47 (m, 1H), 1.78-1.47 (m, 7H); HPLC-MS calculated $C_{28}H_{28}ClNO_6$ (M + H⁺(-THP)): 426.1, found: 426.1. |
| 63 | 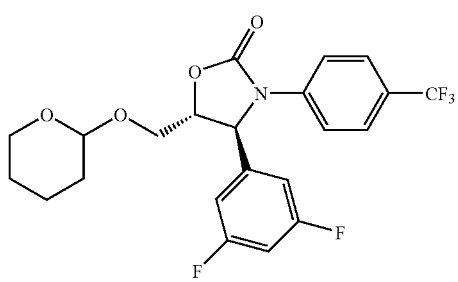 [SMILES: O=C1O[C@@H](COC2CCCCO2)[C@H](c2cc(F)cc(F)c2)N1c1ccc(C(F)(F)F)cc1] | ¹H NMR (acetone-d₆) δ (ppm) 7.78 (d, J = 8.6 Hz, 2H), 7.66 (d, J = 8.6 Hz, 2H), 7.22 (m, 2H), 7.03 (tt, J = 9.1, 2.2 Hz, 1H), 5.74-5.72 (m, 1H), 4.76-4.71 (m, 1H), 4.67-4.66 (m, 1H), 4.15-4.11 (ovlp, d, J = 3.6 Hz, 1H), 3.89-3.82 (m, 2H), 3.53-3.47 (m, 1H), 1.78-1.47 (m, 7H); HPLC-MS calculated $C_{22}H_{20}F_5NO_4$ (M + H⁺(-THP)): 374.1, found: 374.0. |
| 65 | 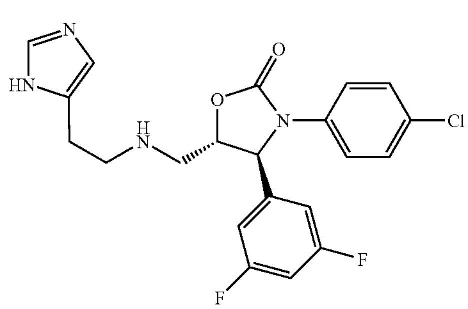 [SMILES: O=C1O[C@@H](CNCCc2cnc[nH]2)[C@H](c2cc(F)cc(F)c2)N1c1ccc(Cl)cc1] | ¹H NMR (acetone-d6) δ (ppm) 8.91 (s, 1H), 7.60 (s, 1H), 7.51-7.49 (m, 2H), 7.35-7.32 (m, 2H), 7.27-7.23 (m, 2H), 7.00 (tt, J = 9.1, 2.3 Hz, 1H), 5.76 (d, J = 6.3 Hz, 1H), 4.65 (ddd, J = 6.8, 6.8, 3.8 Hz, 1H), 3.97-3.81 (m, 2H), 3.79-3.72 (m, 2H), 3.47 (t, J = 6.9 Hz, 2H); HPLC-MS calculated $C_{21}H_{19}ClF_2N_4O_2$ (M + H⁺): 433.1, found: 433.1. |

TABLE 1-continued

| Compound Number | Structure | Physical Data<br>¹H NMR 400 MHz (CDCl₃) and/or MS (m/z) |
|---|---|---|
| 66 | 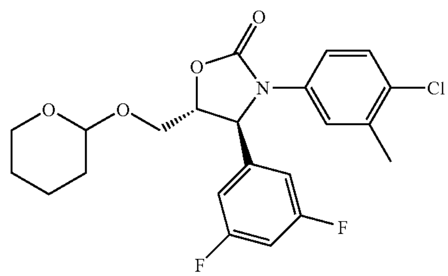 | ¹H NMR (acetone-d₆) δ (ppm) 7.50-7.48 (m, 1H), 7.34 (d, J = 8.7 Hz, 1H), 7.26-7.18 (m, 4H), 5.53-5.51 (m, 1H), 4.72-4.68 (m, 1H), 4.58-4.56 (m, 1H), 3.98-3.92 (m, 1H), 3.81-3.72 (m, 2H), 3.49-3.45 (m, 1H), 2.23 (s, 3H), 1.78-1.47 (m, 7H); HPLC-MS calculated $C_{22}H_{22}ClF_2NO_4$ (M + H⁺(-THP)): 354.1, found: 354.0. |
| 67 | 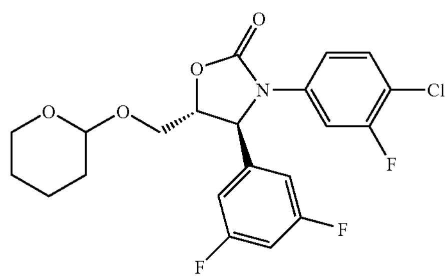 [SMILES: O=C1O[C@@H](COC2CCCCO2)[C@H](c2cc(F)cc(F)c2)N1c1ccc(Cl)c(F)c1] | ¹H NMR (acetone-d₆) δ (ppm) 7.64 (dd, J = 11.7, 2.5 Hz, 1H), 7.54 (t, J = 8.7 Hz, 1H), 7.27-7.19 (m, 4H), 5.56 (d, J = 5.3 Hz, 1H), 4.72-4.68 (m, 1H), 4.60-4.58 (m, 1H), 3.99-3.93 (m, 1H), 3.78-3.72 (m, 2H), 3.49-3.45 (m, 1H), 1.78-1.47 (m, 7H); HPLC-MS calculated $C_{21}H_{19}ClF_3NO_4$ (M + H⁺(-THP)): 358.1, found: 358.0. |
| 68 | 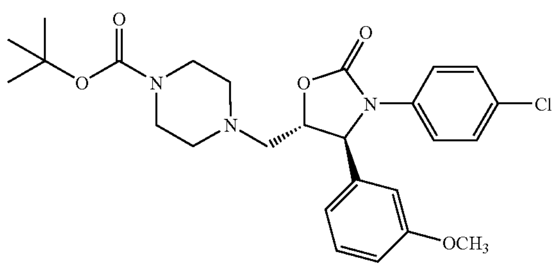 [SMILES: COc1cccc([C@H]2[C@H](CN3CCN(C(=O)OC(C)(C)C)CC3)OC(=O)N2c2ccc(Cl)cc2)c1] | ¹H NMR (acetone-d₆) δ (ppm) 7.52 (d, J = 9.0 Hz, 2H), 7.32-7.28 (m, 3H), 7.03-7.01 (m, 2H), 6.89-6.86 (m, 1H), 5.44 (d, J = 5.7 Hz, 1H), 4.53 (q, J = 5.7 Hz, 1H), 3.77 (s, 3H), 3.39-3.36 (m, 4H), 2.92 (dd, J = 13.5, 5.9 Hz, 1H), 2.86 (dd, part. Obs by HOD, 1H), 2.51 (t, J = 5 Hz, 4H), 1.42 (s, 9H); HPLC-MS calculated $C_{26}H_{32}ClN_3O_5$ (M + H⁺) 502.2, found 502.2. |
| 69 | 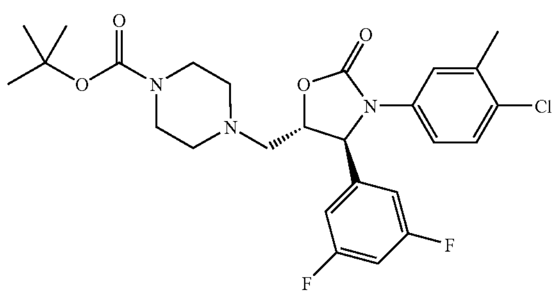 [SMILES: Cc1cc(N2C(=O)O[C@@H](CN3CCN(C(=O)OC(C)(C)C)CC3)[C@@H]2c2cc(F)cc(F)c2)ccc1Cl] | ¹H NMR (acetone-d6) δ (ppm) 7.52 (d, 2.5 Hz, 1H), 7.32 (dd, J = 8.8, 2.5 Hz, 1H), 7.27 (d, J = 8.7 Hz, 1H), 7.23-7.18 (m, 2H), 6.98 (tt, J = 9.1, 2.3 Hz, 1H), 5.58 (d, J = 5.8 Hz, 1H), 4.68 (ddd, J = 5.9, 5.8, 5.8 Hz, 1H) 3.42-3.28 (m, 4H), 2.96 (dd, J = 13.2, 5.8 Hz, 1H), 2.91-2.85 (m, 5H), 2.53 (t, J = 5.2 Hz, 4H), 2.74 (s, 3H), 1.42 (s, 9H); HPLC-MS calculated $C_{26}H_{30}F_2N_3O_4$ (M + H⁺(-tBu): 466.1, found: 466.1. |
| 70 | 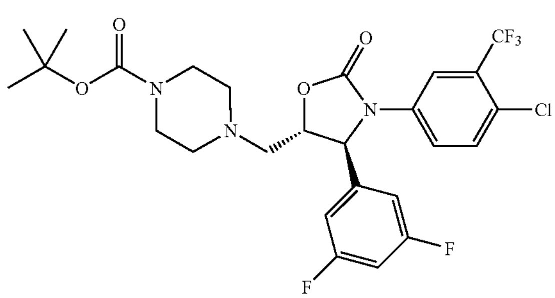 [SMILES: CC(C)(C)OC(=O)N1CCN(C[C@@H]2OC(=O)N(c3ccc(Cl)c(C(F)(F)F)c3)[C@H]2c2cc(F)cc(F)c2)CC1] | ¹H NMR (acetone-d6) δ (ppm) 8.12 (d, J = 2.7 Hz, 1H), 7.66 (dd, J = 8.9, 2.7 Hz, 1H), 7.57 (d, J = 8.8 Hz, 1H), 7.31-7.28 (m, 2H), 7.01 (tt, J = 9.1, 2.3 Hz, 1H) 5.70 (d, J = 5.9 Hz, 1H), 4.68 (ddd, J = 5.9, 5.9, 5.8 Hz, 1H) 3.42-3.28 (m, 4H), 3.06-2.91 (m, 4H), 2.56 (t, J = 5.0 Hz, 4H), 1.42 (s, 9H); HPLC-MS calculated $C_{26}H_{27}F_5N_3O_4$ (M + H⁺(-tBu): 520.1, found: 520.1. |

TABLE 1-continued

| Compound Number | Structure | Physical Data ¹H NMR 400 MHz (CDCl₃) and/or MS (m/z) |
|---|---|---|
| 71 | 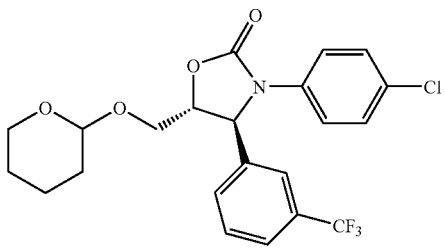 [SMILES: O=C1O[C@@H](COC2CCCCO2)[C@H](c2cccc(C(F)(F)F)c2)N1c1ccc(Cl)cc1] | ¹H NMR (acetone-d₆) δ (ppm) 7.87 (s, 1H), 7.78-7.76 (m, 1H), 7.70-7.63 (m, 2H), 7.59-7.54 (m, 2H), 7.32-7.29 (m, 2H), 5.73 (ovlp d, J = 5.2 Hz, 1H), 4.76-4.72 (m, 1H), 4.65-4.61 (m, 1H), 4.13-4.09 (m, 1H), 3.88-3.83 (m, 2H), 3.52-3.49 (m, 1H), 1.78-1.47 (m, 7H); HPLC-MS calculated $C_{22}H_{21}ClF_3NO_4$ (M + H⁺-THP): 371.1, found: 371.8. |
| 73 | 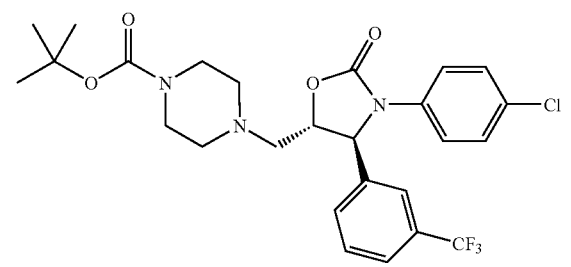 [SMILES: CC(C)(C)OC(=O)N1CCN(C[C@@H]2OC(=O)N(c3ccc(Cl)cc3)[C@H]2c2cccc(C(F)(F)F)c2)CC1] | ¹H NMR (acetone-d6) δ (ppm) 7.88 (s, 1H), 7.80 (d, J = 7.2 Hz, 1H), 7.68-7.62 (m, 2H), 7.56-7.52 (m, 2H), 7.32-7.28 (m, 2H), 5.69 (d, J = 5.6 Hz, 1H), 4.60 (ddd, J = 6.6, 5.6, 5.5 Hz, 1H), 3.44-3.30 (m, 4H), 3.00 (dd, J = 13.6, 6.8 Hz, 1H), 2.89 (dd, J = 13.2, 5.2 Hz, 1H), 2.54-2.51 (m, 4H), 1.42 (s, 9H); HPLC-MS calculated $C_{26}H_{29}ClF_3N_3O_4$ Exact Mass (M + H⁺(-tBu): 483.2, found: 483.9. |
| 74 | 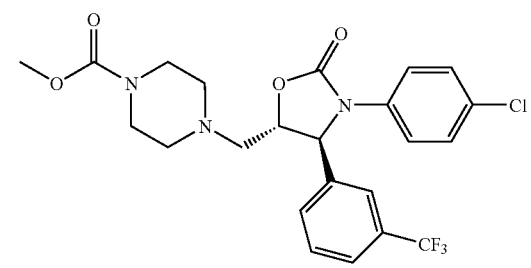 [SMILES: COC(=O)N1CCN(C[C@@H]2OC(=O)N(c3ccc(Cl)cc3)[C@H]2c2cccc(C(F)(F)F)c2)CC1] | ¹H NMR (acetone-d6) δ (ppm) 7.88 (s, 1H), 7.80 (d, J = 7.2 Hz, 1H), 7.68-7.62 (m, 2H), 7.56-7.52 (m, 2H), 7.32-7.28 (m, 2H), 5.69 (d, J = 5.7 Hz, 1H), 4.60 (ddd, J = 6.4, 5.6, 5.6 Hz, 1H), 3.61 (s, 3H), 3.44-3.33 (m, 4H), 3.00 (dd, J = 13.6, 6.8 Hz, 1H), 2.89 (dd, J = 13.6, 5.2 Hz, 1H), 2.60-2.51 (m, 4H); HPLC-MS calculated $C_{23}H_{23}ClF_3N_3O_4$ Exact Mass (M + H⁺): 498.1, found: 498.1. |
| 75 | 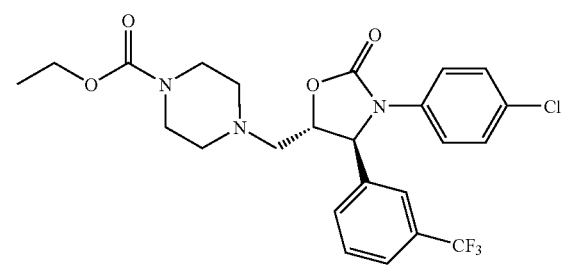 [SMILES: CCOC(=O)N1CCN(C[C@@H]2OC(=O)N(c3ccc(Cl)cc3)[C@H]2c2cccc(C(F)(F)F)c2)CC1] | ¹H NMR (acetone-d6) δ (ppm) 7.88 (s, 1H), 7.80 (d, J = 7.2 Hz, 1H), 7.68-7.62 (m, 2H), 7.56-7.52 (m, 2H), 7.32-7.28 (m, 2H), 5.69 (d, J = 5.6 Hz, 1H), 4.60 (ddd, J = 6.8, 5.6, 5.2 Hz, 1H), 4.11-4.03 (m, 2H), 3.44-3.33 (m, 4H), 3.00 (dd, J = 13.6, 6.6 Hz, 1H), 2.89 (dd, J = 13.6, 5.2 Hz, 1H), 2.60-2.51 (m, 4H), 1.21 (t, J = 7.2 Hz, 3H); HPLC-MS calculated $C_{24}H_{25}ClF_3N_3O_4$ Exact Mass (M + H⁺): 512.1, found: 512.7. |
| 76 | 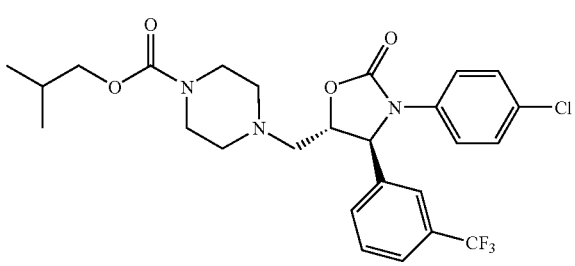 [SMILES: CC(C)COC(=O)N1CCN(C[C@@H]2OC(=O)N(c3ccc(Cl)cc3)[C@H]2c2cccc(C(F)(F)F)c2)CC1] | ¹H NMR (acetone-d6) δ (ppm) 7.89 (s, 1H), 7.80 (d, J = 7.2 Hz, 1H), 7.68-7.62 (m, 2H), 7.56-7.52 (m, 2H), 7.32-7.28 (m, 2H), 5.69 (d, J = 5.7 Hz, 1H), 4.60 (ddd, J = 6.5, 5.6, 5.5 Hz, 1H), 3.81 (d, J = 6.4 Hz, 2H), 3.44-3.33 (m, 4H), 3.00 (dd, J = 13.6, 6.6 Hz, 1H), 2.89 (dd, J = 13.6, 5.2 Hz, 1H), 2.60-2.51 (m, 4H), 1.95-1.86 (m, 1H), 0.92 (t, J = 6.8 Hz, 6H); HPLC-MS calculated $C_{26}H_{29}ClF_3N_3O_4$ Exact Mass (M + H⁺): 540.2, found: 539.8. |

TABLE 1-continued

| Compound Number | Structure | Physical Data <br> ¹H NMR 400 MHz (CDCl₃) and/or MS (m/z) |
|---|---|---|
| 77 | 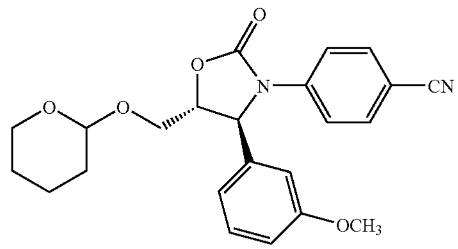 [SMILES: COc1cccc([C@H]2[C@H](COC3CCCCO3)OC(=O)N2c2ccc(C#N)cc2)c1] | ¹H NMR (acetone-d₆) δ (ppm) 7.77-7.75 (m, 2H), 7.70-7.67 (m, 2H), 7.33 (t, J = 7.9 Hz, 1H), 7.05-7.00 (m, 2H), 6.90 (dd, J = 8.2, 1.9 Hz, 1H), 5.58 (ovlp d, J = 4.8 Hz, 1H), 4.76-4.71 (m, 1H), 4.61-4.57 (m, 1H), 4.11-4.07 (m, 1H), 3.88-3.83 (m, 2H), 3.78 (s, 3H), 3.52-3.49 (m, 1H), 1.78-1.47 (m, 7H); HPLC-MS calculated C₂₃H₂₄N₂O₅ (M + H⁺-THP): 325.1, found: 325.1. |
| 78 | 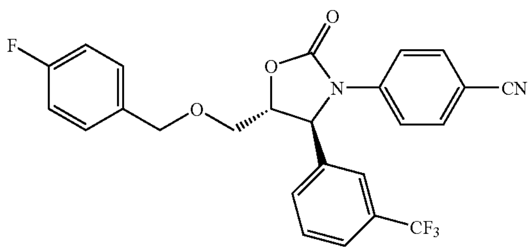 [SMILES: N#Cc1ccc(N2C(=O)O[C@@H](COCc3ccc(F)cc3)[C@@H]2c2cccc(C(F)(F)F)c2)cc1] | ¹H NMR (acetone-d6) δ (ppm) 7.82 (s, 1H), 7.77-7.64 (m, 7H), 7.40-7.36 (m, 2H), 7.09-7.05 (m, 2H), 5.82 (d, J = 4.8 Hz, 1H), 4.70-4.62 (m, 3H), 3.97 (d, J = 4.1 Hz, 2H); HPLC-MS calculated C₂₅H₁₈ClF₄N₂O₃ (M + H⁺: 471.1, found: 470.8. |
| 79 | 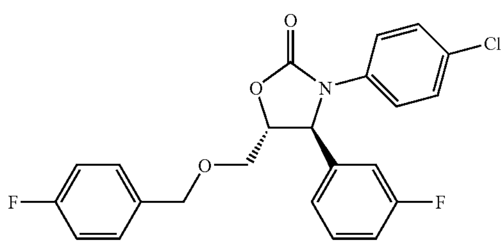 [SMILES: O=C1O[C@@H](COCc2ccc(F)cc2)[C@H](c2cccc(F)c2)N1c1ccc(Cl)cc1] | ¹H NMR (acetone-d₆) δ (ppm) 7.51 (d, J = 9.0 Hz, 2H), 7.46-7.39 (m, 3H), 7.32-7.23 (m, 4H), 7.12-7.07 (m, 3H), 5.57 (d, J = 5.4 Hz, 1H), 4.69-4.62 (gem, d, J = 12.0 Hz, 2H), 4.58 (ddd, J = 5.7, 3.8, 3.4 Hz, 1H), 3.96-3.89 (m, 2H); HPLC-MS calculated C₂₃H₁₈ClF₂NO₃ (M + H⁺) 430.1, found: 430.1. |
| 80 | 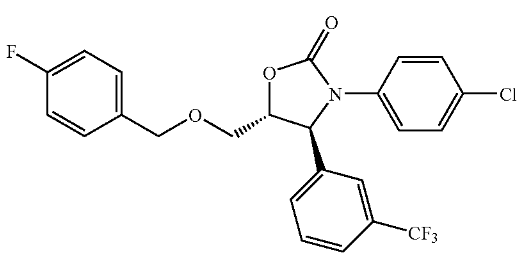 [SMILES: O=C1O[C@@H](COCc2ccc(F)cc2)[C@H](c2cccc(C(F)(F)F)c2)N1c1ccc(Cl)cc1] | ¹H NMR (acetone-d6) δ (ppm) 7.82 (s, 1H), 7.75 (d, J = 7.5 Hz, 1H), 7.68 (d, J = 7.9 Hz, 1H), 7.65-7.61 (m, 1H), 7.56-7.52 (m, 2H), 7.32-7.28 (m, 2H), 7.10-6.97 (m, 2H), 5.71 (d, J = 5.3 Hz, 1H), 4.69-4.60 (m, 3H), 3.95 (d, J = 3.8 Hz, 2H); HPLC-MS calculated C₂₄H₁₈ClF₄N₂O₃ (M + H⁺: 480.1, found: 479.7. |
| 81 | 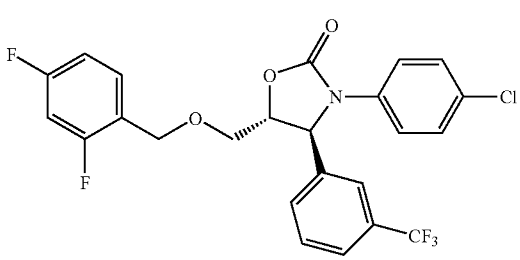 [SMILES: O=C1O[C@@H](COCc2ccc(F)cc2F)[C@H](c2cccc(C(F)(F)F)c2)N1c1ccc(Cl)cc1] | ¹H NMR (acetone-d6) δ (ppm) 7.83 (s, 1H), 7.76 (d, J = 7.6 Hz, 1H), 7.69 (d, J = 7.9 Hz, 1H), 7.65-7.61 (m, 1H), 7.55-7.49 (m, 3H), 7.32-7.28 (m, 2H), 7.07-6.69 (m, 2H), 5.72 (d, J = 5.2 Hz, 1H), 4.73-4.64 (m, 3H), 4.01 (d, J = 3.6 Hz, 2H); HPLC-MS calculated C₂₄H₁₇ClF₅N₂O₃ (M + H⁺: 498.1, found: 497.7. |

Note: chemical formulas in the table should be read as $C_{23}H_{24}N_2O_5$, $C_{25}H_{18}ClF_4N_2O_3$, $C_{23}H_{18}ClF_2NO_3$, $C_{24}H_{18}ClF_4N_2O_3$, $C_{24}H_{17}ClF_5N_2O_3$.

TABLE 1-continued

| Compound Number | Structure | Physical Data<br>¹H NMR 400 MHz (CDCl₃) and/or MS (m/z) |
|---|---|---|
| 82 | 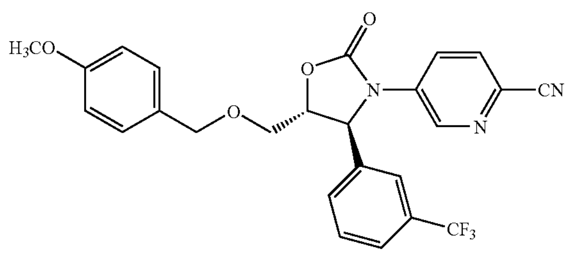 [SMILES: COc1ccc(COC[C@@H]2OC(=O)N(c3ccc(C#N)nc3)[C@H]2c2cccc(C(F)(F)F)c2)cc1] | ¹H NMR (acetone-d6) δ (ppm) 8.85 (d, J = 2.8 Hz, 1H), 8.17 (dd, J = 8.8, 2.8 Hz, 1H), 7.90 (s, 1H), 7.85 (d, J = 8.8 Hz, 1H), 7.80 (d, J = 7.6 Hz, 1H), 7.72 (d, J = 7.6 Hz, 1H), 7.66 (t, J = 7.6 Hz, 1H), 7.26 (d, J = 8.8 Hz, 2H), 6.86 (d, J = 8.8 Hz, 2H), 5.86 (d, J = 5.2 Hz, 1H), 4.73 (ddd, J = 5.1, 3.7, 3.6 Hz, 1H), 4.59-4.53 (m, 2H), 3.94 (d, J = 3.6 Hz, 2H), 3.78 (s, 3H); HPLC-MS calculated C₂₅H₂₀F₃N₃O₄ (M + H⁺: 484.1, found: 484.1. |
| 85 | 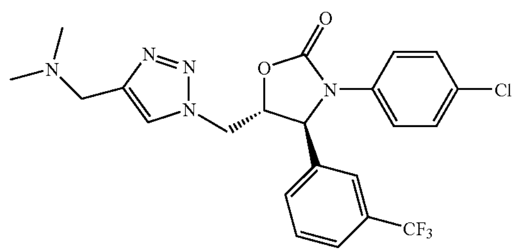 [SMILES: CN(C)Cc1cn(C[C@@H]2OC(=O)N(c3ccc(Cl)cc3)[C@H]2c2cccc(C(F)(F)F)c2)nn1] | ¹H NMR (acetone-d6) δ (ppm) 7.83 (s, 1H), 7.75 (d, J = 7.7 Hz, 1H), 7.69 (d, J = 7.9 Hz, 1H), 7.64 (t, J = 7.7 Hz, 1H), 7.45 (d, J = 8.9 Hz, 2H), 7.30-7.28 (m, 2H), 5.75 (d, J = 5.81 (d, J = 5.0 Hz, 1H), 5.13-5.06 (m, 2H), 5.00 (ddd, J = 5.1, 5.0, 4.5 Hz, 1H), 3.59 (br s, 3H), 3.09 (br s, 3H); HPLC-MS calculated C₂₂H₂₁ClF₃N₅O₂ (M + H⁺: 480.1, found: 480.1. |
| 86 | 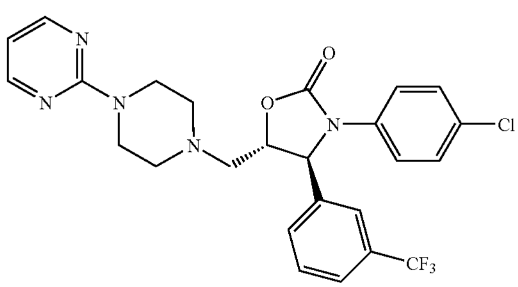 [SMILES: O=C1O[C@@H](CN2CCN(c3ncccn3)CC2)[C@H](c2cccc(C(F)(F)F)c2)N1c1ccc(Cl)cc1] | ¹H NMR (acetone-d6) δ (ppm) 8.32-8.31 (m, 2H), 7.92 (s, 1H), 7.80 (m, 1H), 7.67-7.64 (m, 2H), 7.57-7.55 (m, 2H), 7.32-7.28 (m, 2H), 6.57-6.56 (m, 1H), 5.75-5.74 (m, 1H), 4.67-4.65 (m, 1H), 3.79-3.73 (m, 4H), 3.06-3.02 (m, 1H), 2.94-2.89 (m, 1H), 2.63-2.52 (m, 4H),; HPLC-MS calculated C₂₅H₂₃ClF₃N₅O₂ Exact Mass (M + H⁺): 518.1, found: 518.1. |
| 90 | 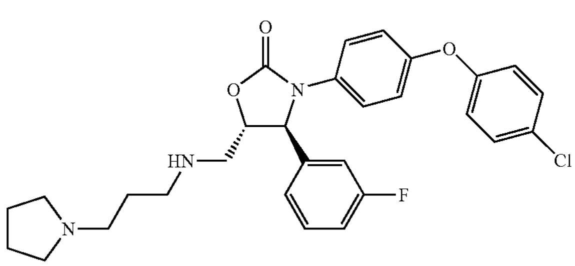 [SMILES: O=C1O[C@@H](CNCCCN2CCCC2)[C@H](c2cccc(F)c2)N1c1ccc(Oc2ccc(Cl)cc2)cc1] | ¹H NMR (CDCl₃) δ (ppm) 7.33-7.40 (m, 4H), 7.24-7.30 (m, 2H), 7.14-7.17 (m, 1H), 6.99-7.07 (m, 2H), 6.86-6.92 (m, 4H), 5.34 (br s, 1H), 4.41 (br s, 1H), 3.12 (d, 1H, J = 13.1 Hz), 2.98 (d, 1H, J = 13.0 Hz), 2.62-2.90 (m, 7H), 1.76-2.3 (m, 7H), 1.26-1.27 (m, 1H). HPLC-MS calculated C₂₉H₃₁ClFN₃O₃ (M + H⁺): 524.2, found: 524.2 |
| 91 | 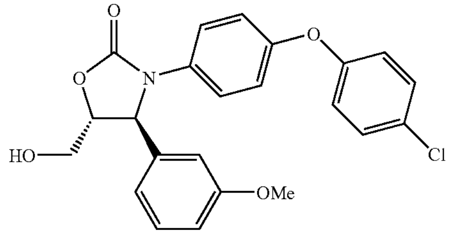 [SMILES: COc1cccc([C@H]2[C@H](CO)OC(=O)N2c2ccc(Oc3ccc(Cl)cc3)cc2)c1] | ¹H NMR (CDCl₃) δ (ppm) 7.33 (d, 2H, J = 9.0 Hz), 7.24-7.30 (m, 4H), 6.83-6.91 (m, 6H), 5.26 (d, 1H, J = 6.5 Hz), 4.40-4.43 (m, 1H), 4.05 (dd, 1H, J = 12.8, 3.0 Hz), 3.81 (dd, 1H, J = 12.8, 3.2 Hz), 3.77 (s, 3H). HPLC-MS calculated C₂₃H₂₀ClNO₅ (M + H⁺): 426.1, found: 426.1. |

TABLE 1-continued

| Compound Number | Structure | Physical Data<br>¹H NMR 400 MHz (CDCl₃) and/or MS (m/z) |
|---|---|---|
| 92 | 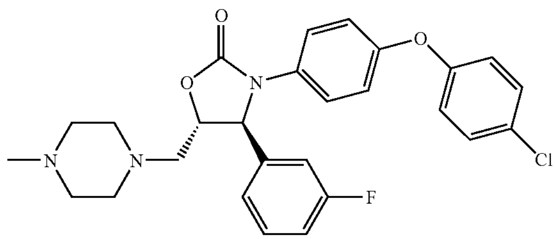 [SMILES: CN1CCN(C[C@@H]2OC(=O)N(c3ccc(Oc4ccc(Cl)cc4)cc3)[C@H]2c2cccc(F)c2)CC1] | ¹H NMR (CDCl₃) δ (ppm) 7.31-7.37 (m, 3H), 7.24-7.28 (m, 2H), 7.10 (d, 1H, J = 7.7 Hz), 6.99-7.04 (m, 2H), 6.86-6.92 (m, 4H), 4.43 (dd, 1H, J = 11.7, 3.0 Hz), 2.78 (d, 2H, J = 5.9 Hz), 2.61 (br s, 4H), 2.47 (br s, 4H), 2.30 (s, 3H). HPLC-MS calculated $C_{27}H_{27}ClFN_3O_3$ (M + H⁺): 496.2, found: 496.2. |
| 93 | 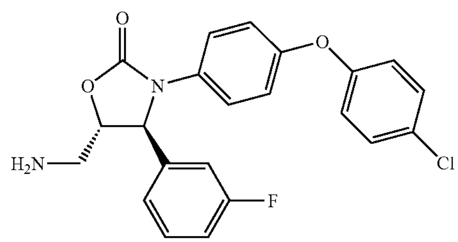 [SMILES: NC[C@@H]1OC(=O)N(c2ccc(Oc3ccc(Cl)cc3)cc2)[C@H]1c1cccc(F)c1] | ¹H NMR (CDCl₃) δ (ppm) 7.30-7.35 (m, 3H), 7.22-7.27 (m, 2H), 7.11 (d, 1H, J = 7.7 Hz), 6.98-7.05 (m, 2H), 6.84-6.87 (m, 4H), 5.29 (d, 1H, J = 6.3 Hz), 4.38-4.42 (m, 1H), 3.30 (dd, 1H, J = 13.7, 3.2 Hz), 3.11 (dd, 1H, J = 13.3, 5.1 Hz), 2.22 (br s, 1H). HPLC-MS calculated $C_{22}H_{18}ClFN_2O_3$ (M + H⁺): 413.2, found: 413.1. |
| 94 | 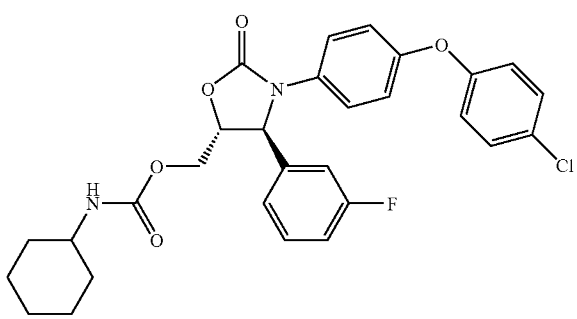 [SMILES: O=C(NC1CCCCC1)OC[C@@H]1OC(=O)N(c2ccc(Oc3ccc(Cl)cc3)cc2)[C@H]1c1cccc(F)c1] | ¹H NMR (acetone-d₆) δ (ppm) 7.43-7.50 (m, 3H), 7.35-7.39 (m, 2H), 7.28-7.33 (m, 2H), 7.11 (dt, 1H, J = 8.5, 2.1 Hz), 6.96 (d, 4H, J = 8.7 Hz), 6.42 (d, 1H, J = 7.5 Hz), 5.48 (d, 1H, J = 5.7 Hz), 4.57-4.61 (m, 1H), 4.48 (dd, 1H, J = 12.5, 4.6 Hz), 4.38 (dd, 1H, J = 12.4, 3.4 Hz), 3.34-3.43 (m, 1H), 1.81-1.89 (m, 2H), 1.69-1.73 (m, 2H), 1.57-1.60 (m, 2H), 1.09-1.36 (m, 4H). HPLC-MS calculated $C_{29}H_{28}ClFN_2O_5$ (M + H⁺): 539.2, found: 539.2. |
| 95 | 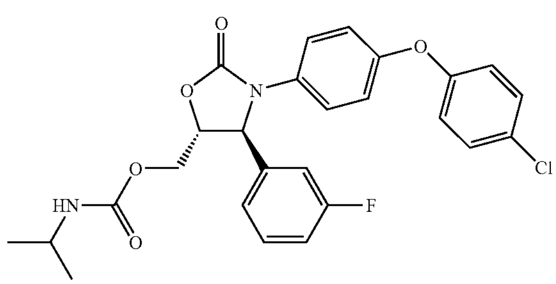 [SMILES: CC(C)NC(=O)OC[C@@H]1OC(=O)N(c2ccc(Oc3ccc(Cl)cc3)cc2)[C@H]1c1cccc(F)c1] | ¹H NMR (acetone-d₆) δ (ppm) 7.43-7.50 (m, 3H), 7.28-7.39 (m, 5H), 7.11 (dt, 1H, J = 8.6, 2.1 Hz), 6.94-6.98 (m, 4H), 6.39 (d, 1H, J = 6.4 Hz), 5.48 (d, 1H, J = 5.7 Hz), 4.58-4.61 (m, 1H), 4.47 (dd, 1H, J = 12.4, 4.6 Hz), 4.38 (dd, 1H, J = 12.4, 3.4 Hz), 3.69-3.77 (sept, 1H, J = 7.0 Hz), 1.12 (m, 6H). HPLC-MS calculated $C_{26}H_{24}ClFN_2O_5$ (M + H⁺): 499.1, found: 499.2. |
| 96 | 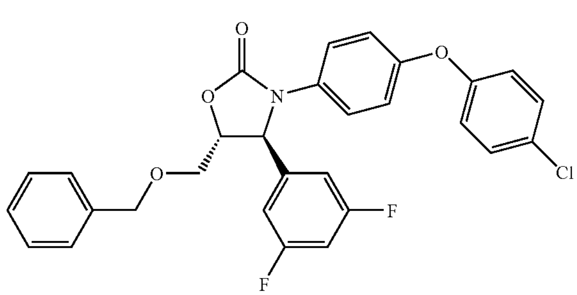 [SMILES: O=C1O[C@@H](COCc2ccccc2)[C@H](c2cc(F)cc(F)c2)N1c1ccc(Oc2ccc(Cl)cc2)cc1] | ¹H NMR (acetone-d₆) δ (ppm) 7.51 (d, J = 9.0 Hz, 2H), 7.38-7.29 (m, 7H), 7.15 (d, J = 6.2 Hz, 2H), 7.02-6.96 (m, 5H), 5.58 (d, J = 5.4 Hz, 1H), 4.71-4.64 (gem, d, J = 12.1 Hz, 2H), 4.67 (ddd, J = 5.6, 3.8, 3.5 Hz, 1H), 3.92 (m, 1H); HPLC-MS calculated $C_{29}H_{22}ClF_2NO_4$ (M + H⁺): 522.1, found: 522.1. |

TABLE 1-continued

| Compound Number | Structure | Physical Data<br>$^1$H NMR 400 MHz (CDCl$_3$) and/or MS (m/z) |
|---|---|---|
| 97 | 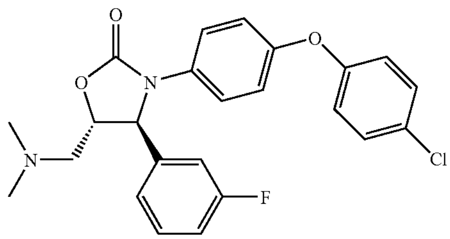 [SMILES: CN(C)C[C@@H]1OC(=O)N(c2ccc(Oc3ccc(Cl)cc3)cc2)[C@H]1c1cccc(F)c1] | $^1$H NMR (CDCl$_3$) δ (ppm) 7.33-7.38 (m, 3H), 7.24-7.27 (m, 2H), 7.10 (d, 1H, J = 7.7 Hz), 6.99-7.03 (m, 2H), 6.86-6.92 (m, 4H), 5.20 (d, 1H, J = 5.5 Hz), 4.39 (dt, 1H, J = 5.7, 5.7 Hz), 2.23 (s, 6H). HPLC-MS calculated C$_{24}$H$_{22}$ClFN$_2$O$_3$ (M + H$^+$): 441.1, found: 441.1. |
| 98 | 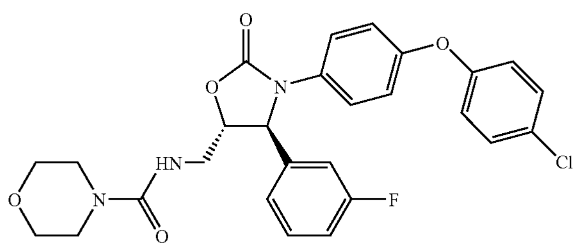 [SMILES: O=C(NC[C@@H]1OC(=O)N(c2ccc(Oc3ccc(Cl)cc3)cc2)[C@H]1c1cccc(F)c1)N1CCOCC1] | $^1$H NMR (CDCl$_3$) δ (ppm) 7.30-7.36 (m, 3H), 7.24-7.28 (m, 2H), 7.17 (d, 1H), 7.06 (d, 1H, J = 9.2 Hz), 7.01 (dt, 1H, J = 8.4, 2.0 Hz), 6.85-6.91 (m, 4H), 5.30 (d, 1H, J = 5.7 Hz), 5.03 (t, 1H, J = 6.1 Hz), 4.41-4.44 (m, 1H), 3.89-3.96 (m, 1H), 3.61-3.66 (m, 5H), 3.29-3.39 (m, 4H). HPLC-MS calculated C$_{27}$H$_{25}$ClFN$_3$O$_5$ (M + H$^+$): 525.1, found: 525.1. |
| 100 | 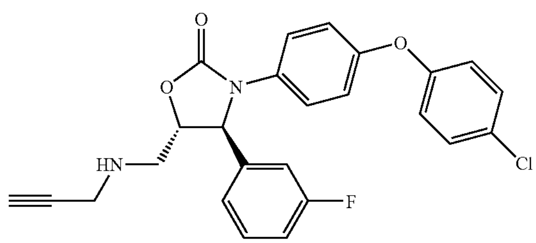 [SMILES: C#CCNC[C@@H]1OC(=O)N(c2ccc(Oc3ccc(Cl)cc3)cc2)[C@H]1c1cccc(F)c1] | $^1$H NMR (CDCl$_3$) δ (ppm) 7.31-7.35 (m, 3H), 7.23-7.27 (m, 2H), 7.10 (d, 1H, J = 7.8 Hz), 6.99-7.04 (m, 2H), 6.86-6.91 (m, 4H), 5.29 (d, 1H, J = 6.3 Hz), 4.42-4.45 (m, 1H), 3.53 (d, 2H, J = 2.3 Hz), 3.19 (dd, 1H, J = 13.1, 4.1 Hz), 3.02 (dd, 1H, J = 13.1, 4.8 Hz), 2.27 (t, 1H, J = 2.4 Hz). HPLC-MS calculated C$_{25}$H$_{20}$ClFN$_2$O$_3$ (M + H$^+$): 451.1, found: 451.1. |
| 102 | 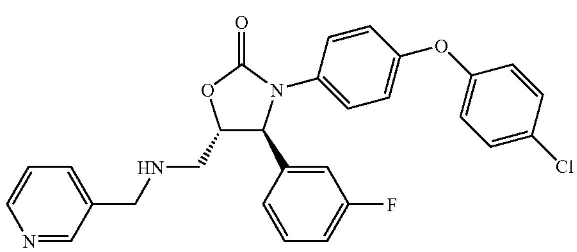 [SMILES: O=C1O[C@@H](CNCc2cccnc2)[C@H](c2cccc(F)c2)N1c1ccc(Oc2ccc(Cl)cc2)cc1] | $^1$H NMR (CDCl$_3$) δ (ppm) 8.60 (d, 1H, J = 1.7 Hz), 8.55 (dd, 1H, J = 4.8, 1.5 Hz), 7.67 (dt, 1H, J = 7.8, 1.7 Hz), 7.24-7.34 (m, 7H), 6.98-7.02 (m, 2H), 6.94 (t, 1H, J = 1.9 Hz), 6.86-6.92 (m, 4H), 5.20 (d, 1H, J = 6.3 Hz), 4.41 (ddd, 1H, J = 6.2, 4.6, 4.6 Hz), 3.95 (d, 1H, J = 13.5 Hz), 3.85 (d, 1H, J = 13.5 Hz), 3.11 (dd, 1H, J = 13.1, 4.0 Hz), 2.90 (dd, 1H, J = 13.1, 4.8 Hz). HPLC-MS calculated C$_{28}$H$_{23}$ClFN$_3$O$_3$ (M + H$^+$): 504.1, found: 504.1. |
| 103 | 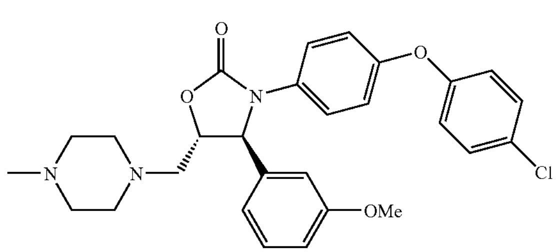 [SMILES: COc1cccc([C@H]2[C@H](CN3CCN(C)CC3)OC(=O)N2c2ccc(Oc3ccc(Cl)cc3)cc2)c1] | $^1$H NMR (acetone-d$_6$) δ (ppm) 7.50-7.54 (m, 2H), 7.34-7.38 (m, 2H), 7.30 (t, 1H, J = 7.8 Hz), 7.01-7.03 (m, 2H), 6.93-6.98 (m, 4H), 6.88 (dd, 1H, J = 8.8, 2.4 Hz), 5.38 (d, 1H, J = 5.7 Hz), 4.48 (app q, 1H, J = 5.8 Hz), 3.78 (s, 3H), 2.75-2.89 (m, 2H), 2.55 (br s, 4H), 2.35 (br s, 4H), 2.17 (s, 3H). HPLC-MS calculated C$_{28}$H$_{30}$ClN$_3$O$_4$ (M + H$^+$): 508.2. found: 508.2. |

TABLE 1-continued

| Compound Number | Structure | Physical Data<br>$^1$H NMR 400 MHz (CDCl$_3$)<br>and/or MS (m/z) |
|---|---|---|
| 104 | 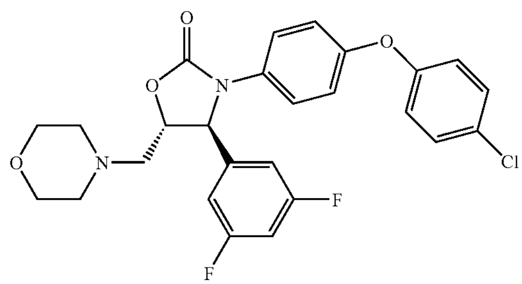 [SMILES: O=C1O[C@@H](CN2CCOCC2)[C@H](c2cc(F)cc(F)c2)N1c1ccc(Oc2ccc(Cl)cc2)cc1] | $^1$H NMR (acetone-d$_6$) δ (ppm) 7.51-7.55 (m, 2H), 7.35-7.39 (m, 2H), 7.20-7.25 (m, 2H), 6.95-7.00 (m, 5H), 5.56 (d, 1H, J = 6.0 Hz), 4.58 (ddd, 1H, J = 6.1, 6.1, 6.0 Hz), 3.55-3.65 (m, 4H), 2.93 (dd, 1H, J = 13.4, 6.2 Hz), 2.85 (dd, 1H, J = 13.4, 5.5 Hz), 2.55 (br s, 4H). HPLC-MS calculated C$_{26}$H$_{23}$ClF$_2$N$_2$O$_4$ (M + H$^+$): 501.1, found: 501.1. |
| 105 | 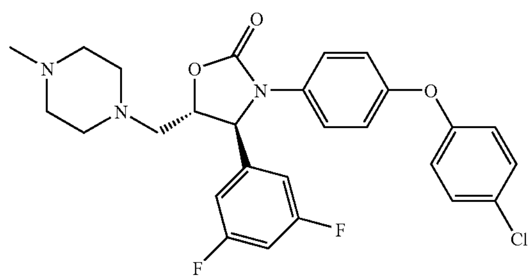 [SMILES: CN1CCN(C[C@@H]2OC(=O)N(c3ccc(Oc4ccc(Cl)cc4)cc3)[C@H]2c2cc(F)cc(F)c2)CC1] | $^1$H NMR (acetone-d6) δ (ppm) 7.50 (d, J = 8.9 Hz, 2H), 7.37 (d, 8.9 Hz, 2H), 7.22 (m, 2H), 7.02-6.96 (m, 5H), 5.55 (d, J = 6.1 Hz, 1J), 4.65 (dd, J = 11.2, 5.9 Hz), −3.68-3.20 (m, 8H), 3.16 (dd, J = 13.9, 4.8 Hz, 1H), 3.10 (dd, 13.8, 6.1 Hz, 1H), 2.93 (s, 3H). HPLC-MS calculated C$_{27}$H$_{26}$ClF$_2$N$_3$O$_3$ (M + H$^+$): 514.2, found: 514.1. |
| 107 | 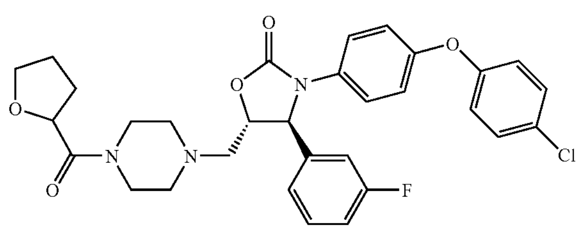 [SMILES: O=C(C1CCCO1)N1CCN(C[C@@H]2OC(=O)N(c3ccc(Oc4ccc(Cl)cc4)cc3)[C@H]2c2cccc(F)c2)CC1] | $^1$H NMR (acetone-d$_6$) δ (ppm) 7.47-7.50 (m, 2H), 7.40-7.45 (m, 1H), 7.30-7.39 (m, 4H), 7.11 (dt, 1H, J = 8.9, 1.8 Hz), 6.94-6.97 (m, 4H), 5.55 (d, 1H, J = 6.4 Hz), 5.02-5.07 (m, 1H), 4.69 (dd, 1H, J = 7.4, 5.4), 3.70-4.06 (m, 8H), 3.25-3.49 (m, 4H), 2.23-2.31 (m, 1H), 1.93-2.01 (m, 1H), 1.82-1.92 (m, 2H). HPLC-MS calculated C$_{31}$H$_{31}$ClFN$_3$O$_5$ (M + H$^+$): 580.2, found: 580.2. |
| 108 | 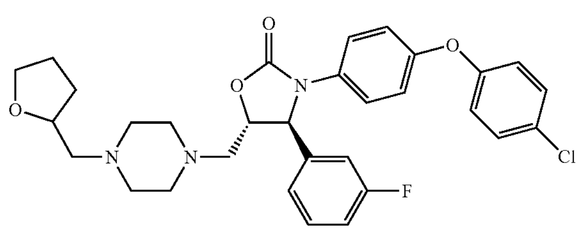 [SMILES: O=C1O[C@@H](CN2CCN(CC3CCCO3)CC2)[C@H](c2cccc(F)c2)N1c1ccc(Oc2ccc(Cl)cc2)cc1] | $^1$H NMR (acetone-d$_6$) δ (ppm) 7.48-7.50 (m, 2H), 7.41-7.45 (m, 1H), 7.34-7.39 (m, 3H), 7.30 (dt, 1H, J = 9.8, 2.2 Hz), 7.10 (dt, 1H, J = 8.3, 2.1 Hz), 6.93-6.97 (m, 4H), 5.53 (d, 1H, J = 6.1 Hz), 4.67 (dq, 1H, J = 6.3, 2.0 Hz), 4.37 (dq, 1H, J = 7.3, 1.6 Hz), 3.86 (q, 1H, J = 7.5 Hz), 3.73-3.78 (m, 1H), 3.40-3.70 (m, 5H), 3.11-3.25 (m, 7H), 2.07-2.16 (m, 1H), 1.83-1.95 (m, 2H), 1.55-1.64 (m, 1H). HPLC-MS calculated C$_{31}$H$_{33}$ClFN$_3$O$_4$ (M + H$^+$): 566.2, found: 566.2. |
| 110 | 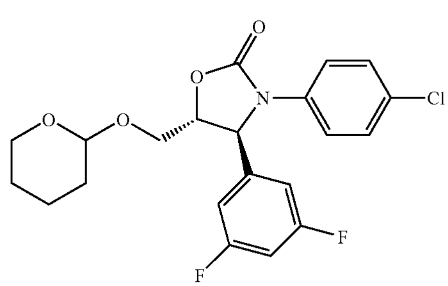 [SMILES: O=C1O[C@@H](COC2CCCCO2)[C@H](c2cc(F)cc(F)c2)N1c1ccc(Cl)cc1] | $^1$H NMR (CDCl$_3$) δ (ppm) 7.33-7.37 (m, 2H), 7.23-7.27 (m, 2H), 6.80-6.86 (m, 2H), 6.76 (tt, J = 8.7, 2.3 Hz, 1H), 5.27 (ovlp d, 1H, J = 5.0 Hz), 4.64-4.70 (m, 1H), 4.40-4.44 (m, 1H), 3.99-4.07 (m, 1H), 3.82-3.89 (m, 1H), 3.75 (ddd, 1H, J = 29.3, 11.5, 4.3 Hz), 3.51-3.57 (m, 1H), 1.70-1.79 (m, 2H), 1.50-1.62 (m, 4H). HPLC-MS calculated C$_{21}$H$_{20}$ClF$_2$NO$_4$ (M + H$^+$): 424.1, found: 424.1. |

TABLE 1-continued

| Compound Number | Structure | Physical Data<br>$^1$H NMR 400 MHz (CDCl$_3$) and/or MS (m/z) |
|---|---|---|
| 111 | 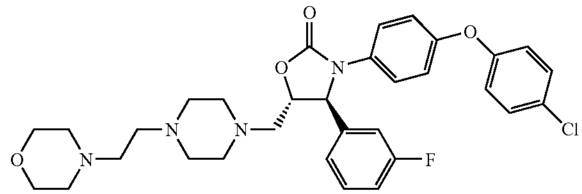 [SMILES: O=C1O[C@@H](CN2CCN(CCN3CCOCC3)CC2)[C@H](c2cccc(F)c2)N1c1ccc(Oc2ccc(Cl)cc2)cc1] | $^1$H NMR (CDCl$_3$) δ (ppm) 7.31-7.36 (m, 3H), 7.24-7.27 (m, 2H), 7.10 (d, 1H, J = 7.8 Hz), 6.98-7.04 (m, 2H), 6.86-6.91 (m, 4H), 5.15 (d, 1H, J = 5.8 Hz), 4.42 (q, 1H, J = 5.8 Hz), 3.71 (t, 4H, J = 4.6 Hz), 2.77 (d, 2H, J = 5.9 Hz), 2.59 (br s, 5H), 2.49-2.52 (m, 11H). HPLC-MS calculated C$_{32}$H$_{36}$ClFN$_4$O$_4$ (M + H$^+$): 595.2, found: 595.2. |
| 112 | 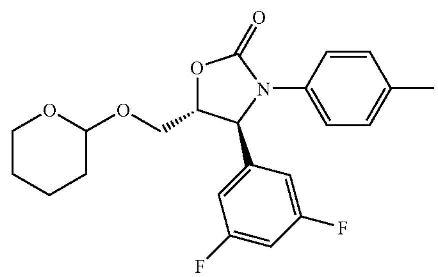 [SMILES: Cc1ccc(N2C(=O)O[C@@H](COC3CCCCO3)[C@@H]2c2cc(F)cc(F)c2)cc1] | $^1$H NMR (CDCl$_3$) δ (ppm) 7.26-7.28 (m, 2H), 7.10 (d, 2H, J = 8.4 Hz), 6.83-6.89 (m, 2H), 6.74 (dddd, 1H, J = 8.7, 8.7, 2.3, 2.3 Hz), 5.28 (ovlp d, 1H, J = 5.1 Hz), 4.67-4.72 (m, 1H), 4.40-4.44 (m, 1H), 3.99-4.08 (m, 1H), 3.84-3.91 (m, 1H), 3.77 (ddd, 1H, J = 27.6, 11.4, 4.4 Hz), 3.53-3.58 (m, 1H), 2.28 (s, 3H), 1.71-1.82 (m, 2H), 1.52-1.64 (m, 4H). HPLC-MS calculated C$_{22}$H$_{23}$F$_2$NO$_4$ (M + H$^+$): 404.2, found: 404.2 |
| 113 | 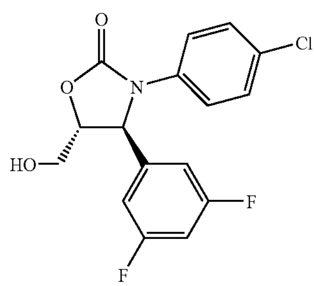 [SMILES: O=C1O[C@@H](CO)[C@H](c2cc(F)cc(F)c2)N1c1ccc(Cl)cc1] | $^1$H NMR (CDCl$_3$) δ (ppm) 7.28-7.31 (m, 2H), 7.21-7.25 (m, 2H), 6.81-6.88 (m, 2H), 6.77 (tt, 1H, J = 8.7, 2.2 Hz), 5.35 (d, 1H, J = 6.1 Hz), 4.35 (ddd, 1H, J = 6.0, 2.9, 2.9), 4.03-4.08 (m, 1H), 3.80 (ddd, 1H, J = 12.7, 7.7, 2.8 Hz), 2.89 (dd, 1H, J = 7.5, 5.2 Hz). HPLC-MS calculated C$_{16}$H$_{12}$ClF$_2$NO$_3$ (M + H$^+$): 340.1, found: 340.2. |
| 114 | 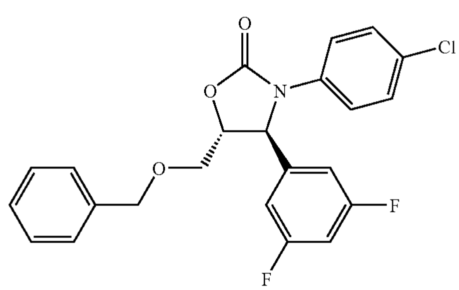 [SMILES: O=C1O[C@@H](COCc2ccccc2)[C@H](c2cc(F)cc(F)c2)N1c1ccc(Cl)cc1] | $^1$H NMR (CDCl$_3$) δ (ppm) 7.29-7.40 (m, 7H), 7.23-7.25 (m, 2H), 6.74-6.77 (m, 3H), 5.22 (d, 1H, J = 5.2 Hz), 4.69 (d, 1H, J = 12.0 Hz), 4.60 (d, 1H, J = 12.0 Hz), 4.38 (q, 1H, J = 4.8 Hz), 3.80 (dd, 1H, J = 10.8, 4.6 Hz), 3.74 (dd, 1H, J = 10.8, 3.5 Hz). HPLC-MS calculated C$_{23}$H$_{18}$ClF$_2$NO$_3$ (M + H$^+$): 430.1, found: 430.1. |
| 115 | 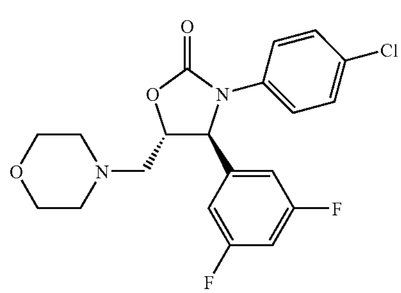 [SMILES: O=C1O[C@@H](CN2CCOCC2)[C@H](c2cc(F)cc(F)c2)N1c1ccc(Cl)cc1] | $^1$H NMR (CDCl$_3$) δ (ppm) 7.35 (d, 2H, J = 8.9 Hz), 7.26 (d, 2H, J = 9.0 Hz), 6.82-6.87 (m, 2H), 6.77 (tt, 1H, J = 8.6, 2.2 Hz), 5.18 (d, 1H, J = 5.5 Hz), 4.40 (q, 1H, J = 5.6 Hz), 3.66-3.75 (m, 4H), 2.73-2.82 (m, 2H), 2.56 (t, 4H, J = 4.6 Hz). HPLC-MS calculated C$_{20}$H$_{19}$ClF$_2$N$_2$O$_3$ (M + H$^+$): 409.1, found: 409.1. |

TABLE 1-continued

| Compound Number | Structure | Physical Data<br>¹H NMR 400 MHz (CDCl₃) and/or MS (m/z) |
|---|---|---|
| 116 | 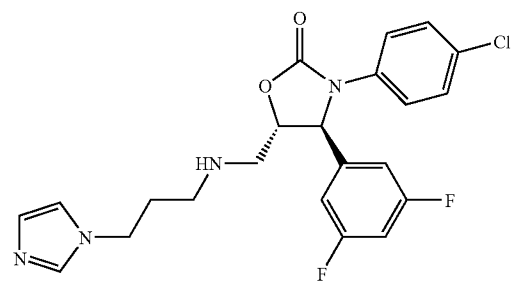 [SMILES: O=C1O[C@@H](CNCCCn2ccnc2)[C@H](c2cc(F)cc(F)c2)N1c1ccc(Cl)cc1] | ¹H NMR (CDCl₃) δ (ppm) 7.48 (s, 1H), 7.31-7.34 (m, 2H), 7.25-7.28 (m, 2H), 7.07 (s, 1H), 6.90 (s, 1H), 6.75-6.84 (m, 3H), 5.17 (d, 1H, J = 6.0 Hz), 4.36 (q, 1H, J = 5.2 Hz), 4.03 (t, 2H, J = 6.8 Hz), 3.05 (dd, 1H, J = 13.2, 4.0 Hz), 2.89 (dd, 1H, J = 13.2, 5.1 Hz), 2.59-2.72 (m, 2H), 1.95 (pentet, 2H). HPLC-MS calculated $C_{22}H_{21}ClF_2N_4O_2$ (M + H⁺): 447.1. found: 447.1. |
| 117 | 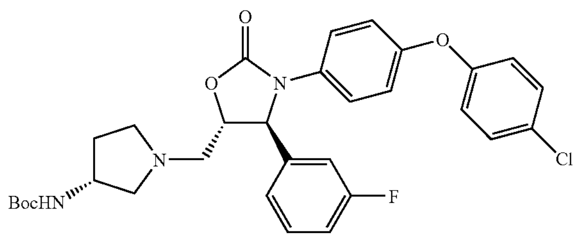 [SMILES: CC(C)(C)OC(=O)N[C@@H]1CCN(C[C@@H]2OC(=O)N(c3ccc(Oc4ccc(Cl)cc4)cc3)[C@H]2c2cccc(F)c2)C1] | ¹H NMR (CDCl₃) δ (ppm) 7.32-7.37 (m, 3H), 7.23-7.27 (m, 2H), 7.10 (d, 1H, J = 7.7 Hz), 6.99-7.03 (m, 2H), 6.86-6.91 (m, 4H), 5.17 (d, 1H, J = 5.6 Hz), 4.69 (d, 1H, J = 6.5 Hz), 4.40 (q, 1H, J = 5.7 Hz), 4.17 (br s, 1H), 2.96 (dd, 1H, J = 13.0, 6.3 Hz), 2.87-2.92 (m, 1H), 2.82 (dd, 1H, J = 13.0, 5.3 Hz), 2.71 (dd, 1H, J = 9.6, 6.5 Hz), 2.58 (d, 1H, J = 8.0 Hz), 2.45 (q, 1H, J = 8.2 Hz), 2.20-2.28 (m, 1H), 1.56-1.64 (m, 1H), 1.44 (s, 9H). HPLC-MS calculated $C_{31}H_{33}ClFN_3O_5$ (M + H⁺): 582.2, found: 582.2. |
| 118 | 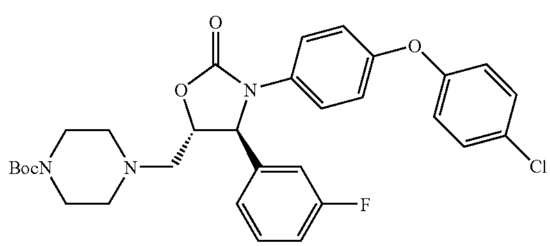 [SMILES: CC(C)(C)OC(=O)N1CCN(C[C@@H]2OC(=O)N(c3ccc(Oc4ccc(Cl)cc4)cc3)[C@H]2c2cccc(F)c2)CC1] | ¹H NMR (CDCl₃) δ (ppm) 7.32-7.37 (m, 3H), 7.24-7.27 (m, 2H), 7.11 (d, 1H, J = 7.7 Hz), 7.00-7.04 (m, 2H), 6.86-6.90 (m, 4H), 5.15 (d, 1H, J = 5.8 Hz), 4.47 (br s, 1H), 3.43 (br s, 4H), 2.83 (br s, 2H), 2.53 (br s, 4H), 1.45 (s, 9H). HPLC-MS calculated $C_{31}H_{33}ClFN_3O_5$ (M + H⁺): 582.2, found: 582.2. |
| 119 | 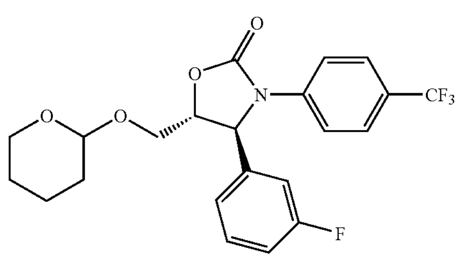 [SMILES: O=C1O[C@@H](COC2CCCCO2)[C@H](c2cccc(F)c2)N1c1ccc(C(F)(F)F)cc1] | ¹H NMR (CDCl₃) δ (ppm) 7.52-7.59 (m, 4H), 7.34-7.39 (m, 1H), 7.10 (d, 1H, J = 6.8 Hz), 7.01-7.06 (m, 2H), 5.35 (ovlp d, 1H, J = 4.9 Hz), 4.67-4.73 (m, 1H), 4.48 (pentet, 1H, J = 4.8 Hz), 4.05 (ddd, 1H, J = 19.6, 11.1, 4.6 Hz), 3.83-3.90 (m, 1H), 3.77 (ddd, 1H, J = 32.1, 11.6, 4.1 Hz), 3.53-3.58 (m, 1H), 1.70-1.77 (m, 2H), 1.52-1.62 (m, 4H). HPLC-MS calculated $C_{22}H_{21}F_4NO_4$ (M + H⁺): 440.1, found: 440.1. |
| 120 | 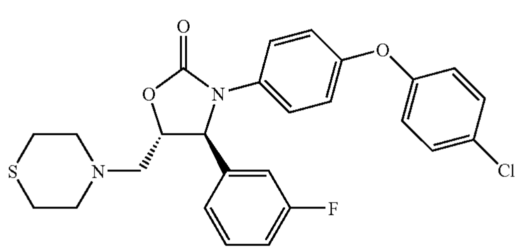 [SMILES: O=C1O[C@@H](CN2CCSCC2)[C@H](c2cccc(F)c2)N1c1ccc(Oc2ccc(Cl)cc2)cc1] | ¹H NMR (CDCl₃) δ (ppm) 7.31-7.38 (m, 3H), 7.24-7.28 (m, 2H), 7.10 (d, 1H, J = 7.7 Hz), 7.00-7.04 (m, 2H), 6.86-6.92 (m, 4H), 5.10 (d, 1H, J = 5.7 Hz), 4.41 (q, 1H, J = 5.8 Hz), 2.81-2.86 (m, 5H), 2.75 (dd, 1H, J = 13.7, 6.1 Hz), 2.60-2.71 (m, 4H). HPLC-MS calculated $C_{26}H_{24}ClFN_2O_3S$ (M + H⁺): 499.1, found: 499.1. |

TABLE 1-continued

| Compound Number | Structure | Physical Data ¹H NMR 400 MHz (CDCl₃) and/or MS (m/z) |
|---|---|---|
| 121 | 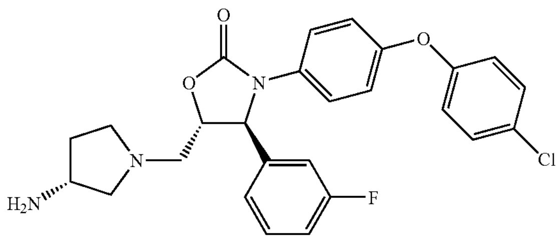 [SMILES: N[C@@H]1CCN(C[C@@H]2OC(=O)N(c3ccc(Oc4ccc(Cl)cc4)cc3)[C@H]2c2cccc(F)c2)C1] | ¹H NMR (CDCl₃) δ (ppm) 7.30-7.36 (m, 3H), 7.23-7.27 (m, 2H), 7.10 (d, 1H, J = 7.7 Hz), 6.98-7.04 (m, 2H), 6.85-6.90 (m, 4H), 5.22 (d, 1H, J = 4.7 Hz), 4.41 (br s, 1H), 3.58 (br s, 1H), 2.76-3.00 (m, 4H), 2.54 (br s, 2H), 2.17 (br s, 1H), 2.00 (br s, 3H), 1.59 (br s, 1H). HPLC-MS calculated $C_{26}H_{25}ClFN_3O_3$ (M + H⁺): 482.2, found: 482.2. |
| 122 | 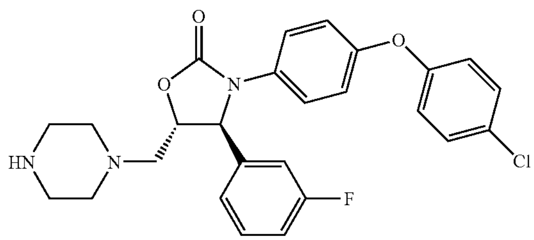 [SMILES: O=C1O[C@@H](CN2CCNCC2)[C@H](c2cccc(F)c2)N1c1ccc(Oc2ccc(Cl)cc2)cc1] | ¹H NMR (CDCl₃) δ (ppm) 7.31-7.37 (m, 3H), 7.24-7.28 (m, 2H), 7.11 (d, 1H, J = 7.7 Hz), 6.99-7.04 (m, 2H), 6.86-6.91 (m, 4H), 5.15 (d, 1H, J = 5.8 Hz), 4.44 (q, 1H, J = 5.9 Hz), 2.94 (br s, 4H), 2.73-2.82 (m, 2H), 2.57 (br s, 4H), 2.37 (br s, 1H). ). HPLC-MS calculated $C_{26}H_{25}ClFN_3O_3$ (M + H⁺): 482.2, found: 482.2. |
| 123 | 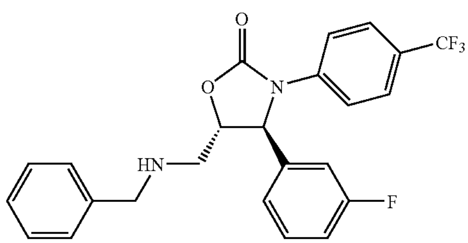 [SMILES: O=C1O[C@@H](CNCc2ccccc2)[C@H](c2cccc(F)c2)N1c1ccc(C(F)(F)F)cc1] | ¹H NMR (CDCl₃) δ (ppm) 7.49-7.54 (m, 4H), 7.27-7.39 (m, 6H), 6.99 (ddd, 1H, J = 8.4, 8.4, 2.5 Hz), 6.94 (d, 1H, J = 7.7 Hz), 6.85 (dt, 1H, J = 9.2, 2.0, 2.0 Hz), 5.28 (d, 1H, J = 6.0 Hz), 4.37 (ddd, 1H, J = 5.9, 4.3, 4.3 Hz), 3.93 (d, 1H, J = 13.2 Hz), 3.82 (d, 1H, J = 13.2 Hz), 3.12 (dd, 1H, J = 13.3, 4.3 Hz), 2.87 (dd, 1H, J = 13.3, 4.3 Hz). HPLC-MS calculated $C_{24}H_{20}F_4N_2O_2$ (M + H⁺): 445.2, found: 445.2. |
| 124 | 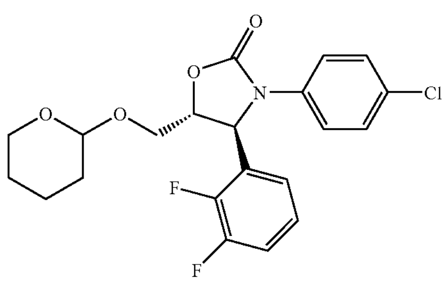 [SMILES: O=C1O[C@@H](COC2CCCCO2)[C@H](c2cccc(F)c2F)N1c1ccc(Cl)cc1] | ¹H NMR (CDCl₃) δ (ppm) 7.37-7.41 (m, 2H), 7.24-7.28 (m, 2H), 7.01-7.18 (m, 3H), 5.65 (ovlp d, 1H, J = 4.4 Hz), 4.70-4.76 (m, 1H), 4.54 (pentet, 1H, J = 4.0 Hz), 4.09 (ddd, 1H, J = 20.1, 11.6, 4.2 Hz), 3.71-3.90 (m, 2H), 3.53-3.58 (m, 1H), 1.66-1.76 (m, 2H), 1.48-1.63 (m, 4H). HPLC-MS calculated $C_{21}H_{20}ClF_2NO_4$ (M + H⁺): 424.1, found: 424.1. |
| 125 | 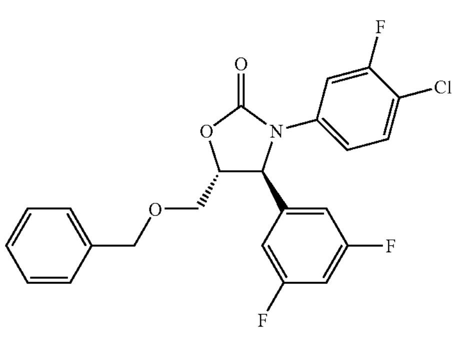 [SMILES: O=C1O[C@@H](COCc2ccccc2)[C@H](c2cc(F)cc(F)c2)N1c1ccc(Cl)c(F)c1] | ¹H NMR (CDCl₃) δ (ppm) 7.31-7.40 (m, 6H), 7.25-7.29 (m, 1H), 7.02 (dddd, 1H, J = 1.1, 1.1, 1.1, 8.9), 6.71-6.80 (m, 3H), 5.18 (d, 1H, J = 5.3 Hz), 4.68 (d, 1H, J = 12.0 Hz), 4.60 (d, 1H, J = 12.0 Hz), 4.38 (q, 1H, J = 4.7 Hz), 3.79 (dd, 1H, J = 10.8, 4.6 Hz), 3.73 (dd, 1H, J = 10.8, 3.4 Hz). HPLC-MS calculated $C_{23}H_{17}ClF_3NO_3$ (M + H⁺): 448.1, found: 448.1. |

TABLE 1-continued

| Compound Number | Structure | Physical Data<br>¹H NMR 400 MHz (CDCl₃) and/or MS (m/z) |
|---|---|---|
| 126 | 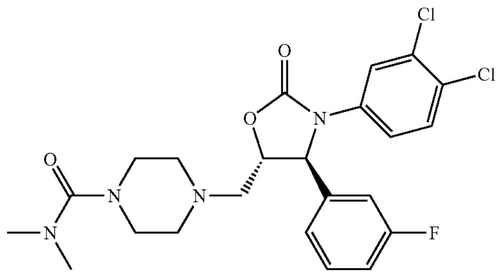 [SMILES: CN(C)C(=O)N1CCN(C[C@@H]2OC(=O)N(c3ccc(Cl)c(Cl)c3)[C@H]2c2cccc(F)c2)CC1] | ¹H NMR (CDCl₃) δ (ppm) 7.64 (d, 1H, J = 2.6 Hz), 7.36 (ddd, 1H, J = 7.9, 7.9, 5.8 Hz), 7.31 (d, 1H, J = 8.9 Hz), 7.20 (dd, 1H, J = 8.9, 2.6 Hz), 7.08 (d, 1H, J = 7.8 Hz), 6.98-7.06 (m, 2H), 5.16 (d, 1H, J = 5.5 Hz), 4.44 (q, 1H, J = 5.8 Hz), 3.18-3.29 (m, 4H), 2.83 (s, 6H), 2.79 (d, 2H, J = 5.8 Hz), 2.55 (t, 4H, J = 4.9 Hz). HPLC-MS calculated $C_{23}H_{25}Cl_2FN_4O_3$ (M + H⁺): 495.1, found: 495.1. |
| 127 | 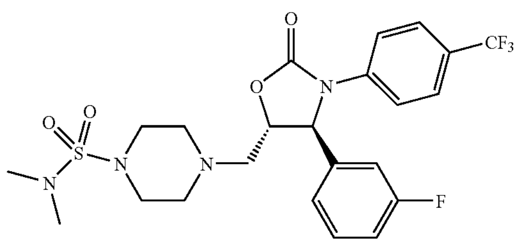 [SMILES: CN(C)S(=O)(=O)N1CCN(C[C@@H]2OC(=O)N(c3ccc(C(F)(F)F)cc3)[C@H]2c2cccc(F)c2)CC1] | ¹H NMR (CDCl₃) δ (ppm) 7.51-7.56 (m, 4H), 7.37 (ddd, 1H, J = 7.9, 7.9, 5.8 Hz), 7.08 (d, 1H, J = 8.0 Hz), 6.99-7.06 (m, 2H), 5.20 (d, 1H, J = 5.5 Hz), 4.44 (q, 1H, J = 5.7 Hz), 3.20-3.30 (m, 4H), 2.82-2.84 (m, 8H), 2.63 (t, 4H, J = 4.9 Hz). ). HPLC-MS calculated $C_{23}H_{26}F_4N_4O_4S$ (M + H⁺): 531.2, found: 531.2. |
| 128 | 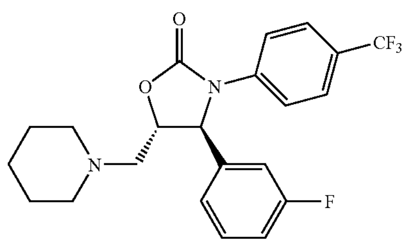 [SMILES: O=C1O[C@@H](CN2CCCCC2)[C@H](c2cccc(F)c2)N1c1ccc(C(F)(F)F)cc1] | ¹H NMR (CDCl₃) δ (ppm) 7.58 (d, 2H, J = 8.8 Hz), 7.52 (d, 2H, J = 7.9 Hz), 7.34 (ddd, 1H, J = 7.9, 7.9, 5.8 Hz), 7.09 (d, 1H, J = 7.8 Hz), 6.99-7.05 (m, 2H), 5.27 (d, 1H, J = 5.0 Hz), 4.42 (ddd, 1H, J = 7.3, 5.1, 5.1 Hz), 2.66-2.77 (m, 2H), 2.47-2.50 (m, 4H), 1.51-1.65 (m, 4H), 1.44-1.48 (m, 2H). HPLC-MS calculated $C_{22}H_{22}F_4N_2O_2$ (M + H⁺): 423.2, found: 423.2. |
| 129 | 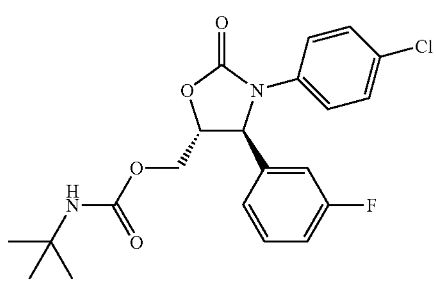 [SMILES: CC(C)(C)NC(=O)OC[C@@H]1OC(=O)N(c2ccc(Cl)cc2)[C@H]1c1cccc(F)c1] | ¹H NMR (CDCl₃) δ (ppm) 7.32-7.37 (m, 3H), 7.21-7.25 (m, 2H), 7.09 (d, 1H, J = 7.8 Hz), 6.98-7.05 (m, 2H), 5.19 (d, 1H, J = 5.4 Hz), 4.79 (s, 1H), 4.43-4.47 (m, 2H), 4.29 (d, 1H, J = 9.3 Hz), 1.29 (s, 9H). HPLC-MS calculated $C_{21}H_{22}ClFN_2O_4$ (M + H⁺): 421.1, found: 421.1. |
| 130 | 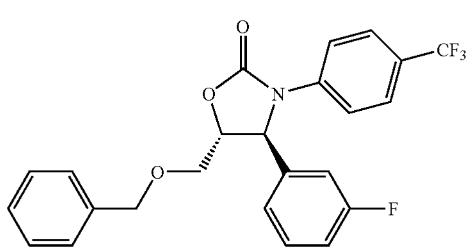 [SMILES: O=C1O[C@@H](COCc2ccccc2)[C@H](c2cccc(F)c2)N1c1ccc(C(F)(F)F)cc1] | ¹H NMR (CDCl₃) δ (ppm) 7.50-7.55 (m, 4H), 7.31-7.39 (m, 6H), 7.00-7.07 (m, 2H), 6.94 (dt, 1H, J = 9.2, 2.0 Hz), 5.30 (d, 1H, J = 5.1 Hz), 4.69 (d, 1H, J = 11.9 Hz), 4.60 (d, 1H, J = 12.0 Hz), 4.43 (q, 1H, J = 4.6 Hz), 3.81 (dd, 1H, J = 10.9, 4.4 Hz), 3.75 (dd, 1H, J = 10.9, 3.4 Hz). HPLC-MS calculated $C_{24}H_{19}F_4NO_3$ (M + H⁺): 446.1, found: 446.1. |

TABLE 1-continued

| Compound Number | Structure | Physical Data<br>¹H NMR 400 MHz (CDCl₃) and/or MS (m/z) |
|---|---|---|
| 131 | 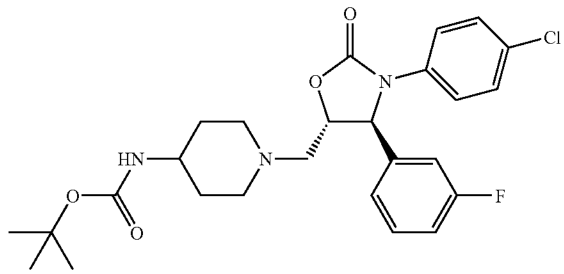 [SMILES: CC(C)(C)OC(=O)NC1CCN(C[C@@H]2OC(=O)N(c3ccc(Cl)cc3)[C@H]2c2cccc(F)c2)CC1] | ¹H NMR (acetone-d₆) δ (ppm) 7.51-7.55 (m, 2H), 7.43 (ddd, 1H, J = 7.9, 7.9, 5.9), 7.25-7.32 (m, 4H), 7.05-7.10 (m, 1H), 5.88 (d, 1H, J = 6.3 Hz), 5.51 (d, 1H, J = 5.7 Hz), 4.51 (q, 1H, J = 5.7 Hz), 3.35 (br s, 1H), 2.80-2.97 (m, 4H), 2.19-2.32 (m, 2H), 1.81 (t, 2H, J = 14.4 Hz), 1.55 (dddd, 1H, J = 11.4, 11.4, 11.4, 3.9 Hz), 1.39-149 (m, 10H). HPLC-MS calculated $C_{26}H_{31}ClFN_3O_4$ (M + H⁺): 504.2, found: 504.2. |
| 132 | 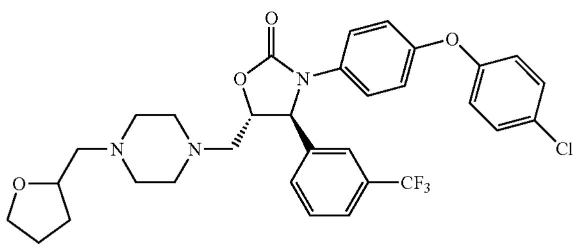 [SMILES: O=C1O[C@@H](CN2CCN(CC3CCCO3)CC2)[C@H](c2cccc(C(F)(F)F)c2)N1c1ccc(Oc2ccc(Cl)cc2)cc1] | ¹H NMR (CDCl₃) δ (ppm) 7.57-7.59 (m, 2H), 7.47-7.52 (m, 2H), 7.31-7.35 (m, 2H), 7.23-7.27 (m, 2H), 6.85-6.91 (m, 4H), 5.26 (dd, 1H, J = 5.6, 2.0 Hz), 4.41 (q, 1H, J = 6.1 Hz), 3.97-4.05 (m, 1H), 3.85-3.91 (m, 1H), 3.71-3.78 (m, 1H), 2.74-2.83 (m, 2H), 2.38-2.66 (m, 10H), 1.94-2.02 (m, 1H), 1.80-1.91 (m, 2H), 1.48 (dddd, 1H, J = 12.0, 8.1, 8.1, 8.1 Hz). HPLC-MS calculated $C_{32}H_{33}ClF_3N_3O_4$ (M + H⁺): 616.2, found: 616.2. |
| 133 | 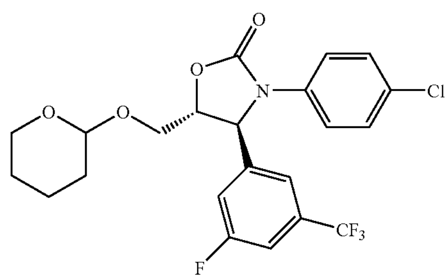 [SMILES: O=C1O[C@@H](COC2CCCCO2)[C@H](c2cc(F)cc(C(F)(F)F)c2)N1c1ccc(Cl)cc1] | ¹H NMR (CDCl₃) δ (ppm) 7.39-7.42 (m, 1H), 7.33-7.37 (m, 2H), 7.25-7.31 (m, 3H), 7.20 (dd, 1H, J = 8.8, 1.5 Hz), 5.40 (ovlp d, 1H, J = 4.9 Hz), 4.65-4.71 (m, 1H), 4.43-4.47 (m, 1H), 4.02-4.10 (m, 1H), 3.75-3.92 (m, 2H), 3.52-3.59 (m, 1H), 1.70-1.82 (m, 2H), 1.51-1.62 (m, 4H). HPLC-MS calculated $C_{22}H_{20}ClF_4NO_4$ (M + H⁺): 474.1, found: 474.1. |
| 134 | 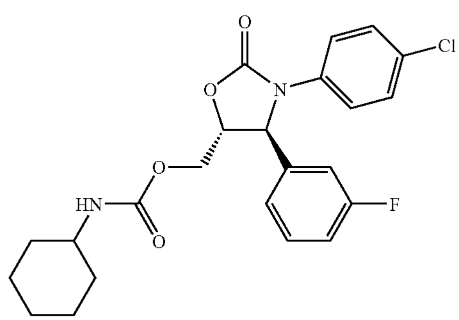 [SMILES: O=C(NC1CCCCC1)OC[C@@H]1OC(=O)N(c2ccc(Cl)cc2)[C@H]1c1cccc(F)c1] | ¹H NMR (CDCl₃) δ (ppm) 7.32-7.37 (m, 3H), 7.22-7.42 (m, 2H), 7.09 (d, 1H, J = 7.8 Hz), 6.98-7.05 (m, 2H), 5.19 (d, 1H, J = 5.2 Hz), 4.73 (d, 1H, J = 7.9 Hz), 4.46-4.51 (m, 2H), 4.31-4.36 (m, 1H), 3.41-3.50 (m, 1H), 1.92 (d, 1H, J = 9.7 Hz), 1.83 (d, 1H, J = 10.2 Hz), 1.67-1.72 (m, 2H), 1.58-1.59 (m, 1H), 1.26-1.38 (m, 2H), 1.03-1.19 (m, 3H). HPLC-MS calculated $C_{23}H_{24}ClFN_2O_4$ (M + H⁺): 447.1, found: 447.1. |
| 136 | 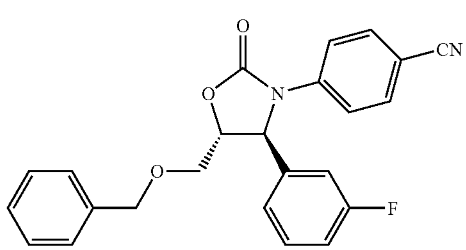 [SMILES: N#Cc1ccc(N2C(=O)O[C@@H](COCc3ccccc3)[C@@H]2c2cccc(F)c2)cc1] | ¹H NMR (CDCl₃) δ (ppm) 7.54 (s, 4H), 7.30-7.38 (m, 6H), 7.00-7.06 (m, 2H), 6.92 (dt, 1H, J = 9.1, 2.0), 5.28 (d, 1H, J = 4.9 Hz), 4.68 (d, 1H, J = 12.0 Hz), 4.60 (d, 1H, J = 12.0 Hz), 4.43 (q, 1H, J = 4.4 Hz), 3.81 (dd, 1H, J = 10.9, 4.3 Hz), 3.75 (dd, 1H, J = 10.9, 3.3 Hz). HPLC-MS calculated $C_{24}H_{19}FN_2O_3$ (M + H⁺): 403.1, found: 403.1. |

TABLE 1-continued

| Compound Number | Structure | Physical Data<br>¹H NMR 400 MHz (CDCl₃)<br>and/or MS (m/z) |
|---|---|---|
| 137 | 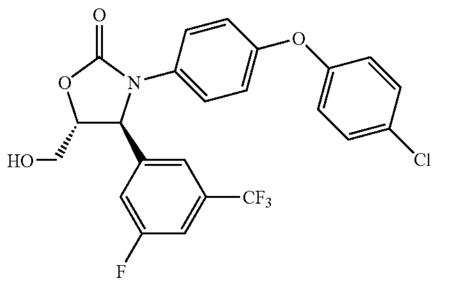 [SMILES: O=C1O[C@@H](CO)[C@H](c2cc(F)cc(C(F)(F)F)c2)N1c1ccc(Oc2ccc(Cl)cc2)cc1] | ¹H NMR (CDCl₃) δ (ppm) 7.39 (s, 1H), 7.24-7.32 (m, 6H), 6.86-6.93 (m, 4H), 5.43 (d, 1H, J = 6.1 Hz), 4.39 (ddd, 1H, J = 6.0, 3.0, 3.0 Hz), 4.07-4.12 (m, 1H), 3.83 (ddd, 1H, J = 12.7, 7.7, 2.8 Hz), 2.74 (dd, 1H, J = 7.7, 5.2 Hz). HPLC-MS calculated $C_{23}H_{16}ClF_4NO_4$ (M + H⁺): 482.1, found: 482.1. |
| 138 | 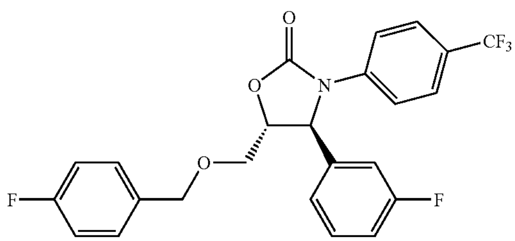 [SMILES: O=C1O[C@@H](COCc2ccc(F)cc2)[C@H](c2cccc(F)c2)N1c1ccc(C(F)(F)F)cc1] | ¹H NMR (acetone-d₆) δ (ppm) 7.74 (d, 2H, J = 8.7 Hz), 7.63 (d, 2H, J = 8.7 Hz), 7.45 (ddd, 1H, J = 8.3, 8.3, 6.2 Hz), 7.37-7.41 (m, 2H), 7.26-7.31 (m, 2H), 7.04-7.14 (m, 3H), 5.67 (d, 1H, J = 5.0), 4.66 (d, 2H, J = 1.7), 4.62 (ddd, 1H, J = 5.0, 3.7, 3.7 Hz), 3.95 (d, 1H, J = 3.7 Hz). HPLC-MS calculated $C_{24}H_{18}F_5NO_3$ (M + H⁺): 464.1, found: 464.1. |
| 139 | 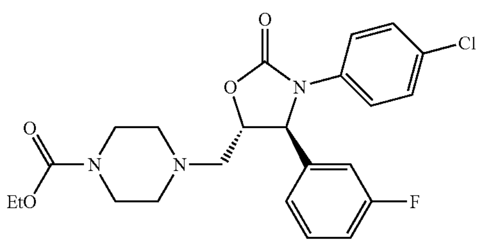 [SMILES: CCOC(=O)N1CCN(C[C@@H]2OC(=O)N(c3ccc(Cl)cc3)[C@H]2c2cccc(F)c2)CC1] | ¹H NMR (acetone-d₆) δ (ppm) 7.53 (m, 2H), 7.44 (ddd, 1H, J = 7.9, 7.9, 5.9 Hz), 7.27-7.35 (m, 4H), 7.09 (m, 1H), 5.55 (d, 1H, J = 5.7 Hz), 4.57 (app q, 1H, J = 5.7 Hz), 4.06 (q, 2H, J = 7.1 Hz), 3.35-3.46 (m, 4H), 2.96 (dd, 1H, J = 13.5, 6.2 Hz), 2.88 (dd, 1H, J = 13.5, 5.5 Hz), 2.54 (t, 4H, J = 10.1 Hz), 1.20 (t, 3H, J = 7.1 Hz). HPLC-MS calculated $C_{23}H_{25}ClF_2N_3O_4$ (M + H⁺): 462.2, found: 462.2. |
| 140 | 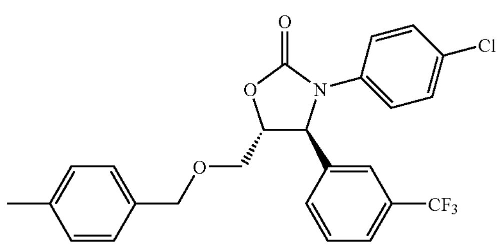 [SMILES: Cc1ccc(COC[C@@H]2OC(=O)N(c3ccc(Cl)cc3)[C@H]2c2cccc(C(F)(F)F)c2)cc1] | ¹H NMR (acetone-d₆) δ (ppm) 7.62 (s, 1H), 7.60 (d, 1H, J = 7.5 Hz), 7.55 (d, 1H, J = 7.8 Hz), 7.50 (t, 1H, J = 7.6 Hz), 7.37-7.41 (m, 2H), 7.15-7.19 (m, 2H), 7.12 (d, 2H, J = 8.0 Hz), 7.01 (d, 2H, J = 7.9 Hz), 5.56 (d, 1H, J = 5.3 Hz), 4.45-4.52 (m, 3H), 3.75-3.81 (m, 2H), 2.18 (s, 3H). HPLC-MS calculated $C_{25}H_{21}ClF_3NO_3$ (M + H⁺): 476.1, found: 476.1. |
| 141 | 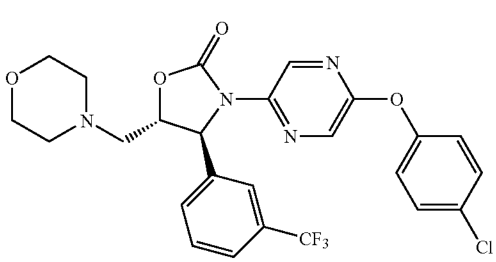 [SMILES: O=C1O[C@@H](CN2CCOCC2)[C@H](c2cccc(C(F)(F)F)c2)N1c1cnc(Oc2ccc(Cl)cc2)cn1] | ¹H NMR (acetone-d₆) 400 MHz δ (ppm) 8.90 (d, J = 1.4 Hz, 1H), 8.06 (d, J = 1.4 Hz, 1H), 7.86 (s, 1H), 7.79 (d, J = 7.6 Hz, 1H), 7.67-7.60 (m, 2H) 7.43 (m, 2H), 7.18 (m, 2H), 5.78 (d, J = 5.3 Hz, 1H), 4.71 (ddd, J = 6.6, 5.9, 5.3 Hz, 1H), 3.64-3.54 (m, 4H), 2.96 (dd, J = 13.3, 6.8 Hz, 1H), 2.87 (dd, J = 13.3, 5.2 Hz, 1H). 2.56-2.54 (m, 4H); HPLC-MS calculated $C_{25}H_{22}ClF_3N_4O_4$ (M + H⁺) 535.1, found 535.1. |

TABLE 1-continued

| Compound Number | Structure | Physical Data<br>$^1$H NMR 400 MHz (CDCl$_3$)<br>and/or MS (m/z) |
|---|---|---|
| 142 | 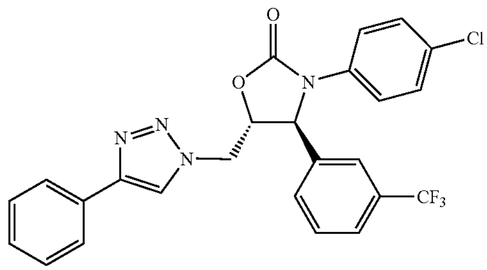 [SMILES: O=C1O[C@@H](Cn2cc(-c3ccccc3)nn2)[C@H](c2cccc(C(F)(F)F)c2)N1c1ccc(Cl)cc1] | $^1$H NMR (acetone-d$_6$) δ (ppm) 8.47 (s, 1H), 7.86-7.88 (m, 3H), 7.78 (d, 1H, J = 7.7 Hz), 7.69 (d, 1H, J = 7.8 Hz), 7.64 (t, 1H, J = 7.7 Hz), 7.41-7.45 (m, 4H), 7.33 (t, 1H, J = 7.4 Hz), 7.26-7.29 (m, 2H), 5.81 (d, 1H, J = 5.3 Hz), 5.13-5.20 (m, 2H), 5.06 (q, 1H, J = 5.4 Hz). HPLC-MS calculated C$_{25}$H$_{18}$ClF$_3$N$_4$O$_2$ (M + H$^+$): 499.1, found: 499.1. |
| 143 | 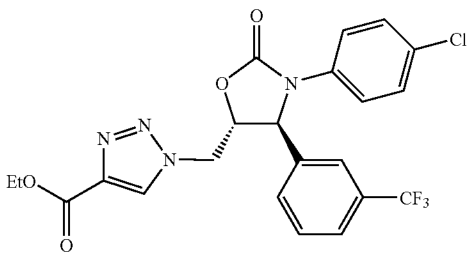 [SMILES: CCOC(=O)c1cn(C[C@@H]2OC(=O)N(c3ccc(Cl)cc3)[C@H]2c2cccc(C(F)(F)F)c2)nn1] | $^1$H NMR (acetone-d$_6$) δ (ppm) 8.6.5 (s, 1H), 7.87 (s, 1H), 7.79 (d, 1H, J = 7.7 Hz), 7.70 (d, 1H, J = 7.8 Hz), 7.65 (t, 1H, J = 7.7 Hz), 7.45-7.48 (m, 2H), 7.29-7.31 (m, 2H), 5.82 (d, 1H, J = 5.3 Hz), 5.22 (s, 1H), 5.21 (s, 1H), 5.09 (q, 1H, J = 5.2 Hz), 4.33 (q, 2H, J = 7.1 Hz), 1.32 (t, 3H, J = 7.1 Hz). HPLC-MS calculated C$_{22}$H$_{18}$ClF$_3$N$_4$O$_4$ (M + H$^+$): 495.1, found: 495.1. |
| 144 | 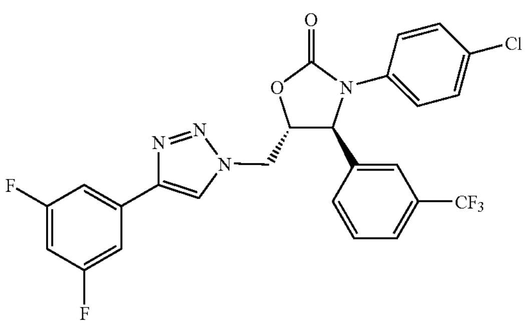 [SMILES: O=C1O[C@@H](Cn2cc(-c3cc(F)cc(F)c3)nn2)[C@H](c2cccc(C(F)(F)F)c2)N1c1ccc(Cl)cc1] | $^1$H NMR (acetone-d$_6$) δ (ppm) 8.64 (s, 1H), 7.87 (s, 1H), 7.79 (d, 1H, J = 7.7 Hz), 7.70 (d, 1H, J = 7.8 Hz), 7.65 (t, 1H, J = 7.7 Hz), 7.50-7.54 (m, 2H), 7.43-7.45 (m, 2H), 7.27-7.29 (m, 2H), 6.99 (tt, 1H, J = 9.2, 2.3 Hz), 5.81 (d, 1H, J = 5.4 Hz), 5.17-5.23 (m, 2H), 5.06 (q, 1H, J = 5.5 Hz). HPLC-MS calculated C$_{25}$H$_{16}$ClF$_5$N$_4$O$_2$ (M + H$^+$): 535.1, found: 535.1. |
| 145 | 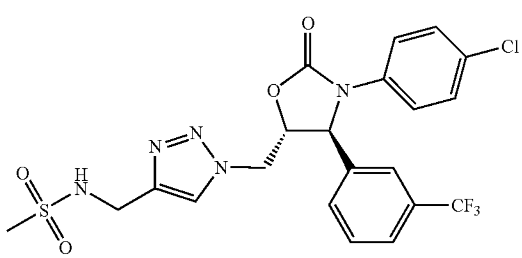 [SMILES: CS(=O)(=O)NCc1cn(C[C@@H]2OC(=O)N(c3ccc(Cl)cc3)[C@H]2c2cccc(C(F)(F)F)c2)nn1] | $^1$H NMR (CD$_3$CN) δ (ppm) 7.86 (s, 1H), 7.71 (s, 1H), 7.61-7.66 (m, 2H), 7.55 (t, 1H, J = 7.7 Hz), 7.25-7.31 (m, 4H), 5.63 (br s, 1H), 5.44 (d, 1H, J = 5.7 Hz), 4.81-4.89 (m, 3H), 4.30 (d, 1H, J = 6.3 Hz), 2.82 (s, 3H). HPLC-MS calculated C$_{21}$H$_{19}$ClF$_3$N$_5$O$_4$S (M + H$^+$): 530.1, found: 530.1. |
| 146 | 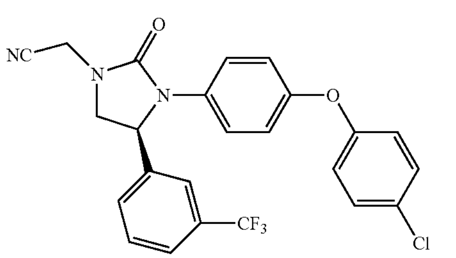 | HPLC-MS calculated for C$_{24}$H$_{17}$ClF$_3$N$_3$O$_2$ (M + H$^+$) 472.1, found 472.1. |

TABLE 1-continued

| Compound Number | Structure | Physical Data ¹H NMR 400 MHz (CDCl₃) and/or MS (m/z) |
|---|---|---|
| 147 | 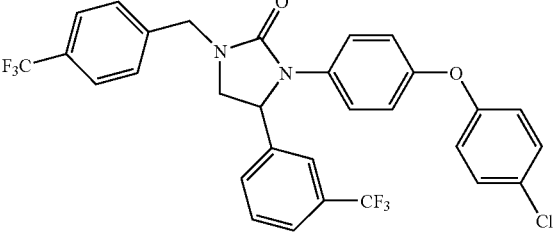 | HPLC-MS calculated for $C_{30}H_{21}ClF_6N_2O_2$ (M + H⁺) 591.1, found 591.1. |
| 148 | 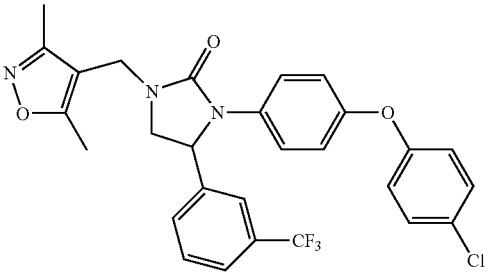 [SMILES: Cc1noc(C)c1CN1CC(c2cccc(C(F)(F)F)c2)N(c2ccc(Oc3ccc(Cl)cc3)cc2)C1=O] | HPLC-MS $C_{28}H_{23}ClF_3N_3O_3$ (M + H⁺) 542.1, found 542.1. |
| 150 | 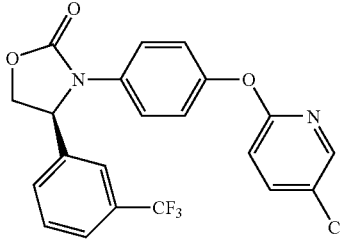 | ¹H NMR (CDCl₃, 400 MHz) δ 8.08 (d, 1H), 7.60~7.65 (m, 2H), 7.58 (s, 1H), 7.53 (d, 2H), 7.40 (d, 2H), 7.04 (d, 2H), 6.83 (d, 1H), 5.43 (dd, 1H), 4.83 (t, 1H), 4.21 (dd, 1H); HPLC-MS calculated for $C_{21}H_{14}ClF_3N_2O_3$ (M + H⁺) 435.1, found 435.1. |
| 152 | 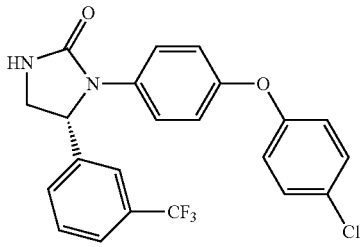 [SMILES: O=C1NC[C@@H](c2cccc(C(F)(F)F)c2)N1c1ccc(Oc2ccc(Cl)cc2)cc1] | ¹H NMR (CDCl₃, 400 MHz) δ 7.45~7.58 (m, 4H), 7.29 (d, 2H), 7.23 (d, 2H), 6.87 (m, 4H), 5.34 (dd, 1H), 4.82 (br, 1H), 4.01 (t, 1H), 3.35 (dd, 1H); HPLC-MS calculated for $C_{22}H_{16}ClF_3N_2O_2$ (M + H⁺) 433.1, found 433.1. |
| 154 | 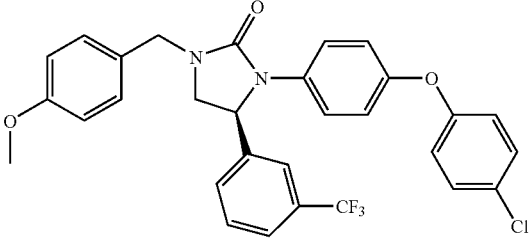 | ¹H NMR (CDCl₃, 400 MHz) δ 7.51 (m, 2H), 7.44 (m, 2H), 7.34 (d, 2H), 7.23 (m, 4H), 6.87 (m, 6H), 5.17 (dd, 1H), 4.53 (d, 1H), 4.37 (d, 1H), 3.79 (s, 3H), 3.76 (t, 1H), 3.07 (dd, 1H); HPLC-MS calculated for $C_{30}H_{24}ClF_3N_2O_3$ (M + H⁺) 553.1, found 553.1. |
| 156 | 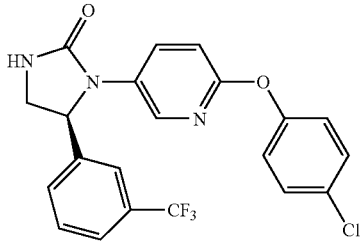 | ¹H NMR (CDCl₃, 400 MHz) δ 8.04 (dd, 1H), 7.87 (d, 1H), 7.45~7.57 (m, 4H), 7.30 (d, 2H), 7.00 (d, 2H), 6.87 (d, 1H), 5.31 (m, 2H), 4.02 (t, 1H), 3.38 (dd, 1H); HPLC-MS calculated for $C_{21}H_{15}ClF_3N_3O_2$ (M + H⁺) 434.1, found 434.1. |

TABLE 1-continued

| Compound Number | Structure | Physical Data<br>$^1$H NMR 400 MHz (CDCl$_3$) and/or MS (m/z) |
|---|---|---|
| 157 | 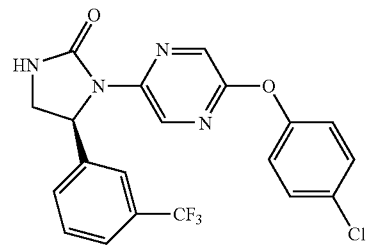 [SMILES: O=C1NC[C@H](c2cccc(C(F)(F)F)c2)N1c1ccc(Oc2ccc(Cl)cc2)nc1] | $^1$H NMR (CDCl$_3$, 400 MHz) δ 9.03 (d, 1H), 7.89 (d, 1H), 7.63 (s, 1H), 7.52~7.57 (m, 2H), 7.45 (m, 1H), 7.32 (d, 2H), 7.02 (d, 2H), 5.75 (dd, 1H), 5.31 (s, 1H), 4.07 (t, 1H), 3.44 (dd, 1H); HPLC-MS calculated for C$_{20}$H$_{14}$ClF$_3$N$_4$O$_2$ (M + H$^+$) 435.1, found 435.1. |
| 158 | 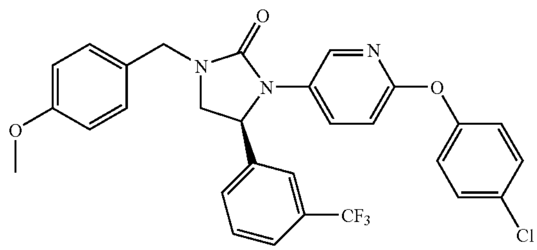 [SMILES: COc1ccc(CN2C[C@H](c3cccc(C(F)(F)F)c3)N(c3ccc(Oc4ccc(Cl)cc4)nc3)C2=O)cc1] | HPLC-MS calculated for C$_{29}$H$_{23}$ClF$_3$N$_3$O$_3$ (M + H$^+$) 554.1, found 554.1. |
| 159 | 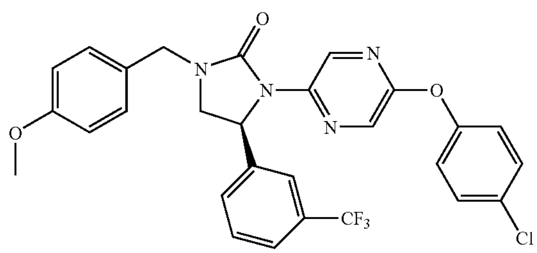 [SMILES: COc1ccc(CN2C[C@H](c3cccc(C(F)(F)F)c3)N(c3cnc(Oc4ccc(Cl)cc4)cn3)C2=O)cc1] | HPLC-MS calculated for C$_{28}$H$_{22}$ClF$_3$N$_4$O$_3$ (M + H$^+$) 555.1, found 555.1. |
| 160 | 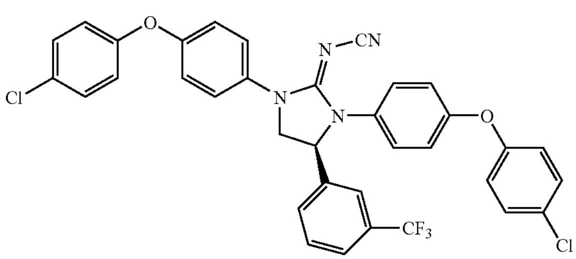 [SMILES: N#C/N=C1/N(c2ccc(Oc3ccc(Cl)cc3)cc2)C[C@H](c2cccc(C(F)(F)F)c2)N1c1ccc(Oc2ccc(Cl)cc2)cc1] | $^1$H NMR (CDCl$_3$, 400 MHz) δ 7.54~7.67 (m, 4H), 7.47 (d, 2H), 7.31 (d, 2H), 7.27 (d, 2H), 7.15 (d, 2H), 7.06 (d, 2H), 6.98 (d, 2H), 6.94 (d, 2H), 6.92 (d, 2H), 6.91 (d, 2H), 5.22 (dd, 1H), 4.49 (t, 1H), 3.95 (dd, 1H); HPLC-MS calculated for C$_{35}$H$_{23}$Cl$_2$F$_3$N$_4$O$_2$ (M + H$^+$) 659.1, found 659.1. |
| 161 | 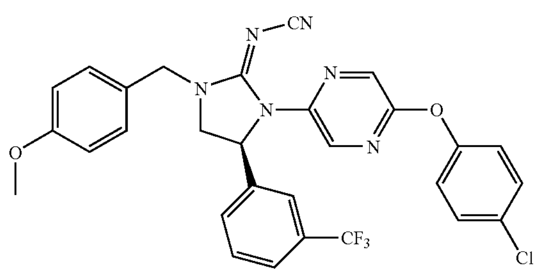 [SMILES: COc1ccc(CN2C[C@H](c3cccc(C(F)(F)F)c3)N(c3cnc(Oc4ccc(Cl)cc4)cn3)/C2=N\C#N)cc1] | $^1$H NMR (CDCl$_3$, 400 MHz) δ 8.51 (s, 1H), 8.06 (s, 1H), 7.54 (d, 1H), 7.40~7.47 (m, 3H), 7.34 (d, 2H), 7.30 (d, 2H), 7.06 (d, 2H), 6.90 (d, 2H), 5.56 (dd, 1H), 4.90 (s, 2H), 3.98 (t, 1H), 3.80 (s, 3H), 3.36 (dd, 1H); HPLC-MS calculated for C$_{29}$H$_{22}$ClF$_3$N$_6$O$_2$ (M + H$^+$) 579.1, found 579.1. |

TABLE 1-continued

| Compound Number | Structure | Physical Data $^1$H NMR 400 MHz (CDCl$_3$) and/or MS (m/z) |
|---|---|---|
| 162 | 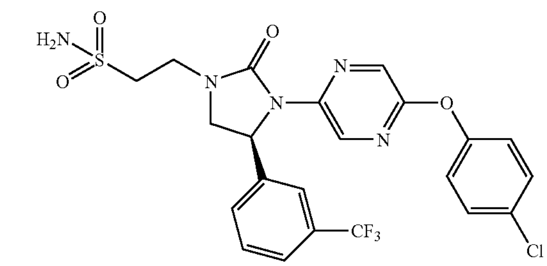 [SMILES: NS(=O)(=O)CCN1C[C@H](c2cccc(C(F)(F)F)c2)N(c2cnc(Oc3ccc(Cl)cc3)cn2)C1=O] | $^1$H NMR (CDCl$_3$, 400 MHz) δ 8.95 (d, 1H), 8.88 (d, 1H), 7.63 (s, 1H), 7.58 (d, 1H), 7.52 (d, 1H), 7.46 (t, 1H), 7.32 (d, 2H), 7.01 (d, 2H), 5.67 (q, 1H), 5.45 (s, 2H), 4.06 (q, 1H), 3.93 (t, 2H), 3.43 (q, 1H), 3.33 (t, 2H); HPLC-MS calculated for C$_{22}$H$_{19}$ClF$_3$N$_5$O$_4$S (M + H$^+$) 542.1, found 542.1. |
| 168 | 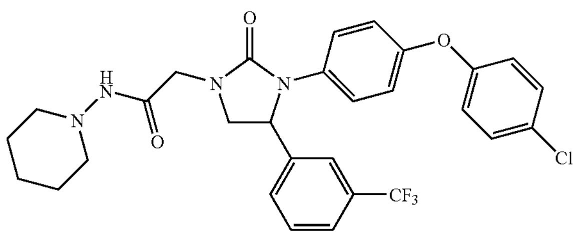 [SMILES: O=C(CN1CC(c2cccc(C(F)(F)F)c2)N(c2ccc(Oc3ccc(Cl)cc3)cc2)C1=O)NN1CCCCC1] | HPLC MS calculated for C$_{29}$H$_{28}$ClF$_3$N$_4$O$_3$ (M + H$^+$) 573.2, found 573.2. |
| 170 | 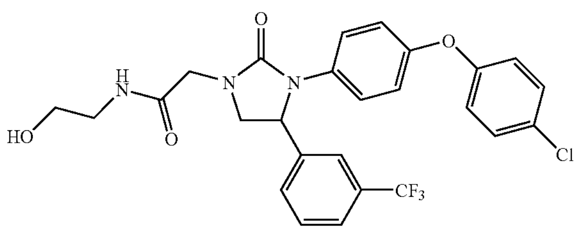 [SMILES: O=C(CN1CC(c2cccc(C(F)(F)F)c2)N(c2ccc(Oc3ccc(Cl)cc3)cc2)C1=O)NCCO] | HPLC-MS calculated for C$_{26}$H$_{23}$ClF$_3$N$_3$O$_4$ (M + H$^+$) 534.1, found 534.1. |
| 171 | 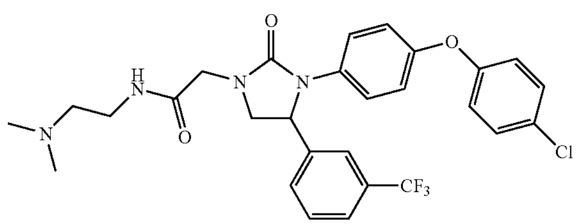 [SMILES: CN(C)CCNC(=O)CN1CC(c2cccc(C(F)(F)F)c2)N(c2ccc(Oc3ccc(Cl)cc3)cc2)C1=O] | HPLC-MS calculated for C$_{28}$H$_{28}$ClF$_3$N$_4$O$_3$ (M + H$^+$) 561.2, found 561.2. |
| 179 | 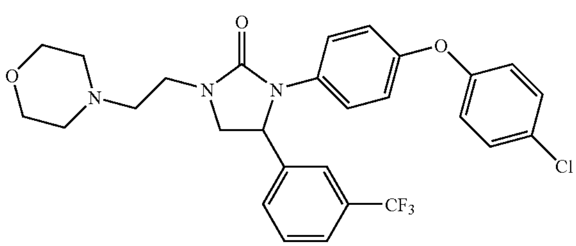 [SMILES: O=C1N(CCN2CCOCC2)CC(c2cccc(C(F)(F)F)c2)N1c1ccc(Oc2ccc(Cl)cc2)cc1] | HPLC-MS calculated for C$_{28}$H$_{27}$ClF$_3$N$_3$O$_3$ (M + H$^+$) 546.2, found 546.2. |
| 180 | 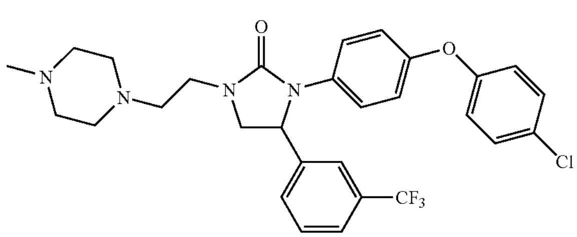 [SMILES: CN1CCN(CCN2CC(c3cccc(C(F)(F)F)c3)N(c3ccc(Oc4ccc(Cl)cc4)cc3)C2=O)CC1] | HPLC-MS calculated for C$_{29}$H$_{30}$ClF$_3$N$_4$O$_2$ (M + H$^+$) 559.2, found 559.2. |

TABLE 1-continued

| Compound Number | Structure | Physical Data<br>$^1$H NMR 400 MHz (CDCl$_3$)<br>and/or MS (m/z) |
|---|---|---|
| 182 | 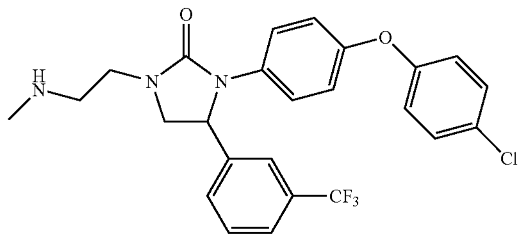 [SMILES: CNCCN1CC(c2cccc(C(F)(F)F)c2)N(c2ccc(Oc3ccc(Cl)cc3)cc2)C1=O] | HPLC-MS calculated for<br>$C_{25}H_{23}ClF_3N_3O_2$ (M + H$^+$)<br>490.1, found 490.1. |
| 183 | 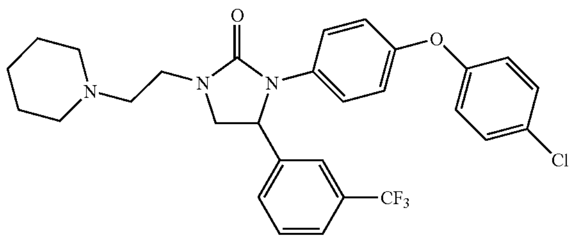 [SMILES: O=C1N(CCN2CCCCC2)CC(c2cccc(C(F)(F)F)c2)N1c1ccc(Oc2ccc(Cl)cc2)cc1] | HPLC-MS calculated for<br>$C_{29}H_{29}ClF_3N_3O_2$ (M + H$^+$)<br>544.2, found 544.2. |
| 186 | 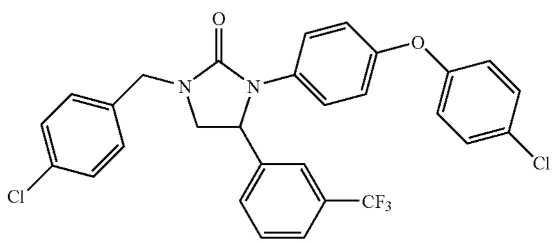 [SMILES: O=C1N(Cc2ccc(Cl)cc2)CC(c2cccc(C(F)(F)F)c2)N1c1ccc(Oc2ccc(Cl)cc2)cc1] | HPLC-MS calculated for<br>$C_{29}H_{21}Cl_2F_3N_2O_2$ (M + H$^+$)<br>557.1, found 557.1. |
| 187 | 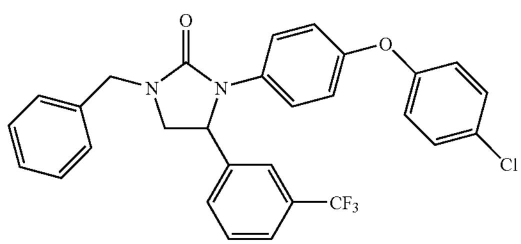 [SMILES: O=C1N(Cc2ccccc2)CC(c2cccc(C(F)(F)F)c2)N1c1ccc(Oc2ccc(Cl)cc2)cc1] | HPLC-MS calculated for<br>$C_{29}H_{22}ClF_3N_2O_2$ (M + H$^+$)<br>523.1, found 523.1. |
| 188 | 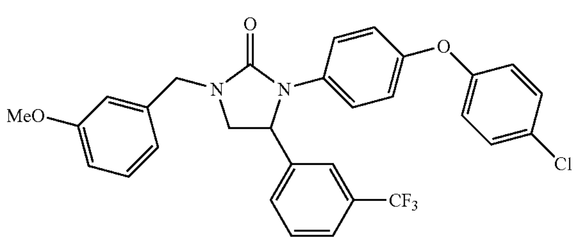 [SMILES: COc1cccc(CN2CC(c3cccc(C(F)(F)F)c3)N(c3ccc(Oc4ccc(Cl)cc4)cc3)C2=O)c1] | HPLC-MS calculated for<br>$C_{30}H_{24}ClF_3N_2O_3$ (M + H$^+$)<br>553.1, found 553.1. |
| 189 | 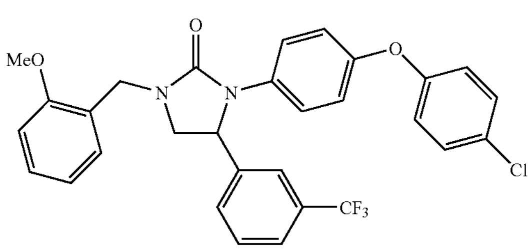 [SMILES: COc1ccccc1CN1CC(c2cccc(C(F)(F)F)c2)N(c2ccc(Oc3ccc(Cl)cc3)cc2)C1=O] | HPLC-MS calculated for<br>$C_{27}H_{21}ClFN_5O_2$ (M + H$^+$):<br>502.1.0, found: 502.1.<br>501.94 |

TABLE 1-continued

| Compound Number | Structure | Physical Data $^1$H NMR 400 MHz (CDCl$_3$) and/or MS (m/z) |
|---|---|---|
| 191 | 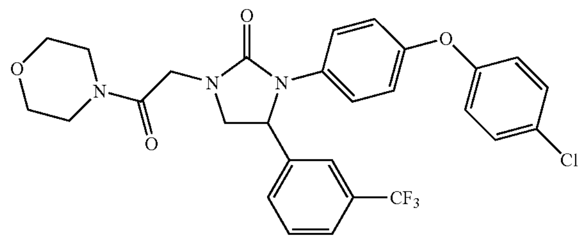 [SMILES: O=C(CN1CC(c2cccc(C(F)(F)F)c2)N(c2ccc(Oc3ccc(Cl)cc3)cc2)C1=O)N1CCOCC1] | HPLC-MS calculated for C$_{28}$H$_{25}$ClF$_3$N$_3$O$_4$ (M + H$^+$) 560.1, found 560.1. |
| 192 | 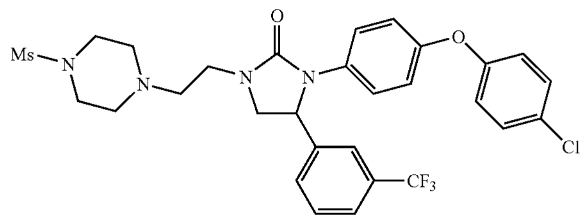 [SMILES: CS(=O)(=O)N1CCN(CCN2CC(c3cccc(C(F)(F)F)c3)N(c3ccc(Oc4ccc(Cl)cc4)cc3)C2=O)CC1] | HPLC-MS calculated for C$_{29}$H$_{30}$ClF$_3$N$_4$O$_4$S (M + H$^+$) 623.2, found 623.2. |
| 193 | 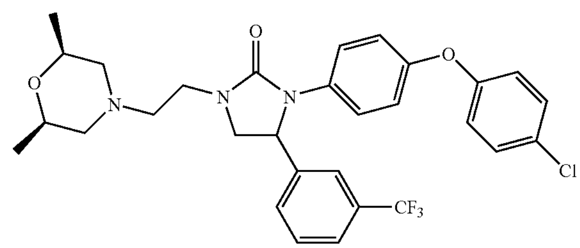 [SMILES: C[C@@H]1CN(CCN2CC(c3cccc(C(F)(F)F)c3)N(c3ccc(Oc4ccc(Cl)cc4)cc3)C2=O)C[C@H](C)O1] | HPLC-MS calculated for C$_{30}$H$_{31}$ClF$_3$N$_3$O$_3$ (M + H$^+$) 574.2, found 574.2. |
| 195 | 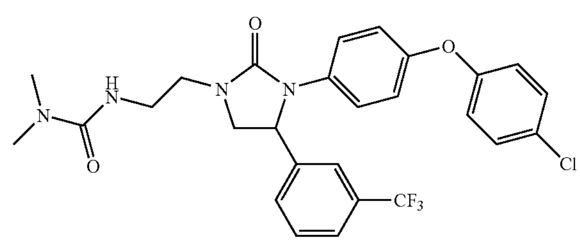 [SMILES: CN(C)C(=O)NCCN1CC(c2cccc(C(F)(F)F)c2)N(c2ccc(Oc3ccc(Cl)cc3)cc2)C1=O] | HPLC-MS calculated for C$_{27}$H$_{26}$ClF$_3$N$_4$O$_3$ (M + H$^+$) 547.2, found 547.2. |
| 196 | 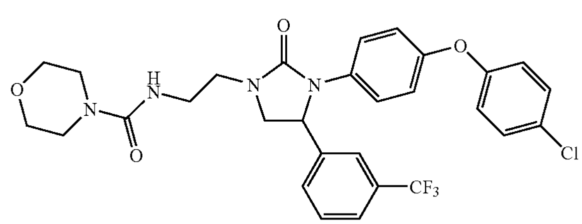 [SMILES: O=C(NCCN1CC(c2cccc(C(F)(F)F)c2)N(c2ccc(Oc3ccc(Cl)cc3)cc2)C1=O)N1CCOCC1] | HPLC-MS calculated for C$_{29}$H$_{28}$ClF$_3$N$_4$O$_4$ (M + H$^+$) 589.2, found 589.2. |
| 197 | 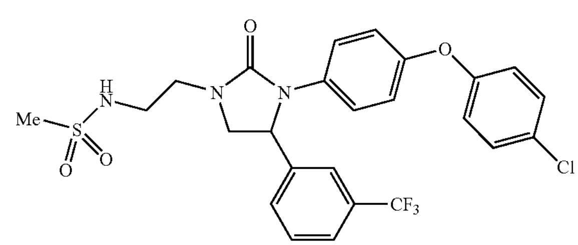 [SMILES: CS(=O)(=O)NCCN1CC(c2cccc(C(F)(F)F)c2)N(c2ccc(Oc3ccc(Cl)cc3)cc2)C1=O] | HPLC-MS calculated for C$_{25}$H$_{23}$ClF$_3$N$_3$O$_4$S (M + H$^+$) 554.1, found 554.1. |

TABLE 1-continued

| Compound Number | Structure | Physical Data<br>$^1$H NMR 400 MHz (CDCl$_3$) and/or MS (m/z) |
|---|---|---|
| 198 | 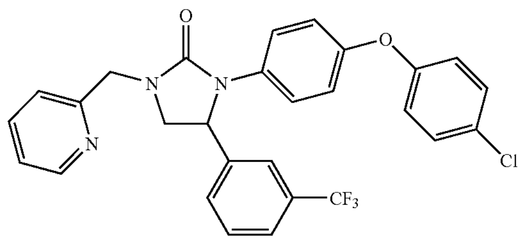 [SMILES: O=C1N(Cc2ccccn2)CC(c2cccc(C(F)(F)F)c2)N1c1ccc(Oc2ccc(Cl)cc2)cc1] | HPLC-MS calculated for C$_{28}$H$_{21}$ClF$_3$N$_3$O$_2$ (M + H$^+$) 524.1, found 524.1. |
| 199 | 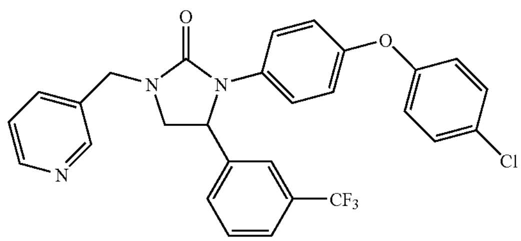 [SMILES: O=C1N(Cc2cccnc2)CC(c2cccc(C(F)(F)F)c2)N1c1ccc(Oc2ccc(Cl)cc2)cc1] | HPLC-MS calculated for C$_{28}$H$_{21}$ClF$_3$N$_3$O$_2$ (M + H$^+$) 524.1, found 524.1. |
| 200 | 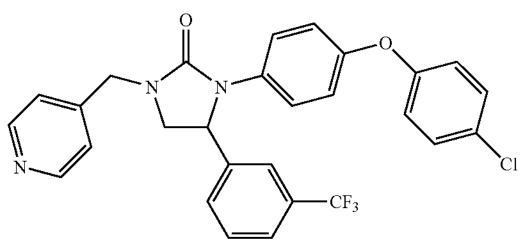 | HPLC-MS calculated for C$_{28}$H$_{21}$ClF$_3$N$_3$O$_2$ (M + H$^+$) 524.1, found 524.1. |
| 202 | 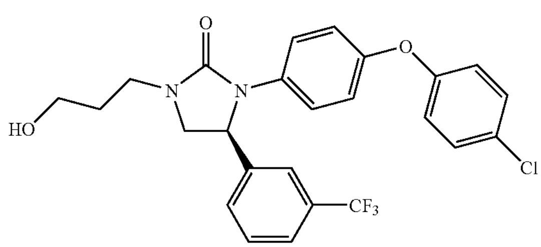 [SMILES: O=C1N(CCCO)C[C@H](c2cccc(C(F)(F)F)c2)N1c1ccc(Oc2ccc(Cl)cc2)cc1] | $^1$H NMR (CDCl$_3$, 400 MHz) δ 7.57 (m, 2H), 7.49 (m, 2H), 7.30 (d, 2H), 7.24 (d, 2H), 6.87 (m, 4H), 5.26 (dd, 1H), 3.97 (t, 1H), 3.67 (q, 2H), 3.50 (m, 2H), 3.26 (dd, 1H), 3.20 (t, 1H), 1.75 (m, 2H); HPLC-MS calculated for C$_{25}$H$_{22}$ClF$_3$N$_2$O$_3$ (M + H$^+$) 491.1, found 491.1. |
| 204 | 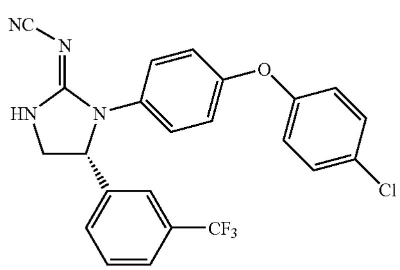 | $^1$H NMR (CDCl$_3$, 400 MHz) δ 7.60 (m, 1H), 7.51 (m, 3H), 7.27 (d, 2H), 7.15 (d, 2H), 6.88 (m, 4H), 6.65 (br, 1H), 5.40 (dd, 1H), 4.21 (t, 1H), 3.63 (dd, 1H); HPLC-MS calculated for C$_{23}$H$_{16}$ClF$_3$N$_4$O (M + H$^+$) 457.1, found 457.1. |
| 205 | 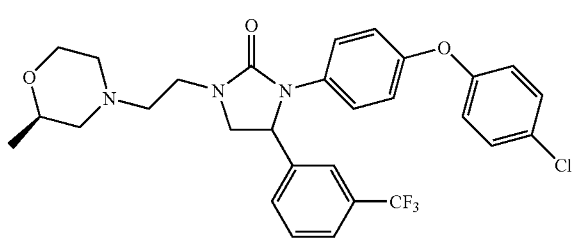 [SMILES: C[C@@H]1CN(CCN2CC(c3cccc(C(F)(F)F)c3)N(c3ccc(Oc4ccc(Cl)cc4)cc3)C2=O)CCO1] | HPLC-MS calculated for C$_{29}$H$_{29}$ClF$_3$N$_3$O$_3$ (M + H$^+$) 560.2, found 560.2. |

TABLE 1-continued

| Compound Number | Structure | Physical Data<br>$^1$H NMR 400 MHz (CDCl$_3$)<br>and/or MS (m/z) |
|---|---|---|
| 206 | 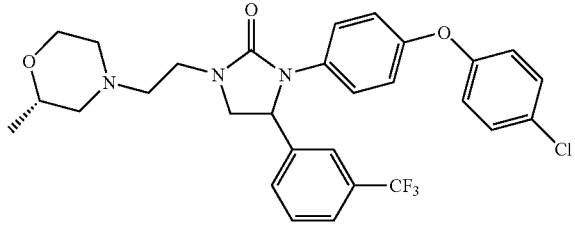 [SMILES: C[C@H]1CN(CCN2CC(c3cccc(C(F)(F)F)c3)N(c3ccc(Oc4ccc(Cl)cc4)cc3)C2=O)CCO1] | HPLC-MS calculated for<br>$C_{29}H_{29}ClF_3N_3O_3$ (M + H$^+$)<br>560.2, found 560.2. |
| 207 | 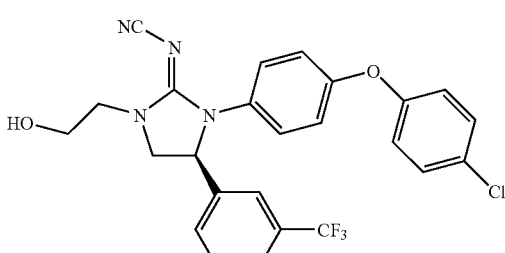 | HPLC-MS calculated for<br>$C_{25}H_{20}ClF_3N_4O_2$ (M + H$^+$)<br>501.1, found 501.1. |
| 209 | 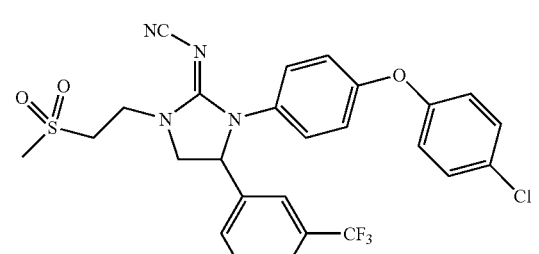 | HPLC-MS calculated for<br>$C_{26}H_{22}ClF_3N_4O_3S$ (M + H$^+$)<br>563.1, found 563.1. |
| 210 | 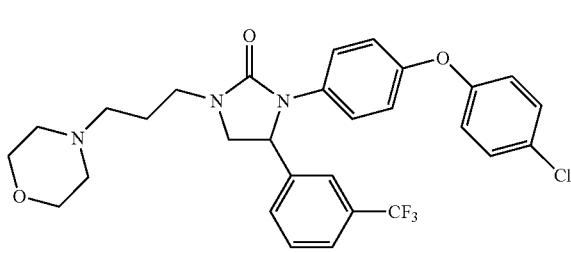 [SMILES: O=C1N(CCCN2CCOCC2)CC(c2cccc(C(F)(F)F)c2)N1c1ccc(Oc2ccc(Cl)cc2)cc1] | HPLC-MS calculated for<br>$C_{29}H_{29}ClF_3N_3O_3$ (M + H$^+$)<br>560.2, found 560.2. |
| 211 | 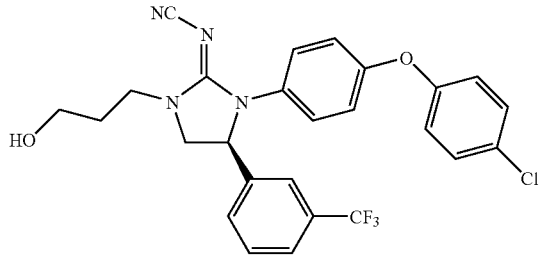 | HPLC-MS calculated for<br>$C_{26}H_{22}ClF_3N_4O_2$ (M + H$^+$)<br>515.1, found 515.1. |
| 212 | 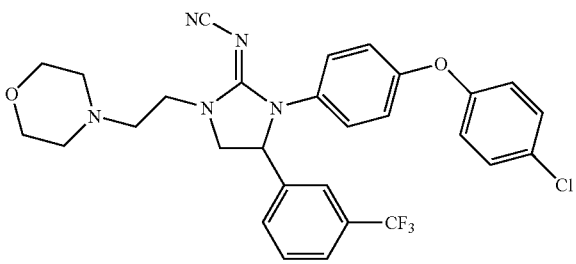 | HPLC-MS calculated for<br>$C_{29}H_{27}ClF_3N_5O_2$ (M + H$^+$)<br>570.2, found 570.2. |

TABLE 1-continued

| Compound Number | Structure | Physical Data $^1$H NMR 400 MHz (CDCl$_3$) and/or MS (m/z) |
|---|---|---|
| 213 | 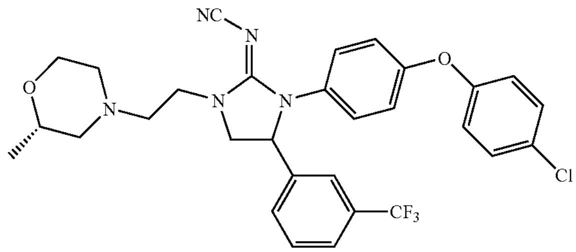 | HPLC-MS calculated for C$_{30}$H$_{29}$ClF$_3$N$_5$O$_2$ (M + H$^+$) 584.2, found 584.2. |
| 214 | 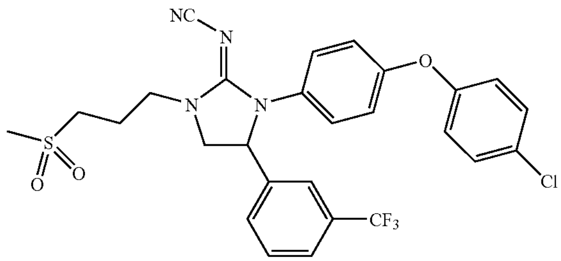 | HPLC-MS calculated for C$_{27}$H$_{24}$ClF$_3$N$_4$O$_3$S (M + H$^+$) 577.1, found 577.1. |
| 215 | 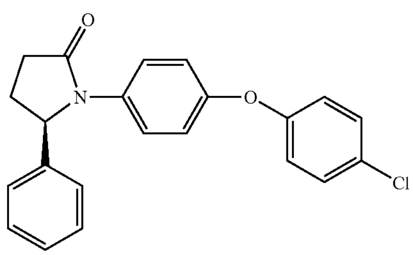 [SMILES: O=C1CC[C@H](c2ccccc2)N1c1ccc(Oc2ccc(Cl)cc2)cc1] | $^1$H NMR (CDCl$_3$) δ (ppm) 7.41-7.32 (m, 4H), 7.31-7.23 (m, 5H), 6.92-6.87 (m, 4H), 5.24 (dd, J = 7.4, 4.6 Hz, 1H), 2.82-2.78 (m, 1H), 2.71-2.58 (m, 2H), 2.10-2.01 (m, 1H). HPLC-MS calculated C$_{22}$H$_{18}$ClNO$_2$ (M + H$^+$): 364.11, found: 364.10. |
| 216 | 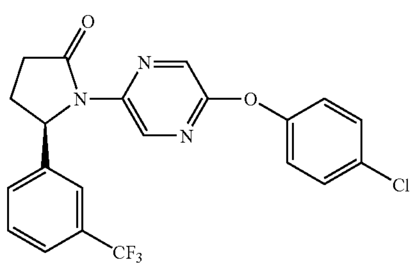 [SMILES: O=C1CC[C@H](c2cccc(C(F)(F)F)c2)N1c1cnc(Oc2ccc(Cl)cc2)cn1] | $^1$H NMR (CDCl$_3$) δ (ppm) 9.13 (d, J = 1.6 Hz, 1H), 7.96 (d, J = 1.2 Hz, 1H), 7.53-7.49 (m, 2H), 7.46-7.31 (m, 4H), 7.08-7.02 (m, 2H), 5.74 (dd, J = 8.2, 3.8 Hz, 1H), 2.91-2.79 (m, 1H), 2.78-2.63 (m, 2H), 2.11-2.00 (m, 1H). HPLC-MS calculated C$_{21}$H$_{15}$ClF$_3$N$_3$O$_2$ (M + H$^+$): 434.08, found: 434.10. |
| 217 | 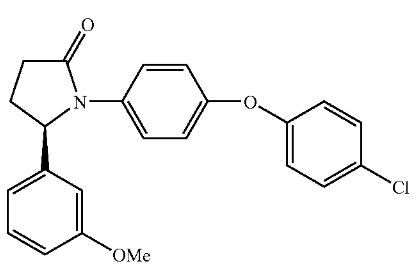 [SMILES: COc1cccc([C@H]2CCC(=O)N2c2ccc(Oc3ccc(Cl)cc3)cc2)c1] | $^1$H NMR (CDCl$_3$) δ (ppm) 7.63-7.38 (m, 2H), 7.32-7.27 (m, 2H), 6.95-6.73 (m, 7H), 5.21 (dd, J = 7.4, 4.6 Hz, 1H), 3.81 (s, 3H), 2.87-2.73 (m, 1H), 2.72-2.60 (m, 2H), 2.10-1.99 (m, 1H). HPLC-MS calculated C$_{23}$H$_{20}$ClNO$_3$ (M + H$^+$): 394.12, found: 394.10. |
| 218 | 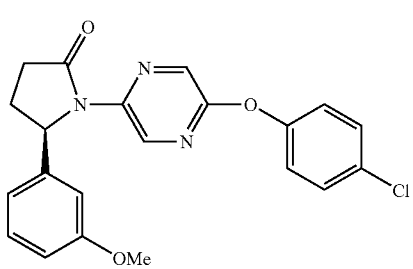 [SMILES: COc1cccc([C@H]2CCC(=O)N2c2cnc(Oc3ccc(Cl)cc3)cn2)c1] | $^1$H NMR (CDCl$_3$) δ (ppm) 9.11 (d, J = 1.2 Hz), 7.99 (d, J = 1.6 Hz, 1H), 7.37-7.31 (m, 1H), 7.22 (t, J = 8.0 Hz, 1H), 7.07-7.02 (m, 2H), 6.81-6.72 (m, 3H), 5.68 (dd, J = 8.2, 3.8 Hz, 1H), 3.77 (s, 3H), 2.89-2.74 (m, 1H), 2.72-2.57 (m, 2H), 2.10-1.99 (m, 1H). HPLC-MS calculated C$_{21}$H$_{18}$ClN$_3$O$_3$ (M + H$^+$): 396.11, found: 396.10. |

TABLE 1-continued

| Compound Number | Structure | Physical Data $^1$H NMR 400 MHz (CDCl$_3$) and/or MS (m/z) |
|---|---|---|
| 219 | 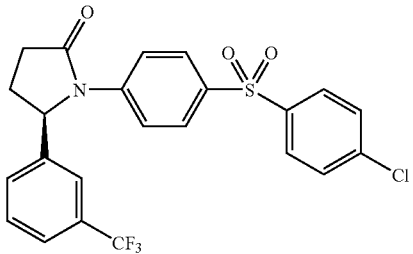 [SMILES: O=C1CC[C@H](c2cccc(C(F)(F)F)c2)N1c1ccc(S(=O)(=O)c2ccc(Cl)cc2)cc1] | HPLC-MS calculated for C$_{23}$H$_{17}$ClF$_3$NO$_3$S (M + H$^+$) 480.06, found 480.06. |
| 220 | 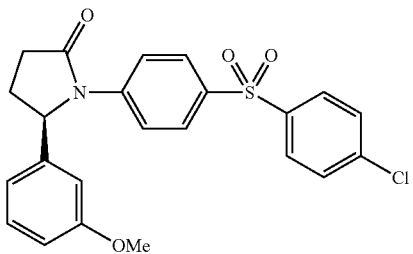 [SMILES: COc1cccc([C@H]2CCC(=O)N2c2ccc(S(=O)(=O)c3ccc(Cl)cc3)cc2)c1] | $^1$H NMR (CDCl$_3$) δ (ppm) 7.84-7.75 (m, 4H), 7.67-7.61 (m, 2H), 7.59-7.41 (m, 2H), 7.24 (t, J = 7.6 Hz, 1H), 6.82-6.77 (m, 1H), 6.77-6.72 (m, 1H), 6.70-6.66 (m, 1H), 5.21 (dd, J = 7.6, 4.0 Hz, 1H), 3.75 (s, 3H), 2.82-2.69 (m, 1H), 2.69-2.54 (m, 2H), 2.04-1.96 (m, 1H). HPLC-MS calculated for C$_{23}$H$_{20}$ClNO$_4$S (M + H$^+$) 442.08, found 442.10. |
| 221 | 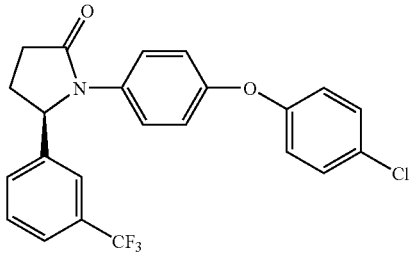 | $^1$H NMR (CDCl$_3$) δ 7.60-7.50 (m, 1H), 7.49-7.37 (m, 3H), 7.34-7.28 (m, 2H), 7.27-7.21 (m, 2H), 6.91-6.67 (m, 4H), 5.28 (dd, J = 6.8, 5.6 Hz, 1H), 2.84-2.59 (m, 3H), 2.07-1.94 (m, 1H). HPLC-MS calculated for C$_{23}$H$_{17}$ClF$_3$NO$_2$ (M + H$^+$) 432.09, found 432.10. |
| 223 | 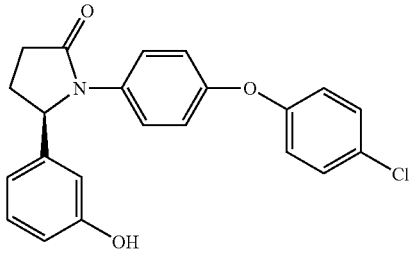 | $^1$H NMR (CDCl$_3$) δ 7.58-7.32 (m, 2H), 7.27-7.16 (m, 3H), 6.88-6.79 (m, 4H), 6.77-6.66 (m, 3H), 5.15 (dd, J = 8.0, 3.2 Hz, 1H), 2.82-2.54 (m, 3H), 2.04-1.92 (m, 1H). HPLC-MS calculated for C$_{22}$H$_{18}$ClNO$_3$ (M + H$^+$) 380.10, found 380.10. |
| 224 | 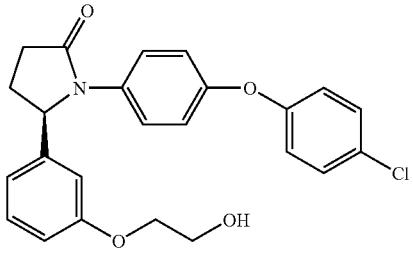 [SMILES: O=C1CC[C@H](c2cccc(OCCO)c2)N1c1ccc(Oc2ccc(Cl)cc2)cc1] | $^1$H NMR (CDCl$_3$) δ 7.62-7.36 (m, 2H), 7.30-7.23 (m, 3H), 6.93-6.71 (m, 7H), 5.19 (dd, J = 7.4, 4.6 Hz, 1H), 4.11-4.00 (m, 2H), 4.00-3.94 (m, 2H), 2.86-2.72 (m, 1H), 2.71-2.58 (m, 2H), 2.10-1.90 (m, 2H). HPLC-MS calculated for C$_{24}$H$_{22}$ClNO$_4$ (M + H$^+$) 424.13, found 424.10. |

TABLE 1-continued
| Compound Number | Structure | Physical Data<br>¹H NMR 400 MHz (CDCl₃) and/or MS (m/z) |
|---|---|---|
| 225 | 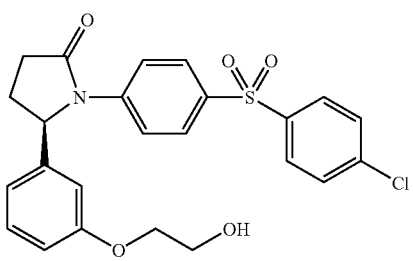 [SMILES: O=C1CC[C@H](c2cccc(OCCO)c2)N1c1ccc(S(=O)(=O)c2ccc(Cl)cc2)cc1] | HPLC-MS calculated for $C_{24}H_{22}ClNO_5S$ (M + H⁺) 472.09, found 472.10. |
| 226 | 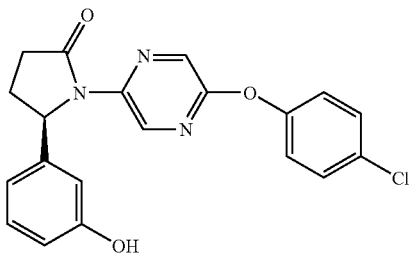 [SMILES: O=C1CC[C@H](c2cccc(O)c2)N1c1cnc(Oc2ccc(Cl)cc2)cn1] | HPLC-MS calculated for $C_{20}H_{16}ClN_3O_3$ (M + H⁺) 382.09, found 382.10 |
| 227 | 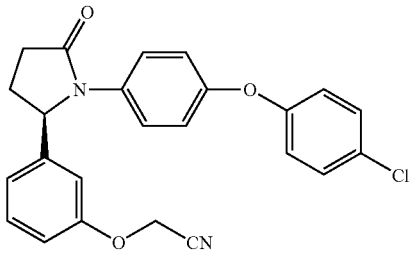 [SMILES: N#CCOc1cccc([C@H]2CCC(=O)N2c2ccc(Oc3ccc(Cl)cc3)cc2)c1] | ¹H NMR (CDCl₃) 7.60-7.22 (m, 5H), 6.98-6.68 (m, 7H), 5.20 (dd, J = 7.2, 4.8 Hz, 1H), 4.73 (s, 2H), 2.83-2.72 (m, 1H), 2.71-2.58 (m, 2H), 2.06-1.97 (m, 1H). HPLC-MS calculated for $C_{24}H_{19}ClN_2O_3$ (M + H⁺) 419.11, found 419.10. |
| 229 | 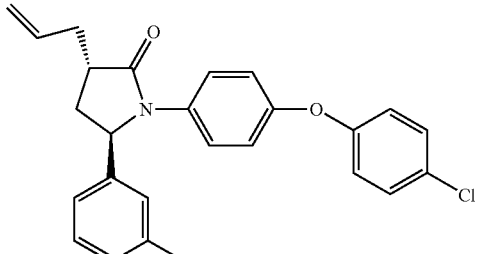 | HPLC-MS calculated for $C_{26}H_{21}ClF_3NO_2$ (M + H⁺) 472.12, found 472.10. |
| 230 | 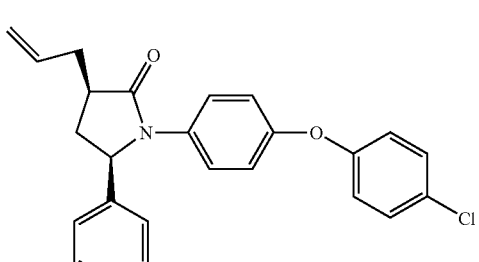 | HPLC-MS calculated for $C_{26}H_{21}ClF_3NO_2$ (M + H⁺) 472.12, found 472.10. |

TABLE 1-continued

| Compound Number | Structure | Physical Data<br>¹H NMR 400 MHz (CDCl₃) and/or MS (m/z) |
|---|---|---|
| 231 | 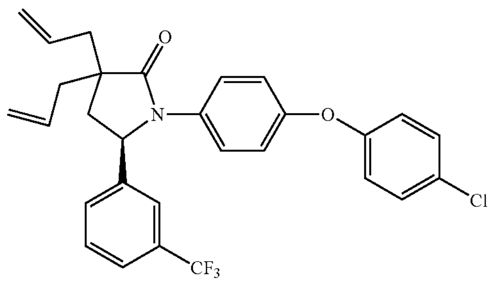 [SMILES: C=CCC1(CC=C)C[C@H](c2cccc(C(F)(F)F)c2)N(c2ccc(Oc3ccc(Cl)cc3)cc2)C1=O] | HPLC-MS calculated for $C_{29}H_{25}ClF_3NO_2$ (M + 2) 513.15, found 513.10. |
| 232 | 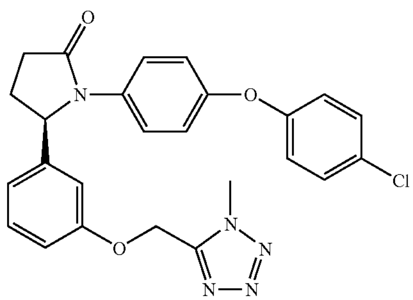 [SMILES: Cn1nnnc1COc1cccc([C@H]2CCC(=O)N2c2ccc(Oc3ccc(Cl)cc3)cc2)c1] | HPLC-MS calculated for $C_{25}H_{22}ClN_5O_3$ (M + H⁺) 476.14, found 476.10. |
| 233 | 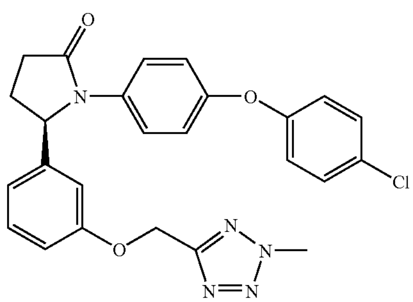 [SMILES: Cn1nnc(COc2cccc([C@H]3CCC(=O)N3c3ccc(Oc4ccc(Cl)cc4)cc3)c2)n1] | HPLC-MS calculated for $C_{25}H_{22}ClN_5O_3$ (M + H⁺) 476.14, found 476.10. |
| 234 | 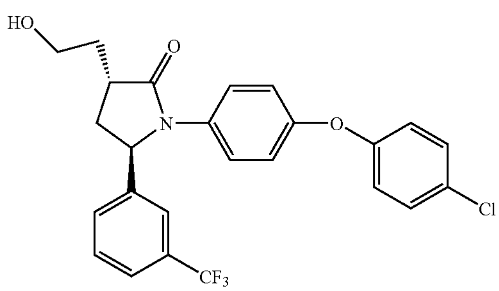 [SMILES: O=C1[C@@H](CCO)C[C@H](c2cccc(C(F)(F)F)c2)N1c1ccc(Oc2ccc(Cl)cc2)cc1] | ¹H NMR (CDCl₃) δ 7.51-7.46 (m, 1H), 7.44-7.37 (m, 2H), 7.36-7.30 (m, 3H), 7.21-7.16 (m, 2H), 6.87-6.78 (m, 4H), 5.21 (dd, J = 10.5, 2.0 Hz, 1H), 3.85-3.68 (m, 2H), 2.97-2.85 (m, 1H), 2.45-2.32 (m, 1H), 2.26-2.15 (m, 2H), 2.10-1.98 (m, 1H), 1.80-1.69 (m, 1H). HPLC-MS calculated for $C_{25}H_{21}ClF_3NO_3$ (M + H⁺) 476.12, found 476.10. |
| 235 | 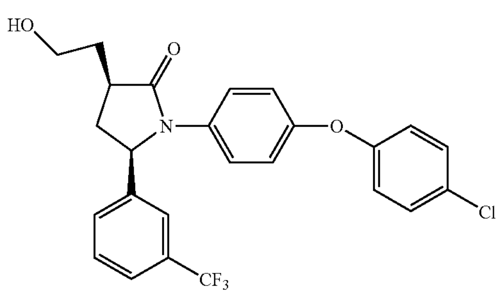 [SMILES: O=C1[C@H](CCO)C[C@H](c2cccc(C(F)(F)F)c2)N1c1ccc(Oc2ccc(Cl)cc2)cc1] | ¹H NMR (CDCl₃) δ 7.46-7.40 (m, 1H), 7.39-7.29 (m, 3H), 7.20-7.11 (m, 4H), 6.82-6.75 (m, 4H), 5.17 (dd, J = 11.5, 8.3 Hz, 1H), 3.87-3.71 (m, 2H), 2.92-2.73 (m, 2H), 2.16-2.01 (m, 2H), 1.86-1.76 (m, 1H), 1.75-1.62 (m, 1H). HPLC-MS calculated for $C_{25}H_{21}ClF_3NO_3$ (M + H⁺) 476.12, found 476.10. |

TABLE 1-continued

| Compound Number | Structure | Physical Data<br>$^1$H NMR 400 MHz (CDCl$_3$)<br>and/or MS (m/z) |
|---|---|---|
| 236 | 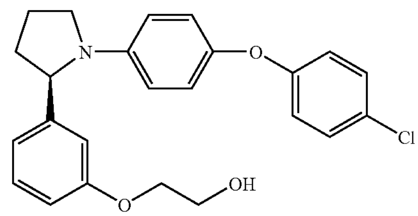 [SMILES: OCCOc1cccc([C@H]2CCCN2c2ccc(Oc3ccc(Cl)cc3)cc2)c1] | HPLC-MS calculated for C$_{24}$H$_{24}$ClNO$_3$ (M + H$^+$) 410.14, found 410.10. |
| 237 | 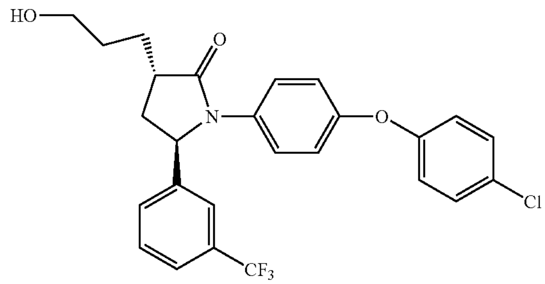 [SMILES: O=C1[C@@H](CCCO)C[C@H](c2cccc(C(F)(F)F)c2)N1c1ccc(Oc2ccc(Cl)cc2)cc1] | $^1$H NMR (CDCl$_3$) δ 7.60-7.51 (m, 1H), 7.50-7.43 (m, 2H), 7.43-7.35 (m, 3H), 7.28-7.22 (m, 2H), 6.93-6.83 (m, 4H), 5.24 (dd, J = 10.5, 3.0 Hz, 1H), 3.70 (t, J = 7.2 Hz, 2H), 2.87-2.75 (m, 1H), 2.45-2.33 (m, 1H), 2.26-2.16 (m, 1H), 2.11-1.98 (m, 1H), 1.87 (s, br, 1H), 1.75-1.58 (m, 3H). HPLC-MS calculated for C$_{26}$H$_{23}$ClF$_3$NO$_3$ (M + H$^+$) 490.13, found 490.10. |
| 238 | 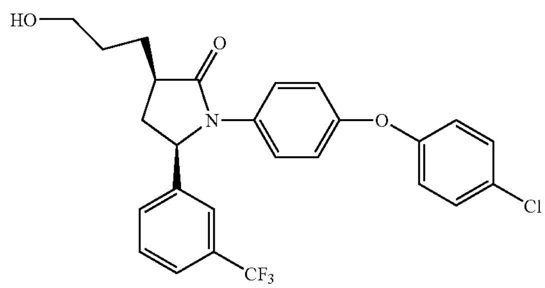 [SMILES: O=C1[C@H](CCCO)C[C@H](c2cccc(C(F)(F)F)c2)N1c1ccc(Oc2ccc(Cl)cc2)cc1] | $^1$H NMR (CDCl$_3$) δ 7.51-7.46 (m, 1H), 7.45-7.34 (m, 3H), 7.26-7.24 (m, 1H), 7.24-7.21 (m, 2H), 7.21-7.19 (m, 1H), 6.89-6.81 (m, 4H), 5.20 (dd, J = 11.3, 8.3 Hz, 1H), 3.73 (t, J = 7.5 Hz, 2H), 2.89-2.71 (m, 2H), 2.18-2.06 (m, 1H), 1.75 (s, br, 1H), 1.74-1.62 (m, 4H). HPLC-MS calculated for C$_{26}$H$_{23}$ClF$_3$NO$_3$ (M + H$^+$) 490.13, found 490.10. |
| 239 | 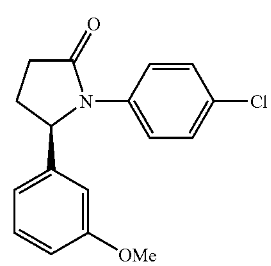 [SMILES: COc1cccc([C@H]2CCC(=O)N2c2ccc(Cl)cc2)c1] | $^1$H NMR (CDCl$_3$) δ 7.44-7.38 (m, 2H), 7.29-7.20 (m, 3H), 6.83-6.77 (m, 2H), 6.75-6.72 (m, 1H), 5.20 (dd, J = 10.0, 5.5 Hz, 1H), 3.77 (s, 3H), 2.84-2.73 (m, 1H), 2.72-2.56 (m, 2H), 2.07-1.96 (m, 1H). HPLC-MS calculated for C$_{17}$H$_{16}$ClNO$_2$ (M + H$^+$) 302.09, found 302.10. |
| 240 | 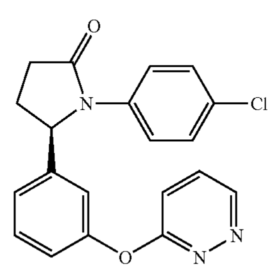 [SMILES: O=C1CC[C@H](c2cccc(Oc3cccnn3)c2)N1c1ccc(Cl)cc1] | $^1$H NMR (CDCl$_3$) δ 8.98 (d, J = 5.0 Hz, 1H), 7.55 (dd, J = 11.0, 5.5 Hz, 1H), 7.41-7.35 (m, 3H), 7.25-7.20 (m, 2H), 7.17 (dd, J = 11.0, 1.0 Hz, 1H), 7.12 (ddd, J = 10.5, 3.0, 1.0 Hz, 1H), 7.09 (d, J = 9.5 Hz, 1H), 7.06-7.02 (m, 1H), 5.23 (dd, J = 10.0, 6.0 Hz, 1H), 2.80-2.52 (m, 3H), 2.11-2.02 (m, 1H). HPLC-MS calculated for C$_{20}$H$_{16}$ClN$_3$O$_2$ (M + H$^+$) 366.09, found 366.00. |

TABLE 1-continued

| Compound Number | Structure | Physical Data<br>¹H NMR 400 MHz (CDCl₃)<br>and/or MS (m/z) |
|---|---|---|
| 241 | 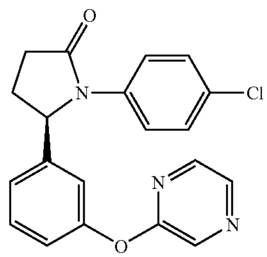 [SMILES: O=C1CC[C@H](c2cccc(Oc3cnccn3)c2)N1c1ccc(Cl)cc1] | ¹H NMR (CDCl₃) δ 8.39 (s, 1H), 8.28 (d, J = 3.0 Hz, 1H), 8.05 (dd, J = 3.0, 1.5 Hz, 1H), 7.41-7.33 (m, 3H), 7.22 (d, J = 11.0 Hz, 2H), 7.12-7.04 (m, 2H), 7.00-6.96 (m, 1H), 5.23 (dd, J = 10.0, 5.5 Hz, 1H), 2.79-2.56 (m, 3H), 2.10-2.02 (m, 1H). HPLC-MS calculated for $C_{20}H_{16}ClN_3O_2$ (M + H⁺) 366.09, found 366.00. |
| 242 | 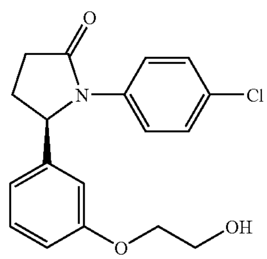 [SMILES: O=C1CC[C@H](c2cccc(OCCO)c2)N1c1ccc(Cl)cc1] | ¹H NMR (CDCl₃) δ 7.39 (d, J = 11.0 Hz, 2H), 7.25-7.17 (m, 3H), 6.83-6.77 (m, 2H), 6.75-6.72 (m, 1H), 5.17 (dd, J = 10.0, 6.0 Hz, 1H), 4.08-3.96 (m, 2H), 3.94 (t, J = 5.5 Hz, 2H), 2.82-2.71 (m, 1H), 2.70-2.55 (m, 2H), 2.05-1.93 (m, 1H), 1.76 (s, br, 1H). HPLC-MS calculated for $C_{18}H_{18}ClNO_3$ (M + H⁺) 332.10, found 332.00. |
| 245 | 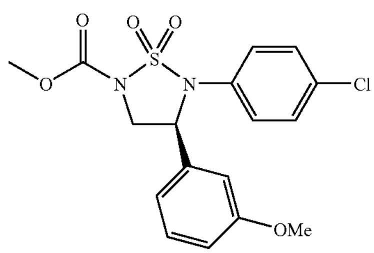 | ¹H NMR (CDCl₃) δ 7.24-7.13 (m, 5H), 6.85 (d, J = 8.5 Hz, 1H), 6.79 (t, J = 4.0 Hz), 6.75 (ddd, J = 10.5, 3.0, 1.0 Hz, 1H), 5.01 (dd, J = 12.5, 8.0 Hz, 1H), 4.20 (dd, J = 12.5, 8.0 Hz, 1H), 3.88 (s, 3H), 3.75 (t, J = 12.5 Hz, 1H), 3.68 (s, 3H), HPLC-MS calculated for $C_{17}H_{17}ClN_2O_5S$ (M + H⁺) 397.05, found 397.10. |
| 246 | 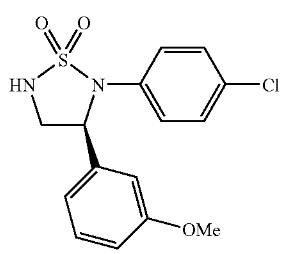 [SMILES: COc1cccc([C@H]2CNS(=O)(=O)N2c2ccc(Cl)cc2)c1] | ¹H NMR (CDCl₃) δ 7.29 (t, J = 10.0 Hz, 1H), 7.23 (d, J = 11.5 Hz, 2H), 7.10 (d, J = 11.5 Hz, 2H), 6.96 (d, J = 8.5 Hz, 1H), 6.89 (d, J = 3.0 Hz, 1H), 6.85 (ddd, J = 10.5, 3.0, 1.0 Hz, 1H), 5.15 (t, J = 7.5 Hz, 1H), 4.75-4.61 (m, 1H), 4.06-3.94 (m, 1H) 3.78 (s, 3H), 3.46 (ddd, J = 15.3, 9.0, 6.5 Hz, 1H). HPLC-MS calculated for $C_{15}H_{15}ClN_2O_3S$ (M + 2) 339.05, found 339.00. |
| 247 | 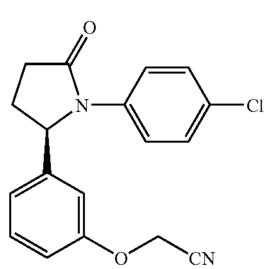 [SMILES: N#CCOc1cccc([C@H]2CCC(=O)N2c2ccc(Cl)cc2)c1] | ¹H NMR (CDCl₃) δ 7.37 (d, J = 11.5 Hz, 2H), 7.31 (t, J = 10.0 Hz, 1H), 7.21 (d, J = 11.5 Hz, 2H), 6.93 (d, J = 10.0 Hz, 1H), 6.87 (ddd, J = 10.0, 3.0, 1.0 Hz, 1H), 6.82-6.78 (m, 1H), 5.21 (dd, J = 9.5, 6.0 Hz, 1H), 4.73 (s, 2H), 2.80-2.70 (m, 1H), 2.70-2.53 (m, 2H), 2.03-1.92 (m, 1H). HPLC-MS calculated for $C_{18}H_{15}ClN_2O_2$ (M + H⁺) 327.08, found 327.10. |

TABLE 1-continued

| Compound Number | Structure | Physical Data $^1$H NMR 400 MHz (CDCl$_3$) and/or MS (m/z) |
|---|---|---|
| 248 | 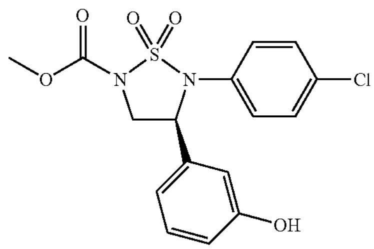 [SMILES: COC(=O)N1C[C@H](c2cccc(O)c2)N(c2ccc(Cl)cc2)S1(=O)=O] | HPLC-MS calculated for C$_{16}$H$_{15}$ClN$_2$O$_5$S (M + H$^+$) 383.04, found 383.10. |
| 249 | 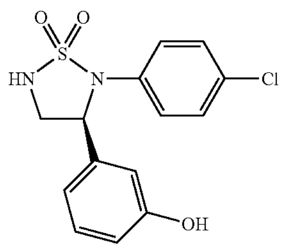 [SMILES: O=S1(=O)NC[C@H](c2cccc(O)c2)N1c1ccc(Cl)cc1] | HPLC-MS calculated for C$_{14}$H$_{13}$ClN$_2$O$_3$S (M + H$^+$) 325.03, found 325.00. |
| 250 | 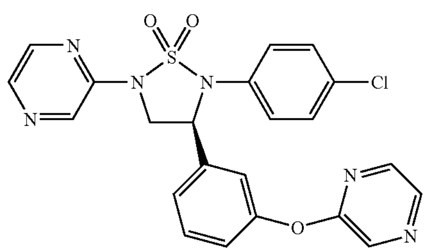 [SMILES: O=S1(=O)N(c2cnccn2)C[C@H](c2cccc(Oc3cnccn3)c2)N1c1ccc(Cl)cc1] | $^1$H NMR (CDCl$_3$) δ 8.83 (s, br, 1H), 8.41 (s, br, 1H), 8.36 (s, br, 1H), 8.30 (s, br, 2H), 8.05 (s, br, 1H), 7.42 (t, J = 10.0 Hz, 1H), 7.35-7.24 (m, 6H), 7.15 (dd, J = 10.0, 2.5 Hz, 1H), 5.32 (dd, J = 11.0, 8.5 Hz, 1H), 4.55 (dd, J = 13.0, 8.5 Hz, 1H), 4.08 (t, J = 12.5 Hz, 1H). HPLC-MS calculated for C$_{22}$H$_{17}$ClN$_6$O$_3$S (M + H$^+$) 481.08, found 481.10. |
| 251 | 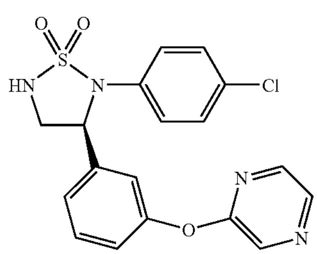 [SMILES: O=S1(=O)NC[C@H](c2cccc(Oc3cnccn3)c2)N1c1ccc(Cl)cc1] | HPLC-MS calculated for C$_{18}$H$_{15}$ClN$_4$O$_3$S (M + H$^+$) 403.06, found 403.00. |
| 252 | 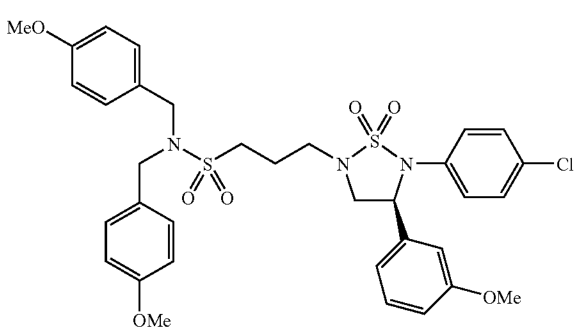 [SMILES: COc1ccc(CN(Cc2ccc(OC)cc2)S(=O)(=O)CCCN2C[C@H](c3cccc(OC)c3)N(c3ccc(Cl)cc3)S2(=O)=O)cc1] | HPLC-MS calculated for C$_{18}$H$_{22}$ClN$_3$O$_5$S$_2$ [(M-2PMB) + H$^+$] 460.07, found 460.10. |

TABLE 1-continued

| Compound Number | Structure | Physical Data<br>$^1$H NMR 400 MHz (CDCl$_3$) and/or MS (m/z) |
|---|---|---|
| 253 | 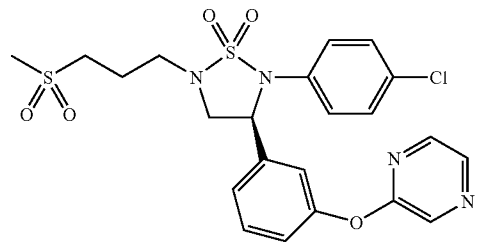 [SMILES: CS(=O)(=O)CCCN1C[C@H](c2cccc(Oc3cnccn3)c2)N(c2ccc(Cl)cc2)S1(=O)=O] | $^1$H NMR (CDCl$_3$) δ 8.41 (s, br, 1H), 8.29 (d, J = 3.5 Hz, 1H), 8.05 (dd, J = 5.0, 2.0 Hz, 1H), 7.41 (t, J = 10.0 Hz, 1H), 7.30-7.22 (m, 3H), 7.20-7.17 (m, 1H), 7.16-7.10 (m, 3H), 5.16 (dd, J = 10.5, 8.0 Hz, 1H), 3.88 (dd, J = 12.0, 8.5 Hz, 1H), 3.47-3.39 (m, 1H), 3.34-3.14 (m, 4H), 2.93 (s, 3H), 2.31-2.20 (m, 2H). HPLC-MS calculated for C$_{22}$H$_{23}$ClN$_4$O$_5$S$_2$ (M + H$^+$) 523.08, found 523.10. |
| 255 | 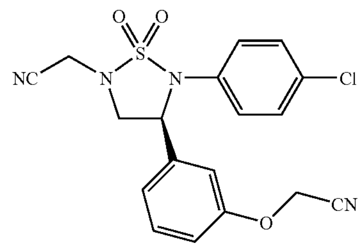 | $^1$H NMR (CDCl$_3$) δ 7.34 (t, J = 10.0 Hz, 1H), 7.31-7.27 (m, 2H), 7.23-7.19 (m, 2H), 7.10 (d, J = 9.5 Hz, 1H), 7.07-7.04 (m, 1H), 6.94 (ddd, J = 10.0, 3.0, 1.0 Hz, 1H), 5.19 (dd, J = 10.5, 8.5 Hz, 1H), 4.75 (s, 2H), 4.16 (s, 2H), 4.02 (dd, J = 12.5, 8.5 Hz, 1H), 3.47 (dd, J = 12.5, 10.5 Hz, 1H). HPLC-MS calculated for C$_{18}$H$_{15}$ClN$_4$O$_3$S (M + H$^+$) 403.06, found 402.90. |
| 256 | 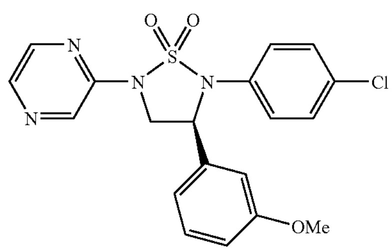 [SMILES: COc1cccc([C@H]2CN(c3cnccn3)S(=O)(=O)N2c2ccc(Cl)cc2)c1] | $^1$H NMR (CDCl$_3$) δ 8.82 (d, J = 2.0 Hz, 1H), 8.35 (d, J = 3.0 Hz, 1H), 8.32 (dd, J = 3.0, 2.0 Hz, 1H), 7.33-7.27 (m, 4H), 7.27-7.23 (m, 1H), 7.00 (d, J = 10.0 Hz, 1H), 6.96-6.93 (m, 1H), 6.85 (ddd, J = 10.0, 3.0, 1.0 Hz, 1H), 5.27 (dd, J = 11.5, 8.0 Hz, 1H), 4.50 (dd, J = 13.0, 8.0 Hz, 1H), 4.04 (dd, J = 13.0, 11.5 Hz, 1H), 3.77 (s, 3H). HPLC-MS calculated for C$_{19}$H$_{17}$ClN$_4$O$_3$S (M + H$^+$) 417.07, found 417.10. |
| 257 | 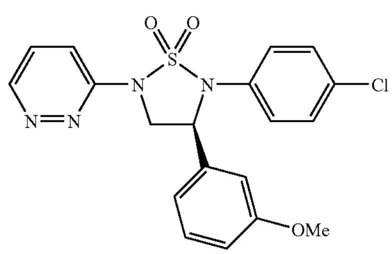 [SMILES: COc1cccc([C@H]2CN(c3cccnn3)S(=O)(=O)N2c2ccc(Cl)cc2)c1] | $^1$H NMR (CDCl$_3$) δ 9.08 (d, J = 5.5 Hz, 1H), 8.03 (d, J = 11.5 Hz, 1H), 7.81 (dd, J = 11.5, 5.5 Hz, 1H), 7.36-7.29 (m, 4H), 7.28-7.24 (m, 1H), 6.99 (d, J = 9.5 Hz, 1H), 6.95-6.91 (m, 1H), 6.86 (ddd, J = 10.5, 3.0, 1.0 Hz, 1H), 5.30 (dd, J = 11.5, 8.0 Hz, 1H), 4.75 (dd, J = 13.5, 8.0 Hz, 1H), 4.20 (dd, J = 13.5, 11.5 Hz, 1H), 3.77 (s, 3H). HPLC-MS calculated for C$_{19}$H$_{17}$ClN$_4$O$_3$S (M + H$^+$) 417.07, found 417.10. |
| 258 | 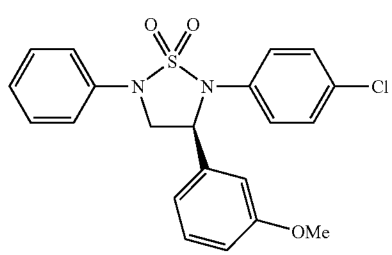 [SMILES: COc1cccc([C@H]2CN(c3ccccc3)S(=O)(=O)N2c2ccc(Cl)cc2)c1] | HPLC-MS calculated for C$_{21}$H$_{19}$ClN$_2$O$_3$S (M + H$^+$) 415.08, found 415.10. |

TABLE 1-continued

| Compound Number | Structure | Physical Data ¹H NMR 400 MHz (CDCl₃) and/or MS (m/z) |
|---|---|---|
| 259 | 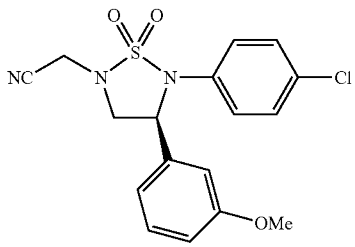 | ¹H NMR (CDCl₃) δ 7.29-7.23 (m, 3H), 7.22-7.17 (m, 2H), 6.95 (d, J = 9.5 Hz, 1H), 6.92-6.89 (m, 1H), 6.84 (ddd, J = 10.5, 3.0, 1.0 Hz, 1H), 5.17 (dd, J = 11.0, 8.5 Hz, 1H), 4.14 (AB, J = 29.5, 22.0 Hz, 2H), 3.97 (dd, J = 12.0, 8.5 Hz, 1H), 3.77 (s, 3H), 3.48 (dd, J = 12.0, 11.0 Hz, 1H). HPLC-MS calculated for $C_{17}H_{16}ClN_3O_3S$ (M + H⁺) 378.06, found 378.10. |
| 260 | 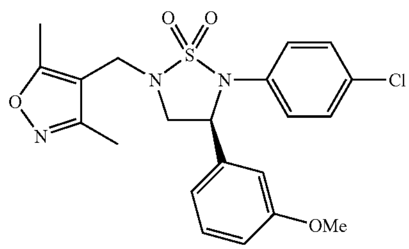 [SMILES: COc1cccc([C@H]2CN(Cc3c(C)noc3C)S(=O)(=O)N2c2ccc(Cl)cc2)c1] | ¹H NMR (CDCl₃) δ ppm) 7.27-7.25 (m, 1H), 7.25-7.22 (m, 2H), 7.16-7.11 (m, 2H), 6.92 (d, J = 9.5 Hz, 1H), 6.89-6.86 (m, 1H), 6.82 (ddd, J = 10.0, 3.0, 1.0 Hz, 1H), 5.02 (dd, J = 9.5, 8.5 Hz, 1H), 4.18 (d, J = 17.5 Hz, 1H), 3.89 (d, J = 17.5 Hz, 1H), 3.76 (s, 3H), 3.62 (dd, J = 11.5, 8.5 Hz, 1H), 3.10 (dd, J = 11.5, 9.5 Hz, 1H), 2.35 (s, 3H), 2.28 (s, 3H). (HPLC-MS calculated for $C_{21}H_{22}ClN_3O_4S$ (M + H⁺) 448.10, found 448.10. |
| 261 | 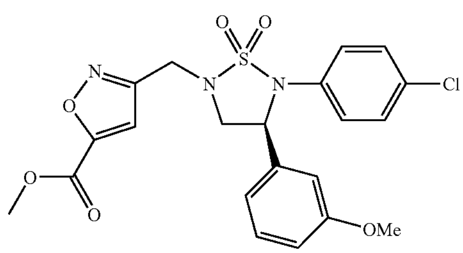 [SMILES: COC(=O)c1cc(CN2C[C@H](c3cccc(OC)c3)N(c3ccc(Cl)cc3)S2(=O)=O)no1] | ¹H NMR (CDCl₃) δ 7.28-7.26 (m, 1H), 7.26-7.21 (m, 2H), 7.18-7.13 (m, 2H), 6.90 (d, J = 10.0 Hz, 1H), 6.87-6.84 (m, 1H), 6.82 (ddd, J = 10.0, 3.5, 1.0 Hz, 1H), 6.81 (s, 1H), 5.07 (dd, J = 10.5, 8.5 Hz, 1H), 4.66 (dd, J = 20.0, 0.5 Hz, 1H), 4.37 (d, J = 20.0 Hz, 1H), 3.98 (s, 3H), 3.88 (dd, J = 12.5 8.5 Hz, 1H), 3.76 (s, 3H), 3.50 (dd, J = 12.5, 10.5 Hz, 1H). HPLC-MS calculated for $C_{21}H_{20}ClN_3O_6S$ (M + H⁺) 478.08, found 478.10. |
| 262 | 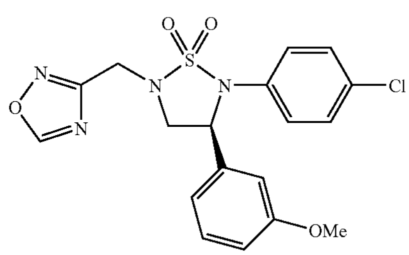 [SMILES: COc1cccc([C@H]2CN(Cc3ncon3)S(=O)(=O)N2c2ccc(Cl)cc2)c1] | ¹H NMR (CDCl₃) δ 8.76 (s, 1H), 7.27-7.26 (m, 1H), 7.25-7.21 (m, 2H), 7.20-7.15 (m, 2H), 6.94 (d, J = 9.5 Hz, 1H), 6.91-6.88 (m, 1H), 6.82 (ddd, J = 10.0, 3.0, 1.0 Hz, 1H), 5.14 (dd, J = 11.0, 8.5 Hz, 1H), 4.72 (d, J = 19.5 Hz, 1H), 4.35 (d, J = 19.5 Hz, 1H), 4.03 (dd, J = 12.0, 8.5 Hz, 1H), 3.76 (s, 3H), 3.43 (dd, J = 12.0, 11.0, 1H). HPLC-MS calculated for $C_{18}H_{17}ClN_4O_4S$ (M + H⁺) 421.07, found 421.10. |
| 263 | 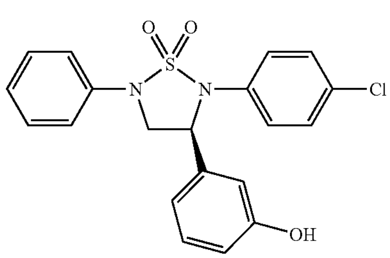 [SMILES: O=S1(=O)N(c2ccccc2)C[C@H](c2cccc(O)c2)N1c1ccc(Cl)cc1] | HPLC-MS calculated for $C_{20}H_{17}ClN_2O_3S$ (M + H⁺) 401.06, found 401.10. |

TABLE 1-continued

| Compound Number | Structure | Physical Data<br>¹H NMR 400 MHz (CDCl₃) and/or MS (m/z) |
|---|---|---|
| 264 | 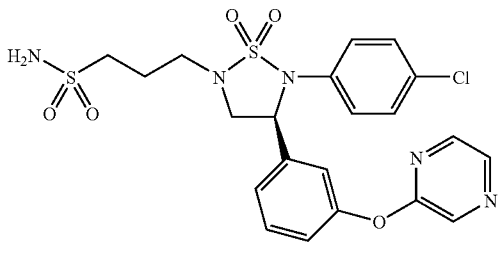 [SMILES: NS(=O)(=O)CCCN1C[C@H](c2cccc(Oc3cnccn3)c2)N(c2ccc(Cl)cc2)S1(=O)=O] | ¹H NMR (CDCl₃) δ 8.41 (d, J = 1.5 Hz, 1H), 8.30 (d, J = 3.5 Hz, 1H), 8.07 (dd, J = 3.5, 1.5 Hz, 1H), 7.44-7.39 (m, 1H), 7.30-7.27 (m, 1H), 7.26-7.23 (m, 2H), 7.21-7.18 (m, 1H), 7.16-7.10 (m, 3H), 5.15 (dd, J = 8.5, 8.0 Hz, 1H), 4.73 (s, br, 2H), 3.88 (dd, J = 11.5, 8.5 Hz, 1H), 3.45-3.20 (m, 5H), 2.27-2.18 (m, 2H). HPLC-MS calculated for $C_{21}H_{22}ClN_5O_5S_2$ (M + H⁺) 524.08, found 524.10. |
| 265 | 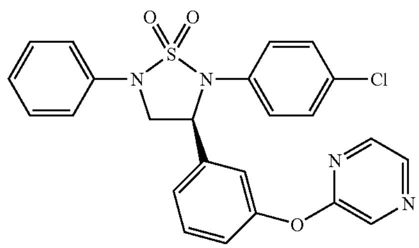 [SMILES: O=S1(=O)N(c2ccccc2)C[C@H](c2cccc(Oc3cnccn3)c2)N1c1ccc(Cl)cc1] | ¹H NMR (CDCl₃) δ 8.42 (d, J = 1.5 Hz, 1H), 8.30 (d, J = 3.5 Hz, 1H), 8.05 (dd, J = 3.5, 1.5 Hz, 1H), 7.46-7.42 (m, 1H), 7.42-7.38 (m, 2H), 7.36-7.27 (m, 6H), 7.27-7.22 (m, 3H), 7.15 (ddd, J = 10.0, 3.0, 1.0 Hz, 1H), 5.30 (dd, J = 10.5, 8.0 Hz, 1H), 4.18 (dd, J = 11.5, 8.0 Hz, 1H), 3.90 (dd, J = 11.5, 10.5 Hz, 1H). HPLC-MS calculated for $C_{24}H_{19}ClN_4O_3S$ (M + H⁺) 479.09, found 479.10. |
| 266 | 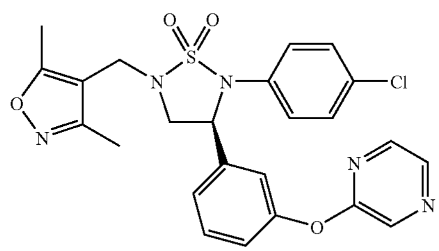 [SMILES: Cc1noc(C)c1CN1C[C@H](c2cccc(Oc3cnccn3)c2)N(c2ccc(Cl)cc2)S1(=O)=O] | ¹H NMR (CDCl₃) δ 8.42 (d, J = 1.5 Hz, 1H), 8.29 (J = 3.5 Hz, 1H), 8.03 (dd, J = 3.5, 1.5 Hz, 1H), 7.43-7.37 (m, 1H), 7.29-7.27 (m, 1H), 7.26-7.20 (m, 2H), 7.19-7.10 (m, 4H), 5.08 (dd, J = 9.5, 8.5 Hz, 1H), 4.18 (d, J = 17.5 Hz, 1H), 3.89 (d, J = 17.5 Hz, 1H), 3.67 (dd, J = 12.0, 8.5 Hz, 1H), 3.15 (dd, J = 12.0, 9.5 Hz, 1H), 2.35 (s, 3H), 2.27 (s, 3H). HPLC-MS calculated for $C_{24}H_{22}ClN_5O_4S$ (M + H⁺) 512.11, found 512.10. |
| 267 | 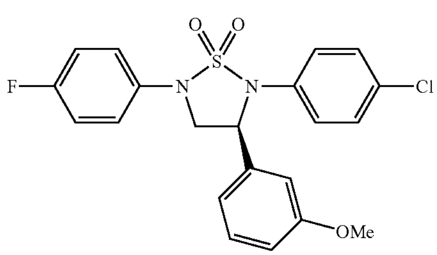 [SMILES: COc1cccc([C@H]2CN(c3ccc(F)cc3)S(=O)(=O)N2c2ccc(Cl)cc2)c1] | ¹H NMR (CDCl₃) δ 7.38-7.32 (m, 2H), 7.31-7.26 (m, 3H), 7.25-7.20 (m, 2H), 7.15-7.08 (m, 2H), 7.02 (d, J = 9.5 Hz, 1H), 6.99-6.96 (m, 1H), 6.85 (ddd, J = 10.0, 3.0, 1.0 Hz, 1H), 5.24 (dd, J = 10.5, 8.0 Hz, 1H), 4.09 (dd, J = 11.5, 8.0 Hz, 1H), 3.83 (dd, J = 11.5, 10.5 MS calculated for $C_{21}H_{18}ClFN_2O_3S$ (M + H⁺) 433.07, found 433.10. |
| 268 | 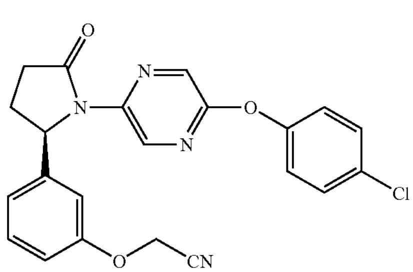 | ¹H NMR (CDCl₃) δ 9.13 (d, J = 1.5 Hz, 1H), 7.99 (d, J = 2.0 Hz, 1H), 7.37-7.32 (m, 2H), 7.32-7.26 (m, 1H), 7.08-7.02 (m, 2H), 6.94 (d, J = 9.5 Hz, 1H), 6.88-6.80 (m, 2H), 5.69 (dd, J = 10.0, 4.0 Hz, 1H), 4.74 (s, 2H), 2.90-2.74 (m, 1H), 2.74-2.60 (m, 2H), 2.11-2.00 (m, 1H). HPLC-MS calculated for $C_{22}H_{17}ClN_4O_3$ (M + H⁺) 421.10, found 420.90. |

| Compound Number | Structure | Physical Data $^1$H NMR 400 MHz (CDCl$_3$) and/or MS (m/z) |
|---|---|---|
| 273 | 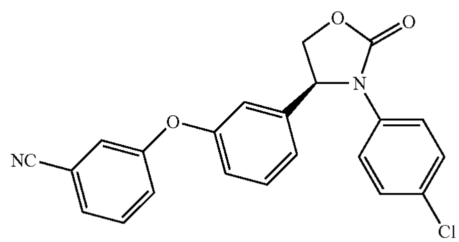 | HPLC-MS calculated for C$_{22}$H$_{15}$ClN$_2$O$_3$ (M + H$^+$): 391.1, found 391.1. |
| 274 | 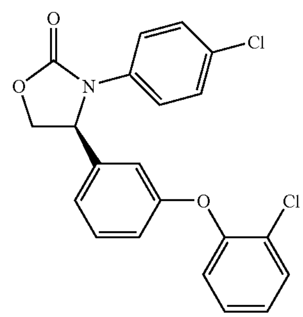 [SMILES: O=C1OC[C@H](c2cccc(Oc3ccccc3Cl)c2)N1c1ccc(Cl)cc1] | $^1$H NMR (CDCl$_3$) δ 7.45 (dd, J = 7.6, 1.6 Hz, 1H), 7.33-7.19 (m, 6H), 7.15-7.11 (m, 1H), 7.01-6.99 (m, 1H), 6.89-6.87 (m, 2H), 6.81 (t, J = 1.6 Hz, 1H), 5.34 (dd, J = 8.8, 6.0 Hz, 1H), 4.78 (t, J = 8.4 Hz, 1H), 4.20 (dd, J = 8.8, 6.4 Hz, 1H); HPLC-MS calculated for C$_{21}$H$_{15}$Cl$_2$NO$_3$ (M + H$^+$): 400.1, found 400.1 |
| 275 | 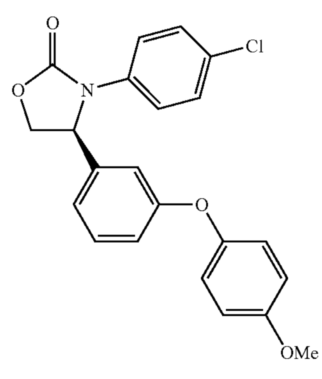 [SMILES: COc1ccc(Oc2cccc([C@H]3COC(=O)N3c3ccc(Cl)cc3)c2)cc1] | $^1$H NMR (CDCl$_3$) δ 7.31-7.23 (m, 5H), 6.95-6.93 (m, 1H), 6.86-6.81 (m, 6H), 6.87 (m, 4H), 6.87-6.84 (m, 1H), 6.82 (t, J = 2.0 Hz, 1H), 5.32 (dd, J = 8.8, 6.4 Hz, 1H), 4.77 (t, J = 8.8 Hz, 1H), 4.20 (dd, J = 8.8, 6.0 Hz, 1H), 3.82 (s, 3H); HPLC-MS calculated for C$_{22}$H$_{18}$ClNO$_4$ (M + H$^+$): 396.1, found 396.1. |
| 277 | 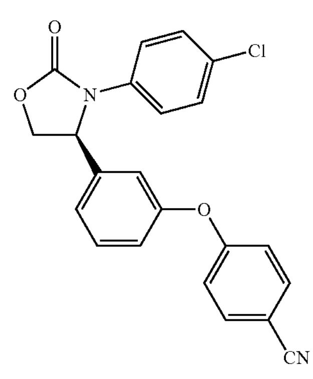 [SMILES: N#Cc1ccc(Oc2cccc([C@H]3COC(=O)N3c3ccc(Cl)cc3)c2)cc1] | HPLC-MS calculated for C$_{22}$H$_{15}$ClN$_2$O$_3$ (M + H$^+$): 391.1, found 391.0. |

TABLE 1-continued

| Compound Number | Structure | Physical Data<br>¹H NMR 400 MHz (CDCl₃) and/or MS (m/z) |
|---|---|---|
| 278 | 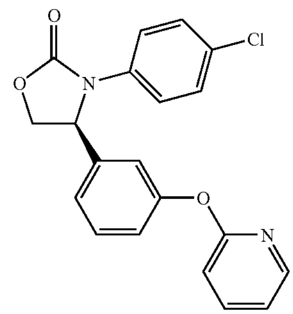 [SMILES: O=C1OC[C@H](c2cccc(Oc3ccccn3)c2)N1c1ccc(Cl)cc1] | HPLC-MS calculated for $C_{20}H_{15}ClN_2O_3$ (M + H⁺): 367.1, 367.0. |
| 281 | 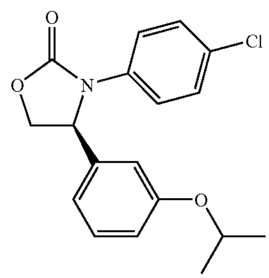 [SMILES: CC(C)Oc1cccc([C@H]2COC(=O)N2c2ccc(Cl)cc2)c1] | HPLC-MS calculated for $C_{18}H_{18}ClNO_3$ (M + H⁺): 332.1, found 332.1. |
| 282 | 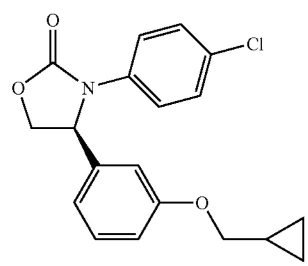 [SMILES: O=C1OC[C@H](c2cccc(OCC3CC3)c2)N1c1ccc(Cl)cc1] | HPLC-MS calculated for $C_{19}H_{18}ClNO_3$ (M + H⁺); 344.1, found 344.1. |
| 283 | 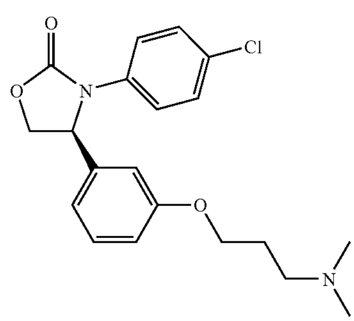 [SMILES: CN(C)CCCOc1cccc([C@H]2COC(=O)N2c2ccc(Cl)cc2)c1] | HPLC-MS calculated for $C_{20}H_{23}ClN_2O_3$ (M + H⁺): 375.1, found 375.1. |
| 284 | 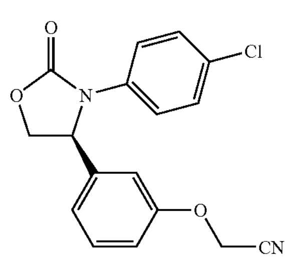 [SMILES: N#CCOc1cccc([C@H]2COC(=O)N2c2ccc(Cl)cc2)c1] | HPLC-MS calculated for $C_{16}H_{13}Cl_2NO_3$ (M + H⁺): 329.0, found 329.0. |

TABLE 1-continued

| Compound Number | Structure | Physical Data $^1$H NMR 400 MHz (CDCl$_3$) and/or MS (m/z) |
|---|---|---|
| 285 | 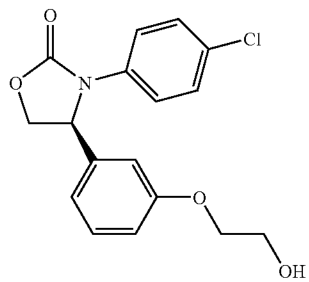 [SMILES: O=C1OC[C@H](c2cccc(OCCO)c2)N1c1ccc(Cl)cc1] | $^1$H NMR (CDCl$_3$) δ 7.38-7.34 (m, 2H), 7.29 (t, J = 8.0 Hz, 1H), 7.25-7.21 (m, 2H), 6.90-6.85 (m, 2H), 6.82 (t, J = 2.0 Hz, 1H), 5.32 (dd, J = 8.8, 6.0 Hz, 1H), 4.78 (t, J = 8.8 Hz, 1H), 4.20 (dd, J = 8.8, 6.0 Hz, 1H), 4.21-4.00 (m, 2H), 3.95 (t, J = 4.0 Hz, 2H); HPLC-MS calculated for C$_{17}$H$_{16}$ClNO$_4$ (M + H$^+$): 334.1, found 334.0. |
| 286 | 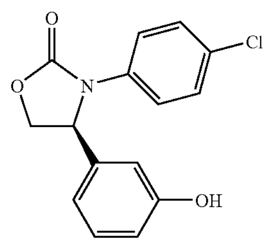 [SMILES: O=C1OC[C@H](c2cccc(O)c2)N1c1ccc(Cl)cc1] | HPLC-MS calculated for C$_{15}$H$_{12}$ClNO$_3$ (M + H$^+$): 290.0, found 290.0. |
| 287 | 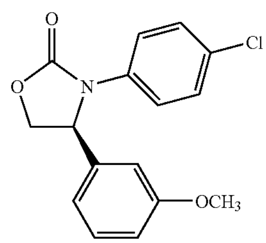 [SMILES: COc1cccc([C@H]2COC(=O)N2c2ccc(Cl)cc2)c1] | $^1$H NMR (CDCl$_3$) δ 7.37-7.34 (2H, m), 7.28 (1H, t, J = 8.0 Hz), 7.24-7.21 (2H, m), 6.87-6.84 (2H, m), 6.79 (1H, t, J = 2.0 Hz), 5.32 (1H, dd, J = 6.0, 8.8 Hz), 4.77 (1H, t, J = 8.8 Hz), 4.20 (1H, dd, J = 6.0, 8.8 Hz), 3.77 (3H, s); HPLC-MS calculated for C$_{16}$H$_{14}$ClNO$_3$ (M + H$^+$) 304.1, found 304.1. |
| 292 | 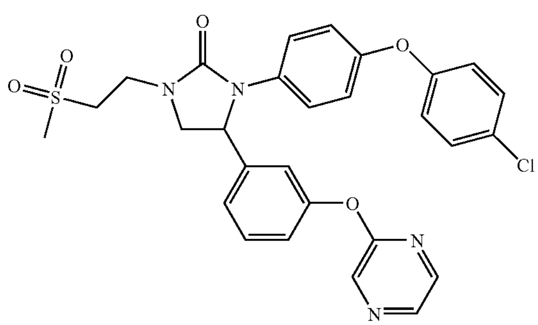 [SMILES: CS(=O)(=O)CCN1CC(c2cccc(Oc3cnccn3)c2)N(c2ccc(Oc3ccc(Cl)cc3)cc2)C1=O] | HPLC-MS calculated for C$_{28}$H$_{25}$ClN$_4$O$_5$S (M + H$^+$): 565.1, found 565.1. |
| 297 | 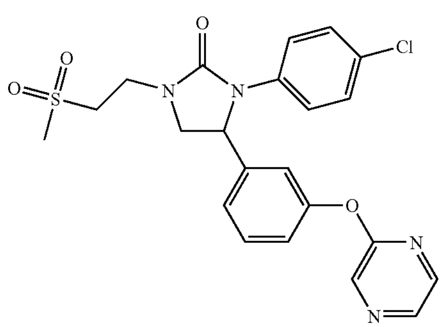 [SMILES: CS(=O)(=O)CCN1CC(c2cccc(Oc3cnccn3)c2)N(c2ccc(Cl)cc2)C1=O] | HPLC-MS calculated for C$_{22}$H$_{21}$ClN$_4$O$_4$S (M + H$^+$): 473.1, found 473.1. |

TABLE 1-continued

| Compound Number | Structure | Physical Data<br>$^1$H NMR 400 MHz (CDCl$_3$) and/or MS (m/z) |
|---|---|---|
| 298 | 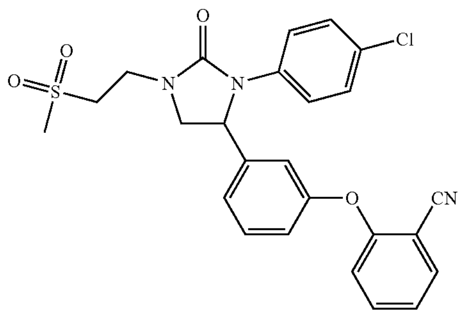 [SMILES: CS(=O)(=O)CCN1CC(c2cccc(Oc3ccccc3C#N)c2)N(c2ccc(Cl)cc2)C1=O] | HPLC-MS calculated for C$_{25}$H$_{22}$ClN$_3$O$_4$S (M + H$^+$): 496.1, found 496.1. |
| 299 | 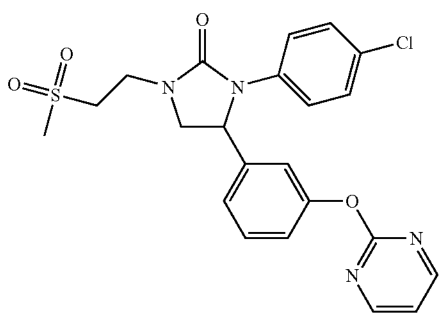 [SMILES: CS(=O)(=O)CCN1CC(c2cccc(Oc3ncccn3)c2)N(c2ccc(Cl)cc2)C1=O] | HPLC-MS calculated for C$_{22}$H$_{21}$ClN$_4$O$_4$S (M + H$^+$): 473.1, found 473.1. |
| 300 | 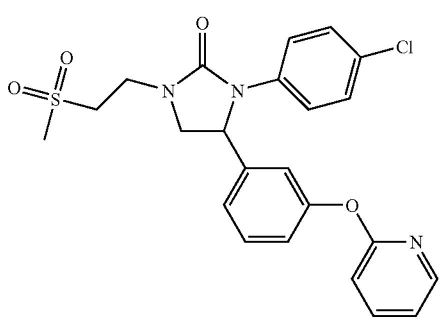 [SMILES: CS(=O)(=O)CCN1CC(c2cccc(Oc3ccccn3)c2)N(c2ccc(Cl)cc2)C1=O] | HPLC-MS calculated for C$_{23}$H$_{22}$ClN$_3$O$_4$S (M + H$^+$): 472.1, found 472.1. |
| 301 | 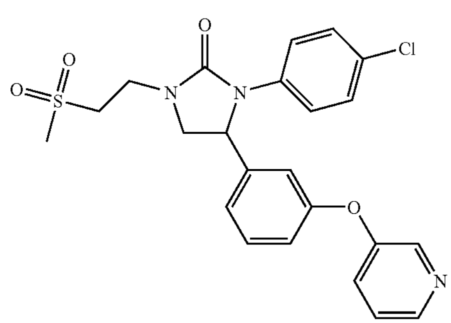 [SMILES: CS(=O)(=O)CCN1CC(c2cccc(Oc3cccnc3)c2)N(c2ccc(Cl)cc2)C1=O] | $^1$H NMR (CDCl$_3$) δ 8.46-8.42 (m, 2H), 7.53-7.48 (m, 2H), 7.44-7.40 (t, J = 8.4 Hz, 1H), 7.30-7.28 (m, 2H), 7.21-7.19 (m, 3H), 7.02-6.99 (m, 2H), 5.24 (dd, J = 6.0, 9.6 Hz, 1H), 4.04 (t, J = 9.2 Hz, 1H), 3.93-3.87 (m, 1H), 3.79-3.72 (m, 1H), 3.48 (dd, J = 8.8, 6.0 Hz, 1H), 3.34-3.30 (m, 2H), 3.00 (s, 3H); HPLC-MS calculated for C$_{23}$H$_{22}$ClN$_3$O$_4$S (M + H$^+$): 472.1, found 472.1. |

TABLE 1-continued

| Compound Number | Structure | Physical Data<br>¹H NMR 400 MHz (CDCl₃) and/or MS (m/z) |
|---|---|---|
| 302 | 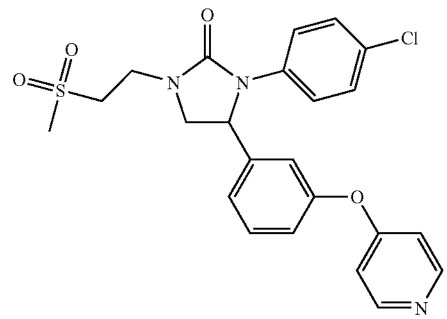 [SMILES: CS(=O)(=O)CCN1CC(c2cccc(Oc3ccncc3)c2)N(c2ccc(Cl)cc2)C1=O] | HPLC-MS calculated for $C_{23}H_{22}ClN_3O_4S$ (M + H⁺): 472.1, found 472.1. |
| 303 | 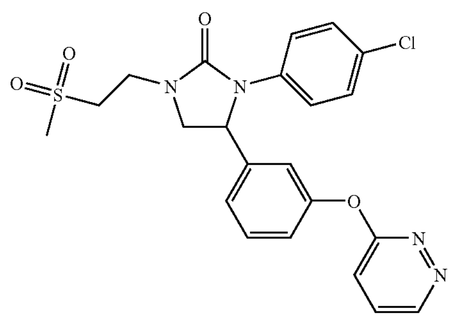 [SMILES: CS(=O)(=O)CCN1CC(c2cccc(Oc3cccnn3)c2)N(c2ccc(Cl)cc2)C1=O] | HPLC-MS calculated for $C_{22}H_{21}ClN_4O_4S$ (M + H⁺): 473.1, found 473.1. |
| 304 | 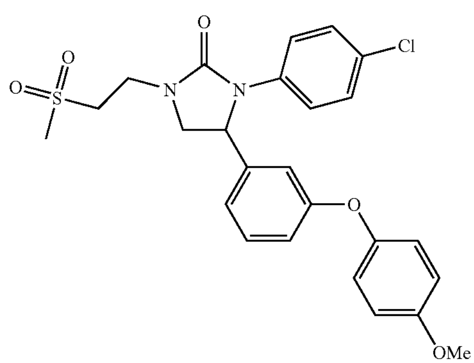 [SMILES: COc1ccc(Oc2cccc(C3CN(CCS(C)(=O)=O)C(=O)N3c3ccc(Cl)cc3)c2)cc1] | HPLC-MS calculated for $C_{25}H_{25}ClN_2O_5S$ (M + H⁺): 501.1, found 501.1. |
| 305 | 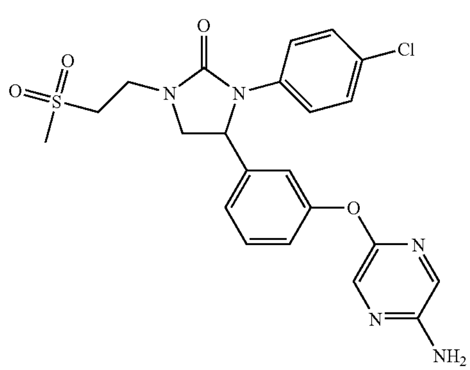 [SMILES: CS(=O)(=O)CCN1CC(c2cccc(Oc3cnc(N)cn3)c2)N(c2ccc(Cl)cc2)C1=O] | HPLC-MS calculated for $C_{22}H_{22}ClN_5O_4S$ (M + H⁺): 488.0, found 488.0. |

TABLE 1-continued

| Compound Number | Structure | Physical Data<br>¹H NMR 400 MHz (CDCl₃) and/or MS (m/z) |
|---|---|---|
| 306 | 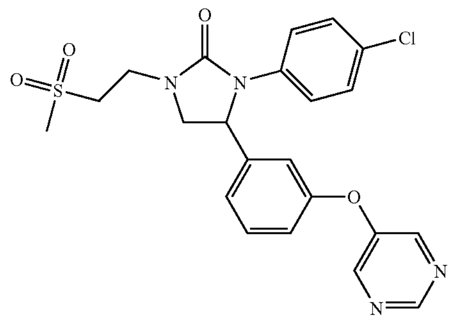 [SMILES: CS(=O)(=O)CCN1CC(c2cccc(Oc3cncnc3)c2)N(c2ccc(Cl)cc2)C1=O] | HPLC-MS calculated for $C_{22}H_{21}ClN_4O_4S$ (M + H⁺): 473.1, found 473.1. |
| 308 | 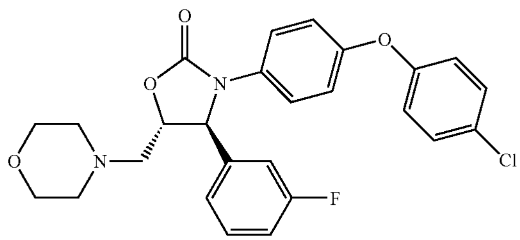 [SMILES: O=C1O[C@@H](CN2CCOCC2)[C@H](c2cccc(C(F)(F)F)c2)N1c1ccc(Oc2ccc(Cl)cc2)cc1] | ¹H NMR (acetone-d₆) δ 7.50-7.54 (m, 2H), 7.44 (ddd, 1H, J = 7.9, 7.9, 5.9 Hz), 7.34-7.38 (m, 3H), 7.30 (dt, 1H, J = 9.8, 2.5 Hz), 7.07-7.12 (m, 1H), 6.94-6.98 (m, 4H), 5.52 (d, 1H, J = 5.9 Hz), 4.55 (q, 1H, J = 5.9 Hz), 3.55-3.64 (m, 4H), 2.91 (dd, 1H, J = 13.4, 6.1 Hz), 2.83 (dd, 1H, J = 13.4, 6.1 Hz), 2.54 (br s, 4H). HPLC-MS calculated $C_{26}H_{24}ClFN_2O_4$ (M + H⁺): 483.1, found: 483.1. |
| 309 | 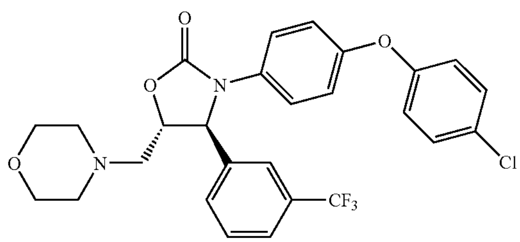 | ¹H NMR (acetone-d₆) δ 7.89 (s, 1H), 7.82 (d, 1H, J = 7.2 Hz), 7.62-7.69 (m, 2H), 7.50-7.54 (m, 2H), 7.34-7.38 (m, 2H), 6.93-6.97 (m, 4H), 5.66 (d, 1H, J = 5.9 Hz), 4.60 (q, 1H, J = 5.5 Hz), 3.53-3.64 (m, 4H), 2.95 (dd, 1H, J = 13.3, 6.7 Hz), 2.85 (dd, 1H, J = 13.3, 6.7 Hz), 2.49-2.57 (m, 4H). HPLC-MS calculated $C_{27}H_{24}ClF_3N_2O_4$ (M + H⁺): 533.1, found: 533.1. |
| 310 | 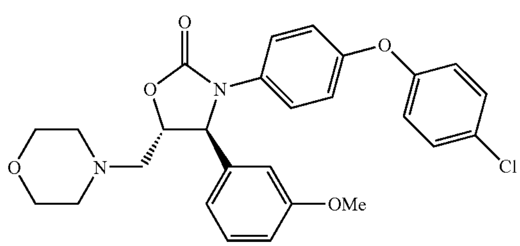 | ¹H NMR (acetone-d₆) δ 7.50-7.54 (m, 2H), 7.34-7.38 (m, 2H), 7.30 (t, 1H, J = 7.8 Hz), 7.01-7.05 (m, 2H), 6.92-6.97 (m, 4H), 6.87 (ddd, 1H, J = 8.3, 2.4, 1.1 Hz), 5.41 (d, 1H, J = 5.8 Hz), 4.51 (q, 1H, J = 5.8 Hz), 3.78 (s, 3H), 3.57-3.64 (m, 4H), 2.88 (dd, 1H, J = 13.4, 5.8 Hz), 2.80 (dd, 1H, J = 13.4, 5.8 Hz), 2.53 (t, 4H, J = 4.5 Hz). HPLC-MS calculated $C_{27}H_{27}ClN_2O_5$ (M + H⁺): 495.2, found: 495.2. |
| 312 | 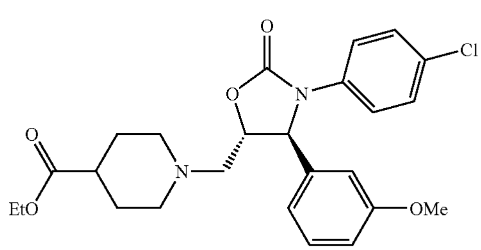 [SMILES: CCOC(=O)C1CCN(C[C@@H]2OC(=O)N(c3ccc(Cl)cc3)[C@H]2c2cccc(OC)c2)CC1] | ¹H NMR (acetone-d₆) δ 7.51-7.55 (m, 2H), 7.27-7.31 (m, 3H), 6.99-7.03 (m, 2H), 6.87 (ddd, 1H, J = 8.3, 2.5, 0.9 Hz), 5.4.2 (d, 1H, J = 5.6 Hz), 4.49 (q, 1H, J = 5.6 Hz), 4.08 (q, 2H, J = 7.1 Hz), 3.77 (s, 3H), 2.76-2.97 (m, 4H), 2.16-2.31 (m, 3H), 1.78-1.86 (m, 2H), 1.57-1.76 (m, 2H), 1.21 (t, 3H, J = 7.1 Hz). HPLC-MS calculated $C_{25}H_{29}ClN_2O_5$ (M + H⁺): 473.2, found: 473.2. |

TABLE 1-continued

| Compound Number | Structure | Physical Data<br>¹H NMR 400 MHz (CDCl₃) and/or MS (m/z) |
|---|---|---|
| 313 | 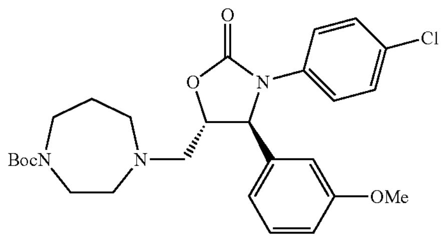 [SMILES: COc1cccc([C@H]2[C@H](CN3CCCN(C(=O)OC(C)(C)C)CC3)OC(=O)N2c2ccc(Cl)cc2)c1] | ¹H NMR (acetone-d₆) δ 7.54 (dd, 2H, J = 8.8, 1.4 Hz), 7.27-7.32 (m, 3H), 6.99-7.01 (m, 2H), 6.86-6.89 (m, 1H), 5.43 (t, 1H, J = 5.4 Hz), 4.45 (q, 1H, J = 5.4 Hz), 3.77 (s, 3H), 3.34-3.48 (m, 4H), 3.02 (dd, 2H, J = 5.8, 3.3 Hz), 2.75-2.88 (m, 4H), 1.68-1.78 (m, 2H), 1.43 (d, 9H, J = 1.4 Hz). HPLC-MS calculated $C_{27}H_{34}ClN_3O_5$ (M + H⁺): 516.2, found: 516.2. |
| 314 | 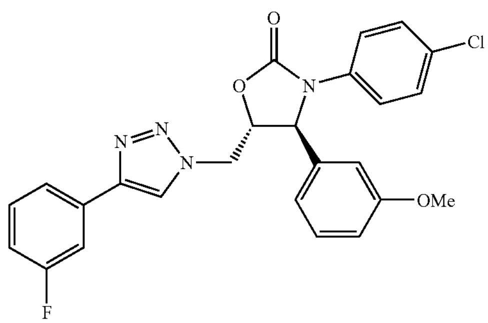 [SMILES: COc1cccc([C@H]2[C@H](Cn3cc(-c4cccc(F)c4)nn3)OC(=O)N2c2ccc(Cl)cc2)c1] | ¹H NMR (acetone-d₆) δ 8.57 (s, 1H), 7.72 (ddd, 1H, J = 7.8, 1.3, 1.3 Hz), 7.64 (ddd, 1H, J = 10.3, 2.6, 1.5 Hz), 7.41-7.50 (m, 3H), 7.25-7.32 (m, 3H), 7.08-7.13 (m, 1H), 6.99-7.03 (m, 2H), 6.89 (ddd, 1H, J = 8.3, 2.5, 1.0 Hz), 5.58 (d, 1H, J = 5.4 Hz), 5.12-5.13 (m, 2H), 4.95 (ddd, 1H, J = 5.5, 5.5, 4.7 Hz), 3.75 (s, 3H). HPLC-MS calculated $C_{25}H_{20}ClFN_4O_3$ (M + H⁺): 479.1, found: 479.1. |
| 315 | 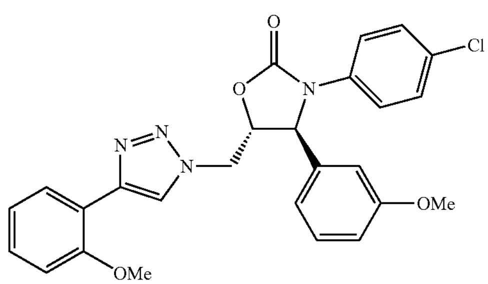 [SMILES: COc1cccc([C@H]2[C@H](Cn3cc(-c4ccccc4OC)nn3)OC(=O)N2c2ccc(Cl)cc2)c1] | ¹H NMR (acetone-d₆) δ 8.49 (s, 1H), 8.25 (dd, 1H, J = 7.7, 1.7 Hz), 7.41-7.45 (m, 2H), 7.25-7.35 (m, 4H), 7.10 (d, 1H, J = 7.6 Hz), 7.05 (ddd, 1H, J = 7.6, 7.6, 1.1 Hz), 6.97-6.99 (m, 2H), 6.88 (ddd, 1H, J = 8.3, 2.4, 1.0 Hz), 5.56 (d, 1H, J = 5.3 Hz), 5.10 (d, 2H, J = 5.1 Hz), 4.94 (q, 1H, J = 5.3 Hz), 3.94 (s, 3H), 3.74 (s, 3H). HPLC-MS calculated $C_{26}H_{23}ClN_4O_4$ (M + H⁺): 491.1, found: 491.1. |
| 316 | 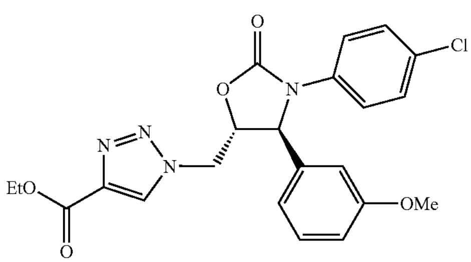 [SMILES: CCOC(=O)c1cn(C[C@@H]2OC(=O)N(c3ccc(Cl)cc3)[C@H]2c2cccc(OC)c2)nn1] | ¹H NMR (acetone-d₆) δ 8.66 (s, 1H), 7.44-7.47 (m, 2H), 7.27-7.32 (m, 3H), 6.99-7.03 (m, 2H), 6.89 (ddd, 1H, J = 8.3, 2.5, 0.9 Hz), 5.59 (d, 1H, J = 5.4 Hz), 5.16 (d, 2H, J = 5.3 Hz), 4.97 (q, 1H, J = 5.4 Hz), 4.32 (q, 2H, J = 7.1 Hz), 3.77 (s, 3H), 1.32 (t, 3H, J = 7.1 Hz). HPLC-MS calculated $C_{22}H_{21}ClN_4O_5$ (M + H⁺): 457.1, found: 457.1. |
| 317 | 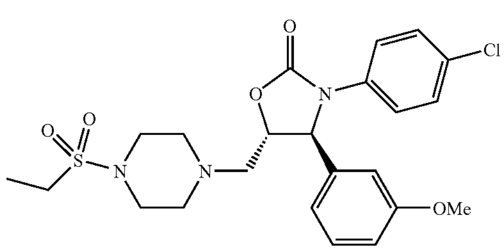 [SMILES: CCS(=O)(=O)N1CCN(C[C@@H]2OC(=O)N(c3ccc(Cl)cc3)[C@H]2c2cccc(OC)c2)CC1] | ¹H NMR (acetone-d₆) δ 7.50-7.54 (m, 2H), 7.27-7.32 (m, 3H), 7.01-7.04 (m, 2H), 6.87 (ddd, 1H, J = 8.3, 2.5, 1.0 Hz), 5.44 (d, 1H, J = 5.8 Hz), 4.54 (q, 1H, J = 5.7 Hz), 3.77 (s, 3H), 3.20-3.30 (m, 4H), 2.88-3.03 (m, 4H), 2.66 (t, 4H, J = 4.9 Hz), 1.28 (t, 3H, J = 7.4 Hz). HPLC-MS calculated $C_{23}H_{28}ClN_3O_5S$ (M + H⁺): 494.1, found: 494.1. |

TABLE 1-continued

| Compound Number | Structure | Physical Data<br>¹H NMR 400 MHz (CDCl₃)<br>and/or MS (m/z) |
|---|---|---|
| 318 | 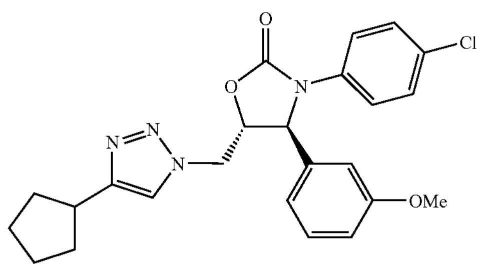 [SMILES: COc1cccc([C@H]2[C@H](Cn3cc(C4CCCC4)nn3)OC(=O)N2c2ccc(Cl)cc2)c1] | ¹H NMR (acetone-d₆) δ 7.80 (s, 1H), 7.39-7.42 (m, 2H), 7.26-7.31 (m, 3H), 6.95-6.96 (m, 1H), 6.92 (d, 1H, J = 7.7 Hz), 6.88 (ddd, 1H, J = 8.3, 2.5, 0.8 Hz), 5.48 (d, 1H, J = 5.0 Hz), 4.92-5.02 (m, 2H), 4.85 (q, 1H, J = 5.1 Hz), 3.76 (m, 3H), 3.08-3.16 (m, 1H), 1.94-2.01 (m, 2H), 1.59-1.72 (m, 5H). HPLC-MS calculated $C_{24}H_{25}ClN_4O_3$ (M + H⁺): 453.2, found: 453.2. |
| 319 | 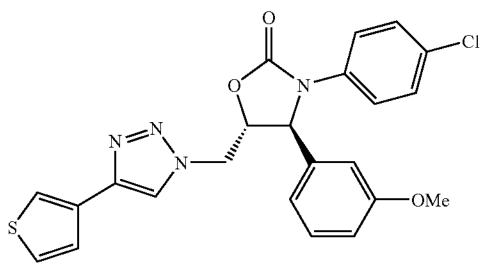 [SMILES: COc1cccc([C@H]2[C@H](Cn3cc(-c4ccsc4)nn3)OC(=O)N2c2ccc(Cl)cc2)c1] | ¹H NMR (acetone-d₆) δ 8.37 (s, 1H), 7.81 (t, 1H, J = 2.3 Hz), 7.53-7.56 (m, 2H), 7.41-7.45 (m, 2H), 7.26-7.33 (m, 3H), 6.99-7.01 (m, 2H), 6.87-6.90 (m, 1H), 5.56 (d, 1H, J = 5.5 Hz), 5.09 (d, 2H, J = 5.1 Hz), 4.92 (q, 1H, J = 5.4 Hz), 3.75 (s, 3H). HPLC-MS calculated $C_{23}H_{19}ClN_4O_3S$ (M + H⁺): 467.1, found: 467.1. |
| 320 | 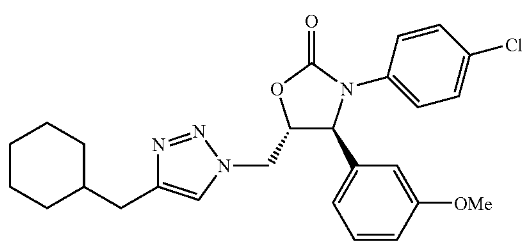 [SMILES: COc1cccc([C@H]2[C@H](Cn3cc(CC4CCCCC4)nn3)OC(=O)N2c2ccc(Cl)cc2)c1] | ¹H NMR (acetone-d₆) δ 7.78 (s, 1H), 7.39-7.43 (m, 2H), 7.26-7.31 (m, 3H), 6.97-6.98 (m, 1H), 6.93 (d, 1H, J = 7.0 Hz), 6.88 (ddd, 1H, J = 8.3, 2.5, 0.8 Hz), 5.48 (d, 1H, J = 4.96 Hz), 4.93-5.03 (m, 2H), 4.85 (q, 1H, J = 5.0 Hz), 3.77 (s, 3H), 2.51 (d, 2H, J = 6.9 Hz), 1.48-1.63 (m, 6H), 1.07-1.21 (m, 3H), 0.83-0.93 (m, 2H). HPLC-MS calculated $C_{26}H_{29}ClN_4O_3$ (M + H⁺): 481.2, found: 481.2. |
| 321 | 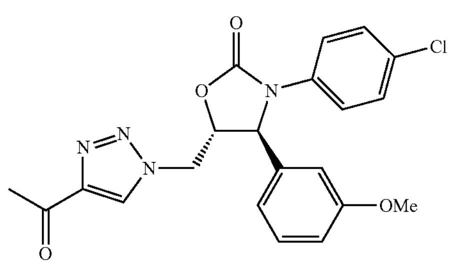 [SMILES: COc1cccc([C@H]2[C@H](Cn3cc(C(C)=O)nn3)OC(=O)N2c2ccc(Cl)cc2)c1] | ¹H NMR (acetone-d₆) δ 8.61 (s, 1H), 7.43-4.47 (m, 2H), 7.28-7.33 (m, 3H), 6.98-7.02 (m, 2H), 6.89 (dd, 1H, J = 8.3, 2.5 Hz), 5.58 (d, 1H, J = 5.4 Hz), 5.16-5.17 (m, 2H), 4.97 (q, 1H, J = 4.9 Hz), 3.77 (s, 3H), 2.55 (s, 3H). HPLC-MS calculated $C_{21}H_{19}ClN_4O_4$ (M + H⁺): 427.1, found: 427.1. |
| 322 | 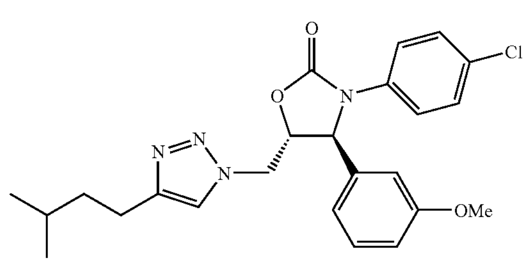 [SMILES: COc1cccc([C@H]2[C@H](Cn3cc(CCC(C)C)nn3)OC(=O)N2c2ccc(Cl)cc2)c1] | ¹H NMR (acetone-d₆) δ 7.80 (s, 1H), 7.39-7.43 (m, 2H), 7.27-7.32 (m, 3H), 6.93-6.96 (m, 2H), 6.87-6.90 (m, 1H), 5.47 (d, 1H, J = 5.0 Hz), 4.93-5.02 (m, 2H), 4.83-4.86 (m, 1H), 3.77 (m, 3H), 2.64 (t, 2H, J = 7.8 Hz), 1.44-1.55 (m, 3H), 0.87-0.89 (m, 6H). HPLC-MS calculated $C_{24}H_{27}ClN_4O_3$ (M + H⁺): 455.2, found: 455.2. |

TABLE 1-continued

| Compound Number | Structure | Physical Data ¹H NMR 400 MHz (CDCl₃) and/or MS (m/z) |
|---|---|---|
| 323 | 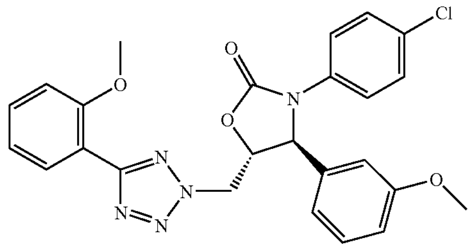 [SMILES: COc1cccc([C@H]2[C@H](Cn3nnc(-c4ccccc4OC)n3)OC(=O)N2c2ccc(Cl)cc2)c1] | HPLC-MS calculated: $C_{25}H_{22}ClN_5O_4$ (M + H⁺): 492.1, found: 492.1 |
| 325 | 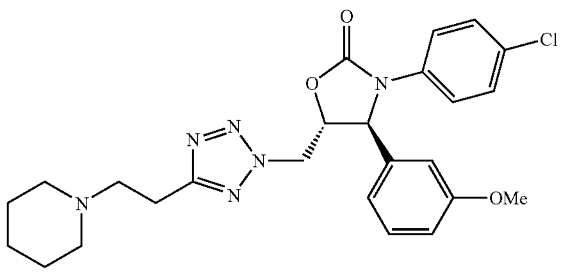 [SMILES: COc1cccc([C@H]2[C@H](Cn3nnc(CCN4CCCCC4)n3)OC(=O)N2c2ccc(Cl)cc2)c1] | ¹H NMR (acetone-d₆) δ 7.43-7.47 (m, 2H), 7.28-7.33 (m, 3H), 7.04 (t, 1H, J = 2.1 Hz), 6.98 (d, 1H, J = 7.7 Hz), 6.91 (ddd, 1H, J = 8.3, 2.6, 0.9 Hz), 5.61 (d, 1H, J = 5.0 Hz), 5.32 (dd, 1H, J = 14.6, 5.6 Hz), 5.25 (dd, 1H, J = 14.6, 5.6 Hz), 4.99 (ddd, 1H, J = 5.0, 5.0, 4.2 Hz), 3.78 (s, 3H), 2.93 (t, 2H, J = 7.6 Hz), 2.50-2.57 (m, 2H), 2.37 (br s, 4H), 1.49 (pentet, 4H, J = 5.8 Hz), 1.37-1.41 (m, 2H). HPLC-MS calculated $C_{25}H_{29}ClN_6O_3$ (M + H⁺): 497.2, found: 497.2. |
| 327 | 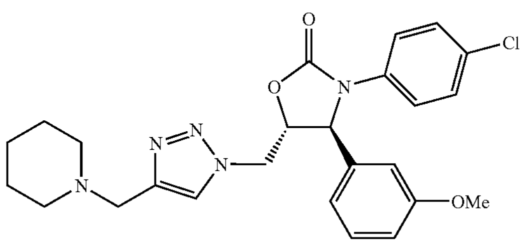 | ¹H NMR (acetone-d₆) δ 8.06 (br s, 1H), 7.42-7.46 (m, 2H), 7.26-7.31 (m, 3H), 6.98-6.99 (m, 1H), 6.95 (d, 1H, J = 7.7 Hz), 6.88 (ddd, 1H, J = 8.3, 2.5, 0.8 Hz), 5.51 (d, 1H, J = 4.9 Hz), 4.99-5.09 (m, 2H), 4.89 (q, 1H, J = 5.0 Hz), 3.77 (s, 3H), 3.12 (t, 1H, J = 5.7 Hz), 2.44 (br s, 3H), 1.84-1.90 (m, 1H), 1.66-1.70 (m, 1H), 1.53 (br s, 4H), 1.37 (br s, 2H). HPLC-MS calculated $C_{25}H_{28}ClN_5O_3$ (M + H⁺): 482.2, found: 482.2. |
| 328 | 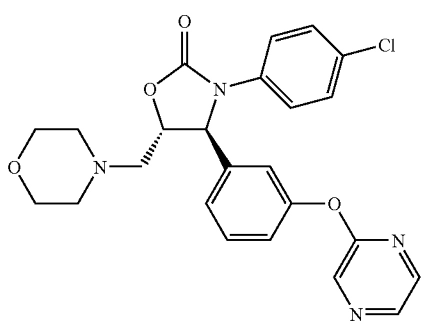 [SMILES: O=C1O[C@@H](CN2CCOCC2)[C@H](c2cccc(Oc3cnccn3)c2)N1c1ccc(Cl)cc1] | ¹H NMR (acetone-d₆) δ 8.41 (d, 1H, J = 1.3 Hz), 8.33 (d, 1H, J = 2.6 Hz), 8.11 (dd, 1H, J = 2.6, 1.4 Hz), 7.50-7.54 (m, 2H), 7.47 (t, 1H, J = 8.1 Hz), 7.35-7.37 (m, 2H), 7.29-7.33 (m, 2H), 7.17 (ddd, 1H, J = 8.1, 2.3, 1.1 Hz), 5.53 (d, 1H, J = 5.8 Hz), 4.58 (q, 1H, J = 5.7 Hz), 3.52-3.61 (m, 4H), 2.91 (dd, 1H, J = 13.6, 6.5 Hz), 2.82 (dd, 1H, J = 13.6, 6.5 Hz), 2.53 (t, 4H, J = 4.5 Hz). HPLC-MS calculated $C_{24}H_{23}ClN_4O_4$ (M + H⁺): 467.1, found: 467.1. |
| 329 | 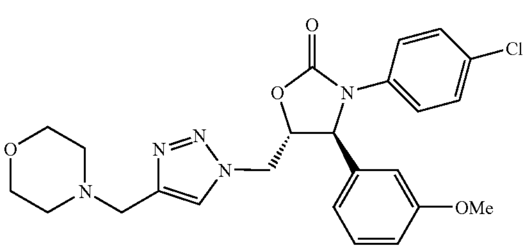 [SMILES: COc1cccc([C@H]2[C@H](Cn3cc(CN4CCOCC4)nn3)OC(=O)N2c2ccc(Cl)cc2)c1] | ¹H NMR (acetone-d₆) δ 7.96 (s, 1H), 7.39-7.43 (m, 2H), 7.26-7.31 (m, 3H), 6.97-6.98 (m, 1H), 6.94 (d, 1H, J = 7.7 Hz), 6.88 (ddd, 1H, J = 8.3, 2.5, 0.8 Hz), 5.50 (d, 1H, J = 4.9 Hz), 5.03 (m, 2H), 4.88 (q, 1H, J = 5.0 Hz), 3.77 (s, 3H), 3.57 (s, 2H), 3.50-3.53 (m, 4H), 2.33 (t, 4H, J = 4.3 Hz). HPLC-MS calculated $C_{24}H_{26}ClN_5O_4$ (M + H⁺): 484.2, found: 484.2. |

| Compound Number | Structure | Physical Data $^1$H NMR 400 MHz (CDCl$_3$) and/or MS (m/z) |
|---|---|---|
| 330 | 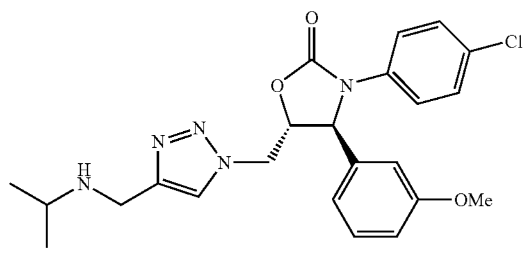 [SMILES: COc1cccc([C@H]2[C@H](Cn3cc(CNC(C)C)nn3)OC(=O)N2c2ccc(Cl)cc2)c1] | $^1$H NMR (acetone-d$_6$) δ 8.00 (s, 1H), 7.41-7.45 (m, 2H), 7.26-7.31 (m, 3H), 6.98-6.99 (m, 1H), 6.95 (d, 1H, J = 7.7 Hz), 6.88 (ddd, 1H, J = 8.3, 2.5, 0.9 Hz), 5.50 (d, 1H, J = 5.2 Hz), 5.01-5.03 (m, 2H), 4.86 (q, 1H, J = 5.2 Hz), 3.87 (s, 2H), 3.77 (s, 3H), 2.79 (septet, 1H, J = 6.3 Hz), 1.03 (d, 3H, J = 6.2 Hz), 1.02 (d, 3H, J = 6.2 Hz). HPLC-MS calculated C$_{23}$H$_{26}$ClN$_5$O$_3$ (M + H$^+$): 456.2, found: 456.2. |
| 331 | 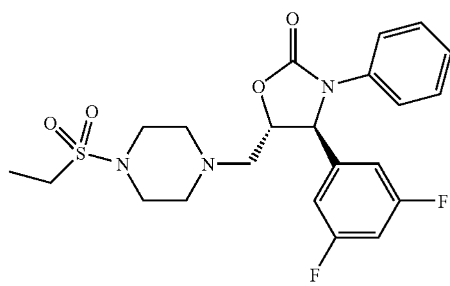 | $^1$H NMR (acetone-d$_6$) δ 7.51-7.55 (m, 2H), 7.30-7.34 (m, 2H), 7.17-7.23 (m, 2H), 6.98 (tt, 1H, J = 9.1, 2.3 Hz), 5.57 (d, 1H, J = 5.8 Hz), 4.61 (q, 1H, J = 5.7 Hz), 3.20-3.31 (m, 4H), 2.92-3.05 (m, 4H), 2.69 (t, 4H, J = 4.9 Hz), 1.28 (t, 3H, J = 7.4 Hz). HPLC-MS calculated C$_{22}$H$_{24}$ClF$_2$N$_3$O$_4$S (M + H$^+$): 500.1, found: 500.1. |
| 332 | 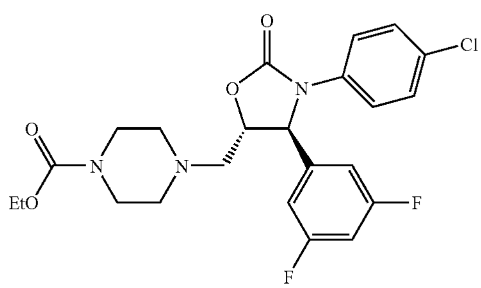 [SMILES: CCOC(=O)N1CCN(C[C@@H]2OC(=O)N(c3ccc(Cl)cc3)[C@H]2c2cc(F)cc(F)c2)CC1] | $^1$H NMR (acetone-d$_6$) δ 7.52-7.55 (m, 2H), 7.30-7.34 (m, 2H), 7.17-7.23 (m, 2H), 6.97 (tt, 1H, J = 9.1, 2.3 Hz), 5.59 (d, 1H, J = 5.8 Hz), 4.60 (q, 1H, J = 5.7 Hz), 4.06 (q, 2H, J = 7.1 Hz), 3.35-3.47 (m, 4H), 2.98 (dd, 1H, J = 13.5, 6.2 Hz), 2.89 (dd, 1H, J = 13.5, 6.2 Hz), 2.56 (t, 4H, J = 5.0 Hz), 1.20 (t, 3H, J = 7.1 Hz). HPLC-MS calculated C$_{23}$H$_{24}$ClF$_2$N$_3$O$_4$ (M + H$^+$): 480.1, found: 480.1. |
| 333 | 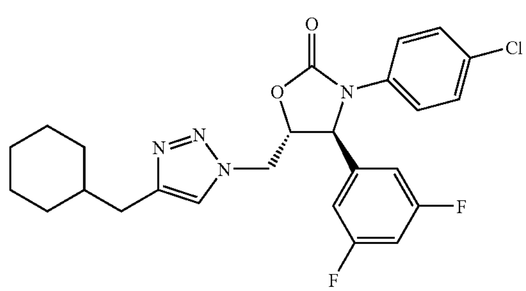 [SMILES: O=C1O[C@@H](Cn2cc(CC3CCCCC3)nn2)[C@H](c2cc(F)cc(F)c2)N1c1ccc(Cl)cc1] | $^1$H NMR (acetone-d$_6$) δ 7.78 (s, 1H), 7.40-7.44 (m, 2H), 7.28-7.32 (m, 2H), 7.10-7.19 (m, 2H), 6.97-7.02 (m, 1H), 5.62 (d, 1H, J = 4.9 Hz), 5.01-5.04 (m, 2H), 4.92-4.96 (m, 1H), 2.51 (d, 2H, J = 6.9 Hz), 1.5-1.63 (m, 6H), 1.08-1.20 (m, 3H), 0.85-0.94 (m, 2H). HPLC-MS calculated C$_{25}$H$_{25}$ClF$_2$N$_4$O$_2$ (M + H$^+$): 487.2, found: 487.2. |
| 335 | 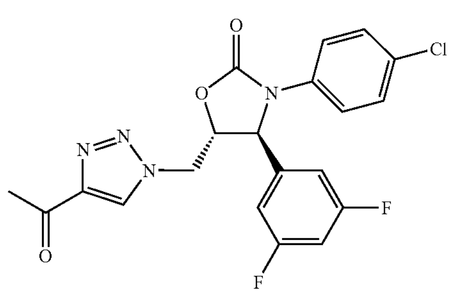 [SMILES: CC(=O)c1cn(C[C@@H]2OC(=O)N(c3ccc(Cl)cc3)[C@H]2c2cc(F)cc(F)c2)nn1] | $^1$H NMR (acetone-d$_6$) δ 8.59 (s, 1H), 7.45-7.49 (m, 2H), 7.31-7.34 (m, 2H), 7.17-7.22 (m, 2H), 7.02 (tt, 1H, J = 9.1, 2.2 Hz), 5.72 (d, 1H, J = 5.5 Hz), 5.20-5.21 (m, 2H), 5.05 (q, 1H, J = 5.2 Hz), 2.55 (s, 3H). HPLC-MS calculated C$_{20}$H$_{15}$ClF$_2$N$_4$O$_3$ (M + H$^+$): 433.1, found: 433.1. |

TABLE 1-continued

| Compound Number | Structure | Physical Data $^1$H NMR 400 MHz (CDCl$_3$) and/or MS (m/z) |
|---|---|---|
| 337 | 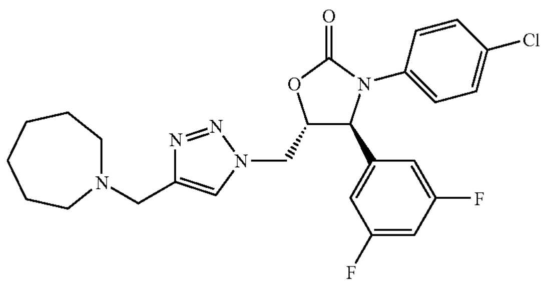 [SMILES: O=C1O[C@@H](Cn2cc(CN3CCCCCC3)nn2)[C@H](c2cc(F)cc(F)c2)N1c1ccc(Cl)cc1] | $^1$H NMR (acetone-d$_6$) δ 7.94 (s, 1H), 7.43 (d, 2H, J = 8.8 Hz), 7.30 (d, 2H, J = 8.8 Hz), 7.12-7.17 (m, 2H), 7.00 (tt, 1H, J = 9.1, 2.1 Hz), 5.63 (d, 1H, J = 5.0 Hz), 5.01-5.11 (m, 2H), 4.96 (q, 1H, J = 4.8 Hz), 3.74 (s, 2H), 2.56 (s, 4H), 1.53 (br s, 8H). HPLC-MS calculated C$_{25}$H$_{26}$ClF$_2$N$_5$O$_2$ (M + H$^+$): 502.2, found: 502.2. |
| 338 | 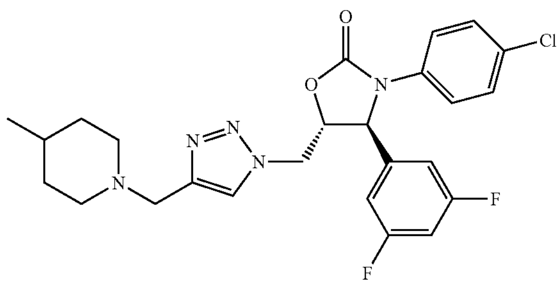 [SMILES: CC1CCN(Cc2cn(C[C@@H]3OC(=O)N(c4ccc(Cl)cc4)[C@H]3c3cc(F)cc(F)c3)nn2)CC1] | $^1$H NMR (acetone-d$_6$) δ 7.91 (s, 1H), 7.41-7.44 (m, 2H), 7.29-7.31 (m, 2H), 7.12-7.17 (m, 2H), 6.97-7.02 (m, 1H), 5.62 (d, 1H, J = 4.9 Hz), 5.01-5.11 (m, 2H), 4.96 (q, 1H, J = 3.9 Hz), 3.57 (s, 2H), 2.76 (d, 2H, J = 11.3 Hz), 1.91 (t, 2H, J = 11.5 Hz), 1.50 (d, 2H, J = 11.9 Hz), 1.18-1.25 (m, 1H), 1.03-1.16 (m, 2H), 0.86 (d, 3H, J = 6.4 Hz). HPLC-MS calculated C$_{25}$H$_{26}$ClF$_2$N$_5$O$_2$ (M + H$^+$): 502.2, found: 502.2. |
| 339 | 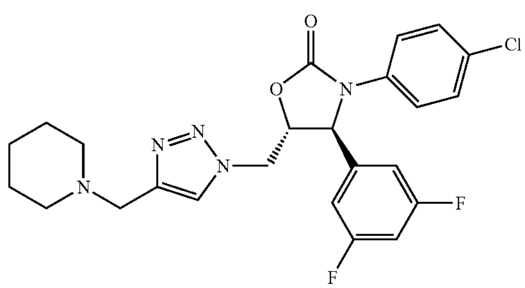 | $^1$H NMR (acetone-d$_6$) δ 7.92 (s, 1H), 7.42-7.45 (m, 2H), 729-7.32 (m, 2H), 7.11-1.17 (m, 2H), 7.00 (tt, 1H, J = 9.1, 2.3 Hz), 5.64 (d, 1H, J = 5.0 Hz), 5.01-5.11 (m, 2H), 4.96 (q, 1H, J = 5.1 Hz), 3.55 (s, 2H), 2.32 (br s, 4H), 1.43-1.49 (m, 4H), 1.31-1.37 (m, 2H). HPLC-MS calculated C$_{24}$H$_{24}$ClF$_2$N$_5$O$_2$ (M + H$^+$): 488.2, found: 488.2. |
| 340 | 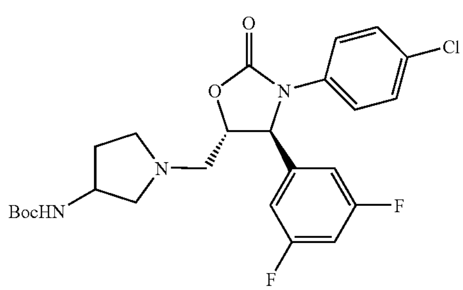 [SMILES: CC(C)(C)OC(=O)NC1CCN(C[C@@H]2OC(=O)N(c3ccc(Cl)cc3)[C@H]2c2cc(F)cc(F)c2)C1] | $^1$H NMR (acetone-d$_6$) δ 7.52 (m, 2H), 7.32 (m, 2H), 7.15-7.19 (m, 2H), 6.94-6.99 (m, 1H), 5.91-5.99 (m, 1H), 5.60-5.61 (m, 1H), 4.52 (q, 1H, J = 5.3 Hz), 4.03-4.10 (m, 1H), 3.04-3.11 (m, 1H), 2.75-2.91 (m, 2H), 2.51-2.62 (m, 2H), 2.10-2.20 (m, 1H), 1.62-1.69 (m, 1H), 1.39 (s, 9H). HPLC-MS calculated C$_{25}$H$_{28}$ClF$_2$N$_3$O$_4$ (M + H$^+$): 508.2, found: 508.2. |
| 341 | 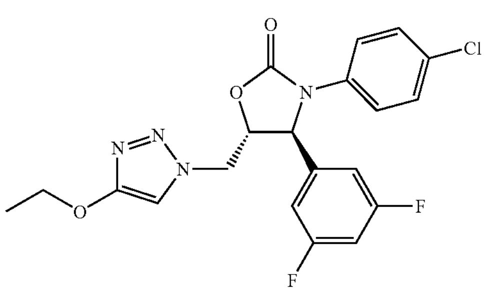 [SMILES: CCOc1cn(C[C@@H]2OC(=O)N(c3ccc(Cl)cc3)[C@H]2c2cc(F)cc(F)c2)nn1] | $^1$H NMR (acetone-d$_6$) δ 7.52 (s, 1H), 7.43-7.46 (m, 2H), 7.29-7.35 (m, 2H), 7.11-7.17 (m, 2H), 7.00 (tt, 1H, J = 9.1, 2.3 Hz), 5.62 (d, 1H, J = 5.0 Hz), 4.92-4.98 (m, 3H), 4.16 (q, 2H, J = 7.0 Hz), 1.31 (t, 3H, J = 7.0 Hz). HPLC-MS calculated C$_{20}$H$_{17}$ClF$_2$N$_4$O$_3$ (M + H$^+$): 435.1, found: 435.1. |

TABLE 1-continued

| Compound Number | Structure | Physical Data<br>$^1$H NMR 400 MHz (CDCl$_3$)<br>and/or MS (m/z) |
|---|---|---|
| 342 | 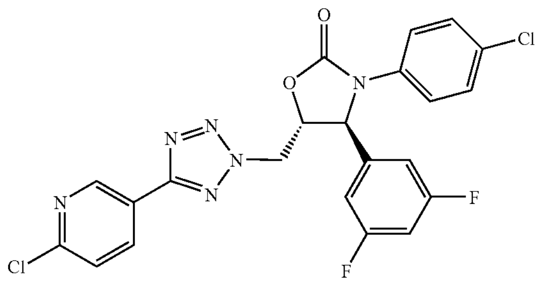 [SMILES: O=C1O[C@@H](Cn2nnc(-c3ccc(Cl)nc3)n2)[C@H](c2cc(F)cc(F)c2)N1c1ccc(Cl)cc1] | $^1$H NMR (acetone-d$_6$) δ 8.99 (d, 1H, J = 2.3 Hz), 8.37 (dd, 1H, J = 8.3, 2.4 Hz), 7.63 (d, 1H, J = 8.3 Hz), 7.45 (d, 2H, J = 8.9 Hz), 7.23-7.29 (m, 4H), 7.03 (tt, 1H, J = 9.0, 2.2 Hz), 5.87 (d, 1H, J = 5.0 Hz), 5.56 (dd, 1H, J = 14.7, 5.8 Hz), 5.48 (dd, 1H, J = 14.7, 5.8 Hz), 5.21 (q, 1H, J = 5.2 Hz). HPLC-MS calculated C$_{23}$H$_{15}$Cl$_2$F$_2$N$_5$O$_2$ (M + H$^+$): 503.1, found: 503.1. |
| 343 | 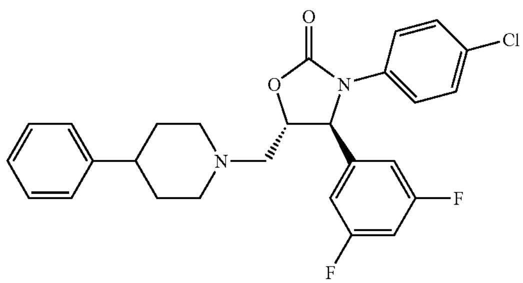 [SMILES: O=C1O[C@@H](CN2CCC(c3ccccc3)CC2)[C@H](c2cc(F)cc(F)c2)N1c1ccc(Cl)cc1] | $^1$H NMR (acetone-d$_6$) δ 7.55-7.58 (m, 2H), 7.32-7.35 (m, 2H), 7.21-7.31 (m, 6H), 7.18 (tt, 1H, J = 6.6, 1.4 Hz), 6.99 (tt, 1H, J = 9.1, 2.3 Hz), 5.61 (d, 1H, J = 5.9 Hz), 4.60 (q, 1H, J = 5.6 Hz), 3.11-3.15 (m, 1H), 2.85-2.99 (m, 3H), 2.48-2.56 (m, 1H), 2.34-2.41 (m, Hz), 1.78-1.84 (m, 2H), 1.69-1.74 (m, 1H), 1.62 (dq, 1H, J = 12.0, 3.9 Hz). HPLC-MS calculated C$_{27}$H$_{25}$ClF$_2$N$_2$O$_2$ (M + H$^+$): 483.2, found: 483.2. |
| 345 | 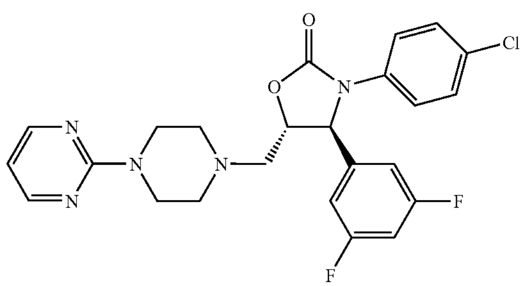 [SMILES: O=C1O[C@@H](CN2CCN(c3ncccn3)CC2)[C@H](c2cc(F)cc(F)c2)N1c1ccc(Cl)cc1] | $^1$H NMR (acetone-d$_6$) δ 8.32 (d, 2H, J = 4.7 Hz), 7.53-7.57 (m, 2H), 7.30-7.35 (m, 2H), 7.21-7.27 (m, 2H), 6.99 (tt, 1H, J = 9.1, 2.3 Hz), 6.57 (t, 1H, J = 4.7 Hz), 5.64 (d, 1H, J = 5.8 Hz), 4.64 (q, 1H, J = 5.6 Hz), 3.72-3.84 (m, 4H), 3.02 (dd, 1H, J = 13.4, 6.4 Hz), 2.91 (dd, 1H, J = 13.4, 6.4 Hz), 2.64 (t, 4H, J = 5.1 Hz). HPLC-MS calculated C$_{24}$H$_{22}$ClF$_2$N$_5$O$_2$ (M + H$^+$): 486.1, found: 486.1. |
| 346 | 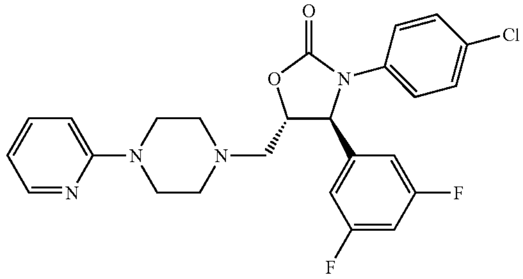 | $^1$H NMR (acetone-d$_6$) δ 8.12 (ddd, J = 4.9, 2.0, 0.8 Hz, 1H), 7.53-7.57 (m, 2H), 7.50 (ddd, J = 8.9, 7.1, 2.0 Hz, 1H) 7.31-7.34 (m, 2H), 7.21-7.24 (m, 2H), 6.99 (tt, 1H, J = 9.1, 2.3 Hz), 6.77 (d, 1H, J = 8.6 Hz), 6.61 (ddd, J = 6.8, 5.6, 0.7 Hz, 1H), 5.63 (d, 1H, J = 5.8 Hz), 4.64 (q, 1H, J = 5.6 Hz), 3.47-3.58 (m, 4H), 3.02 (dd, 1H, J = 13.4, 6.4 Hz), 2.92 (dd, 1H, J = 13.4, 6.4 Hz), 2.64 (t, 4H, J = 5.1 Hz). HPLC-MS calculated C$_{25}$H$_{23}$ClF$_2$N$_4$O$_2$ (M + H$^+$): 485.2, found: 485.0. |

TABLE 1-continued

| Compound Number | Structure | Physical Data<br>¹H NMR 400 MHz (CDCl₃) and/or MS (m/z) |
|---|---|---|
| 347 | 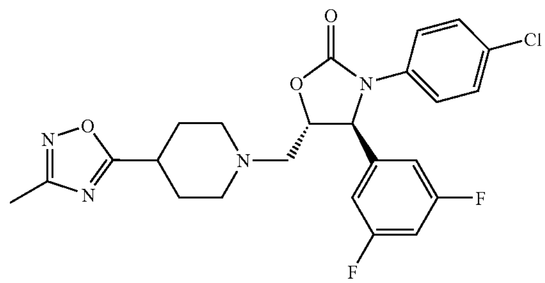 [SMILES: Cc1noc(C2CCN(C[C@@H]3OC(=O)N(c4ccc(Cl)cc4)[C@H]3c3cc(F)cc(F)c3)CC2)n1] | ¹H NMR (acetone-d₆) δ 7.53-7.57 (m, 2H), 7.30-7.34 (m, 2H), 7.17-7.24 (m, 2H), 6.98 (tt, 1H, J = 9.1, 2.3 Hz), 5.60 (d, 1H, J = 5.8 Hz), 4.59 (q, 1H, J = 5.6 Hz), 3.04-3.07 (m, 1H), 2.94-3.01 (m, 3H), 2.88 (dd, 1H, J = 13.4, 5.3 Hz), 2.43 (dt, 1H, J = 11.2, 2.3 Hz), 2.35 (dt, 1H, J = 11.3, 2.4), 2.30 (s, 3H), 1.99-2.07 (m, 2H), 1.85-1.95 (m, 1H), 1.72-1.82 (m, 1H). HPLC-MS calculated $C_{24}H_{23}ClF_2N_4O_3$ (M + H⁺): 489.2, found: 489.2. |
| 348 | 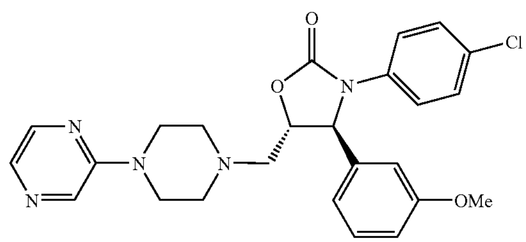 [SMILES: COc1cccc([C@H]2[C@H](CN3CCN(c4cnccn4)CC3)OC(=O)N2c2ccc(Cl)cc2)c1] | ¹H NMR (acetone-d₆) δ 8.24 (d, 1H, J = 1.4 Hz), 8.04 (dd, 1H, J = 2.6, 1.6 Hz), 7.81 (d, 1H, J = 2.6 Hz), 7.51-7.56 (m, 2H), 7.27-7.33 (m, 3H), 7.04-7.06 (m, 2H), 6.86-6.89 (m, 1H), 5.49 (d, 1H, J = 5.7 Hz), 4.58 (q, 1H, J = 5.7 Hz), 3.77 (s, 3H), 3.56-3.67 (m, 4H), 2.98 (dd, 1H, J = 13.5, 5.9 Hz), 2.89 (dd, 1H, J = 13.5, 5.7 Hz), 2.7 (t, 4H, J = 5.1 Hz). HPLC-MS calculated $C_{25}H_{26}ClN_5O_3$ (M + H⁺): 480.2, found: 480.2. |
| 349 | 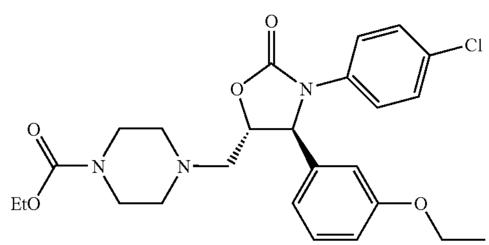 [SMILES: CCOC(=O)N1CCN(C[C@@H]2OC(=O)N(c3ccc(Cl)cc3)[C@H]2c2cccc(OCC)c2)CC1] | ¹H NMR (acetone-d₆) δ 7.50-7.54 (m, 2H), 7.27-7.31 (m, 3H), 7.00-7.02 (m, 2H), 6.84-6.87 (m, 1H), 5.44 (d, 1H, J = 5.7 Hz), 4.53 (q, 1H, J = 5.7 Hz), 3.97-4.09 (m, 4H), 3.36-3.46 (m, 4H), 2.93 (dd, 1H, J = 13.5, 5.8 Hz), 2.85 (dd, 1H, J = 13.5, 5.8 Hz), 2.54 (t, 4H, J = 5.0 Hz), 1.32 (t, 3H, J = 7.0 Hz), 1.20 (t, 3H, J = 7.1 Hz). HPLC-MS calculated $C_{25}H_{30}ClN_3O_5$ (M + H⁺): 488.2, found 488.2. |
| 350 | 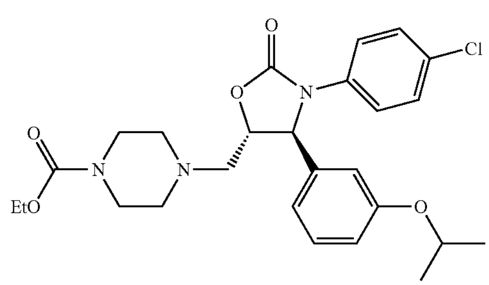 [SMILES: CCOC(=O)N1CCN(C[C@@H]2OC(=O)N(c3ccc(Cl)cc3)[C@H]2c2cccc(OC(C)C)c2)CC1] | ¹H NMR (acetone-d₆) δ 7.51-7.54 (m, 2H), 7.26-7.32 (m, 3H), 6.99-7.00 (m, 2H), 6.84 (ddd, 1H, J = 8.2, 2.5, 0.9 Hz), 5.43 (d, 1H, J = 5.7 Hz), 4.61 (septet, 1H, J = 6.0 Hz), 4.53 (q, 1H, J = 5.7 Hz), 4.06 (q, 2H, J = 7.1 Hz), 3.40-3.43 (m, 4H), 2.93 (dd, 1H, J = 13.5, 5.8 Hz), 2.85 (dd, 1H, J = 13.5, 5.8 Hz), 2.54 (t, 4H, J = 5.0 Hz), 1.26 (d, 3H, J = 6.0 Hz), 1.21 (d, 3H, J = 6.0 Hz), 1.20 (t, 3H, J = 7.1 Hz). HPLC-MS calculated $C_{26}H_{32}ClN_3O_5$ (M + H⁺): 502.2. found: 502.2. |

| Compound Number | Structure | Physical Data<br>$^1$H NMR 400 MHz (CDCl$_3$) and/or MS (m/z) |
|---|---|---|
| 351 | 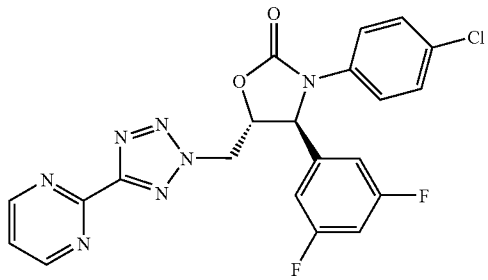 | HPLC-MS calculated C$_{21}$H$_{14}$ClF$_2$N$_7$O$_2$ (M + H$^+$) calc'd 470.1, found: 470.1 |
| 352 | 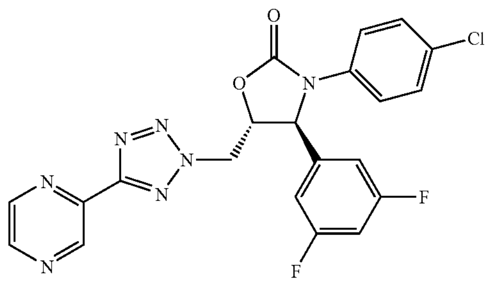 [SMILES: O=C1O[C@@H](Cn2nnc(-c3cnccn3)n2)[C@H](c2cc(F)cc(F)c2)N1c1ccc(Cl)cc1] | HPLC-MS calculated C$_{21}$H$_{14}$ClF$_2$N$_7$O$_2$ (M + H$^+$) calc'd 470.1, found: 470.1 |
| 353 | 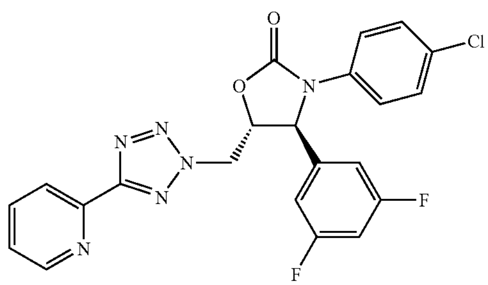 [SMILES: O=C1O[C@@H](Cn2nnc(-c3ccccn3)n2)[C@H](c2cc(F)cc(F)c2)N1c1ccc(Cl)cc1] | $^1$H NMR (acetone-d$_6$) δ 8.74 (ddd, 1H, J = 4.8, 1.7, 0.9 Hz), 8.12 (dt, 1H, J = 7.9, 1.0 Hz), 7.97 (dt, 1H, J = 7.7, 1.8 Hz), 7.52 (ddd, 1H, J = 7.6, 4.8, 1.2 Hz), 7.46-7.50 (m, 2H), 7.27-7.32 (m, 4H), 7.02 (tt, 1H, J = 9.1, 2.3 Hz), 5.90 (d, 1H, J = 5.2 Hz), 5.54 (dd, 1H, J = 14.6, 6.0 Hz), 5.47 (dd, 1H, J = 14.6, 4.2 Hz), 5.18-5.22 (m, 1H). HPLC-MS calculated C$_{22}$H$_{15}$ClF$_2$N$_6$O$_2$ (M + H$^+$): 469.1. found: 469.1. |
| 354 | 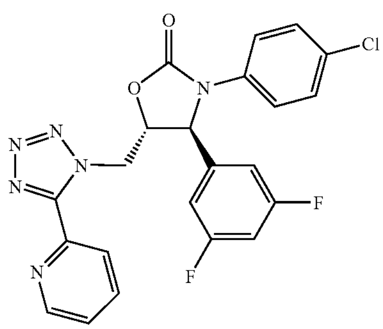 [SMILES: O=C1O[C@@H](Cn2nnnc2-c2ccccn2)[C@H](c2cc(F)cc(F)c2)N1c1ccc(Cl)cc1] | $^1$H NMR (acetone-d$_6$) δ 8.37-8.39 (m, 1H), 8.32 (dt, 1H, J = 7.9, 1.0 Hz), 8.08 (dt, 1H, J = 7.8, 1.7 Hz), 7.58 (ddd, 1H, J = 7.7, 4.9, 1.2 Hz), 7.50-7.54 (m, 2H), 7.32-7.36 (m, 2H), 7.23-7.29 (m, 2H), 7.06 (tt, 1H, J = 9.1, 2.3 Hz), 5.85 (d, 1H, J = 6.0 Hz), 5.67-5.69 (m, 2H), 5.17 (ddd 1H, J = 6.2, 6.2, 5.2 Hz). HPLC-MS calculated C$_{22}$H$_{15}$ClF$_2$N$_6$O$_2$ (M + H$^+$): 469.1, found: 469.1. |
| 355 | 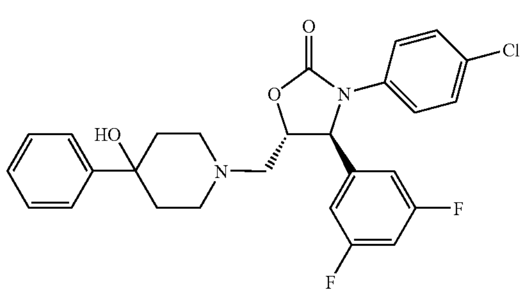 [SMILES: O=C1O[C@@H](CN2CCC(O)(c3ccccc3)CC2)[C@H](c2cc(F)cc(F)c2)N1c1ccc(Cl)cc1] | $^1$H NMR (acetone-d$_6$) δ 7.56-7.60 (m, 2H), 7.48-7.51 (m, 2H), 7.29-7.36 (m, 4H), 7.24-7.29 (m, 2H), 7.21 (tt, 1H, J = 6.8, 1.3 Hz), 6.99 (tt, 1H, J = 9.1, 2.3 Hz), 5.63 (d, 1H, J = 5.8 Hz), 4.61 (q, 1H, J = 5.7 Hz), 3.86 (s, 1H), 2.90-3.02 (m, 2H), 2.78-2.86 (m, 2H), 2.66-2.71 (m, 2H), 2.14 (dt, 1H, J = 13.2, 5.0 Hz), 1.90-1.98 (m, 1H), 1.68 (dq, 1H, J = 13.3, 2.6 Hz), 1.61 (dq, 1H, J = 13.3, 2.4 Hz). HPLC-MS calculated C$_{27}$H$_{25}$ClF$_2$N$_2$O$_3$ (M + H$^+$): 499.2, found: 499.2. |

TABLE 1-continued

| Compound Number | Structure | Physical Data<br>$^1$H NMR 400 MHz (CDCl$_3$) and/or MS (m/z) |
|---|---|---|
| 356 | 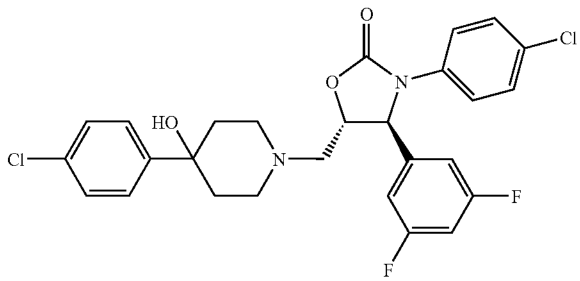 [SMILES: O=C1O[C@@H](CN2CCC(O)(c3ccc(Cl)cc3)CC2)[C@H](c2cc(F)cc(F)c2)N1c1ccc(Cl)cc1] | $^1$H NMR (acetone-d$_6$) δ 7.54-7.59 (m, 2H), 7.48-7.52 (m, 2H), 7.31-7.36 (m, 4H), 7.23-7.29 (m, 2H), 6.99 (tt, 1H, J = 9.1, 2.3 Hz), 5.62 (d, 1H, J = 5.7 Hz), 4.61 (ddd, 1H, J = 6.4, 5.6, 5.6 Hz), 4.01 (s, 1H), 2.99 (dd, 1H, J = 13.2, 6.6 Hz), 2.92 (dd, 1H, J = 13.2, 6.6 Hz), 2.64-2.88 (m, 4H), 2.11 (dt, 1H, J = 12.9, 4.8 Hz), 1.91 (dt, 1H, J = 13.2, 5.1 Hz), 1.68 (dq, 1H, J = 13.3, 2.6 Hz), 1.60 (dq, 1H, J = 13.3, 2.6 Hz). HPLC-MS calculated C$_{27}$H$_{24}$Cl$_2$F$_2$N$_2$O$_3$ (M + H$^+$): 533.1, found: 533.1. |
| 357 | 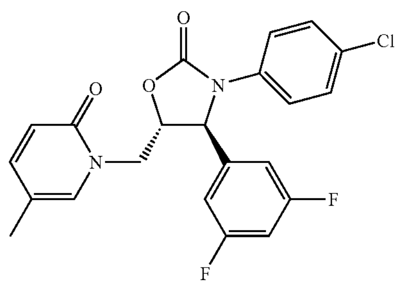 [SMILES: Cc1ccc(=O)n(C[C@@H]2OC(=O)N(c3ccc(Cl)cc3)[C@H]2c2cc(F)cc(F)c2)c1] | $^1$H NMR (acetone-d$_6$) δ 7.54 (d, 1H, J = 7.0 Hz), 7.42-7.46 (m, 2H), 7.30-7.34 (m, 2H), 7.19-7.25 (m, 2H), 7.00 (tt, 1H, J = 9.1, 2.3 Hz), 6.23 (s, 1H), 6.11 (dd, 1H, J = 7.0, 1.9 Hz), 5.64 (d, 1H, J = 6.3 Hz), 4.82 (ddd, 1H, J = 6.1, 6.1, 4.0 Hz), 4.56 (dd, 1H, J = 14.2, 3.9 Hz), 4.47 (dd, 1H, J = 14.1, 4.0 Hz), 2.15 (d, 3H, J = 0.9 Hz). HPLC-MS calculated C$_{22}$H$_{17}$ClF$_2$N$_2$O$_3$ (M + H$^+$): 431.1. found: 431.1. |
| 358 | 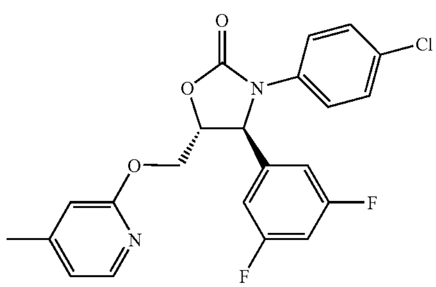 [SMILES: Cc1ccnc(OC[C@@H]2OC(=O)N(c3ccc(Cl)cc3)[C@H]2c2cc(F)cc(F)c2)c1] | $^1$H NMR (acetone-d$_6$) δ 7.99 (d, 1H, J = 5.2 Hz), 7.54-7.58 (m, 2H), 7.32-7.36 (m, 2H), 7.21-7.27 (m, 2H), 7.01 (tt, 1H, J = 9.1, 2.3 Hz), 6.83 (d, 1H, J = 5.2 Hz), 6.62 (s, 1H), 5.75 (d, 1H, J = 5.5 Hz), 4.82 (ddd, 1H, J = 5.5, 4.1, 4.1 Hz), 4.69-4.77 (m, 2H), 2.29 (s, 3H). HPLC-MS calculated C$_{22}$H$_{17}$ClF$_2$N$_2$O$_3$ (M + H$^+$): 431.1. found: 431.1. |
| 359 | 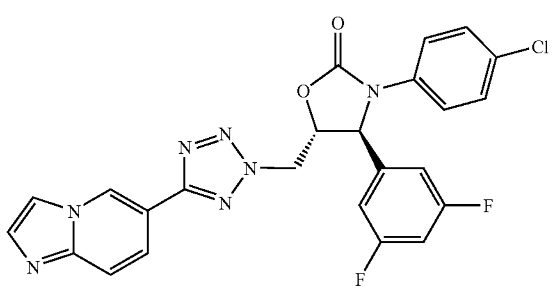 [SMILES: O=C1O[C@@H](Cn2nnc(-c3ccc4nccn4c3)n2)[C@H](c2cc(F)cc(F)c2)N1c1ccc(Cl)cc1] | $^1$H NMR (acetone-d$_6$) δ 9.21 (t, 1H, J = 1.4 Hz), 8.04 (s, 1H), 7.75 (dd, 1H, J = 9.4, 1.7 Hz), 7.64-7.66 (m, 2H), 7.46-7.50 (m, 2H), 7.26-7.31 (m, 4H), 7.05 (tt, 1H, J = 9.1, 2.3 Hz), 5.89 (d, 1H, J = 5.2 Hz), 5.54 (dd, 1H, J = 14.7, 5.9 Hz), 5.46 (dd, 1H, J = 14.7, 3.9 Hz), 5.20 (ddd, 1H, J = 5.6, 5.6, 3.9 Hz). HPLC-MS calculated C$_{24}$H$_{16}$ClF$_2$N$_7$O$_2$ (M + H$^+$): 508.1. found: 508.1. |
| 360 | 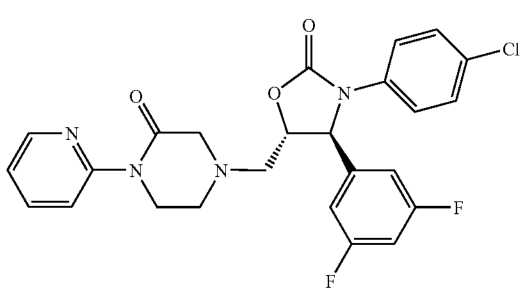 [SMILES: O=C1CN(C[C@@H]2OC(=O)N(c3ccc(Cl)cc3)[C@H]2c2cc(F)cc(F)c2)CCN1c1ccccn1] | $^1$H NMR (acetone-d$_6$) δ 8.41-8.42 (m, 1H), 8.00-8.03 (m, 1H), 7.73-7.78 (m, 1H), 7.53-7.56 (m, 2H), 7.29-7.36 (m, 2H), 7.21-7.26 (m, 2H), 7.15-7.19 (m, 1H), 6.95-7.01 (m, 1H), 5.68 (d, 1H, J = 5.9 Hz), 4.70 (q, 1H, J = 5.8 Hz), 3.92-4.02 (m, 2H), 3.43-3.54 (m, 2H), 3.15 (dd, 1H, J = 13.6, 5.7 Hz), 3.02-3.07 (m, 3H). HPLC-MS calculated C$_{25}$H$_{21}$ClF$_2$N$_4$O$_3$ (M + H$^+$): 499.1. found: 499.1. |

TABLE 1-continued

| Compound Number | Structure | Physical Data $^1$H NMR 400 MHz (CDCl$_3$) and/or MS (m/z) |
|---|---|---|
| 361 | 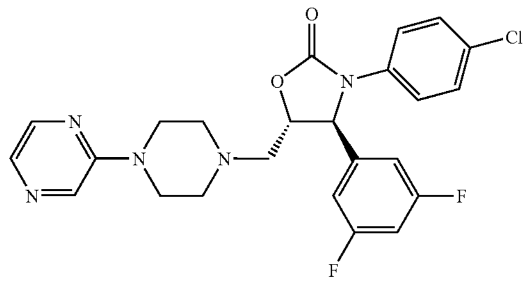 [SMILES: O=C1O[C@@H](CN2CCN(c3cnccn3)CC2)[C@H](c2cc(F)cc(F)c2)N1c1ccc(Cl)cc1] | $^1$H NMR (acetone-d$_6$) δ 8.25 (d, 1H, J = 1.5 Hz), 8.04 (dd, 1H, J = 2.5, 1.5 Hz), 7.81 (d, 1H, J = 2.6 Hz), 7.53-7.60 (m, 2H), 7.30-7.34 (m, 2H), 7.21-7.27 (m, 2H), 6.99 (tt, 1H, J = 9.1, 2.3 Hz), 5.64 (d, 1H, J = 5.8 Hz), 4.65 (q, 1H, J = 5.8 Hz), 3.55-3.67 (m, 4H), 3.04 (dd, 1H, J = 13.5, 6.3 Hz), 13.5, 5.4 Hz), 2.93 (dd, 1H, J = 13.5, 5.4 Hz), 2.72 (t, 4H, J = 5.1 Hz). HPLC-MS calculated C$_{24}$H$_{22}$ClF$_2$N$_5$O$_2$ (M + H$^+$): 486.2. found: 486.2. |
| 362 | 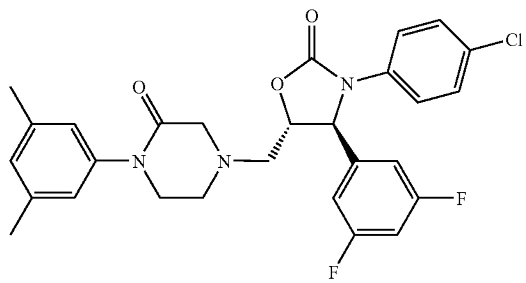 [SMILES: Cc1cc(C)cc(N2CCN(C[C@@H]3OC(=O)N(c4ccc(Cl)cc4)[C@H]3c3cc(F)cc(F)c3)CC2=O)c1] | $^1$H NMR (acetone-d$_6$) δ 7.54-7.58 (m, 2H), 7.31-7.35 (m, 2H), 7.22-7.29 (m, 2H), 6.99 (tt, 1H, J = 9.1, 2.3 Hz), 6.89 (s, 3H), 5.67 (d, 1H, J = 5.9 Hz), 4.68 (q, 1H, J = 5.7 Hz), 3.57-3.69 (m, 2H), 3.32-3.43 (m, 2H), 3.13 (dd, 1H, J = 13.6, 5.8 Hz), 3.01-3.07 (m, 3H), 2.27 (s, 6H). HPLC-MS calculated C$_{28}$H$_{26}$ClF$_2$N$_3$O$_3$ (M + H$^+$): 526.2. found: 526.2. |
| 364 | 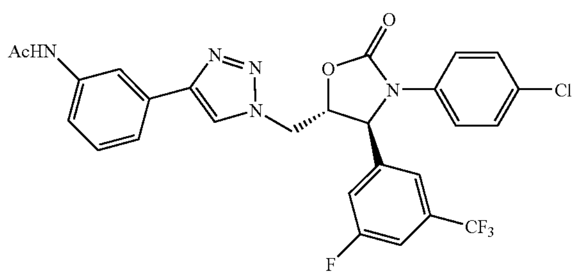 [SMILES: CC(=O)Nc1cccc(-c2cn(C[C@@H]3OC(=O)N(c4ccc(Cl)cc4)[C@H]3c3cc(F)cc(C(F)(F)F)c3)nn2)c1] | $^1$H NMR (CDCl$_3$) δ 9.21 (s, 1H), 8.41 (s, 1H), 8.17 (s, 1H), 7.75 (s, 1H), 7.67-7.62 (m, 2H), 7.52-7.44 (m, 4H), 7.34-7.28 (m, 3H), 5.85 (d, J = 5.5 Hz, 1H), 5.17-5.07 (m, 2H), 4.26 (dd, J = 6.6, 6.6 Hz, 1H), 2.10 (ovlp s, 3H); HPLC-MS calculated C$_{27}$H$_{20}$ClF$_4$N$_5$O$_3$ (M + H$^+$): 574.1, found: 574.1. |
| 365 | 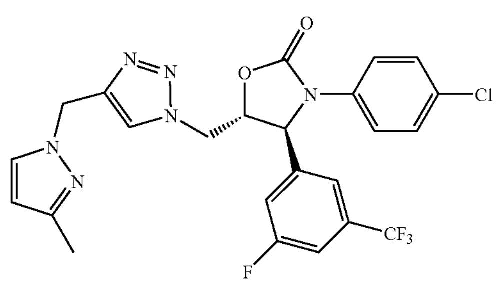 [SMILES: Cc1ccn(Cc2cn(C[C@@H]3OC(=O)N(c4ccc(Cl)cc4)[C@H]3c3cc(F)cc(C(F)(F)F)c3)nn2)n1] | $^1$H NMR (CDCl$_3$) δ 8.00 (s, 1H), 7.73 (s, 1H), 7.64 (m, 1H), 7.51 (d, J = 8.4 Hz, 1H), 7.46-7.42 (m, 3H), 7.33-7.29 (m, 2H), 5.96 (d, J = 2.2 Hz, 1H), 5.78 (d, J = 5.4 Hz, 1H), 5.29 (s, 2H), 5.12-5.10 (m, 2H), 5.03 (ddd, J = 5.8, 5.5, 4.2 Hz, 1H), 4.91 (d, J = 2.6 Hz, 1H), 2.14 (s, 3H); HPLC-MS calculated C$_{24}$H$_{19}$ClF$_4$N$_6$O$_2$ (M + H$^+$): 535.1, found: 535.1. |
| 366 | 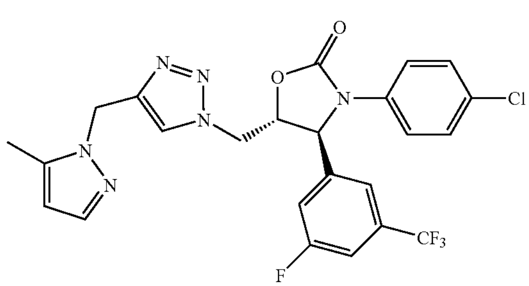 [SMILES: Cc1ccnn1Cc1cn(C[C@@H]2OC(=O)N(c3ccc(Cl)cc3)[C@H]2c2cc(F)cc(C(F)(F)F)c2)nn1] | $^1$H NMR (CDCl$_3$) δ 7.90 (s, 1H), 7.74 (s, 1H), 7.66-7.63 (m, 1H), 7.52 (d, J = 8.4 Hz, 1H), 7.47-7.43 (m, 2H), 7.34-7.31 (m, 2H), 7.28-7.26 (m, 1H), 6.04-5.98 (m, 1H), 5.79 (d, J = 5.2 Hz, 1H), 5.33 (s, 2H), 5.12-5.10 (m, 2H), 5.03 (ddd, J = 5.8, 5.5, 4.2 Hz, 1H), 4.96 (d, J = 2.4 Hz, 1H), 2.32 (s, 3H); HPLC-MS calculated C$_{24}$H$_{19}$ClF$_4$N$_6$O$_2$ (M + H$^+$): 535.1, found: 535.1. |

TABLE 1-continued

| Compound Number | Structure | Physical Data $^1$H NMR 400 MHz (CDCl$_3$) and/or MS (m/z) |
|---|---|---|
| 367 | 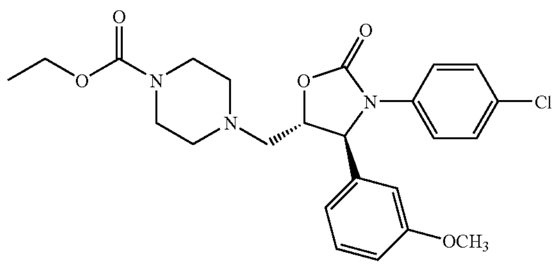 | $^1$H NMR (acetone-d$_6$) δ 7.54-7.50 (m, 2H), 7.32-7.28 (m, 3H), 7.03-7.01 (m, 2H), 6.89-6.86 (m, 1H), 5.44 (d, J = 5.7 Hz, 1H), 4.53 (q, J = 5.7 Hz, 1H), 4.07 (q, J = 6.8 Hz, 2H), 3.77 (s, 3H), 3.42-3.39 (m, 4H), 2.95 (dd, J = 13.5, 5.9 Hz, 1H), 2.86 (dd, part. Obs by HOD, 1H), 2.51 (t, J = 4.8 Hz, 4H), 1.20 (t, J = 6.8 Hz, 3H); HPLC-MS calculated C$_{24}$H$_{28}$ClN$_3$O$_5$ (M + H$^+$) 474.2, found 474.2. |
| 369 | 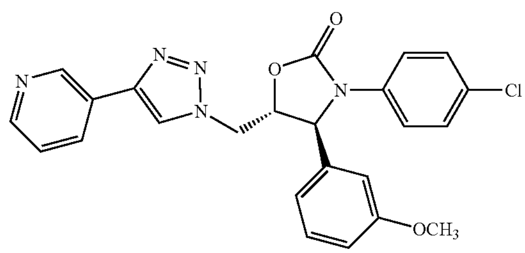 [SMILES: COc1cccc([C@H]2[C@H](Cn3cc(-c4cccnc4)nn3)OC(=O)N2c2ccc(Cl)cc2)c1] | $^1$H NMR (acetone-d$_6$) δ 9.07 (d, J = 1.6 Hz, 1H), 8.62 (s, 1H), 8.54 (dd, J = 4.8, 1.6 Hz, 1H), 8.21 (dt, J = 7.9, 2.1 Hz, 1H), 7.45-7.41 (m, 3H), 7.32-7.26 (m, 3H), 7.03-6.99 (m, 2H), 6.89 (ddd, J = 8.3, 2.6, 0.9 Hz, 1H), 5.58 (d, J = 5.4 Hz, 1H), 5.16-5.14 (m, 2H), 4.95 (ddd, J = 5.5, 5.5, 4.6 Hz, 1H), 3.76 (s, 3H); HPLC-MS calculated C$_{24}$H$_{20}$ClN$_5$O$_3$ (M + H$^+$) 462.1, found 462.1. |
| 370 | 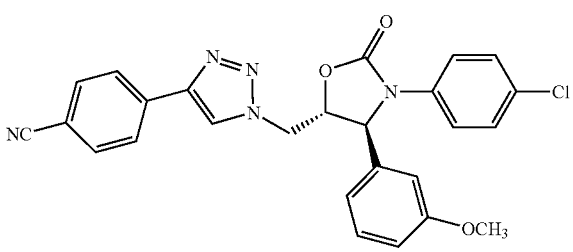 | $^1$H NMR (acetone-d$_6$) δ 8.56 (s, 1H), 7.98-7.95 (m, 2H), 7.73-7.71 (m, 2H), 7.31-7.28 (m, 2H), 7.19-7.13 (m, 3H), 6.90-6.87 (m, 2H), 6.76 (ddd, J = 8.3, 2.6, 0.9 Hz, 1H), 5.45 (d, J = 5.4 Hz, 1H), 5.04-5.02 (m, 2H), 4.84 (ddd, J = 5.5, 5.5, 4.6 Hz, 1H), 3.63 (s, 3H); HPLC-MS calculated C$_{26}$H$_{20}$ClN$_5$O$_3$ (M + H$^+$) 486.1, found 486.1. |
| 371 | 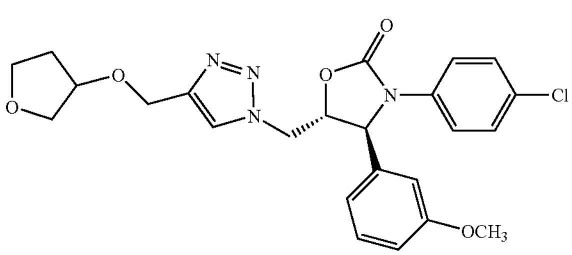 [SMILES: COc1cccc([C@H]2[C@H](Cn3cc(COC4CCOC4)nn3)OC(=O)N2c2ccc(Cl)cc2)c1] | $^1$H NMR (acetone-d$_6$) δ 8.05 (s, 1H), 7.43-7.41 (m, 2H), 7.32-7.28 (m, 3H), 6.99-6.95 (m, 2H), 6.88 (ddd, J = 8.3, 2.6, 0.9 Hz, 1H), 5.52 (d, J = 5.2 Hz, 1H), 5.05-5.04 (m, 2H), 4.88 (ddd, J = 5.2, 5.2, 4.6 Hz, 1H), 4.60-4.53 (m, 2H), 4.20-4.16 (m, 1H), 3.77 (s, 3H), 3.75-3.65 (m, 4H), 1.95-1.88 (m, 2H); HPLC-MS calculated C$_{24}$H$_{25}$ClN$_4$O$_5$ (M + H$^+$) 485.2, found 485.1. |
| 372 | 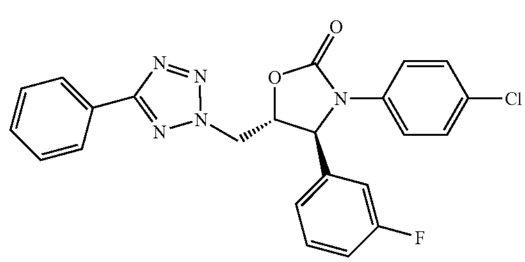 [SMILES: O=C1O[C@@H](Cn2nnc(-c3ccccc3)n2)[C@H](c2cccc(F)c2)N1c1ccc(Cl)cc1] | $^1$H NMR (acetone-d$_6$) δ 8.07-8.04 (m, 2H), 7.59-7.55 (m, 3H), 7.54-7.45 (m, 3H), 7.42-7.38 (m, 2H), 7.30-7.26 (m, 2H), 7.18-7.13 (m, 1H), 5.85 (d, J = 5.0 Hz, 1H), 5.50 (dd, J = 14.7, 5.9 Hz, 1H), 5.43 (dd, J = 14.7, 4.0 Hz, 1H), 5.19-5.15 (m, 1H), HPLC-MS calculated C$_{23}$H$_{17}$ClFN$_5$O$_2$ (M + H$^+$) 450.1, found 450.1. |

TABLE 1-continued

| Compound Number | Structure | Physical Data<br>¹H NMR 400 MHz (CDCl₃)<br>and/or MS (m/z) |
|---|---|---|
| 373 | 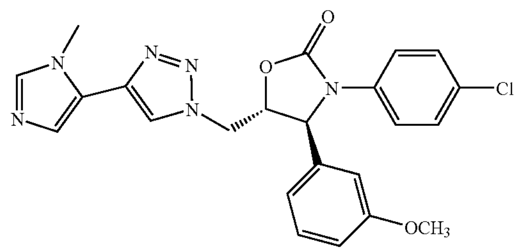 [SMILES: COc1cccc([C@H]2[C@H](Cn3cc(-c4cncn4C)nn3)OC(=O)N2c2ccc(Cl)cc2)c1] | ¹H NMR (acetone-d₆) δ 8.38 (s, 1H0, 7.61 (br s, 1H), 7.47-7.42 (m, 2H), 7.33-7.27 (m, 3H), 7.21 (br s, 1H), 7.03 (t, J = 2.0 Hz, 1H), 6.99 (d, J = 7.7 Hz, 1H), 6.89 (dd, J = 8.3, 2.5 Hz, 1H), 5.59 (d, J = 5.3 Hz, 1H), 5.16 (dd, J = 14.7, 5.9 Hz, 1H), 5.11 (dd, J = 14.7, 4.3 Hz, 1H), 4.95 (ddd, J = 5.5, 5.5, 4.3 Hz, 1H), 3.82 (s, 3H), 3.76 (s, 3H); HPLC-MS calculated C₂₃H₂₁ClN₆O₃ (M + H⁺) 465.1, found 465.1. |
| 374 | 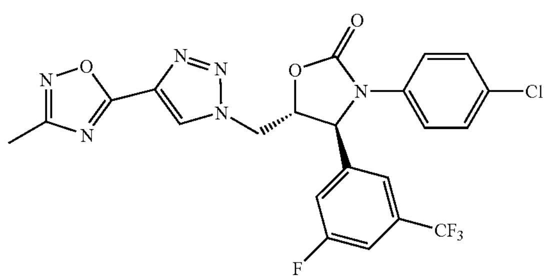 [SMILES: Cc1noc(-c2cn(C[C@@H]3OC(=O)N(c4ccc(Cl)cc4)[C@H]3c3cc(F)cc(C(F)(F)F)c3)nn2)n1] | ¹H NMR (CDCl₃) δ 8.92 (s, 1H), 7.71 (s, 1H), 7.72-7.69 (m, 1H), 7.52 (d, J = 8.4 Hz, 1H), 7.50-7.46 (m, 2H), 7.33-7.20 (m, 2H), 5.90 (d, J = 5.6 Hz, 1H), 5.34-5.33 (m, 2H), 5.18 (ddd, J = 5.7, 5.7, 4.7 Hz, 1H), 2.40 (s, 3H); HPLC-MS calculated C₂₂H₁₅ClF₄N₆O₃ (M + H⁺): 523.1, found: 523.1. |
| 375 | 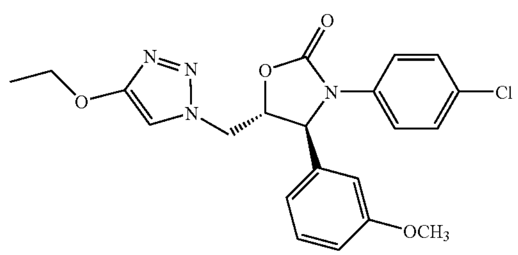 [SMILES: CCOc1cn(C[C@@H]2OC(=O)N(c3ccc(Cl)cc3)[C@H]2c2cccc(OC)c2)nn1] | ¹H NMR (acetone-d₆) δ 7.54 (s, 1H), 7.44-7.42 (m, 2H), 7.32-7.28 (m, 3H), 6.99-6.95 (m, 2H), 6.88 (ddd, J = 8.3, 2.5, 0.9 Hz, 1H), 5.48 (d, J = 5.2 Hz, 1H), 4.94-4.92 (m, 2H), 4.85 (ddd, J = 5.5, 5.1, 4.4 Hz, 1H), 4.15 (q, J = 7.1 Hz, 2H), 3.77 (s, 3H), 1.31 (t, J = 7.1 Hz, 3H); HPLC-MS calculated C₂₁H₂₁ClN₄O₄ (M + H⁺) 429.1, found 429.1. |
| 376 | 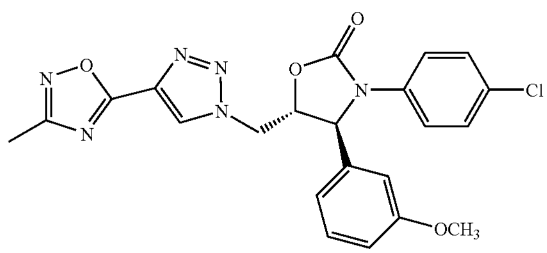 [SMILES: COc1cccc([C@H]2[C@H](Cn3cc(-c4nc(C)no4)nn3)OC(=O)N2c2ccc(Cl)cc2)c1] | ¹H NMR (acetone-d₆) δ 8.93 (s, 1H), 7.47-7.44 (m, 2H), 7.33-7.28 (m, 3H), 7.05-7.00 (m, 2H), 6.88 (ddd, J = 7.9, 2.5, 0.8 Hz, 1H), 5.62 (d, J = 5.0 Hz, 1H), 5.25-5.24 (m, 2H), 5.03 (ddd, J = 5.7, 5.5, 4.9 Hz, 1H) 3.76 (s, 3H), 2.40 (s, 3H); HPLC-MS calculated C₂₂H₁₉ClN₆O₄ (M + H⁺) 467.1, found 467.1.1. |
| 378 | 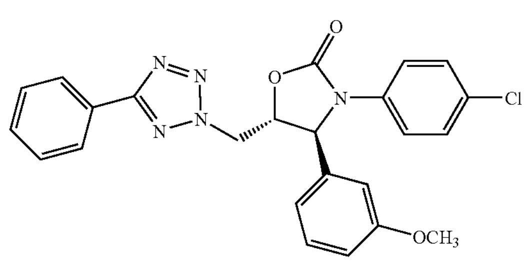 [SMILES: COc1cccc([C@H]2[C@H](Cn3nnc(-c4ccccc4)n3)OC(=O)N2c2ccc(Cl)cc2)c1] | ¹H NMR (acetone-d₆) δ 8.05-8.03 (m, 2H), 7.54-7.50 (m, 3H), 7.47-7.43 (m, 2H), 7.32 (t, J = 7.9 Hz, 1H), 7.30-7.24 (m, 2H), 7.09 (t, J = 2.08 Hz, 1H), 7.05-7.03 (app d, J = 7.8 Hz, 1H), 6.90 (ddd, J = 8.3, 2.6, 0.9 Hz, 1H), 5.72 (d, J = 5.1 Hz, 1H), 5.50 (dd, J = 14.7, 8.7 Hz, 1H), 5.43 (dd, J = 14.7, 10.6 Hz, 1H), 5.12-5.08 (m, 1H), 3.76 (s, 3H), HPLC-MS calculated C₂₄H₂₀ClN₅O₃ (M + H⁺) 462.1, found 462.1. |

TABLE 1-continued

| Compound Number | Structure | Physical Data<br>¹H NMR 400 MHz (CDCl₃) and/or MS (m/z) |
|---|---|---|
| 379 | 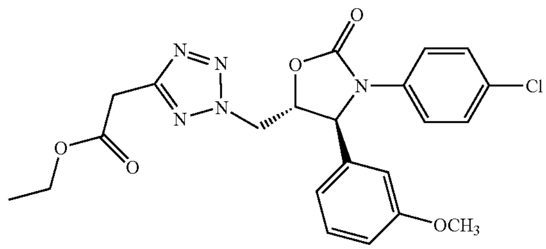 [SMILES: CCOC(=O)Cc1nnn(C[C@@H]2OC(=O)N(c3ccc(Cl)cc3)[C@H]2c2cccc(OC)c2)n1] | ¹H NMR (acetone-$d_6$) δ 7.48-7.44 (m, 2H), 7.34-7.29 (m, 3H), 7.07 (app t, J = 2.1 Hz, 1H), 7.02-6.99 (app d, J = 7.7 Hz, 1H), 6.90 (ddd, J = 8.3, 2.6, 0.9 Hz, 1H), 5.61 (d, J = 5.4 Hz, 1H), 5.40 (dd, J = 14.6, 6.4 Hz, 1H), 5.30 (dd, J = 14.6, 4.0 Hz, 1H), 5.02 (ddd, J = 6.4, 5.4, 4.1 Hz, 1H), 4.12 (q, J = 7.1 Hz, 2H), 3.94 (gem, d, J = 16.4 Hz, 2H), 3.78 (s, 3H), 1.20 (t, J = 7.1 Hz, 3H); HPLC-MS calculated $C_{22}H_{22}ClN_5O_5$ (M + H⁺) 472.1, found 472.1. |
| 383 | 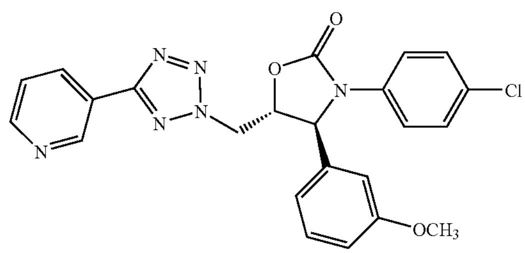 [SMILES: COc1cccc([C@H]2[C@H](Cn3nnc(-c4cccnc4)n3)OC(=O)N2c2ccc(Cl)cc2)c1] | ¹H NMR (acetone-$d_6$) δ 9.20 (dd, J = 2.2, 0.9 Hz, 1H), 8.71 (dd, J = 4.8, 1.7 Hz, 1H), 8.32 (ddd, J = 8.0, 2.2, 1.8 Hz, 1H), 7.52 (ddd, J = 7.9, 4.8, 0.9, Hz, 1H), 7.46-7.42 (m, 2H), 7.32 (t, J = 7.9 Hz, 1H), 7.27-7.24 (m, 2H), 7.09 (app t, J = 2.1 Hz, 1H), 7.04 (d, J = 7.7 Hz, 1H), 6.92 (ddd, J = 8.3, 2.6, 0.9 Hz, 1H), 5.72 (d, J = 5.1 Hz, 1H), 5.51 (dd, J = 14.7, 6.0 Hz, 1H), 5.45 (dd, J = 14.7, 4.0 Hz, 1H), 5.12 (ddd, J = 5.9, 5.2, 4.1 Hz, 1H), 3.77 (s, 3H), HPLC-MS calculated $C_{23}H_{19}ClN_6O_3$ (M + H⁺) 463.1, found 463.1. |
| 385 | 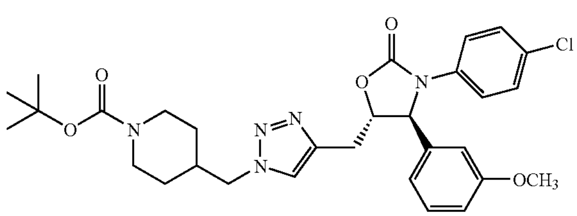 [SMILES: COc1cccc([C@H]2[C@H](Cc3cn(CC4CCN(C(=O)OC(C)(C)C)CC4)nn3)OC(=O)N2c2ccc(Cl)cc2)c1] | ¹H NMR (acetone-$d_6$) δ 7.87 (s, 1H), 7.46-7.42 (m, 2H), 7.29-7.25 (m, 3H), 6.92-6.88 (m, 2H), 6.85 (ddd, J = 8.2, 2.5, 0.9 Hz, 1H), 5.47 (d, J = 4.8 Hz, 1H), 4.67 (ddd, J = 5.4, 5.4, 4.9 Hz, 1H), 4.28 (d, J = 7.2 Hz, 2H), 4.06-3.96 (m, 4H), 3.76 (s, 3H), 3.33 (d, J = 5.4 Hz, 2H), 2.67-2.52 (m, 4H), 1.50-1.42 (m, 1H), 1.41 (s, 9H); HPLC-MS calculated $C_{30}H_{36}ClN_5O_5$ (M + H⁺-Boc) 482.2, found 482.2. |
| 388 | 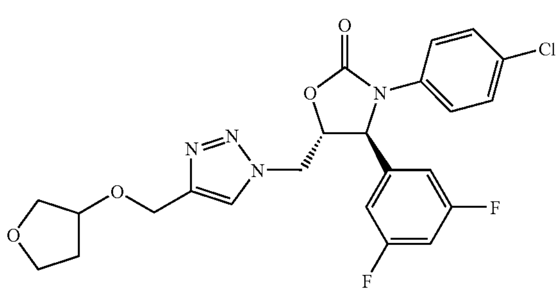 [SMILES: O=C1O[C@@H](Cn2cc(COC3CCOC3)nn2)[C@H](c2cc(F)cc(F)c2)N1c1ccc(Cl)cc1] | ¹H NMR (acetone-$d_6$) δ 8.03 (s, 1H), 7.46-7.42 (m, 2H), 7.32-7.30 (m, 2H), 7.19-7.15 (m, 2H), 7.00 (dddd, J = 9.1, 9.1, 2.3, 2.3 Hz, 1H), 5.64 (d, J = 5.3 Hz, 1H), 5.09-5.08 (m, 2H), 4.95 (ddd, J = 5.4, 5.4, 4.3 Hz, 1H), 4.58-4.53 (m, 2H), 4.22-4.18 (m, 1H), 3.77-3.64 (m, 6H); HPLC-MS calculated $C_{23}H_{21}ClF_2N_4O_4$ (M + H⁺): 491.1, found: 491.1. |

TABLE 1-continued

| Compound Number | Structure | Physical Data<br>$^1$H NMR 400 MHz (CDCl$_3$) and/or MS (m/z) |
|---|---|---|
| 390 | 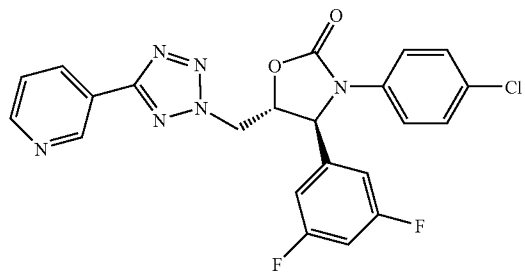 [SMILES: O=C1O[C@@H](Cn2nnc(-c3cccnc3)n2)[C@H](c2cc(F)cc(F)c2)N1c1ccc(Cl)cc1] | $^1$H NMR (acetone-d$_6$) δ 9.20 (br s, 1H), 8.72 (d, J = 4.1, 1H), 8.34 (ddd, J = 8.0, 1.9, 1.9 Hz, 1H), 7.52 (ddd, J = 7.9, 4.8, Hz, 1H), 7.46-7.42 (m, 2H), 7.29-7.24 (m, 2H), 7.02 (dddd, J = 9.1, 9.1, 2.2, 2.2 Hz, 1H), 5.87 (d, J = 5.1 Hz, 1H), 5.51 (dd, J = 14.7, 5.7 Hz, 1H), 5.46 (dd, J = 14.7, 4.0 Hz, 1H), 5.12 (ddd, J = 5.4, 5.4, 4.0 Hz, 1H), HPLC-MS calculated C$_{22}$H$_{15}$ClF$_2$N$_6$O$_2$ (M + H$^+$) 469.1, found 469.1. |
| 393 | 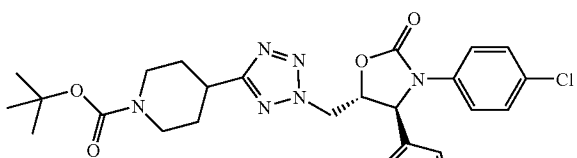 | $^1$H NMR (acetone-d$_6$) δ 7.48-7.45 (m, 2H), 7.34-7.31 (m, 2H), 7.20-7.18 (m, 2H), 7.02 (dddd, J = 9.1, 9.1, 2.3, 2.3 Hz, 1H), 5.76 (d, J = 4.8 Hz, 1H), 5.38 (dd, J = 14.7, 5.4 Hz, 1H), 5.30 (dd, J = 14.7, 4.2 Hz, 1H), 5.12 (ddd, J = 5.2, 5.1, 4.1 Hz, 1H), 4.05-3.98 (m, 2H), 3.06 (dddd, J = 11.1, 11.1, 4.0, 4.0 Hz, 1H), 1.85-1.80 (m, 2H), 1.63-1.53 (m, 2H), 1.41 (s, 9H), HPLC-MS calculated C$_{27}$H$_{29}$ClF$_2$N$_6$O$_2$ (M + H$^+$-Boc) 475.2, found 475.2. |
| 394 | 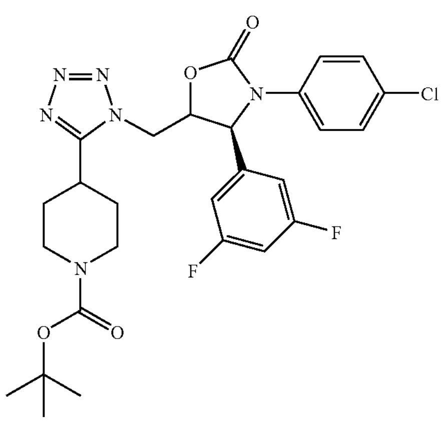 [SMILES: CC(C)(C)OC(=O)N1CCC(c2nnnn2CC2OC(=O)N(c3ccc(Cl)cc3)[C@H]2c2cc(F)cc(F)c2)CC1] | $^1$H NMR (acetone-d$_6$) δ 7.52-7.48 (m, 2H), 7.38-7.32 (m, 2H), 7.26-7.23 (m, 2H), 7.02 (dddd, J = 9.1, 9.1, 2.3, 2.3 Hz, 1H), 5.76 (d, J = 5.2 Hz, 1H), 5.27-5.17 (m, 3H), 5.03 (ddd, J = 6.0, 5.3, 4.3 Hz, 1H), 4.17-4.13 (m, 2H), 3.06 (dddd, J = 11.1, 11.1, 3.3, 3.3 Hz, 1H), 1.99-1.95 (m, 2H), 1.84-1.73 (m, 2H), 1.46 (s, 9H), HPLC-MS calculated C$_{27}$H$_{29}$ClF$_2$N$_6$O$_4$ (M + H$^+$-Boc) 475.2, found 475.2. |
| 395 | 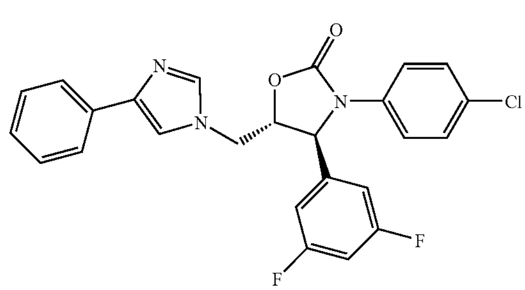 [SMILES: O=C1O[C@@H](Cn2cnc(-c3ccccc3)c2)[C@H](c2cc(F)cc(F)c2)N1c1ccc(Cl)cc1] | $^1$H NMR (acetone-d$_6$) δ 7.78-7.76 (m, 2H), 7.66 (s, 1H), 7.45 (d, J = 8.9 Hz, 1H), 7.36-7.27 (m, 3H), 7.20-7.14 (m, 2H), 7.01-6.87 (m, 1H), 5.60 (d, J = 5.5 Hz, 1H), 4.93-4.89 (m, 1H), 4.75-4.74 (m, 2H); HPLC-MS calculated C$_{25}$H$_{18}$ClF$_2$N$_3$O$_2$ (M + H$^+$) 466.1, found 466.1. (Proton count short) |

TABLE 1-continued

| Compound Number | Structure | Physical Data<br>¹H NMR 400 MHz (CDCl₃) and/or MS (m/z) |
|---|---|---|
| 396 | 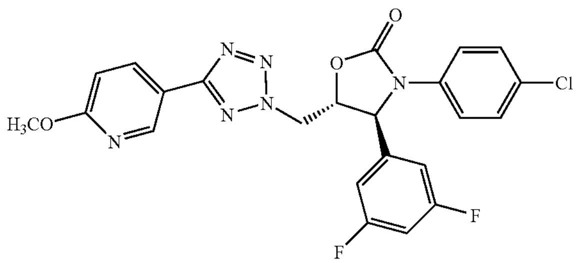 [SMILES: COc1ccc(-c2nnn(C[C@@H]3OC(=O)N(c4ccc(Cl)cc4)[C@H]3c3cc(F)cc(F)c3)n2)cn1] | ¹H NMR (acetone-d₆) δ 8.79 (m, 1H), 8.21 (ddd, J = 8.7, 2.4, 1.3 Hz, 1H), 7.45 (d, J = 9.0 Hz, 2H) 7.29-7.24 (m, 4H), 7.05-7.00 (m, 1H), 6.90 (d, J = 8.7 Hz, 1H), 5.87 (d, J = 4.9 Hz, 1H), 5.49 (dd, J = 14.7, 5.6 Hz, 1H), 5.43 (dd, J = 14.7, 4.1 Hz, 1H), 5.12 (ddd, J = 5.3, 5.0, 4.2 Hz, 1H), 3.97 (s, 3H), HPLC-MS calculated $C_{23}H_{17}ClF_2N_6O_3$ (M + H⁺) 499.1, found 499.0. |
| 397 | 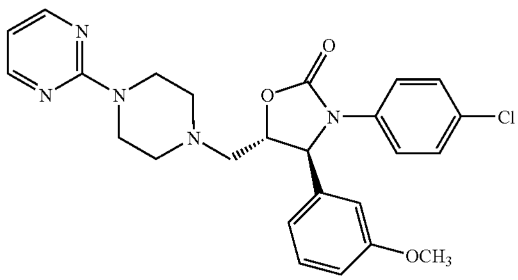 [SMILES: COc1cccc([C@H]2[C@H](CN3CCN(c4ncccn4)CC3)OC(=O)N2c2ccc(Cl)cc2)c1] | ¹H NMR (acetone-d₆) δ 8.32 (d, J = 4.7 Hz, 2H), 7.55-7.53 (m, 2H), 7.33-7.29 (m, 3H), 7.06-7.04 (m, 2H), 6.87 (ddd, J = 8.3, 2.5, 0.8 Hz, 1H), 6.57 (t, J = 4.7 Hz, 1H), 5.49 (d, J = 5.7 Hz, 1H), 4.57 (q, J = 5.7 Hz, 1H), 3.80-3.77 (m, 7H), 2.98 (dd, J = 13.4, 6.1 Hz, 1H), 2.86 (dd, J = 13.4, 5.6 Hz, 1H), 2.62 (t, J = 5.1 Hz, 4H); HPLC-MS calculated $C_{25}H_{26}ClN_5O_3$ (M + H⁺) 480.1, found 480.1. |
| 398 | 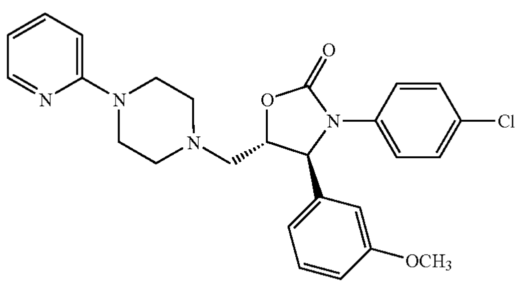 [SMILES: COc1cccc([C@H]2[C@H](CN3CCN(c4ccccn4)CC3)OC(=O)N2c2ccc(Cl)cc2)c1] | ¹H NMR (acetone-d₆) δ 8.12 (dddd, J = 4.1, 2.0, 1.2, 0.8 Hz, 1H), 7.56-7.48 (m, 3H), 7.32-7.28 (m, 3H), 7.06-7.04 (m, 2H), 6.90-6.76 9m, 1H), 6.77 (d, J = 8.6 Hz, 1H), 6.61 (ddd, J = 6.8, 5.6, 0.7 Hz, 1H), 5.49 (d, J = 5.6 Hz, 1H), 4.57 (q, J = 5.8 Hz, 1H), 3.77 (s, 3H), 3.55-3.51 (m, 4H), 2.96 (dd, J = 13.4, 6.1 Hz, 1H), 2.87 (dd, J = 13.4, 5.6 Hz, 1H), 2.67 (t, J = 5.0 Hz, 4H); HPLC-MS calculated $C_{26}H_{27}ClN_4O_3$ (M + H⁺) 479.2, found 479.1. |
| 401 | 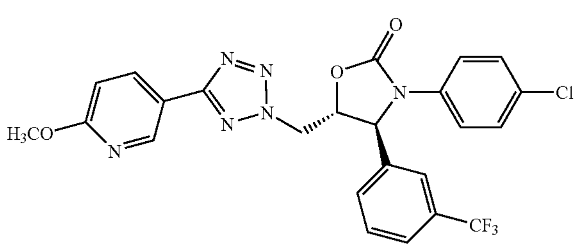 [SMILES: COc1ccc(-c2nnn(C[C@@H]3OC(=O)N(c4ccc(Cl)cc4)[C@H]3c3cccc(C(F)(F)F)c3)n2)cn1] | ¹H NMR (acetone-d₆) δ 8.79 (dd, J = 2.4, 0.8 Hz, 1H), 8.19 (dd, J = 8.7, 2.4 Hz, 1H), 7.94 (s, 1H), 7.83 (d, J = 7.7 Hz, 1H), 7.73-7.65 (m, 2H), 7.46-7.43 (m, 2H), 7.26-7.24 (m, 2H), 6.90 (dd, J = 8.7, 0.8 Hz, 1H), 5.95 (d, J = 4.8 Hz, 1H), 5.52 (dd, J = 14.6, 5.6 Hz, 1H), 5.43 (dd, J = 14.6, 4.1 Hz, 1H), 5.12 (ddd, J = 5.6, 4.8, 4.1 Hz, 1H), 3.96 (s, 3H), HPLC-MS calculated $C_{24}H_{18}ClF_3N_6O_3$ (M + H⁺) 531.1, found 531.1. |

TABLE 1-continued

| Compound Number | Structure | Physical Data<br>$^1$H NMR 400 MHz (CDCl$_3$)<br>and/or MS (m/z) |
|---|---|---|
| 402 | 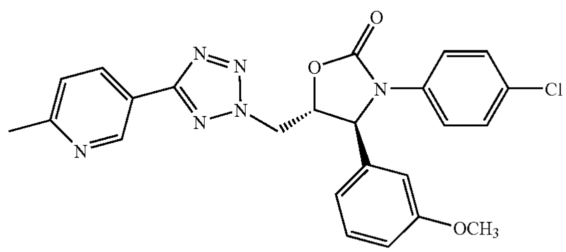 | $^1$H NMR (acetone-d$_6$) δ 9.06 (d, J = 2.3 Hz, 1H), 8.19 (dd, J = 8.1, 2.3 Hz, 1H), 7.44-7.41 (m, 2H), 7.38 (d, J = 8.1 Hz, 1H), 7.32 (t, J = 7.9 Hz, 1H), 7.25-7.23 (m, 2H), 7.08 (app t, J = 2.1 Hz, 1H), 7.03 (d, J = 7.7 Hz, 1H), 6.92 (ddd, J = 8.3, 2.6, 0.9 Hz, 1H), 5.71 (d, J = 5.1 Hz, 1H), 5.48 (dd, J = 14.6, 5.9 Hz, 1H), 5.40 (dd, J = 14.6, 4.0 Hz, 1H), 5.12 (ddd, J = 5.9, 5.1, 4.1 Hz, 1H), 3.76 (s, 3H), 2.56 (s, 3H), HPLC-MS calculated C$_{24}$H$_{21}$ClN$_6$O$_3$ (M + H$^+$) 477.1, found 477.1. |
| 403 | 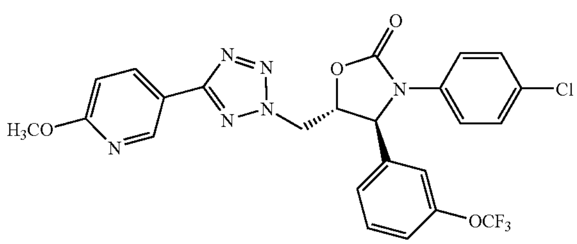 | $^1$H NMR (acetone-d$_6$) δ 8.78 (dd, J = 2.4, 0.8 Hz, 1H), 8.19 (dd, J = 8.7, 2.4 Hz, 1H), 7.59-7.54 (m, 3H), 7.46-7.43 (m, 2H), 7.35-7.32 (m, 1H), 7.27-7.24 (m, 2H), 6.90 (dd, J = 8.7, 0.8 Hz, 1H), 5.89 (d, J = 4.8 Hz, 1H), 5.49 (dd, J = 14.7, 5.6 Hz, 1H), 5.43 (dd, J = 14.6, 4.0 Hz, 1H), 5.12 (ddd, J = 5.6, 4.8, 4.1 Hz, 1H), 3.96 (s, 3H), HPLC-MS calculated C$_{24}$H$_{18}$ClF$_3$N$_6$O$_4$ (M + H$^+$) 547.1, found 547.0. |
| 404 | 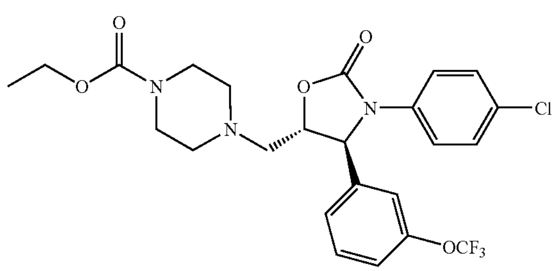 | $^1$H NMR (acetone-d$_6$) δ 7.55-7.48 (m, 5H), 7.33-7.28 (m, 3H), 5.62 (d, J = 5.7 Hz, 1H), 4.60 (ddd, J = 6.4, 5.5, 5.5 Hz, 1H), 4.07 (q, J = 7.1 Hz, 2H), 3.45-3.34 (m, 4H), 2.98 (dd, J = 13.5, 6.4 Hz, 1H), 2.86 (dd, J = 13.5, 5.3 Hz, 1H), 2.55 (t, J = 5.1 Hz, 4H), 1.20 (t, J = 7.1 Hz, 3H); HPLC-MS calculated C$_{24}$H$_{25}$ClF$_3$N$_3$O$_5$ (M + H$^+$) 528.1, found 528.1. |
| 405 | 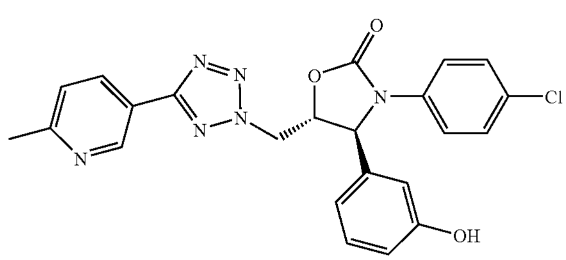 [SMILES: Cc1ccc(-c2nnn(C[C@@H]3OC(=O)N(c4ccc(Cl)cc4)[C@H]3c3cccc(O)c3)n2)cn1] | $^1$H NMR (acetone-d$_6$) δ 9.07 (m, 1H), 8.58 (s, 1H), 8.19 (dd, J = 8.1, 2.2 Hz, 1H), 7.44-7.41 (m, 2H), 7.38 (d, J = 8.1 Hz, 1H), 7.36-7.22, 6.96 (d, J = 7.7 Hz, 1H), 6.92 (s, 1H), 6.83 (ddd, J = 8.1, 2.4, 1.3 Hz, 1H), 5.65 (d, J = 4.6 Hz, 1H), 5.48 (dd, J = 14.6, 5.8 Hz, 1H), 5.40 (dd, J = 14.6, 3.9 Hz, 1H), 5.12 (ddd, J = 5.7, 5.4, 4.3 Hz, 1H), 2.56 (s, 3H), HPLC-MS calculated C$_{23}$H19Cl$_6$O$_3$ (M + H$^+$) 463.1, found 462.9. |

TABLE 1-continued

| Compound Number | Structure | Physical Data $^1$H NMR 400 MHz (CDCl$_3$) and/or MS (m/z) |
|---|---|---|
| 406 | 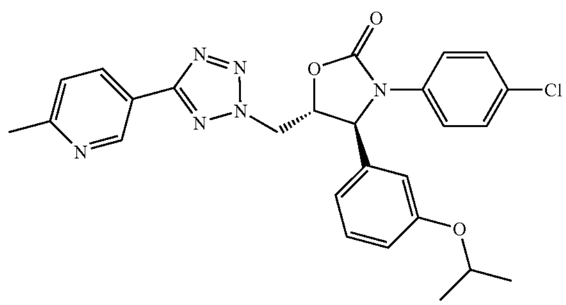 [SMILES: Cc1ccc(-c2nnn(C[C@@H]3OC(=O)N(c4ccc(Cl)cc4)[C@H]3c3cccc(OC(C)C)c3)n2)cn1] | $^1$H NMR (acetone-d$_6$) δ 9.08 (d, J = 2.2 Hz, 1H), 8.19 (dd, J = 8.1, 2.3 Hz, 1H), 7.47-7.42 (m, 2H), 7.38 (d, J = 8.1 Hz, 1H), 7.32 (t, J = 8.0 Hz, 1H), 7.26-7.24 (m, 2H), 7.05 (app t, J = 2.0 Hz, 1H), 7.03 (d, J = 7.7 Hz, 1H), 6.92 (ddd, J = 8.3, 2.5, 0.8 Hz, 1H), 5.70 (d, J = 5.0 Hz, 1H), 5.48 (dd, J = 14.6, 5.8 Hz, 1H), 5.41 (dd, J = 14.6, 4.1 Hz, 1H), 5.12 (ddd, J = 5.7, 5.0, 4.2 Hz, 1H), 4.61 (septet, J = 6.0 Hz, 1H), 1.25 (d, J = 6.0 Hz, 3H), 1.21 (d, J = 6.0 Hz, 3H), HPLC-MS calculated C$_{26}$H$_{25}$ClN$_6$O$_3$ (M + H$^+$) 505.2, found 505.2. |
| 407 | 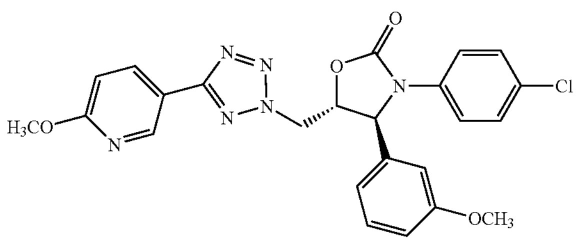 [SMILES: COc1cccc([C@H]2[C@H](Cn3nnc(-c4ccc(OC)nc4)n3)OC(=O)N2c2ccc(Cl)cc2)c1] | $^1$H NMR (acetone-d$_6$) δ 8.78 (dd, J = 2.4, 0.7 Hz, 1H), 8.20 (dd, J = 8.7, 2.4 Hz, 1H), 7.47-7.42 (m, 2H), 7.32 (t, J = 8.0 Hz, 1H), 7.26-7.24 (m, 2H), 7.08 (app t, J = 2.0 Hz, 1H), 7.03 (d, J = 7.7 Hz, 1H), 6.92-6.89 (m, 2H), 5.70 (d, J = 5.0 Hz, 1H), 5.46 (dd, J = 14.6, 5.8 Hz, 1H), 5.39 (dd, J = 14.6, 4.1 Hz, 1H), 5.12 (ddd, J = 5.7, 5.0, 4.1 Hz, 1H), 3.96 (s, 3H), 3.77 (s, 3H); HPLC-MS calculated C$_{24}$H$_{21}$ClN$_6$O$_4$ (M + H$^+$) 493.1, found 492.9. |
| 408 | 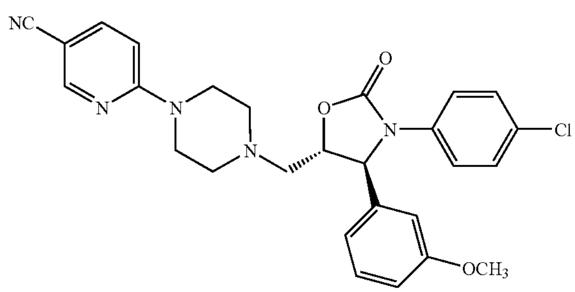 | $^1$H NMR (acetone-d$_6$) δ 8.42 (d, J = 2.3 Hz, 1H), 7.76 (dd, J = 9.1, 2.4 Hz, 1H), 7.55-7.52 (m, 2H), 7.33-7.28 (m, 3H), 7.06-7.04 (m, 2H), 6.90-6.87 (m, 2H), 5.49 (d, J = 5.7 Hz, 1H), 4.57 (q, J = 5.7 Hz, 1H), 3.77 (s, 3H), 3.72 (ddd, J = 5.4, 5.0, 5.0 Hz, 4H), 2.98 (dd, J = 13.5, 5.8 Hz, 1H), 2.87 (dd, J = 13.5, 5.7 Hz, 1H), 2.67 (t, J = 5.0 Hz, 4H); HPLC-MS calculated C$_{27}$H$_{26}$ClN$_5$O$_3$ (M + H$^+$) 504.2, found 504.0. |
| 409 | 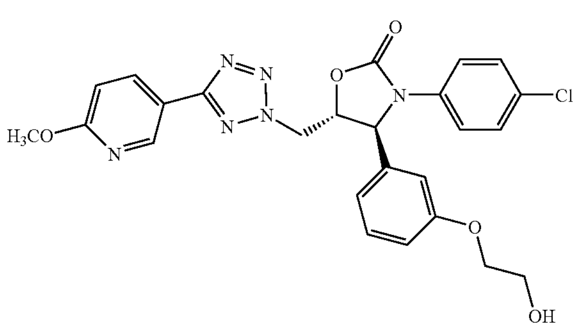 [SMILES: COc1ccc(-c2nnn(C[C@@H]3OC(=O)N(c4ccc(Cl)cc4)[C@H]3c3cccc(OCCO)c3)n2)cn1] | $^1$H NMR (acetone-d$_6$) δ 8.78 (d, J = 2.3 Hz, 1H), 8.20 (dd, J = 8.7, 2.4 Hz, 1H), 7.47-7.42 (m, 2H), 7.31 (t, J = 8.0 Hz, 1H), 7.26-7.24 (m, 2H), 7.08 (br s, 1H), 7.03 (d, J = 7.6 Hz, 1H), 6.92-6.89 (m, 2H), 5.70 (d, J = 4.9 Hz, 1H), 5.46 (dd, J = 14.6, 5.9 Hz, 1H), 5.39 (dd, J = 14.6, 4.1 Hz, 1H), 5.12 (ddd, J = 5.1, 4.9, 4.6 Hz, 1H), 4.06-4.00 (m, 2H), 3.99 (s, 3H), 3.82 (q, J = 5.2 Hz, 2H); HPLC-MS calculated C$_{25}$H$_{23}$ClN$_6$O$_5$ (M + H$^+$) 523.1, found 522.9. |

TABLE 1-continued

| Compound Number | Structure | Physical Data ¹H NMR 400 MHz (CDCl₃) and/or MS (m/z) |
|---|---|---|
| 410 | 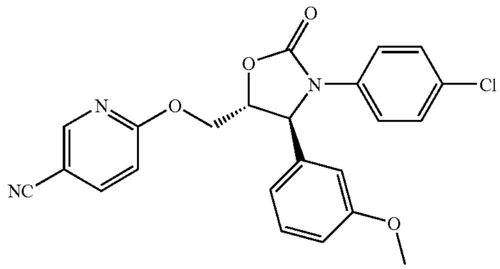 | ¹H NMR (acetone-d₆) δ 8.62 (d, J = 1.7 Hz, 1H), 8.09 (dd, J = 8.7, 2.3 Hz, 1H), 7.56-7.53 (m, 2H), 7.34-7.29 (m, 3H), 7.08 (dd, J = 2.3, 1.8 Hz, 1H), 7.05 (d, J = 7.7 Hz, 1H), 6.90 (ddd, J = 8.3, 2.5, 0.8 Hz, 1H), 5.64 (d, J = 5.2 Hz, 1H), 4.86-4.79 (m, 3H), 3.77 (s, 3H); HPLC-MS calculated C₂₃H₁₈ClN₃O₄ (M + H⁺) 436.1, found 436.1. |
| 413 | 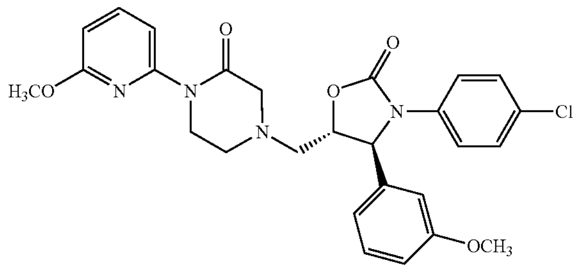 [SMILES: COc1cccc([C@H]2[C@H](CN3CCN(c4cccc(OC)n4)C(=O)C3)OC(=O)N2c2ccc(Cl)cc2)c1] | ¹H NMR (acetone-d₆) δ 7.69-7.64 (m, 2H), 7.55-7.53 (m, 2H), 7.31-7.26 (m, 3H), 7.07 (dd, J = 2.2, 1.9 Hz, 1H), 7.03 (d, J = 7.7 Hz, 1H, 6.87 (ddd, J = 8.3, 2.6, 0.8 Hz, 1H), 6.55 (dd, J = 6.2, 2.5 Hz, 1H), 5.54 (d, J = 5.8 Hz, 1H), 4.62 (q, J = 5.7 Hz, 1H), 4.01 (ddd, J = 6.8, 4.2, 3.0 Hz, 2H), 3.87 (s, 3H), 3.77 (s, 3H), 3.48 (d, J = 16.6 Hz, 1H), 3.43 (d, J = 16.6 Hz, 1H), 3.10 (dd, J = 13.5, 5.6 Hz, 1H), 3.06-2.97 (m, 3H); HPLC-MS calculated C₂₇H₂₇ClN₄O₅ (M + H⁺) 523.2, found 523.0. |
| 414 | 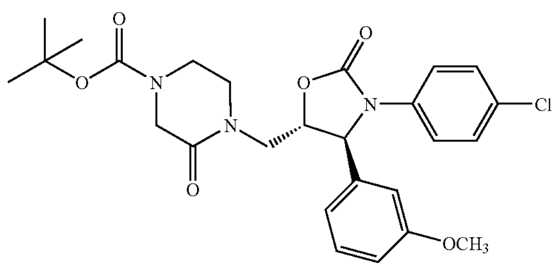 [SMILES: COc1cccc([C@H]2[C@H](CN3CCN(C(=O)OC(C)(C)C)CC3=O)OC(=O)N2c2ccc(Cl)cc2)c1] | ¹H NMR (acetone-d₆) δ 7.47-7.44 (m, 2H), 7.31-7.27 (m, 3H), 7.05 (t, J = 2.0 Hz, 1H), 7.01 (d, J = 7.7 Hz, 1H), 6.85 (ddd, J = 8.3, 2.6, 0.7 Hz, 1H), 5.45 (d, J = 6.1 Hz, 1H), 4.64 (ddd, J = 5.9, 5.1, 5.0 Hz, 1H), 3.99-3.95 (m, 4H), 3.77 (s, 3H), 3.64-3.55 (m, 4H), 1.42 (s, 9H); HPLC-MS calculated C₂₉H₃₀ClN₃O₆ (M + Na⁺) 538.0 found 538.0. |
| 415 | 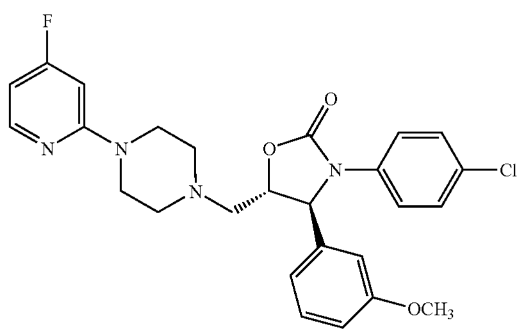 [SMILES: COc1cccc([C@H]2[C@H](CN3CCN(c4cc(F)ccn4)CC3)OC(=O)N2c2ccc(Cl)cc2)c1] | ¹H NMR (acetone-d₆) δ 8.10 (dd, J = 9.8, 5.6 Hz, 1H), 7.56-7.52 (m, 2H), 7.32-7.27 (m, 3H), 7.05-7.03 (m, 2H), 6.89-6.86 (m, 1H), 6.52 (dd, J = 13.2, 2.1 Hz, 1H), 6.44 (ddd, J = 8.2, 6.9, 2.1 Hz, 1H), 5.48 (d, J = 5.7 Hz, 1H), 4.57 (q, J = 5.7 Hz, 1H), 3.77 (s, 3H), 3.57 (dddd, J = 13.0, 13.0, 10.0, 5.0 Hz, 4H), 2.97 (dd, J = 13.5, 6.0 Hz, 1H), 2.87 (dd, J = 13.4, 5.6 Hz, 1H), 2.67 (t, J = 5.1 Hz, 4H); HPLC-MS calculated C₂₆H₂₆ClFN₄O₃ (M + H⁺) 497.2, found 497.0. |
| 417 | 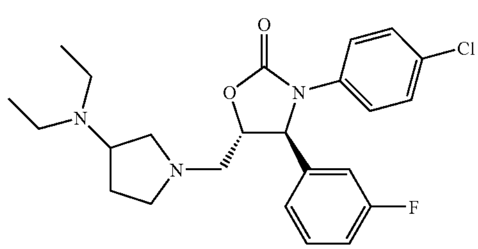 [SMILES: CCN(CC)C1CCN(C[C@@H]2OC(=O)N(c3ccc(Cl)cc3)[C@H]2c2cccc(F)c2)C1] | HPLC-MS calculated C₂₄H₃₀ClFN₃O₂ (M + H): 446.19, found: 446.20. |

TABLE 1-continued

| Compound Number | Structure | Physical Data <sup>1</sup>H NMR 400 MHz (CDCl₃) and/or MS (m/z) |
|---|---|---|
| 418 | 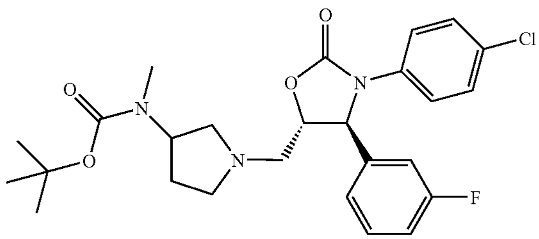 [SMILES: CN(C(=O)OC(C)(C)C)C1CCN(C[C@@H]2OC(=O)N(c3ccc(Cl)cc3)[C@H]2c2cccc(F)c2)C1] | HPLC-MS calculated C$_{26}$H$_{31}$ClFN$_3$O$_4$ (M + H): 504.20, found: 504.20. |
| 420 | 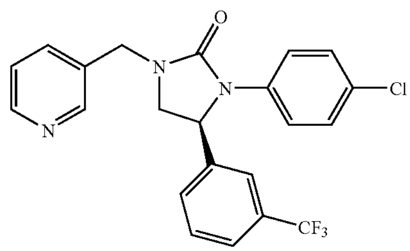 [SMILES: O=C1N(Cc2cccnc2)C[C@H](c2cccc(C(F)(F)F)c2)N1c1ccc(Cl)cc1] | HPLC-MS calculated for C$_{22}$H$_{18}$Cl$_3$F$_3$N$_3$O (M + H$^+$) 432.1, found 432.0. |
| 421 | 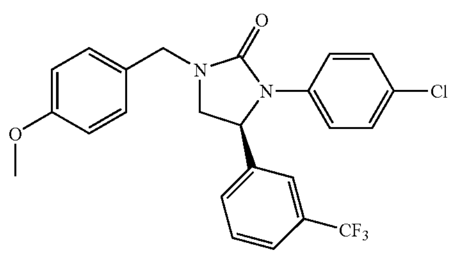 [SMILES: COc1ccc(CN2C[C@H](c3cccc(C(F)(F)F)c3)N(c3ccc(Cl)cc3)C2=O)cc1] | HPLC-MS calculated for C$_{24}$H$_{21}$ClF$_3$N$_2$O$_2$ (M + H$^+$) 461.1, found 461.0. |
| 422 | 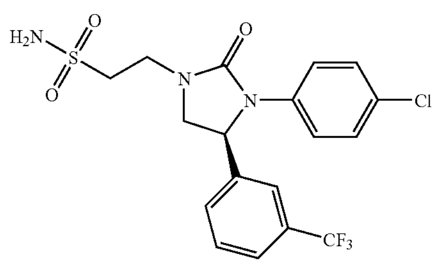 [SMILES: NS(=O)(=O)CCN1C[C@H](c2cccc(C(F)(F)F)c2)N(c2ccc(Cl)cc2)C1=O] | HPLC-MS calculated for C$_{18}$H$_{18}$ClF$_3$N$_3$O$_3$S (M + H$^+$) 448.0, found 448.0. |
| 423 | 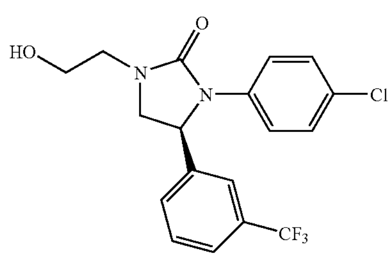 [SMILES: O=C1N(CCO)C[C@H](c2cccc(C(F)(F)F)c2)N1c1ccc(Cl)cc1] | 1H NMR (CDCl3, 400 MHz) δ 7.50-7.39 (m, 4H), 7.23 (d, J = 8.8 Hz, 2H), 7.13 (d, J = 9.2 Hz, 2H), 5.22 (dd, J = 9.2, 6.4 Hz, 1H), 3.99 (t, J = 9.2 Hz, 1H), 3.78 (t, J = 5.0 Hz, 2H), 3.51-3.32 (m, 2H), 3.30 (dd, J = 9.0, 6.2 Hz, 1H); HPLC-MS calculated for C$_{18}$H$_{17}$ClF$_3$N$_2$O$_2$ (M + H$^+$) 385.0, found 385.0. |
| 424 | 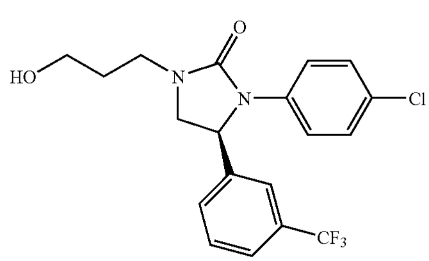 [SMILES: O=C1N(CCCO)C[C@H](c2cccc(C(F)(F)F)c2)N1c1ccc(Cl)cc1] | HPLC-MS calculated for C$_{19}$H$_{19}$ClF$_3$N$_2$O$_2$ (M + H$^+$) 399.1, found 399.0. |

TABLE 1-continued

| Compound Number | Structure | Physical Data<br>$^1$H NMR 400 MHz (CDCl$_3$)<br>and/or MS (m/z) |
|---|---|---|
| 425 | 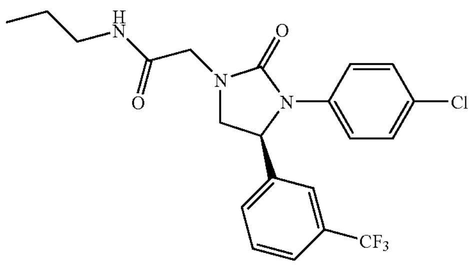 [SMILES: CCCNC(=O)CN1C[C@H](c2cccc(C(F)(F)F)c2)N(c2ccc(Cl)cc2)C1=O] | HPLC-MS calculated for<br>C$_{21}$H$_{22}$ClF$_3$N$_3$O$_2$ (M + H$^+$)<br>440.1, found 440.0. |
| 426 | 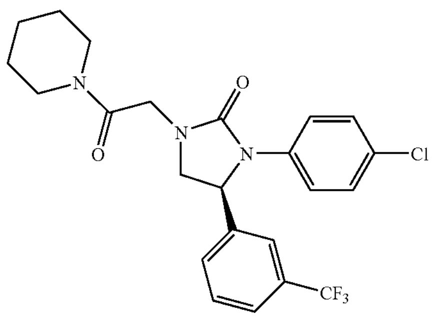 [SMILES: O=C(CN1C[C@H](c2cccc(C(F)(F)F)c2)N(c2ccc(Cl)cc2)C1=O)N1CCCCC1] | HPLC-MS calculated for<br>C$_{23}$H$_{24}$ClF$_3$N$_3$O$_2$ (M + H$^+$)<br>466.1, found 466.0. |
| 427 | 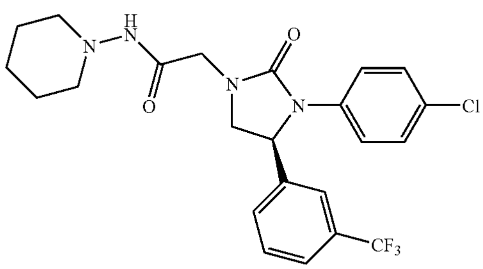 [SMILES: O=C(CN1C[C@H](c2cccc(C(F)(F)F)c2)N(c2ccc(Cl)cc2)C1=O)NN1CCCCC1] | HPLC-MS calculated for<br>C$_{23}$H$_{25}$ClF$_3$N$_4$O$_2$ (M + H$^+$)<br>481.1, found 481.0. |
| 428 | 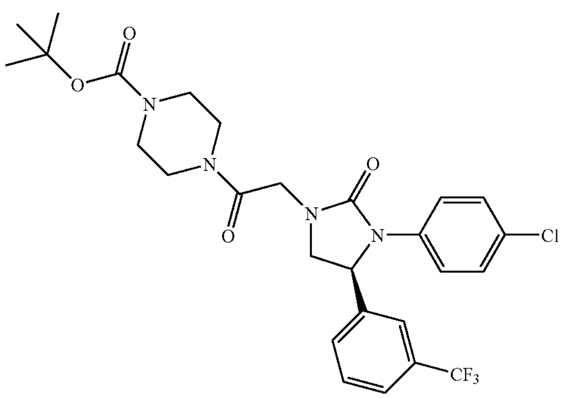 [SMILES: CC(C)(C)OC(=O)N1CCN(C(=O)CN2C[C@H](c3cccc(C(F)(F)F)c3)N(c3ccc(Cl)cc3)C2=O)CC1] | HPLC-MS calculated for<br>C$_{27}$H$_{31}$ClF$_3$N$_4$O$_4$ (M + H$^+$)<br>567.1, found 467.0. |
| 429 | 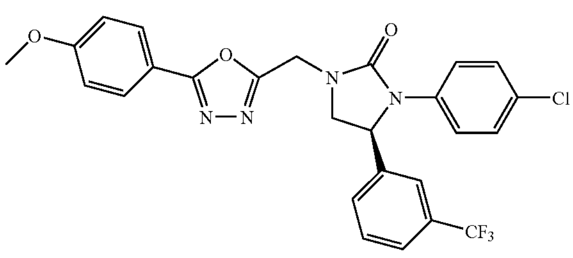 | HPLC-MS calculated for<br>C$_{26}$H$_{21}$ClF$_3$N$_4$O$_3$ (M + H$^+$)<br>425.1, found 425.1. |

TABLE 1-continued

| Compound Number | Structure | Physical Data $^1$H NMR 400 MHz (CDCl$_3$) and/or MS (m/z) |
|---|---|---|
| 430 | 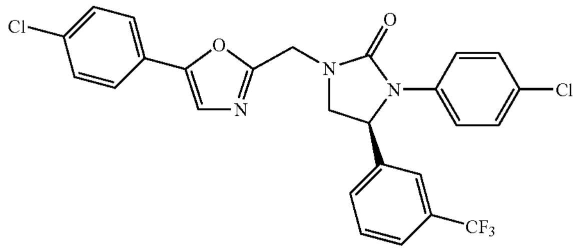 [SMILES: O=C1N(Cc2ncc(-c3ccc(Cl)cc3)o2)C[C@H](c2cccc(C(F)(F)F)c2)N1c1ccc(Cl)cc1] | HPLC-MS calculated for C$_{26}$H$_{19}$Cl$_2$F$_3$N$_3$O$_2$ (M + H$^+$) 532.0, found 532.0. |
| 431 | 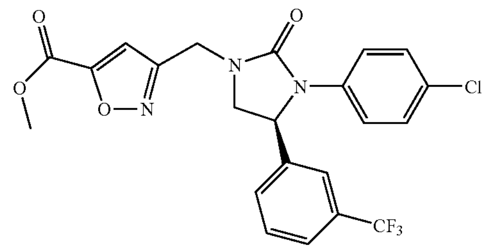 [SMILES: COC(=O)c1cc(CN2C[C@H](c3cccc(C(F)(F)F)c3)N(c3ccc(Cl)cc3)C2=O)no1] | $^1$H NMR (CD$_3$OD, 400 MHz) δ 7.65 (s, 1H), 7.61-7.52 (m, 3H), 7.42 (d, J = 8.8 Hz, 2H), 7.25 (d, J = 9.2 Hz, 2H), 6.76 (s, 1H), 5.59 (dd, J = 9.2, 6.0 Hz, 1H), 4.79 (m, 2H), 4.07 (t, J = 9.2 Hz, 1H), 3.94 (s, 3H), 3.36 (m, 1H); HPLC-MS calculated for C$_{22}$H$_{18}$ClF$_3$N$_3$O$_4$ (M + H$^+$) 480.0, found 480.0. |
| 433 | 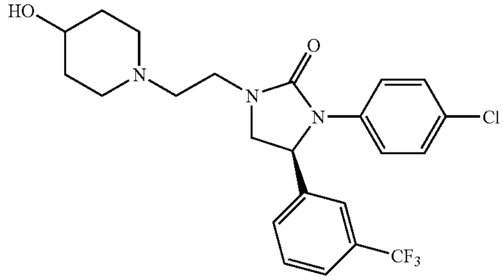 [SMILES: O=C1N(CCN2CCC(O)CC2)C[C@H](c2cccc(C(F)(F)F)c2)N1c1ccc(Cl)cc1] | HPLC-MS calculated for C$_{23}$H$_{26}$ClF$_3$N$_3$O$_2$ (M + H$^+$) 468.1, found 468.0. |
| 434 | 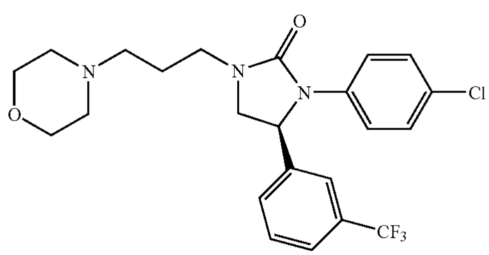 [SMILES: O=C1N(CCCN2CCOCC2)C[C@H](c2cccc(C(F)(F)F)c2)N1c1ccc(Cl)cc1] | HPLC-MS calculated for C$_{23}$H$_{26}$ClF$_3$N$_3$O$_2$ (M + H$^+$) 468.1, found 468.0. |
| 435 | 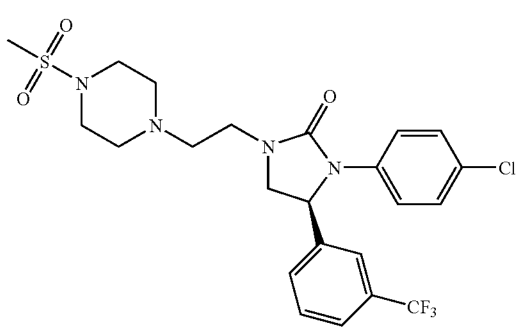 [SMILES: CS(=O)(=O)N1CCN(CCN2C[C@H](c3cccc(C(F)(F)F)c3)N(c3ccc(Cl)cc3)C2=O)CC1] | HPLC-MS calculated for C$_{23}$H$_{27}$ClF$_3$N$_4$O$_3$S (M + H$^+$) 531.1, found 531.1. |

TABLE 1-continued

| Compound Number | Structure | Physical Data<br>¹H NMR 400 MHz (CDCl₃)<br>and/or MS (m/z) |
|---|---|---|
| 436 | 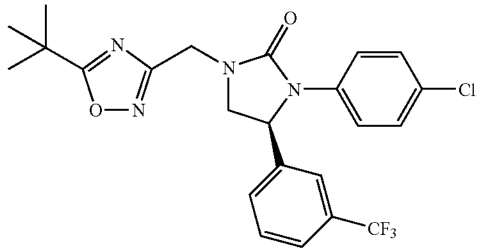 [SMILES: CC(C)(C)c1nc(CN2C[C@H](c3cccc(C(F)(F)F)c3)N(c3ccc(Cl)cc3)C2=O)no1] | ¹H NMR (CD₃OD, 400 MHz) δ 7.60 (s, 1H), 7.56-7.41 (m, 3H), 7.30 (d, J = 8.8 Hz, 2H), 7.13 (d, J = 9.2 Hz, 2H), 5.49 (dd, J = 9.2, 6.0 Hz, 1H), 4.64-4.45 (m, 2H), 4.03 (t, J = 9.2 Hz, 1H), 3.37 (dd, J = 9.2, 6.0 Hz, 1H), 1.31 (s, 9H); HPLC-MS calculated for C₂₃H₂₃ClF₃N₄O₂ (M + H⁺) 479.1, found 479.1. |
| 437 | 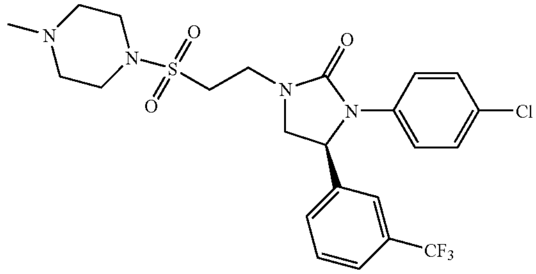 [SMILES: CN1CCN(S(=O)(=O)CCN2C[C@H](c3cccc(C(F)(F)F)c3)N(c3ccc(Cl)cc3)C2=O)CC1] | HPLC-MS calculated for C₂₃H₂₇ClF₃N₄O₃S (M + H⁺) 531.1, found 531.1. |
| 439 | 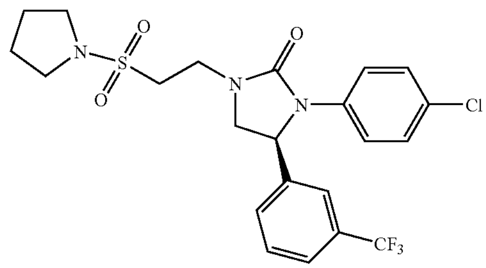 [SMILES: O=C1N(CCS(=O)(=O)N2CCCC2)C[C@H](c2cccc(C(F)(F)F)c2)N1c1ccc(Cl)cc1] | ¹H NMR (CD₃OD, 400 MHz) δ 7.70 (s, 1H), 7.65-7.51 (m, 3H), 7.38 (d, J = 8.8 Hz, 2H), 7.24 (d, J = 8.8 Hz, 2H), 5.54 (dd, J = 9.6, 6.4 Hz, 1H), 4.09 (t, J = 9.2 Hz, 1H), 3.82-3.75 (m, 2H), 3.46 (dd, J = 8.8, 6.4 Hz, 1H), 3.38-3.34 (m, 6H), 1.96-1.93 (m, 4H); HPLC-MS calculated for C₂₂H₂₄ClF₃N₃O₃S (M + H⁺) 502.1, found 502.1. |
| 440 | 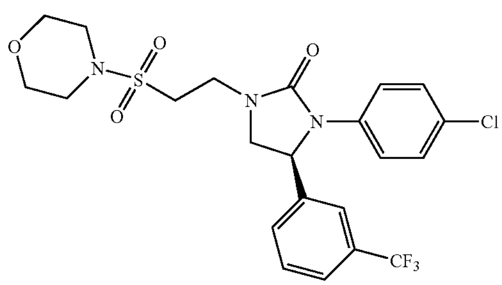 [SMILES: O=C1N(CCS(=O)(=O)N2CCOCC2)C[C@H](c2cccc(C(F)(F)F)c2)N1c1ccc(Cl)cc1] | HPLC-MS calculated for C₂₂H₂₄ClF₃N₃O₄S (M + H⁺) 518.1, found 518.1. |
| 441 | 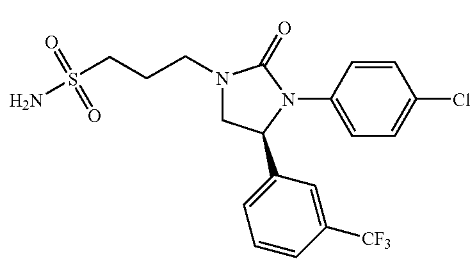 [SMILES: NS(=O)(=O)CCCN1C[C@H](c2cccc(C(F)(F)F)c2)N(c2ccc(Cl)cc2)C1=O] | HPLC-MS calculated for C₁₉H₂₀ClF₃N₃O₃S (M + H⁺) 462.0, found 462.0. |

TABLE 1-continued

| Compound Number | Structure | Physical Data $^1$H NMR 400 MHz (CDCl$_3$) and/or MS (m/z) |
|---|---|---|
| 442 | 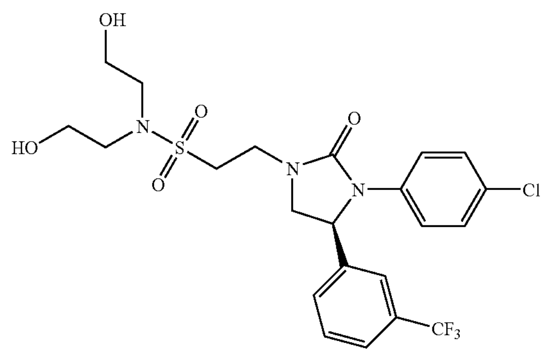 [SMILES: O=C1N(CCS(=O)(=O)N(CCO)CCO)C[C@H](c2cccc(C(F)(F)F)c2)N1c1ccc(Cl)cc1] | HPLC-MS calculated for C$_{22}$H$_{26}$Cl F$_3$N$_3$O$_5$S (M + H$^+$) 536.1, found 536.1. |
| 443 | 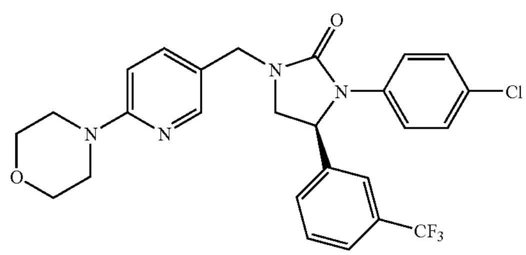 [SMILES: O=C1N(Cc2ccc(N3CCOCC3)nc2)C[C@H](c2cccc(C(F)(F)F)c2)N1c1ccc(Cl)cc1] | HPLC-MS calculated for C$_{26}$H$_{25}$Cl F$_3$N$_4$O$_2$ (M + H$^+$) 517.1, found 517.1. |
| 444 | 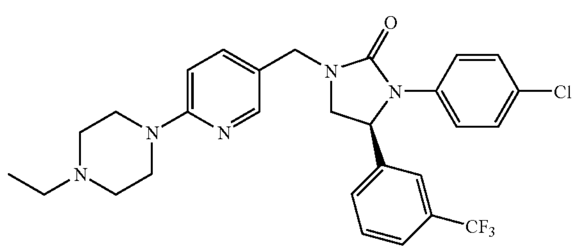 [SMILES: CCN1CCN(c2ccc(CN3C[C@H](c4cccc(C(F)(F)F)c4)N(c4ccc(Cl)cc4)C3=O)cn2)CC1] | HPLC-MS calculated for C$_{28}$H$_{30}$Cl F$_3$N$_5$O (M + H$^+$) 544.2, found 544.2. |
| 446 | 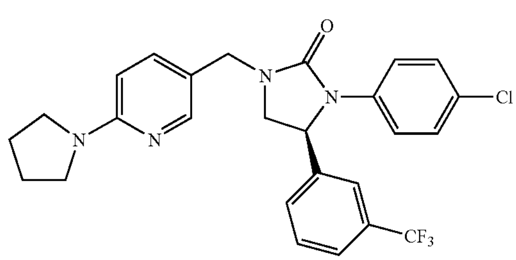 [SMILES: O=C1N(Cc2ccc(N3CCCC3)nc2)C[C@H](c2cccc(C(F)(F)F)c2)N1c1ccc(Cl)cc1] | HPLC-MS calculated for C$_{26}$H$_{25}$Cl F$_3$N$_4$O (M + H$^+$) 501.1, found 501.1. |
| 447 | 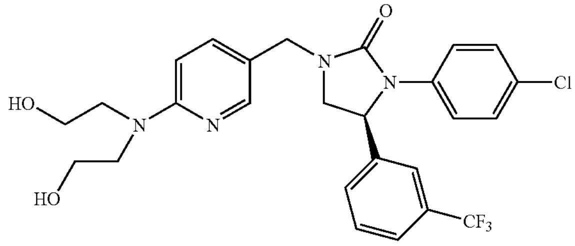 [SMILES: O=C1N(Cc2ccc(N(CCO)CCO)nc2)C[C@H](c2cccc(C(F)(F)F)c2)N1c1ccc(Cl)cc1] | HPLC-MS calculated for C$_{26}$H$_{27}$Cl F$_3$N$_4$O$_3$ (M + H$^+$) 535.1, found 535.1. |

TABLE 1-continued

| Compound Number | Structure | Physical Data $^1$H NMR 400 MHz (CDCl$_3$) and/or MS (m/z) |
|---|---|---|
| 448 | 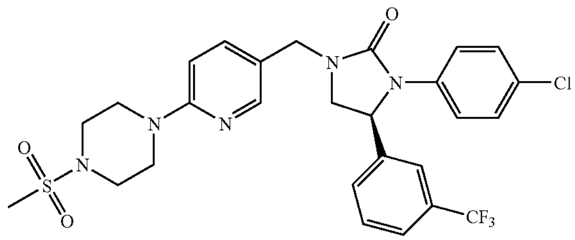 [SMILES: CS(=O)(=O)N1CCN(c2ccc(CN3C[C@H](c4cccc(C(F)(F)F)c4)N(c4ccc(Cl)cc4)C3=O)cn2)CC1] | HPLC-MS calculated for C$_{27}$H$_{28}$Cl F$_3$N$_5$O$_3$S (M + H$^+$) 594.1, found 594.1. |
| 449 | 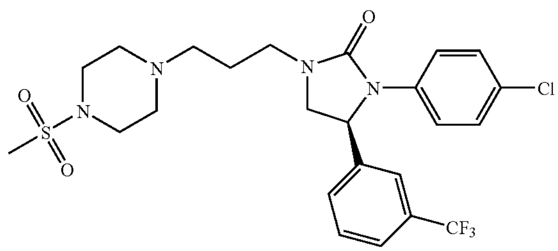 [SMILES: CS(=O)(=O)N1CCN(CCCN2C[C@H](c3cccc(C(F)(F)F)c3)N(c3ccc(Cl)cc3)C2=O)CC1] | HPLC-MS calculated for C$_{24}$H$_{29}$Cl F$_3$N$_4$O$_3$S (M + H$^+$) 545.1, found 545.1. |
| 450 | 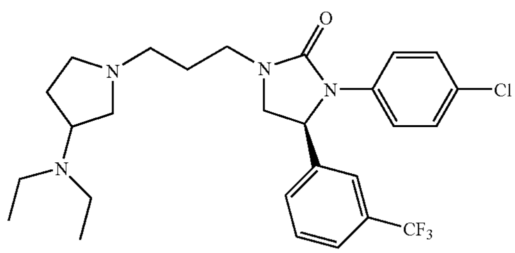 [SMILES: CCN(CC)C1CCN(CCCN2C[C@H](c3cccc(C(F)(F)F)c3)N(c3ccc(Cl)cc3)C2=O)C1] | HPLC-MS calculated for C$_{27}$H$_{35}$Cl F$_3$N$_4$O (M + H$^+$) 523.2, found 523.2. |
| 452 | 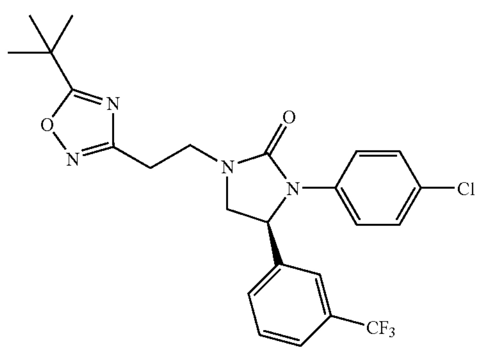 [SMILES: CC(C)(C)c1nc(CCN2C[C@H](c3cccc(C(F)(F)F)c3)N(c3ccc(Cl)cc3)C2=O)no1] | $^1$H NMR (CD$_3$OD, 400 MHz) δ 7.56 (s, 1H), 7.49-7.40 (m, 3H), 7.24 (d, J = 9.2 Hz, 2H), 7.10 (d, J = 9.2 Hz, 2H), 5.41 (dd, J = 9.4, 6.2 Hz, 1H), 3.95 (t, J = 9.4 Hz, 1H), 3.71-3.50 (m, 2H), 3.26 (dd, J = 8.8, 6.4 Hz, 1H), 2.97-2.85 (m, 2H), 1.27 (s, 9H); HPLC-MS calculated for C$_{24}$H$_{25}$Cl F$_3$N$_4$O$_2$ (M + H$^+$) 493.1, found 493.1. |
| 453 | 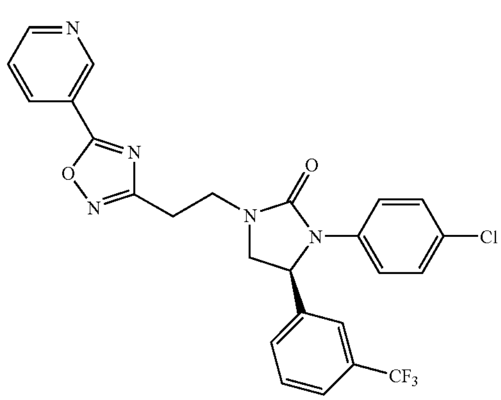 [SMILES: O=C1N(CCc2noc(-c3cccnc3)n2)C[C@H](c2cccc(C(F)(F)F)c2)N1c1ccc(Cl)cc1] | HPLC-MS calculated for C$_{25}$H$_{20}$Cl F$_3$N$_5$O$_2$ (M + H$^+$) 514.1, found 514.1. |

TABLE 1-continued

| Compound Number | Structure | Physical Data $^1$H NMR 400 MHz (CDCl$_3$) and/or MS (m/z) |
|---|---|---|
| 454 | 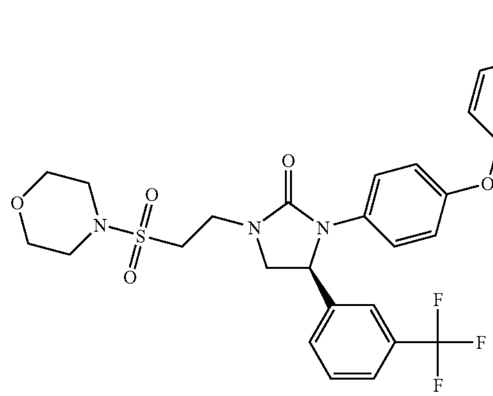 | HPLC-MS calculated for C$_{28}$H$_{27}$ClF$_3$N$_3$O$_5$S (M + H$^+$) 610.1, found 610.1. |
| 456 | 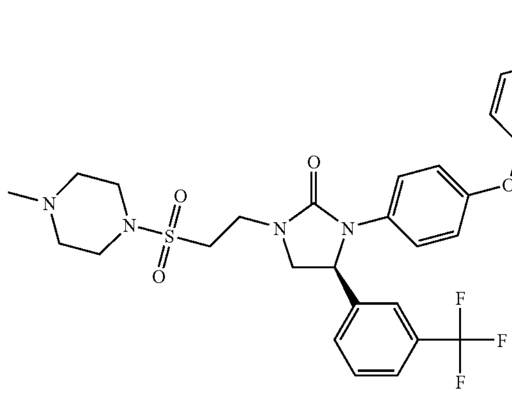 | $^1$H NMR (CDCl$_3$, 400 MHz) δ 7.40-7.60 (m, 4H), 7.27 (d, J = 8.8 Hz, 2H), 7.23 (d, J = 8.8 Hz, 2H), 6.87 (d, J = 8.8 Hz, 2H), 6.83 (d, J = 8.8 Hz, 2H), 5.26 (dd, J = 6.8 Hz, 9.2 Hz, 1H), 4.11 (t, J = 9.2 Hz, 1H), 3.80-3.90 (m, 1H), 3.65-3.76 (m, 1H), 3.39 (dd, J = 6.8 Hz, 8.8 Hz, 1H), 3.32 (t, J = 4.4 Hz, 4H), 3.15-3.25 (m, 2H), 2.50 (b, 4H), 2.33 (s, 3H); HPLC-MS calculated for C$_{29}$H$_{30}$ClF$_3$N$_4$O$_4$S (M + H$^+$) 623.2, found 623.2. |
| 461 | 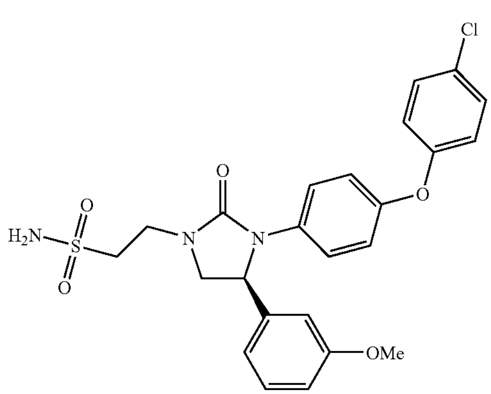 [SMILES: COc1cccc([C@H]2CN(CCS(N)(=O)=O)C(=O)N2c2ccc(Oc3ccc(Cl)cc3)cc2)c1] | HPLC-MS calculated for C$_{24}$H$_{24}$ClN$_3$O$_5$S (M + H$^+$) 501.1, found 501.1. |

TABLE 1-continued

| Compound Number | Structure | Physical Data<br>¹H NMR 400 MHz (CDCl₃) and/or MS (m/z) |
|---|---|---|
| 465 | 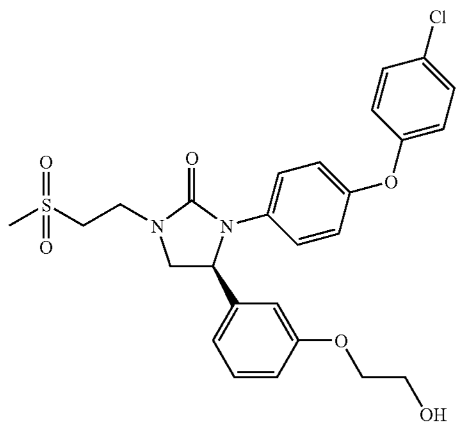 [SMILES: CS(=O)(=O)CCN1C[C@H](c2cccc(OCCO)c2)N(c2ccc(Oc3ccc(Cl)cc3)cc2)C1=O] | ¹H NMR (CDCl₃, 400 MHz) δ 7.31 (d, J = 8.8 Hz, 2H), 7.20-7.26 (m, 3H), 6.81-6.90 (m, 7H), 5.15 (dd, , J = 6.4 Hz, 9.2 Hz, 1H), 3.92-4.04 (m, 5H), 3.81 (t, J = 6.4 Hz, 2H), 3.30-3.36 (m, 3H), 2.99 (s, 3H), 2.15 (t, J = 5.6 Hz, 1H); HPLC-MS calculated for $C_{26}H_{27}ClN_2O_6S$ (M + H⁺) 531.1, found 531.1. |
| 466 | 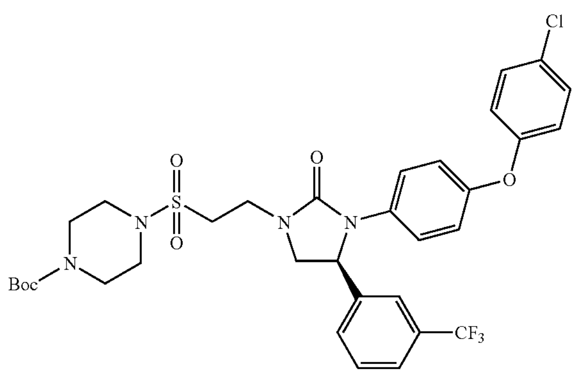 [SMILES: CC(C)(C)OC(=O)N1CCN(S(=O)(=O)CCN2C[C@H](c3cccc(C(F)(F)F)c3)N(c3ccc(Oc4ccc(Cl)cc4)cc3)C2=O)CC1] | HPLC-MS calculated for $C_{33}H_{36}ClF_3N_4O_6S$ (M + H⁺) 709.2, found 609.2. |
| 467 | 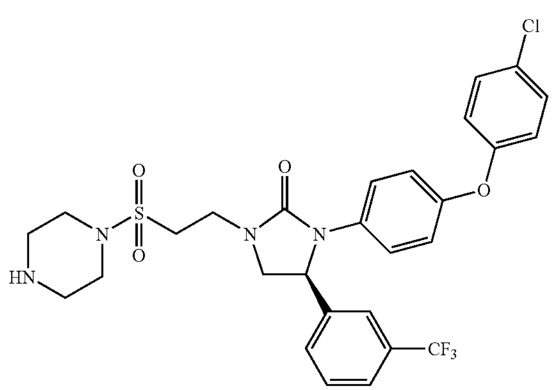 [SMILES: O=C1N(CCS(=O)(=O)N2CCNCC2)C[C@H](c2cccc(C(F)(F)F)c2)N1c1ccc(Oc2ccc(Cl)cc2)cc1] | ¹H NMR (CDCl₃, 400 MHz) δ 7.40-7.60 (m, 4H), 7.27 (d, J = 8.8 Hz, 2H), 7.23 (d, J = 9.2 Hz, 2H), 6.87 (d, J = 8.8 Hz, 2H), 6.83 (d, J = 8.8 Hz, 2H), 5.26 (dd, J = 6.4 Hz, 9.2 Hz, 1H), 4.11 (t, J = 9.2 Hz, 1H), 3.80-3.90 (m, 1H), 3.65-3.76 (m, 1H), 3.39 (dd, J = 6.8 Hz, 8.8 Hz, 1H), 3.20-3.30 (m, 4H), 3.15-3.25 (m, 2H), 2.90-2.98 (m, 4H); HPLC-MS calculated for $C_{28}H_{28}ClF_3N_4O_4S$ (M + H⁺) 609.2, found 609.2. |
| 469 | 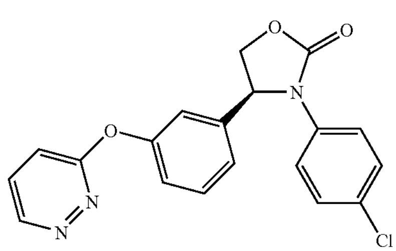 [SMILES: O=C1OC[C@H](c2cccc(Oc3cccnn3)c2)N1c1ccc(Cl)cc1] | ¹H NMR (CDCl₃, 400 MHz) δ 8.96 (d, J = 3.6 Hz, 1H), 7.51 (dd, , J = 4.4 Hz, 8.8 Hz, 1H), 7.42 (t, J = 8.4 Hz, 1H), 7.34 (d, J = 8.8 Hz, 2H), 7.13-7.23 (m, 6H), 5.36 (dd, , J = 6.0 Hz, 8.8 Hz, 1H), 4.80 (t, J = 8.8 Hz, 1H), 4.28 (dd, , J = 5.6 Hz, 8.4 Hz, 1H); HPLC-MS calculated for $C_{19}H_{14}ClN_3O_3$ (M + H⁺) 368.1, found 368.1. |

TABLE 1-continued

| Compound Number | Structure | Physical Data<br>¹H NMR 400 MHz (CDCl₃)<br>and/or MS (m/z) |
|---|---|---|
| 470 | 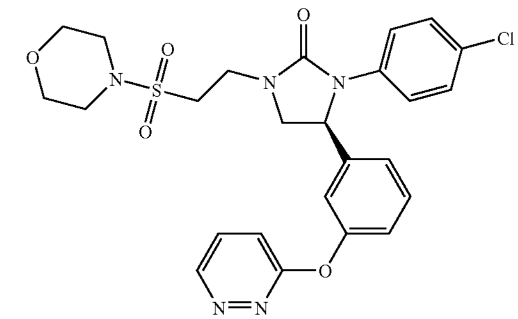 [SMILES: O=C1N(CCS(=O)(=O)N2CCOCC2)C[C@H](c2cccc(Oc3cccnn3)c2)N1c1ccc(Cl)cc1] | HPLC-MS calculated for<br>$C_{25}H_{26}ClN_5O_5S$ (M + H⁺)<br>544.1, found 544.1. |
| 471 | 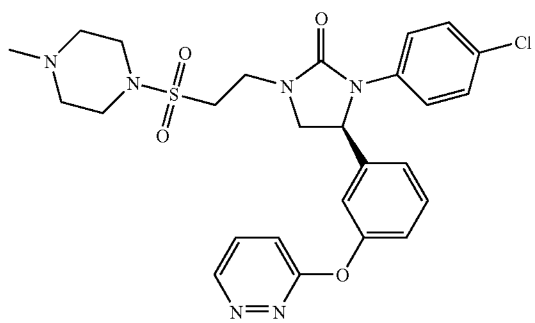 [SMILES: CN1CCN(S(=O)(=O)CCN2C[C@H](c3cccc(Oc4cccnn4)c3)N(c3ccc(Cl)cc3)C2=O)CC1] | HPLC-MS calculated for<br>$C_{26}H_{29}ClN_6O_4S$ (M + H⁺)<br>557.2, found 557.2. |
| 472 | 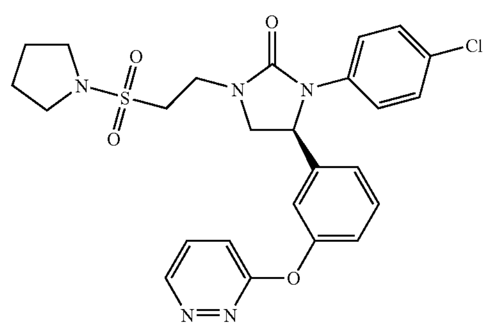 [SMILES: O=C1N(CCS(=O)(=O)N2CCCC2)C[C@H](c2cccc(Oc3cccnn3)c2)N1c1ccc(Cl)cc1] | HPLC-MS calculated for<br>$C_{25}H_{26}ClN_5O_4S$ (M + H⁺)<br>528.1, found 528.1. |
| 473 | 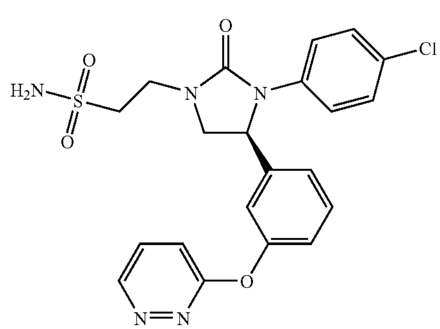 [SMILES: NS(=O)(=O)CCN1C[C@H](c2cccc(Oc3cccnn3)c2)N(c2ccc(Cl)cc2)C1=O] | HPLC-MS calculated for<br>$C_{21}H_{20}ClN_5O_4S$ (M + H⁺)<br>474.1, found 474.1. |

TABLE 1-continued

| Compound Number | Structure | Physical Data<br>¹H NMR 400 MHz (CDCl₃)<br>and/or MS (m/z) |
| --- | --- | --- |
| 474 | 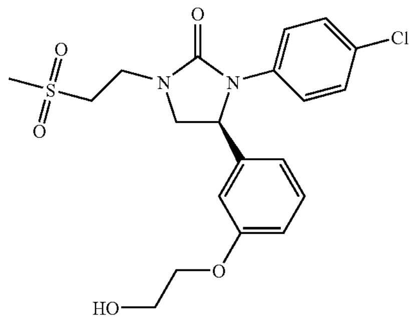 [SMILES: CS(=O)(=O)CCN1C[C@H](c2cccc(OCCO)c2)N(c2ccc(Cl)cc2)C1=O] | HPLC-MS calculated for<br>$C_{20}H_{23}ClN_2O_5S$ (M + H⁺)<br>439.1, found 439.1. |
| 475 | 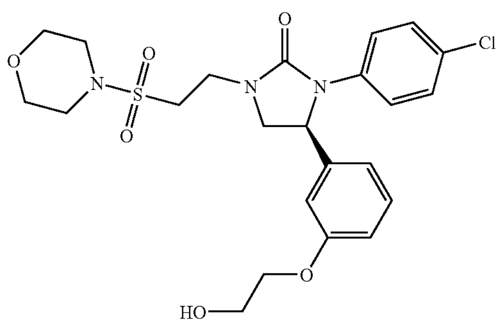 [SMILES: O=C1N(CCS(=O)(=O)N2CCOCC2)C[C@H](c2cccc(OCCO)c2)N1c1ccc(Cl)cc1] | HPLC-MS calculated for<br>$C_{23}H_{28}ClN_3O_6S$ (M + H⁺)<br>510.1, found 510.1. |
| 476 | 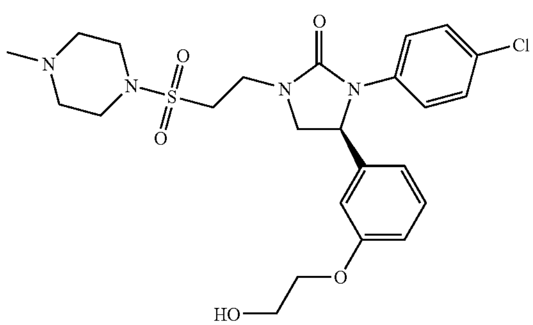 [SMILES: CN1CCN(S(=O)(=O)CCN2C[C@H](c3cccc(OCCO)c3)N(c3ccc(Cl)cc3)C2=O)CC1] | HPLC-MS calculated for<br>$C_{24}H_{31}ClN_4O_5S$ (M + H⁺)<br>523.2, found 523.2. |
| 477 | 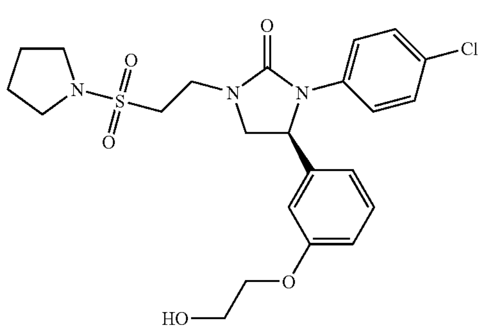 [SMILES: O=C1N(CCS(=O)(=O)N2CCCC2)C[C@H](c2cccc(OCCO)c2)N1c1ccc(Cl)cc1] | HPLC-MS calculated for<br>$C_{23}H_{28}ClN_3O_5S$ (M + H⁺)<br>494.1, found 494.1. |

TABLE 1-continued

| Compound Number | Structure | Physical Data $^1$H NMR 400 MHz (CDCl$_3$) and/or MS (m/z) |
|---|---|---|
| 478 | 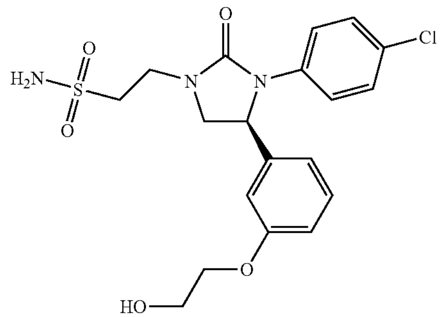 [SMILES: NS(=O)(=O)CCN1C[C@H](c2cccc(OCCO)c2)N(c2ccc(Cl)cc2)C1=O] | HPLC-MS calculated for C$_{19}$H$_{22}$ClN$_3$O$_5$S (M + H$^+$) 440.1, found 440.1. |
| 479 | 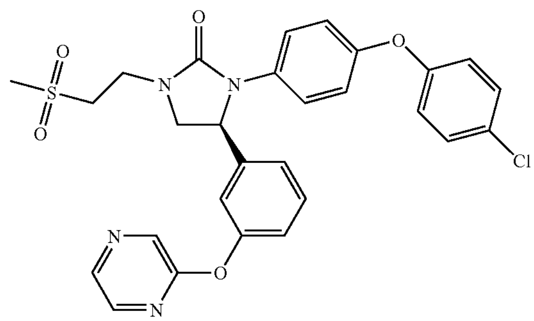 [SMILES: CS(=O)(=O)CCN1C[C@H](c2cccc(Oc3cnccn3)c2)N(c2ccc(Oc3ccc(Cl)cc3)cc2)C1=O] | HPLC-MS calculated for C$_{28}$H$_{25}$ClN$_4$O$_5$S (M + H$^+$) 565.1, found 565.1. |
| 480 | 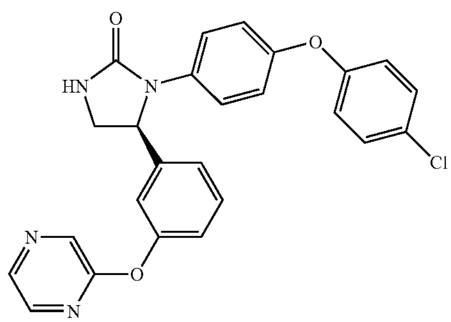 [SMILES: O=C1NC[C@H](c2cccc(Oc3cnccn3)c2)N1c1ccc(Oc2ccc(Cl)cc2)cc1] | HPLC-MS calculated for C$_{25}$H$_{19}$ClN$_4$O$_3$ (M + H$^+$) 459.1, found 459.1. |
| 481 | 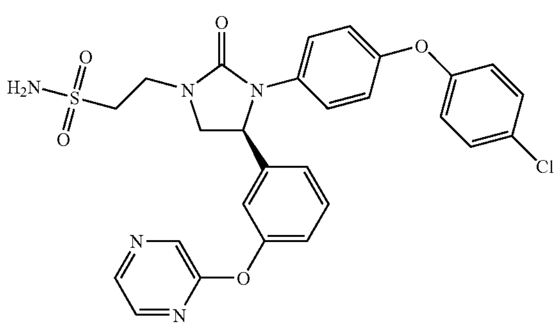 [SMILES: NS(=O)(=O)CCN1C[C@H](c2cccc(Oc3cnccn3)c2)N(c2ccc(Oc3ccc(Cl)cc3)cc2)C1=O] | HPLC-MS calculated for C$_{27}$H$_{24}$ClN$_5$O$_5$S (M + H$^+$) 566.1, found 566.1. |
| 482 | 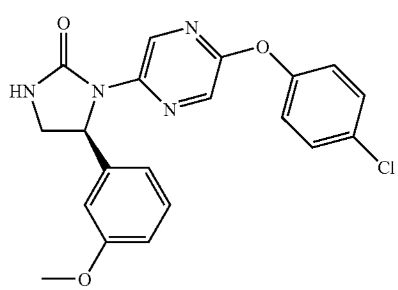 [SMILES: COc1cccc([C@H]2CNC(=O)N2c2cnc(Oc3ccc(Cl)cc3)cn2)c1] | HPLC-MS calculated for C$_{20}$H$_{17}$ClN$_4$O$_3$ (M + H$^+$) 397.1, found 397.1. |

TABLE 1-continued

| Compound Number | Structure | Physical Data<br>¹H NMR 400 MHz (CDCl₃)<br>and/or MS (m/z) |
|---|---|---|
| 483 | 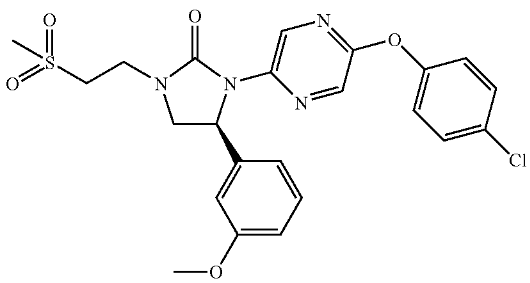 [SMILES: COc1cccc([C@H]2CN(CCS(C)(=O)=O)C(=O)N2c2cnc(Oc3ccc(Cl)cc3)cn2)c1] | HPLC-MS calculated for<br>$C_{23}H_{23}ClN_4O_5S$ (M + H⁺)<br>503.1, found 503.1. |
| 484 | 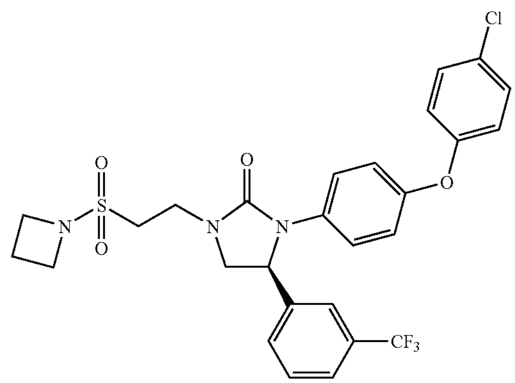 [SMILES: O=C1N(CCS(=O)(=O)N2CCC2)C[C@H](c2cccc(C(F)(F)F)c2)N1c1ccc(Oc2ccc(Cl)cc2)cc1] | HPLC-MS calculated for<br>$C_{27}H_{25}ClF_3N_3O_4S$ (M + H⁺)<br>580.1, found 580.1. |
| 485 | 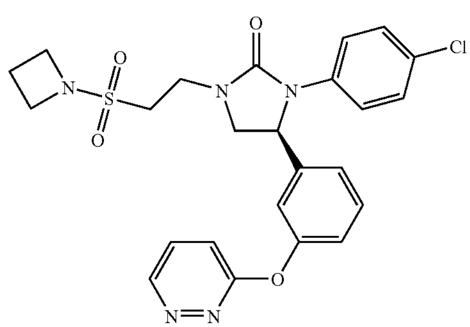 [SMILES: O=C1N(CCS(=O)(=O)N2CCC2)C[C@H](c2cccc(Oc3cccnn3)c2)N1c1ccc(Cl)cc1] | HPLC-MS calculated for<br>$C_{24}H_{24}ClN_5O_4S$ (M + H⁺)<br>514.1, found 514.1. |
| 486 | 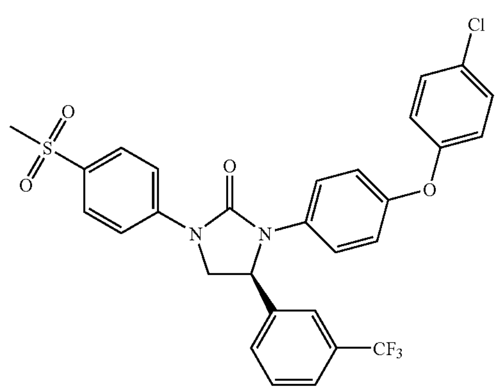 [SMILES: CS(=O)(=O)c1ccc(N2C[C@H](c3cccc(C(F)(F)F)c3)N(c3ccc(Oc4ccc(Cl)cc4)cc3)C2=O)cc1] | HPLC-MS calculated for<br>$C_{29}H_{22}ClF_3N_2O_4S$ (M + H⁺)<br>587.1, found 587.1. |

TABLE 1-continued

| Compound Number | Structure | Physical Data<br>¹H NMR 400 MHz (CDCl₃) and/or MS (m/z) |
|---|---|---|
| 487 | 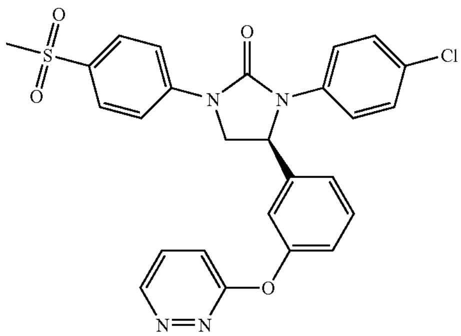 [SMILES: CS(=O)(=O)c1ccc(N2C[C@H](c3cccc(Oc4cccnn4)c3)N(c3ccc(Cl)cc3)C2=O)cc1] | HPLC-MS calculated for $C_{26}H_{21}ClN_4O_4S$ (M + H⁺) 521.1, found 521.1. |
| 488 | 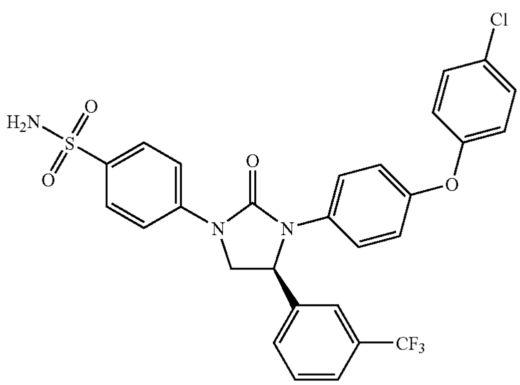 [SMILES: NS(=O)(=O)c1ccc(N2C[C@H](c3cccc(C(F)(F)F)c3)N(c3ccc(Oc4ccc(Cl)cc4)cc3)C2=O)cc1] | HPLC-MS calculated for $C_{28}H_{21}ClF_3N_3O_4S$ (M + H⁺) 588.1, found 588.1. |
| 489 | 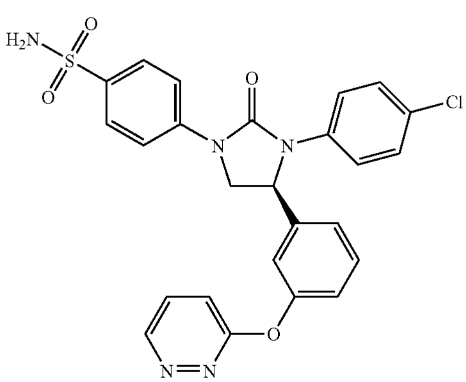 [SMILES: NS(=O)(=O)c1ccc(N2C[C@H](c3cccc(Oc4cccnn4)c3)N(c3ccc(Cl)cc3)C2=O)cc1] | HPLC-MS calculated for $C_{25}H_{20}ClN_5O_4S$ (M + H⁺) 522.1, found 522.1. |
| 491 | 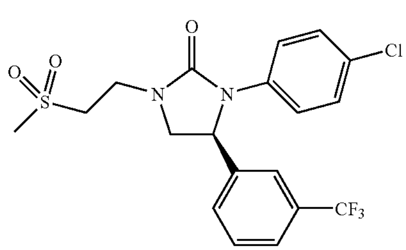 [SMILES: CS(=O)(=O)CCN1C[C@H](c2cccc(C(F)(F)F)c2)N(c2ccc(Cl)cc2)C1=O] | HPLC-MS calculated for $C_{19}H_{18}ClF_3N_2O_3S$ (M + H⁺) 447.1, found 447.1. |

TABLE 1-continued

| Compound Number | Structure | Physical Data<br>$^1$H NMR 400 MHz (CDCl$_3$)<br>and/or MS (m/z) |
|---|---|---|
| 492 | 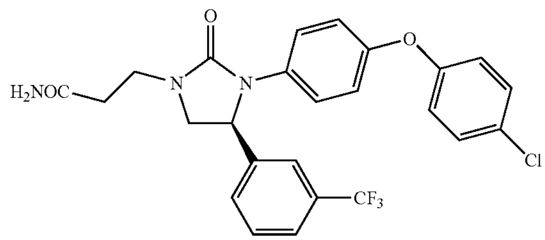 [SMILES: NC(=O)CCN1C[C@H](c2cccc(C(F)(F)F)c2)N(c2ccc(Oc3ccc(Cl)cc3)cc2)C1=O] | $^1$H NMR (CDCl$_3$, 400 MHz) δ 7.55 (m, 2H), 7.47 (m, 2H), 7.25 (m, 4H), 6.86 (m, 4H), 6.33 (br, 1H), 5.65 (br, 1H), 5.24 (dd, J = 9.2, 6.4 Hz, 1H), 4.03 (t, J = 9.2 Hz, 1H), 3.70 (dt, J = 14.4, 6.0 Hz, 1H), 3.57 (dt, J = 14.4, 6.0 Hz, 1H), 3.31 (dd, J = 9.2, 6.4 Hz, 1H), 2.60 (t, J = 6.0 Hz, 2H); HPLC-MS calculated for C$_{25}$H$_{21}$ClF$_3$N$_3$O$_3$ (M + H$^+$) 504.1, found 504.1. |
| 494 | 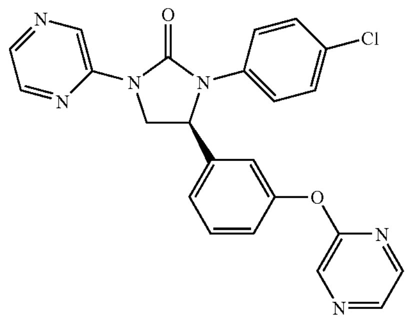 [SMILES: O=C1N(c2cnccn2)C[C@H](c2cccc(Oc3cnccn3)c2)N1c1ccc(Cl)cc1] | HPLC-MS calculated for C$_{23}$H$_{17}$ClN$_6$O$_2$ (M + H$^+$) 445.1, found 445.1. |
| 496 | 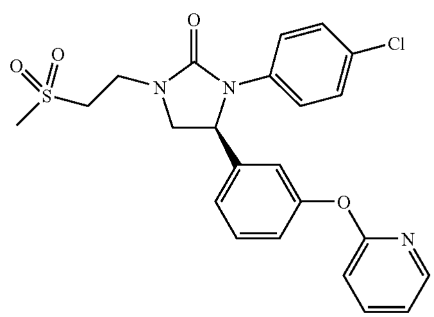 [SMILES: CS(=O)(=O)CCN1C[C@H](c2cccc(Oc3ccccn3)c2)N(c2ccc(Cl)cc2)C1=O] | HPLC-MS calculated for C$_{23}$H$_{22}$ClN$_3$O$_4$S (M + H$^+$) 472.1, found 472.1. |
| 497 | 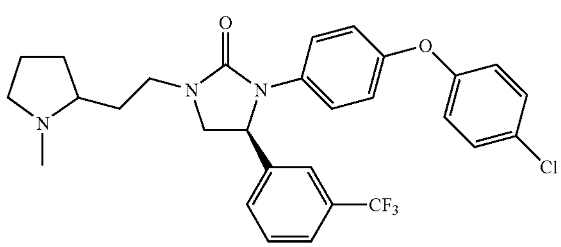 [SMILES: CN1CCCC1CCN1C[C@H](c2cccc(C(F)(F)F)c2)N(c2ccc(Oc3ccc(Cl)cc3)cc2)C1=O] | HPLC-MS calculated for C$_{29}$H$_{29}$ClF$_3$N$_3$O$_2$ (M + H$^+$) 544.2, found 544.2. |
| 498 | 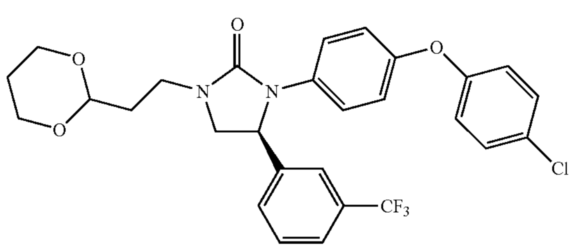 [SMILES: O=C1N(CCC2OCCCO2)C[C@H](c2cccc(C(F)(F)F)c2)N1c1ccc(Oc2ccc(Cl)cc2)cc1] | $^1$H NMR (CDCl$_3$, 400 MHz) δ 7.56-7.44 (m, 4H), 7.29 (d, J = 9.2 Hz, 2H), 7.23 (d, J = 9.2 Hz, 2H), 6.85 (m, 4H), 5.20 (dd, J = 9.2, 6.0 Hz, 1H), 4.64 (t, J = 4.8 Hz, 1H), 4.07 (m, 2H), 3.92 (t, J = 9.2 Hz, 1H), 3.74 (m, 2H), 3.45 (m, 2H), 3.27 (dd, J = 9.2, 6.0 Hz, 1H), 2.05 (m, 1H), 1.86 (td, J = 6.8, 4.8 Hz, 2H), 1.33 (m, 1H); HPLC-MS calculated for C$_{28}$H$_{26}$ClF$_3$N$_2$O$_4$ (M + H$^+$) 547.2, found 547.2. |

TABLE 1-continued

| Compound Number | Structure | Physical Data $^1$H NMR 400 MHz (CDCl$_3$) and/or MS (m/z) |
|---|---|---|
| 499 | 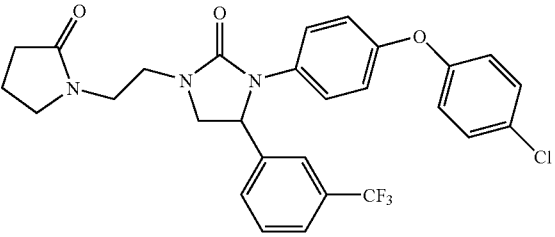 [SMILES: O=C1CCCN1CCN1CC(c2cccc(C(F)(F)F)c2)N(c2ccc(Oc3ccc(Cl)cc3)cc2)C1=O] | HPLC-MS calculated for C$_{28}$H$_{25}$ClF$_3$N$_3$O$_3$ (M + H$^+$) 544.2, found 544.2. |
| 500 | 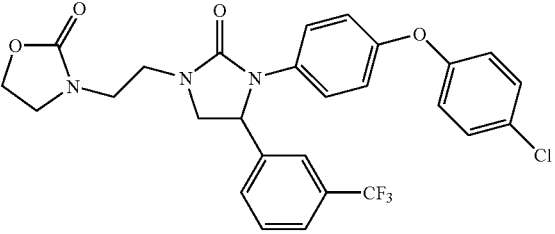 [SMILES: O=C1OCCN1CCN1CC(c2cccc(C(F)(F)F)c2)N(c2ccc(Oc3ccc(Cl)cc3)cc2)C1=O] | $^1$H NMR (CDCl$_3$, 400 MHz) δ 7.55-7.45 (m, 4H), 7.23 (m, 4H), 6.86 (m, 4H), 5.23 (dd, J = 9.2, 7.2 Hz, 1H), 4.34 (t, J = 8.0 Hz, 2H), 4.09 (t, J = 9.2 Hz, 1H), 3.83-3.58 (m, 4H), 3.36 (m, 3H); HPLC-MS calculated for C$_{27}$H$_{23}$ClF$_3$N$_3$O$_4$ (M + H$^+$) 546.1, found 546.1. |
| 501 | 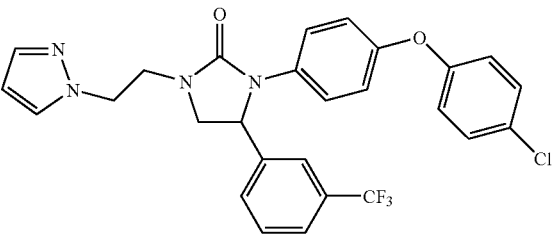 [SMILES: O=C1N(CCn2cccn2)CC(c2cccc(C(F)(F)F)c2)N1c1ccc(Oc2ccc(Cl)cc2)cc1] | HPLC-MS calculated for C$_{27}$H$_{22}$ClF$_3$N$_4$O$_2$ (M + H$^+$) 527.1, found 527.1. |
| 502 | 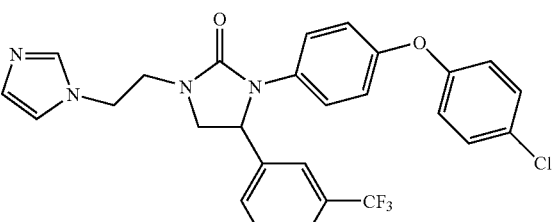 | HPLC-MS calculated for C$_{27}$H$_{22}$ClF$_3$N$_4$O$_2$ (M + H$^+$) 527.1, found 527.1. |
| 504 | 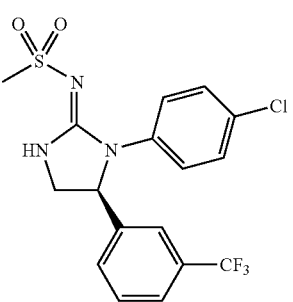 [SMILES: CS(=O)(=O)/N=C1\NC[C@H](c2cccc(C(F)(F)F)c2)N1c1ccc(Cl)cc1] | HPLC-MS calculated for C$_{17}$H$_{15}$ClF$_3$N$_3$O$_2$S (M + H$^+$) 418.1, found 418.1 |

TABLE 1-continued

| Compound Number | Structure | Physical Data $^1$H NMR 400 MHz (CDCl$_3$) and/or MS (m/z) |
|---|---|---|
| 505 | 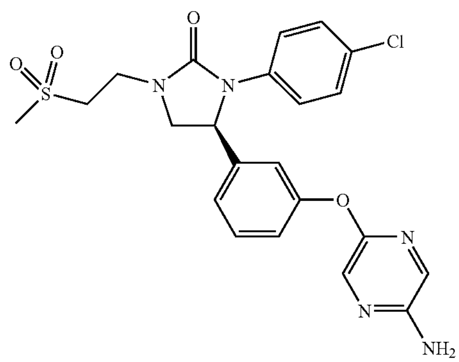 [SMILES: CS(=O)(=O)CCN1C[C@H](c2cccc(Oc3cnc(N)cn3)c2)N(c2ccc(Cl)cc2)C1=O] | HPLC-MS calculated for C$_{22}$H$_{22}$ClN$_5$O$_4$S (M + H$^+$) 488.1, found 488.1. |
| 506 | 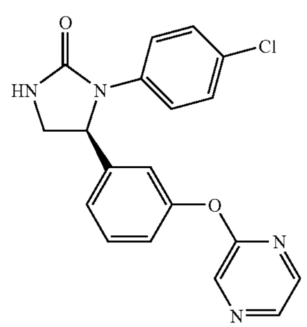 [SMILES: O=C1NC[C@H](c2cccc(Oc3cnccn3)c2)N1c1ccc(Cl)cc1] | HPLC-MS calculated for C$_{19}$H$_{15}$ClN$_4$O$_2$ (M + H$^+$) 367.1, found 367.1. |
| 508 | 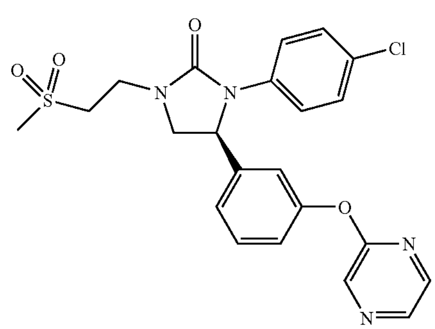 [SMILES: CS(=O)(=O)CCN1C[C@H](c2cccc(Oc3cnccn3)c2)N(c2ccc(Cl)cc2)C1=O] | $^1$H NMR (CDCl$_3$, 400 MHz) δ 8.40 (s, 1H), 8.28 (d, J = 2.0 Hz, 1H), 8.08 (d, J = 2.0 Hz, 1H), 7.40 (t, J = 8.0 Hz, 1H), 7.29 (d, J = 9.2 Hz, 2H), 7.18 (m, 3H), 7.09 (m, 2H), 5.23 (dd, J = 8.8, 6.0 Hz, 1H), 4.05 (t, J = 8.8 Hz, 1H), 3.81 (m, 2H), 3.43 (dd, J = 8.8, 6.0 Hz, 1H), 3.33 (m, 2H), 2.97 (s, 3H); HPLC-MS calculated for C$_{22}$H$_{21}$ClN$_4$O$_4$S (M + H$^+$) 473.1, found 473.1. |
| 509 | 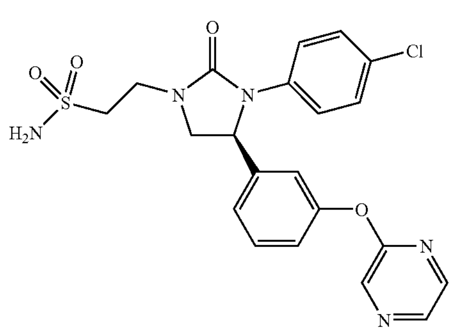 [SMILES: NS(=O)(=O)CCN1C[C@H](c2cccc(Oc3cnccn3)c2)N(c2ccc(Cl)cc2)C1=O] | HPLC-MS calculated for C$_{21}$H$_{20}$ClN$_5$O$_4$S (M + H$^+$) 474.1, found 474.1. |

TABLE 1-continued

| Compound Number | Structure | Physical Data<br>$^1$H NMR 400 MHz (CDCl$_3$)<br>and/or MS (m/z) |
|---|---|---|
| 510 | 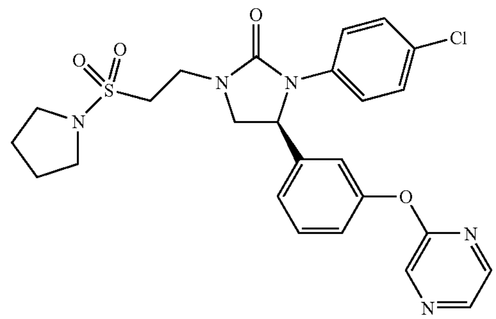 [SMILES: O=C1N(CCS(=O)(=O)N2CCCC2)C[C@H](c2cccc(Oc3cnccn3)c2)N1c1ccc(Cl)cc1] | HPLC-MS calculated for<br>$C_{25}H_{26}ClN_5O_4S$ (M + H$^+$)<br>528.1, found 528.1. |
| 511 | 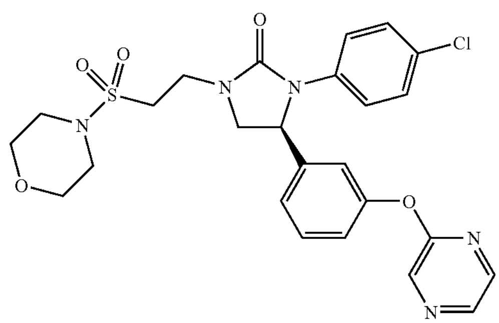 [SMILES: O=C1N(CCS(=O)(=O)N2CCOCC2)C[C@H](c2cccc(Oc3cnccn3)c2)N1c1ccc(Cl)cc1] | HPLC-MS calculated for<br>$C_{25}H_{26}ClN_5O_5S$ (M + H$^+$)<br>544.1, found 544.1. |
| 512 | 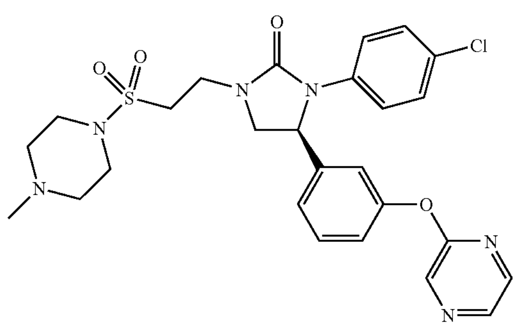 [SMILES: CN1CCN(S(=O)(=O)CCN2C[C@H](c3cccc(Oc4cnccn4)c3)N(c3ccc(Cl)cc3)C2=O)CC1] | HPLC-MS calculated for<br>$C_{26}H_{29}ClN_6O_4S$ (M + H$^+$)<br>557.2, found 557.2. |
| 513 | 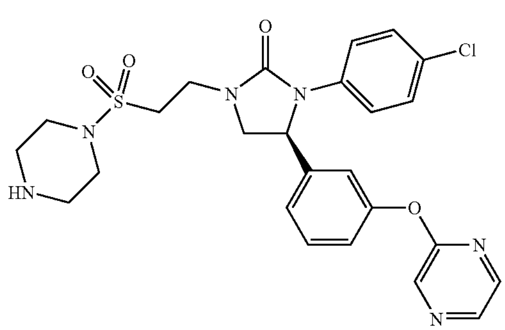 [SMILES: O=C1N(CCS(=O)(=O)N2CCNCC2)C[C@H](c2cccc(Oc3cnccn3)c2)N1c1ccc(Cl)cc1] | HPLC-MS calculated for<br>$C_{25}H_{27}ClN_6O_4S$ (M + H$^+$)<br>543.2, found 543.2. |

TABLE 1-continued

| Compound Number | Structure | Physical Data $^1$H NMR 400 MHz (CDCl$_3$) and/or MS (m/z) |
|---|---|---|
| 514 | 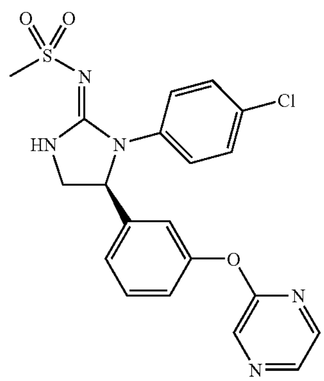 [SMILES: CS(=O)(=O)/N=C1\NC[C@H](c2cccc(Oc3cnccn3)c2)N1c1ccc(Cl)cc1] | HPLC-MS calculated for C$_{20}$H$_{18}$ClN$_5$O$_3$S (M + H$^+$) 444.1, found 444.1 |
| 515 | 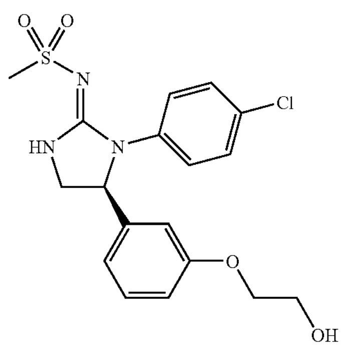 [SMILES: CS(=O)(=O)/N=C1\NC[C@H](c2cccc(OCCO)c2)N1c1ccc(Cl)cc1] | HPLC-MS calculated for C$_{18}$H$_{20}$ClN$_3$O$_4$S (M + H$^+$) 410.1, found 410.1. |
| 516 | 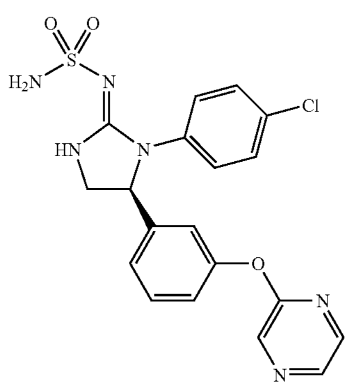 [SMILES: NS(=O)(=O)/N=C1\NC[C@H](c2cccc(Oc3cnccn3)c2)N1c1ccc(Cl)cc1] | HPLC-MS calculated for C$_{19}$H$_{17}$ClN$_6$O$_3$S (M + H$^+$) 445.1, found 445.1. |
| 517 | 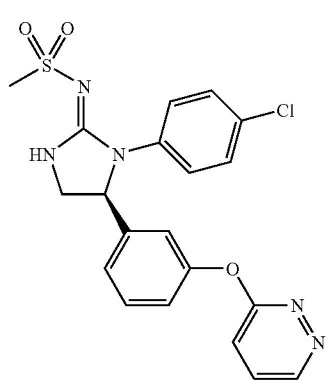 [SMILES: CS(=O)(=O)/N=C1\NC[C@H](c2cccc(Oc3cccnn3)c2)N1c1ccc(Cl)cc1] | HPLC-MS calculated for C$_{20}$H$_{18}$ClN$_5$O$_3$S (M + H$^+$) 444.1, found 444.1. |

TABLE 1-continued

| Compound Number | Structure | Physical Data $^1$H NMR 400 MHz (CDCl$_3$) and/or MS (m/z) |
|---|---|---|
| 518 | 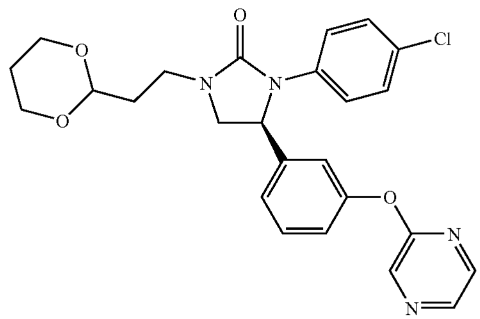 [SMILES: O=C1N(CCC2OCCCO2)C[C@H](c2cccc(Oc3cnccn3)c2)N1c1ccc(Cl)cc1] | HPLC-MS calculated for C$_{25}$H$_{25}$ClN$_4$O$_4$ (M + H$^+$) 481.2, found 481.2. |
| 519 | 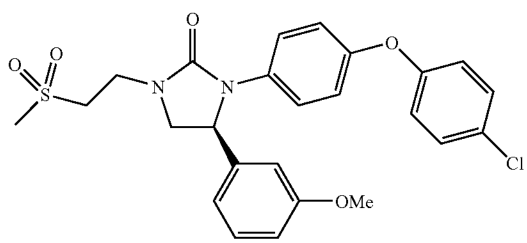 [SMILES: COc1cccc([C@H]2CN(CCS(C)(=O)=O)C(=O)N2c2ccc(Oc3ccc(Cl)cc3)cc2)c1] | HPLC-MS calculated for C$_{25}$H$_{25}$ClN$_2$O$_5$S (M + H$^+$) 501.1, found 501.1. |
| 520 | 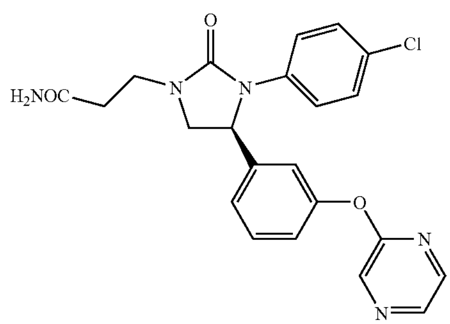 [SMILES: NC(=O)CCN1C[C@H](c2cccc(Oc3cnccn3)c2)N(c2ccc(Cl)cc2)C1=O] | $^1$H NMR (CDCl$_3$, 400 MHz) δ 8.41 (s, 1H), 8.28 (d, J = 2.0 Hz, 1H), 8.03 (d, J = 2.0 Hz, 1H), 7.41 (t, J = 8.0 Hz, 1H), 7.31 (d, J = 8.8 Hz, 2H), 7.18 (m, 3H), 7.09 (d, J = 8.0 Hz, 1H), 7.03 (s, 1H), 6.42 (br, 1H), 5.67 (br, 1H), 5.17 (dd, J = 8.8, 5.2 Hz, 1H), 4.00 (t, J = 8.8 Hz, 1H), 3.61 (t, J = 6.0 Hz, 2H), 3.35 (dd, J = 8.8, 5.2 Hz, 1H), 2.51 (m, 2H); HPLC-MS calculated for C$_{22}$H$_{20}$ClN$_5$O$_3$ (M + H$^+$) 438.1, found 438.1. |
| 523 | 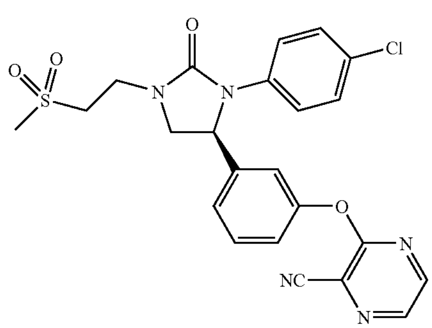 | HPLC-MS calculated for C$_{23}$H$_{20}$ClN$_5$O$_4$S (M + H$^+$) 498.1, found 498.1. |
| 524 | 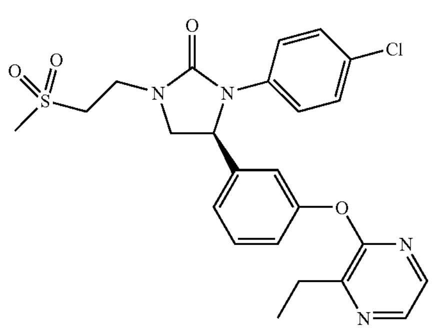 [SMILES: CCc1nccnc1Oc1cccc([C@H]2CN(CCS(C)(=O)=O)C(=O)N2c2ccc(Cl)cc2)c1] | HPLC-MS calculated for C$_{24}$H$_{25}$ClN$_4$O$_4$S (M + H$^+$) 501.1, found 501.1. |

TABLE 1-continued

| Compound Number | Structure | Physical Data $^1$H NMR 400 MHz (CDCl$_3$) and/or MS (m/z) |
|---|---|---|
| 525 | 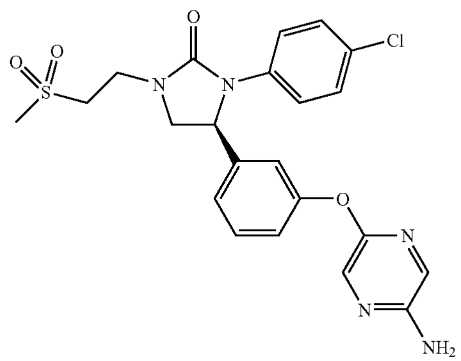 [SMILES: CS(=O)(=O)CCN1C[C@H](c2cccc(Oc3cnc(N)cn3)c2)N(c2ccc(Cl)cc2)C1=O] | HPLC-MS calculated for C$_{22}$H$_{22}$ClN$_5$O$_4$S (M + H$^+$) 488.1, found 488.1. |

CBI Biological Assays

Homogenized membranes are prepared from CHO cell clones stably expressing a human cannabinoid receptor 1 (CB1) or human cannabinoid receptor 2 (CB2). Cells are grown and scrapped from 15 cm tissue culture plates, and then subsequently centrifuged down. Cells are washed once with cold PBS, and resuspended in ≦20 ml of Buffer A (20 mM HEPES, pH 7.4, 10 mM EDTA, EDTA-free complete protease inhibitor cocktail [1 tablet/25 ml]). The cell suspension is homogenized on ice, using a Polytron homogenizer at 25000 rpm at three intervals of 15 seconds each. The homogenate is first centrifuged at 2000 rpm on a tabletop low speed centrifuge for 10 minutes. The supernatant, after passing through a cell strainer, is then centrifuged at 50,000×g for 25 minutes at 4° C. The pellet is resuspended into buffer B (15% glycerol, 20 mM HEPES, pH 7.4, 0.1 mM EDTA, EDTA-free complete protease inhibitor cocktail [1 tablet/10 ml]). Protein concentration of the prep is determined using the BCA Protein Assay kit using BSA as standard. The membranes are aliquoted and kept frozen at −80° C.

[$^3$H]-CP55940 ligand binding assay: Solutions of test compounds ranging from 100 μM to 0.01 nM are prepared in DMSO. The desired amount of membrane prep is diluted with ice-cold assay buffer (50 mM Tris-HCl, 2.5 mM EDTA, 5 mM MgCl$_2$, 0.05% BSA, pH 7.4) and vortexed well. 2 μl or less of compound is distributed into each well of a round-bottom 96-well polystyrene assay plate, followed by addition of 100 μl of diluted membranes (3-10 μg/well) and the mixture is kept on ice until the addition of hot CP55940 (final concentration of 0.5 nM). [$^3$H]-CP55940 is diluted 1:6300 (v/v) with cold assay buffer and 100 μl is added into each well. The reaction is carried out at room temperature for 120 minutes before the membranes are harvested onto a PerkinElmer Unifilter GF/B-96 filter plate using a Packard Filtermate Harvester. After nine washes with wash buffer (50 mM Tris-HCl, 2.5 mM EDTA, 5 mM MgCl$_2$, 0.05% BSA, pH 7.), the filter is dried in a 37° C. oven for 30 minutes. MicroScint-20 is added and the plate sealed for scintillation counting on TopCount. EC$_{50}$ values are obtained by fitting the data with the sigmoidal dose response curve-fitting tool of GraphPad Prism. Eight or twelve different concentrations are used to generate a concentration response curve (using three data points per concentration).

GTPγS binding assay: Solutions of test compounds ranging from 100 μM to 0.01 nM are prepared in DMSO. The desired amount of membrane prep is diluted with ice-cold assay buffer (20 mM HEPES, pH 7.4, 100 mM NaCl, 10 mM MgCl$_2$, 0.1% Fatty acid-free BSA, 5 μM GDP) and vortexed well. 2 μl or less of compound is distributed into each well of a round-bottom 96-well polystyrene assay plate, followed by addition of 100 μl of diluted membranes (3-10 μg/well) and the mixture is kept on ice until the addition of hot GTPγS. [$^{35}$S]-GTPγS (Perkin Elmer NEG030H; 1 μCi/μl, 1250 Ci/mmol) is diluted 1:1000 (v/v) with cold assay buffer and 100 μl is added into each well. The reaction is carried out at room temperature for 90 minutes before the membranes are harvested onto PerkinElmer Unifilter GF/B-96 filter plate using a Packard Filtermate Harvester. After several washes with wash buffer (20 mM HEPES, pH 7.4, 100 mM NaCl, 10 mM MgCl$_2$), and a rinse with 95% ethanol, the filter is dried in a 37° C. oven for 30 minutes. MicroScint-20 is added and the plate sealed for scintillation counting on TopCount. EC$_{50}$ values are obtained by fitting the GTP [γ-$^{35}$S] binding data with the sigmoidal dose response curve-fitting tool of GraphPad Prism. Six or twelve different concentrations are used to generate a concentration response curve (using three data points per concentration).

For each assay, a Cheng-Prusoff correction (Cheng and Prusoff, 1973, Biochem. Pharmacol., 22: 3099-3103) is used to convert the EC$_{50}$ to inhibition constant K$_i$. Thus, $$K_i = \frac{EC_{50}}{1 + [L]/K_d}$$

where [L] is the concentration of the radio-ligand used in the assay, and K$_d$ is the equilibrium binding dissociation constant for the radio-ligand.

Food Intake and Body Weight Gain

To evaluate the efficacy of compounds of the invention on inhibition of food intake and body weight gain, genetically obese (Lep$^{ob}$/Lep$^{ob}$) mice and diet-induced obese (DIO) mice are used in acute and sub-chronic models, respectively.

Male ob/ob mice (age 7-8 weeks old, Jackson Labs, Bar Harbor, Me.) are housed in groups of four and fed commercial standard pellet diet (Lab Diet 5001, PMI Nutrition International, LLC). Diet-induced obese mice are generated using 6-7 weeks old C57BL6 mice (Jackson Labs, Bar Harbor, Me.) placed on high fat diet (D12331, Research Diets) for 12-17 weeks. All mice are maintained on a 12-hour light/dark cycle (lights on at 06:00) in a humidity- and temperature-controlled environment with free access to food and water.

The week prior to the start of each study, mice are singly housed and a habituation to treatment is performed to establish baseline food consumption and body weight. Animals are randomized into treatment groups based on their initial body weight and food consumption.

To determine the acute effects of a single administration of a compound of the invention (test compound) on food consumption, ob/ob mice are treated with either vehicle, a known antagonist as a positive control, or with test compound(s). Similarly, to determine more chronic effects of test compound on food consumption and body weight gain, DIO mice are treated with either vehicle, a known antagonist as a positive control, or with test compound(s) for up to 7-35 days. Test compounds are dosed at ranges between 0.1 up to 100 mg/kg. Animals are treated one hour prior to the start of the dark cycle. Food intake and body weight are recorded manually using an electronic balance prior to treatment, 16 hours post-treatment, followed by daily measurements for up to 7-35 days after the start of study. Compound efficacy is determined by comparing food intake and body weight data between vehicle treated, standard positive control treated, and test compound treated mice.

Compounds of Formula I, in free form or in pharmaceutically acceptable salt form, exhibit valuable pharmacological properties, for example, as indicated by the in vitro tests described in this application. Compound of the invention show a $K_i$ of between $1\times10^{-5}$ and $1\times10^{-10}$M, preferably less than 500 nM, more preferably less than 100 nM. Additionally, compounds of the invention show a 10 fold, preferably 20, 50 and 100 fold, selectivity for CB1 over CB2.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula I:

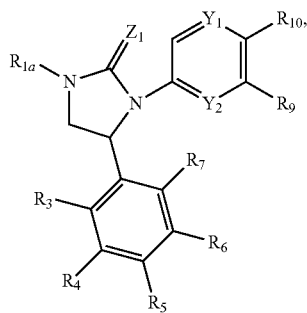

or a pharmaceutically acceptable salt thereof,
in which:
$Y_1$ is selected from N and $CR_{11}$;
$Y_2$ is selected from N and $CR_8$;
$Z_1$ is selected from S, O, NH, CH—$NO_2$, $NS(O)_2NH_2$, $NC(O)NH_2$, $NS(O)_2CH_3$, N(OH) and N(CN); or C=$Z_1$ of Formula I is replaced with $CH_2$ or $S(O)_2$;
$R_{1a}$ is selected from cyano, $C_{1-6}$alkyl, cyano-substituted-$C_{1-6}$alkyl, $C_{2-6}$alkenyl, —$X_1R_{12}$, —$X_1NR_{13}S(O)_2R_{13}$, —$X_1OS(O)_2R_{13}$, —$X_1NR_{13}X_1OR_{13}$, —$X_1OR_{13}$, —$X_1C(O)OR_{13}$, —$X_1S(O)_2R_{12}$, —$X_1S(O)_2NR_{13}C(O)R_{13}$, —$X_1S(O)_2R_{13}$, —$X_1C(O)R_{12}$, —$X_1NR_{13}R_{13}$, —$X_1S(O)_2NR_{13}R_{13}$, —$X_1OC(O)NR_{13}R_{13}$, —$X_1C(O)NR_{12}R_{13}$, —$X_1NR_{13}X_1C(O)R_{12}$, —$X_1NR_{13}X_1C(O)NR_{13}R_{13}$, —$X_1C(O)NR_{13}X_1C(O)OR_{13}$, —$X_1C(O)NR_{13}X_1NR_{13}R_{13}$, —$X_1C(O)NR_{13}X_1OR_{13}$ and —$X_1C(O)NR_{13}R_{13}$; wherein
$R_{12}$ is selected from $C_{6-10}$aryl, $C_{5-10}$heteroaryl, $C_{3-12}$cycloalkyl and $C_{3-10}$heterocycloalkyl; wherein said aryl, heteroaryl, cycloalkyl or heterocycloalkyl of $R_{12}$ is optionally substituted by 1 to 3 radicals independently selected from halo, hydroxy, bis-hydroxy-$C_{1-6}$alkyl-amino, $C_{1-6}$alkyl-amino, di-ethyl-amino, $C_{1-6}$alkyl, $C_{1-6}$alkoxy, $C_{1-6}$alkoxy-carbonyl, $C_{1-6}$alkyl-sulphoxy, $C_{1-6}$alkyl-carboxy, $C_{1-6}$alkyl-sulfonyl, amino-sulfonyl, halo-substituted-$C_{1-6}$alkyl, halo-substituted-$C_{1-6}$alkoxy, $C_{3-12}$cycloalkyl, $C_{3-10}$heterocycloalkyl, $C_{5-10}$heteroaryl and $C_{6-10}$aryl optionally substituted with 1 to 3 halo radicals; wherein said cycloalkyl, heterocycloalkyl, heteroaryl and aryl substituents of $R_{12}$ can be further optionally substituted with 1 to 3 $C_{1-6}$alkyl radicals, or methyl-sulfonyl, methoxy-carbonyl, and methoxy;
each $R_{13}$ is independently selected from hydrogen, $C_{1-6}$alkyl, hydroxy-$C_{1-6}$alkyl, $C_{6-10}$aryl, $C_{3-10}$heterocycloalkyl; wherein said aryl or heterocycloalkyl of $R_{13}$ is optionally substituted with a group selected from $C_{1-6}$alkyl and $C_{1-6}$alkoxy;
each $X_1$ is $C_{1-4}$alkylene;
$R_3$, $R_5$, $R_6$ and $R_7$ are each independently selected from hydrogen, halo and amino;
$R_4$ is selected from halo, cyano, dimethyl-amino-propyl, hydroxy, $C_{1-6}$alkyl, $C_{1-6}$alkoxy, halo-substituted-$C_{1-6}$alkyl, halo-substituted-$C_{1-6}$alkoxy, hydroxy-substituted-$C_{1-6}$alkyl, hydroxy-substituted-$C_{1-6}$alkoxy, cyano-substituted-$C_{1-6}$alkyl, cyano-substituted-$C_{1-6}$alkoxy, and —$OX_5R_{4a}$; wherein $X_5$ is selected from a bond and $C_{1-4}$alkylene; $R_{4a}$ is selected from $C_{1-6}$alkyl, $C_{3-8}$cycloalkyl, $C_{6-10}$aryl and $C_{5-10}$heteroaryl; wherein any cycloalkyl, aryl or heteroaryl of $R_{4a}$ is optionally substituted with 1 to 3 radicals independently selected from halo, cyano, amino, $C_{1-6}$alkyl, $C_{1-6}$alkoxy, halo-substituted-$C_{1-6}$alkyl, halo-substituted-$C_{1-6}$alkoxy, hydroxy-substituted-$C_{1-6}$alkyl, hydroxy-substituted-$C_{1-6}$alkoxy, cyano-substituted-$C_{1-6}$alkyl and cyano-substituted-$C_{1-6}$alkoxy;
$R_8$, $R_9$, and $R_{11}$ are each independently selected from hydrogen, halo, $C_{1-6}$alkyl, $C_{1-6}$alkoxy, halo-substituted-$C_{1-6}$alkyl and halo-substituted-$C_{1-6}$alkoxy;
$R_{10}$ is selected from halo, cyano, $C_{1-6}$alkyl, $C_{1-6}$alkoxy, halo-substituted-$C_{1-6}$alkyl, halo-substituted-$C_{1-6}$alkoxy, benzoyl, —$X_4OR_{17}$, —$X_4S(O)_{0-2}R_{17}$ and —$X_4R_{17}$; wherein $X_4$ is selected from a bond and $C_{1-4}$alkylene; and $R_{17}$ is selected from $C_{6-10}$aryl and $C_{5-10}$hetyeroaryl; wherein $R_{17}$ is optionally substituted with 1 to 3 halo radicals.

2. The compound of claim 1 in which $R_{1a}$ is selected from cyano, methyl-carbonyl-amino-sulfonyl-ethyl, pyrrolidin-2-onyl-ethyl, imidazolyl-ethyl, oxazolidinonly-ethyl, 1-pyrazolyl, cyano-methyl, 1,3-dioxanyl-ethyl, allyl, piperazinyl-sulfonyl-ethyl, azetidinyl-sulfonyl-ethyl, morpholino-sulfonyl-ethyl, pyrrolidinyl-sulfonyl-ethyl, pyrrolidinyl-propyl, pyrrolidinyl-ethyl, piperazinyl-propyl, piperidinyl-sulfonyl-ethyl, (5-(4-methoxyphenyl)-1,2,4-oxadiazol-3-yl) methyl, piperidinyl-carbonyl-methyl, 3-(N,N-bis(4-methoxyphenyl)sulfamoyl)propyl, 2 oxo-2-(piperidin-1- ylamino)ethyl, propyl-amino-carbonyl-methyl, 2-(carboxymethylamino)-2-oxoethyl), bis-hydroxyethyl-amino-sulfonyl-ethyl, carboxy-methyl-amino-carbonyl-methyl, amino-carbonyl-ethyl, amino-sulfonyl-ethyl, amino-sulfonyl-propyl, methyl-amino-ethyl, piperidinyl-ethyl, piperazinyl-ethyl, methyl-sulfonyl-ethyl, carboxy-methyl, tetrazole-methyl, benzyl, 1,2,4-oxadiazole-methyl, 1,2,4-oxadiazole-ethyl, isoxazole-methyl, 2-(2-hydroxyethylamino)-2-oxoethyl, dimethylamino-ethyl-amino-carbonyl-methyl, hydroxyl-ethyl, methoxy-ethyl, hydroxyl-ethyl-amino-ethyl, morpholino-ethyl, methyl-piperazinyl-ethyl, 2-(carbamoyloxy)ethyl, methyl-sulfonyl-oxy-ethyl, morpholino-carbonyl-methyl, methyl-sulfonyl-piperazinyl-ethyl, 2-morpholinoethyl, amino-ethyl, 2-(3,3-dimethylureido)ethyl, morpholino-carbonyl-amino-ethyl, methyl-sulfonyl-amino-ethyl, pyridinyl-methyl, hydroxyl-propyl, 2-(2,6-dimethylmorpholino)ethyl, 2-(2-methylmorpholino)ethyl, methyl-sulfonyl-propyl and morpholino-propyl; wherein said ring systems of $R_{1a}$ are optionally substituted with 1 to 3 radicals independently selected from halo, trifluoromethyl, methyl, bis-hydroxy-ethyl-amino, t-butyl, t-butoxy-carbonyl, hydroxy, methyl-sulfonyl, amino-sulfonyl, diethyl-amino, morpholino, cyclohexyl, pyridinyl, piperidinyl, pyrrolidinyl, piperazinyl optionally substituted with ethyl or methyl-sulfonyl, methoxy-carbonyl and methoxy.

3. The compound of claim 2 in which $R_3$, $R_5$, $R_6$ and $R_7$ are each independently hydrogen.

4. The compound of claim 3 in which $R_4$ is selected from: trifluoro-methyl; halo; hydroxy; cyano-methoxy; dimethyl-amino-propyl; cyano; cyclopropyl-methoxy; pyrazinyl-oxy optionally substituted with amino; pyridinyl-oxy; pyrimidinyl-oxy; benzoxy; phenoxy optionally substituted with methyl or cyano; ethoxy; tetrazolyl-methoxy optionally substituted with methyl; pyridazinyl-oxy; pyrazinyl-oxy; hydroxy-ethoxy; and methoxy.

5. The compound of claim 4 in which $R_8$, $R_9$ and $R_{11}$ are each independently selected from hydrogen, halo, trifluoromethyl and methyl.

6. The compound of claim 5 in which $R_{10}$ is selected from halo, cyano, methoxy, trifluoromethyl, pyridinyl-oxy, benzoyl, phenoxy, benzyl, pyridazinyl-oxy, phenyl-sulfonyl and pyrimidinyl-oxy; wherein said pyridinyl-oxy, phenyl-sulfonyl, phenoxy, benzoyl, benzyl, pyridazinyl-oxy and pyrimidinyl-oxy can be optionally substituted with 1 to 3 halo radicals.

7. The compound of claim 1 selected from:
3-[4-(4-chloro-phenoxy)-phenyl]-1-methyl-4-(3-trifluoromethyl-phenyl)-imidazolidin-2-one;
ethyl 2-(3-(4-(4-chlorophenoxy)phenyl)-2-oxo-4-(3-(trifluoromethyl)phenyl)imidazolidin-1-yl)acetate;
(S)-2-(3-(4-(4-chlorophenoxy)phenyl)-2-oxo-4-(3-(trifluoromethyl)phenyl)imidazolidin-1-yl)acetonitrile;
3-(4-(4-chlorophenoxy)phenyl)-1-(4-(trifluoromethyl)benzyl)-4-(3-(trifluoromethyl)phenyl)imidazolidin-2-one;
3-[4-(4-Chloro-phenoxy)-phenyl]-1-(3,5-dimethyl-isoxazol-4-ylmethyl)-4-(3-trifluoromethyl-phenyl)-imidazolidin-2-one;
(S)-3-(4-(4-chlorophenoxy)phenyl)-1-(4-methoxybenzyl)-4-(3-(trifluoromethyl)phenyl)imidazolidin-2-one;
(S)-3-[6-(4-Chloro-phenoxy)-pyridin-3-yl]-1-(4-methoxy-benzyl)-4-(3-trifluoromethyl-phenyl)-imidazolidin-2-one;
(S)-3-[5-(4-Chloro-phenoxy)-pyrazin-2-yl]-1-(4-methoxy-benzyl)-4-(3-trifluoromethyl-phenyl)-imidazolidin-2-one;
(S)-3-[5-(4-Chloro-phenoxy)-pyrazin-2-yl]-1-(4-methoxy-benzyl)-4-(3-trifluoromethyl-phenyl)-imidazolidin-2-ylidene-cyanamide;
(S)-2-(3-(5-(4-chlorophenoxy)pyrazin-2-yl)-2-oxo-4-(3-(trifluoromethyl)phenyl)imidazolidin-1-yl)ethanesulfonamide;
(S)-3-[4-(4-Chloro-phenoxy)-phenyl]-1-(2-methanesulfonyl-ethyl)-4-(3-trifluoromethyl-phenyl)-imidazolidin-2-one;
(S)-2-(3-(4-(4-chlorophenoxy)phenyl)-2-oxo-4-(3-(trifluoromethyl)phenyl)imidazolidin-1-yl)ethanesulfonamide;
2-(3-(4-(4-chlorophenoxy)phenyl)-2-oxo-4-(3-(trifluoromethyl)phenyl)imidazolidin-1-yl)acetic acid;
1-((1H-tetrazol-5-yl)methyl)-3-(4-(4-chlorophenoxy)phenyl)-4-(3-(trifluoromethyl)phenyl)imidazolidin-2-one;
2-(3-(4-(4-chlorophenoxy)phenyl)-2-oxo-4-(3-(trifluoromethyl)phenyl)imidazolidin-1-yl)-N-propylacetamide;
2-(3-(4-(4-chlorophenoxy)phenyl)-2-oxo-4-(3-(trifluoromethyl)phenyl)imidazolidin-1-yl)-N-(piperidin-1-yl)acetamide;
2-(2-(3-(4-(4-chlorophenoxy)phenyl)-2-oxo-4-(3-(trifluoromethyl)phenyl)-imidazolidin-1-yl)acetamido)acetic acid;
2-(3-(4-(4-chlorophenoxy)phenyl)-2-oxo-4-(3-(trifluoromethyl)phenyl)imidazolidin-1-yl)-N-(2-hydroxyethyl)acetamide;
2-(3-(4-(4-chlorophenoxy)phenyl)-2-oxo-4-(3-(trifluoromethyl)phenyl)imidazolidin-1-yl)-N-(2-(dimethylamino)ethyl)acetamide;
3-(4-(4-chlorophenoxy)phenyl)-1-(2-hydroxyethyl)-4-(3-(trifluoromethyl)phenyl)-imidazolidin-2-one;
2-(3-(4-(4-chlorophenoxy)phenyl)-2-oxo-4-(3-(trifluoromethyl)phenyl)imidazolidin-1-yl)ethyl methanesulfonate;
3-(4-(4-chlorophenoxy)phenyl)-1-(2-methoxyethyl)-4-(3-(trifluoromethyl)phenyl)-imidazolidin-2-one;
3-(4-(4-chlorophenoxy)phenyl)-1-(2-(2-hydroxyethylamino)ethyl)-4-(3-(trifluoromethyl)-phenyl)imidazolidin-2-one;
3-(4-(4-chlorophenoxy)phenyl)-1-(2-morpholinoethyl)-4-(3-(trifluoromethyl)phenyl)imidazolidin-2-one;
3-(4-(4-chlorophenoxy)phenyl)-1-(2-(4-methylpiperazin-1-yl)ethyl)-4-(3-(trifluoromethyl)phenyl)imidazolidin-2-one;
2-(3-(4-(4-chlorophenoxy)phenyl)-2-oxo-4-(3-(trifluoromethyl)phenyl)imidazolidin-1-yl)ethyl carbamate;
3-(4-(4-chlorophenoxy)phenyl)-1-(2-(methylamino)ethyl)-4-(3-(trifluoromethyl)phenyl)imidazolidin-2-one;
3-(4-(4-chlorophenoxy)phenyl)-1-(2-(piperidin-1-yl)ethyl)-4-(3-(trifluoromethyl)phenyl)imidazolidin-2-one;
3-(4-(4-chlorophenoxy)phenyl)-1-(2-(piperazin-1-yl)ethyl)-4-(3-(trifluoromethyl)phenyl)-imidazolidin-2-one;
1-(4-chlorobenzyl)-3-(4-(4-chlorophenoxy)phenyl)-4-(3-(trifluoromethyl)phenyl)imidazolidin-2-one;
1-benzyl-3-(4-(4-chlorophenoxy)phenyl)-4-(3-(trifluoromethyl)phenyl)imidazolidin-2-one;
3-(4-(4-chlorophenoxy)phenyl)-1-(3-methoxybenzyl)-4-(3-(trifluoromethyl)phenyl)imidazolidin-2-one;
3-(4-(4-chlorophenoxy)phenyl)-1-(2-methoxybenzyl)-4-(3-(trifluoromethyl)phenyl)imidazolidin-2-one;

3-(4-(4-chlorophenoxy)phenyl)-1-(2-morpholino-2-oxo-ethyl)-4-(3-(trifluoromethyl)phenyl)imidazolidin-2-one;
3-(4-(4-chlorophenoxy)phenyl)-1-(2-(4-(methylsulfonyl)piperazin-1-yl)ethyl)-4-(3-(trifluoromethyl)phenyl)imidazolidin-2-one;
3-(4-(4-chlorophenoxy)phenyl)-1-(2-((2S,6R)-2,6-dimethylmorpholino)ethyl)-4-(3-(trifluoromethyl)phenyl)imidazolidin-2-one;
1-(2-aminoethyl)-3-(4-(4-chlorophenoxy)phenyl)-4-(3-(trifluoromethyl)phenyl)imidazolidin-2-one;
3-(2-(3-(4-(4-chlorophenoxy)phenyl)-2-oxo-4-(3-(trifluoromethyl)phenyl)imidazolidin-1-yl)ethyl)-1,1-dimethylurea;
N-(2-(3-(4-(4-chlorophenoxy)phenyl)-2-oxo-4-(3-(trifluoromethyl)phenyl)imidazolidin-1-yl)ethyl)morpholine-4-carboxamide;
N-(2-(3-(4-(4-chlorophenoxy)phenyl)-2-oxo-4-(3-(trifluoromethyl)phenyl)imidazolidin-1-yl)ethyl)methanesulfonamide;
3-(4-(4-chlorophenoxy)phenyl)-1-(pyridin-2-ylmethyl)-4-(3-(trifluoromethyl)phenyl)imidazolidin-2-one;
3-(4-(4-chlorophenoxy)phenyl)-1-(pyridin-3-ylmethyl)-4-(3-(trifluoromethyl)phenyl)imidazolidin-2-one;
3-(4-(4-chlorophenoxy)phenyl)-1-(pyridin-4-ylmethyl)-4-(3-(trifluoromethyl)phenyl)imidazolidin-2-one;
(S)-3-(4-(4-chlorophenoxy)phenyl)-1-(3-hydroxypropyl)-4-(3-(trifluoromethyl)phenyl)imidazolidin-2-one;
3-(4-(4-chlorophenoxy)phenyl)-1-(2-((R)-2-methylmorpholino)ethyl)-4-(3-(trifluoromethyl)phenyl)imidazolidin-2-one;
3-(4-(4-chlorophenoxy)phenyl)-1-(2-((S)-2-methylmorpholino)ethyl)-4-(3-(trifluoromethyl)phenyl)imidazolidin-2-one;
(S)—N-(3-(4-(4-chlorophenoxy)phenyl)-1-(2-hydroxyethyl)-4-(3-(trifluoromethyl)phenyl)imidazolidin-2-ylidene)cyanamide;
(S)-3-(4-(4-chlorophenoxy)phenyl)-1-(3-(methylsulfonyl)propyl)-4-(3-(trifluoromethyl)phenyl)imidazolidin-2-one;
N-(3-(4-(4-chlorophenoxy)phenyl)-1-(2-(methylsulfonyl)ethyl)-4-(3-(trifluoromethyl)phenyl)imidazolidin-2-ylidene)cyanamide;
3-(4-(4-chlorophenoxy)phenyl)-1-(3-morpholinopropyl)-4-(3-(trifluoromethyl)phenyl)imidazolidin-2-one;
(S)—N-(3-(4-(4-chlorophenoxy)phenyl)-1-(3-hydroxypropyl)-4-(3-(trifluoromethyl)phenyl)imidazolidin-2-ylidene)cyanamide;
N-(3-(4-(4-chlorophenoxy)phenyl)-1-(2-morpholinoethyl)-4-(3-(trifluoromethyl)phenyl)imidazolidin-2-ylidene)cyanamide;
N-(3-(4-(4-chlorophenoxy)phenyl)-1-(2-((S)-2-methylmorpholino)ethyl)-4-(3-(trifluoromethyl)phenyl)imidazolidin-2-ylidene)cyanamide;
N-(3-(4-(4-chlorophenoxy)phenyl)-1-(3-(methylsulfonyl)propyl)-4-(3-(trifluoromethyl)phenyl)imidazolidin-2-ylidene)cyanamide;
(S)—N,N-bis(4-methoxybenzyl)-3-(5-(4-chlorophenyl)-4-(3-methoxyphenyl)-1,1-dioxo-1,2,5-thiadiazolidin-2-yl)propanesulfamide;
(S)-2-(4-chlorophenyl)-1,1-dioxo-5-(3-(methylsulfonyl)propyl)-3-(3-(pyrazin-2-yloxy)phenyl)-1,2,5-thiadiazolidine;
(S)-2-(5-(4-chlorophenyl)-4-(3-(cyanomethoxy)phenyl)-1,1-dioxo-1,2,5-thiadiazolidin-2-yl)acetonitrile;
(S)-2-(5-(4-chlorophenyl)-4-(3-methoxyphenyl)-1,1-dioxo-1,2,5-thiadiazolidin-2-yl)acetonitrile;
(S)-2-(4-chlorophenyl)-3-(3-methoxyphenyl)-1,1-dioxo-5-((3,5-dimethylisoxazol-4-yl)methyl)-1,2,5-thiadiazolidine;
(S)-methyl 3-((5-(4-chlorophenyl)-4-(3-methoxyphenyl)-1,1-dioxo-1,2,5-thiadiazolidin-2-yl)methyl)isoxazole-5-carboxylate;
(S)-3-((5-(4-chlorophenyl)-4-(3-methoxyphenyl)-1,1-dioxo-1,2,5-thiadiazolidin-2-yl)methyl)-1,2,4-oxadiazole;
(S)-3-(5-(4-chlorophenyl)-1,1-dioxo-4-(3-(pyrazin-2-yloxy)phenyl)-1,2,5-thiadiazolidin-2-yl)propane-1-sulfonamide;
(S)-4-((5-(4-chlorophenyl)-4-(3-(pyrazin-2-yloxy)phenyl)-1,2,5-thiadiazolidin-2-yl)methyl)-3,5-dimethylisoxazole;
3-(4-(4-chlorophenoxy)phenyl)-4-(3-(benzyloxy)phenyl)-1-(2-(methylsulfonyl)ethyl)imidazolidin-2-one;
3-(4-(4-chlorophenoxy)phenyl)-4-(3-hydroxyphenyl)-1-(2-(methylsulfonyl)ethyl)imidazolidin-2-one;
3-(4-(4-chlorophenoxy)phenyl)-1-(2-(methylsulfonyl)ethyl)-4-(3-(pyridin-2-yloxy)phenyl)imidazolidin-2-one;
3-(4-(4-chlorophenoxy)phenyl)-1-(2-(methylsulfonyl)ethyl)-4-(3-(pyrazin-2-yloxy)phenyl)imidazolidin-2-one;
4-(3-(2-cyanophenoxy)phenyl)-3-(4-(4-chlorophenoxy)phenyl)-1-(2-(methylsulfonyl)ethyl)imidazolidin-2-one;
4-(3-(benzyloxy)phenyl)-3-(4-chlorophenyl)-1-(2-(methylsulfonyl)ethyl)imidazolidin-2-one;
3-(4-chlorophenyl)-4-(3-hydroxyphenyl)-1-(2-(methylsulfonyl)ethyl)imidazolidin-2-one;
3-(4-chlorophenyl)-1-(2-(methylsulfonyl)ethyl)-4-(3-(pyrazin-2-yloxy)phenyl)imidazolidin-2-one;
4-(3-(2-cyanophenoxy)phenyl)-3-(4-chlorophenyl)-1-(2-(methylsulfonyl)ethyl)imidazolidin-2-one;
3-(4-chlorophenyl)-1-(2-(methylsulfonyl)ethyl)-4-(3-(pyrimidin-2-yloxy)phenyl)imidazolidin-2-one;
3-(4-chlorophenyl)-1-(2-(methylsulfonyl)ethyl)-4-(3-(pyridin-2-yloxy)phenyl)imidazolidin-2-one;
3-(4-chlorophenyl)-1-(2-(methylsulfonyl)ethyl)-4-(3-(pyridin-3-yloxy)phenyl)imidazolidin-2-one;
3-(4-chlorophenyl)-1-(2-(methylsulfonyl)ethyl)-4-(3-(pyridin-4-yloxy)phenyl)imidazolidin-2-one;
3-(4-chlorophenyl)-1-(2-(methylsulfonyl)ethyl)-4-(3-(pyridazin-3-yloxy)phenyl)imidazolidin-2-one;
4-(3-(4-methoxyphenoxy)phenyl)-3-(4-chlorophenyl)-1-(2-(methylsulfonyl)ethyl)imidazolidin-2-one;
4-(3-(5-aminopyrazin-2-yloxy)phenyl)-3-(4-chlorophenyl)-1-(2-(methylsulfonyl)ethyl)imidazolidin-2-one;
3-(4-chlorophenyl)-1-(2-(methylsulfonyl)ethyl)-4-(3-(pyrimidin-5-yloxy)phenyl)imidazolidin-2-one;
(S)-3-(4-chlorophenyl)-1-((5-(4-methoxyphenyl)-1,2,4-oxadiazol-3-yl)methyl)-4-(3-(trifluoromethyl)phenyl)imidazolidin-2-one;
(S)-3-(4-chlorophenyl)-1-(pyridin-3-ylmethyl)-4-(3-(trifluoromethyl)phenyl)imidazolidin-2-one;
(S)-3-(4-chlorophenyl)-1-(4-methoxybenzyl)-4-(3-(trifluoromethyl)phenyl)imidazolidin-2-one;
(S)-2-(3-(4-chlorophenyl)-2-oxo-4-(3-(trifluoromethyl)phenyl)imidazolidin-1-yl)ethanesulfonamide;
(S)-3-(4-chlorophenyl)-1-(2-hydroxyethyl)-4-(3-(trifluoromethyl)phenyl)imidazolidin-2-one;
(S)-3-(4-chlorophenyl)-1-(3-hydroxypropyl)-4-(3-(trifluoromethyl)phenyl)imidazolidin-2-one;
(S)-2-(3-(4-chlorophenyl)-2-oxo-4-(3-(trifluoromethyl)phenyl)imidazolidin-1-yl)-N-propylacetamide;

(S)-3-(4-chlorophenyl)-1-(2-oxo-2-(piperidin-1-yl) ethyl)-4-(3-(trifluoromethyl)phenyl)imidazolidin-2-one;

(S)-2-(3-(4-chlorophenyl)-2-oxo-4-(3-(trifluoromethyl) phenyl)imidazolidin-1-yl)-N-(piperidin-1-yl)acetamide;

(S)-tert-butyl 4-(2-(3-(4-chlorophenyl)-2-oxo-4-(3-(trifluoromethyl)phenyl)imidazolidin-1-yl)acetyl)piperazine-1-carboxylate;

(S)-3-(4-chlorophenyl)-1-((5-(4-methoxyphenyl)-1,3,4-oxadiazol-2-yl)methyl)-4-(3-(trifluoromethyl)phenyl) imidazolidin-2-one;

(S)-3-(4-chlorophenyl)-1-((5-(4-chlorophenyl)oxazol-2-yl)methyl)-4-(3-(trifluoromethyl)phenyl)imidazolidin-2-one;

(S)-methyl 3-((3-(4-chlorophenyl)-2-oxo-4-(3-(trifluoromethyl)phenyl)imidazolidin-1-yl)methyl)isoxazole-5-carboxylate;

(S)-3-(4-chlorophenyl)-1-(2-morpholinoethyl)-4-(3-(trifluoromethyl)phenyl)imidazolidin-2-one;

(S)-3-(4-chlorophenyl)-1-(2-(4-hydroxypiperidin-1-yl) ethyl)-4-(3-(trifluoromethyl)phenyl)imidazolidin-2-one;

(S)-3-(4-chlorophenyl)-1-(3-morpholinopropyl)-4-(3-(trifluoromethyl)phenyl)imidazolidin-2-one;

(S)-3-(4-chlorophenyl)-1-(2-(4-(methylsulfonyl)piperazin-1-yl)ethyl)-4-(3-(trifluoromethyl)phenyl)imidazolidin-2-one;

(S)-1-((5-tert-butyl-1,2,4-oxadiazol-3-yl)methyl)-3-(4-chlorophenyl)-4-(3-(trifluoromethyl)phenyl)imidazolidin-2-one;

(S)-3-(4-chlorophenyl)-1-(2-(4-methylpiperazin-1-ylsulfonyl)ethyl)-4-(3-(trifluoromethyl)phenyl)imidazolidin-2-one;

(S)-3-(4-chlorophenyl)-1-(2-(piperidin-1-ylsulfonyl) ethyl)-4-(3-(trifluoromethyl)phenyl)imidazolidin-2-one;

(S)-3-(4-chlorophenyl)-1-(2-(pyrrolidin-1-ylsulfonyl) ethyl)-4-(3-(trifluoromethyl)phenyl)imidazolidin-2-one;

(S)-3-(4-chlorophenyl)-1-(2-(morpholinosulfonyl)ethyl)-4-(3-(trifluoromethyl)phenyl)imidazolidin-2-one;

(S)-3-(3-(4-chlorophenyl)-2-oxo-4-(3-(trifluoromethyl) phenyl)imidazolidin-1-yl)propane-1-sulfonamide;

(S)-2-(3-(4-chlorophenyl)-2-oxo-4-(3-(trifluoromethyl) phenyl)imidazolidin-1-yl)-N,N-bis(2-hydroxyethyl) ethanesulfonamide;

(S)-3-(4-chlorophenyl)-1-((6-morpholinopyridin-3-yl) methyl)-4-(3-(trifluoromethyl)phenyl)imidazolidin-2-one;

(S)-3-(4-chlorophenyl)-1-((6-(4-ethylpiperazin-1-yl)pyridin-3-yl)methyl)-4-(3-(trifluoromethyl)phenyl)imidazolidin-2-one;

(S)-3-(4-chlorophenyl)-1-((6-(piperidin-1-yl)pyridin-3-yl)methyl)-4-(3-(trifluoromethyl)phenyl)imidazolidin-2-one;

(S)-3-(4-chlorophenyl)-1-((6-(pyrrolidin-1-yl)pyridin-3-yl)methyl)-4-(3-(trifluoromethyl)phenyl)imidazolidin-2-one;

(S)-1-((6-(bis(2-hydroxyethyl)amino)pyridin-3-yl)methyl)-3-(4-chlorophenyl)-4-(3-(trifluoromethyl)phenyl) imidazolidin-2-one;

(S)-3-(4-chlorophenyl)-1-((6-(4-(methylsulfonyl)piperazin-1-yl)pyridin-3-yl)methyl)-4-(3-(trifluoromethyl) phenyl)imidazolidin-2-one;

(S)-3-(4-chlorophenyl)-1-(3-(4-(methylsulfonyl)piperazin-1-yl)propyl)-4-(3-(trifluoromethyl)phenyl)imidazolidin-2-one;

(4S)-3-(4-chlorophenyl)-1-(3-(3-(diethylamino)pyrrolidin-1-yl)propyl)-4-(3-(trifluoromethyl)phenyl)imidazolidin-2-one;

(S)-3-(4-chlorophenyl)-1-(2-(5-cyclohexyl-1,2,4-oxadiazol-3-yl)ethyl)-4-(3-(trifluoromethyl)phenyl)imidazolidin-2-one;

(S)-1-(2-(5-tert-butyl-1,2,4-oxadiazol-3-yl)ethyl)-3-(4-chlorophenyl)-4-(3-(trifluoromethyl)phenyl)imidazolidin-2-one;

(S)-3-(4-chlorophenyl)-1-(2-(5-(pyridin-3-yl)-1,2,4-oxadiazol-3-yl)ethyl)-4-(3-(trifluoromethyl)phenyl)imidazolidin-2-one;

(S)-3-(4-(4-chlorophenoxy)phenyl)-1-(2-(morpholinosulfonyl)ethyl)-4-(3-(trifluoromethyl)phenyl)imidazolidin-2-one;

(S)-3-(3-(4-(4-chlorophenoxy)phenyl)-2-oxo-4-(3-(trifluoromethyl)phenyl)imidazolidin-1-yl)propane-1-sulfonamide;

(S)-3-(4-(4-chlorophenoxy)phenyl)-1-(2-(4-methylpiperazin-1-ylsulfonyl)ethyl)-4-(3-(trifluoromethyl)phenyl) imidazolidin-2-one;

(S)-2-(3-(4-(4-chlorophenoxy)phenyl)-2-oxo-4-(3-(trifluoromethyl)phenyl)imidazolidin-1-yl)-N-(2-hydroxyethyl)ethanesulfonamide;

(S)-2-(3-(4-(4-chlorophenoxy)phenyl)-2-oxo-4-(3-(trifluoromethyl)phenyl)imidazolidin-1-yl)-N,N-bis(2-hydroxyethyl)ethanesulfonamide;

(S)-2-(3-(4-(4-chlorophenoxy)phenyl)-4-(3-methoxyphenyl)-2-oxoimidazolidin-1-yl)ethanesulfonamide;

(S)-2-(3-(4-(4-chlorophenoxy)phenyl)-4-(3-(2-hydroxyethoxy)phenyl)-2-oxoimidazolidin-1-yl)ethanesulfonamide;

(S)—N-(2-(3-(4-(4-chlorophenoxy)phenyl)-2-oxo-4-(3-(trifluoromethyl)phenyl)imidazolidin-1-yl)ethylsulfonyl)acetamide;

(S)-3-(4-(4-chlorophenoxy)phenyl)-4-(3-(2-hydroxyethoxy)phenyl)-1-(2-(methylsulfonyl)ethyl)imidazolidin-2-one;

tert-butyl 4-((2-((S)-3-(4-(4-chlorophenoxy)phenyl)-4-(3-(trifluoromethyl)phenyl)-2-oxoimidazolidin-1-yl) ethyl)sulfonyl)piperazine-1-carboxylate;

(S)-3-(4-(4-chlorophenoxy)phenyl)-4-(3-(trifluoromethyl)phenyl)-1-(2-((piperazin-1-yl)sulfonyl)ethyl)imidazolidin-2-one;

(S)-3-(4-chlorophenyl)-1-(2-(morpholinosulfonyl)ethyl)-4-(3-(pyridazin-3-yloxy)phenyl)imidazolidin-2-one;

(S)-3-(4-chlorophenyl)-1-(2-(4-methylpiperazin-1-ylsulfonyl)ethyl)-4-(3-(pyridazin-3-yloxy)phenyl)imidazolidin-2-one;

(S)-3-(4-chlorophenyl)-4-(3-(pyridazin-3-yloxy)phenyl)-1-(2-(pyrrolidin-1-ylsulfonyl)ethyl)imidazolidin-2-one;

(S)-2-(3-(4-chlorophenyl)-2-oxo-4-(3-(pyridazin-3-yloxy)phenyl)imidazolidin-1-yl)ethanesulfonamide;

(S)-3-(4-chlorophenyl)-4-(3-(2-hydroxyethoxy)phenyl)-1-(2-(methylsulfonyl)ethyl)imidazolidin-2-one;

(S)-3-(4-chlorophenyl)-4-(3-(2-hydroxyethoxy)phenyl)-1-(2-(morpholinosulfonyl)ethyl)imidazolidin-2-one;

(S)-3-(4-chlorophenyl)-4-(3-(2-hydroxyethoxy)phenyl)-1-(2-(4-methylpiperazin-1-ylsulfonyl)ethyl)imidazolidin-2-one;

(S)-3-(4-chlorophenyl)-4-(3-(2-hydroxyethoxy)phenyl)-1-(2-(pyrrolidin-1-ylsulfonyl)ethyl)imidazolidin-2-one;

(S)-2-(3-(4-chlorophenyl)-4-(3-(2-hydroxyethoxy)phenyl)-2-oxoimidazolidin-1-yl)ethanesulfonamide;
(S)-3-(4-(4-chlorophenoxy)phenyl)-1-(2-(methylsulfonyl)ethyl)-4-(3-(pyrazin-2-yloxy)phenyl)imidazolidin-2-one;
(S)-2-(3-(4-(4-chlorophenoxy)phenyl)-2-oxo-4-(3-(pyrazin-2-yloxy)phenyl)imidazolidin-1-yl)ethanesulfonamide;
(S)-3-(5-(4-chlorophenoxy)pyrazin-2-yl)-4-(3-methoxyphenyl)-1-(2-(methylsulfonyl)ethyl)imidazolidin-2-one;
(S)-1-(2-(azetidin-1-ylsulfonyl)ethyl)-3-(4-(4-chlorophenoxy)phenyl)-4-(3-(trifluoromethyl)phenyl)imidazolidin-2-one;
(S)-1-(2-(azetidin-1-ylsulfonyl)ethyl)-3-(4-chlorophenyl)-4-(3-(pyridazin-3-yloxy)phenyl)imidazolidin-2-one;
(S)-methyl 3-(3-(4-(4-chlorophenoxy)phenyl)-2-oxo-4-(3-(trifluoromethyl)phenyl)imidazolidin-1-yl)propanoate;
(S)-3-(4-chlorophenyl)-1-(2-(methylsulfonyl)ethyl)-4-(3-(trifluoromethyl)phenyl)imidazolidin-2-one;
(S)-3-(3-(4-(4-chlorophenoxy)phenyl)-2-oxo-4-(3-(trifluoromethyl)phenyl)imidazolidin-1-yl)propanamide;
(S)-3-(4-chlorophenyl)-1-(2-(methylsulfonyl)ethyl)-4-(3-(pyridin-2-yloxy)phenyl)imidazolidin-2-one;
(4S)-3-(4-(4-chlorophenoxy)phenyl)-1-(2-(1-methylpyrrolidin-2-yl)ethyl)-4-(3-(trifluoromethyl)phenyl)imidazolidin-2-one;
(S)-1-(2-(1,3-dioxan-2-yl)ethyl)-3-(4-(4-chlorophenoxy)phenyl)-4-(3-(trifluoromethyl)phenyl)imidazolidin-2-one;
3-(4-(4-chlorophenoxy)phenyl)-1-(2-(2-oxopyrrolidin-1-yl)ethyl)-4-(3-(trifluoromethyl)phenyl)imidazolidin-2-one;
3-(2-(3-(4-(4-chlorophenoxy)phenyl)-2-oxo-4-(3-(trifluoromethyl)phenyl)imidazolidin-1-yl)ethyl)oxazolidin-2-one;
1-(2-(1H-pyrazol-1-yl)ethyl)-3-(4-(4-chlorophenoxy)phenyl)-4-(3-(trifluoromethyl)phenyl)imidazolidin-2-one;
1-(2-(1H-imidazol-1-yl)ethyl)-3-(4-(4-chlorophenoxy)phenyl)-4-(3-(trifluoromethyl)phenyl)imidazolidin-2-one;
(S)-3-(4-chlorophenyl)-1-(2-(methylsulfonyl)ethyl)-4-(3-(pyrazin-2-yloxy)phenyl)imidazolidin-2-one;
(S)-2-(3-(4-chlorophenyl)-2-oxo-4-(3-(pyrazin-2-yloxy)phenyl)imidazolidin-1-yl)ethanesulfonamide;
(S)-3-(4-chlorophenyl)-4-(3-(pyrazin-2-yloxy)phenyl)-1-(2-(pyrrolidin-1-ylsulfonyl)ethyl)imidazolidin-2-one;
(S)-3-(4-chlorophenyl)-1-(2-(morpholinosulfonyl)ethyl)-4-(3-(pyrazin-2-yloxy)phenyl)imidazolidin-2-one;
(S)-3-(4-chlorophenyl)-1-(2-(4-methylpiperazin-1-ylsulfonyl)ethyl)-4-(3-(pyrazin-2-yloxy)phenyl)imidazolidin-2-one;
(S)-3-(4-chlorophenyl)-1-(2-(piperazin-1-ylsulfonyl)ethyl)-4-(3-(pyrazin-2-yloxy)phenyl)imidazolidin-2-one;
(S)-1-(2-(1,3-dioxan-2-yl)ethyl)-3-(4-chlorophenyl)-4-(3-(pyrazin-2-yloxy)phenyl)imidazolidin-2-one;
(S)-3-(4-(4-chlorophenoxy)phenyl)-4-(3-methoxyphenyl)-1-(2-(methylsulfonyl)ethyl)imidazolidin-2-one;
(S)-3-(3-(4-chlorophenyl)-2-oxo-4-(3-(pyrazin-2-yloxy)phenyl)imidazolidin-1-yl)propanamide;
(S)—N-(3-(4-(4-chlorophenoxy)phenyl)-1-cyano-4-(3-(trifluoromethyl)phenyl)imidazolidin-2-ylidene)cyanamide;
(S)-1-(2-(1H-1,2,4-triazol-3-yl)ethyl)-3-(4-chlorophenyl)-4-(3-(pyrazin-2-yloxy)phenyl)imidazolidin-2-one;
(S)-3-(3-(3-(4-chlorophenyl)-1-(2-(methylsulfonyl)ethyl)-2-oxoimidazolidin-4-yl)phenoxy)pyrazine-2-carbonitrile;
(S)-3-(4-chlorophenyl)-4-(3-(3-ethylpyrazin-2-yloxy)phenyl)-1-(2-(methylsulfonyl)ethyl)imidazolidin-2-one; and
(S)-4-(3-(5-aminopyrazin-2-yloxy)phenyl)-3-(4-chlorophenyl)-1-(2-(methylsulfonyl)ethyl)imidazolidin-2-one.

8. A composition comprising a pharmaceutically acceptable carrier and a compound selected from a compound of claim 1.

* * * * *